(12) United States Patent
Kahvejian et al.

(10) Patent No.: US 9,644,180 B2
(45) Date of Patent: *May 9, 2017

(54) SYNTHETIC MEMBRANE-RECEIVER COMPLEXES

(71) Applicant: RUBIUS THERAPEUTICS, INC., Cambridge, MA (US)

(72) Inventors: Avak Kahvejian, Arlington, MA (US); Jordi Mata-Fink, Somerville, MA (US); John Round, Cambridge, MA (US); David Arthur Berry, Cambridge, MA (US); Noubar B. Afeyan, Lexington, MA (US)

(73) Assignee: RUBIUS THERAPEUTICS, INC., Cambridge, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/738,414

(22) Filed: Jun. 12, 2015

(65) Prior Publication Data

US 2015/0306212 A1 Oct. 29, 2015

Related U.S. Application Data

(63) Continuation of application No. 14/581,486, filed on Dec. 23, 2014, which is a continuation of application No. PCT/US2014/065304, filed on Nov. 12, 2014.

(60) Provisional application No. 62/059,100, filed on Oct. 2, 2014, provisional application No. 62/025,367, filed on Jul. 16, 2014, provisional application No. 62/006,825, filed on Jun. 2, 2014, provisional application No. 62/006,829, filed on Jun. 2, 2014, provisional application No. 62/006,832, filed on Jun. 2, 2014, provisional application No. 61/991,319, filed on May 9, 2014, provisional application No. 61/973,764, filed on Apr. 1, 2014, provisional application No. 61/919,432, filed on Dec. 20, 2013, provisional application No. 61/962,867, filed on Nov. 18, 2013.

(51) Int. Cl.

| | | |
|---|---|---|
| *C12N 9/88* | (2006.01) | |
| *C12N 15/07* | (2006.01) | |
| *C12N 5/078* | (2010.01) | |
| *A61K 38/17* | (2006.01) | |
| *A61K 39/44* | (2006.01) | |
| *A61K 31/7088* | (2006.01) | |
| *A61K 47/48* | (2006.01) | |
| *A61K 9/00* | (2006.01) | |
| *A61K 35/18* | (2015.01) | |
| *A61K 39/00* | (2006.01) | |
| *A61K 39/385* | (2006.01) | |
| *A61K 39/42* | (2006.01) | |
| *C07K 16/08* | (2006.01) | |
| *A61K 35/12* | (2015.01) | |

(52) U.S. Cl.
CPC .......... *C12N 5/0641* (2013.01); *A61K 9/0019* (2013.01); *A61K 31/7088* (2013.01); *A61K 35/18* (2013.01); *A61K 38/177* (2013.01); *A61K 38/1774* (2013.01); *A61K 39/001* (2013.01); *A61K 39/385* (2013.01); *A61K 39/42* (2013.01); *A61K 39/44* (2013.01); *A61K 47/48053* (2013.01); *A61K 47/48776* (2013.01); *A61K 47/48792* (2013.01); *C07K 16/082* (2013.01); *C12N 9/88* (2013.01); *A61K 2035/124* (2013.01); *A61K 2039/622* (2013.01); *C07K 2317/622* (2013.01); *C12N 2510/00* (2013.01); *C12Y 204/02004* (2013.01); *C12Y 304/22* (2013.01); *C12Y 403/01024* (2013.01)

(58) Field of Classification Search
CPC .......... C12Y 403/01024; C12N 5/0641; C12N 2510/00
USPC .......... 435/69.1, 70.1; 514/1.1, 5.5
See application file for complete search history.

(56) References Cited

U.S. PATENT DOCUMENTS

| | | |
|---|---|---|
| 4,327,710 A | 5/1982 | DeLoach et al. |
| 5,258,499 A | 11/1993 | Konigsberg et al. |
| 5,648,248 A | 7/1997 | Zenke et al. |
| 5,676,954 A | 10/1997 | Brigham |
| 5,677,176 A | 10/1997 | Nicolau et al. |
| 5,753,221 A | 5/1998 | Magnani et al. |
| 5,811,301 A | 9/1998 | Cameron |
| 5,891,468 A | 4/1999 | Martin et al. |
| 6,139,836 A | 10/2000 | Magnani et al. |
| 6,165,787 A | 12/2000 | Crabtree et al. |
| 6,326,205 B1 | 12/2001 | Murray et al. |
| 6,350,466 B1 | 2/2002 | Li et al. |
| 6,361,998 B1 | 3/2002 | Bell et al. |
| 6,660,525 B2 | 12/2003 | Martin et al. |
| 6,984,379 B1 | 1/2006 | Kohn et al. |

(Continued)

FOREIGN PATENT DOCUMENTS

| | | |
|---|---|---|
| DE | 102004054536 A1 | 5/2006 |
| WO | 2006016247 A2 | 2/2006 |

(Continued)

OTHER PUBLICATIONS

Liu et al., "Membrane Remodeling During Reticulocyte Maturation", Blood, 115(10):2021-7, Mar. 11, 2010.
Rossi et al., "Erythrocyte-Mediated Delivery of Phenylalanine Ammonia Lyase for the Treatment of Phenylketonuria in BTBR-Pahenu2 mice", Journal of Controlled Release, 194:37-44, Nov. 28, 2014.
Sprandel et al., "Biochemical Studies of Phenylalanine Ammonia-Lyase Encapsulated in Erythrocytes", Biochemical Society Transactions, 18(4):654-655, Aug. 1990.
Aledort, L. M. et al., "Efficacy and Safety of Intravenous Anti-D Immunoglobulin (Rhophylac) in Chronic Immune Thrombocytopenic Purpura," Hematology (Amsterdam, Netherlands), 2007, pp. 289-295, vol. 12, No. 4. doi:10.1080/10245330701383908.

(Continued)

*Primary Examiner* — David Lukton
(74) *Attorney, Agent, or Firm* — Lando & Anastasi, LLP

(57) ABSTRACT

Compositions comprising synthetic membrane-receiver complexes, methods of generating synthetic membrane-receiver complexes, and methods of treating or preventing diseases, disorders or conditions therewith.

21 Claims, 50 Drawing Sheets

(56) References Cited

U.S. PATENT DOCUMENTS

| | | | |
|---|---|---|---|
| 7,427,603 | B2 | 9/2008 | Zon et al. |
| 7,462,485 | B2 | 12/2008 | Glaser |
| 7,531,341 | B1 | 5/2009 | Vellard et al. |
| 7,534,595 | B2 | 5/2009 | Vellard et al. |
| 7,537,923 | B2 | 5/2009 | Kakkis et al. |
| 7,560,263 | B2 | 7/2009 | Kakkis et al. |
| 8,211,656 | B2 | 7/2012 | Hyde et al. |
| 8,529,944 | B2 | 9/2013 | de Almeida Moreira et al. |
| 8,617,840 | B2 | 12/2013 | Godfrin |
| 2008/0008695 | A1* | 1/2008 | Vellard .......... C12N 9/88 424/94.3 |
| 2008/0274092 | A1 | 11/2008 | Godfrin et al. |
| 2010/0310612 | A1 | 12/2010 | DuFour et al. |
| 2010/0316620 | A1 | 12/2010 | Bourgeaux et al. |
| 2012/0009140 | A1 | 1/2012 | Godfrin et al. |
| 2012/0207745 | A1 | 8/2012 | Godfrin et al. |
| 2013/0028962 | A1 | 1/2013 | Zhang et al. |
| 2014/0010795 | A1 | 1/2014 | Bourgeaux et al. |
| 2014/0024118 | A1 | 1/2014 | Nakamura et al. |

FOREIGN PATENT DOCUMENTS

| | | |
|---|---|---|
| WO | 2006114691 A1 | 11/2006 |
| WO | 2007042647 A1 | 4/2007 |
| WO | 2009019317 A1 | 2/2009 |
| WO | 2009080837 A1 | 7/2009 |
| WO | 2009101467 A1 | 8/2009 |
| WO | 2009112493 A1 | 9/2009 |
| WO | 2010052315 A1 | 5/2010 |
| WO | 2010075072 A2 | 7/2010 |
| WO | 2010115880 A1 | 10/2010 |
| WO | 2011051346 A1 | 5/2011 |
| WO | 2013121296 A1 | 8/2013 |
| WO | 2013139906 A1 | 9/2013 |
| WO | 2014181309 A1 | 11/2014 |
| WO | 2014183071 A2 | 11/2014 |

OTHER PUBLICATIONS

Asherson, R. A., "Multiorgan Failure and Antiphospholipid Antibodies: the Catastrophic Antiphospholipid (Asherson's) Syndrome," Immunobiology, doi:10.1016/j.imbio.2005.10.002, 2005, pp. 727-733, vol. 210, No. 10.

Banzato, A. et al., "Clinical Relevance of Beta-2-Glycoprotein-1 Plasma Levels in Antiphospholipid Syndrome (APS)," Current Rheumatology Reports, 2014, 424, 5 pages, vol. 16, No. 6. doi:10.1007/s11926-014-0424-9.

Beck, L. et al., "M-Type Phospholipase A2 Receptor as Target Antigen in Idiopathic Membranous Nephropathy," New England Journal of Medicine, Jul. 2, 2009, pp. 11-21, vol. 361, No. 1. Retrieved from http://www.nejm.org/doi/ful1/1 0.1056/NEJMoa081 0457.

Beck, L. H. & Salant, D. J. "Review Series: Membranous Nephropathy: from Models to Man," Journal of Clinical Investigation, 2014, pp. 2307-2314, vol. 124, No. 6. doi:10.1172/JCI72270. Review.

Bhowmik, D. et al., "Clinical Approach to Rapidly Progressive Renal Failure: Role of Kidney Biopsy," J Assoc Physicians India, Jan. 2011, pp. 38-41, vol. 59.

Bollmann, F. Mathias, "Rheumatic Autoimmune Diseases: Proposed Elimination of Autoreactive B-cells with Magnetic Nanoparticle-Linked Antigens", Medical Hypotheses Eden Press Penrith US, vol. 78, No. 4, Jan. 6, 2012.

Booth, C. et al., "Pegademase Bbovine (PEG-ADA) for the Treatment of Infants and Children with Severe Combined Immunodeficiency ( SCID )," Biologics, 2009, pp. 349-358, vol. 3.

Caras, I. W. et al., "Analysis of the Signal for Attachment of a Glycophospholipid Membrane Anchor," Journal of Cell Biology, Apr. 1989, pp. 1387-1396, vol. 108.

Chen, E. H. et al., "Hereditary Overexpression of Adenosine Deaminase in Erythrocytes: Studies in Erythroid Cell Lines and Transgenic Mice," Blood, 1994, pp. 2346-2353, vol. 84, No. 7.

Chen, Z. et al., "Circulation DNA: Biological Implications for Cancer Metastasis and Immunology," Medical Hypotheses, 2005, pp. 956-961, vol. 65, No. 5. doi:1 0.1 016/j.mehy.2005.04.042.

Cremel, M. et al., "Red Blood Cells as Innovative Antigen Carrier to Induce Specific Immune Tolerance," International Journal of Pharmaceutics, 2013, pp. 39-49, vol. 443, No. 1-2. doi:10.1016/j.ijpharm.2012.12.044.

Dember, L., "Emerging Treatment Approaches for the Systemic Amyloidoses," Kidney International, 2005, pp. 1377-1390, vol. 68, No. 3.

Ferri, C. et al., "Mixed Cryoglobulinemia: Demographic, Clinical, and Serologic Features and Survival in 231 Patients," Semin Arthritis Rheum, 2004, pp. 355-374, vol. 33, No. 6. doi:10.1053/S0049-0172(03)00179-3.

Fujimi, A. et al., "Ex Vivo Large-Scale Generation of Human Red Blood Cells from Cord Blood CD34+ Cells by Co-Culturing with Macrophages," International Journal of Hematology, 2008, pp. 339-350, vol. 87, No. 4. doi:10.1007/s12185-008-0062-y.

Furtado, P. B. et al., "The Partly Folded Back Solution Structure Arrangement of the 30 SCR Domains in Human Complement Receptor Type 1 (CR1) Permits Access to its C3b and C4b Ligands," Journal of Molecular Biology, 2008, pp. 102-118, vol. 375, No. 1. doi: 10.1 016/j.jmb.2007.09.085.

Giarratana, M.C. et al., "Ex Vivo Generation of Fully Mature Human Red Blood Cells from Hematopoietic Stem Cells," Nature Biotechnology, 2005, pp. 69-74, vol. 23, No. 1. doi:10.1038/nbt1047.

Giarratana, M.C. et al., "Proof of Principle for Transfusion of in Vitro-Generated Red Blood Cells," Blood, 2011, pp. 5071-5079, vol. 118, No. 19. doi:10.1182/blood-2011-06-362038.

Hattangadi, S.M. et al., "From Stem Cell to Red Cell: Regulation of Erythropoiesis at Multiple Levels by Multiple Proteins, RNAs, and Chromatin Modifications," Blood, 2011, pp. 6258-6668, vol. 118, No. 24. doi:10.1182/blood-2011-07-356006.

Hebert, L.A. et al., "Differential Diagnosis of Glomerular Disease: a Systematic and Inclusive Approach," American Journal of Nephrology, 2013, pp. 253-266, vol. 38, No. 3. doi: 10.1159/000354390.

Hu, C.M. J. et al., "Erythrocyte Membrane-Camouflaged Polymeric Nanoparticles as a Biomimetic Delivery Platform," Proceedings of the National Academy of Sciences of the United States of America, 2011, pp. 10980-10985, vol. 108, No. 27. doi:1 0.1 073/pnas.11 06634108.

Hu, J. et al., "Isolation and Functional Characterization of Human Erythroblasts at Distinct Stages: Implications for Understanding of Normal and Disordered Erythropoiesis in Vivo," Blood, 2013, pp. 3246-3253, vol. 121, No. 16. doi:10.1182/blood-2013-01-476390.

Huang, X. et al., "Extensive Ex Vivo Expansion of Functional Human Erythroid Precursors Established from Umbilical Cord Blood Eells by Defined Factors," Molecular Therapy: the Journal of the American Society of Gene Therapy, 2014, pp. 451-463, vol. 22, No. 2. doi:10.1038/mt.2013.201.

Inada, Y. et al., "In Vivo Binding of Circulating Immune Complexes by C3b Receptors ( CR1) of Transfused Erythrocytes," Annals of the Rheumatic Disease, 1989, pp. 287-294, vol. 48, No. 4.

International Search Report and Written Opinion from International Application No. PCT/US2014/065304 dated Jun. 22, 2015.

Kallenberg, C. G. M. et al., "Complement is Crucial in the Pathogenesis of ANCA Associated Vasculitis," Kidney international, 2013, pp. 16-18, vol. 83, No. 1. doi:1 0.1 038/ki.2012.371.

Keerthivasan, G. et al., "Erythroblast Enucleation," Stem Cells International, 2011, Article ID139851, pp. 1-9. doi:10.4061/2011/139851.

Kim, J. Y. et al., "Treatment of Myasthenia Gravis Based on its Immunopathogenesis Symptom-Relieving Treatments," Journal of Clinical Neurology, 2011, pp. 173-183, vol. 7, No. 4.

Kontos, S. et al., "Engineering Antigens for in situ Erythrocyte Binding Induces T-cell Deletion," Proceedings of the National Academy of Sciences of the United States of America, 2013, pp. E60-E68, vol. 110, No. 1. doi:10.1073/pnas.1216353110.

(56) References Cited

OTHER PUBLICATIONS

Leberbauer, C. et al., "Different Steroids Co-Regulate Long-Term Expansion Versus Terminal Differentiation in Primary Human Erythroid Progenitors," Blood, 2005, pp. 85-94, vol. 105, No. 1. doi:10.1182/blood-2004-3-1002.

Liepkalns, J. S. et al., "Resistance of a Subset of Red Blood Cells to Clearance by Antibodies in a Mouse Model of Incompatible Transfusion," Transfusion, 2013, pp. 1319-1327, vol. 53, No. 6. doi:10.1111/j.1537-2995.2012.03910.x.

Ma, F. et al., "Generation of Functional Erythrocytes from Human Embryonic Stem Cell-Derived Definitive Hematopoiesis," Proceedings of the National Academy of Sciences of the United States of America, 2008, pp. 13087-11392, vol. 105, No. 35.

McCaughan, J. A. et al., "The Complement Cascade in Kidney Disease: from Sideline to Center Stage," American Journal of Kidney Diseases : the Official Journal of the National Kidney Foundation, 2013, pp. 604-614, vol. 62, No. 3. doi:1 0.1 053/j.ajkd. 2012.12.033.

McGrogan, A. et al., "The Incidence of Primary Glomerulonephritis Worldwide: a Systematic Review of the Literature," Nephrology, Dialysis, Transplantation: Official Publication of the European Dialysis and Transplant Association—European Renal Association, 2011, pp. 414-430, vol. 26, No. 2. doi:1 0.1 093/ndt/gfq665.

Miharada, K. et al., "Efficient Enucleation of Erythroblasts Differentiated In Vitro from Hematopoietic Stem and Progenitor Cells," Nature Biotechnology, 2006, pp. 1255-1256, vol. 24, No. 10. doi: 10.1 038/nbt1245.

Millan, C.G. et al., "Drug, Enzyme and Peptide Delivery Using Erythrocytes as Carriers", Journal of Controlled Release, Elsevier, Amsterdam, NL, vol. 95, No. 1, Feb. 20, 2004.

Mukthavaram, R. et al., "Targeting and Depletion of Circulating Leukocytes and Cancer Cells by Lipophilic Antibody-Modified Erythrocytes," Journal of Controlled Release: Official Journal of the Controlled Release Society, 2014, pp. 146-153, vol. 183. doi: 10.1 016/j.jconrel.2014.03.038.

Murciano, J. et al., "Prophylactic Fibrinolysis Through Selective Dissolution of Nascent Clots by tPA-Carrying Erythrocytes," Nature Biotechnology, 2003, pp. 891-896, vol. 21, No. 8.

Muzykantov, V. R., "Drug Delivery by Red Blood Cells: Vascular Carriers Designed by Mother Nature," Expert Opinion on Drug Delivery, 2011, pp. 403-427, vol. 7, No. 4. doi:1 0.1517/ 1742524100361 0633.Drug.

Muzykantov, V. R., "Drug Delivery Carriers on the Fringes: Natural Red Blood Cells Versus Synthetic Multilayered Capsules," Expert Opinion on Drug Delivery, 2013, pp. 1-4, vol. 10, No. 1.

Neildez-Nguyen, T. M.A. et al., "Human Erythroid Cells Produced Ex Vivo at Large Scale Differentiate into Red Blood Cells In Vivo," Nature Biotechnology, 2002, pp. 467-472, vol. 20, No. 5.

Olivier, E. N. et al., "Large-Scale Production of Embryonic Red Blood Cells from Human Embryonic Stem Cells," Experimental Hematology, 2006, pp. 1635-1642, vol. 34, No. 12. doi:10.1016/j. exphem.2006.07.003.

Pasini, E. M. et al., "Red Blood Cell (RBC) Membrane Proteomics—Part 1: Proteomics and RBC Physiology," Journal of Proteomics, 2010, pp. 403-442, vol. 73, No. 3. doi:1 0.1 016/j.jprot.2009. 06.005.

Plaimauer, B. et al., "Recombinant ADAMTS13 Normalizes von Willebrand Factor-Cleaving Activity in Plasma of Acquired TTP Patients by Overriding Inhibitory Antibodies," Journal of Thrombosis and Haemostasis: JTH, 2011, pp. 936-944, vol. 9, No. 5. doi:10.1111/j.1538-7836.2011.04224.x.

Polmar, S.H. et al., "Enzyme Replacement Therapy for Adenosine Deaminase Deficiency and Severe Combined Immunodeficiency," The New England Journal of Medicine, Dec. 9, 1976, pp. 1337-1343.

Popov, M. et al., "Transmembrane Folding of the Human Erythrocyte Anion Exchanger (AE1, Band 3) Determined by Scanning and Insertional N-Giycosylation Mutagenesis," Biochem J, 1999, pp. 269-279, vol. 339.

Rahman, A. et al., "Systemic Lupus Erythematosus," New England Journal of Medicine, 2008, pp. 929-939, vol. 358, No. 9.

Repik, A. et al., "A Transgenic Mouse Model for Studying the Clearance of Blood-Borne Pathogens Via Human Complement Receptor 1 (CR 1 )," Clinical and Experimental Immunology, 2005, pp. 230-240, vol. 140, No. 2. doi:10.1111/j.1365-2249.2005. 02764.x.

Rodriguez De Cordoba, S. et al. "Complement Dysregulation and Disease: From Genes and Proteins to Diagnostics and Drugs," Immunobiology, 2012, pp. 1034-1046, vol. 217.

Rother, B. R. P. et al., "Expression of Recombinant Transmembrane CD59 in Paroxysmal Nocturnal Hemoglobinuria B Cells Confers Resistance to Human Complement," Blood, 1994, pp. 2604-2611, vol. 84, No. 8.

Ryan, J. J. et al., "Expression and Characterization of Recombinant Rat a 3 (IV) NC1 and its Use in Induction of Experimental Autoimmune Glomerulonephritis," Nephrology, Dialysis, Transplantation: Official Publication of the European Dialysis and Transplant Association—European Renal Association, 2001, pp. 253-261, vol. 16, No. 2.

Sherer, Y. et al., "Intravenous Immunoglobulin Therapy of Antiphospholipid Syndrome," Rheumatology, 2000, pp. 421-446, vol. 39, No. 4.

Shi, J. et al., "Engineered Red Blood Cells as Carriers for Systemic Delivery of a Wide Array of Functional Probes," Proceedings of the National Academy of Sciences of the United States of America, 2014, pp. 10131-10136, vol. 111, No. 28. doi:1 0.1 073/pnas. 1409861111.

Shiozawa, Y. et al., "Cancer Stem Cells and Their Role in Metastasis", Pharmacology & Therapeutics, 2013, pp. 285-293, vol. 138, No. 2. doi:1 0.1 016/j.pharmthera.2013.01.014.

Smith, B. W. et al., "The Aryl Hydrocarbon Receptor Directs Hematopoietic Progenitor Cell Expansion and Differentiation," Blood, 2013, pp. 376-385, vol. 122, No. 3. doi:1 0.1182/blood-2012-11-466722.

Stein, S. C. et al., "Erythrocyte-Bound Tissue Plasminogen Activator is Neuroprotective in Experimental Traumatic Brain Injury," Journal of Neurotrauma, 2009, pp. 1585-1592, vol. 26, No. 9.

Suzuki, H. et al., "The Pathophysiology of IgA Nephropathy," Journal of the American Society of Nephrology: JASN, 2011, pp. 1795-1803, vol. 22, No. 10. doi:1 0.1681/ASN.2011050464.

Timmins, N. E. et al., "Manufactured RBC—rivers of blood, or an oasis in the desert?", Biotechnology Advances, 2011, pp. 661-666, vol. 29, No. 6. doi:1 0.1 016/j.biotechadv.2011.05.002.

Toong, C. et al., "Clearing the Complexity: Immune Complexes and Their Treatment in Lupus Nephritis," International Journal of Nephrology and Renovascular Disease, 2011, pp. 17-28, vol. 4. doi:10.2147/IJNRD.S10233.

Wang, J. et al., "In Vitro Hematopoietic Differentiation of Human Embryonic Stem Cells Induced by Co-Culture with Human Bone Marrow Stromal Cells and Low Dose Cytokines," Cell Biology International, 2005, pp. 654-661, vol. 29, No. 8. doi:1 0.1 016/j. cellbi.2005.03.019.

Weisman, H. F. et al., "Soluble Human Complement Receptor Type 1: In Vivo Inhibitor of Complement Suppressing Post-Ischemic Myocardial Inflammation and Necrosis," Science, 1990, pp. 146-151, vol. 249, No. 4965.

Yew, N. S. et al., "Erythrocytes Encapsulated with Phenylalanine Hydroxylase Exhibit Improved Pharmacokinetics and Lowered Plasma Phenylalanine Levels in Normal Mice," Molecular Genetics and Metabolism, 2013, pp. 339-344, vol. 109, No. 4. doi:1 0.1 016/j.ymgme.2013.05.011.

Zimring, J.C., "Fresh Versus Old Blood: Are There Differences and Do They Matter?", Hematology—The Education Program of the American Society of Hematology, 2013, pp. 651-655. doi: 10.1182/ asheducation-2013.1.651.

\* cited by examiner

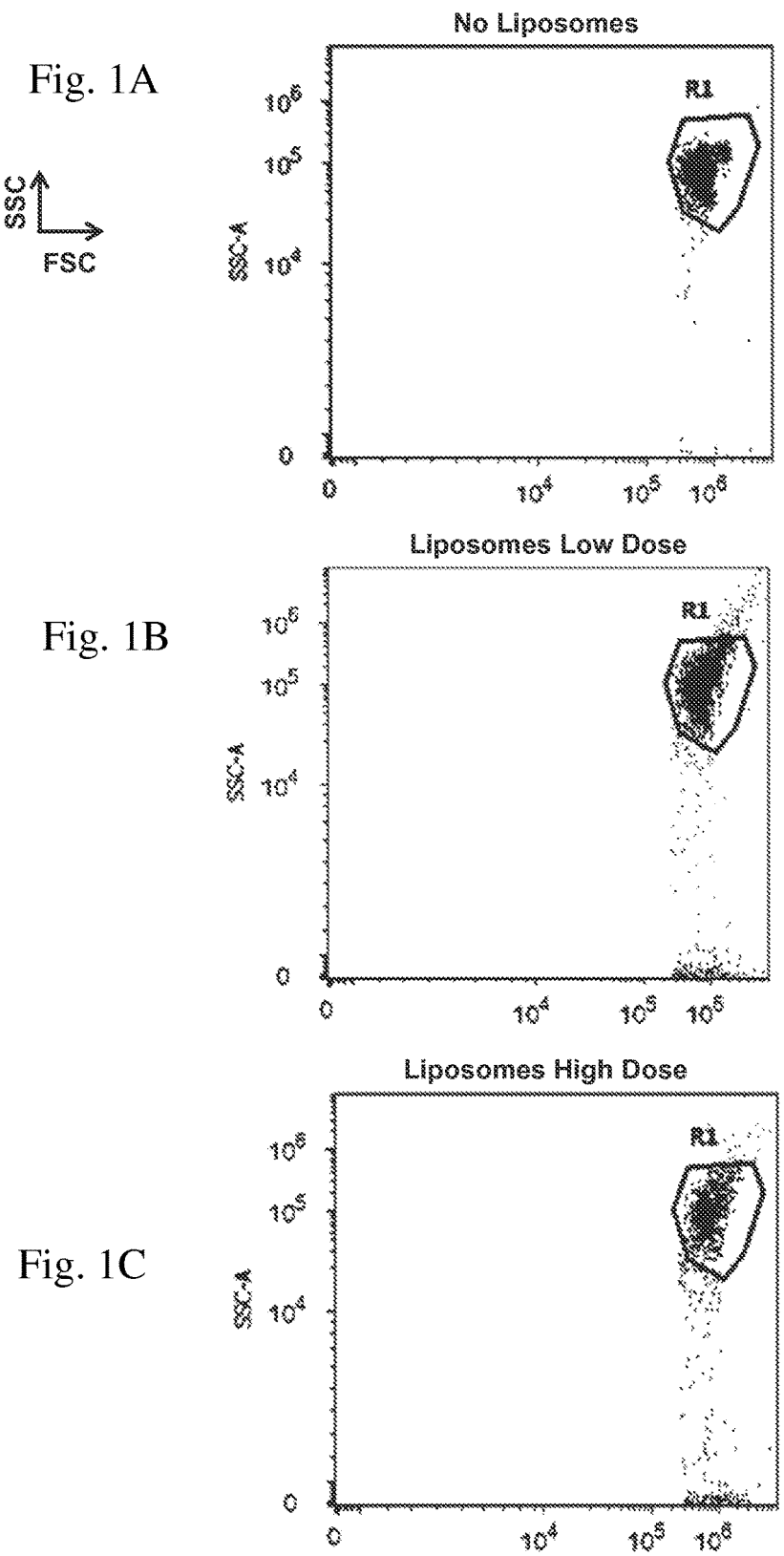

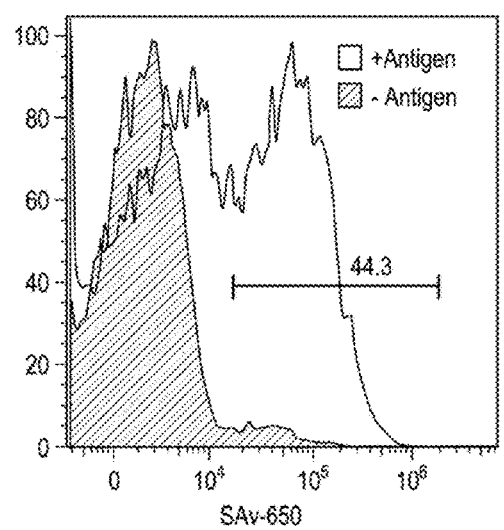
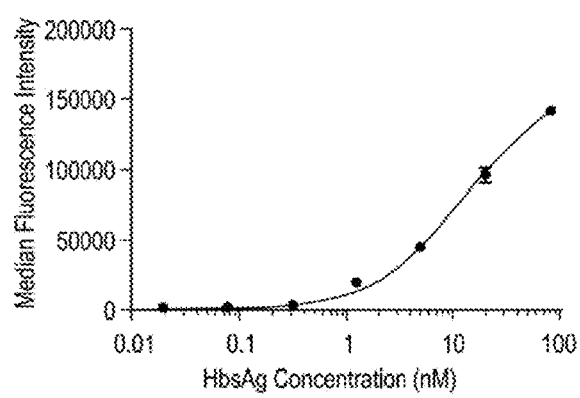
Fig. 7A
Fig. 7B

Anti-HA Western Blot

Fig 13A   Metabolite flux across membrane of complex
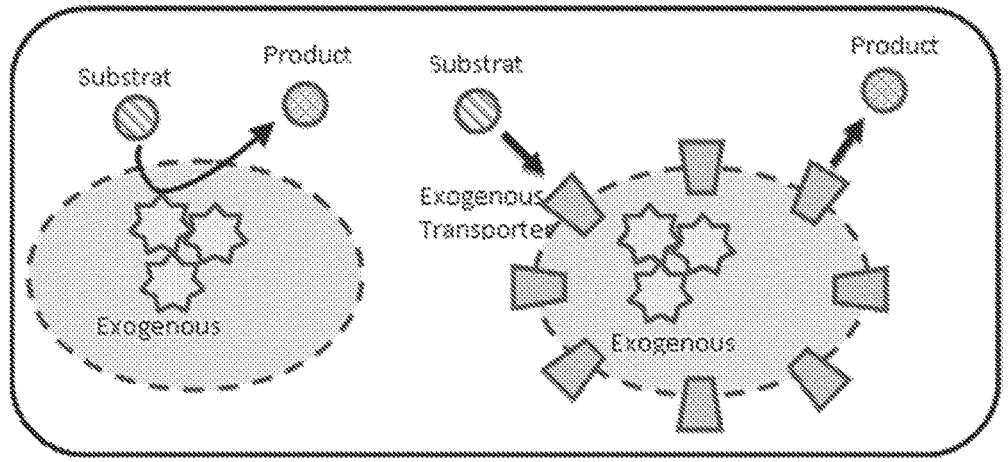
Fig 13B   Exogenous enzyme on surface of complex
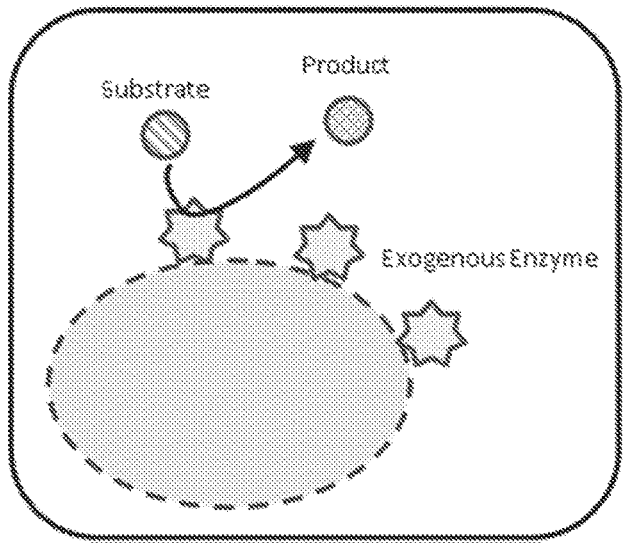
Fig 13C   Complex Destruction and Payload release
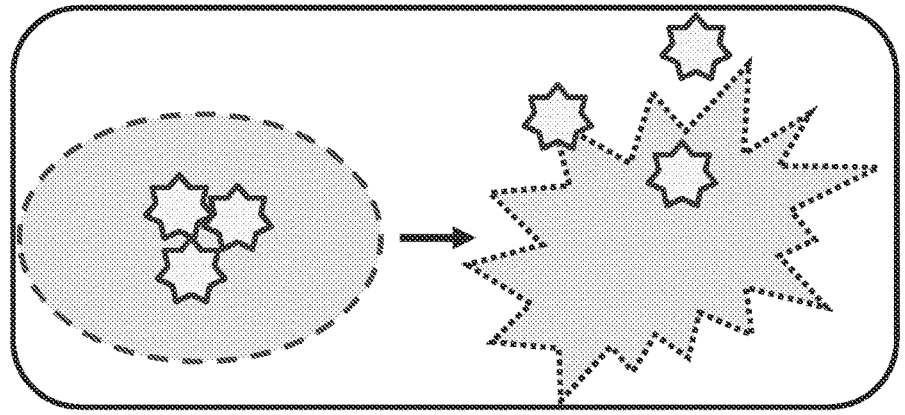

Fig 14A    Methods of Exogenous Polypeptide Expression
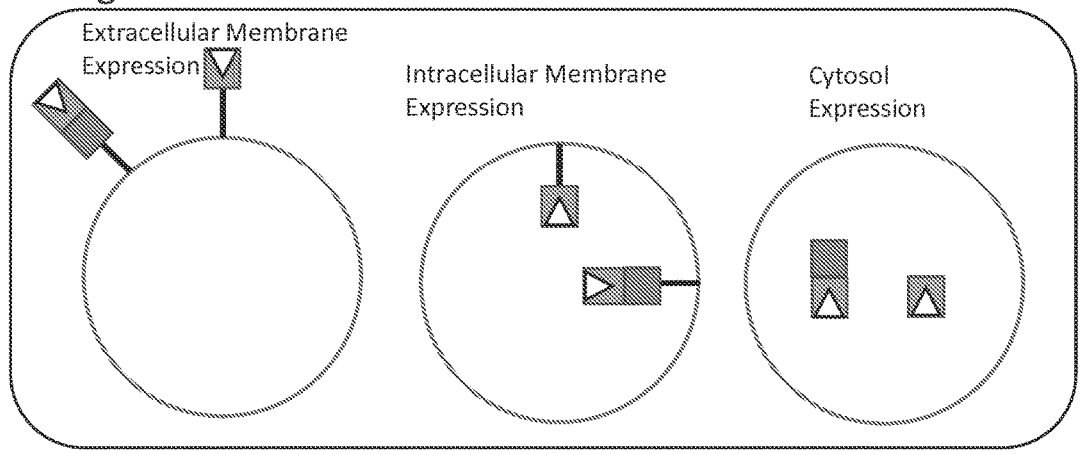
Fig 14B    Methods of Circulating Clearance
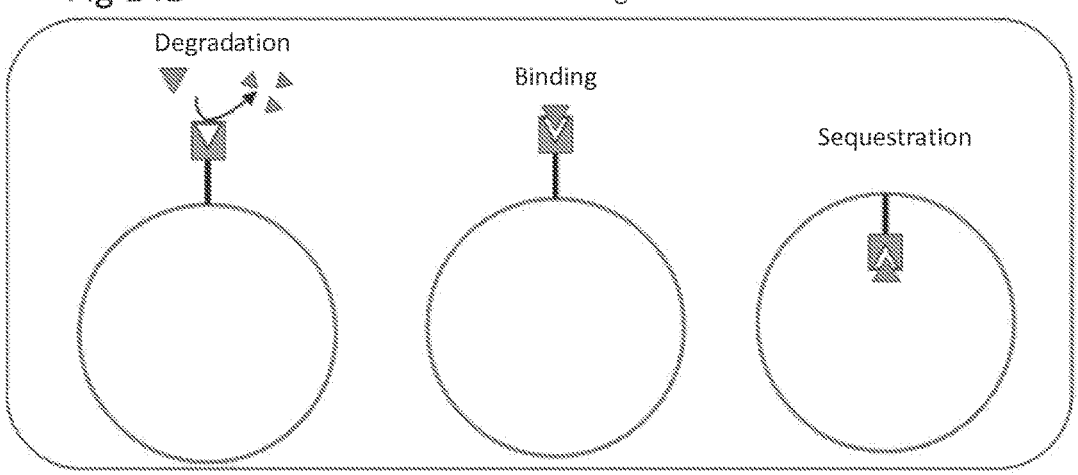
Fig 14C    Autocatalytic Fusion Example
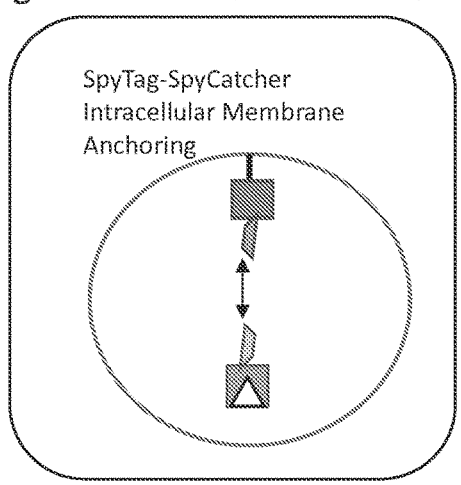
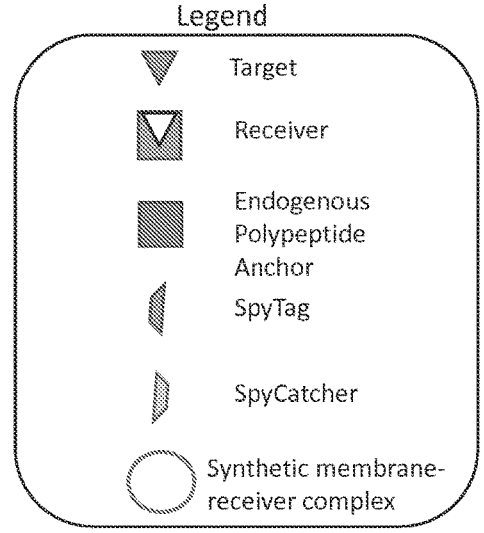

SYNTHETIC MEMBRANE-RECEIVER COMPLEXES

RELATED APPLICATIONS

This application is a continuation U.S. patent application Ser. No. 14/581,486, filed Dec. 23, 2014, which is a continuation of International Application No. PCT/US2014/065304, filed Nov. 12, 2014, entitled "Synthetic Membrane-Receiver Complexes", which claims the benefit of U.S. Provisional Application No. 61/962,867, filed Nov. 18, 2013; U.S. Provisional Application No. 61/919,432, filed Dec. 20, 2013; U.S. Provisional Application No. 61/973,764, filed Apr. 1, 2014; U.S. Provisional Application No. 61/991,319, filed May 9, 2014; U.S. Provisional Application No. 62/006,825, filed Jun. 2, 2014; U.S. Provisional Application No. 62/006,829, filed Jun. 2, 2014; U.S. Provisional Application No. 62/006,832, filed Jun. 2, 2014; U.S. Provisional Application No. 62/025,367, filed Jul. 16, 2014; U.S. Provisional Application No. 62/059,100, filed Oct. 2, 2014, all of which are incorporated by reference herein in their entirety.

SEQUENCE LISTING

The instant application contains a Sequence Listing which has been submitted electronically in ASCII format and is hereby incorporated by reference in its entirety. Said ASCII copy, created on Feb. 17, 2015, is named 28345US_CRF_sequencelisting.txt and is 67,497 bytes in size.

FIELD OF THE INVENTION

The field of the invention is pharmaceutical compositions for the treatment of diseases and disorders.

BACKGROUND

The circulatory system permits blood and lymph circulation to transport, e.g., nutrients, oxygen, carbon dioxide, cellular waste products, hormones, cytokines, blood cells, and pathogens to and from cells in the body. Blood is a fluid comprising, e.g., plasma, red blood cells, white blood cells, and platelets that is circulated by the heart through the vertebrate vascular system. The circulatory system becomes a reservoir for many toxins and pathogenic molecules upon their introduction to or production by the body. The circulatory system also serves as a reservoir for cellular secretions or detritus from within the body. The perpetual or aberrant circulation and proliferation of such molecules and entities can drive disease and/or exacerbate existing conditions.

The efficacy of therapeutic compositions that alleviate or prevent diseases and conditions associated with the circulatory system is often limited by their half-life, which is typically up to a few days. The short half-life often necessitates repeated injections and hospitalizations. It is thought that the short half-life may be due to both renal clearance, e.g., of proteins smaller than 60 kDa, and non-renal clearance, e.g., via liver excretion or immune-mediated removal. The activity of therapies is also often limited by an immune reaction elicited against them (see, e.g., Wang et al., Leukemia 2003, 17:1583). Several approaches are practiced in the art.

One approach includes the use of "erythrocyte ghosts" that are derived from a hemolyzed red blood cell. To prepare erythrocyte ghosts, red blood cells undergo hypotonic lysis. The red blood cells are exposed to low ionic strength buffer causing them to burst. The resulting lysed cell membranes are isolated by centrifugation. The pellet of lysed red blood cell membranes is resuspended and incubated in the presence of the therapeutic agent, for example, such as an antibiotic or chemotherapeutic agent in a low ionic strength buffer. The therapeutic agent distributes within the cells. Erythrocyte ghosts and derivatives used to encapsulate payloads, such as therapeutic agents, can shield those payloads from the immune system, but the erythrocyte ghosts themselves are subject to rapid clearance by the reticulo-endothelial system (see, e.g., Loegering et al. 1987 Infect Immun 55(9):2074). Erythrocyte ghosts also elicit an immune response in mammalian subjects. These vesicles are typically constituted of both lipids and proteins, including potentially high amounts of phosphatidylserine, which is normally found on the inner leaflet of the plasma membrane. This leads to potential immunological reactions in the recipient mammalian subjects. The undesirable effects seriously limit the potential for therapeutic applications of technologies based on erythrocyte ghosts.

Another approach for drug encapsulation includes the use of exosomes. "Exosomes" include cell-derived vesicles that are present in many and perhaps all biological fluids, including blood, urine, and cultured medium of cell cultures. The reported diameter of exosomes is between 30 and 100 nm, which is larger than low-density lipoprotein (LDL), but smaller than, for example, red blood cells. Exosomes are either released from the cell when multivesicular bodies fuse with the plasma membrane or they are released directly from the plasma membrane. Exosome delivery methods require a better understanding of their biology, as well as the development of production, characterization, targeting and cargo-loading nanotechnologies. Attempts have been made to manufacture exosomes using human embryonic stem cell derived mesenchymal stem cells (hESC-MSCs). However, as hESC-MSCs are not infinitely expansible, large scale production of exosomes would require replenishment of hESC-MSC through derivation from hESCs and incur recurring costs for testing and validation of each new batch (Chen et al. 2011 Journal of Translational Medicine 9:47). Clinical translation is also hindered by the lack of suitable and scalable nanotechnologies for the purification and loading of exosomes (Lakhal and Wood 2011 BioEssays 33(10):737). Current ultracentrifugation protocols are commercially unreproducible, as they produce a heterogeneous mix of exosomes, other cellular vesicles and macromolecular complexes. Therefore, purification methods based on the use of specific, desired markers, such as the expression of a targeting moiety on the surface of the exosome, are required. In addition, siRNA loading into exosomes is relatively inefficient and cost-ineffective, highlighting the need for the development of transfection reagents tailored for nanoparticle applications. Further, exosomes are rapidly cleared from circulation and substantially accumulate in the liver within 24 hours of administration (Ohno et al., 2013 Mol Therapy 21(1):185), limiting their application for long-term drug delivery to the circulatory of a subject.

Polyethylene glycol-coated liposomes are presently used as carriers for in vivo drug delivery. A "liposome" includes an artificially-prepared spherical vesicle composed of a lamellar phase lipid bilayer. The liposome can be used as a vehicle for administration of nutrients and pharmaceutical agents. Liposomes can be prepared by disrupting biological membranes, e.g., by sonication. Liposomes are often composed of phosphatidylcholine-enriched phospholipids and may also contain mixed lipid chains with surfactant properties such as egg phosphatidylethanolamine. A liposome design may employ surface ligands for attaching to a target, e.g., unhealthy tissue. Types of liposomes include the multilamellar vesicle (MLV), the small unilamellar liposome vesicle (SUV), the large unilamellar vesicle (LUV), and the cochleate vesicle. Liposomes as cariers of anthracycline antibiotics have been a subject of a great number of studies. As a result, liposome formulations of daunorubicin (DaunoXome™) and doxorubicin (Doxil™) are now commercially available. The pharmacokinetics of the liposomal forms of anthracycline antibiotics differ from that of their free forms in higher peak concentrations and longer circulations times of the drugs. The kinetics of DaunoXome and Doxil clearance from plasma is close to mono-exponential. The half-life of DaumoXome in patient plasma is on the order of a few hours. In Doxil, polyethylene glycol-coated liposomes are used. The immune system poorly recognizes such liposomes; therefore the plasma half-life of Doxil is in the order of tens of hours.

Red blood cells have been considered for use, e.g., to degrade toxic metabolites or inactivate xenobiotics, as drug delivery systems, as carriers of antigens for vaccination, and in other biomedical applications (Magnani Ed. 2003, Erythrocyte Engineering for Drug Delivery and Targeting). Many of these applications require procedures for the transient opening of pores across the red cell membrane. Drugs have commonly been loaded into freshly isolated red blood cells, without culturing, using disruptive methods based on hypotonic shock. Hypotonic dialysis can induce a high degree of hemolysis, irreversible modifications in the morphology of the cells and phosphotidyl serine exposure, which has been recognized as an important parameter associated with premature red blood cells removal and induction of transfusion-related pathologies (Favretto 2013 J Contr Rel).

Many drugs, particularly protein therapeutics, stimulate immunogenic responses that include B cell antibody production, T cell activation, and macrophage phagocytosis. The causes of immunogenicity can be extrinsic or intrinsic to the protein. Extrinsic factors are drug formulation, aggregate formation, degradation products, contaminants and dosing. The administration mode, as well as the drug regimen, also strongly influences how immunogenicity is assessed. That is, immunogenicity will have different effects for drugs that are given in acute indications compared to drugs to treat chronic diseases. In the latter case, patients are exposed to the drug over a longer period of time and as such can mount a complete response. Pegylation is a technology designed to prolong the half-life, as well as minimize immunogenic responses. In contrast to assumptions that polyethylene glycol (PEG) is non-immunogenic and non-antigenic, certain animal studies show that uricase, ovalbumin and some other PEGylated agents can elicit antibody formation against PEG (anti-PEG). In humans, anti-PEG may limit therapeutic efficacy and/or reduce tolerance of PEG-asparaginase (PEG-ASNase) in patients with acute lymphoblastic leukemia and of pegloticase in patients with chronic gout, but did not impair hyposensitization of allergic patients with mPEG-modified ragweed extract or honeybee venom or the response to PEG-IFN in patients with hepatitis C. Anti-PEG antibodies can be found in 22-25% of healthy blood donors. Two decades earlier, the occurrence was 0.2%. This increase may be due to an improvement of the limit of detection of antibodies and to greater exposure to PEG and PEG-containing compounds in cosmetics, pharmaceuticals and processed food products. These results raise concerns regarding the efficacy of PEG-conjugated drugs for a subset of patients (Garay, Expert Opin Drug Deliv, 2012 9(11):1319).

Attempts in the art to create passive half-life improvement methods focus on increasing the apparent hydrodynamic radius of a drug. The kidney's glomerular filtration apparatus is the primary site in the body where blood components are filtered, see for reference e.g., Osicka et al. Clin Sci 1997 93:65 and Myers et al. Kidney Int 1982 21:633. The main determinant of filtration is the hydrodynamic radius of the molecule in the blood; smaller molecules (<80 kDa) are filtered out of the blood to a higher extent than larger molecules. Researchers have used this generalized rule to modify drugs to exhibit a larger hydrodynamic radius and thus longer half-life, mainly via chemical conjugation to large molecular weight water-soluble polymers, such as polyethylene glycol (PEG). Numerous PEGylated protein and small molecule therapeutics are currently offered in the clinic (Pasut and Veronese, 2009 Adv Drug Deliv Rev 61(13):1177; Fishburn, 2008 J Pharm Sci 97(10):4167). Though effective in many cases in increasing circulation half-life, especially as the hydrodynamic radius of the graft or fusion increases (Gao, Liu, et al., 2009 PNAS 106(36): 15231), these methods offer challenges in manufacturing and maintenance of biological effector function. Heterogeneities in conjugation reactions can cause complex product mixtures with varying biological activities, due mostly to the utilization of site-unspecific chemistries. Extensive biochemical characterization often follows precise purification methods to retain a homogenous therapeutic product (Huang, Gough, et al, 2009 Anal Chem 81(2):567; Bailon, Palleroni, et al., 2001 Bioconj Chem 12(2):195; Dhalluin, Ross, et al., 2005 Bioconj Chem 16(3):504). Furthermore, attachment of large moieties, such as branched PEGs, to reactive zones of proteins can lead to decreased receptor affinity (Fishburn, 2008 J Pharm Sci 97(10):4167).

Albumin may be used to bind a therapeutic protein for increased circulation of the drug (Dennis et al, 2002 J Bil Chem 277(38):35035; Walker, Dunlevy, et al., 2010 Prot Engr Des Sel 23(4):271) to increase the apparent size of the therapeutic by engineering it to bind another protein in the blood. In this manner, the drug attains its large molecular size only after administration into the blood stream. The addition of affinity-matured serum albumin-binding peptides to antibody fragments increased their circulation time 24 fold in mice (Dennis et al, 2002 J Bil Chem 277(38):35035). This method is complicated by the dynamics of albumin recycle by the neonatal Fc receptor (FcRn) and the use of cysteine-constrained cyclic peptides for functionality. Alternatively, recombinant addition of large antibody fragments may be made to a protein drug. This may cause structural as well as manufacturing complications, e.g., because of the use of complex cyclic or large domains for functionality. Despite high affinity for albumin, they require the physical constraint of correctly forming a cyclic structure prior to use. Methods of fusing larger antibody fragments may not be amendable to proteins with an already complex folding structure or low expression yield.

The potential of chimeric antigen receptor T-cell therapies, antibody-coupled T-cell receptor (ACTR) therapies and other adoptive T-cell therapies in effecting complete and durable responses has been demonstrated in a number of malignant and infectious diseases. The development of more potent T cells is limited, however, by safety concerns, highlighted by the occurrence of on-target and off-target toxicities that, although uncommon, have been fatal on occasions. Timely pharmacological intervention can be effective in the management of adverse events but adoptively transferred T cells can persist long term, along with any unwanted effects. T cells targeting differentiation antigens can be expected to also recognize nonmalignant cells that express the same antigens, resulting in adverse events. For example, melanoma patients treated with T cells targeting melanocyte differentiation antigens, such as MART-1 and gp100, often develop vitiligo and uveitis. These on-target toxicities have been observed across all forms of therapeutic approaches, including tumor-infiltrating cells, in vitro-expanded T-cell clones and TCR-transgenic cells. In general, on-target autoimmunity is associated with tumor regression and is more prominent in treatment approaches that are more efficacious. On-target but off-tumour toxicities can be immediately life-threatening. For example, patients with colorectal cancer with lung and liver metastases may develop respiratory distress within 15 min of HER2-specific CAR T-cell infusion and may subsequently die from multi-organ failure 5 days later. As T-cell therapy becomes more effective, acute toxicities have also become more evident. Cytokine release syndrome, which is characterized by fevers, rigors, hypotension and hypoxia, has been observed in a number of CD19 CAR T-cell studies as a result of large-scale T-cell activation upon the recognition of CD19+ malignant cells.

There is an ongoing need to provide therapeutic compositions through the circulatory system that alleviate or prevent such diseases and conditions. There is a further a need for methods and compositions that increase the half-life, safety profile, and/or efficacy of such therapeutic compositions. Aspects of the invention address one or more of the shortcomings of current methods and compositions.

SUMMARY OF THE INVENTION

In some aspects, disclosed herein is a method of reducing the circulatory concentration of a target self-antibody. The method comprises the steps of administering to a human subject suffering from or at risk of developing a self-antibody mediated disease, disorder or condition, a pharmaceutical composition comprising a synthetic membrane-receiver polypeptide complex, wherein the pharmaceutical composition is administered in an amount effective to substantially reduce the circulatory concentration of the target self-antibody.

In certain embodiments, the synthetic membrane-receiver polypeptide complex has a volume of distribution equal to the plasma volume of the subject.

In other embodiments, the synthetic membrane-receiver polypeptide complex has a volume of distribution of less than 0.09 l/kg.

In certain embodiments, the method comprises administering the pharmaceutical composition at least twice over a treatment period such that the self-antibody mediated disease, disorder or condition is treated, or a symptom thereof is decreased.

In other embodiments, the method comprises administering the pharmaceutical composition at least twice over a treatment period such that the self-antibody mediated disease, disorder or condition is prevented.

In yet other embodiments, the method comprises administering the pharmaceutical composition a sufficient number of times over a treatment period such that the circulatory concentration of the target self-antibody is substantially decreased during the treatment period.

In yet other embodiments, the method comprises administering the pharmaceutical composition a sufficient number of times over a treatment period such that the circulatory concentration of the target self-antibody is substantially decreased during the treatment period such that one or more symptoms of the self-antibody mediated disease, disorder or condition is prevented, decreased or delayed.

In yet other embodiments, the method comprises administering the pharmaceutical composition a sufficient number of times over a treatment period such that the circulatory concentration of the target self-antibody is decreased at a rate greater than i) the endogenous clearance rate of the target self-antibody by the human subject, or ii) the endogenous production rate of the target self-antibody by the human subject, or iii) both i) and ii).

In some embodiments, the circulatory concentration of the target self-antibody is decreased by at least about 1%, 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, 99.5%, 99.9%, 99.99%, or greater than 99.99% during part or the entirety of the treatment period.

In other embodiments, the circulatory concentration of the target self-antibody is decreased by at least about 1%, 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, 99.5%, 99.9%, 99.99%, or greater than 99.99% within about 1, 5, 10, 15, 20, 30, 40, or 50 minutes, or about 1, 2, 3, 4, 5, 6, 7, 8, 9, 10, 11, 12, 13, 14, 15, 16, 17, 18, 19, 20, 21, 22, or 23 hours, or 1, 2, 3, 4, 5, or 6 days or about 1, 2, 3, 4, 5, or 6 weeks of the administration.

In some embodiments, the method comprises administering the pharmaceutical composition a sufficient number of times a treatment period such that the circulatory concentration of the target self-antibody is substantially decreased for at least about one week, two weeks, three weeks, four weeks, one month, two months, three months, four months, five months, six months, or greater than six months.

In other embodiments, the method comprises administering the pharmaceutical composition a sufficient number of times a treatment period such that the circulatory concentration of the target self-antibody is substantially decreased for a period of time at least as long as the treatment period.

In some embodiments, the treatment period is not longer than a year, six months, three months, two months, one month, two weeks, one week, three days, two days, one day.

In some embodiments, the time interval between administrations within a treatment period is no longer than the period in which the number of synthetic membrane-receiver polypeptide complexes in circulation is reduced to less than about 5%, 10%, 15%, 20%, 25%, 30%, 35%, 40%, 45%, 50%, 55%, 60%, 65%, 70%, 75%, 80%, 85%, 90%, or 95% of the number of synthetic membrane-receiver polypeptide complexes present in the administered pharmaceutical composition.

In other embodiments, the frequency of administration is sufficient to effectively reduce the circulatory concentration of the target self-antibody below a level that is associated with a symptom of the self-antibody mediated disease, disorder or condition.

In some embodiments, the administering of the pharmaceutical composition reduces the concentration of unbound target self-antibody or the concentration of total target self-antibody in the circulatory system of the subject.

In some embodiments, the concentration of total target self-antibody is approximately equal to the concentration of unbound and bound target self-antibody in the circulatory system of the subject.

In certain embodiments, the pharmaceutical composition further comprises a pharmaceutically active agent.

In certain embodiments, the method further comprises the step of administering a pharmaceutically active agent, wherein the pharmaceutically active agent is administered prior to, after, or concurrent with the pharmaceutical composition.

In some embodiments, the pharmaceutical composition is administered topically or parenterally.

In some embodiments, the pharmaceutically active agent is selected from a biological agent, a small molecule agent, or a nucleic acid agent.

In some embodiments, the pharmaceutical composition further comprises a pharmaceutically acceptable carrier.

In some embodiments, the method further comprises the step of selecting for treatment a subject suffering from or at risk of a self-antibody mediated disease, disorder or condition selected from the group consisting of: type I diabetes, multiple sclerosis, ulcerative colitis, lupus, immune thrombocytopenia purpura, warm antibody hemolytic anemia, cold agglutinin disease, Goodpasture syndrome, antiphospholipid antibody syndrome, and membranous glomerulonephritis.

In some embodiments, the synthetic membrane-receiver polypeptide complex is formulated for short-term duration in the circulatory system of the subject.

In other embodiments, the synthetic membrane-receiver polypeptide complex is formulated for long-term duration in the circulatory system of the subject.

In some embodiments, the receiver polypeptide is not substantially disassociated from the membrane in the circulatory system of the subject.

In some embodiments, the receiver polypeptide is present in the circulatory system for at least 21 days.

In certain embodiments, the synthetic membrane-receiver polypeptide complex comprises phosphatidylcholine, sphingomyelin, lysophosphatidylcholine, phosphatidylethanolamine, phosphatidylserine, phosphatidylinositol, or phosphatidic acid.

In some embodiments, the synthetic membrane-receiver polypeptide complex further comprises i) a CD47, CD55, or CD59 polypeptide or a functional fragment thereof, or ii) a cell membrane polypeptide, or iii) both i) and ii).

In some embodiments, the synthetic membrane-receiver polypeptide complex comprises a CD47, CD55, or CD59 polypeptide or a functional fragment thereof in an amount effective for the polypeptide complex to reside in the circulatory system for long-term duration.

In some embodiments, the synthetic membrane-receiver polypeptide complex does not contain a substantial amount of a replicating nucleic acid.

In some embodiments, the synthetic membrane-receiver polypeptide complex comprises at least 10 copies, 100 copies, 1,000 copies, 10,000 copies, 25,000 copies, 50,000 copies, or 100,000 copies of the receiver polypeptide, and/or wherein the synthetic membrane-receiver polypeptide complex comprises a ratio of the receiver polypeptide relative to a membrane lipid selected from the group consisting of phosphatidylcholine, sphingomyelin, lysophosphatidylcholine, phosphatidylethanolamine, phosphatidylserine, phosphatidylinositol, or phosphatidic acid.

In certain embodiments, the synthetic membrane-receiver polypeptide complex comprises at least a second polypeptide in addition to the receiver polypeptide.

In certain embodiments, the synthetic membrane-receiver polypeptide complex has catalytic activity for more than one substrate independent of the receiver polypeptide.

In some embodiments, the second polypeptide is associated with the membrane.

In certain embodiments, the receiver polypeptide is encoded by an exogenous nucleic acid.

In certain embodiments, the exogenous nucleic acid is not substantially retained by the synthetic membrane-receiver polypeptide complex.

In some embodiments, the expression of the receiver polypeptide is effectively terminated.

In some embodiments, the receiver polypeptide is associated with the membrane.

In other embodiments, the receiver polypeptide is a fusion or a chimera.

In some embodiments, the fusion or chimera comprises at least one of an S domain, an A domain or a U domain, wherein the S domain is a surface domain exposed to the environment around the synthetic membrane-receiver polypeptide complex, wherein the A domain is an anchor, wherein the U domain faces the unexposed side of the synthetic membrane-receiver polypeptide complex, and wherein the S domain, the A domain, and/or the U domain are of different polypeptide origin.

In some embodiments, the S domain and/or the A domain comprises at least 6 or at least 30 amino acids.

In certain embodiments, the target self-antibody specifically recognizes glycoprotein (GP Ib-IX, IIb-IIIa, IV, or Ia-IIa), the NC1 domain of collagen α3 (IV), B2 glycoprotein-1, or phospholipase A2 receptor.

In certain embodiments, the receiver polypeptide comprises an antigenic polypeptide selected from the group consisting of glycoprotein (GP Ib-IX, IIb-IIIa, IV, or Ia-IIa), the NC1 domain of collagen α3 (IV), B2 glycoprotein-1, or phospholipase A2 receptor, or an antigenic fragment thereof.

In some embodiments, the S domain comprises the antigenic polypeptide or antigenic fragment thereof.

In some aspects, provided herein is a pharmaceutical composition administered by the methods disclosed herein.

In certain embodiments, the pharmaceutical composition further comprises a pharmaceutically acceptable carrier.

In certain embodiments, the pharmaceutical composition comprises a population of synthetic membrane-receiver polypeptide complexes.

In some embodiments, the pharmaceutical composition comprises at least $1 \times 10^5$ synthetic membrane-receiver polypeptide complexes. In certain embodiments, the synthetic membrane-receiver polypeptide complexes are provided in a volume of about 10 nl, 100 nl, 1 µl, 10 µl, 100 µl, 1 ml, 10 ml, 20 ml, or 50 ml.

In certain embodiments, the pharmaceutical composition comprises at least $1 \times 10^{11}$ synthetic membrane-receiver polypeptide complexes. In certain embodiments, the synthetic membrane-receiver polypeptide complexes are provided in a volume of about 1 ml, 10 ml, 20 ml, 50 ml, 100 ml, 250 ml, or 500 ml.

In certain embodiments, the pharmaceutical composition is a composition formulated for long-term storage.

In certain embodiments, the pharmaceutical composition is a composition which is frozen.

In some embodiments, the pharmaceutical composition comprises a pharmaceutically active agent.

In certain embodiments, the pharmaceutically active agent is selected from a biological agent, a small molecule agent, or a nucleic acid agent.

In some aspects, provided herein is a dosage form comprising the compositions disclosed herein formulated as a liquid suspension for intravenous injection.

In some aspects, provided herein is a medical device comprising a container holding the pharmaceutical compositions disclosed herein and an applicator for intravenous injection of the pharmaceutical composition to the subject.

In some aspects, provided herein is a medical kit comprising the pharmaceutical compositions disclosed herein and a medical device for intravenous injection of the pharmaceutical composition to the subject.

In some aspects, provided herein is the synthetic membrane-receiver polypeptide complex of the pharmaceutical composition administered by the methods disclosed herein.

In some aspects, provided herein is a population of synthetic membrane-receiver polypeptide complexes as disclosed herein.

In some embodiments, the population of synthetic membrane-receiver polypeptide complexes are formulated as a liquid.

In other embodiments, the population of synthetic membrane-receiver polypeptide complexes are frozen.

In some aspects, provided herein is an isolated receiver polypeptide of the synthetic membrane-receiver polypeptide complex as disclosed herein.

In some aspects, provided herein is an exogenous nucleic acid encoding the receiver polypeptide disclosed herein.

In some aspects, provided herein is a synthetic membrane-receiver polypeptide complex comprising: a receiver polypeptide capable of interacting with a target, and a membrane comprising a second polypeptide, wherein the synthetic membrane-receiver polypeptide complex has catalytic activity independent of the receiver.

In some embodiments, the synthetic membrane-receiver polypeptide complex is formulated for intravenous administration to the circulatory system of a mammalian subject, which for example can be a human.

In certain embodiments, the receiver polypeptide is capable of reducing the concentration of unbound target or total target in the circulatory system of the subject.

In certain embodiments, the synthetic membrane-receiver polypeptide complex has a volume of distribution approximately equal or equivalent to the plasma volume of the subject.

In some embodiments, the synthetic membrane-receiver polypeptide complex has a volume of distribution of less than 0.091/kg.

In some embodiments, the receiver polypeptide is present in the circulatory system for substantially the duration of the synthetic membrane-receiver polypeptide complex in the circulatory system of the subject.

In some embodiments, the synthetic membrane-receiver polypeptide complex is formulated for short-term duration in the circulatory system of the subject.

In some embodiments, the synthetic membrane-receiver polypeptide complex is formulated for long-term duration in the circulatory system of the subject.

In certain embodiments, the receiver polypeptide is present in the circulatory system for at least about 21 days.

In certain embodiments, the synthetic membrane-receiver polypeptide complex comprises phosphatidylcholine, sphingomyelin, lysophosphatidylcholine, phosphatidylethanolamine, phosphatidylserine, phosphatidylinositol, or phosphatidic acid.

In other embodiments, the synthetic membrane-receiver polypeptide complex further comprises a CD47, CD55, or CD59 polypeptide or a functional fragment thereof.

In other embodiments, the synthetic membrane-receiver polypeptide complex comprises a CD47, CD55, or CD59 polypeptide or a functional fragment thereof in an amount effective for the complex to reside in the circulatory system for long-term duration.

In some embodiments, the interaction of the complex with a target comprises binding, degrading, cleaving and/or sequestering the target.

In other embodiments, the interaction of the complex with a target comprises altering an activity of the target.

In other embodiments, the interaction of the complex with a target comprises reducing an activity of the target.

In other embodiments, the interaction of the complex with a target comprises inactivating the target.

In some embodiments, the target is a self-antibody, a complement protein, an immune complex, a serum amyloid protein, a metabolite or a toxin.

In other embodiments, the target is an inflammatory molecule, a cytokine or a chemokine.

In other embodiments, the target is a lipid or a carbohydrate, an amino acid.

In other embodiments, the target is a virus, a viral antigen, an envelope antigen or a capsid antigen.

In other embodiments, the target is a bacterium, a bacterial antigen, a bacterial surface antigen, a secreted bacterial toxin, or a secreted bacterial antigen.

In other embodiments, the target is a fungus, a fungal antigen, a fungal cell surface antigen, a secreted fungal toxin, or a secreted fungal antigen.

In other embodiments, the target is DNA or RNA.

In other embodiments, the target is a circulating cell, an inflammatory cell, a tumor cell, or a metastatic cancer cell.

In certain embodiments, the receiver polypeptide is a complement receptor 1 (CR1) polypeptide, a variant or functional fragment thereof.

In some embodiments, the CR1 polypeptide comprises one or more Short Consensus Repeats (SCRs), Complement Control Proteins (CCPs) and/or Long Homologous Repeats (LHRs).

In certain embodiments, the receiver polypeptide is a duffy antigen receptor complex (DARC), a variant or functional fragment thereof.

In other embodiments, the receiver polypeptide is an antibody, a single-chain variable fragment, a nanobody, a diabody, or a DARPin.

In other embodiments, the receiver polypeptide is a lyase, a hydrolase, a protease, or a nuclease.

In other embodiments, the receiver polypeptide is exposed to the environment around the synthetic receiver polypeptide complex.

In other embodiments, the receiver polypeptide is located at the unexposed side of the synthetic receiver polypeptide complex.

In other embodiments, the receiver polypeptide is associated with the membrane.

In other embodiments, the receiver polypeptide is a fusion or a chimera.

In certain embodiments, the fusion or chimera comprises at least one of an S domain, an A domain or a U domain, wherein the S domain is a surface domain exposed to the environment around the synthetic membrane-receiver polypeptide complex, wherein the A domain is an anchor, wherein the U domain faces the unexposed side of the synthetic membrane-receiver polypeptide complex, and wherein the S domain, the A domain, and/or the U domain are of different polypeptide origin.

In some embodiments, the S domain and/or the A domain comprises at least 6 or at least 30 amino acids.

In certain embodiments, the synthetic membrane-receiver polypeptide complex comprises at least 10 copies, 100 copies, 1,000 copies, 10,000 copies, 25,000 copies, 50,000 copies, or 100,000 copies of the receiver polypeptide, and/or wherein the synthetic membrane-receiver polypeptide complex comprises a ratio of the receiver polypeptide relative to a membrane lipid selected from the group consisting of phosphatidylcholine, sphingomyelin, lysophosphatidylcholine, phosphatidylethanolamine, phosphatidylserine, phosphatidylinositol, or phosphatidic acid.

In certain embodiments, the receiver polypeptide is encoded by a recombinant nucleic acid.

In certain embodiments, the recombinant nucleic acid is not retained by the synthetic membrane-receiver polypeptide complex.

In certain embodiments, the expression of the receiver polypeptide is effectively terminated.

In certain embodiments, the synthetic membrane-receiver polypeptide complex does not contain a substantial amount of a replicating nucleic acid.

In some aspects, provided herein is a pharmaceutical composition comprising a population of synthetic membrane-receiver polypeptide complexes as disclosed herein and a pharmaceutically acceptable carrier.

In certain embodiments, the pharmaceutical composition comprises at least $1 \times 10^5$ synthetic membrane-receiver complexes.

In some embodiments, the synthetic membrane-receiver complexes are provided in a volume of about 10 nl, 100 nl, 1 µl, 10 µl, 100 µl, 1 ml, 10 ml, 20 ml, or 50 ml.

In certain embodiments, the pharmaceutical composition comprises at least $1 \times 10^{11}$ synthetic membrane-receiver complexes.

In some embodiments, the synthetic membrane-receiver complexes are provided in a volume of about 1 ml, 10 ml, 20 ml, 50 ml, 100 ml, 250 ml, or 500 ml.

In some embodiments, the pharmaceutical composition is a composition formulated for long-term storage.

In some embodiments, the pharmaceutical composition is a composition which is frozen.

In certain embodiments, the pharmaceutical composition comprises a pharmaceutically active agent.

In some embodiments, the pharmaceutically active agent is selected from a biological agent, a small molecule agent, or a nucleic acid agent.

In some aspects, provided herein is a dosage form comprising the pharmaceutical compositions disclosed herein formulated as a liquid suspension for intravenous injection.

In some aspects, provided herein is a medical device comprising a container holding the pharmaceutical composition disclosed herein and an applicator for intravenous injection of the pharmaceutical composition to a subject.

In some aspects, provided herein is a medical kit comprising the pharmaceutical composition disclosed herein and a medical device for intravenous injection of the pharmaceutical composition to a subject.

In some aspects, provided herein is a method of treating or preventing a disease, disorder or condition associated with the presence of or the concentration of a target in the circulatory system of a mammalian subject. The method comprises administering intravenously to the subject the pharmaceutical compositions disclosed herein in an amount effective to treat or prevent disease, disorder or condition.

In certain embodiments, the target is associated with the disease, disorder or condition.

In some aspects, provided herein is a method of modulating the circulatory concentration of a target. The method comprises administering to a mammalian subject suffering from or at risk of developing a disease, disorder or condition associated with the presence, absence, elevated or depressed concentration of the target in the circulatory system of the subject, a pharmaceutical composition comprising a synthetic membrane-receiver polypeptide complex in an amount effective to substantially modulate the circulatory concentration of the target.

In certain embodiments, the synthetic membrane-receiver polypeptide complex has a volume of distribution equal to the plasma volume of the subject.

In certain embodiments, the administration is repeated when the amount of synthetic membrane-receiver polypeptide complexes in circulation is reduced to 50% of i) the concentration of the complexes that were first administered or ii) Cmax of the synthetic membrane-receiver polypeptide complexes in circulation.

In certain embodiments, the synthetic membrane-receiver polypeptide complex interacts with the target in circulation.

In certain embodiments, the interaction with the target comprises binding, degrading, cleaving and/or sequestering the target.

In other embodiments, the interaction with a target comprises altering an activity of the target.

In other embodiments, the interaction with the target comprises reducing an activity of the target.

In other embodiments, the interaction with the target comprises inactivating the target.

In other embodiments, the interaction with the target comprises catalytically converting the target.

In certain embodiments, modulating consists of reducing the circulatory concentration of the target.

In certain embodiments, the presence or elevated level of the target in the circulatory system of the subject is associated with the disease, disorder or condition.

In certain embodiments, the method further comprises increasing the circulatory concentration of a non-target compound.

In certain embodiments, the absence or depressed level of the non-target compound in the circulatory system of the subject is associated with the disease, disorder or condition.

In certain embodiments, the target is a biological compound, an inorganic compound, an organic compound, a gaseous compound or an element.

In certain embodiments, the target is less than 1000 Da, less than 500 Da, less than 250 Da, or less than 100 Da.

In certain embodiments, the target is more than 1 kDa.

In certain embodiments, the target is a polypeptide, a lipid, a carbohydrate, a nucleic acid, an amino acid, metabolite, or a small molecule.

In other embodiments, the target is an antibody, a complement factor, an immune complex, a serum amyloid protein, a bacterial pathogen, a fungal pathogen, a viral pathogen, or an infected, pathogenic, apoptotic, necrotic, aberrant or oncogenic mammalian cell.

In other embodiments, the target is an amyloid polypeptide.

In other embodiments, the target is a complement polypeptide.

In certain embodiments, the substantial modulation of the circulatory concentration of the target is reversible.

In other embodiments, the substantial modulation of the circulatory concentration of the target is temporally restricted.

In other embodiments, the substantial modulation of the circulatory concentration of the target is spatially restricted.

In some aspects, disclosed herein is a method of reducing the circulatory concentration of a target serum amyloid protein. The method comprises the steps of administering to a mammalian subject suffering from or at risk of developing an amyloidosis, a pharmaceutical composition comprising a synthetic membrane-receiver complex, wherein the pharmaceutical composition is administered in an amount effective to substantially reduce the circulatory concentration of the target serum amyloid protein.

In certain embodiments, the synthetic membrane-receiver complex has a volume of distribution equal to the plasma volume of the subject. In some embodiments, the synthetic membrane-receiver complex has a volume of distribution of less than 0.09 l/kg.

In certain embodiments, the method comprises administering the pharmaceutical composition at least twice over a treatment period such that the amyloidosis is treated, or a symptom thereof is decreased.

In other embodiments, the method comprises administering the pharmaceutical composition at least twice over a treatment period such that the amyloidosis is prevented.

In yet other embodiments, the method comprises administering the pharmaceutical composition a sufficient number of times over a treatment period such that the circulatory concentration of the target serum amyloid protein is substantially decreased during the treatment period.

In yet other embodiments, the method comprises administering the pharmaceutical composition a sufficient number of times over a treatment period such that the circulatory concentration of the target serum amyloid protein is substantially decreased during the treatment period such that one or more symptom of the amyloidosis is prevented, decreased or delayed.

In yet other embodiments, the method comprises administering the pharmaceutical composition a sufficient number of times over a treatment period such that the circulatory concentration of the target serum amyloid protein is decreased at a rate greater than i) the endogenous clearance rate of the target serum amyloid protein by the mammalian subject, or ii) the endogenous production rate of the target serum amyloid protein by the mammalian subject, or iii) both i) and ii).

In some embodiments, the circulatory concentration of the target serum amyloid protein is decreased by at least about 1%, 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, 99.5%, 99.9%, 99.99%, or greater than 99.99% during part or the entirety of the treatment period.

In other embodiments, the circulatory concentration of the target serum amyloid protein is decreased by at least about 1%, 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, 99.5%, 99.9%, 99.99%, or greater than 99.99% within about 1, 5, 10, 15, 20, 30, 40, or 50 minutes, or about 1, 2, 3, 4, 5, 6, 7, 8, 9, 10, 11, 12, 13, 14, 15, 16, 17, 18, 19, 20, 21, 22, or 23 hours, or 1, 2, 3, 4, 5, or 6 days or about 1, 2, 3, 4, 5, or 6 weeks of the administration.

In some embodiments, the method comprises administering the pharmaceutical composition a sufficient number of times a treatment period such that the circulatory concentration of the target serum amyloid protein is substantially decreased for at least about one week, two weeks, three weeks, four weeks, one month, two months, three months, four months, five months, six months, or greater than six months.

In other embodiments, the method comprises administering the pharmaceutical composition a sufficient number of times a treatment period such that the circulatory concentration of the target serum amyloid protein is substantially decreased for a period of time at least as long as the treatment period.

In some embodiments, the treatment period is not longer than a year, six months, three months, two months, one month, two weeks, one week, three days, two days, one day.

In some embodiments, the time interval between administrations within a treatment period is no longer than the period in which the number of synthetic membrane-receiver complexes in circulation is reduced to less than about 5%, 10%, 15%, 20%, 25%, 30%, 35%, 40%, 45%, 50%, 55%, 60%, 65%, 70%, 75%, 80%, 85%, 90%, or 95% of the number of synthetic membrane-receiver complexes present in the administered pharmaceutical composition.

In other embodiments, the frequency of administration is sufficient to effectively reduce the circulatory concentration of the target serum amyloid protein below a level that is associated with a symptom of the amyloidosis.

In some embodiments, the administering of the pharmaceutical composition reduces the concentration of unbound target serum amyloid protein or the concentration of total target serum amyloid protein in the circulatory system of the subject.

In some embodiments, the concentration of total target serum amyloid protein is approximately equal to the concentration of unbound and bound target serum amyloid protein in the circulatory system of the subject.

In some embodiments, the method further comprises the step of selecting for treatment a subject suffering from or at risk of an amyloidosis selected from the group consisting of: A amyloidosis (AA), Ig light chain amyloidosis (AL), transthyretin (TTR) amyloidosis, and fibrinogen amyloidosis.

In certain embodiments, the target serum amyloid protein is selected from the group consisting of: amyloid P protein, amyloid A protein, light chain, misfolded transthyretin, and fibrinogen alpha chain.

In some embodiments, the receiver is associated with the membrane. Optionally, the receiver is a fusion or a chimera. If desired, the fusion or chimera may comprise at least one of an S domain, an A domain or a U domain, wherein the S domain is a surface domain exposed to the environment around the synthetic membrane-receiver complex, wherein the A domain is an anchor, wherein the U domain faces the unexposed side of the synthetic membrane-receiver complex, and wherein the S domain, the A domain, and/or the U domain are of different polypeptide origin. In some embodiments, the S domain and/or the A domain comprise a polypeptide comprising at least 6 or at least 30 amino acids. In some embodiments, the S domain comprises the antigenic polypeptide or antigenic fragment thereof.

In some aspects, disclosed herein is a method of reducing the circulatory concentration of a target immune complex. The method comprises the steps of administering to a mammalian subject suffering from or at risk of developing an immune complex-associated disease, disorder or condition, a pharmaceutical composition comprising a synthetic membrane-complement receptor 1 (CR1) receiver complex, wherein the pharmaceutical composition is administered in an amount effective to substantially reduce the circulatory concentration of the target immune complex.

In certain embodiments, the synthetic membrane-CR1 receiver complex has a volume of distribution equal to the plasma volume of the subject. In some embodiments, the synthetic membrane-CR1 receiver complex has a volume of distribution of less than 0.09 l/kg.

In certain embodiments, the method comprises administering the pharmaceutical composition at least twice over a treatment period such that the immune complex-associated disease, disorder or condition is treated, or a symptom thereof is decreased.

In other embodiments, the method comprises administering the pharmaceutical composition at least twice over a treatment period such that the immune complex-associated disease, disorder or condition is prevented.

In yet other embodiments, the method comprises administering the pharmaceutical composition a sufficient number of times over a treatment period such that the circulatory concentration of the target immune complex is substantially decreased during the treatment period.

In yet other embodiments, the method comprises administering the pharmaceutical composition a sufficient number of times over a treatment period such that the circulatory concentration of the target immune complex is substantially decreased during the treatment period such that one or more symptom of the a immune complex-associated disease, disorder or condition is prevented, decreased or delayed.

In yet other embodiments, the method comprises administering the pharmaceutical composition a sufficient number of times over a treatment period such that the circulatory concentration of the target immune complex is decreased at a rate greater than i) the endogenous clearance rate of the target immune complex by the mammalian subject, or ii) the endogenous production rate of the target immune complex by the mammalian subject, or iii) both i) and ii).

In some embodiments, the circulatory concentration of the target immune complex is decreased by at least about 1%, 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, 99.5%, 99.9%, 99.99%, or greater than 99.99% during part or the entirety of the treatment period.

In other embodiments, the circulatory concentration of the target immune complex is decreased by at least about 1%, 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, 99.5%, 99.9%, 99.99%, or greater than 99.99% within about 1, 5, 10, 15, 20, 30, 40, or 50 minutes, or about 1, 2, 3, 4, 5, 6, 7, 8, 9, 10, 11, 12, 13, 14, 15, 16, 17, 18, 19, 20, 21, 22, or 23 hours, or 1, 2, 3, 4, 5, or 6 days or about 1, 2, 3, 4, 5, or 6 weeks of the administration.

In some embodiments, the method comprises administering the pharmaceutical composition a sufficient number of times a treatment period such that the circulatory concentration of the target immune complex is substantially decreased for at least about one week, two weeks, three weeks, four weeks, one month, two months, three months, four months, five months, six months, or greater than six months.

In other embodiments, the method comprises administering the pharmaceutical composition a sufficient number of times a treatment period such that the circulatory concentration of the target immune complex is substantially decreased for a period of time at least as long as the treatment period.

In some embodiments, the treatment period is not longer than a year, six months, three months, two months, one month, two weeks, one week, three days, two days, one day.

In some embodiments, the time interval between administrations within a treatment period is no longer than the period in which the number of synthetic membrane-CR1 receiver complexes in circulation is reduced to less than about 5%, 10%, 15%, 20%, 25%, 30%, 35%, 40%, 45%, 50%, 55%, 60%, 65%, 70%, 75%, 80%, 85%, 90%, or 95% of the number of synthetic membrane—CR1 receiver complexes present in the administered pharmaceutical composition.

In other embodiments, the frequency of administration is sufficient to effectively reduce the circulatory concentration of the target immune complex below a level that is associated with a symptom of the immune complex-associated disease, disorder or condition.

In some embodiments, the administering of the pharmaceutical composition reduces the concentration of unbound target immune complex or the concentration of total target immune complex in the circulatory system of the subject.

In some embodiments, the concentration of total target immune complex is approximately equal to the concentration of unbound and bound target immune complex in the circulatory system of the subject.

In some embodiments, the method further comprises the step of selecting for treatment a subject suffering from or at risk of a immune complex-associated disease, disorder or condition selected from the group consisting of: IgA nephropathy and lupus nephritis.

In certain embodiments, the target immune complex comprises i) IgM or IgG, and ii) C3b and/or C4b.

In some embodiments, the receiver is associated with the membrane. Optionally, the receiver is a fusion or a chimera. If desired, the fusion or chimera may comprise at least one of an S domain, an A domain or a U domain, wherein the S domain is a surface domain exposed to the environment around the synthetic membrane—CR1 receiver complex, wherein the A domain is an anchor, wherein the U domain faces the unexposed side of the synthetic membrane—CR1 receiver complex, and wherein the S domain, the A domain, and/or the U domain are of different polypeptide origin. In some embodiments, the S domain and/or the A domain comprise a polypeptide comprising at least 6 or at least 30 amino acids. In some embodiments, the S domain comprises the antigenic polypeptide or antigenic fragment thereof.

In certain embodiments, the CR1 receiver polypeptide comprises one or more of any one of a complement control protein (CCP) module, a short consensus repeat (SCR), and/or a long homologous repeat (LHRs)

In some aspects, disclosed herein is a method of reducing the circulatory concentration of a target complement protein. The method comprises the steps of administering to a mammalian subject suffering from or at risk of developing a disease, disorder or condition associated with the dysregulation of a complement protein, a pharmaceutical composition comprising a synthetic membrane-receiver complex, wherein the pharmaceutical composition is administered in an amount effective to substantially reduce the circulatory concentration of the target complement protein.

In certain embodiments, the synthetic membrane-receiver complex has a volume of distribution equal to the plasma volume of the subject. In some embodiments, the synthetic membrane-receiver complex has a volume of distribution of less than 0.091/kg.

In certain embodiments, the method comprises administering the pharmaceutical composition at least twice over a treatment period such that the disease, disorder or condition associated with the dysregulation of a complement protein is treated, or a symptom thereof is decreased.

In other embodiments, the method comprises administering the pharmaceutical composition at least twice over a treatment period such that the disease, disorder or condition associated with the dysregulation of a complement protein is prevented.

In yet other embodiments, the method comprises administering the pharmaceutical composition a sufficient number of times over a treatment period such that the circulatory concentration of the target complement protein is substantially decreased during the treatment period.

In yet other embodiments, the method comprises administering the pharmaceutical composition a sufficient number of times over a treatment period such that the circulatory concentration of the target complement protein is substantially decreased during the treatment period such that one or more symptom of the disease, disorder or condition associated with the dysregulation of a complement protein is prevented, decreased or delayed.

In yet other embodiments, the method comprises administering the pharmaceutical composition a sufficient number of times over a treatment period such that the circulatory concentration of the target complement protein is decreased at a rate greater than i) the endogenous clearance rate of the target complement protein by the mammalian subject, or ii) the endogenous production rate of the target complement protein by the mammalian subject, or iii) both i) and ii)).

In some embodiments, the circulatory concentration of the target complement protein is decreased by at least about 1%, 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, 99.5%, 99.9%, 99.99%, or greater than 99.99% during part or the entirety of the treatment period.

In other embodiments, the circulatory concentration of the target complement protein is decreased by at least about 1%, 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, 99.5%, 99.9%, 99.99%, or greater than 99.99% within about 1, 5, 10, 15, 20, 30, 40, or 50 minutes, or about 1, 2, 3, 4, 5, 6, 7, 8, 9, 10, 11, 12, 13, 14, 15, 16, 17, 18, 19, 20, 21, 22, or 23 hours, or 1, 2, 3, 4, 5, or 6 days or about 1, 2, 3, 4, 5, or 6 weeks of the administration.

In some embodiments, the method comprises administering the pharmaceutical composition a sufficient number of times a treatment period such that the circulatory concentration of the target complement protein is substantially decreased for at least about one week, two weeks, three weeks, four weeks, one month, two months, three months, four months, five months, six months, or greater than six months.

In other embodiments, the method comprises administering the pharmaceutical composition a sufficient number of times a treatment period such that the circulatory concentration of the target complement protein is substantially decreased for a period of time at least as long as the treatment period.

In some embodiments, the treatment period is not longer than a year, six months, three months, two months, one month, two weeks, one week, three days, two days, one day.

In some embodiments, the time interval between administrations within a treatment period is no longer than the period in which the number of synthetic membrane-receptor complexes in circulation is reduced to less than about 5%, 10%, 15%, 20%, 25%, 30%, 35%, 40%, 45%, 50%, 55%, 60%, 65%, 70%, 75%, 80%, 85%, 90%, or 95% of the number of synthetic membrane-receptor complexes present in the administered pharmaceutical composition.

In other embodiments, the frequency of administration is sufficient to effectively reduce the circulatory concentration of the target complement protein below a level that is associated with a symptom of the disease, disorder or condition associated with the dysregulation of a complement protein.

In some embodiments, the administering of the pharmaceutical composition reduces the concentration of unbound target complement protein or the concentration of total target complement protein in the circulatory system of the subject.

In some embodiments, the concentration of total target complement protein is approximately equal to the concentration of unbound and bound target complement protein in the circulatory system of the subject.

In some embodiments, the method further comprises the step of selecting for treatment a subject suffering from or at risk of a disease, disorder or condition associated with the dysregulation of a complement protein selected from the group consisting of: atypical hemolytic-uremic syndrome (aHUS), paroxysmal nocturnal hemoglobinuria (PNH), age-related macular degeneration, autoimmune hemolytic anemia, complement factor I deficiency, and non-alcoholic steatohepatitis.

In certain embodiments, the target complement protein is selected from the group consisting of: C1q, C1r, C1s, C2, C3, C4, C5, C6, C7, C8, and C9.

In some aspects, disclosed herein is a method of modulating the circulatory concentration of a target metabolite. The method comprises the steps of administering to a mammalian subject suffering from or at risk of developing a metabolic disease, disorder or condition, a pharmaceutical composition comprising a synthetic membrane-receiver complex, wherein the pharmaceutical composition is administered in an amount effective to substantially modulate the circulatory concentration of the target metabolite.

In certain embodiments, the synthetic membrane-receiver complex has a volume of distribution equal to the plasma volume of the subject. In some embodiments, the synthetic membrane-receiver complex has a volume of distribution of less than 0.091/kg.

In certain embodiments, the method comprises administering the pharmaceutical composition at least twice over a treatment period such that the metabolic disease, disorder or condition is treated, or a symptom thereof is decreased.

In other embodiments, the method comprises administering the pharmaceutical composition at least twice over a treatment period such that the metabolic disease, disorder or condition is prevented.

In yet other embodiments, the method comprises administering the pharmaceutical composition a sufficient number of times over a treatment period such that the circulatory concentration of the target metabolite is substantially decreased during the treatment period.

In yet other embodiments, the method comprises administering the pharmaceutical composition a sufficient number of times over a treatment period such that the circulatory concentration of a metabolite is substantially increased during the treatment period.

In yet other embodiments, the method comprises administering the pharmaceutical composition a sufficient number of times over a treatment period such that the circulatory concentration of the target metabolite is substantially decreased during the treatment period such that one or more symptom of the a metabolic disease, disorder or condition is prevented, decreased or delayed.

In yet other embodiments, the method comprises administering the pharmaceutical composition a sufficient number of times over a treatment period such that the circulatory concentration of a metabolite is substantially increased during the treatment period such that one or more symptom of the a metabolic disease, disorder or condition is prevented, decreased or delayed.

In yet other embodiments, the method comprises administering the pharmaceutical composition a sufficient number of times over a treatment period such that the circulatory concentration of the target metabolite is decreased at a rate greater than i) the endogenous clearance rate of the target metabolite by the mammalian subject, or ii) the endogenous production rate of the target metabolite by the mammalian subject, or iii) both i) and ii).

In yet other embodiments, the method comprises administering the pharmaceutical composition a sufficient number of times over a treatment period such that the circulatory concentration of a metabolite is increased at a rate greater than i) the endogenous clearance rate of a metabolite by the mammalian subject, or ii) the endogenous production rate of a metabolite by the mammalian subject, or iii) both i) and ii).

In some embodiments, the circulatory concentration of the target metabolite is decreased by at least about 1%, 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, 99.5%, 99.9%, 99.99%, or greater than 99.99% during part or the entirety of the treatment period.

In some embodiments, the circulatory concentration of a metabolite is increased by at least about 1%, 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, 99.5%, 99.9%, 99.99%, or greater than 99.99% during part or the entirety of the treatment period.

In other embodiments, the circulatory concentration of the target metabolite is decreased by at least about 1%, 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, 99.5%, 99.9%, 99.99%, or greater than 99.99% within about 1, 5, 10, 15, 20, 30, 40, or 50 minutes, or about 1, 2, 3, 4, 5, 6, 7, 8, 9, 10, 11, 12, 13, 14, 15, 16, 17, 18, 19, 20, 21, 22, or 23 hours, or 1, 2, 3, 4, 5, or 6 days or about 1, 2, 3, 4, 5, or 6 weeks of the administration.

In other embodiments, the circulatory concentration of a metabolite is increased by at least about 1%, 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, 99.5%, 99.9%, 99.99%, or greater than 99.99% within about 1, 5, 10, 15, 20, 30, 40, or 50 minutes, or about 1, 2, 3, 4, 5, 6, 7, 8, 9, 10, 11, 12, 13, 14, 15, 16, 17, 18, 19, 20, 21, 22, or 23 hours, or 1, 2, 3, 4, 5, or 6 days or about 1, 2, 3, 4, 5, or 6 weeks of the administration.

In some embodiments, the method comprises administering the pharmaceutical composition a sufficient number of times a treatment period such that the circulatory concentration of the target metabolite is substantially decreased for at least about one week, two weeks, three weeks, four weeks, one month, two months, three months, four months, five months, six months, or greater than six months.

In some embodiments, the method comprises administering the pharmaceutical composition a sufficient number of times a treatment period such that the circulatory concentration of a metabolite is substantially increased for at least about one week, two weeks, three weeks, four weeks, one month, two months, three months, four months, five months, six months, or greater than six months.

In other embodiments, the method comprises administering the pharmaceutical composition a sufficient number of times a treatment period such that the circulatory concentration of the target metabolite is substantially decreased for a period of time at least as long as the treatment period.

In other embodiments, the method comprises administering the pharmaceutical composition a sufficient number of times a treatment period such that the circulatory concentration of a metabolite is substantially increased for a period of time at least as long as the treatment period.

In some embodiments, the treatment period is not longer than a year, six months, three months, two months, one month, two weeks, one week, three days, two days, one day.

In some embodiments, the time interval between administrations within a treatment period is no longer than the period in which the number of synthetic membrane-receiver complexes in circulation is reduced to less than about 5%, 10%, 15%, 20%, 25%, 30%, 35%, 40%, 45%, 50%, 55%, 60%, 65%, 70%, 75%, 80%, 85%, 90%, or 95% of the number of synthetic membrane-receiver complexes present in the administered pharmaceutical composition.

In other embodiments, the frequency of administration is sufficient to effectively reduce the circulatory concentration of the target metabolite below a level that is associated with a symptom of the metabolic disease, disorder or condition.

In other embodiments, the frequency of administration is sufficient to effectively increase the circulatory concentration of a metabolite above a level that is associated with a symptom of the metabolic disease, disorder or condition.

In some embodiments, the administering of the pharmaceutical composition reduces the concentration of unbound target metabolite or the concentration of total target metabolite in the circulatory system of the subject.

In some embodiments, the concentration of total target metabolite is approximately equal to the concentration of unbound and bound target metabolite in the circulatory system of the subject.

In some embodiments, the administering of the pharmaceutical composition increases the concentration of an unbound metabolite or the concentration of total metabolite in the circulatory system of the subject.

In some embodiments, the method further comprises the step of selecting for treatment a subject suffering from or at risk of a metabolic disease, disorder or condition selected from the group consisting of: Phenylketonuria (PKU), Adenosine Deaminase Deficiency-Severe Combined Immunodeficiency (ADA-SCID), Mitochondrial Neurogastrointestinal Encephalopathy (MNGIE), Primary Hyperoxaluria, Alkaptonuria, and Thrombotic Thrombocytopenic Purpura (TTP).

In certain embodiments, the target metabolite is selected from the group consisting of: Phenylalanine, Adenosine, Thymidine, Deoxyuridine, Oxalate, Homogentisate, von Willenbrand Factor.

In some embodiments, the receiver is associated with the membrane. Optionally, the receiver is a fusion or a chimera. If desired, the fusion or chimera may comprise at least one of an S domain, an A domain or a U domain, wherein the S domain is a surface domain exposed to the environment around the synthetic membrane-receiver complex, wherein the A domain is an anchor, wherein the U domain faces the unexposed side of the synthetic membrane-receiver complex, and wherein the S domain, the A domain, and/or the U domain are of different polypeptide origin. In some embodiments, the S domain and/or the A domain comprise a polypeptide comprising at least 6 or at least 30 amino acids. In some embodiments, the S domain comprises the antigenic polypeptide or antigenic fragment thereof.

In certain embodiments, the receiver polypeptide is selected from the group consisting of: Phenylalanine Hydroxylase, Adenosine Deaminase, Thymidine Phosphorylase, Glyoxalate Reductase, Homogentisate Reductase, ADAMTS13.

Aspects of the invention relate to synthetic membrane receiver complexes that comprise non-polypeptide receivers, such as nucleic acids, lipids, carbohydrates and/or small molecules. In some embodiments, the receiver is associated with the membrane. Optionally, the receiver is a fusion or a chimera with a polypeptide. If desired, the fusion or chimera may comprise at least one of an S domain, an A domain or a U domain, wherein the S domain is a surface domain exposed to the environment around the synthetic membrane-receiver complex, wherein the A domain is an anchor, wherein the U domain faces the unexposed side of the synthetic membrane-receiver complex, and wherein the S domain, the A domain, and/or the U domain are of different origin. In some embodiments, the S domain and/or the A domain comprise a polypeptide comprising at least 6 or at least 30 amino acids. In some embodiments, the S domain comprises the antigenic polypeptide or antigenic fragment thereof.

In certain embodiments, the pharmaceutical compositions described herein comprise a population of synthetic membrane-receiver complexes such as at least $1 \times 10^5$ synthetic membrane-receiver complexes, optionally in a volume of about 10 nl, 100 nl, 1 µl, 10 µl, 100 µl, 1 ml, 10 ml, 20 ml, or 50 ml. In certain embodiments, the pharmaceutical compositions described herein comprise a population of synthetic membrane-receiver complexes such as at least $1 \times 10^{11}$ synthetic membrane-receiver complexes, optionally in a volume of about 1 ml, 10 ml, 20 ml, 50 ml, 100 ml, 250 ml, or 500 ml.

In some aspects, provided herein is the synthetic membrane-receiver complex of the pharmaceutical composition administered by the methods disclosed herein.

In some aspects, provided herein is a population of synthetic membrane-receiver complexes as disclosed herein. Optionally, the population of synthetic membrane-receiver complexes is formulated as a liquid. Alternatively, the population of synthetic membrane-receiver complexes is frozen.

In some aspects, provided herein is an isolated receiver of the synthetic membrane-receiver complex as disclosed herein.

In some aspects, provided herein is an exogenous nucleic acid encoding the receiver disclosed herein.

In some aspects, provided herein is a synthetic membrane-receiver complex comprising: a receiver capable of interacting with a target, and a membrane comprising a polypeptide that is not the receiver, wherein the synthetic membrane-receiver complex has catalytic activity independent of the receiver.

In some embodiments, the synthetic membrane-receiver complex comprises a receiver that is not a polypeptide.

In some embodiments, any synthetic membrane-receiver complex described herein, including those comprising a polypeptide receiver, optionally comprise a payload, such as a therapeutic agent.

Aspects of the invention relate to isolated, enucleated erythroid cell comprising a receiver polypeptide that is functionally active when the enucleated erythroid cell is administered to the circulatory system of a subject. In some embodiments, the erythroid cell is a human cell.

Aspects of the invention relate to isolated, functional erythroid precursor cell comprising a receiver polypeptide that is encoded by an exogenous nucleic acid, wherein the expression of the receiver polypeptide does not substantially alter: the expression of a surface marker, selected from the group consisting of GPA, cKit, and TR when the functional erythroid precursor cell differentiates; the rate of enucleation when the functional erythroid precursor cell terminally matures; and/or the rate of expansion when the functional erythroid precursor cell expands in culture, wherein the alteration is compared to an isolated, uncultured erythroid precursor cell of the same stage and lineage not comprising the polypeptide receiver.

Aspects of the invention relate to isolated erythroid cell populations comprising a plurality of functional erythroid cells comprising a receiver polypeptide localized to an exterior surface of the erythroid cells, wherein the population is substantially free of non-erythroid cells. In some embodiments, the population comprises greater than 5-95% of enucleated erythroid cells.

Aspects of the invention relate to isolated erythroid cell populations comprising a plurality of functional erythroid cells comprising a receiver polypeptide encoded by an exogenous nucleic acid, wherein during enucleation the receiver polypeptide is retained by the erythroid cell whereas the exogenous nucleic acid is not retained. In some embodiments, the population comprises greater than 5-95% of enucleated erythroid cells, optionally in the absence of: i) an enrichment step and/or ii) co-culturing with non-erythroid cells.

Aspects of the invention relate to isolated erythroid cell populations comprising a plurality of functional erythroid cells comprising a receiver polypeptide encoded by an exogenous nucleic acid, wherein during enucleation the receiver polypeptide is retained by the erythroid cell whereas the exogenous nucleic acid is not retained, and wherein the resulting functional enucleated erythroid cell exhibits substantially the same osmotic membrane fragility as an isolated, uncultured erythroid cell not comprising the polypeptide receiver.

Aspects of the invention relate to isolated erythroid cell populations comprising a plurality of functional erythroid precursor cells in substantially the same stage of differentiation and/or cell cycle stage, wherein the precursor cells comprise an exogenous nucleic acid encoding a receiver polypeptide, and wherein a majority of erythrocyte precursor cells is capable of differentiating into mature erythrocytes that retain the receiver polypeptide without retaining the exogenous nucleic acid.

Aspects of the invention relate to isolated erythroid cell populations comprising a plurality of functional erythroid cells comprising a receiver polypeptide, wherein an exogenous nucleic acid encoding the receiver polypeptide is introduced into a cultured or freshly isolated erythroid cell precursor and wherein after introduction of the exogenous nucleic acid the functional erythroid cells expand from the precursor cells by more than 20,000-fold in culture. In some embodiments, the population comprises greater than 5-95% of enucleated erythroid cells, optionally in the absence of: i) an enrichment step and/or ii) co-culturing with non-erythroid cells.

Aspects of the invention relate to an isolated erythroid cell population that is cultured from a functional erythrocyte precursor cell comprising an exogenous nucleic acid, the population comprising: a pyrenocyte, a functional nucleated erythroid cell and a functional enucleated erythroid cell, wherein the functional nucleated erythroid cell and the functional enucleated erythroid cell comprise an receiver polypeptide encoded by the exogenous nucleic acid, and wherein the receiver polypeptide is retained by the functional enucleated erythroid cell, whereas the exogenous nucleic acid is not retained by the enucleated erythroid cell. In some embodiments, the enucleated, functional erythroid cell exhibits substantially the same osmotic membrane fragility as an isolated, uncultured erythroid cell not comprising the polypeptide receiver.

In some embodiments, the erythroid cell populations described herein comprise greater than 1%, 2%, 3%, 4%, 5%, 6%, 7%, 8%, 9% or greater than 10% fetal hemoglobin.

In some embodiments, the functional erythroid cell exhibits at least 10 copies, 100 copies, 1,000 copies, 10,000 copies, 25,000 copies, 50,000 copies, or 100,000 copies of the receiver polypeptide per cell.

In certain embodiments, a plurality of functional erythroid cells loses a substantial portion of its cell membrane after being administered to the circulatory system of a subject.

In certain embodiments, the functional erythroid cells comprise a receiver polypeptide that interacts with a target. In some embodiments, interacting with a target comprises binding to the target, degrading the target, cleaving the target, and/or sequestering the target.

In some embodiments, the receiver polypeptide is displayed on the cell surface. In other embodiments, the receiver polypeptide is localized in the interior of the functional erythroid cell.

In certain embodiments, the functional erythroid cells comprise a receiver polypeptide that is selected from the group consisting of: an antibody, a single-chain variable fragment, a nanobody, a diabody, a darbin, a lyase, a hydrolase, a protease, a nuclease, and a DNase.

In some embodiments, the functional erythroid cells comprise a receiver polypeptide that interacts with a target that is selected from the group consisting of: an immune complex, an inflammatory molecule, an inflammatory cell, a lipid, a carbohydrate, an amino acid, a virus, a bacterium, a bacterial toxin, a fungus, a fungal toxin, a DNA, an RNA, a cell, a circulating cell, a tumor cell, a metastatic cancer cell, a metabolite, a plant toxin, a cytokine, a chemokine, a complement cascade factor, and a clotting cascade factor.

In some embodiments, the functional erythroid cells comprise a receiver polypeptide that is fused to an endogenous polypeptide. In certain embodiments, the endogenous polypeptide is an intracellular polypeptide. In some embodiments, the endogenous polypeptide is an extracellular polypeptide. In some embodiments, the endogenous polypeptide is membrane-bound.

In some embodiments, the functional erythroid cells comprise a receiver polypeptide that is fused to an endogenous extracellular polypeptide.

In some embodiments, the functional erythroid cells comprise a receiver polypeptide that conjugated to the erythroid cell.

In some embodiments, the functional erythroid cells comprise a receiver polypeptide that interacts with the target intercellularly.

In some embodiments, the functional erythroid cells comprise a receiver polypeptide that is localized in the cytosol of the erythroid cell.

In some embodiments, the functional erythroid cells comprise a receiver polypeptide that is located in the cell membrane of the erythroid cell.

In certain embodiments, the functional erythroid cells comprise a plurality of receiver polypeptides. In some embodiments, a first receiver polypeptide is located in the cytosol of the functional erythroid cell and a second receiver polypeptide is located on the cell surface of the functional erythroid cell.

In some embodiments, the functional erythroid cells comprise a receiver polypeptide that is an Fv portion of an antibody that binds a botulinum toxin and the target is a botulinum toxin.

In other embodiments, the functional erythroid cells comprise a receiver polypeptide that is a complement receptor 1 and the target is a circulating immune complex.

In yet other embodiments, the functional erythroid cells comprise a receiver polypeptide that is a duffy antigen receptor complex (DARC) and the target is a circulating chemokine.

In some embodiments, the functional erythroid cells comprise a receiver polypeptide that is phenylalanine hydroxylase (PAH) and the target is phenylalanine.

In some embodiments, the functional erythroid cells comprise a receiver polypeptide that is expressed as a fusion of the C-terminus of a cytoplasmic beta globin protein.

In other embodiments, the functional erythroid cells comprise a receiver polypeptide that is an exonuclease and wherein the target is a circulating cell-free DNA molecule.

In yet other embodiments, the functional erythroid cells comprise a receiver polypeptide that is expressed as a fusion of the N-terminus of endogenous glycophorin A.

In some embodiments, the functional erythroid cells comprise a receiver polypeptide that is attached extracellularly on the erythroid cell by covalent bond formation. In some embodiments, the covalent bond is formed by an isopeptidase. In some embodiments, the isopeptidase is SpyTag/SpyCatcher. In some embodiments, the SpyTag is expressed on the surface of the cell. In some embodiments, the SpyTag is fused to an extracellular terminus of a transmembrane protein. In some embodiments, the SpyTag is an in-frame fusion in an extracellular region of a multi-pass membrane protein. In some embodiments, the SpyTag is fused to a GPI-linked protein. In some embodiments, the SpyCatcher is fused to the receiver polypeptide. In some embodiments, the receiver polypeptide fused to SpyCatcher is expressed and/or secreted in the same functional erythroid cell that expresses the SpyTag fusion. In some embodiments, the receiver polypeptide fused to SpyCatcher is expressed by an exogenous protein production system and then contacted with the functional erythroid cell that expresses the SpyTag fusion. In some embodiments, the SpyTag is replaced with SpyCatcher and the SpyCatcher is replaced with SpyTag. In some embodiments, the receiver polypeptide is anchored intracellularly in the functional erythroid cell by covalent bond formation. In some embodiments, the covalent bond is formed by an isopeptidase. In some embodiments, the isopeptidase is SpyTag/SpyCatcher. In some embodiments, the SpyTag is expressed in the intracellular space of the cell. In some embodiments, the SpyTag is fused to an intracellular terminus of a membrane protein. In some embodiments, the SpyTag is an in-frame fusion in an intracellular region of a multi-pass membrane protein. In some embodiments, the SpyTag is fused to an endogenous intracellular protein. In some embodiments, the SpyTag is fused to a cytoskeletal protein. In some embodiments, the SpyCatcher is fused to the receiver polypeptide. In some embodiments, the receiver polypeptide fused to SpyCatcher is expressed in the intracellular space of the same functional erythroid cell that expresses the SpyTag fusion. In some embodiments, the SpyTag is replaced with SpyCatcher and the SpyCatcher is replaced with SpyTag.

Aspects of the invention relate to methods of generating functional erythroid cells comprising a receiver polypeptide, the methods comprising contacting an erythroid cell with a receiver and exposing the erythroid cell to a controlled cell injury. In certain embodiments, the controlled cell injury is cell deformation, electroporation, sonoporation, liposomal transfection, or salt-based transfection. In some embodiments, the cell is contacted with an mRNA that encodes the receiver polypeptide. In some embodiments, the contacting results in an uptake and translation of the mRNA encoding the receiver polypeptide by the erythroid cell or erythroid cell precursor.

In certain embodiments, the populations of erythroid cells described herein are maintained and/or propagated in vitro. In other embodiments, the populations of erythroid cells described herein are lyophilized. In yet other embodiments, the populations of erythroid cells described herein are frozen.

Aspects of the invention relate to methods of contacting a target comprising: introducing into a biological sample or a subject the erythroid cell populations described herein, and maintaining the contact of the erythroid cell population with the sample or subject for a time sufficient for a functional erythroid cell from the population to interact with a target in the sample or subject. In some embodiments, interacting with a target comprises binding to the target, degrading the target, cleaving the target, and/or sequestering the target. In certain embodiments, the methods of contacting a target are carried out in vitro. In other embodiments, the methods of contacting a target are carried out in vivo, e.g. in an animal. In some embodiments, the methods of contacting a target further comprise contacting the target with an assayable moiety. In some embodiments, the assayable moiety is used to determine the rate and/or degree of interaction between the functional erythroid cell and the target.

Aspects of the invention relate to pharmaceutical compositions comprising the erythroid cell populations comprising the functional erythroid cells comprising a receiver described herein. Optionally, the pharmaceutical compositions comprising the erythroid cell populations further comprise a pharmaceutically acceptable carrier. Optionally the the pharmaceutical compositions comprising the erythroid cell populations further comprise a therapeutic agent.

Aspects of the invention relate to methods of treating, preventing, or managing a disease or condition, comprising administering to a subject in need of such treatment, prevention or management, a therapeutically or prophylactically effective amount of the pharmaceutical composition comprising a population of functional erythroid cells comprising a receiver, thereby treating, preventing, or managing the disease or condition.

Aspects of the invention relate to pharmaceutical compositions comprising a population of functional erythroid cells comprising a receiver for use in any of the methods of treatment or prevention described herein. In some embodiments, the receiver polypeptide interacts with a target residing in the circulatory system of the subject. In some embodiments, the presence, absence, elevated or depressed level of the target is associated with a disease, disorder or condition. In some embodiments, interacting with a target comprises binding to the target, degrading the target, cleaving the target, and/or sequestering the target. In some embodiments, the administration of the pharmaceutical compositions comprising a population of functional erythroid cells comprising a receiver results in a substantial reduction of the concentration or number of the target in the circulatory system of the subject.

Aspects of the invention relate to pharmaceutical compositions comprising a plurality of functional erythroid cells comprising a receiver polypeptide, wherein the erythroid cells exhibit the receiver polypeptide in or on the cell, and wherein the receiver polypeptide when the functional erythroid cell is administered to the circulatory system of a subject: does not substantially affect the circulation clearance time of the functional erythroid cell when compared to a unmodified erythroid cell in a control animal, and/or does not activate fibrinogen breakdown, measured by circulating levels of fibrinopeptide A and/or fibrinopeptide B, compared to an unmodifed erythroid cell.

Aspects of the invention relate to methods for culturing the functional erythroid cell population of described herein, comprising using one or more culturing factors selected from the group consisting of stem cell factor, IL-3, IL-6, insulin, transferrin, erythropoietin, hydrocortisone, and estrogens to culture the functional erythroid cells.

Aspects of the invention relate to populations of at least $10^{10}$ cells comprising at least 10% reticulocytes of the same blood group, wherein a plurality of the reticulocytes comprises areceiver polypeptide.

Aspects of the invention relate to a pharmaceutical composition comprising a synthetic membrane-receiver polypeptide complex for use in the treatment of any of the diseases, disorders, or conditions disclosed herein.

Aspects of the invention relate to a pharmaceutical composition comprising a synthetic membrane-receiver polypeptide complex for use in the treatment of a disease, disorder, or condition associated with the presence of or the concentration of a target in the circulatory system of a mammalian subject.

Aspects of the invention relate to a pharmaceutical composition comprising a synthetic membrane-receiver polypeptide complex for use in the modulation of the circulatory concentration of a target.

BRIEF DESCRIPTION OF THE FIGURES

The figures are meant to be illustrative of one or more features, aspects, or embodiments of the invention and are not intended to be limiting.

FIG. 3 A

FIG. 3A—Expression of glycophorin A with an HA epitope tag at the cytoplasmic C terminus assessed by expression of co-translated GFP.

FIG. 3I—Expression of antibody scFv fused to N-terminus of CD55-derived fragment of 37 amino acids, assessed by anti-HA Western blot.

FIG. 3J—Cytoplasmic expression of adenosine deaminase fused to HA tag assessed by anti-HA Western blot. Expected size approximately 40 kDa.

FIG. 3K—Cytoplasmic expression of phenylalanine hydroxylase fused to HA tag assessed by anti-HA Western blot. Expected size approximately 33 kDa.

FIG. 3N—Cytoplasmic expression of phenylalanine hydroxylase fused to the intracellular C terminus of glycophorin A assessed by anti-HA Western blot. Expected size approximately 50 kDa.

FIG. 3O-FIG. 3AJ shows the exogenous expression of surface and cytoplasmic proteins on nucleated cultured erythroid precursor cells.

FIG. 3O—Expression of glycophorin A with an HA epitope tag at the cytoplasmic C terminus assessed by expression of co-translated GFP.

FIG. 3AA—Expression of antibody scFv fused to C terminus of Kell-derived fragment of 79 amino acids assessed by anti-HA staining.

FIG. 3AB—Expression of CD55 with HA epitope tag at the extracellular N terminus after the leader sequence assessed by anti-HA staining.

FIG. 3AC—Expression of CD59 with HA epitope tag at the extracellular N terminus after the leader sequences assessed by anti-HA staining.

FIG. 3AD—Expression of antibody scFv fused to N-terminus of CD55-derived fragment of 37 amino acids, assessed by anti-HA staining.

FIG. 3AE—Expression of antibody scFv fused to N-terminus of CD59 assessed by anti-HA staining.

FIG. 3AF—Cytoplasmic expression of adenosine deaminase fused to HA tag assessed by anti-HA Western blot. Expected size approximately 40 kDa.

FIG. 3AG—Cytoplasmic expression of phenylalanine hydroxylase fused to HA tag assessed by anti-HA Western blot. Expected size approximately 33 kDa.

FIG. 3AH—Cytoplasmic expression of phenylalanine hydroxylase fused to adenosine deaminase and an HA tag assessed by flow cytometry for fluorescence from co-translated GFP.

FIG. 3AI—Cytoplasmic expression of adenosine deaminase fused to the intracellular C terminus of glycophorin A assessed by anti-HA Western blot. Expected size approximately 55 kDa.

FIG. 3AJ—Cytoplasmic expression of phenylalanine hydroxylase fused to the intracellular C terminus of glycophorin A assessed by anti-HA Western blot. Expected size approximately 50 kDa.

FIG. 3AK-FIG. 3AP shows the exogenous expression of surface and cytoplasmic proteins on K562 erythroleukemia cells.

FIG. 3AK—Overexpression of complement receptor 1 assessed by anti-CR1 staining.

FIG. 3AL—Expression of antibody scFv as N terminal fusion to glycophorin A assessed by anti-HA staining.

FIG. 3AM—Expression of antibody scFv fused to N-terminus of CD55-derived fragment of 37 amino acids, assessed by anti-HA staining.

FIG. 3AN—Expression of antibody scFv fused to N-terminus of CD59 assessed by anti-HA staining.

FIG. 3AO—Cytoplasmic expression of adenosine deaminase fused to HA tag assessed by anti-HA Western blot. Expected size approximately 40 kDa.

FIG. 3AP—Cytoplasmic expression of phenylalanine hydroxylase fused to HA tag assessed by anti-HA Western blot. Expected size approximately 33 kDa.

(FIG. 4A) Untransfected platelets. (FIG. 4B) Platelets transfected with 3 ug GFP mRNA. (FIG. 4C) Platelets transfected with 6.8 ug GFP mRNA.

(FIG. 5A) is a Western blot of exogenously expressed adenosine deaminase detected with an anti-HA antibody over the course of differentiation, from nucleated precursor cells ("Diff I D5") through to enucleated erythroid cells ("Diff III D8"). (FIG. 5B) is a bar chart of inosine produced from adenosine by intact adenosine deaminase-expressing 293T cells. (FIG.

5C) is a Western blot of the exogenously expressed phenylalanine hydroxylase detected with an anti-HA antibody at various time points over the course of differentiation, from nucleated precursor cells ("Diff I D5") through to enucleated erythroid cells ("Diff III D8").

(FIG. 6A) is a flow cytometry plot that shows the capture of fluorescent immune complexes (white histogram) and complement-deficient immune complexes (shaded histogram) by cultured erythroid cells that overexpress CR1. (FIG. 6B) is a bar chart of flow cytometry data assessing the uptake of fluorescent immune complexes (hashed bars), complement deficient immune complexes (gray bars), or no immune complexes (black bars) by macrophages (left set) or macrophages incubated with cultured erythroid cells that overexpress CR1 (right set).

FIG. 7A-FIG. 7D shows the activity of an antibody scFv that binds hepatitis B surface antigen (scFv) on the surface of a cultured erythroid cell. (FIG. 7A) is a flow cytometry histogram showing binding of 450 nM antigen (white histogram) or no antigen (gray histogram). (FIG. 7B) is a titration of binding signal assessed by flow cytometry for a range of antigen concentrations. (FIG. 7C-FIG. 7D) are flow cytometry plots of blood cells from mice that had been injected with fluorescent antigen and cultured erythroid cells that (FIG. 7C) do not or (FIG. 7D) do express scFv. The y-axis measures antigen fluorescence. The x-axis measures fluorescence of the cultured cells.

(FIG. 8A) is a set of flow cytometry plots that show no binding (left) and binding (right) of circulating Dylight650-labeled mouse anti-HA antibody to CFSE-labeled cultured human erythroid cells isolated from a recipient mouse that either do not (left) or do (right) express HA epitope tag on their surface. The x-axis measures CFSE fluorescence. The y-axis measures anti-HA antibody Dylight650 fluorescence. (FIG. 8B) is data from an HA epitope tag substrate ELISA comparing anti-HA antibody levels over time in plasma collected from mice injected with anti-HA antibody (open circles, solid line), anti-HA antibody followed by cultured human erythroid cells that do not express HA epitope tag (dashed line), or anti-HA antibody followed by cultured human erythroid cells that do express HA epitope tag (dotted line). (FIG. 8C) is a set of flow cytometry plots that show no binding (left) and binding (right) of Dylight650-labeled mouse anti-biotin antibody to CFSE-labeled primary human erythrocytes that either are not (left) or are (right) conjugated with biotin on their surface. The x-axis measures CFSE fluorescence. The y-axis measures anti-biotin antibody Dylight650 fluorescence. (FIG. 8D) is data from a biotin substrate ELISA comparing anti-biotin antibody levels over time in plasma collected from mice injected with anti-biotin antibody (open circles, solid line), anti-biotin antibody followed by cultured human erythroid cells that are not conjugated to biotin (dashed line), or anti-biotin antibody followed by cultured human erythroid cells that are conjugated to biotin (dotted line).

(FIG. 9A) is a representative flow cytometry dot-plot of drawn blood, stained for human glycophorin A (y-axis) and CFSE (x-axis), in which human cultured cells are double-positive. (FIG. 9B) is a plot of the clearance rate over time as a percentage of double-positive cells remaining after NSG mice were injected with with human red blood cells (solid circles), cultured enucleated erythroid cells (dashed diamonds), cultured enucleated erythroid cells that express an intracellular exogenous protein (dotted squares) and cultured enucleated erythroid cells that express a surface exogenous protein (open triangles).

(FIG. 10A-FIG. 10B) show levels of (FIG. 10A) fibrinopeptide A and (FIG. 10B) fibrinopeptide B assessed by ELISA in plasma collected from mice 20 minutes (black), 6 hours (gray), and 48 hours (white) after injection with (1) human red blood cells, (2) cultured human erythroid cells, (3) cultured human erythroid cells expressing an exogenous cytoplasmic protein, (4) cultured human erythroid cells expressing an exogenous surface transgene, or (5) recombinant protein. (FIG. 10C-FIG. 10D) show microscope images of histologically stained sections of spleen for mice injected with (FIG. 10C) cultured human erythroid cells and (FIG. 10D) recombinant protein.

(FIG. 11A) is flow cytometry data of blood drawn from a mouse that was injected with cultured human erythroid cells expressing an exogenous surface protein, showing the percent of cultured human erythroid cells that are HA-positive over time. (FIG. 11B) is a Western blot of blood drawn from two mice, wherein one mouse was injected with cultured human erythroid cells expressing an exogenous cytoplasmic protein, and wherein the other mouse was injected with the purified recombinantly-produced exogenous protein in the absence of any cells, showing the level of HA-containing protein in the blood over time.

(FIG. 12A) is a plot of expansion rates for distinct cultures of in vitro differentiated erythroid cells that contain transgenes (dashed line and dotted line) and cells that do not contain a transgene (solid line). (FIG. 12B) is a flow cytometry plot of cell surface markers GPA and CKIT for distinct cultures of cultured human erythroid cells that do not (left) or do (right) contain a transgene. (FIG. 12C) is a flow cytometry plot of cultured human erythroid cells that do not (left) or do (right) contain a transgene, wherein the cells are stained with DNA stain DRAQ5 (y-axis) and anti-glycophorin A (x-axis), which identifies distinct populations of (1) enucleated cells, (2) nucleated cells, and (3) nuclei.

FIG. 13A is a schematic of a synthetic membrane-receiver complex comprising a receiver polypeptide. The left panel depicts the flux of a target substrate across the membrane of the synthetic membrane-receiver complex. The target substrate is altered by an internally localized enzymatic receiver polypeptide and the resulting product of the enzymatic reaction either remains in the synthetic membrane-receiver complex or exits through the membrane. The right panel depicts a synthetic membrane-receiver complex that contains at least two receivers (e.g., receiver polypeptides), one being localized on the surface and one being internally localized. In this example, the surface-localized receiver aids a substrate to enter the synthetic membrane-receiver complex, e.g., by carrying out a transporter function. The second receiver, localized internally, alters the substrate enzymatically. The resulting product of the enzymatic reaction either remains in the synthetic membrane-receiver complex or exits through the membrane, optionally aided by the first surface-localized receiver.

FIG. 13B is a schematic of another synthetic membrane-receiver complex comprising a receiver polypeptide. FIG. 13B depicts a receiver polypeptide localized on the surface of the synthetic membrane-receiver complex. As shown, a target substrate can be acted upon directly by the receiver. In the exemplified configuration, the target substrate does not need to cross the membrane to be enzymatically converted to a product. Optionally, the surface-localized enzymatic receiver polypeptide can be made cleavable, e.g., if the complex enters a specific microenvironment. In that instance, the receiver polypeptide will be cleaved and become active in the extracellular space.

FIG. 13C is a schematic of yet another synthetic membrane-receiver complex comprising a receiver. FIG. 13C depicts the lysis of a synthetic membrane-receiver complex containing internally-localized receiver (e.g., a polypeptide) and optional payload (e.g., a therapeutic agent) which may result from a variety of stimuli. Upon lysis, the internally-localized receiver and optional payload is released into the microenvironment where it may act on a target substrate.

FIG. 14A is a schematic of three ways in which a receiver may be localized in a synthetic membrane-receiver complex. FIG. 14B is a schematic of three ways in which a receiver localized in or on a synthetic membrane-receiver complex may act on a target in circulation. FIG. 14C is a schematic of an auto-catalytic fusion of an endogenous polypeptide anchor to a receiver utilizing a SpyTag-SpyCatcher mechanism.

DETAILED DESCRIPTION OF THE INVENTION

Figure 1D:
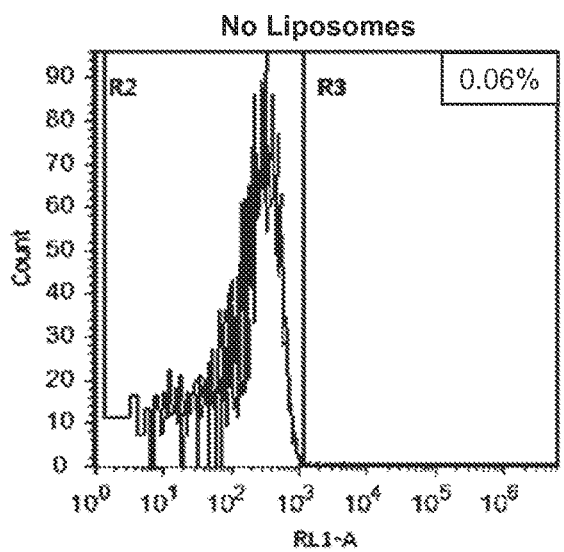
FIG. 1A-FIG. 1D is a collection of flow cytometry plots of red blood cells contacted with fluorescently labeled IgG encapsulated within liposomes. Cells are shown that are incubated with no liposomes (FIG. 1A, FIG. 1D), a low dose of liposomes (FIG. 1B, FIG. 1E), and a high dose of liposomes (FIG. 1C, FIG. 1F). On the bottom histograms, the percentage of cells that are fluorescent is shown.
Figure 1E:
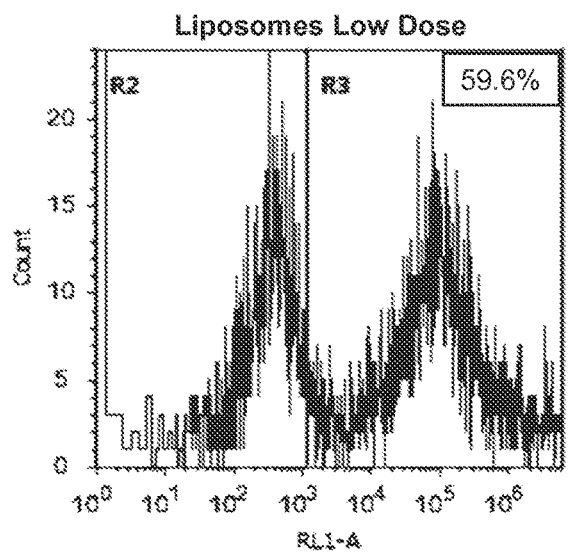
Figure 1F:
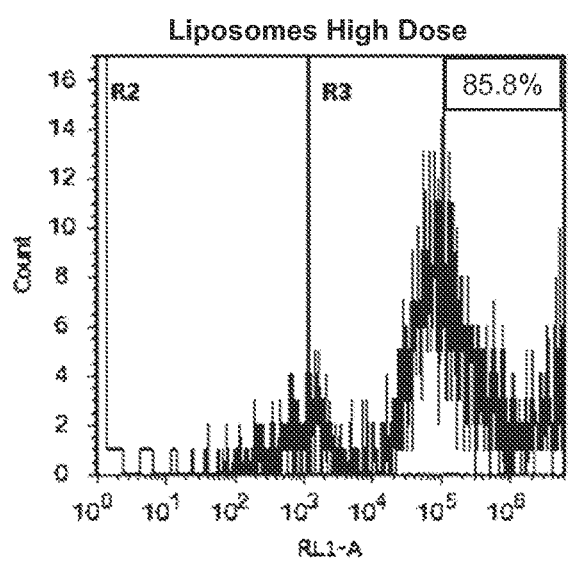

Therapeutic technologies attempting to employ circulating agents have been developed in the past to address some of the challenges in delivering treatments such as pharmaceutical drugs to patients. None possess one or many of the features and benefits of the synthetic membrane-receiver complexes provided herein. Aspects of the invention provide compositions capable of multiple, distinct utilities, which utilize biochemical and biophysical mechanisms not previously addressed. Aspects of the invention relate to compositions and methods for performing, e.g., functions related to circulating clearance and functions related to metabolic enzyme delivery, and methods for treating or preventing a variety of diseases, disorders and conditions. Accordingly, the compositions and methods disclosed herein address the long sought after need for therapeutic compositions that are distributed through the circulatory system that have increased half-life, safety profile, and/or efficacy that avoid shortcomings associated with previous approaches such as undesirable immunological reactions, short half-life due to rapid clearance from the circulation, and off-target effects, among others.

Functions related to circulating clearance include activities characterized by, e.g., the specific binding, degradation, and/or sequestration of a target (e.g., a pathogenic substance or toxic molecule) in the circulatory system of a subject by a synthetic membrane-receiver complex comprising a receiver capable of interacting with a target as described herein. Synthetic membrane-receiver complexes are introduced or capable of being introduced into the circulation of a subject. In some embodiments, the bound or sequestered targets are guided to the liver, spleen, or any other site in which they may be removed from the circulatory system.

Functions related to metabolic enzyme delivery include activities characterized by, e.g., removal of a target (e.g., a pathogenic substance or toxic molecule), in circulation of a subject by a synthetic membrane-receiver complex as described herein that comprises, e.g., one or more metabolic enzyme receiver polypeptides within the complex or on the surface of the complex, such that the receiver polypeptide interacts with and modifies the target. Modification of the target includes, e.g., alteration of the bioavailability of the target, cleaving, degrading, and/or otherwise inactivating the target by the receiver. In some embodiments, the enzymatic polypeptide is protected from the immune system. In some embodiments, the half-life of the enzyme is extended and/or an immunogenic reaction is reduced when administered in the subject.

It is to be understood that this invention is not limited to particular methods, reagents, compounds, compositions or biological systems, which can, of course, vary. It is also to be understood that the terminology used herein is for the purpose of describing particular aspects only, and is not intended to be limiting.

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

Many modifications and other embodiments of the inventions set forth herein will easily come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

As used in this specification and the appended claims, the singular forms "a", "an" and "the" include plural references unless the content clearly dictates otherwise.

The use of the alternative (e.g., "or") should be understood to mean either one, both, or any combination thereof of the alternatives.

The term "about" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

As used herein, any concentration range, percentage range, ratio range, or integer range is to be understood to include the value of any integer within the recited range and, when appropriate, fractions thereof (such as one tenth and one hundredth of an integer), unless otherwise indicated.

"Comprise," "comprising," and "comprises" and "comprised of" as used herein are synonymous with "include", "including", "includes" or "contain", "containing", "contains" and are inclusive or open-ended terms that specifies the presence of what follows e.g. component and do not exclude or preclude the presence of additional, non-recited components, features, element, members, steps, known in the art or disclosed therein.

As used herein, the terms "such as", "for example" and the like are intended to refer to exemplary embodiments and not to limit the scope of the present disclosure.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, preferred materials and methods are described herein.

All publications and patent applications cited in this specification are herein incorporated by reference in their entirety for all purposes as if each individual publication or patent application were specifically and individually indicated to be incorporated by reference for all purposes. The publications discussed herein are provided solely for their disclosure prior to the filing date of the present application. Nothing herein is to be construed as an admission that the inventors described herein are not entitled to antedate such disclosure by virtue of prior invention or for any other reason.

DEFINITIONS

"Administration," "administering" and variants thereof means introducing a composition, such as a synthetic membrane-receiver complex, or agent into a subject and includes concurrent and sequential introduction of a composition or agent. The introduction of a composition or agent into a subject is by any suitable route, including orally, pulmonarily, intranasally, parenterally (intravenously, intramuscularly, intraperitoneally, or subcutaneously), rectally, intralymphatically, or topically. Administration includes self-administration and the administration by another. A suitable route of administration allows the composition or the agent to perform its intended function. For example, if a suitable route is intravenous, the composition is administered by introducing the composition or agent into a vein of the subject. Administration can be carried out by any suitable route, "Anchor" or "anchor domain" or "A domain" is used to refer to the portion of a receiver polypeptide, including a fusion or chimeric receiver polypeptide that is in contact with the lipid layer of a synthetic membrane-receiver polypeptide complex. The receiver polypeptide may interact with the lipid layer via a phospholipid tail insertion, covalent binding to a lipid layer constituent, an ionic bond, hydrogen bond, or via a single or multi-pass transmembrane polypeptide domain that cross one or more of the lipid layers.

As used herein, the term "antibody" encompasses an immunoglobulin whether natural or partly or wholly synthetically produced, and fragments thereof. The term also covers any protein having a binding domain which is homologous to an immunoglobulin binding domain. These proteins can be derived from natural sources, or partly or wholly synthetically produced. "Antibody" further includes a polypeptide comprising a framework region from an immunoglobulin gene or fragments thereof that specifically binds and recognizes an antigen. Use of the term antibody is meant to include whole antibodies, polyclonal, monoclonal and recombinant antibodies, fragments thereof, and further includes single-chain antibodies, humanized antibodies; murine antibodies; chimeric, mouse-human, mouse-primate, primate-human monoclonal antibodies, anti-idiotype antibodies, antibody fragments, such as, e.g., scFv, (scFv)2, Fab, Fab', and F(ab')2, F(ab1)2, Fv, dAb, and Fd fragments, diabodies, and antibody-related polypeptides. Antibody includes bispecific antibodies and multispecific antibodies so long as they exhibit the desired biological activity or function.

The term "antigen binding fragment" used herein refers to fragments of an intact immunoglobulin, and any part of a polypeptide including antigen binding regions having the ability to specifically bind to the antigen. For example, the antigen binding fragment may be a F(ab')2 fragment, a Fab' fragment, a Fab fragment, a Fv fragment, or a scFv fragment, but is not limited thereto. A Fab fragment has one antigen binding site and contains the variable regions of a light chain and a heavy chain, the constant region of the light chain, and the first constant region CH1 of the heavy chain. A Fab' fragment differs from a Fab fragment in that the Fab' fragment additionally includes the hinge region of the heavy chain, including at least one cysteine residue at the C-terminal of the heavy chain CH1 region. The F(ab')2 fragment is produced whereby cysteine residues of the Fab' fragment are joined by a disulfide bond at the hinge region. A Fv fragment is the minimal antibody fragment having only heavy chain variable regions and light chain variable regions, and a recombinant technique for producing the Fv fragment is well known in the art. Two-chain Fv fragments may have a structure in which heavy chain variable regions are linked to light chain variable regions by a non-covalent bond. Single-chain Fv (scFv) fragments generally may have a dimer structure as in the two-chain Fv fragments in which heavy chain variable regions are covalently bound to light chain variable regions via a peptide linker or heavy and light chain variable regions are directly linked to each other at the C-terminal thereof. The antigen binding fragment may be obtained using a protease (for example, a whole antibody is digested with papain to obtain Fab fragments, and is digested with pepsin to obtain F(ab')2 fragments), and may be prepared by a genetic recombinant technique. A dAb fragment consists of a VH domain. Single-chain antibody molecules may comprise a polymer with a number of individual molecules, for example, dimmer, trimer or other polymers.

"Applicator" refers to any device used to connect to a subject. This includes, e.g., needles, cannulae, catheters, and tubing.

"Associated with" when used to describe the relationships among multiple compounds or molecules encompasses such as, e.g., any interaction between a receiver and a target or between a synthetic membrane-receiver complex and a target. This includes enzymatic interaction, ionic binding, covalent binding, non-covalent binding, hydrogen bonding, London forces, van der Waals forces, hydrophobic interaction, lipophilic interactions, magnetic interactions, electrostatic interactions, and the like.

"Associated with" when used to describe the relationships among a target, entity, compound, agent, or molecule and a disease, disorder, condition, symptom or phenotype is any link that may reasonably be made between them, including a causal link, or a statistical significant link, an empirically established link, a suggested link, whether or not causative of the disease, disorder, condition, symptom or phenotype.

"Autoimmune disorders" generally are conditions in which a subject's immune system attacks the body's own cells, causing tissue destruction. Autoimmune disorders may be diagnosed using blood tests, cerebrospinal fluid analysis, electromyogram (measures muscle function), and magnetic resonance imaging of the brain, but antibody testing in the blood, for self-antibodies (or auto-antibodies) is particularly useful. Usually, IgG class antibodies are associated with autoimmune diseases.

"Binding" describes an interaction among compounds or molecules, e.g., between a receiver and a target or between a synthetic membrane-receiver complex and a target, that comes about by covalent binding or non-covalent binding, including ionic binding, electrostatic interactions, hydrogen bonding, London forces, van der Waals forces, hydrophobic interaction, lipophilic interactions, and similar.

The "biological activity of a polypeptide" refers to any molecular activity or phenotype (such as, e.g., binding, signal transduction, catalytic, etc.) that is caused by the polypeptide, such as a receiver polypeptide.

As used herein, the term "biological sample" refers to any type of material of biological origin isolated from a subject, including, for example, DNA, RNA, lipids, carbohydrates, and protein. The term "biological sample" includes tissues, cells and biological fluids isolated from a subject. Biological samples include, e.g., but are not limited to, whole blood, plasma, serum, semen, saliva, tears, urine, fecal material, sweat, buccal, skin, cerebrospinal fluid, bone marrow, bile, hair, muscle biopsy, organ tissue or other material of biological origin known by those of ordinary skill in the art. Biological samples can be obtained from, e.g., biopsies of internal organs or from cancers. Biological samples can be obtained from subjects for diagnosis or research or can be obtained from healthy subjects, as controls or for basic research.

The "clearance rate" as used herein is calculated by measuring the amount or concentration of, e.g., target, receiver, target-receiver, or synthetic membrane-receiver complexes remaining in the circulatory system of a subject over time. For example, 1%, 2%, 3%, 4%, 5%, 10%, 15%, 20%, 30%, 40%, 50%, 60%, 70%, 80%, 90%, 95%, or 99% of target detected in a first sample may still be detected in a second sample that is taken 1 hour, 5 hours, 10 hours, 24 hours, 2 days, 3 days, 4 days, 5 days, 6 days, 7 days, 2 weeks, 3 weeks, 4 weeks, 2 months, 3 months, 4 months, 5 months, 6 months, 7 months, 8 months, 9 months, 10 months, 11 months, 12 months, 2 years, 3 years, 4 years, or 5 years later. The clearance rate may alternatively be expressed as: number of entities (e.g., target/receiver) per unit of time (e.g., per day). An increase in clearance rate is a rate greater than that exhibited in an untreated or healthy suitable control subject. A decrease in clearance rate is a rate less than that exhibited in an untreated or healthy suitable control subject. The increase or decrease may be 1%, 2%, 3%, 4%, 5%, 10%, 15%, 20%, 30%, 40%, 50%, 60%, 70%, 80%, 90%, 100%, 150%, 200%, 500%, 1000% or may be 1.1-fold, 1.2-fold, 1.3 fold, 1.4-fold, 1.5-fold, 2-fold, 3-fold, 4-fold, 5-fold, 10-fold, 20-fold, 50-fold, 100-fold, 500-fold, or 1000-fold. An increase in clearance rate of a target includes, e.g., a slow down in the accumulation of a target, a reaching of a new equilibrium of generation and degradation, and a reversal of an accumulation, e.g., a decrease in the number or concentration of the target in circulation.

"Cleaving" as used herein is a process that disrupts a bonding interaction present in a target, such as a polypeptide or nucleic e.g., to produce two or more entities that after cleaving can be separated from one another. The separation can involve, e.g., disrupt an ionic bond, a covalent bond, a polar covalent bond, a non-polar covalent bond, or a metallic bond. As cleaving applies to polypeptide targets, cleavage can involve breaking one or more peptide bonds. As cleaving applies to small molecule targets, cleavage can involve breaking one or more carbon or sulfide bonds. As cleaving applies to nucleotide sequences, cleavage can involve breaking one or more phosphodiester bonds. As cleaving applies to microbes such as bacteria, fungi, or viruses, cleavage can involve lysis of a membrane or capsid structure. Cleaving can be carried out by an enzyme, e.g., a catalytically active receiver polypeptide. Receivers can comprise, e.g., exonuclease, endonuclease, or protease activity.

The "circulatory system of a subject," as used herein, encompasses the space occupied by whole blood and optionally the lymphatic system in a human, inclusive of plasma and all circulating cells and molecules, and distributed throughout arteries, veins, capillaries, and lymphatic vessels of all tissues. The "circulatory concentration" is the concentration of a target, e.g., a cell, polypeptide (such as an antibody, pathogenic antigen, etc.), therapeutic agent, small molecule, metabolite or other entity, a receiver or a synthetic membrane-receiver complex in the space defined as the circulatory system. In certain embodiments, the concentration may be defined as the number of free (unbound) entities in a given volume. In other embodiments, the concentration may be defined as the total number of entities in a given volume.

The term "complementarity determining region (CDR)" used herein refers to an amino acid sequence found in the variable region of a heavy chain or a light chain of an immunoglobulin. The CDRs determine the specificity of an antibody and may provide a contact residue for binding to a specific epitope of an antigen. The heavy chain and the light chain may respectively include three CDRs (CDRH1, CDRH2, and CDRH3, and CDRL1, CDRL2, and CDRL3). Four framework regions, which have more highly conserved amino acid sequences than the CDRs, separate the CDR regions in the VH or VL.

A "complex" as used herein comprises an association of two or more entities. A complex may comprise one or more polypeptides, nucleic acid, lipids, carbohydrates, inorganic compounds, organic compounds, and the like. A complex can be functional (multiunit polypeptides) or non-functional (e.g., aggregates or precipitates) and may have beneficial or detrimental properties (e.g., immune complexes). Complexes may be naturally occurring or may be man-made or synthetic. Synthetic complexes include higher order entities, e.g., subcellular structures and cells if they comprise a synthetic compound or molecule. For example, a synthetic membrane-receiver complex includes a cell comprising a receiver.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. As used herein the term "conservative amino acid substitution" is illustrated by a substitution among amino acids within each of the following groups: (1) glycine, alanine, valine, leucine, and isoleucine, (2) phenylalanine, tyrosine, and tryptophan, (3) serine and threonine, (4) aspartate and glutamate, (5) glutamine and asparagine, and (6) lysine, arginine and histidine.

"Decrease," in the context of a symptom of a treated disease, disorder or condition, refers to a reduction in measurable or conveyable parameters associated with the disease or condition that manifest as symptoms. Examples of measurable parameters are a reduction in the subject's body temperature, a reduction in the concentration of targets in a sample taken from the subject, reduction in the intensity of inflammation or size of an inflamed area, reduction in the number of infiltrating cells, reduction in the number of episodes associated with the disease, disorder or condition, increase/decrease in organ size, weight gain/loss, etc. Examples of conveyable parameters are, e.g., the subject's own assessment of well being and quality of life. For example, for self-antibody mediated diseases, the decrease may be quantified as one, or a combination of, the following parameters: reduced inflammation, reduced flare-ups, reduced fatigue, reduced blood clotting, reduced swelling, increased energy, or increased hair growth, etc. The parameters that may be quantified are those appropriate for assessing the specific disease, disorder or condition that is being treated. Delay, in the context of symptoms of a treated disease, disorder or condition, refers to the significant extension of a manageable health condition that would otherwise become exacerbated, using a treatment.

"Degrading" is defined as the process in which a target is either directly, or indirectly, reduced, inactivated, decomposed, deconstructed, lysed, dissolved, broken, lessened, impaired, weakened, deteriorated, diminished, or partitioned.

"Different polypeptide origin" refers to the organism or species from which a genetic sequence encoding the polypeptide, the polypeptide, or portion thereof, is sourced. In certain embodiments, a fusion comprising polypeptides of different polypeptide origin may include a receiver polypeptide that is encoded by the genetic sequence for human adenosine deaminase and the genetic sequence for phenylalanine hydroxylase from *chromobacterium violaceum*.

A "domain" is a part of a polypeptide, such as a receiver polypeptide that is generally having a 3-dimensional structure and may exhibit a distinct activity, function, such as, e.g., a catalytic, an enzymatic, a structural role, or a binding function.

Duration refers to the period of time that a portion of the synthetic membrane-receiver polypeptide complex exists in a specific tissue or an organism as a whole. This applies to 0.1% 1%, 5%, 10%, 20%, 30%, 40%, 50%, 60%, 70%, 80%, 90%, or 100% of the initial dose or concentration of the synthetic membrane-receiver polypeptide complex. In some embodiments, the synthetic membrane-receiver complex is formulated for long-term duration. In some embodiments, the synthetic membrane-receiver complex is formulated for short-term duration.

By an "enriched population of cells" it is meant a population of cells that is substantially comprised of a particular cell of interest. In an enriched population, 50% or more of the cells in the population are the cells of interest, e.g., 50%, 60%, 70%, usually 80%, 85%, 90%, more usually 92%, 95%, 96%, 97%, 98%, or 99%, sometimes as much as 100% of the cells in the population. The separation of cells of interest from a complex mixture or heterogeneous culture of cells may be performed by any convenient means known in the art, for example, by affinity separation techniques such as magnetic separation using magnetic beads coated with an affinity reagent, affinity chromatography, or "panning" with an affinity reagent attached to a solid matrix, e.g., plate, or other convenient technique. Other techniques providing accurate separation include fluorescence activated cell sorters, which can have varying degrees of sophistication, such as multiple color channels, low angle and obtuse light scattering detecting channels, impedance channels, etc. The cells may be selected against dead cells by employing dyes associated with dead cells. Any technique may be employed which is not unduly detrimental to the viability of the desired cells.

"Enucleation" is the rendering of a cell to a non-replicative state, either through inactivation or removal of the nucleus.

An "epitope" includes any segment on an antigen to which an antibody or other ligand or binding molecule binds. An epitope may consist of chemically active surface groupings of molecules such as amino acids or sugar side chains and usually have specific three dimensional structural characteristics, as well as specific charge characteristics. In some embodiments, receivers comprise specific epitopes. In some embodiments, targets comprise specific epitopes.

"Erythroid cells" as used herein, include nucleated red blood cells, red blood cell precursors, and enucleated red blood cells and those listed in Table 2. For example, the erythroid cells are a cord blood stem cell, a CD34+ cell, a hematopoietic stem cell (HSC), a spleen colony forming (CFU-S) cell, a common myeloid progenitor (CMP) cell, a blastocyte colony-forming cell, a burst forming unit-erythroid (BFU-E), a megakaryocyte-erythroid progenitor (MEP) cell, an erythroid colony-forming unit (CFU-E), a reticulocyte, an erythrocyte, an induced pluripotent stem cell (iPSC), a mesenchymal stem cell (MSC), a polychromatic normoblast, an orthochromatic normoblast, or a combination thereof. In some embodiments, the erythroid cells are immortal or immortalized cells. For example, immortalized erythroblast cells can be generated by retroviral transduction of CD34+ hematopoietic progenitor cells to express Oct4, Sox2, Klf4, cMyc, and suppress TP53 (e.g., as described in Huang et al., Mol Ther 2013, epub ahead of print September 3). In addition, the cells may be intended for autologous use or provide a source for allogeneic transfusion. Erythroid cells can be contacted with a receiver to generate a synthetic membrane-receiver complex. Erythroid cells comprising a receiver are one example of a synthetic membrane-receiver complex. In some embodiments, erythroid cells arecultured. In some embodiments, erythroid progenitor cells are contacted with a receiver to generate a synthetic membrane-receiver complex.

As used herein, the term "excipient" refers to an inert substance added to a pharmaceutical composition to further facilitate administration of a compound. Examples of excipients include, but are not limited to, calcium carbonate, calcium phosphate, various sugars and types of starch, cellulose derivatives, gelatin, vegetable oils, anti-coagulants, and polyethylene glycols.

The receiver, including a receiver polypeptide is "exogenous" or "heterologous", thus it may either not naturally exist, such as a fusion or chimera comprising domains of different polypeptide or species origin, it may not naturally occur in a naturally occurring cell, such as an unmodified erythrocyte or platelet, it may not function in the same way as a naturally occurring polypeptide would, or it may not naturally occur in the quantity that the receiver polypeptide occurs, e.g., in embodiments in which the synthetic membrane-receiver polypeptide complex is a cell-derived polypeptide receiver that is overexpressed as compared to the expression of a naturally occurring polypeptide in an unmodified cell. In some embodiments, the polypeptide receiver is expressed from an exogenous nucleic acid. In some embodiments, the receiver is isolated from a source and loaded into or conjugated to a synthetic membrane-receiver complex.

The term "exogenous" when used in the context of nucleic acid includes a transgene and recombinant nucleic acids.

As used herein, the term "expression" refers to the process to produce a polypeptide, such as a receiver polypeptide including transcription and translation. Expression may be, e.g., increased by a number of approaches, including: increasing the number of genes encoding the polypeptide, increasing the transcription of the gene (such as by placing the gene under the control of a constitutive promoter), increasing the translation of the gene, knocking out of a competitive gene, or a combination of these and/or other approaches.

A synthetic membrane-receiver complex that is "formulated for long-term duration" is, in some embodiments, one that is part of a population of synthetic membrane-receiver complexes wherein a substantial fraction of the population resides in the circulatory system for more than 10 days, e.g., 15, 21, 25, 35, 45, 50, 60, 90, 100, 110, or 120 days. In some embodiments, the population may have an increased half-life, e.g., 1.5×, 2×, 5×, 10×, 20×, 50×, 100× more time in circulation, when formulated for long-term duration compared to the duration exhibited by a population of unformulated complexes. In some embodiments, an entity such as a receiver may have an increased half-life, e.g., 1.5×, 2×, 5×, 10×, 20×, 50×, 100× more time in circulation, when formulated for long-term duration compared to the duration that entity would exhibit in an unmodified state.

A synthetic membrane-receiver complex that is "formulated for short-term duration" is, in some embodiments, one that is part of a population of synthetic membrane-receiver complexes wherein a substantial fraction of the population resides in the circulatory system for less than 10 days, e.g., 9, 8, 7, 6, 5, 4, 3, 2 days, 1 day, 12 hours, or 6 hours. In some embodiments, the population may have a decreased half-life, e.g., 5%, 10%, 20%, 30%, 40%, 50%, 60%, 70%, 80%, 90%, 99% less time in circulation, when formulated for short-term duration compared to the duration exhibited by a population of unformulated complexes. In some embodiments, an entity such as a receiver may have a reduced half-life, e.g., 5%, 10%, 20%, 30%, 40%, 50%, 60%, 70%, 80%, 90%, 99% less time in circulation, when formulated for short-term duration compared to the duration that entity would exhibit in an unmodified state.

"Formulated for residency in the circulatory system", as used herein, describes one or more modifications to an entity, such as a synthetic membrane-receiver complex formulated for administration to the circulatory system of a subject that substantially decrease recognition, modification, degradation, and/or destruction of the entity by components of the circulatory system (e.g., circulating immune cells, antibodies, enzymatic activities) thereby increasing the half-life of the entity when compared to an unmodified entity.

A "functional" receiver or synthetic membrane-receiver complex refers to a synthetic membrane-receiver complex or a receiver that exhibits a desired or specified activity or characteristic, including enzymatic, catalytic or metabolic activity, structural integrity, immunogenic complementarity, target binding, and correct localization or is capable of promoting a desired or specified effect or phenotype.

"Fusion or chimera" is defined as a polypeptide sequence, or corresponding encoding nucleotide sequence, that is derived from the combination of two or more sequences that are not found together in nature. This may be a combination of separate sequences derived from separate genes within the same genome, or from heterologous genes derived from distinctly different species' genomes.

"Genetic material" refers to nucleic acid molecules having nucleotide sequences of adenosine, thymine, uracil, cytosine, and guanine capable of encoding a gene.

The term "heavy chain" used herein is understood to include a full-length heavy chain including a variable region (VH) having amino acid sequences that determine specificity for antigens and a constant region having three constant domains (CH1, CH2, and CH3), and fragments thereof. In addition, the term "light chain" used herein is understood to include a full-length light chain including a variable region (VL) having amino acid sequences that determine specificity for antigens and a constant region (CL), and fragments thereof.

The term "homolog" indicates polypeptides, including receiver polypeptide that have the same or conserved residues at a corresponding position in their primary, secondary or tertiary structure. Functional homologs include receivers and other polypeptides that exhibit similar function and/or specificity (e.g., for a particular target).

A naturally occurring intact antibody, or immunoglobulin, includes four polypeptides: two full-length light chains and two full-length heavy chains, in which each light chain is linked to a heavy chain by disulfide bonds. Each heavy chain has a constant region and a variable region. Similarly, each light chain has a constant region and a variable region. There are five heavy chain classes (isotypes): gamma ($\gamma$), mu ($\mu$), alpha ($\alpha$), delta ($\delta$), or epsilon ($\epsilon$), and additionally several subclasses gamma 1 ($\gamma$1), gamma 2 ($\gamma$2), gamma 3 ($\gamma$3), gamma 4 ($\gamma$4), alpha 1 ($\alpha$1), and alpha 2 ($\alpha$2). The light chain constant region can be either kappa ($\kappa$) or lambda ($\lambda$) type. The variable regions differ in sequence among antibodies and are used in the binding and specificity of a given antibody to its particular antigen.

As used herein, the term "increase," "enhance," "stimulate," and/or "induce" (and like terms) generally refers to the act of improving or increasing, either directly or indirectly, a concentration, level, function, activity, or behavior relative to the natural, expected, or average, or relative to a control condition.

As used herein, the term "inhibit," "suppress," "decrease," "interfere," and/or "reduce" (and like terms) generally refers to the act of reducing, either directly or indirectly, a concentration, level, function, activity, or behavior relative to the natural, expected, or average, or relative to a control condition.

A "library" as used herein includes a collection of nucleic acid molecules (e.g., DNA, RNA) having diverse nucleic acid sequences, a genetically diverse collection of clones, a collection of diverse polypeptides, a diverse collection of cells, etc.

As used herein, "a mammalian subject" includes all mammals, including without limitation, humans, domestic animals (e.g., dogs, cats and the like), farm animals (e.g., cows, sheep, pigs, horses and the like) and laboratory animals (e.g., monkey, rats, mice, rabbits, guinea pigs and the like). The terms "individual," "subject," "host," and "patient," are used interchangeably herein and refer to any mammalian subject for whom diagnosis, treatment, or therapy is desired, particularly humans. The methods described herein are applicable to both human therapy and veterinary applications. In some embodiments, the subject is a mammal, and in other embodiments the subject is a human.

"Medical device" refers to any device, apparatus or machine used to deliver a dose of a synthetic membrane-receiver complex and/or a therapeutic agent. This includes containers, bottles, vials, syringes, bags, cartridges, cassettes, magazines, cylinders, or canisters.

"Medical kit" refers to a packaged unit that includes a medical device, applicator, appropriate dosage of synthetic membrane-receiver complex optionally including a therapeutic agent, and relevant labeling and instructions.

As used herein, the term "modulate," "modulating", "modify," and/or "modulator" generally refers to the ability to alter, by increase or decrease, e.g., directly or indirectly promoting/stimulating/upregulating or interfering with/inhibiting/downregulating a specific concentration, level, expression, function or behavior, such as, e.g., to act as an antagonist or agonist. In some instances a modulator may increase and/or decrease a certain concentration, level, activity or function relative to a control, or relative to the average level of activity that would generally be expected or relative to a control level of activity.

"Membrane" as used herein is a boundary layer that separates an interior space from an exterior space comprising one or more biological compounds, typically lipids, and optionally polypeptides. Membranes can be lipid bilayers. In certain embodiments, membranes comprise one or more of phosphatidylcholine, sphingomyelin, lysophosphatidylcholine, phosphatidylethanolamine, phosphatidylserine, phosphatidylinositol, or phosphatidic acid. In some embodiments, membranes comprise one or more polypeptides such as ankyrin and coenzyme Q10. Included in the definition of membrane are cell membranes comprising, e.g., a phospholipid bilayer and cell membrane associated polypeptides. The synthetic membrane-receiver complex comprises a membrane as defined herein.

The phrase "nucleic acid molecule" refers to a single or double-stranded polymer of deoxyribonucleotide or ribonucleotide bases. It includes chromosomal DNA and self-replicating plasmids, vectors, mRNA, tRNA, siRNA, etc. which may be recombinant and from which exogenous polypeptides may be expressed when the nucleic acid is introduced into a cell.

Orthologs are defined as genes in different species that evolved from a common ancestral gene by speciation.

The term "pharmaceutically-acceptable" and grammatical variations thereof, refers to compositions, carriers, diluents and reagents capable of administration to or upon a subject without the production of undesirable physiological effects to a degree that would prohibit administration of the composition. For example, "pharmaceutically-acceptable excipient" includes an excipient that is useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous.

As used herein, the term "pharmaceutically acceptable carrier" includes any of the standard pharmaceutical carriers, such as a phosphate buffered saline solution, water, emulsions such as an oil/water or water/oil, and various types of wetting agents. The term also encompasses any of the agents approved by a regulatory agency of the US Federal government or listed in the US Pharmacopeia for use in animals, including humans, as well as any carrier or diluent that does not cause significant irritation to a subject and does not abrogate the biological activity and properties of the administered compound.

Some agents may be administered as "pharmaceutically acceptable salt", e.g., prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like. Salts can also be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines. Any ordinary skilled person in the art will know how to select a proper pharmaceutically acceptable carrier, a pharmaceutically acceptable salt thereof for implementing this invention without undue experimentation.

As used herein, the term "pharmaceutical composition" refers to one or more of the compounds described herein, such as, e.g., a synthetic membrane-receiver polypeptide complex mixed or intermingled with, or suspended in one or more other chemical components, such as physiologically acceptable carriers and excipients. One purpose of a pharmaceutical composition is to facilitate administration of a compound to a subject.

Certain embodiments provide various polypeptide molecules having sequences associated with a desired function or activity, such as receiver polypeptides. A polypeptide is a term that refers to a chain of amino acid residues, regardless of post-translational modification (e.g., phosphorylation or glycosylation) and/or complexation with additional polypeptides, synthesis into multisubunit complexes, with nucleic acids and/or carbohydrates, or other molecules. Proteoglycans therefore also are referred to herein as polypeptides. In certain embodiments, the synthetic membrane-receiver complex comprises a polypeptide receiver and is referred to a "synthetic membrane-receiver polypeptide complex." In certain embodiments, the synthetic membrane-receiver complex comprises one or more non-receiver polypeptides that are optionally membrane-associated and that exhibit catalytic and/or metabolic activity independent of the receiver. For example, the non-receiver polypeptides may have catalytic activity for an organic compound including a metabolite. In certain embodiments, the synthetic membrane-receiver complex comprises a sufficient number of non-receiver polypeptides (and optionally non-protein co-factors) to support a metabolic pathway.

The term "pharmaceutically active agent" or "pharmaceutical agent" is defined as any compound, e.g., a small molecule drug, or a biologic (e.g., a polypeptide drug or a nucleic acid drug) that when administered to a subject has a measurable or conveyable effect on the subject, e.g., it alleviates or decreases a symptom of a disease, disorder or condition. In some embodiments, the pharmaceutical agent may be administered prior to, in combination with, or following the delivery of a synthetic membrane-receiver polypeptide complex. In some embodiments, the pharmaceutically active agent exerts a synergistic treatment effect with the synthetic membrane-receiver polypeptide complex. In some embodiments, the pharmaceutically active agents exerts an additive treatment effect with the synthetic membrane-receiver polypeptide complex.

A "promoter" is defined as an array of nucleic acid control sequences that direct transcription of an operably linked nucleic acid. Promoters include necessary nucleic acid sequences near the start site of transcription. A promoter also optionally includes distal enhancer or repressor elements. A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

A "receiver," as used herein, is an entity capable of interacting with a target, e.g., to associate with or bind to a target. A receiver can comprise or can consist essentially of a polypeptide. In some embodiments, the receiver comprises a polypeptide, a carbohydrate, a nucleic acid, a lipid, a small molecule, or a combination thereof. In embodiments in which a receiver is a naturally occurring compound or molecule, the receiver is "synthetic" in the sense that it is an exogenous or heterologous compound or molecule with regard to its presence in the synthetic membrane-receiver complex. In other embodiments the receiver is "synthetic" in the sense that it is a man-made compound or molecule, such as a fusion or chimera, a non-naturally occurring polypeptide, carbohydrate, nucleic acid, lipid, or combination thereof, or a man-made small molecule or other therapeutic agent. For example, the receiver may comprise a fusion or chimera comprising one or more of an S domain, an A domain and a U domain. The S domain is a surface domain exposed to the environment around the synthetic membrane-receiver complex, such as the circulatory system of a subject. The A domain is an anchor domain that attaches the S domain to the synthetic membrane of the synthetic membrane-receiver polypeptide complex. The U domain faces the unexposed side of or is located within the synthetic membrane-receiver complex, i.e. the side that is not exposed to the external environment of the circulatory system of a subject. Irrespective of any domains, a receiver may be located on the surface of the synthetic membrane-receiver polypeptide complex or may be located within the complex. The receiver may be associated with the membrane of the synthetic membrane-receiver complex, e.g., the receiver is anchored in, conjugated to or otherwise bound to the membrane. In some embodiments, the receiver may be conjugated to the membrane of the synthetic membrane-receiver complex by chemical or enzymatic conjugation. In other embodiments, the receiver is not conjugated to the membrane. In some embodiments, the receiver is not associated with the membrane of the synthetic membrane-receiver complex and is located within the membrane-encapsulated volume of the complex. In some embodiments, a receiver located within the synthetic membrane-receiver complex does not substantially diffuse out of the complex and/or may not permeate the membrane. In other embodiments, the receiver may substantially diffuse out of the complex and/or may permeate the membrane. In some embodiments, the receiver is loaded, e.g., introduced into or put onto the synthetic membrane-receiver complex. A receiver that is loaded is not biologically synthesized by the synthetic membrane-receiver complex. A receiver suitable for loading may be e.g., produced in a cell-based expression system, isolated from a biological sample, or chemically or enzymatically synthesized, and then loaded into or onto the synthetic membrane-receiver complex. In some embodiments, the receiver may be further modified by the synthetic membrane-receiver complex after loading. In other embodiments, the receiver is not modified after loading. In some embodiments, the receiver polypeptide is not loaded onto or into the complex. In some embodiments, the receiver is made, e.g., biologically synthesized by the synthetic membrane-receiver complex. Typically a receiver polypeptide is expressed by the synthetic membrane-receiver complex from an exogenous nucleic acid molecule (e.g., a DNA or mRNA) that was introduced into the complex. The receiver may bind to and/or sequester a target. Alternatively or in addition the receiver may exhibit a catalytic activity toward the target, e.g., the receiver may convert or modify the target, or may degrade the target. A product may then optionally be released from the receiver.

"Residency" of a synthetic membrane-receiver complex refers to the period of time it spends in a physiological location. The specific location of the synthetic membrane-receiver complex may change during its lifetime and "residency" applies to the period of time spent in various environments, including vascular circulation, peripheral tissues, capillaries, digestive system, pulmonary system, nasal tissues, epidermal surface, and interstitial tissue. In specific embodiments, the synthetic membrane-receiver complex resides in the circulatory system of a subject.

"Replicating nucleic acid" refers to deoxyribonucleic acid (DNA) that is capable of being copied by enzymes dedicated to the increasing the number of copies of the DNA. Usually, DNA replication leads to the production of two identical replicas from one original DNA molecule. DNA replication comprises the incorporation of nucleotides into a growing DNA strand by DNA polymerase matched to the template strand one at a time via the creation of phosphodiester bonds.

"Sequestering" is defined as cloistering, occluding, separating, segregating, hiding, insulating, or isolating of a target and preventing it from freely interacting with its environment.

"Specifically binding" or "specifically interacting", as used herein, describes any interaction between two entities (e.g., a target with a receiver, such as an antibody with an antigen, a receptor with a ligand, an enzyme with a substrate, biotin with avidin, etc.) that is saturable, often reversible and so competitive, as these terms are understood by those of ordinary skill in the chemical and biochemical arts. e.g., Specific binding involving biological molecules such as, e.g., proteins, peptides and nucleic acid occurs when one member of the binding pair has a site with a shape and distribution of charged, polar, or hydrophobic moieties such that the interaction of the cognate ligand with that site is characterized by favorable energetics (i.e., a negative free energy of binding). The specificity of the interaction may be measured or expressed as a binding constant (Kd). The Kd may range from a mM range to a pM range, including μM ranges and nM ranges. Typical Kd values are below about $10^{-6}$M, below about $10^{-7}$M, below about $10^{-8}$M, and in some embodiments below about $10^{-9}$ M.

As used herein, the term "substantially" or "substantial" refers, e.g., to the presence, level, or concentration of an entity in a particular space, the effect of one entity on another entity, or the effect of a treatment. For example, an activity, level or concentration of an entity is substantially increased if the increase is 2-fold, 3-fold, 4-fold, 5-fold, 10-fold, 50-fold, 100-fold, or 1000-fold relative to a baseline. An activity, level or concentration of an entity is also substantially increased if the increase is 5%, 10%, 20%, 30%, 40%, 50%, 60%, 70%, 80%, 90%, 100%, 200%, or 500% relative to a baseline. An entity may be substantially present in a particular space if it can be detected by methods known in the art. An entity may not be substantially present in a particular space if it is present at levels below the limit of detection for assays and methods known in the art. In some embodiments, an entity may not be substantially present in a particular space if it is barely detectable but only in non-functional quantities or minute quantities that do not cause or change a phenotype. In other embodiments, an entity may not be substantially present in a particular population if it is present and can be detected only in a small number of constituents making up the population, e.g., less than 10%, 9%, 8%, 7%, 6%, 5%, 4%, 3% 2% or less than 1%, 0.5%, 0.1% of constituents of the population. For example, an exogenous nucleic acid may not be retained upon enucleation, the cell is rendered non-replicative, and the enucleated cell is incapable of continued expression of the receiver polypeptide encoded by the exogenous nucleic acid. The loss of the ability of the cell to continue to significantly translate the exogenous polypeptide "effectively terminates" protein expression. In certain embodiments, the synthetic membrane-receiver complex is substantially incapable of self-replication, e.g., the replication of nucleic acids. For example, the synthetic membrane-receiver polypeptide complex does not substantially incorporate a nucleoside if contacted with labeled nucleoside, such as thymidine, in an incorporation assay. In some embodiments, the synthetic membrane-receiver polypeptide complex does not contain a substantial amount of self-replicating nucleic acids. The term "substantial identity" of polynucleotide or nucleic acid sequences means that a polynucleotide comprises a sequence that has at least 25% sequence identity. Alternatively, percent identity can be any integer from 25% to 100%. More preferred embodiments include at least: 25%, 30%, 35%, 40%, 45%, 50%, 55%, 60%, 65%, 70%, 75%, 80%, 85%, 90%, 95%, or 99% compared to a reference sequence using the programs described herein; preferably BLAST using standard parameters.

"Synthetic" refers to a compound or molecule that is either man-made and non-naturally occurring, or if it is naturally occurring is placed in a context or location that it would not naturally exist, or if it naturally exists in the context or location is in a state of purity, or is present in an amount, concentration or number that it would not naturally be present in the context or location. Synthetic entities can be isolated or purified compounds that are optionally chemically or enzymatically modified from their natural state, exogenous nucleic acids, exogenous (heterologous) receivers, and the like. The presence of a synthetic compound or molecule, as defined herein, in any entity renders the entire entity "synthetic". For example, a cell comprising a receiver is a synthetic cell.

A "target," as used herein, is an entity capable of interacting with a receiver, e.g., to associate with or bind to a receiver. A "target" includes, but is not limited to a polypeptide (e.g., an antibody or antibody-related polypeptide, a complement constituent, an amyloid protein, a pathogen, a toxin, a prion), a molecule (e.g., a metabolite, a steroid, a hormone, a carbohydrate; an oligosaccharide; a chemical; a polysaccharide, a DNA; an RNA; a lipid, an amino acid, an element, a toxin or pathogen), a complex (e.g., an immune complex), or a cell (e.g., a cancer cell, a macrophage, a bacterium, a fungus, a virus, or a parasite). A target is intended to be detected, diagnosed, impaired, destroyed or altered (e.g., functionally complemented) by the methods provided herein. The specific target may occur free or is associated with other entities in the circulatory system of a subject.

A "target self-antibody," as used herein, is a self-antibody associated with an autoimmune disease. Such self-antibodies may be detected and analyzed using antibody binding tests involving contacting the subject's antibodies to samples of the subject's own tissue, usually thyroid, stomach, liver, and kidney tissue. Antibodies binding to the "self" tissue (comprising self-antigens) indicate an autoimmune disorder.

"Transgene" or "exogenous nucleic acid" refers to a foreign or native nucleotide sequence that is introduced into a synthetic membrane-receiver complex. Transgene and exogenous nucleic acid are used interchangeably herein and encompass recombinant nucleic acids.

As used herein, "treat," "treating," and/or "treatment" are an approach for obtaining beneficial or desired clinical results, pharmacologic and/or physiologic effect, e.g., alleviation of the symptoms, preventing or eliminating said symptoms, and refer to both therapeutic treatment and prophylactic or preventative treatment of the specific disease, disorder or condition. Beneficial or desired clinical results, pharmacologic and/or physiologic effect include, but are not limited to, preventing the disease, disorder or condition from occurring in a subject that may be predisposed to the disease, disorder or condition but does not yet experience or exhibit symptoms of the disease (prophylactic treatment), alleviation of symptoms of the disease, disorder or condition, diminishment of extent of the disease, disorder or condition, stabilization (i.e., not worsening) of the disease, disorder or condition, preventing spread of the disease, disorder or condition, delaying or slowing of the disease, disorder or condition progression, amelioration or palliation of the disease, disorder or condition, and combinations thereof, as well as prolonging survival as compared to expected survival if not receiving treatment.

A "therapeutic agent" or "therapeutic molecule" includes a compound or molecule that, when present in an effective amount, produces a desired therapeutic effect, pharmacologic and/or physiologic effect on a subject in need thereof.

The term "therapeutically effective amount" or "effective amount" is an amount of an agent being administered to a subject sufficient to effect beneficial or desired clinical results, pharmacologic and/or physiologic effects. An effective amount can be administered in one or more administrations. An effective amount is typically sufficient to palliate, ameliorate, stabilize, reverse, slow or delay the progression of the disease state. The effective amount thus refers to a quantity of an agent or frequency of administration of a specific quantity of an agent sufficient to reasonably achieve a desired therapeutic and/or prophylactic effect. For example, it may include an amount that results in the prevention of, treatment of, or a decrease in, the symptoms associated with a disease or condition that is being treated, e.g., the diseases or medical conditions associated with a target polypeptide. The amount of a therapeutic composition administered to the subject will depend on the type and severity of the disease and on the characteristics of the individual, such as general health, pathologic conditions, diets, age, sex, body weight and tolerance to drugs. It will also depend on the degree, severity and type of disease. Further, the effective amount will depend on the methods of formulation and administration used, e.g., administration time, administration route, excretion speed, and reaction sensitivity. The skilled artisan will be able to determine appropriate dosages depending on these and other factors. The compositions can also be administered in combination with one or more additional therapeutic compounds. A desirable dosage of the pharmaceutical composition may be in the range of about 0.001 to 100 mg/kg for an adult. In one example, an intravenous administration is initiated at a dose which is minimally effective, and the dose is increased over a pre-selected time course until a positive effect is observed. Subsequently, incremental increases in dosage are made limiting to levels that produce a corresponding increase in effect while taking into account any adverse affects that may appear. Non-limited examples of suitable dosages can range, for example, from $1\times10^{10}$ to $1\times10^{14}$, from $1\times10^{11}$ to $1\times10^{13}$, or from $5\times10^{11}$ to $5\times10^{12}$ synthetic membrane-receiver polypeptide complexes of the present invention. Specific examples include about $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, $1\times10^{12}$, or more synthetic membrane-receiver polypeptide complexes of the present invention. Each dose of synthetic membrane-receiver polypeptide complexes can be administered at intervals such as once daily, once weekly, twice weekly, once monthly, or twice monthly.

"Unbound" refers to the state of a target with which the receiver is capable of interacting. An unbound target is not associated with another entity or a receiver. An unbound receiver is not associated with another entity or a target. A target is considered "bound" once it is associated with the receiver or another entity. Unbound targets include soluble forms of the target in circulation. Bound targets include targets that are embedded, associated with, linked to, or otherwise interacting with entities in circulation or peripheral tissue. Entities with which a target may interact include circulating cells, peripheral endothelial tissue, immune complexes, glycolipids, microbes, immunoglobulins, serum albumin, clotting factors, lipoproteins, and electrolytes.

A "variant" is a polypeptide which differs from the original protein by one or more amino acid substitutions, deletions, insertions, or other modifications. These modifications do not significantly change the biological activity of the original protein. In many cases, a variant retains at least 10%, 20%, 30%, 40%, 50%, 60%, 70%, 80%, 90%, 95%, or 100% of the biological activity of original protein. The biological activity of a variant can also be higher than that of the original protein. A variant can be naturally-occurring, such as by allelic variation or polymorphism, or be deliberately engineered.

The amino acid sequence of a variant is substantially identical to that of the original protein. In many embodiments, a variant shares at least 50%, 60%, 70%, 80%, 85%, 90%, 95%, 99%, or more global sequence identity or similarity with the original protein. Sequence identity or similarity can be determined using various methods known in the art, such as Basic Local Alignment Tool (BLAST), dot matrix analysis, or the dynamic programming method. In one example, the sequence identity or similarity is determined by using the Genetics Computer Group (GCG) programs GAP (Needleman-Wunsch algorithm). The amino acid sequences of a variant and the original protein can be substantially identical in one or more regions, but divergent in other regions.

As used herein, the term "vector" is a nucleic acid molecule, preferably self-replicating, which transfers and/or replicates an inserted nucleic acid molecule, such as a transgene or exogenous nucleic acid into and/or between host cells. It includes a plasmid or viral chromosome into whose genome a fragment of recombinant DNA is inserted and used to introduce recombinant DNA, or a transgene, into a synthetic membrane-receiver polypeptide complex.

The "volume of distribution" (VD) is a pharmacological, theoretical volume that the total amount of administered drug would have to occupy (if it were uniformly distributed), to provide the same concentration as it is in blood plasma. A VD greater than the blood plasma indicates that an agent is distributed in tissue in the rest of the body. The VD is influenced by solubility, charge, size, etc. Generally, non-polar agents with high lipid solubility, agents with low rates of ionization or low plasma binding capabilities have higher volumes of distribution than agents that are more polar, more highly ionized or exhibit high plasma binding. The volume of distribution is given by the following equation: $V_D$=total amount of drug in the body/drug blood plasma concentration. The units for Volume of Distribution are typically reported in (nil or liter)/kg body weight. A volume of distribution "equal to plasma volume" is relative to the volume of the circulatory system exclusive of circulating cells.

Synthetic Membrane-Receiver Complexes

Provided herein are synthetic membrane-receiver complexes, populations, pharmaceutical compositions, and dosage forms thereof, as well as medical devices and kits comprising a formulation of the synthetic membrane-receiver complexes.

The synthetic membrane-receiver complexes described herein comprise a receiver (e.g., a polypeptide) that is capable of interacting with a target and further comprise a membrane comprising a polypeptide that is not the receiver. The synthetic membrane-receiver complex has catalytic activity independent of the receiver. Optionally, the synthetic membrane-receiver complexes comprise a payload, for example a therapeutic agent.

In some embodiments, synthetic membrane-receiver complex are generated using cells as a source material. In certain embodiments, generating a synthetic membrane-receiver complex comprises the step of contacting an erythroid cell and platelets with a receiver. In certain embodiments, generating a synthetic membrane-receiver complex comprises the step of contacting a cell derived from a hematopoietic stell cell with a receiver.

In certain embodiments, synthetic membrane-receiver complexes are administered, e.g., intravenously to the circulatory system of a mammalian subject, such as a human. In some embodiments, the membrane-receiver complexes provide a natural barrier between a receiver and optionally a payload (e.g., therapeutic agent) and the immune system. In some embodiments, the synthetic membrane-receiver complexes are capable of residing in the circulatory system of a subject for an extended period of time allowing delivery of a therapeutic effect for a longer period of time than what can be achieved by delivery through other methods currently used.

Synthetic membrane-receiver complexes may interact with a target in the circulatory system of the subject. In some embodiments, the concentration of an unbound target or total target in the circulatory system of the subject is reduced subsequent to its interaction with the receiver exhibited in or on the synthetic membrane-receiver complex. In certain embodiments, the presence or elevated concentration of a target in circulation is associated with a disease, disorder or condition and reducing the concentration of the target leads to a reduction in disease burden, may alleviate a symptom of the disease or has some other treatment effect. In some embodiments, a reduction in the concentration of the target prevents the onset of a disease, disorder or condition.

Biodistribution is a substantial hurdle in drug delivery and efficacy. After a drug enters the systemic circulation, it is distributed to the body's tissues. Distribution is generally uneven because of differences in blood perfusion, tissue binding (e.g., because of lipid content), regional pH, and permeability of cell membranes. The entry rate of a drug into a tissue depends on the rate of blood flow to the tissue, tissue mass, and partition characteristics between blood and tissue. Distribution equilibrium (when entry and exit rates are the same) between blood and tissue is reached more rapidly in richly vascularized areas, unless diffusion across cell membranes is the rate-limiting step. After equilibrium, drug concentrations in tissues and in extracellular fluids are reflected by the plasma concentration. Metabolism and excretion occur simultaneously with distribution, making the process dynamic and complex.

The synthetic membrane-receiver complexes when formulated in a pharmaceutical compositions suitable for administration into the circulatory system of a subject can have a volume of distribution equal to the plasma volume of the subject. Advantages of the volume of distribution characteristic of the synthetic membrane-receiver complexes include that the biodistribution of the receiver when administered as a synthetic membrane-receiver complex into the circulatory system of a subject may be accurately predicted and/or that potential adverse extravascular effects of the receiver (e.g., an inflammatory response, an immune response, toxicity, etc.) are substantially reduced.

Distribution of a therapeutic composition out of the bloodstream and into surrounding tissue increases the apparent volume of distribution to be greater than the plasma volume of the subject. Therapeutic compositions that exit the bloodstream and interact with surrounding tissue, e.g., adipose tissue or muscle, may interact with those tissues in unpredictable ways and trigger adverse events. A therapeutic composition, such as a composition comprising a synthetic membrane-receiver complex described herein, whose volume of distribution does not substantially exceed the plasma volume of the subject typically has a safety profile that is superior to a therapeutic composition with a large volume of distribution. Further, the amount of a therapeutic composition that must be loaded to be effective (the effective amount) is in part dependent on the bioavailability of the therapeutic composition. Bioavailability is related to the composition's profile and rate of distribution into extravascular tissues, and thus its volume of distribution. By maintaining a precise and predictable volume of distribution, typically a therapeutic composition, such as a composition comprising a synthetic membrane-receiver complex described herein, will have a more precise and predictable dose-effect relationship than a therapeutic composition with a less precise and predictable volume of distribution.

For example, the drug distribution rate for interstitial fluids of most tissues is determined primarily by perfusion. For poorly perfused tissues (e.g., muscle, fat), distribution is very slow, especially if the tissue has a high affinity for the drug. Endothelial cells lining the vessel wall are connected by adherens, tight and gap junctions. These junctional complexes are related to those found at epithelial junctions but with notable changes in terms of specific molecules and organization. Endothelial junctional proteins play important roles in tissue integrity but also in vascular permeability, leukocyte extravasation and angiogenesis. Small molecules, protein therapeutics, and viruses measure 1-30 nm and are capable of diffusing far beyond the vasculature based on lipophilicity, ability to bind plasma proteins, and charge. A drug that is confined to the vasculature has a lesser volume of tissue to occupy and thus may remain at an effective, therapeutic concentration. In addition, the drug is unable to interact with peripheral tissues and potential off-target toxicity effects are limited. Larger circulatory agents (e.g., between 1 micron and 20 microns) do not pass through endothelial tight junctions which are less than 100 nm in width and endothelial cells are incapable of facilitating the transcytosis of agents of that size. In some embodiments, the synthetic membrane-receiver complexes described herein measure between 1 micon and 20 microns. The vascular properties of these agents limit their diffusive capabilities to the bloodstream and concentrate the therapeutic effect of any receiver or payload.

The synthetic membrane-receiver complexes described herein, in some embodiments, exhibit advantageous clearance properties. In some embodiments, synthetic membrane-receiver complexes may be degraded using a natural degradation process, through the reticulo-endothelial system. Such degradation typically does not cause any or little side effects. In some embodiments, receivers displayed on the synthetic membrane-receiver complexes can be selectively trapped by organs of the reticulo-endothelial system.

The synthetic membrane-rceiver complexes described herein are, in some embodiments, incapable of self-replication. In some embodiments, the synthetic membrane-receiver complexes do not contain self-replicating nucleic acids. Thus, such complexes do not carry a risk of uncontrolled cellular division, undesired protein expression and/or the potential of triggering cytokine release syndrome.

Membrane Compositions of the Synthetic Membrane-Receiver Complexes

1. Lipids

In one embodiment, the synthetic membrane-receiver polypeptide complex comprises a membrane that has a mass of approximately $1 \times 10^{-12}$ g and a density of approximately 1.15 g/cm$^3$. The mass of the membrane component can be assessed by separating it from the remainder of the complex using hypotonic solutions of mildly alkaline buffer, see e.g., protocols in Dodge et al 1963, Arch Biochem Biophys 100:119.

The synthetic membrane-receiver complex comprises a membrane. In some embodiments, the membrane comprises phosphatidylcholine, sphingomyelin, lysophosphatidylcholine, phosphatidylethanolamine, phosphatidylserine, phosphatidylinositol, or phosphatidic acid. In some embodiments, the membrane is a cell membrane.

In one embodiment the synthetic membrane-receiver polypeptide complex comprises lipid molecules of the class of choline phospholipids, acidic phospholipids, and phosphatidylethanolamine.

In one embodiment the synthetic membrane-receiver polypeptide complex comprises phosphatidylcholine, sphingomyelin, lysophosphatidylcholine, phosphatidylethanolamine, phosphatidylserine, phosphatidylinositol, or phosphatidic acid.

In one embodiment the synthetic membrane-receiver polypeptide complex comprises choline phospholipids in an approximate amount of 50%, 51%, 52%, 53%, 54%, 55%, 56%, 57%, 58%, 59%, 60%, 61%, 62%, 63%, 64%, or 65% relative to the total lipid content of the complex.

In one embodiment the synthetic membrane-receiver polypeptide complex comprises acidic phospholipids in an approximate amount of 5%, 6%, 7%, 8%, 9%, 10%, 11%, 12%, 13%, 14%, 15%, 16%, 17%, 18%, 19%, or 20% relative to the total lipid content of the complex.

In one embodiment the synthetic membrane-receiver polypeptide complex comprises phosphatidylcholine in an amount greater than 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%. 39%, 40%, 41%, 42%, 43%, 44%, 45%, 46%, 47%, 48%, 49%, 50%, or greater than 50% relative to the total lipid content of the complex.

In one embodiment the synthetic membrane-receiver polypeptide complex comprises sphingomyelin in an amount greater than 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%. 39%, 40%, 41%, 42%, 43%, 44%, 45%, 46%, 47%, 48%, 49%, 50%, or greater than 50% relative to the total lipid content of the complex.

In one embodiment the synthetic membrane-receiver polypeptide complex comprises lysophosphatidylcholine in an amount greater than 0.1%, 0.2%, 0.3%, 0.4%, 0.5%, 0.6%, 0.7%, 0.8%, 0.9%, 1%, 1.5%, 2%, 2.5%, 3%, 4%, 5%, 6%, 7%, 8%, 9%, 10%, or greater than 10% relative to the total lipid content of the complex.

In one embodiment the synthetic membrane-receiver polypeptide complex comprises phosphatidylethanolamine in an amount greater than 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%. 39%, 40%, 41%, 42%, 43%, 44%, 45%, 46%, 47%, 48%, 49%, 50%, or greater than 50% relative to the total lipid content of the complex.

In one embodiment the synthetic membrane-receiver polypeptide complex comprises phosphatidylserine in an amount greater than 1%, 1.5%, 2%, 2.5%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%. 39%, 40%, 41%, 42%, 43%, 44%, 45%, 46%, 47%, 48%, 49%, 50%, or greater than 50% relative to the total lipid content of the complex.

In one embodiment the synthetic membrane-receiver polypeptide complex comprises phosphatidylinositol in an amount greater than 0.1%, 0.2%, 0.3%, 0.4%, 0.5%, 0.6%, 0.7%, 0.8%, 0.9%, 1%, 1.5%, 2%, 2.5%, 3%, 4%, 5%, 6%, 7%, 8%, 9%, 10%, or greater than 10% relative to the total lipid content of the complex.

In one embodiment the synthetic membrane-receiver polypeptide complex comprises phosphatidic acid in an amount greater than 0.1%, 0.2%, 0.3%, 0.4%, 0.5%, 0.6%, 0.7%, 0.8%, 0.9%, 1%, 1.5%, 2%, 2.5%, 3%, 4%, 5%, 6%, 7%, 8%, 9%, 10%, or greater than 10% relative to the total lipid content of the complex.

In one embodiment the synthetic membrane-receiver polypeptide complex comprises molecules from at least one, two, or three, of the following classes of molecules, including, but not limited to, choline phospholipids, acidic phospholipids, and phosphatidylethanolamine.

In one embodiment the molar ratio of choline phospholipids to acidic phospholipids in the synthetic membrane-receiver polypeptide complex is less than 1:1000, approximately 1:1000, approximately 1:500, approximately 1:250, approximately 1:100, approximately 1:50, approximately 1:25, approximately 1:10, approximately 1:9, approximately 1:8, approximately 1:7, approximately 1:6, approximately 1:5, approximately 1:4, approximately 1:3, approximately 1:2, approximately 1:1, approximately 2:1, approximately 3:1, approximately 4:1, approximately 5:1, approximately 6:1, approximately 7:1, approximately 8:1, approximately 9:1, approximately 10:1, approximately 25:1, approximately 50:1, approximately 100:1, approximately 250:1, approximately 500:1, approximately 1000:1, or greater than approximately 1000:1.

In one embodiment the molar ratio of choline phospholipids to phosphatidyl ethanolamine in the synthetic membrane-receiver polypeptide complex is less than 1:1000, approximately 1:1000, approximately 1:500, approximately 1:250, approximately 1:100, approximately 1:50, approximately 1:25, approximately 1:10, approximately 1:9, approximately 1:8, approximately 1:7, approximately 1:6, approximately 1:5, approximately 1:4, approximately 1:3, approximately 1:2, approximately 1:1, approximately 2:1, approximately 3:1, approximately 4:1, approximately 5:1, approximately 6:1, approximately 7:1, approximately 8:1, approximately 9:1, approximately 10:1, approximately 25:1, approximately 50:1, approximately 100:1, approximately 250:1, approximately 500:1, approximately 1000:1, or greater than approximately 1000:1.

In one embodiment the molar ratio of phosphatidylethanolamine to acidic phospholipids in the synthetic membrane-receiver polypeptide complex is less than 1:1000, approximately 1:1000, approximately 1:500, approximately 1:250, approximately 1:100, approximately 1:50, approximately 1:25, approximately 1:10, approximately 1:9, approximately 1:8, approximately 1:7, approximately 1:6, approximately 1:5, approximately 1:4, approximately 1:3, approximately 1:2, approximately 1:1, approximately 2:1, approximately 3:1, approximately 4:1, approximately 5:1, approximately 6:1, approximately 7:1, approximately 8:1, approximately 9:1, approximately 10:1, approximately 25:1, approximately 50:1, approximately 100:1, approximately 250:1, approximately 500:1, approximately 1000:1, or greater than approximately 1000:1.

In one embodiment the synthetic membrane-receiver polypeptide complex comprises molecules from at least one, two, three, four, five, six, or seven of the following classes of molecules, including, but not limited to, phosphatidylcholine, sphingomyelin, lysophosphatidylcholine, phosphatidylethanolamine, phosphatidylserine, phosphatidylinositol, or phosphatidic acid.

The lipid composition of the synthetic membrane-receiver polypeptide complex can be experimentally measured using methods known in the art including, e.g., gas-liquid chromatography or thin layer chromatography, see for example Dodge & Phillips, J Lipid Res 1967 8:667.

In one embodiment, the synthetic membrane-receiver polypeptide complex comprises a lipid bilayer composed of an inner leaflet and an outer leaflet. The composition of the inner and outer leaflet can be determined by transbilayer distribution assays known in the art, see e.g., Kuypers et al. Biohim Biophys Acta 1985 819:170. In one embodiment, the composition of the outer leaflet is between approximately 70-90% choline phospholipids, between approximately 0-15% acidic phospholipids, and between approximately 5-30% phosphatidylethanolamine. In one embodiment, the composition of the inner leaflet is between approximately 15-40% choline phospholipids, between approximately 10-50% acidic phospholipids, and between approximately 30-60% phosphatidylethanolamine.

2. Cholesterol

In one embodiment the synthetic membrane-receiver polypeptide complex comprises cholesterol. In one embodiment the cholesterol content is between approximately 3.0-5.5 nmol cholesterol per $10^7$ complexes. In one embodiment, the cholesterol content is between approximately 1.8-3.5 nmol cholesterol per $10^7$ complexes. In one embodiment the molar ratio of cholesterol to phospholipids in the complex is between approximately 0.5-1.5. In a preferred embodiment the molar ratio of cholesterol to phospholipids is between approximately 0.8-1.2. In a preferred embodiment the molar ratio of cholesterol to phospholipids is between approximately 0.84-0.9. In a preferred embodiment the molar ratio of cholesterol to phospholipids is between approximately 0.5-0.75. In a preferred embodiment the molar ratio of cholesterol to phospholipids is between approximately 0.55-0.6.

3. Lipids, Proteins, and Carbohydrates

In one embodiment, the synthetic membrane-receiver polypeptide complex comprises polypeptides other than the receiver polypeptide. In one embodiment, approximately 52% of the membrane mass is protein, approximately 40% is lipid, and approximately 8% is carbohydrate. In one embodiment, approximately 7% of the carbohydrate content is comprised of glycosphingolipids and approximately 93% of the carbohydrate content is comprised of O-linked and N-linked oligosaccharides on membrane-associated polypeptides.

In one embodiment the mass ratio of lipid to protein in the synthetic membrane-receiver polypeptide complex is less than 1:1000, approximately 1:1000, approximately 1:500, approximately 1:250, approximately 1:100, approximately 1:50, approximately 1:25, approximately 1:10, approximately 1:9, approximately 1:8, approximately 1:7, approximately 1:6, approximately 1:5, approximately 1:4, approximately 1:3, approximately 1:2, approximately 1:1, approximately 2:1, approximately 3:1, approximately 4:1, approximately 5:1, approximately 6:1, approximately 7:1, approximately 8:1, approximately 9:1, approximately 10:1, approximately 25:1, approximately 50:1, approximately 100:1, approximately 250:1, approximately 500:1, approximately 1000:1, or greater than approximately 1000:1.

In one embodiment the mass ratio of lipid to carbohydrate in the synthetic membrane-receiver polypeptide complex is less than 1:1000, approximately 1:1000, approximately 1:500, approximately 1:250, approximately 1:100, approximately 1:50, approximately 1:25, approximately 1:10, approximately 1:9, approximately 1:8, approximately 1:7, approximately 1:6, approximately 1:5, approximately 1:4, approximately 1:3, approximately 1:2, approximately 1:1, approximately 2:1, approximately 3:1, approximately 4:1, approximately 5:1, approximately 6:1, approximately 7:1, approximately 8:1, approximately 9:1, approximately 10:1, approximately 25:1, approximately 50:1, approximately 100:1, approximately 250:1, approximately 500:1, approximately 1000:1, or greater than approximately 1000:1.

In one embodiment the mass ratio of carbohydrate to protein in the synthetic membrane-receiver polypeptide complex is less than 1:1000, approximately 1:1000, approximately 1:500, approximately 1:250, approximately 1:100, approximately 1:50, approximately 1:25, approximately 1:10, approximately 1:9, approximately 1:8, approximately 1:7, approximately 1:6, approximately 1:5, approximately 1:4, approximately 1:3, approximately 1:2, approximately 1:1, approximately 2:1, approximately 3:1, approximately 4:1, approximately 5:1, approximately 6:1, approximately 7:1, approximately 8:1, approximately 9:1, approximately 10:1, approximately 25:1, approximately 50:1, approximately 100:1, approximately 250:1, approximately 500:1, approximately 1000:1, or greater than approximately 1000:1.

In one embodiment the area occupancy of protein in the synthetic membrane-receiver polypeptide complex is approximately 23% and the area occupancy of lipid in the synthetic membrane-receiver polypeptide complex is approximately 77%.

In one embodiment the synthetic membrane-receiver polypeptide complex comprises a polypeptide selected from the following list, including but not limited to, spectrin, myosin-like polypeptide, band 3, SLC4A1, actin, actin-like polypeptide, glyceraldehyde 3-P dehydrogenase (G3PD).

In one embodiment the synthetic membrane-receiver polypeptide complex comprises at least one, two, three, four, five, six, or seven of the polypeptides selected from the following list, including but not limited to, spectrin, myosin-like polypeptide, band 3, SLC4A1, actin, actin-like polypeptide, glyceraldehyde 3-P dehydrogenase (G3PD).

4. Additional Polypeptides

In some embodiments, the synthetic membrane-receiver complex comprises at least one polypeptide that is not the receiver. In some embodiments, the synthetic membrane-receiver complex comprises at least two, at least three, at least four, at least five, at least six, at least seven, at least eight, at least nine or at least ten polypeptides that are not the receiver. In certain instances, the polypeptide is capable of an enzymatic or catalytic function independent of the receiver. The non-receiver polypeptide may be associated with the membrane of the synthetic membrane-receiver complex.

In some embodiments, the non-receiver polypeptide may, e.g., stabilize the synthetic membrane-receiver complex, target the synthetic membrane-receiver complex to particular cells and tissues, engage the reticulo-endothelial system, protect the synthetic membrane-receiver complex from macrophages and other phagocytic cells, and/or evade other components of the innate immune system. Suitable polypeptides include, e.g., complement regulatory polypeptides, inhibitors of cell-mediated degradation (e.g., CD47, CD55, and CD59), and anti-inflammatory polypeptides. Alternatively or in addition, non-receiver polypeptides may shorten or control the half-life of the complex, including targeting to macrophages or other phagocytic cells. Suitable non-receiver polypeptides may promote apoptosis or otherwise trigger opsonization. In some embodiments, non-receiver polypeptides include polypeptide carriers, pumps, and channels; Glut1, Band3, aquaporin 1, RhAH, NA/K ATPase, Ca ATPase, Na—H exchanger, KCa3.1, KCl cotransporter, and coenzyme Q10.

As many drugs are systemically delivered to the blood circulatory system, the answer to the problem of effective drug delivery often focuses on maintaining the drug in the blood for extended periods of time. Thus, the development of long-circulating (long half-life) therapeutics that remain biologically available in the blood for extended time periods is an unmet need. The synthetic membrane-receiver complexes described herein can be modified to increase or decrease their half-life in circulation. In some embodiments, the half-life of the receiver and optionally the payload in circulation may be modified by altering the half-life of the synthetic membrane-receiver complex. In some instances, the ahlf-life is increased and the increase may be, for instance from about 1.5-fold to 20-fold increase in serum half-life.

In some embodiments, receivers may reside in circulation and may remain functional and active for substantially the duration of the synthetic membrane-receiver complex in circulation. In some embodiments, receivers may reside in circulation and may remain functional and active for more than 21 days in circulation. In some instances, synthetic membrane-receiver complexes and receivers may reside in circulation for 30 days, 45 days, 60 days, 100 days, 120 days, or longer. In other embodiments, the synthetic membrane-receiver complexes and receivers may reside in circulation for several hours to several days, such as 1, 2, 3, 4, 5, 6, 7, 8, 9, or 10 days. Residency in the circulatory system, in certain embodiments, is determined by the presence or absence of certain polypeptides on the synthetic membrane-receiver complex. For example, the synthetic membrane-receiver complex may comprise a CD47, CD55, or CD59 polypeptide or a functional fragment thereof.

CD47 is a membrane protein that interacts with the myeloid inhibitory immunoreceptor SIRPα (also termed CD172a or SHPS-1) that is present, e.g., on macrophages. Engagement of SIRPα by CD47 provides a down-regulatory signal that inhibits host cell phagocytosis. For example, high levels of CD47 allow cancer cells to avoid phagocytosis despite the presence pro-phagocytic signals, such as high levels of calreticulin. CD47 also has further roles in cell adhesion, e.g., by acting as an adhesion receptor for THBS1 on platelets and in the modulation of integrins. CD47 interaction with SIRPα further prevents maturation of immature dendritic cells, inhibits cytokine production by mature dendritic cells. CD47 interaction with SIRPγ mediates cell-cell adhesion, enhances superantigen-dependent T-cell-mediated proliferation and co-stimulates T-cell activation.

CD47 is a 50 kDa membrane receptor that has extracellular N-terminal IgV domain, five transmembrane domains, and a short C-terminal intracellular tail. There are four alternatively spliced isoforms of CD47 that differ only in the length of their cytoplasmic tail. In some embodiments, the synthetic membrane-receiver complex may comprise a CD47 or a functional fragment thereof comprising one or more of: the extracellular N-terminal IgV domain, one, two, three, four, or five transmembrane domains, and/or the short C-terminal intracellular tail. The cytoplasmic tail can be found as four different splice isoforms ranging from 4 to 36 amino acids. The 16 amino acid form 2 is expressed in all cells of hematopoietic origin and in endothelial and epithelial cells. The 36 amino acid form 4 is expressed primarily in neurons, intestine, and testis. The 4 amino acid form 1 is found in epithelial and endothelial cells. The expression pattern of the 23 amino acid form 3 resembles that of form 4. In some embodiments, the synthetic membrane-receiver complex comprises CD47 or a functional fragment thereof that is of one of form 1, from 2, form 3, or from 4. In some embodiments, the synthetic membrane-receiver complex does not comprise form 2. In some embodiments, the synthetic membrane-receiver complex comprises CD47 polypeptide or a functional polypeptide fragment thereof in an amount or copy number sufficient to reside in circulation for 15 days, 21 days, 30 days, 45 days, 60 days, 100 days, 120 days, or longer. In some embodiments, the synthetic membrane-receiver complex comprises a modified CD47, such as a conformational change. For example, a conformational change in CD47 is introduced so that the modified CD47 is capable of interacting with TSP-1. In one embodiment, the modified CD47 comprising the conformational change creates a different binding site for SIRPα. In some embodiments, the synthetic membrane-receiver complex comprises a modified CD47 polypeptide or a functional polypeptide fragment thereof comprising a conformational change in an amount or copy number sufficient to reside in circulation for less than 10, 9, 8, 7, 6, 5, 4, 3, 2, or less than 1 day. In certain embodiments, the synthetic membrane-receiver complex comprises a fusion of a CD47 isoform to the extracellular domain of a native erythroid polypeptide. For example, the N terminus of glycophorin A may be fused to the CD47 polypeptide or functional fragment thereof, which may lead to a reduction of the SIRPα-mediated signal to macrophages to phagocytose the synthetic membrane-receiver complex.

In some embodiments, generating synthetic membrane-receiver complexes includes the step of contacting a receiver (e.g., a polypeptide) with a cell, such as an erythroid cell or a platelet. CD47 is expressed in erythrocytes and platelets to mediate phagocytosis. In some embodiments, the natural levels of CD47 are altered in erythrocytes or platelets, e.g., by over-expression or inhibition of CD47 expression using any suitable method, such as the introduction of exogenous nucleic acids (e.g., expression vectors, CD47 mRNA, CD47 siRNA, and the like). In some embodiments, the natural levels of CD47 are altered such that the synthetic membrane-receiver complex resides in circulation for 15 days, 21 days, 30 days, 45 days, 60 days, 100 days, 120 days, or longer. In some embodiments, the natural levels of CD47 are altered such that the synthetic membrane-receiver complex resides in circulation for less than 10, 9, 8, 7, 6, 5, 4, 3, 2, or less than 1 day.

For example, synthetic membrane-receiver complexes that are administered to a subject may comprise elevated CD47 levels when compared to native levels of a suitable control. Elevated CD47 levels may be achieved, e.g., by exogenous expression by the synthetic membrane-receiver complex of CD47 from an exogenous nucleic acid, by loading of CD47 mRNA into the complex, or by conjugating CD47 polypeptide to the surface of the complex. Elevated CD47 levels are useful to increase the half-life of the population of synthetic membrane-receiver complexes in the circulatory system of the subject. The synthetic membrane-receiver complexes comprise a receiver and optionally a payload, such as a therapeutic agent. In some embodiments, increasing the half-life of the synthetic membrane-receiver complex increases the half-life of the receiver and/or the optional payload in circulation, thereby potentially increasing the therapeutic window in which the receiver and/or payload is active. In one instance, a population of $10^{11}$ synthetic membrane-receiver polypeptide complexes comprises an adenosine deaminase receiver and an exogenous CD47 polypeptide on its surface. When administered to a subject with an enzyme deficiency, such as ADA-SCID, the half-life of the synthetic membrane-receiver polypeptide complex is extended beyond that of a complex not comprising exogenous CD47 polypeptide and the subject requires less frequent dosing. Half-life extension is a particular advantage when compared to current enzyme therapies not involving synthetic membrane-receiver polypeptide complexes.

In some embodiments, CD47 is altered by heparin and/or chondroitin sulfate glycosaminoglycan (GAG) chains. In some embodiments, the synthetic membrane-receiver complex expresses CD47 as a proteoglycan. In some embodiments, the synthetic membrane-receiver complex comprises a CD47 proteoglycan that is conjugated to the complex. In one embodiment, the CD47 proteoglycan comprises heparin and/or chondroitin sulfate glycosaminoglycan (GAG) chains. In one embodiment, that CD47 proteoglycan has a size of greater than 150 kDa, 200 kDa, or greater than 250 kDa. In one embodiment, CD47 comprises one or more GAG chains at Ser64.

In some embodiments, the residency of a synthetic membrane-receiver complex, e.g., generated using erythroid cells or platelets can be further modulated by changing the amount or number of oxidized lipids on the membrane of the synthetic membrane-receiver complex. In one embodiment, the synthetic membrane-receiver complex comprises oxidized lipids in an amount effective to reside in circulation for less than 10, 9, 8, 7, 6, 5, 4, 3, 2, or less than 1 day. In one embodiment, the synthetic membrane-receiver complex comprises oxidized lipids in an amount effective to reside in circulation for 15 days, 21 days, 30 days, 45 days, 60 days, 100 days, 120 days, or longer. In some embodiments, the amount of oxidized lipids in the membrane are altered such that mobility of CD47 is increased or decreased, thereby aiding or hindering, respectively the ability of CD47 to cluster on the membrane. (See, Olsson, Department of Integrative Medical Biology, Section for Histology and Cell Biology, Umeå University, Umeå, Sweden, 2008).

CD55, also known as complement decay-accelerating factor or DAF, is a 70 kDa membrane protein. CD55 recognizes C4b and C3b fragments of the complement system that are created during C4 (classical complement pathway and lectin pathway) and C3 (alternate complement pathway) activation. It is thought that interaction of CD55 with cell-associated C4b and C3b proteins interferes with their ability to catalyze the conversion of C2 and factor B to active C2a and Bb and thereby prevents the formation of C4b2a and C3bBb, the amplification convertases of the complement cascade. CD55 is thought to block the formation of membrane attack complexes. CD55 may prevent lysis by the complement cascade. In some embodiments, the synthetic membrane-receiver complex comprises CD55 polypeptide or a functional polypeptide fragment thereof in an amount or copy number sufficient to reside in circulation for 15 days, 21 days, 30 days, 45 days, 60 days, 100 days, 120 days, or longer. In some embodiments, the synthetic membrane-receiver complex comprises an exogenous CD55 polypeptide and an exogenous CD47 polypeptide or functional polypeptide fragments thereof in an amount, copy number and/or ratio sufficient to reside in circulation for 15 days, 21 days, 30 days, 45 days, 60 days, 100 days, 120 days, or longer.

CD59 glycoprotein also known as MAC-inhibitory protein (MAC-IP), membrane inhibitor of reactive lysis (MIRL), protectin, or HRF is a protein that attaches to host cells via a glycophosphatidylinositol (GPI) anchor. When complement activation leads to deposition of C5b678 on host cells, CD59 can prevent C9 from polymerizing and forming the complement membrane attack complex. CD59 may prevent lysis by the complement cascade. In some embodiments, the synthetic membrane-receiver complex comprises CD59 polypeptide or a functional polypeptide fragment thereof in an amount or copy number sufficient to reside in circulation for 15 days, 21 days, 30 days, 45 days, 60 days, 100 days, 120 days, or longer. In some embodiments, the synthetic membrane-receiver complex comprises an exogenous CD59 polypeptide and an exogenous CD47 polypeptide or functional polypeptide fragments thereof in an amount, copy number and/or ratio sufficient to reside in circulation for 15 days, 21 days, 30 days, 45 days, 60 days, 100 days, 120 days, or longer.

In some embodiments, the synthetic membrane-receiver complex comprises one or more of an exogenous CD55 polypeptide, an exogenous CD59 polypeptide and/or an exogenous CD47 polypeptide or functional polypeptide fragments thereof in an amount, copy number and/or ratio sufficient to reside in circulation for 15 days, 21 days, 30 days, 45 days, 60 days, 100 days, 120 days, or longer.

Effective amounts of CD47, CD55, and CD59 include $10^2$, $10^3$, $10^4$, $10^5$, $10^6$, $10^7$, $10^9$ polypeptides per synthetic membrane-receiver complex. Alternatively, an effective amount is the amount capable of extending the synthetic membrane-receiver polypeptide complex's half-life by 10%, 20%, 30%, 40%, 50%, 60%, 70%, 80%, 90%, 100%, 200%, 400%, 800%, 1,000%, or 10,000% relative to the half-life that the synthetic membrane-receiver polypeptide complex would exhibit without the polypeptides.

Receivers

Provided herein are receivers that are exhibited by synthetic membrane-receiver complexes. In some embodiments, a receiver is capable of interacting with a target, e.g., to associate with or bind to a target. A receiver can comprise or may consist essentially of a polypeptide. In some embodiments, the receiver comprises a polypeptide, a carbohydrate, a nucleic acid, a lipid, a small molecule, or a combination thereof. In some embodiments receivers do not interact with a target but act as payloads to be delivered by the synthetic membrane-receiver complex to a cell, tissue or other site in the body of a subject.

In some embodiments, receivers comprise polypeptides. Receiver polypeptides may range in size from 6 amino acids to 3000 amino acids and may exceed 6, 10, 15, 20, 25, 30, 35, 40, 50, 60, 70, 80, 90, 100, 150, 200, 300, 400 or may exceed 500 amino acids. Receiver polypeptides may range in size from about 20 amino acids to about 500 amino acids, from about 30 amino acids to about 500 amino acids or from about 40 amino acids to about 500 amino acids.

In some embodiments, the receiver polypeptide comprises a chimeric or fusion protein which may comprise two or more distinct protein domains. These chimeric receivers are heterologous or exogenous in the sense that the various domains are derived from different sources, and as such, are not found together in nature and can be encoded e.g., by exogenous nucleic acids. Receiver polypeptides can be produced by a number of methods, many of which are well known in the art and also described herein. For example, receiver polypeptides can be obtained by extraction (e.g., from isolated cells), by expression of an exogenous nucleic acid encoding the receiver polypeptide, or by chemical synthesis. Receiver polypeptides can be produced by, for example, recombinant technology, and expression vectors encoding the polypeptide introduced into host cells (e.g., by transformation or transfection) for expression of the encoded receiver polypeptide.

There are a variety of conservative changes that can generally be made to an amino acid sequence without altering activity. These changes are termed conservative substitutions or mutations; that is, an amino acid belonging to a grouping of amino acids having a particular size, charge or other characteristic can be substituted for another amino acid. Substitutions for an amino acid sequence may be selected from other members of the class to which the amino acid belongs. For example, the nonpolar (hydrophobic) amino acids include alanine, leucine, isoleucine, valine, proline, phenylalanine, tryptophan, methionine, and tyrosine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Such alterations are not expected to substantially affect apparent molecular weight as determined by polyacrylamide gel electrophoresis or isoelectric point. Conservative substitutions also include substituting optical isomers of the sequences for other optical isomers, specifically D amino acids for L amino acids for one or more residues of a sequence. Moreover, all of the amino acids in a sequence may undergo a D to L isomer substitution. Exemplary conservative substitutions include, but are not limited to, Lys for Arg and vice versa to maintain a positive charge; Glu for Asp and vice versa to maintain a negative charge; Ser for Thr so that a free ~OH is maintained; and Gln for Asn to maintain a free $NH_2$. Moreover, point mutations, deletions, and insertions of the polypeptide sequences or corresponding nucleic acid sequences may in some cases be made without a loss of function of the polypeptide or nucleic acid fragment. Substitutions may include, e.g., 1, 2, 3, or more residues. Any teaching of a specific amino acid sequence or an exogenous nucleic acid encoding the polypeptide or teaching of the name of the name thereof includes any conservative substitution point mutations, deletions, and insertions of those polypeptide sequences or corresponding nucleic acid sequences and any sequence depositied for the protein or gene in a database that can be made without a loss of function of the polypeptide or nucleic acid fragment.

In some embodiments, the receiver polypeptide is associated with the membrane of the synthetic membrane-receiver polypeptide complex. In other embodiments, the receiver polypeptide is not associated with the membrane of the synthetic membrane-receiver polypeptide complex.

In one embodiment the mass ratio of lipid to receiver in the synthetic membrane-receiver polypeptide complex is less than 1:1000, approximately 1:1000, approximately 1:500, approximately 1:250, approximately 1:100, approximately 1:50, approximately 1:25, approximately 1:10, approximately 1:9, approximately 1:8, approximately 1:7, approximately 1:6, approximately 1:5, approximately 1:4, approximately 1:3, approximately 1:2, approximately 1:1, approximately 2:1, approximately 3:1, approximately 4:1, approximately 5:1, approximately 6:1, approximately 7:1, approximately 8:1, approximately 9:1, approximately 10:1, approximately 25:1, approximately 50:1, approximately 100:1, approximately 250:1, approximately 500:1, approximately 1000:1, approximately 10,000:1, approximately 100,000:1, approximately 1,000,000:1, approximately 10,000,000:1, approximately 100,000,000:1, approximately 1,000,000,000:1 or greater than approximately 1,000,000,000:1.

In one embodiment the mass ratio of non-receiver polypeptide to receiver in the synthetic membrane-receiver polypeptide complex is less than 1:1000, approximately 1:1000, approximately 1:500, approximately 1:250, approximately 1:100, approximately 1:50, approximately 1:25, approximately 1:10, approximately 1:9, approximately 1:8, approximately 1:7, approximately 1:6, approximately 1:5, approximately 1:4, approximately 1:3, approximately 1:2, approximately 1:1, approximately 2:1, approximately 3:1, approximately 4:1, approximately 5:1, approximately 6:1, approximately 7:1, approximately 8:1, approximately 9:1, approximately 10:1, approximately 25:1, approximately 50:1, approximately 100:1, approximately 250:1, approximately 500:1, approximately 1000:1, approximately 10,000:1, approximately 100,000:1, approximately 1,000,000:1, approximately 10,000,000:1, approximately 100,000,000:1, approximately 1,000,000,000:1 or greater than approximately 1,000,000,000:1.

In certain embodiments, the polypeptide receiver is located on the surface and is exposed to the environment around the synthetic membrane-receiver polypeptide complex. In some embodiments, the polypeptide receiver is located inside and faces the unexposed side of the synthetic membrane-receiver polypeptide complex.

In certain embodiments, the polypeptide receiver comprises at least one of the following domains, an S domain (surface), an A domain (anchor), and/or a U domain (unexposed), wherein the S domain is a surface domain exposed to the environment around the synthetic membrane-receiver polypeptide complex, wherein the A domain is an anchor, and wherein the U domain is located within and/or faces the unexposed side of the synthetic membrane-receiver polypeptide complex.

Optionally the receiver polypeptide comprises i) one or more additional S domains, termed S' domains, or ii) one or more additional U domains, termed U' domains.

In some embodiments, the S domain and the A domain form part of the same polypeptide chain.

In some embodiments, the A domain and the U domain form part of the same polypeptide chain.

In some embodiments, any one or more of the S, A, U domain is added to the synthetic membrane-receiver polypeptide complex externally.

In some embodiments, any one or more of the S, A, U domain is produced within the synthetic membrane-receiver polypeptide complex.

In some embodiments, any one or more of the S, A, U domain is a polypeptide.

In some embodiments, any one or more of the S, A, U domain is not a polypeptide.

Schematics of exemplary conformations of receivers within or on synthetic membrane-receiver complexes are shown in FIGS. 14A, 14B, and 14C.

1. The a Domain

In certain embodiments, the A domain is a membrane polypeptide. The A domain can be, e.g., an integral membrane polypeptide or a membrane associated polypeptide.

The A domain may be selected from one of the following classes, including but not limited to, for example, alpha-helical bitopic, alpha-helical polytopic, beta-barrel transmembrane, all alpha monotopic/peripheral, all beta monotopic/peripheral, alpha/beta monotopic/peripheral, alpha+beta monotopic/peripheral, alpha helical peptides, beta-hairpin peptides, beta-helical peptides, type 1 transmembrane protein (N-terminus extracellular), type 2 transmembrane protein (N-terminus intracellular), type 3 transmembrane protein, type 4A transmembrane protein, type 4B transmembrane protein, lipid-anchored protein, glycosylphosphatidylinositol (GPI) anchored protein, prenyl chain anchored protein, or peptides of nonregular structure.

In certain embodiments, the A domain is endogenous, e.g., endogenous to an erythroid cell, a platelet, or a hematopoietic cell. In some embodiments, the A domain is endogenous to a mammalian cell.

In certain embodiments, the A domain is exogenous, e.g., exogenous to an erythroid cell, a platelet, or a hematopoietic cell. In some embodiments, the A domain is exogenous to a mammalian cell.

The A domain may be selected from the the following molecules or fragments thereof, including but not limited to, CD1, CD2, CD3, CD4, CD5, CD6, CD7, CD8, CD9, CD10, CD11a, CD11b, CD11c, CD12w, CD13, CD14, CD15, CD16, CDw17, CD18, CD19, CD20, CD21, CD22, CD23, CD24, CD25, CD26, CD27, CD28, CD29, CD30, CD31, CD32, CD33, CD34, CD35, CD36, CD37, CD38, CD39, CD40, CD41, CD42, CD43, CD44, CD45, CD46, CD47, CD48, CD49a, CD49b, CD49c, CD49d, CD49e, CD49f, CD53, CD54, CD55, CD56, CD57, CD58, CD59, CD61, CD62E, CD62L, CD62P, CD63, CD68, CD69, CD71, CD72, CD73, CD74, CD80, CD81, CD82, CD83, CD86, CD87, CD88, CD89, CD90, CD91, CD95, CD96, CD100, CD103, CD105, CD106, CD107, CD107a, CD107b, CD109, CD117, CD120, CD122, CD123, CD127, CD132, CD133, CD134, CD135, CD138, CD141, CD142, CD143, CD144, CD147, CD151, CD152, CD154, CD155, CD156, CD158, CD163, CD165, CD166, CD168, CD184, CDw186, CD195, CD197, CDw199, CD209, CD202a, CD220, CD221, CD235a, CD271, CD279, CD303, CD304, CD309, CD326, Ras-Related protein 1A, semaporin 7A precursor, Calcium and integrin-binding protein 1, 55 kDa erythrocyte membrane protein, Flotillin-1, Flotillin-2, Erythroid membrane-associated protein, eukaryotic translation initiation factor 2C 2, cytochrome b5 reductase, cell division control protein 42 homolog, KIAA1363 protein, band3, annexin VII, aquaporin, Ecto-ADP-ribosyltransferase 4, Kell, LFA-3, soulute carrier family 2 member 1, LGALS3 protein, Urea transporter, Rh blood CE group antigen poypeptide, Rh-associated glycoprotein, Dematin, ABO blood groups, Aquaporin 3, Aubergers, Band 3, Basigin, C41, CD44, Cis AB, Colton antigen, Complement Component 4, CR1, DAF, Diego, Duffy, Hh/Bombay antigen, ii antigen, Indian blood group, Kell, Kidd, Lewis antigen, Lutheran antigen, MNS antigen system, Cost group, Er group, Dematin, Stomatin, Tropomyosin, Glucose transporter, Adducin, Rabphilin, C1 tetrahydrofolate synthase, Vel group, Lan antigen, At antigen, Jr antigen, AnWj antigen, Sd antigen, Batty, Bilkes, Box, Christiansen, HJK, HOFM, JFV, JONEs, Jensen, Katagiri, Livesay, Milne, Oldeide, Peters, Rasmussen, Reid, REIT, SARA, Rhesus blood D group, Aldolase, Tropomodulin, Arginase, Creatine kinase, B-Cam protein, RaplA, Bennett-Goodspeed, P antigen system, Rh blood groupXg antigen system, XK protein, Yt/Cartwright antigen system, CD58, Rh, Scianna, Radin, DARC (Duffy), CR1 Knops-McCoy, DAF Cromer, Gerbich (GYPC), CD47, Glycophorin A, Band 3 (AE3), GYPB Ss, C4A, C4B Chido, Rodgers C4 component of complement, HLA Bg HLA class I, RHAG Rh-associated Ammonium transport, Glycoprotein, Colton (Co) Water channel protein, ACHE Cartwright (Yt) Acetylcholinesterase, Glutathione transferase, Glycophorin C, Aquaporin, Erythroblast associated membrane protein, CD44, Synaptobrevin 2, Ribonuclease, Duodenal cytochrome B, ABO glycosyl transferases, CD59, CD44 Indian (In), AnWj Adhesion receptor, MER2, DOK Dombrock ADP-ribosyltransferase, SEMA7A JMH Putative adhesion receptor, UMOD Sda Tamm-Horsfall protein (uromodulin), Diego (Di), Wright (Wr) Anion channel protein (band 3, AE1), Kidd (Jk) Urea transporter, FUT3 Lewis (Le) alpha(1,3) fucosyltransferase, OK Oka Neurothelin, putative adhesion molecule, LW Adhesion receptor, FUT2 Secretor (Se) alpha(1,2) fucosyltransferase, FUT1 Hh alpha(1,2) fucosyltransferase, LU Lutheran (Lu) Adhesion receptor, P1 Glycosyltransferase, XK Kx Putative neurotransmitter transporter, XG Xg formerly called PBDX, MIC2, Hemoglobin, Ankyrin, Spectrin, KEL Kell (forms K, k, Kp, Js) Metalloproteinase, Torkildsen antigen, coenzyme Q10, Rab 35, Ral A binding protein, Zona pellucida binding protein, Lyn B protein, KIaa1741 protein, DC38, Calcium transporting ATPase, GPIX, GPIba, GPIbb, GPV, GPIb-IX-V, GPVI, GPIa/IIa, GPIIb/IIIa, GPV/IIa.

2. The S Domain

In some embodiments, the S domain is a protein or a polypeptide. In other embodiments, the S domain is a nucleic acid. In some embodiments, the S domain is a chemical. In certain embodiment the S domain is a small molecule.

In some embodiments, the S domain is a polypeptide selected from or derived from one or more of the following classes, including but not limited to, a flexible linker, an epitope tag, an enzyme, a protease, a nuclease, a receiver, an antibody-like molecule, a ligand of an antibody, a growth factor, a cytokine, a chemokine, a growth factor receptor, a cytokine receptor, a chemokine receptor, an enzymatic recognition sequence, a transpeptidase recognition sequence, a protease recognition sequence, a cleavable domain, an intein, a DNA binding protein, and RNA binding protein, a complement regulatory molecule, a complement cascade molecule, a clotting cascade molecule, a chelator, a complement regulatory domain, an SCR domain, a CCP domain, an immunoglobulin or immunogloblulin-like domain, an armadillo repeat, a leucine zipper, a dealth effector domain, a cadherein repeat, an EF hand, a phosphotyrosine binding domain, a pleckstrin homology domain, an SCR homology 2 domain, a zinc finger domain, a cyclic peptide, a cell-penetrating peptide.

In some embodiments, the S domain is a non-polypeptide molecule, for example a nucleic acid, a carbohydrate, or a small molecule. In some embodiments, the S domain is a nucleic acid selected from one or more of the following classes, including but not limited to, a DNA aptamer, an RNA aptamer, an siRNA, a shRNA, a single-strand RNA probe, a single strand DNA probe, an mRNA, a chemically modified oligonucleotide. In some embodiments, the S domain is a small molecule selected from one or more of the following classes, including but not limited to, a chelator, DOTA, a radionuclide, an isotope, an imaging agent, a fluorescent molecule, a chemiluminescent molecule, a gas.

3. The U Domain

In some embodiments, the U domain is a protein or a polypeptide. In other embodiments, the U domain is a nucleic acid. In some embodiments, the U domain is a chemical. In certain embodiment the U domain is a small molecule.

In some embodiments, the U domain is a polypeptide selected from or derived from one or more of the following classes, including but not limited to, a flexible linker, an epitope tag, an enzyme, a protease, a nuclease, a receiver, an antibody-like molecule, a ligand of an antibody, a growth factor, a cytokine, a chemokine, a growth factor receptor, a cytokine receptor, a chemokine receptor, an enzymatic recognition sequence, a transpeptidase recognition sequence, a protease recognition sequence, a cleavable domain, an intein, a DNA binding protein, and RNA binding protein, a complement regulatory molecule, a complement cascade molecule, a clotting cascade molecule, a chelator, a complement regulatory domain, an SCR domain, a CCP domain, an immunoglobulin or immunogloblulin-like domain, an armadillo repeat, a leucine zipper, a dealth effector domain, a cadherein repeat, an EF hand, a phosphotyrosine binding domain, a pleckstrin homology domain, an SCR homology 2 domain, a zinc finger domain, a cyclic peptide, a cell-penetrating peptide, a kinase domain, aphosphatase domain, a cytoskeletal protein, a protein that interacts with the cytoskeletal protein, a G-protein coupled receptor, a tyrosine kinase, an ITIM domain, an ITAM domain.

In some embodiments, the U domain is a non-polypeptide molecule, for example a nucleic acid, a carbohydrate, or a small molecule. In some embodiments, the U domain is a nucleic acid selected from one or more of the following classes, including but not limited to, a DNA aptamer, an RNA aptamer, an siRNA, a shRNA, a single-strand RNA probe, a single strand DNA probe, an mRNA, a chemically modified oligonucleotide. In some embodiments, the U domain is a small molecule selected from one or more of the following classes, including but not limited to, a chelator, DOTA, a radionuclide, an isotope, an imaging agent, a fluorescent molecule, a chemiluminescent molecule, a gas.

Examples of Receiver Polypeptides

Examples of receiver polypeptides include: the polypeptide receiver comprises glycophorin A with HA epitope tag at the N terminus; the polypeptide receiver comprises the leader sequence of glycophorin A, HA epitope tag, and the body sequence of glycophorin A; the polypeptide receiver comprises complement receptor 1 (CR1); the polypeptide receiver comprises the leader sequence of CR1, HA epitope tag, the body sequence of CR1; the polypeptide receiver comprises the leader sequence of CR1, HA epitope tag, six SCR domains of LHR-A and LHR-B of CR1, the membrane proximal two SCR domains of CR1, the transmembrane region of CR1, and the intracellular region of CR1; the polypeptide receiver comprises the leader sequence of CR1, HA epitope tag, nine SCR domains of LHR-A and LHR-B and LHR-C of CR1, the membrane proximal two SCR domains of CR1, the transmembrane region of CR1, and the intracellular region of CR1; the polypeptide receiver comprises the leader sequence of CR1, LHR-A of CR1, LHR-B of CR1, LHR-C of CR1, the membrane proximal two SCR domains of CR1, the transmembrane region of CR1, and the intracellular region of CR1; the polypeptide receiver comprises leader sequence of CR1, LHR-A of CR1, LHR-B of CR1, LHR-C of CR1, the membrane proximal two SCR domains of CR1, the transmembrane region and intracellular region of glycophorin A; the polypeptide receiver comprises the leader sequence of glycophorin A, an antibody scFv against hepatitis B surface antigen (scFv), a (Gly3Ser)2 (SEQ ID NO: 23) flexible linker, HA epitope tag, and the body of glycophorin A; the polypeptide receiver comprises Kell, a (Gly3Ser)2 (SEQ ID NO: 23) flexible linker, HA epitope tag, and scFv; the polypeptide receiver comprises Kell and HA epitope tag; the polypeptide receiver comprises a 71-amino acid N-terminal fragment of Kell and an HA epitope tag; the polypeptide receiver comprises a 71-amino acid N-terminal fragment of Kell, a (Gly3Ser)2 (SEQ ID NO: 23) flexible linker, and an HA epitope tag; the polypeptide receiver comprises a 79-amino acid N-terminal fragment of Kell and an HA epitope tag; the polypeptide receiver comprises a 79-amino acid N-terminal fragment of Kell, a (Gly3Ser)2 (SEQ ID NO: 23) flexible linker, and an HA epitope tag; the polypeptide receiver comprises a 71-amino acid N-terminal fragment of Kell, a (Gly3Ser)2 (SEQ ID NO: 23) flexible linker, scFv, and an HA epitope tag; the polypeptide receiver comprises a 79-amino acid N-terminal fragment of Kell, a (Gly3Ser)2 (SEQ ID NO: 23) flexible linker, scFv, and an HA epitope tag; the polypeptide receiver comprises the leader sequence of CD55, scFv, an HA epitope tag, and the terminal 37 amino acids of CD55; the polypeptide receiver comprises the leader sequence of CD55, an HA epitope tag, and the body of CD55. In one embodiment, the polypeptide receiver comprises the leader sequence of CD59, scFv, an HA epitope tag, and the body of CD59; the polypeptide receiver comprises the leader sequence of CD59, and HA epitope tag, and the body of CD59; the polypeptide receiver comprises adenosine deaminase and an HA epitope tag; the polypeptide receiver comprises phenylalanine hydroxylase and an HA epitope tag; the polypeptide receiver comprises adenosine deaminase, a (Gly3Ser)2 (SEQ ID NO: 23) flexible linker, phenylalanine hydroxylase, and an HA epitope tag; the polypeptide receiver comprises glycophorin A, adenosine deaminase at the cytoplasmic C terminus, and an HA epitope tag; the polypeptide receiver comprises glycophorin A, phenylalanine hydroxylase at the cytoplasmic C terminus, and an HA epitope tag.

In certain embodiments, the receiver is capable or interacting with a macrophage. The receiver polypeptide may comprise one or more of: the complement receptor (Rieu et al., J. Cell Biol. 127:2081-2091 (1994)), the scavenger receptor (Brasseur et al., Photochem. Photobiol. 69:345-352 (1999)), the transferrin receptor (Dreier et al., Bioconjug. Chem. 9:482-489 (1998); Hamblin et al., J. Photochem. Photobiol. 26:4556 (1994)); the Fc receptor (Rojanasakul et al., Pharm. Res. 11:1731-1733 (1994)); and the mannose receptor (Frankel et al., Carbohydr. Res. 300:251-258 (1997); Chakrabarty et al., J. Protozool. 37:358-364 (1990)).

Other receivers capable or interacting with a macrophages include: low density lipoproteins (Mankertz et al., Biochem. Biophys. Res. Commun. 240:112-115 (1997); von Baeyer et al., Int. J. Clin. Pharmacol. Ther. Toxicol. 31:382-386 (1993)), very low density lipoproteins (Tabas et al., J. Cell Biol. 115:1547-1560 (1991)), mannose residues and other carbohydrate moieties (Pittet et al., Nucl. Med. Biol. 22:355-365 (1995)), poly-cationic molecules, such as poly-L-lysine (Hamblin et al., J. Photochem. Photobiol. 26:45-56 (1994)), liposomes (Bakker-Woudenberg et al., J. Drug Target. 2:363-371 (1994); Betageri et al., J. Pharm. Pharmacol. 45:48-53 (1993)) and 2-macroglobulin (Chu et al., J. Immunol. 152:1538-1545 (1994)).

In some embodiments, the synthetic membrane-receiver complex does not comprise a receiver comprising an extracellular domain of an HIV coreceptor. In some embodiments, the synthetic membrane-receiver complex does not comprise a receiver capable of binding to a virus. In some embodiments, the synthetic membrane-receiver complex does not comprise a receiver comprising CD4. In some embodiments, the synthetic membrane-receiver complex does not comprise a receiver comprising an HIV coreceptor. In some embodiments, the synthetic membrane-receiver complex does not comprise a receiver comprising CXCR4, CCR5, CCR1, CCR2, CCR3, CCR4, CCR8, CXCR1, CXCR2, CXCR3, CXCR6, GPR15, APJ, CMKLR1, or CX3CR1 or a combination thereof.

In some embodiments, the synthetic membrane-receiver complex does not contain an exogenous nucleic acid encoding an adenosine deaminase receiver. In some embodiments, the synthetic membrane-receiver complex does not comprise a receiver comprising adenosine deaminase (ADA).

In some embodiments, the synthetic membrane-receiver complex does not comprise an exogenous nucleic acid encoding an oncogene. In some embodiments, the synthetic membrane-receiver complex does not comprise a receiver comprising oncogene.

In some embodiments, the synthetic membrane-receiver complex does not contain an exogenous nucleic acid encoding cdx1, cdx2, or cdx4. In some embodiments, the synthetic membrane-receiver complex does not comprise a receiver comprising cdx1, cdx2, or cdx4, or a combination thereof.

In some embodiments, the synthetic membrane-receiver complex does not comprise a receiver comprising a chimeric polypeptide comprising a ligand binding domain. In some embodiments, the synthetic membrane-receiver complex does not comprise a receiver comprising an S domain that is capable of binding a ligand. In some embodiments, the synthetic membrane-receiver complex does not comprise a receiver comprising CD3ξ, CD3η, an IL-2 receptor, an IL-3 receptor, an IL-4 receptor, an IL-7 receptor, an IL-11 receptor, an IL-13 receptor, a GM-CSF receptor, a LIF receptor, a CNTF receptor, an oncostatin M receptor, a TGF-β receptor, an EGF receptor, ATR2/neu, a HER2/neu, a HER3/c-erbB-3, Xmrk, an insulin receptor, an IGF-1 receptor, IRR, PDGF receptor, a CSF-1 receptor, c-kit, STK-1/flk-2, an FGF receptor, flg, bek, an NGF receptor, Ror1 and Ror2.

In some embodiments, the synthetic membrane-receiver complex does not comprise a receiver comprising E6 or E7 genes of human papillomavirus.

In some embodiments, the synthetic membrane-receiver complex does not comprise a receiver comprising a tumor antigen.

In some embodiments, the synthetic membrane-receiver complex does not comprise a receiver comprising glucocerebrosidase.

In some embodiments, the synthetic membrane-receiver complex does not comprise a receiver comprising asparaginase.

In some embodiments, the synthetic membrane-receiver complex does not comprise a receiver comprising arginine deiminase.

Provided herein are compositions containing functional erythroid cells comprising a receiver having functional activities that are either i) not present in native erythroid cells of the same lineage, or ii) present in native erythroid cells of the same lineage in reduced levels or reduced activity levels as compared to the erythroid cells comprising the receiver. Such functional activities include complement inhibition, immune complex clearance, artificial antigen presentation, modulation of the coagulation cascade, oxygen transfer, drug delivery, cytotoxin adsorption, avoidance of phagocytosis, and extension of circulation time.

In some embodiments, functional erythroid cells have higher levels of a complement receptor polypeptide, such as CR1, than native erythroid cells of the same lineage by virtue of comprising a CR-1 receiver. In an alternative embodiment, the functional erythroid cells comprising a receiver have higher levels of a complement receptor agonist polypeptide or complement associated polypeptide than native erythroid cells of the same lineage, including hut not limited to, the polypeptides listed in table 7 and table 10. The complement receptor receiver polypeptide comprises a human Complement Receptor-1 (CR1) polypeptide, variant, or functional fragment thereof. The CR1 receiver polypeptide may be derived from one or more than one of the native alleles of CR1, e.g., the A allele (also termed the F allele or CR1*1 allele), the B allele (also termed the S allele or CR1*2 allele), the C allele (also termed the F' allele or CR1*3 allele), or the D allele (also termed the CR1*4 allele). The sequences and database accession numbers for these native forms are provided in table 4. In some embodiments, the CR1 receiver polypeptide contains a domain of a CR1 polypeptide. For example, the CR1 polypeptide may comprise one or more short consensus repeat (SCR) domains, also termed complement control protein (CCP) modules or Sushi domains, e.g., Genbank accession number AAV65577.1. In one embodiment, the CR1 receiver polypeptide comprises one or more Short Consensus Repeats (SCRs), e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44 or greater than 44 SCRs. In another embodiment, the CR1 receiver polypeptide comprises one or more long homologous repeat (LHR) units of CR1, e.g., LHR-A, LHR-B, LHR-C, or LHR-D, e.g., 1, 2, 3, 4, 5, 6 or greater than 6 LHR domains. In another embodiment, the CR1 receiver polypeptide may comprise one or more than one extracellular domains of CR1 fused to another cell membrane protein, e.g., glycophorin A, glycophorin B, glycophorin C, glycophorin D, kell, band 3, aquaporin 1, glut 1, kidd antigen protein, rhesus antigen, including, but not limited to the cell surface moieties listed in table 1 and table 7.

In some embodiments, a functional erythroid cell contains an exogenous nucleic acid encoding a complement receptor receiver polypeptide, or alternatively or in combination, a complement receptor agonist receiver polypeptide or complement associated receiver polypeptide including but not limited to, the polypeptides, and agonists to the polypeptides, listed in table 10. In some embodiments, the functional erythroid cells further contain an exogenous decay-accelerating factor (CD59, GenBank: CAG46523.1) polypeptide, or an exogenous membrane cofactor (CD46, GenBank: BAA12224.1) polypeptide, or a variant or functional fragment thereof, or a combination thereof.

CR1 activities include binding to C3b-containing immune complexes and shuttling of these immune complexes from circulation to liver and spleen macrophages of the reticuloendothelial system. Upon encounter with cells of the reticuloendothelial system, the immune complex is endocytosed by the phyagocytic cell but the red blood cell is spared to continue its circulation. The removal of the immune complex sometimes results in proteolytic cleavage of CR1 from the surface of the red blood cell. To measure binding activity, one can perform an in vitro binding assay between erythroid cells and immune complexes. To measure sparing of the erythroid cell, one can perform an in vitro phagocytosis assay with phagocytic cells and immune complex-loaded erythroid cells. To measure in vivo clearance of circulating immune complexes to the liver, one can perform a clearance and biodistribution assay using radiolabeled immune complexes.

Provided are compositions containing functional erythroid cells containing a receiver comprising a native polypeptide at a level greater than that of a hematopoietic cell of the same lineage not comprising the receiver polypeptide. For example, populations of functional erythroid cells contain receivers, such as complement receptor 1 levels at least about 1.1, e.g., 1.2, 1.3, 1.4, 1.5, 1.6, 1.7, 1.8, 1.9, 2, 3, 4, 5, 6, 7, 8, 9, 10, 15, 20, 25, 30, 35, 40, 45, 50, 60, 70, 80, 90, 100, 150, 200, 250, 300, 350, 400, 450, 500, 600, 700, 800, 900, 1000, 2000, 3000, 4000, 5000, 6000, 7000, 8000, 9000, 10000, or more than 10000 times greater than corresponding hematopoietic cells of the same lineage that lack the CR1 receiver polypeptide. CR1 levels on reticulocytes and erythrocytes are typically between 50-2000 molecules per cell (Lach-Trifilieff, J Immunol 1999, 162:7549). Provided are compositions that contain populations of functional erythroid cells with CR1 levels of at least about 2500, 5000, 6000, 7000, 8000, 9000, 10000, 15000, 20000, 25000, 30000, 40000, 50000, 100000, 200000, 300000, 400000, 500000, 600000, 700000, 800000, 900000, 1000000, or more than 1000000 molecules per cell. CR1 levels in wild-type and synthetic membrane-receiver polypeptide complexes can be measured and quantified by, for example, flow cytometry with antibodies specific for CR1.

In some embodiments, the receiver interacts with a circulating pathogen, such as a virus or a bacterium. In some embodiments, the functional erythroid cell expresses an exogenous gene encoding an antibody, scFv, or nanobody specific for the circulating pathogen. The antibody, scFv, or nanobody may be expressed as a fusion protein. In other embodiments, the antibody, scFv, or nanobody receiver or another receiver with affinity to circulating pathogens is loaded into or onto the erythroid cell. The antibody, scFv, or nanobody receiver or the other receiver with affinity to circulating pathogens may be localized intracellularly or extracellularly. In some embodiments, the receiver is specific for a viral or bacterial antigen, such as a surface, envelope or capsid antigen.

In some embodiments, the receiver interacts with a toxin, preferably a foreign toxin, such as derived from a pathogen or otherwise from the environment. In some embodiments, the functional erythroid cell expresses a exogenous gene encoding a receiver comprising an amino acid sequence derived from lipopolysaccharide-binding protein (LBP), bactericidal/permeability-increasing protein (BPI), amyloid P component, or a cationic protein. Toxin-binding receivers may be expressed as a fusion protein. In other embodiments, toxin-binding receivers may be loaded into or onto the erythroid cell. Toxin-binding receivers may be localized intracellularly or extracellularly. In some embodiments, the toxin binding receiver is specific for a bacterial toxin such as botulinum or anthrax.

Further, synthetic membrane-receiver complexes may express a receiver capable of enhancing its ability to sequester a target. Potential sequestration enhancement receivers include the polypeptide transporters including, but not limited to, those in table 1.

In one embodiment, the receiver comprises a polypeptide that comprises an amino acid sequence derived from Duffy Antigen Receptor for Chemokines (DARC). In one embodiment, the functional erythroid cell expresses a exogenous gene encoding an amino acid sequence derived from Duffy Antigen Receptor for Chemokines (DARC). The DARC receiver may be expressed as a full-length protein or a fragment thereof. DARC may be expressed as a fusion protein. In other embodiments, DARC protein is loaded into or onto the erythroid cell. In some embodiments, the loaded DARC is additionally functionalized or otherwise modified. The DARC receiver molecule may be localized intracellularly or extracellularly.

DARC was identified as a potent multi-ligand chemokine receptor. DARC belongs to the family of rhodopsin-like seven-helix transmembrane proteins. Besides erythrocytes DARC is expressed in post capillary venular endothelial cells, which are the primary site of leukocyte transmigration in most tissues. DARC provides a highly specific binding site for both CC and CXC chemokines. DARC is thought to possess a higher affinity for ELR motif CXC chemokines. CXC chemokines are neutrophil chemoattractants and may potentially be pro-angiogenic.

Interaction between DARC and CXCL8 has demonstrated a dissociation constant (Kd) of 5 nmol/L and receptor binding sites estimated at 1000-9000 per erythrocyte (Hadley, Blood, 1997) Unlike other seven-transmembrane chemokine receptors, DARC lacks the highly conserved G protein coupling motif located in the second cytoplasmic loop (Meny, Immunohematology, 2010). DARC is not G-protein coupled and has no known alternative signaling mechanism. The biological role of DARC is not fully understood. DARC is thought to be a) multi-specific; b) unable to initiate intracellular signals, and c) chemokines bound to erythrocyte surface are believed to be inaccessible to their normal target inflammatory cells (Neote, J Biol Chem, 1993). Erythrocytes may play a role in the regulation of inflammatory processes through the presence of DARC Inflammatory signaling molecules, such as cytokines, can trigger local and systemic tissue damage when present in high concentrations. Bursts of cytokines are implicated in the pathogenesis of bacterial sepsis, rheumatoid arthritis, and several other inflammatory diseases. Functional erythroid cells that exogenously express natural cytokine receptors or synthetic antibody-like receptor mimics can sequester the inflammatory cytokines. An exemplary chemokine receptor is DARC. Provided herein are functional erythroid cells comprising a receiver that is a cytokine receptor or chemokine receptor, including, but not limited to DARC. For example, functional erythroid cells expressing DARC receiver (thereby increasing the amount present on native erythrocytes) may be used to modulate chemokine levels in circulation and/or within the body's peripheral tissues. The functional erythroid cells comprising a DARC receiver can either be marked for destruction or can slowly release the inflammatory mediators back into circulation, but at a low and diffuse concentration. The functional erythroid cell comprising a receiver that comprises a chemokine or cytokine receptor may act as a reservoir for signal transduction peptides.

In one embodiment, the receiver comprises a polypeptide that comprises an amino acid sequence derived from an antibody. In one embodiment, the functional erythroid cell expresses a exogenous gene encoding an amino acid sequence derived from an antibody. The antibody receiver may be expressed as a full-length protein or a fragment thereof. The antibody may be expressed as a fusion protein. In other embodiments, the antibody protein is loaded into or onto the erythroid cell. In some embodiments, the loaded antibody is additionally functionalized or otherwise modified. The antibody receiver may be localized intracellularly or extracellularly. In one embodiment, the receiver comprises an antibody amino acid sequence that is specific for a desired target. In some embodiments, the antibody is a scFv. In other embodiments, the antibody is a nanobody.

In certain embodiments, the functional erythroid cells comprise a receiver that comprises an antibody or fragment thereof that is specific for a target and is located on the cell surface. For example, a variable fragment (Fv) of an antibody specific for botulinum toxin binding is expressed on the surface of the erythroid cell. Botulinum toxin binding antibodies are known in the art (Amersdorfer, Inf and Immunity, 1997), as is the expression of the Fv portion of an antibody (Hoedemaeker, Journ of Bio Chemistry, 1997). Upon binding, the toxin is retained by the erythroid cell through the Fv region, sequestered and shuttled via the circulatory system to the liver for clearance from the body.

In one embodiment, the receiver comprises a polypeptide that comprises an amino acid sequence derived from a scFv antibody. In one embodiment, the functional erythroid cell expresses a exogenous gene encoding an amino acid sequence derived from a scFv antibody. The scFv antibody receiver may be expressed as a full-length protein or a fragment thereof. The scFv antibody may be expressed as a fusion protein. In other embodiments, the scFv protein is loaded into or onto the erythroid cell. Suitable scFv receiver polypeptides that may be expressed by functional erythroid cells include, but are not limited to, those listed in table 7.

scFv antibodies have been constructed mainly from hybridoma, spleen cells from immunized mice, and B lymphocytes from human. The variable region of an antibody is formed by the noncovalent heterodimer of the variable domains of the V(H) and V(L) domains, which can then be used in the construction of a recombinant scFv antibody.

The production of scFvs is known in the art and require mRNA to first be isolated from hybridoma (or also from the spleen, lymph cells, and bone marrow) followed by reverse transcription into cDNA to serve as a template for antibody gene amplification (PCR). With this method, large libraries with a diverse set of antibody-derived scFvs (a set comparable to that of the original antibodies from which the scFvs are modeled) can be created.

The scFv receiver may be made specific to any target molecule including, but not limited to, those in table 5.

In one example, a scFv receiver specific for anthrax toxin may be expressed on a functional erythroid cell. Upon administration to a subject in need thereof an effective dose of a population of erythroid cell comprising a receiver molecule specific for anthrax toxin can be used to capture and sequester the anthrax toxin. The erythroid cell migrates to the liver where clearance occurs.

In certain embodiments, erythrocytes comprise a receiver comprising a camelid-derived nanobody expressed on the surface of the cell. Nanobodies are usually 12-15 kDa. They are considerably smaller than antibodies and scFv. Nanobodies may thus be easier to transfect, and the nanobody receiver will be more easily expressed, translated and or transported to the cell surface in an erythroid cell. In certain embodiments, nanobody receivers are employed to minimize immunogenic effects caused by a specific receiver. Nanobodies because of their small size will offer reduced immunogenic potential. In certain embodiments, receiver nanobodies are employed because they limit changes in the mechanical and morphological behavior of the plasma membrane of the functional erythroid cell. This may allow the functional erythroid cell to exhibit normal circulatory red blood cell behavior. In certain embodiments, receiver nanobodies are employed because they have an increased ability to recognize hidden or uncommon epitopes compared to standard antibodies. For example, they can bind to small enzymatic cavities of a target and modulate the molecular behavior of the target.

In certain embodiments, functional erythroid cells comprise receiver nanobodies with specificity to target epitopes of molecules in the human complement system. Such functional erythroid cells may be administered to a subject in need thereof to selectively deplete one or more over-active factors of the complement system. For example, C5 may be targeted by erythroid cells comprising receiver nanobodies with specificity to target epitopes of C5 and cleared from the system by the erythroid cells upon administration of the cells into a subject. This approach is suitable to provide a therapeutic effect, e.g., for a complement disorder, such as paroxysmal nocturnal hemoglobinuria. In certain embodiments, functional erythroid cells comprise receiver nanobodies with specificity to target epitopes of molecules including, but not limited to, those listed in table 5.

In some embodiments, the receiver comprises a polypeptide that comprises an amino acid sequence derived from one of proteases, nucleases, amylase, lyase (sucrase) or hydrolase (DNase, lipase). In one embodiment, the functional erythroid cell expresses a exogenous gene encoding an amino acid sequence derived from one of proteases, nucleases, amylase, lyase (sucrase) or hydrolase (DNase, lipase). Receiver proteases, nucleases, amylases, lyases and hydrolases may be expressed as a full-length protein or a fragment thereof. Receiver proteases, nucleases, amylases, lyases and hydrolases may be expressed as a fusion protein. In other embodiments, receiver proteases, nucleases, amylases, lyases or hydrolases are loaded into or onto the erythroid cell. In some embodiments, the loaded receiver proteases, nucleases, amylases, lyases or hydrolases are additionally functionalized or otherwise modified. The receiver protease, nuclease, amylase, lyase or hydrolase receiver molecule may be localized intracellularly or extracellularly.

In certain embodiments, functional erythroid cells comprise a receiver comprising a protease, a nuclease, an amylase, a lyase or a hydrolase. The functional erythroid cell comprising a protease, a nuclease, an amylase, a lyase or a hydrolase receiver is capable of degrading a target on the erythroid cell independent of circulatory clearance, e.g., by macrophages in the liver. In certain embodiments, functional erythroid cells comprising a receiver comprising a protease, a nuclease, an amylase, a lyase or a hydrolase may be administered to a subject in need thereof to treat a cancer by selectively degrading metabolites that are essential for cancer cell growth. For example, asparaginase is used to decrease local asparagine levels to treat acute lymphoblastic leukemia and acute myeloid leukemia. Suitable receivers may, e.g., comprise one or both of the two major classes of enzymes capable of degrading target molecules, lyases and hydrolases. In certain embodiments, functional erythroid cells are provided comprising a receiver comprising a molecule including but not limited to those listed in table 7.

In certain embodiments, erythrocytes comprise a receiver comprising a lyase. In one embodiment, the lyase is valine decarboxylase. Valine decarboxylase receiver may be expressed within the intracellular space of the erythroid cell. Functional erythroid cells comprising a valine decarboxylase receiver may be administered to a subject in need thereof to modulate valine levels within the blood. Erythroid cells comprising a valine decarboxylase receiver are suitable to treat valinemia, an inherited disorder that increases levels of the amino acid valine in the blood. Affected individuals typically develop vomiting, failure to thrive, intellectual disability, and fatigue. Valinemia is caused by a deficiency of the valine transaminase enzyme and has an autosomal recessive pattern of inheritance.

In certain embodiments, erythrocytes comprise a receiver comprising a hydrolase. In one embodiment, the hydrolase is deoxyribonuclease I (DNase I). DNase I receiver may be expressed on the surface of the erythroid cell. Functional erythroid cells comprising a DNase I receiver may be administered to a subject in need thereof to preferentially cleave circulating DNA at phosphodiester linkages adjacent to a pyrimidine nucleotide, yielding 5'-phosphate-terminated polynucleotides with a free hydroxyl group on position 3'. On average tetra-nucleotides are produced. Erythroid cells comprising a DNase I receiver are suitable to treat conditions exacerbated by high levels of immunogenic DNA in circulation, such as systemic lupus erythematosus (SLE).

In certain embodiments the receiver is capable of responding to an external stimulus, e.g., upon binding to a ligand or contacting the stimulus, wherein responding entails, for example, moving, re-folding, changing conformation, forming a dimer, forming a homodimer, forming a heterodimer, forming a multimer, transducing a signal, emitting energy in a detectable form (e.g., fluorescence), functionally interacting with another receiver, or functionally interacting with a non-receiver polypeptide.

In some embodiments, the synthetic membrane-receiver complex does not comprise a fusion molecule capable of promoting fusion of the synthetic membrane-receiver complex to a target cell that is i) different from and/or ii) acts independent of the receiver, wherein the receiver is capable of interacting with a target. In some embodiments, the synthetic membrane-receiver complex does not comprise a receiver comprising Syncytin-1.

In some embodiments, the synthetic membrane-receiver complex does not comprise a photosensitive synthetic compound, such as, e.g. a compound that can be activated by photons or quenchable compounds. In some embodiments, the synthetic membrane-receiver complex does not comprise an activatable molecular detection agent capable of producing a detectable response. In some embodiments, the synthetic membrane-receiver complex does not comprise a diagnostic compound. In some embodiments, the synthetic membrane-receiver complex does not comprise a virus or bacterium.

Receiver Contacting

In certain embodiments, the polypeptide receiver is expressed within the synthetic membrane-receiver polypeptide complex. The polypeptide receiver may be exhibited on the surface of the synthetic membrane-receiver polypeptide complex or may reside within the synthetic membrane-receiver polypeptide complex.

In certain embodiments, the polypeptide receiver is conjugated to the synthetic membrane-receiver polypeptide complex. The polypeptide receiver usually is conjugated to the surface of the synthetic membrane-receiver polypeptide complex. Conjugation may be achieved chemically or enzymatically, by methods known in the art and described herein. Non-polypeptide receivers may also be conjugated to a synthetic membrane-receiver complex. In some embodiments, the receiver is not conjugated to the synthetic membrane-receiver complex.

In certain embodiments, the polypeptide receiver is loaded into the synthetic membrane-receiver polypeptide complex. Non-polypeptide receivers may also be loaded within a synthetic membrane-receiver complex. In some embodiments, the receiver is not loaded into or onto the synthetic membrane-receiver complex.

In some embodiments, the synthetic membrane-receiver complex comprises a receiver that is optionally expressed from an exogenous nucleic acid, conjugated to the complex, loaded into or onto the complex, and any combination thereof. Optionally, the synthetic membrane-receiver complex comprises a therapeutic agent or other payload.

In some embodiments, the synthetic membrane-receiver complex is generated by contacting a suitable isolated cell, e.g., an erythroid cell, a reticulocyte, an erythroid cell precursor, a platelet, or a platelet precursor, with an exogenous nucleic acid encoding a receiver polypeptide. In some embodiments, the receiver polypeptide is encoded by a DNA, which is contacted with a nucleated erythroid precursor cell or a nucleated platelet precursor cell. In some embodiments, the receiver polypeptide is encoded by an RNA, which is contacted with a platelet, a nucleate erythroid cell, a nucleated platelet precursor cell, or a reticulocyte. In some embodiments, the receiver is a polypeptide, which is contacted with a primary platelet, a nucleated erythroid cell, a nucleated platelet precursor cell, a reticulocyte, or an erythrocyte.

A receiver polypeptide may be expressed from a transgene introduced into an erythroid cell by electroporation, chemical or polymeric transfection, viral transduction, mechanical membrane disruption, or other method; a receiver polypeptide that is expressed from mRNA that is introduced into a cell by electroporation, chemical or polymeric transfection, viral transduction, mechanical membrane disruption, or other method; a receiver polypeptide that is over-expressed from the native locus by the introduction of an external factor, e.g., a transcriptional activator, transcriptional repressor, or secretory pathway enhancer; and/or a receiver polypeptide that is synthesized, extracted, or produced from a production cell or other external system and incorporated into the erythroid cell.

In certain embodiments, the polypeptide receiver is expressed within the synthetic membrane-receiver polypeptide complex. The polypeptide receiver may be exhibited on the surface of the synthetic membrane-receiver polypeptide complex or may reside within the synthetic membrane-receiver polypeptide complex.

In certain embodiments, the synthetic membrane-receiver polypeptide complex is a cell, e.g., an erythroid cell or a platelet expressing a receiver polypeptide. Receiver polypeptides can be introduced by transfection of single or multiple copies of genes, transduction with a virus, or electroporation in the presence of DNA or RNA. Methods for expression of exogenous proteins in mammalian cells are well known in the art. For example, expression of exogenous factor IX in hematopoietic cells is induced by viral transduction of CD34+ progenitor cells, see Chang et al., Nat Biotechnol 2006, 24:1017.

Nucleic acids such as DNA expression vectors or mRNA for producing the receiver polypeptide may be introduced into progenitor cells (e.g., an erythroid cell progenitor or a platelet progenitor and the like) that are suitable to produce the synthetic membrane-receiver polypeptide complexes described herein. The progenitor cells can be isolated from an original source or obtained from expanded progenitor cell population via routine recombinant technology as provided herein. In some instances, the expression vectors can be designed such that they can incorporate into the genome of cells by homologous or non-homologous recombination by methods known in the art.

In some instances, e.g., for a synthetic membrane-receiver polypeptide complex that is an erythroid cell comprising a receiver polypeptide, a nucleic acid encoding a non-receiver polypeptide that can selectively target and cut the genome, for example a CRISPR/Cas9, transcriptional activator-like effector nuclease (TALEN), or zinc finger nuclease, is used to direct the insertion of the exogenous nucleic acid of the expression vector encoding the receiver polypeptide to a particular genomic location, for example the CR1 locus (1q32.2), the hemoglobin locus (11p15.4), or another erythroid-associated protein including, but not limited to, those listed in table 1 and table 3.

In some instances, the exogenous nucleic acid is an RNA molecule, or a DNA molecule that encodes for an RNA molecule, that silences or represses the expression of a target gene. For example, the molecule can be a small interfering RNA (siRNA), an antisense RNA molecule, or a short hairpin RNA (shRNA) molecule.

Methods for transferring expression vectors into progenitor cells that are suitable to produce the synthetic membrane-receiver polypeptide complexes described herein include, but are not limited to, viral mediated gene transfer, liposome mediated transfer, transformation, gene guns, transfection and transduction, e.g., viral mediated gene transfer such as the use of vectors based on DNA viruses such as adenovirus, adenoassociated virus and herpes virus, as well as retroviral based vectors. Examples of modes of gene transfer include e.g., naked DNA, $CaPO_4$ precipitation, DEAE dextran, electroporation, protoplast fusion, lipofection, and cell microinjection.

A progenitor cell subject to transfer of an exogenous nucleic acid that encodes a polypeptide receiver can be cultured under suitable conditions allowing for differentiation into mature enucleated red blood cells, e.g., the in vitro culturing process described herein. The resulting enucleated red blood cells display proteins associated with mature erythrocytes, e.g., hemoglobin, glycophorin A, and receiver polypeptides which can be validated and quantified by standard methods (e.g., Western blotting or FACS analysis). Isolated mature enucleated red blood cells comprising a receiver and platelets comprising a receiver are two examples of synthetic membrane-receiver polypeptide complexes of the invention.

In some embodiments, the synthetic membrane-receiver complex is generated by contacting a reticulocyte with an exogenous nucleic acid encoding a receiver polypeptide. In some embodiments, the receiver polypeptide is encoded by an RNA which is contacted with a reticulocyte. In some embodiments, the receiver is a polypeptide which is contacted with a reticulocyte.

Isolated reticulocytes may be transfected with mRNA encoding a receiver polypeptide to generate a synthetic membrane-receiver comple. Messenger RNA may be derived from in vitro transcription of a cDNA plasmid construct containing the coding sequence corresponding to the receiver polypeptide. For example, the cDNA sequence corresponding to the receiver polypeptide may be inserted into a cloning vector containing a promoter sequence compatible with specific RNA polymerases. For example, the cloning vector ZAP Express® pBK-CMV (Stratagene, La Jolla, Calif., USA) contains T3 and T7 promoter sequence compatible with T3 and T7 RNA polymerase, respectively. For in vitro transcription of sense mRNA, the plasmid is linearized at a restriction site downstream of the stop codon(s) corresponding to the end of the coding sequence of the receiver polypeptide. The mRNA is transcribed from the linear DNA template using a commercially available kit such as, for example, the RNAMaxx® High Yield Transcription Kit (from Stratagene, La Jolla, Calif., USA). In some instances, it may be desirable to generate 5'-m7GpppG-capped mRNA. As such, transcription of a linearized cDNA template may be carried out using, for example, the mMESSAGE mMACHINE High Yield Capped RNA Transcription Kit from Ambion (Austin, Tex., USA). Transcription may be carried out in a reaction volume of 20-100 µl at 37° C. for 30 min to 4 h. The transcribed mRNA is purified from the reaction mix by a brief treatment with DNase I to eliminate the linearized DNA template followed by precipitation in 70% ethanol in the presence of lithium chloride, sodium acetate or ammonium acetate. The integrity of the transcribed mRNA may be assessed using electrophoresis with an agarose-formaldehyde gel or commercially available Novex pre-cast TBE gels (e.g., Novex, Invitrogen, Carlsbad, Calif., USA).

Messenger RNA encoding the receiver polypeptide may be introduced into reticulocytes using a variety of approaches including, for example, lipofection and electroporation (van Tandeloo et al., Blood 98:49-56 (2001)). For lipofection, for example, 5 µg of in vitro transcribed mRNA in Opti-MEM (Invitrogen, Carlsbad, Calif., USA) is incubated for 5-15 min at a 1:4 ratio with the cationic lipid DMRIE-C(Invitrogen). Alternatively, a variety of other cationic lipids or cationic polymers may be used to transfect cells with mRNA including, for example, DOTAP, various forms of polyethylenimine, and polyL-lysine (Sigma-Aldrich, Saint Louis, Mo., USA), and Superfect (Qiagen, Inc., Valencia, Calif., USA; See, e.g., Bettinger et al., Nucleic Acids Res. 29:3882-3891 (2001)). The resulting mRNA/lipid complexes are incubated with cells (1-2×10$^6$ cells/ml) for 2 h at 37° C., washed and returned to culture. For electroporation, for example, about 5 to 20×10$^6$ cells in 500 µl of Opti-MEM (Invitrogen, Carlsbad, Calif., USA) are mixed with about 20 µg of in vitro transcribed mRNA and electroporated in a 0.4-cm cuvette using, for example, and Easyject Plus device (EquiBio, Kent, United Kingdom). In some instances, it may be necessary to test various voltages, capacitances and electroporation volumes to determine the useful conditions for transfection of a particular mRNA into a reticulocyte. In general, the electroporation parameters required to efficiently transfect cells with mRNA appear to be less detrimental to cells than those required for electroporation of DNA (van Tandeloo et al., Blood 98:49-56 (2001)).

Alternatively, mRNA may be transfected into a reticulocyte using a peptide-mediated RNA delivery strategy (See, e.g., Bettinger et al., Nucleic Acids Res. 29:3882-3891 (2001)). For example, the cationic lipid polyethylenimine 2 kDA (Sigma-Aldrich, Saint Louis, Mo., USA) may be combined with the melittin peptide (Alta Biosciences, Birmingham, UK) to increase the efficiency of mRNA transfection, particularly in post-mitotic primary cells. The melittin peptide may be conjugated to the PEI using a disulfide cross-linker such as, for example, the hetero-bifunctional cross-linker succinimidyl 3-(2-pyridyldithio) propionate. In vitro transcribed mRNA is preincubated for 5 to 15 min with the mellitin-PEI to form an RNA/peptide/lipid complex. This complex is then added to cells in serum-free culture medium for 2 to 4 h at 37° C. in a 5% $CO_2$ humidified environment and then removed and the transfected cells allowed to continue growing in culture.

In some embodiments, the synthetic membrane-receiver complex is generated by contacting a suitable isolated erythroid cell precursor or a platelet precursor with an exogenous nucleic acid encoding a receiver polypeptide. In some embodiments, the receiver polypeptide is encoded by a DNA, which is contacted with a nucleated erythroid precursor cell or a nucleated platelet precursor cell. In some embodiments, the receiver polypeptide is encoded by an RNA, which is contacted with a platelet, a nucleate erythroid cell, or a nucleated platelet precursor cell.

Receivers may be genetically introduced into erythroid cell precursors, platelet precursor, or nucleated erythroid cells prior to terminal differentiation using a variety of DNA techniques, including transient or stable transfections and gene therapy approaches. The receiver polypeptides may be expressed on the surface and/or in the cytoplasm of mature red blood cell or platelet.

Viral gene transfer may be used to transfect the cells with DNA encoding a receiver polypeptide. A number of viruses may be used as gene transfer vehicles including Moloney murine leukemia virus (MMLV), adenovirus, adeno-associated virus (AAV), herpes simplex virus (HSV), lentiviruses such as human immunodeficiency virus 1 (HIV 1), and spumaviruses such as foamy viruses, for example (See, e.g., Osten et al., HEP 178:177-202 (2007)). Retroviruses, for example, efficiently transduce mammalian cells including human cells and integrate into chromosomes, conferring stable gene transfer.

A receiver polypeptide may be transfected into an erythroid cell precursor, a platelet precursor, or a nucleated erythroid cell, expressed and subsequently retained and exhibited in a mature red blood cell or platelet. A suitable vector is the Moloney murine leukemia virus (MMLV) vector backbone (Malik et al., Blood 91:2664-2671 (1998)). Vectors based on MMLV, an oncogenic retrovirus, are currently used in gene therapy clinical trials (Hossle et al., News Physiol. Sci. 17:87-92 (2002)). For example, a DNA construct containing the cDNA encoding a receiver polypeptide can be generated in the MMLV vector backbone using standard molecular biology techniques. The construct is transfected into a packaging cell line such as, for example, PA317 cells and the viral supernatant is used to transfect producer cells such as, for example, PG13 cells. The PG13 viral supernatant is incubated with an erythroid cell precursor, a platelet precursor, or a nucleated erythroid cell that has been isolated and cultured or has been freshly isolated as described herein. The expression of the receiver polypeptide may be monitored using FACS analysis (fluorescence-activated cell sorting), for example, with a fluorescently labeled antibody directed against the receiver polypeptide, if it is located on the surface of the synthetic membrane-receiver polypeptide complex. Similar methods may be used to express a receiver polypeptide that is located in the inside of the synthetic membrane-receiver polypeptide complex.

Optionally, a fluorescent tracking molecule such as, for example, green fluorescent protein (GFP) may be transfected using a viral-based approach (Tao et al., Stem Cells 25:670-678 (2007)). Ecotopic retroviral vectors containing DNA encoding the enhanced green fluorescent protein (EGFP) or a red fluorescent protein (e.g., DsRed-Express) are packaged using a packaging cell such as, for example, the Phoenix-Eco cell line (distributed by Orbigen, San Diego, Calif.). Packaging cell lines stably express viral proteins needed for proper viral packaging including, for example, gag, pol, and env. Supernatants from the Phoenix- Eco cells into which viral particles have been shed are used to transduce e.g., erythroid cell precursors, platelet precursors, or a nucleated erythroid cells. In some instances, transduction may be performed on a specially coated surface such as, for example, fragments of recombinant fibronectin to improve the efficiency of retroviral mediated gene transfer (e.g., RetroNectin, Takara Bio USA, Madison, Wis.). Cells are incubated in RetroNectin-coated plates with retroviral Phoenix-Eco supernatants plus suitable co-factors. Transduction may be repeated the next day. In this instance, the percentage of cells expressing EGFP or DsRed-Express may be assessed by FACS. Other reporter genes that may be used to assess transduction efficiency include, for example, beta-galactosidase, chloramphenicol acetyltransferase, and luciferase as well as low-affinity nerve growth factor receptor (LNGFR), and the human cell surface CD24 antigen (Bierhuizen et al., Leukemia 13:605-613 (1999)).

Nonviral vectors may be used to introduce genetic material into suitable erythroid cells, platelets or precursors thereof to generate synthetic membrane-receiver polypeptide complexes. Nonviral-mediated gene transfer differs from viral-mediated gene transfer in that the plasmid vectors contain no proteins, are less toxic and easier to scale up, and have no host cell preferences. The "naked DNA" of plasmid vectors is by itself inefficient in delivering genetic material encoding a receiver polypeptide to a cell and therefore is combined with a gene delivery method that enables entry into cells. A number of delivery methods may be used to transfer nonviral vectors into suitable erythroid cells, platelets or precursors thereof including chemical and physical methods.

A nonviral vector encoding a receiver polypeptide may be introduced into suitable erythroid cells, platelets or precursors thereof using synthetic macromolecules such as cationic lipids and polymers (Papapetrou et al., Gene Therapy 12:S118-S130 (2005)). Cationic liposomes, for example form complexes with DNA through charge interactions. The positively charged DNA/lipid complexes bind to the negative cell surface and are taken up by the cell by endocytosis. This approach may be used, for example, to transfect hematopoietic cells (See, e.g., Keller et al., Gene Therapy 6:931-938 (1999)). For erythroid cells, platelets or precursors thereof the plasmid DNA (approximately 0.5 µg in 25-100 µL of a serum free medium, such as, for example, OptiMEM (Invitrogen, Carlsbad, Calif.)) is mixed with a cationic liposome (approximately 4 µg in 25 µL of serum free medium) such as the commercially available transfection reagent Lipofectamine™ (Invitrogen, Carlsbad, Calif.) and allowed to incubate for at least 20 min to form complexes. The DNA/liposome complex is added to suitable erythroid cells, platelets or precursors thereof and allowed to incubate for 5-24 h, after which time transgene expression or the receiver polypeptide may be assayed. Alternatively, other commercially available liposome tranfection agents may be used (e.g., In vivo GeneSHUTTLE™, Qbiogene, Carlsbad, Calif.).

Optionally, a cationic polymer such as, for example, polyethylenimine (PEI) may be used to efficiently transfect erythroid cell progenitor cells, for example hematopoietic and umbilical cord blood-derived CD34+ cells (See, e.g., Shin et al., Biochim. Biophys. Acta 1725:377-384 (2005)). Human CD34+ cells are isolated from human umbilical cord blood and cultured in Iscove's modified Dulbecco's medium supplemented with 200 ng/ml stem cell factor and 20% heat-inactivated fetal bovine serum. Plasmid DNA encoding the receiver polypeptide is incubated with branched or linear PEIs varying in size from 0.8 K to 750 K (Sigma Aldrich, Saint Louis, Mo., USA; Fermetas, Hanover, Md., USA). PEI is prepared as a stock solution at 4.2 mg/ml distilled water and slightly acidified to pH 5.0 using HCl. The DNA may be combined with the PEI for 30 min at room temperature at various nitrogen/phosphate ratios based on the calculation that 1 µg of DNA contains 3 nmol phosphate and 1 µl of PEI stock solution contains 10 nmol amine nitrogen. The isolated CD34+ cells are seeded with the DNA/cationic complex, centrifuged at 280×g for 5 min and incubated in culture medium for 4 or more h until gene expression of the receiver polypeptide is assessed.

A plasmid vector may be introduced into suitable erythroid cells, platelets or precursors thereof using a physical method such as particle-mediated transfection, "gene gun", biolistics, or particle bombardment technology (Papapetrou, et al., (2005) Gene Therapy 12:S118-S130). In this instance, DNA encoding the receiver polypeptide is absorbed onto gold particles and administered to cells by a particle gun. This approach may be used, for example, to transfect erythroid progenitor cells, e.g., hematopoietic stem cells derived from umbilical cord blood (See, e.g., Verma et al., Gene Therapy 5:692-699 (1998)). As such, umbilical cord blood is isolated and diluted three fold in phosphate buffered saline. CD34+ cells are purified using an anti-CD34 monoclonal antibody in combination with magnetic microbeads coated with a secondary antibody and a magnetic isolation system (e.g., Miltenyi MiniMac System, Auburn, Calif., USA). The CD34+ enriched cells may be cultured as described herein. For transfection, plasmid DNA encoding the receiver polypeptide is precipitated onto a particle, for example gold beads, by treatment with calcium chloride and spermidine. Following washing of the DNA-coated beads with ethanol, the beads may be delivered into the cultured cells using, for example, a Biolistic PDS-1000/He System (Bio-Rad, Hercules, Calif., USA). A reporter gene such as, for example, beta-galactosidase, chloramphenicol acetyltransferase, luciferase, or green fluorescent protein may be used to assess efficiency of transfection.

Optionally, electroporation methods may be used to introduce a plasmid vector into suitable erythroid cells, platelets or precursors thereof. Electroporation creates transient pores in the cell membrane, allowing for the introduction of various molecules into the cells including, for example, DNA and RNA as well as antibodies and drugs. As such, CD34+ cells are isolated and cultured as described herein. Immediately prior to electroporation, the cells are isolated by centrifugation for 10 min at 250×g at room temperature and resuspended at $0.2\text{-}10\times10^{\wedge}6$ viable cells/ml in an electroporation buffer such as, for example, X-VIVO 10 supplemented with 1.0% human serum albumin (HSA). The plasmid DNA (1-50 µg) is added to an appropriate electroporation cuvette along with 500 µl of cell suspension. Electroporation may be done using, for example, an ECM 600 electroporator (Genetronics, San Diego, Calif., USA) with voltages ranging from 200 V to 280 V and pulse lengths ranging from 25 to 70 milliseconds. A number of alternative electroporation instruments are commercially available and may be used for this purpose (e.g., Gene Pulser Xcell™, BioRad, Hercules, Calif.; Celljet Duo, Thermo Science, Milford, Mass.). Alternatively, efficient electroporation of isolated CD34+ cells may be performed using the following parameters: 4 mm cuvette, 1600 µF, 550 V/cm, and 10 µg of DNA per 500 µl of cells at $1\times10^5$ cells/ml (Oldak et al., Acta Biochimica Polonica 49:625-632 (2002)).

Nucleofection, a form of electroporation, may also be used to transfect suitable erythroid cells, platelets or precursors thereof. In this instance, transfection is performed using electrical parameters in cell-type specific solutions that enable DNA (or other reagents) to be directly transported to the nucleus thus reducing the risk of possible degradation in the cytoplasm. For example, a Human CD34 Cell Nucleofector™ Kit (from amaxa inc.) may be used to transfect suitable erythroid cells, platelets or precursors thereof. In this instance, 1-5×10$^6$ cells in Human CD34 Cell Nucleofector™ Solution are mixed with 1-5 μg of DNA and transfected in the Nucleofector™ instrument using preprogrammed settings as determined by the manufacturer.

Erythroid cells, platelets or precursors thereof may be non-virally transfected with a conventional expression vector which is unable to self-replicate in mammalian cells unless it is integrated in the genome. Alternatively, erythroid cells, platelets or precursors thereof may be transfected with an episomal vector which may persist in the host nucleus as autonomously replicating genetic units without integration into chromosomes (Papapetrou et al., Gene Therapy 12:S118-S130 (2005)). These vectors exploit genetic elements derived from viruses that are normally extrachromosomally replicating in cells upon latent infection such as, for example, EBV, human polyomavirus BK, bovine papilloma virus-1 (BPV-1), herpes simplex virus-1 (HSV) and Simian virus 40 (SV40). Mammalian artificial chromosomes may also be used for nonviral gene transfer (Vanderbyl et al., Exp. Hematol. 33:1470-1476 (2005)).

Exogenous nucleic acids encoding a polypeptide receiver may be assembled into expression vectors by standard molecular biology methods known in the art, e.g., restriction digestion, overlap-extension PCR, and Gibson assembly.

Exogenous nucleic acids may comprise a gene encoding a polypeptide receiver that is not normally expressed on the cell surface, e.g., of an erythroid cell, fused to a gene that encodes an endogenous or native membrane protein, such that the receiver polypeptide is expressed on the cell surface. For example, a exogenous gene encoding a receiver polypeptide can be cloned at the N terminus following the leader sequence of a type 1 membrane protein, at the C terminus of a type 2 membrane protein, or upstream of the GPI attachment site of a GPI-linked membrane protein.

Standard cloning methods can be used to introduce flexible amino acid linkers between two fused genes. For example, the flexible linker is a poly-glycine poly-serine linker such as [Gly4Ser]3_(SEQ ID NO: 24) commonly used in generating single-chain antibody fragments from full-length antibodies (Antibody Engineering: Methods & Protocols, Lo 2004), or ala-gly-ser-thr polypeptides such as those used to generate single-chain Arc repressors (Robinson & Sauer, PNAS 1998). In some embodiments, the flexible linker provides the receiver polypeptide with more flexibility and steric freedom than the equivalent construct without the flexible linker. This added flexibility is useful in applications that require binding to a target, e.g., an antibody or protein, or an enzymatic reaction of the receiver for which the active site must be accessible to the substrate (e.g., the target).

An epitope tag may be placed between two fused genes, such as, e.g., a nucleic acid sequence encoding an HA epitope tag—amino acids YPYDVPDYA (Seq. ID No. 4), a CMyc tag—amino acids EQKLISEEDL (Seq. ID No. 5), or a Flag tag—amino acids DYKDDDDK (Seq. ID No. 6). The epitope tag may be used for the facile detection and quantification of expression using antibodies against the epitope tag by flow cytometry, western blot, or immunoprecipitation.

In some embodiments, the synthetic membrane-receiver polypeptide comprises a receiver polypeptide and at least one other heterologous polypeptide. The second polypeptide can be a fluorescent protein. The fluorescent protein can be used as a reporter to assess transduction efficiency. In some embodiments, the fluorescent protein is used as a reporter to assess expression levels of the receiver polypeptide if both are made from the same transcript. In some embodiments, the at least one other polypeptide is heterologous and provides a function, such as, e.g., multiple antigens, multiple capture targets, enzyme cascade. In one embodiment, the recombinant nuceic acid comprises a gene encoding a receiver and a second gene, wherein the second gene is separated from the gene encoding the receiver by a viral-derived T2A sequence (gagggcagaggaagtcttctaacatgcggtgacgtggaggsgsstcccggccct (Seq. ID No. 7)) that is post-translationally cleaved into two mature proteins.

In some embodiments, the receiver polypeptide is complement receptor 1 (CR-1). The gene sequence for complement receptor 1 is amplified using PCR. In some embodiments, the exogenous nucleic acid encoding a receiver polypeptide comprises a gene sequence for a scFv against hepatitis B antigen that is fused to the 3' end of the sequence for Kell and amplified using PCR. In some embodiments, the exogenous nucleic acid encoding a receiver polypeptide comprises a gene sequence for a scFv against hepatitis B antigen that is fused to a poly-glycine/serine linker, followed by the 3' end of the sequence for Kell, and amplified using PCR. In some embodiments, the exogenous nucleic acid encoding a receiver polypeptide comprises the 3' end of a gene sequence for a scFv against hepatitis B antigen that is fused to an epitope tag sequence, of which may be one, or a combination of, an; HA-tag, Green fluorescent protein tag, Myc-tag, chitin binding protein, maltose binding protein, glutathione-S-transferase, poly(His)tag, thioredoxin, poly(NANP), FLAG-tag, V5-tag, AviTag, Calmodulin-tag, polyglutamate-tag, E-tag, S-tag, SBP-tag, Softag-1, Softag-3, Strep-tag, TC-tag, VSV-tag, Xpress-tag, Isopeptag, SpyTag, biotin carboxyl carrier protein, Nus-tag, Fc-tag, or Ty-tag. The entire construct is fused to the 3' end of the sequence for Kell and then amplified using PCR. The exogenous gene constructs encoding the various receiver polypeptides are, for example, subsequently loaded into a lentiviral vector and used to transduce a CD34+ cell population.

In one embodiment, the gene comprising an adenosine deaminase receiver is placed in the pSP64 vector. The vector is linearized and RNA polymerase generates mRNA coding for the receiver polypeptide. In one embodiment, a population of neutrophils is electroporated using an Ingenio electroporation kit such that 10, 100, 1,000, 10,000 TU/ml of mRNA coding for surface expression of GluN1 receiver to generate a synthetic membrane-receiver polypeptide complex. In one embodiment, a population of platelet cells is incubated with Trans-IT mRNA and 10, 100, or 1000 TU/ml (transducing units/ml) of mRNA coding for thymidine phosphorylase protein receiver to generate a synthetic membrane-receiver polypeptide complex. In one embodiment, a population of erythroid cells is incubated with lentiviral vectors comprising exogenous nucleic acid encoding a receiver polypeptide, specific plasmids of which may include; pLKO.1 puro, PLKO.1—TRC cloning vector, pSico, FUGW, pLVTHM, pLJM1, pLion11, pMD2.G, pCMV-VSV-G, pCI-VSVG, pCMV-dR8.2 dvpr, psPAX2, pRSV-Rev, and pMDLg/pRRE to generate a synthetic membrane-receiver polypeptide complex. The vectors may be administered at 10, 100, 1,000, 10,000 pfu and incubated for 12 hrs.

In one embodiment, a population of erythroid cells is incubated with Lipofectamine 2000 and 10, 100, or 1000 TU/ml (transducing units/rill) of DNA coding for oxalase receiver.

In certain embodiments, the polypeptide receiver is conjugated to the synthetic membrane-receiver polypeptide complex. The polypeptide receiver usually is conjugated to the surface of the synthetic membrane-receiver polypeptide complex. Conjugation may be achieved chemically or enzymatically. Non-polypeptide receivers may also be conjugated to a synthetic membrane-receiver complex.

In some embodiments, the synthetic membrane-receiver complex comprises a receiver that is chemically conjugated. Chemical conjugation of a receiver may be accomplished by covalent bonding of the receiver to another molecule, with or without use of a linker. The formation of such conjugates is within the skill of artisans and various techniques are known for accomplishing the conjugation, with the choice of the particular technique being guided by the materials to be conjugated. The addition of amino acids to the polypeptide (C- or N-terminal) which contain ionizable side chains, e.g., aspartic acid, glutamic acid, lysine, arginine, cysteine, histidine, or tyrosine, and are not contained in the active portion of the polypeptide sequence, serve in their unprotonated state as a potent nucleophile to engage in various bioconjugation reactions with reactive groups attached to polymers, e.g., homo- or hetero-bi-functional PEG (e.g., Lutolf and Hubbell, Biomacromolecules 2003; 4:713-22, Hermanson, Bioconjugate Techniques, London. Academic Press Ltd; 1996). Receiver conjugation is not not restricted to polypeptides, e.g., a peptide ligand, an antibody, an antibody fragment, or aptamer but is applicable also for non-polypeptide receivers, e.g., lipids, carbohydrates, nucleic acids, and small molecules.

In an embodiment, the receiver may be bound to the surface of a synthetic membrane-receiver complex through a biotin-streptavidin bridge. For example, a biotinylated antibody receiver may be linked to a non-specifically biotinylated surface of the synthetic membrane-receiver complex through a streptavidin bridge. Antibodies can be conjugated to biotin by a number of chemical means (See, e.g., Hirsch et al., Methods Mol. Biol. 295: 135-154 (2004)). Any surface membrane proteins of a synthetic membrane-receiver complex may be biotinylated using an amine reactive biotinylation reagent such as, for example, EZ-Link Sulfo-NHS—SS-Biotin (sulfosuccinimidyl 2-(biotinamido)-ethyl-1,3-dithiopropionate; Pierce-Thermo Scientific, Rockford, Ill., USA; See, e.g., Jaiswal et al., Nature Biotech. 21:47-51 (2003)). For example, isolated erythroid cells may be incubated for 30 min at 4° C. in 1 mg/nil solution of sulfo-NHS-SS in phosphate-buffered saline. Excess biotin reagent is removed by washing the cells with Tris-buffered saline. The biotinylated cells are then reacted with the biotinylated antibody receiver in the presence of streptavidin to form the synthetic membrane-receiver complex.

In another embodiment, the receiver may be attached to the surface of, e.g., an erythroid cell or platelet with a bispecific antibody to generate the synthetic membrane-receiver complex. For example, the bispecific antibody can have specificity for the erythroid cell or platelet and the receiver.

In another embodiment, the receiver is attached to, e.g., an erythroid cell or platelet via a covalent attachment to generate a synthetic membrane-receiver complex. For example, the receiver may be derivatized and bound to the erythroid cell or platelet using a coupling compound containing an electrophilic group that will react with nucleophiles on the erythroid cell or platelet to form the interbonded relationship. Representative of these electrophilic groups are $\alpha,\beta$ unsaturated carbonyls, alkyl halides and thiol reagents such as substituted maleimides. In addition, the coupling compound can be coupled to a receiver polypeptide via one or more of the functional groups in the polypeptide such as amino, carboxyl and tryosine groups. For this purpose, coupling compounds should contain free carboxyl groups, free amino groups, aromatic amino groups, and other groups capable of reaction with enzyme functional groups. Highly charged receivers can also be prepared for immobilization on, e.g., erythroid cells or platelets through electrostatic bonding to generate synthetic membrane-receiver complexes. Examples of these derivatives would include polylysyl and polyglutamyl enzymes.

The choice of the reactive group embodied in the derivative depends on the reactive conditions employed to couple the electrophile with the nucleophilic groups on the erythroid cell or platelet for immobilization. A controlling factor is the desire not to inactivate the coupling agent prior to coupling of the receiver immobilized by the attachment to the erythroid cell or platelet. Such coupling immobilization reactions can proceed in a number of ways. Typically, a coupling agent can be used to form a bridge between the receiver and the erythroid cell or platelet. In this case, the coupling agent should possess a functional group such as a carboxyl group which can be caused to react with the receiver. One way of preparing the receiver for conjugation includes the utilization of carboxyl groups in the coupling agent to form mixed anhydrides which react with the receiver, in which use is made of an activator which is capable of forming the mixed anhydride. Representative of such activators are isobutylchloroformate or other chloroformates which give a mixed anhydride with coupling agents such as 5,5'-(dithiobis(2-nitrobenzoic acid) (DTNB), p-chloromercuribenzoate (CMB), or m-maleimidobenzoic acid (MBA). The mixed anhydride of the coupling agent reacts with the receiver to yield the reactive derivative which in turn can react with nucleophilic groups on the erythroid cell or platelet to immobilize the receiver.

Functional groups on a receiver polypeptide, such as carboxyl groups can be activated with carbodiimides and the like activators. Subsequently, functional groups on the bridging reagent, such as amino groups, will react with the activated group on the receiver polypeptide to form the reactive derivative. In addition, the coupling agent should possess a second reactive group which will react with appropriate nucleophilic groups on the erythroid cell or platelet to form the bridge. Typical of such reactive groups are alkylating agents such as iodoacetic acid, $\alpha, \beta$ unsaturated carbonyl compounds, such as acrylic acid and the like, thiol reagents, such as mercurials, substituted maleimides and the like.

Alternatively, functional groups on the receiver can be activated so as to react directly with nucleophiles on, e.g., erythroid cells or platelets to obviate the need for a bridge-forming compound. For this purpose, use is made of an activator such as Woodward's Reagent K or the like reagent which brings about the formation of carboxyl groups in the receiver into enol esters, as distinguished from mixed anhydrides. The enol ester derivatives of receivers subsequently react with nucleophilic groups on, e.g., an erythroid cell or platelet to effect immobilization of the receiver, thereby creating a synthetic membrane-receiver complex.

In some embodiments, the synthetic membrane-receiver complex is generated by contacting an erythroid cell with a receiver and optionally a payload, wherein contacting does not include conjugating the receiver to the erythroid cell using an attachment site comprising Band 3 (CD233), aquaporin-1, Glut-1, Kidd antigen, RhAg/R1i50 (CD241), Rli (CD240), Rh30CE (CD240CE), Rh30D (CD240D), Kx, glycophorin B (CD235b), glycophorin C (CD235c), glycophorin D (CD235d), Kell (CD238), Duffy/DARCi (CD234), CR1 (CD35), DAF (CD55), Globoside, CD44, ICAM-4 (CD242), Lu/B-CAM (CD239), XG1/XG2 (CD99), EMMPRIN/neurothelin (CD147), JMH, Glycosyltransferase, Cartwright, Dombrock, C4A/CAB, Scianna, MER2, stomatin, BA-1 (CD24), GPIV (CD36), CD108, CD139, or H antigen (CD173).

In some embodiments, the synthetic membrane-receiver complex comprises a receiver that is enzymatically conjugated.

In specific embodiments, the receiver can be conjugated to the surface of, e.g., an erythroid cell or platelet by various chemical and enzymatic means, including but not limited to those listed in table 9 to generate a synthetic membrane-receiver complex. These methods include chemical conjugation with bifunctional cross-linking agents such as, e.g., an NHS ester-maleimide heterobifunctional crosslinker to connect a primary amine group with a reduced thiol group. These methods also include enzymatic strategies such as, e.g., transpeptidase reaction mediated by a sortase enzyme to connect one polypeptide containing the acceptor sequence LPXTG (SEQ ID NO: 25) or LPXTA (SEQ ID NO: 26) with a polypeptide containing the N-terminal donor sequence GGG, see e.g., Swee et al., PNAS 2013. The methods also include combination methods, such as e.g., sortase-mediated conjugation of Click Chemistry handles (an azide and an alkyne) on the antigen and the cell, respectively, followed by a cyclo-addition reaction to chemically bond the antigen to the cell, see e.g., Neves et al., Bioconjugate Chemistry, 2013.

If desired, a catalytic bond-forming polypeptide domain can be expressed on or in e.g., an erythroid cell or platelet, either intracellularly or extracellularly. Many catalytic bond-forming polypeptides exist, including transpeptidases, sortases, and isopeptidases, including those derived from Spy0128, a protein isolated from Streptococcus pyogenes.

It has been demonstrated that splitting the autocatalytic isopeptide bond-forming subunit (CnaB2 domain) of Spy0128 results in two distinct polypeptides that retain catalytic activity with specificity for each other. The polypeptides in this system are termed SpyTag and SpyCatcher. Upon mixing, SpyTag and SpyCatcher undergo isopeptide bond formation between Asp117 on SpyTag and Lys31 on SpyCatcher (Zakeri and Howarth, JACS 2010, 132:4526). The reaction is compatible with the cellular environment and highly specific for protein/peptide conjugation (Zakeri, B.; Fierer, J. O.; Celik, E.; Chittock, E. C.; Schwarz-Linek, U.; Moy, V. T.; Howarth, M. Proc. Natl. Acad. Sci. U.S.A. 2012, 109, E690-E697). SpyTag and SpyCatcher has been shown to direct post-translational topological modification in elastin-like protein. For example, placement of SpyTag at the N-terminus and SpyCatcher at the C-terminus directs formation of circular elastin-like proteins (Zhang et al, Journal of the American Chemical Society, 2013).

The components SpyTag and SpyCatcher can be interchanged such that a system in which molecule A is fused to SpyTag and molecule B is fused to SpyCatcher is functionally equivalent to a system in which molecule A is fused to SpyCatcher and molecule B is fused to SpyTag. For the purposes of this document, when SpyTag and SpyCatcher are used, it is to be understood that the complementary molecule could be substituted in its place.

A catalytic bond-forming polypeptide, such as a SpyTag/SpyCatcher system, can be used to attach the receiver to the surface of, e.g., an erythroid cell, to generate a synthetic membrane-receiver complex. The SpyTag polypeptide sequence can be expressed on the extracellular surface of the erythroid cell. The SpyTag polypeptide can be, for example, fused to the N terminus of a type-1 or type-3 transmembrane protein, e.g., glycophorin A, fused to the C terminus of a type-2 transmembrane protein, e.g., Kell, inserted in-frame at the extracellular terminus or in an extracellular loop of a multi-pass transmembrane protein, e.g., Band 3, fused to a GPI-acceptor polypeptide, e.g., CD55 or CD59, fused to a lipid-chain-anchored polypeptide, or fused to a peripheral membrane protein. The nucleic acid sequence encoding the SpyTag fusion can be expressed within a synthetic membrane-receiver complex. A receiver polypeptide can be fused to SpyCatcher. The nucleic acid sequence encoding the SpyCatcher fusion can be expressed and secreted from the same erythroid cell that expresses the SpyTag fusion. Alternatively, the nucleic acid sequence encoding the SpyCatcher fusion can be produced exogenously, for example in a bacterial, fungal, insect, mammalian, or cell-free production system. Upon reaction of the SpyTag and SpyCatcher polypeptides, a covalent bond will be formed that attaches the receiver to the surface of the erythroid cell to form a synthetic membrane-receiver complex. An erythroid cell comprising the receiver polypeptide fusion is an example of a synthetic membrane-receiver polypeptide complex that comprises a conjugated receiver.

In one embodiment, the SpyTag polypeptide may be expressed as a fusion to the N terminus of glycophorin A under the control of the Gata1 promoter in an erythroid cell. A receiver polypeptide, for example complement receptor 1 and the receivers listed in table 7, fused to the SpyCatcher polypeptide sequence can be expressed under the control of the Gata1 promoter in the same erythroid cell. Upon expression of both fusion polypeptides, an isopeptide bond will be formed between the SpyTag and SpyCatcher polypeptides, forming a covalent bond between the erythroid cell surface and the receiver polypeptide. An erythroid cell comprising the receiver polypeptide fusion is an example of a synthetic membrane-receiver polypeptide complex that comprises a conjugated receiver.

In another embodiment, the SpyTag polypeptide may be expressed as a fusion to the N terminus of glycophorin A under the control of the Gata1 promoter in an erythroid cell. A receiver polypeptide, for example complement receptor 1, fused to the SpyCatcher polypeptide sequence can be expressed in a suitable mammalian cell expression system, for example HEK293 cells. Upon expression of the SpyTag fusion polypeptide on the erythroid cell, the SpyCatcher fusion polypeptide can be brought in contact with the cell. Under suitable reaction conditions, an isopeptide bond will be formed between the SpyTag and SpyCatcher polypeptides, forming a covalent bond between the erythroid cell surface and the receiver polypeptide. An erythroid cell comprising the receiver polypeptide fusion is an example of a synthetic membrane-receiver polypeptide complex that comprises a conjugated receiver.

A catalytic bond-forming polypeptide, such as a SpyTag/SpyCatcher system, can be used to anchor a receiver molecule to the intracellular space of an erythroid cell. The SpyTag polypeptide sequence can be expressed in the intracellular space of the erythroid cell by a number of methods, including direct expression of the transgene, fusion to an endogenous intracellular protein such as, e.g., hemoglobin, fusion to the intracellular domain of endogenous cell surface proteins such as, e.g., Band 3, glycophorin A, Kell, or fusion to a structural component of the erythroid cytoskeleton. The SpyTag sequence is not limited to a polypeptide terminus and may be integrated within the interior sequence of an endogenous polypeptide such that polypeptide translation and localization is not perturbed. A receiver polypeptide can be fused to SpyCatcher. The nucleic acid sequence encoding the SpyCatcher fusion can be expressed within the same erythroid cell that expresses the SpyTag fusion. Upon reaction of the SpyTag and SpyCatcher polypeptides, a covalent bond will be formed that acts to anchor the receiver polypeptide in the intracellular space of the erythroid cell. An erythroid cell comprising the receiver polypeptide fusion is an example of a synthetic membrane-receiver polypeptide complex that comprises a conjugated receiver.

In one embodiment, an erythroid cell may express SpyTag fused to hemoglobin beta intracellularly. The erythroid cell may be genetically modified with a gene sequence that includes a hemoglobin promoter, beta globin gene and a SpyTag sequence such that upon translation, intracellular beta globin is fused to SpyTag at is C terminus. In addition, the erythroid cell expresses a Gata 1 promoter-led gene that codes for SpyCatcher driving phenylalanine hydroxylase (PAH) expression such that upon translation, intracellular PAH is fused to SpyCatcher at its N terminus. Upon expression of both fusion proteins the SpyTag bound beta globin is linked through an isopeptide bond to the SpyCatcher bound PAH in the intracellular space, allowing PAH to be anchored to beta globin and retained during maturation. An erythroid cell comprising the receiver polypeptide fusion is an example of a synthetic membrane-receiver polypeptide complex that comprises a conjugated receiver.

In another embodiment, the SpyTag polypeptide can be expressed as a fusion to the receiver polypeptide within an erythroid cell. The SpyCatcher polypeptide can be expressed as a fusion to the C terminus (intracellular) of glycophorin A within the same erythroid cell. Upon expression of both fusion polypeptides, an isopeptide bond will be formed between the SpyTag and SpyCatcher polypeptides, forming a covalent bond between the membrane-anchored endogenous erythroid polypeptide and the receiver molecule. An erythroid cell comprising the receiver polypeptide fusion is an example of a synthetic membrane-receiver polypeptide complex that comprises a conjugated receiver.

Other molecular fusions may be formed between polypeptides and include direct or indirect conjugation. The polypeptides may be directly conjugated to each other or indirectly through a linker. The linker may be a peptide, a polymer, an aptamer, or a nucleic acid. The polymer may be, e.g., natural, synthetic, linear, or branched. Receiver polypeptides can comprise a heterologous fusion protein that comprises a first polypeptide and a second polypeptide with the fusion protein comprising the polypeptides directly joined to each other or with intervening linker sequences and/or further sequences at one or both ends. The conjugation to the linker may be through covalent bonds or ionic bonds.

In certain embodiments, the polypeptide receiver is loaded into the synthetic membrane-receiver polypeptide complex. Non-polypeptide receivers may also be loaded within a synthetic membrane-receiver complex. In some embodiments, synthetic membrane-receiver complexes are generated by loading, e.g., erythroid cells or platelets with one or more receivers, such that the one or more receivers are internalized within the erythroid cells or platelets. Optionally, the erythroid cells or platelets may additionally be loaded with a payload, such as, e.g., a therapeutic agent.

A number of methods may be used to load, e.g., erythroid cells or platelets with a receiver and optionally a payload (e.g., a therapeutic agent). Suitable methods include, for example, hypotonic lysis, hypotonic dialysis, osmosis, osmotic pulsing, osmotic shock, ionophoresis, electroporation, sonication, microinjection, calcium precipitation, membrane intercalation, lipid mediated transfection, detergent treatment, viral infection, diffusion, receptor mediated endocytosis, use of protein transduction domains, particle firing, membrane fusion, freeze-thawing, mechanical disruption, and filtration. Any one such method or a combination thereof may be used to generate the synthetic membrane-receiver complexes described herein.

For hypotonic lysis, e.g., erythroid cell are exposed to low ionic strength buffer causing them to burst. The receiver or the payload (e.g., a therapeutic agent) distributes within the cells. Erythroid cell, specifically red blood cells may be hypotonically lysed by adding 30-50 fold volume excess of 5 mM phosphate buffer (pH 8) to a pellet of isolated red blood cells. The resulting lysed cell membranes are isolated by centrifugation. The pellet of lysed red blood cell membranes is resuspended and incubated in the presence of the receiver and/or therapeutic agent in a low ionic strength buffer, e.g., for 30 min. Alternatively, the lysed red blood cell membranes may be incubated with the receiver or the payload (e.g., a therapeutic agent) for as little as one minute or as long as several days, depending upon the best conditions determined to efficiently load the erythroid cells.

Alternatively, erythroid cells, specifically red blood cells may be loaded with a receiver and optionally a payload (e.g., a therapeutic agent) using controlled dialysis against a hypotonic solution to swell the cells and create pores in the cell membrane (See, e.g., U.S. Pat. Nos. 4,327,710; 5,753,221; and 6,495,351). For example, a pellet of isolated red blood cells is resuspended in 10 mM HEPES, 140 mM NaCl, 5 mM glucose pH 7.4 and dialyzed against a low ionic strength buffer containing 10 mM $NaH_2PO_4$, 10 mM $NaHCO_3$, 20 mM glucose, and 4 mM $MgCl_2$, pH 7.4. After 30-60 min, the red blood cells are further dialyzed against 16 mM $NaH_2PO_4$, pH 7.4 solution containing the receiver or the payload (e.g., a therapeutic agent) for an additional 30-60 min. All of these procedures may be advantageously performed at a temperature of 4° C. In some instances, it may be beneficial to load a large quantity of erythroid cells, specifically red blood cells with a therapeutic agent by a dialysis approach and a specific apparatus designed for this purpose may be used (See, e.g., U.S. Pat. Nos. 4,327,710, 6,139,836 and 6,495,351 B2).

The loaded erythroid cells, specifically red blood cells can be resealed by gentle heating in the presence of a physiological solution such as, for example, 0.9% saline, phosphate buffered saline, Ringer's solution, cell culture medium, blood plasma or lymphatic fluid. For example, well-sealed membranes may be generated by treating the disrupted erythroid cells, specifically red blood cells for 1-2 min in 150 mM salt solution of, for example, 100 mM phosphate (pH 8.0) and 150 mM sodium chloride at a temperature of 60° C. Alternatively, the cells may be incubated at a temperature of 25-50° C. for 30 min to 4 h (See, e.g., U.S. Patent Application 2007/0243137 A1). Alternatively, the disrupted red blood cells may be resealed by incubation in 5 mM adenine, 100 mM inosine, 2 mM ATP, 100 mM glucose, 100 mM Na-pyruvate, 4 mM MgCl2, 194 mM NaCl, 1.6 M KCl, and 35 mM $NaH_2PO_4$, pH 7.4 at a temperature of 37° C. for 20-30 min (See, e.g., U.S. Pat. No. 5,753,221).

For electroporation, e.g., erythroid cells or platelets are exposed to an electrical field which causes transient holes in the cell membrane, allowing the receiver and optional payload (e.g., therapeutic agent) to diffuse into the cell (See, e.g., U.S. Pat. No. 4,935,223). Erythroid cells, specifically red blood cells, for example, are suspended in a physiological and electrically conductive media such as platelet-free plasma to which the receiver and optional payload (e.g., therapeutic agent) is added. The mixture in a volume ranging from 0.2 to 1.0 ml is placed in an electroporation cuvette and cooled on ice for 10 min. The cuvette is placed in an electroporation apparatus such as, for example, an ECM 830 (from BTX Instrument Division, Harvard Apparatus, Holliston, Mass.). The cells are electroporated with a single pulse of approximately 2.4 milliseconds in length and a field strength of approximately 2.0 kV/cm. Alternatively, electroporation of erythroid cells, specifically red blood cells may be carried out using double pulses of 2.2 kV delivered at 0.25 µF using a Bio-Rad Gene Pulsar apparatus (Bio-Rad, Hercules, Calif., USA) to achieve a loading capacity of over 60% (Flynn et al., Cancer Lett. 82:225-229 (1994)). The cuvette is returned to the ice bath for 10-60 min and then placed in a 37° C. water bath to induce resealing of the cell membrane. Any suitable electroporation method may be used to generate the synthetic membrane-receiver complexes described herein.

For sonication, erythroid cells are, for example, exposed to high intensity sound waves, causing transient disruption of the cell membrane allowing the receiver and optional payload (e.g., therapeutic agent) to diffuse into the cell. Any suitable sonication method may be used to generate the synthetic membrane-receiver complexes described herein.

For detergent treatment, erythroid cells, for example, are treated with a mild detergent which transiently compromises the cell membrane by creating holes through which the receiver and optional payload (e.g., therapeutic agent) may diffuse. After cells are loaded, the detergent is washed from the cells. For example, the detergent may be saponin. Any suitable detergent treatment method may be used to generate the synthetic membrane-receiver complexes described herein.

For receptor mediated endocytosis, erythroid cells, for example, may have a surface receptor which upon binding of the receiver or payload (e.g., therapeutic agent) induces internalization of the receptor and the associated receiver or payload (e.g., therapeutic agent). Any suitable endocytosis method may be used to generate the synthetic membrane-receiver complexes described herein.

In some embodiments, the receiver and optional payload (e.g., therapeutic agent) may be loaded, e.g., into an erythroid cell or platelet by fusing or conjugating the receiver or payload to proteins and/or polypeptides capable of crossing or translocating the plasma membrane (See, e.g., U.S. Patent Application 2002/0151004 A1). Examples of protein domains and sequences that are capable of translocating a cell membrane include, for example, sequences from the HIV-1-transactivating protein (TAT), the *Drosophila* Antennapedia homeodomain protein, the herpes simplex-1 virus VP22 protein, and transportin, a fusion between the neuropeptide galanin and the wasp venom peptide mastoparan. For example, a payload may be fused or conjugated to all or part of the TAT peptide. A receiver fusion protein containing all or part of the TAT peptide and/or a fusion protein containing all or part of the TAT peptide and the payload (e.g., a therapeutic agent, such as an antibody, enzyme, or peptide) may be generated using standard recombinant DNA methods. Alternatively, all or part of the TAT peptide (including receivers comprising all or part of the TAT peptide) may be chemically coupled to a functional group associated with the payload (e.g., therapeutic agent) such as, for example, a hydroxyl, carboxyl or amino group. In some instances, the link between the TAT peptide and the payload may be pH sensitive such that once the conjugate or fusion has entered the intracellular environment, the therapeutic agent is separated from the TAT peptide.

In some embodiments, the synthetic membrane-receiver complex is generated by contacting an erythroid cell with a receiver and optionally a payload without lysing and resealing the cells to incorporate the receiver and/or payload. In some embodiments, the synthetic membrane-receiver complex is generated by contacting an erythroid cell with a receiver and optionally a payload, wherein contacting does not comprise hypotonic dialysis.

In some embodiments, the synthetic membrane-receiver complex is generated by contacting an erythroid cell with a receiver and optionally a payload, wherein contacting does not include loading the receiver and/or payload into or onto the erythroid cell. In some embodiments, the receiver is generated in an entity that is not the erythroid cell to be contacted and/or the receiver is isolated from a sample that does not comprise the erythroid cell to be contacted. For example, for a polypeptide receiver suitable entities include a cell line, an in vitro expression system, a bacterial expression system, etc.

For mechanical firing, erythroid cells, for example, may be bombarded with the receiver and optional payload (e.g., therapeutic agent) attached to a heavy or charged particle such as, for example, gold microcarriers and are mechanically or electrically accelerated such that they traverse the cell membrane. Microparticle bombardment may be achieved using, for example, the Helios Gene Gun (from, e.g., Bio-Rad, Hercules, Calif., USA). Any suitable microparticle bombardment method may be used to generate the synthetic membrane-receiver complexes described herein.

In some embodiments, erythroid cells or platelets may be loaded with a receiver and optional payload (e.g., therapeutic agent) by fusion with a synthetic vesicle such as, for example, a liposome. In this instance, the vesicles themselves are loaded with the receiver and optional payload using one or more of the methods described herein or known in the art. Alternatively, the receiver and optional payload (e.g., therapeutic agent) may be loaded into the vesicles during vesicle formation. The loaded vesicles are then fused with the erythroid cells or platelets under conditions that enhance cell fusion. Fusion of a liposome, for example, with a cell may be facilitated using various inducing agents such as, for example, proteins, peptides, polyethylene glycol (PEG), and viral envelope proteins or by changes in medium conditions such as pH (See, e.g., U.S. Pat. No. 5,677,176). Any suitable liposomal fusion method may be used to generate the synthetic membrane-receiver complexes described herein.

For filtration, erythroid cells or platelets and the receiver and optional payload (e.g., therapeutic agent) may be forced through a filter of pore size smaller than the cell causing transient disruption of the cell membrane and allowing the receiver and optional therapeutic agent to enter the cell. Any suitable filtration method may be used to generate the synthetic membrane-receiver complexes described herein.

For freeze thawing, erythroid cells are subjected to several freeze thaw cycles, resulting in cell membrane disruption (See, e.g., U.S. Patent Application 2007/0243137 A1). In this instance, a pellet of packed red blood cells (0.1-1.0 ml)

is mixed with an equal volume (0.1-1.0 ml) of an isotonic solution (e.g., phosphate buffered saline) containing the receiver and optional payload (e.g., therapeutic agent). The red blood cells are frozen by immersing the tube containing the cells and receiver and optional payload into liquid nitrogen. Alternatively, the cells may be frozen by placing the tube in a freezer at −20° C. or −80° C. The cells are then thawed in, e.g., a 23° C. water bath and the cycle repeated if necessary to increase loading. Any suitable freeze-thaw method may be used to generate the synthetic membrane-receiver complexes described herein.

The receiver and optional payload (e.g., therapeutic agent) may be loaded into a cell, e.g., an erythroid cell or platelet in a solubilized form, e.g., solubilized in an appropriate buffer prior to loading into erythroid cells or platelets.

Alternatively, the receiver and optional payload (e.g., therapeutic agent) may be loaded into a cell, e.g., an erythroid cell or platelet in a particulate form as a solid microparticulate (See, e.g., U.S. Patent Applications 2005/0276861 A1 and U.S. 2006/0270030 A1). In this instance, the receiver or payload may be poorly water-soluble with a solubility of less than 1-10 mg/ml. Microparticles of poorly water-soluble receivers or payloads can be made of less than 10 µm using a variety of techniques such as, for example, energy addition techniques such as milling (e.g., pearl milling, ball milling, hammer milling, fluid energy milling, jet milling), wet grinding, cavitation or shearing with a microfluidizer, and sonication; precipitation techniques such as, for example, microprecipitation, emulsion precipitation, solvent-antisolvent precipitation, phase inversion precipitation, pH shift precipitation, infusion precipitation, temperature shift precipitation, solvent evaporation precipitation, reaction precipitation, compressed fluid precipitation, protein microsphere precipitation; and other techniques such as spraying into cryogenic fluids (See, e.g., U.S. Patent Application 2005/0276861 A1). Water soluble receivers or payloads may also be used to form solid microparticles in the presence of various polymers such as, for example, polylactate-polyglycolate copolymer (PLGA), polycyanoacrylate, albumin, and/or starch (See, e.g., U.S. Patent Application 2005/0276861 A1). Alternatively, a water soluble receivers or payloads may be encapsulated in a vesicle to form a microparticle. The microparticles composed of the receiver and optional payload (e.g., therapeutic agent) may be incorporated into a cell, such as an erythroid cell or platelet using the methods described herein.

In specific embodiments, synthetic membrane-receiver complexes are generated from erythrocytes. For example, erythrocytes may be loaded with a receiver polypeptide or mRNA encoding a receiver polypetide by controlled cell injury. The cell injury can be caused by, for example, pressure induced by mechanical strain or shear forces, subjecting the cell to deformation, constriction, rapid stretching, rapid compression, or pulse of high shear rate. The controlled cell injury leads to uptake of material, e.g., a receiver and optionally a payload into the cytoplasm of the cell from the surrounding cell medium. Any suitable controlled injury method may be used to generate the synthetic membrane-receiver complexes described herein.

Using controlled cell injury based on controlled cell deformation (e.g., mechanical deformation of the cell as it passes through the constriction) leads to uptake of material, e.g., a receiver and optionally a payload by diffusion rather than endocytosis. The material, e.g., a receiver and optionally a payload is present in the cytoplasm rather than in endosomes following cellular uptake upon the controlled injury thereby making the material readily available to the cell. Controlled cell injury, e.g., by controlled deformation, preserves cell viability (e.g., greater than 50%, 70%, or greater than 90%). In certain embodiments, controlled cell injury, e.g., by controlled deformation, preserves the state of cellular differentiation and activity. If desired, a combination treatment is used, e.g., controlled injury by deformation followed by or preceded by, e.g., electroporation or another cell membrane permeability increasing method. Optionally, surfactants may be used.

Mechanical deformation methods are particularly suitable for cells that do not tolerate other membrane permeability increasing methods well, e.g., show decreased viability or a different state of differentiation after performing such methods. Mechanical deformation methods are also suitable for material, e.g., a receiver and optionally a payload that does not tolerate other membrane permeability increasing methods well. Alternatively or in addition, the receiver or payload may not be sufficiently introduced into the cell using alternative methods, e.g., because of e.g., charge, hydrophobicity, or size of the payload.

One exemplar method of controlled injury by deformation and devices suitable for such methods is described, e.g., in PCT Publication No. WO2013059343 INTRACELLULAR DELIVERY, incorporated herein by reference.

In a specific embodiment, a population of reticulocytes is provided that has been subjected to controlled cell injury by controlled deformation to introduce a receiver, thereby generating a synthetic membrane-receiver complex. The cells can, e.g., be compressed and deformed by passage through a micro-channel having a diameter less than that of an individual reticulocyte, thereby causing perturbations in the cell membrane such that the membrane becomes porous. Cells are moved, e.g., pushed, through the channels or conduits by application of pressure. The compression and deformation occurs in a delivery medium comprising, e.g., receiver polypeptide or oligonucleotide (e.g., DNA, RNA, such as mRNA) and optionally a payload. For example, the delivery medium may comprise a receiver including but not limited to those listed in table 7 or coding mRNA thereof. Upon deformation the reticulocyte takes up and retains the exogenous material. Following controlled injury to the cell by constriction, stretching, and/or a pulse of high shear rate, the cells are optionally incubated in a delivery medium that contains the material, e.g., a receiver and optionally a payload. The cells may be maintained in the delivery medium for a few minutes to recover, e.g., to close the injury caused by passing through the constriction. This may occur at room temperature.

Controlled cell injury as used herein includes: i) virus-mediated transfection (e.g., Herpes simplex virus, Adeno virus, Adeno-associated virus, Vaccinia virus, or Sindbis virus), ii) chemically-mediated transfection, e.g., cationic polymer, calcium phosphate, cationic lipid, polymers, and nanoparticles, such as cyclodextrin, liposomes, cationic liposomes, DEAE-dextran, polyethyleneimine, dendrimer, polybrene, calcium phosphate, lipofectin, DOTAP, lipofectamine, CTAB/DOPE, DOTMA; and iii) physically-mediated transfection, including direct injection, biolistic particle delivery, electroporation, laser-irradiation, sonoporation, magnetic nanoparticles, and controlled deformation (e.g., cell squeezing), as exemplified by micro-needle, nano-needle, femtosyringe, atomic-force microscopy (AFM) tip, gene gun (e.g., gold nanoparticles), Amaxa Nucleofector, phototransfection (multi-photon laser), impalefection, and magnetofection, and other suitable methods known in the art. Any suitable method may be used to obtain a synthetic membrane-receiver complex described herein comprising one or more DNA, RNA (e.g., mRNA encoding a receiver polypeptide), or receiver polypeptides and optionally a payload (e.g., a therapeutic agent).

Polypeptide receivers can be detected on the synthetic membrane-receiver complex. The presence of the receiver polypeptide can be validated and quantified using standard molecular biology methods, e.g., Western blotting or FACS analysis. Receiver polypeptides present in the intracellular environment may be quantified upon cell lysis or using fluorescent detection.

For example, a population of erythroid cells is loaded with adenosine deaminase (ADA) using the Pro-Ject protein transfection reagent kit to generate a synthetic membrane-ADA receiver complex. The population of synthetic membrane-ADA receiver complexes is then characterized for active enzyme loading using LCMS to quantify adenosine and inosine.

Alternatively, the population of erythroid cells is incubated in a solution of 10 mM, 100 mM, 500 mM chlorpromazine and 0.01, 0.1, 1.0, 10, 100 mg/ml of adenosine deaminase (ADA). The population of synthetic membrane-ADA receiver complexes are then washed and fluorescent imaging is used to quantify ADA loading.

In one embodiment, a population of erythrocytes is incubated in a hypotonic salt solution containing a concentration of 0.01, 0.1, 1.0, 10 mg/ml of asparaginase to generate a synthetic membrane-asparaginase receiver complex. The cell population is incubated for 1 hr and then resealed by incubation in a hypertonic solution for 10 min. The population of synthetic membrane—asparaginase receiver complexes is then incubated in an asparagine solution for 1 hr and the asparagine and aspartate concentrations are quantified using LCMS.

To generate a synthetic membrane—thymidine phosphorylase receiver complex, a population of erythrocytes is incubated in a PBS solution containing a concentration of 0.01, 0.1, 1.0, 10 mg/ml of thymidine phosphorylase that has been fused via both the C and N termini to one or more cell penetrating peptides, including; Penetratin, Antenapedia, TAT, SynB1, SynB3, PTD-4, PTD-5, FHV Coat-(35-49), BMV Gag-(7-25), HTLV-II Rex-(4-16), D-TAT, R9-Tat, Transportan, MAP, SBP, FBP, MPG ac, MPG(NLS), Pep-1, Pep-2, polyarginines, polylysines, (RAca)6R, (RAbu)6R, (RG)6R, (RM)6R, R10, (RA)6R, R7. Following incubation, synthetic membrane—thymidine phosphorylase receiver complexes are placed in a solution of thymidine for 1 hr and samples are quantified for thymine and thymidine content using LCMS.

Cells may be loaded using a microfluidic device that transiently porates the cells, allowing a payload to enter when the cells are pressured through the system. In one embodiment, a population of erythrocytes is pressured through a system of microfluidic channels in a buffer solution containing 0.01, 0.1, 1.0, 10 mg/ml of phenylalanine ammonia hydroxylase. The cell suspension is then characterized for enzymatic activity using LCMS to quantify phenylalanine and trans-cinnamic acid.

In one embodiment, a synthetic cell membrane-receiver complexes are incubated in a hypotonic solution containing 1 mM of adenosine deaminase for 1 hr. The synthetic membrane-receiver complexes are then transferred to an isotonic solution and allowed to equilibrate and seal in the soluble protein.

Payloads for Synthetic Membrane-Receiver Complexes

Synthetic membrane-receiver complexes may optionally be loaded with payloads such as peptides, proteins, DNA, RNA, siRNA, and other macromolecules and small therapeutic molecules. In some embodiments, the payload is transferred to a cell, e.g., an erythroid cell or platelet by applying controlled injury to the cell for a predetermined amount of time in order to cause perturbations in the cell membrane such that the payload can be delivered to the inside of the cell (e.g., cytoplasm).

The payload may be a therapeutic agent selected from a variety of known small molecule pharmaceuticals. Alternatively, the payload may be may be a therapeutic agent selelcted from a variety of macromolecules, such as, e.g., an inactivating peptide nuclei acid (PNA), an RNA or DNA oligonucleotide aptamer, an interfering RNA (iRNA), a peptide, or a protein.

In some embodiments, the synthetic membrane-receiver complex is generated from a reticulocyte. For example, reticulocytes may be loaded with an mRNA encoding for a therapeutic exogenous polypeptide by controlled cell injury. The mRNA may be naked or modified, as desired. mRNA modification that improve mRNA stability and/or decrease immunogenicity include, e.g., ARCA: anti-reverse cap analog ($m_2^{7.3'-O}$ $GP_3G$), $GP_3G$ (Unmethylated Cap Analog), $m^7GP_3G$ (Monomethylated Cap Analog), $m_3^{2.2.7}GP_3G$ (Trimethylated Cap Analog), m5CTP (5'-methyl-cytidine triphosphate), m6ATP (N6-methyl-adenosine-5'-triphosphate), s2UTP (2-thio-uridine triphosphate), and Ψ (pseudouridine triphosphate).

Synthetic membrane-receiver complexes may comprise two or more payloads, including mixtures, fusions, combinations and conjugates, of atoms, molecules, etc. as disclosed herein, for example including but not limited to, a nucleic acid combined with a polypeptide; two or more polypeptides conjugated to each other; a protein conjugated to a biologically active molecule (which may be a small molecule such as a prodrug); and the like.

In some embodiments, the pharmaceutical composition comprises one or more therapeutic agents and the synthetic membrane-receiver complex described herein. In some embodiments, the synthetic membrane-receiver complexes are co-administered with of one or more separate therapeutic agents, wherein co-administration includes administration of the separate therapeutic agent before, after or concurrent with administration of the synthetic membrane-receiver complex.

Suitable payloads include, without limitation, pharmacologically active drugs and genetically active molecules, including antineoplastic agents, anti-inflammatory agents, hormones or hormone antagonists, ion channel modifiers, and neuroactive agents. Examples of suitable payloads of therapeutic agents include those described in, "The Pharmacological Basis of Therapeutics," Goodman and Gilman, McGraw-Hill, New York, N.Y., (1996), Ninth edition, under the sections: Drugs Acting at Synaptic and Neuroeffector Junctional Sites; Drugs Acting on the Central Nervous System; Autacoids: Drug Therapy of Inflammation; Water, Salts and Ions; Drugs Affecting Renal Function and Electrolyte Metabolism; Cardiovascular Drugs; Drugs Affecting Gastrointestinal Function; Drugs Affecting Uterine Motility; Chemotherapy of Parasitic Infections; Chemotherapy of Microbial Diseases; Chemotherapy of Neoplastic Diseases; Drugs Used for Immunosuppression; Drugs Acting on Blood-Forming organs; Hormones and Hormone Antagonists; Vitamins, Dermatology; and Toxicology, all incorporated herein by reference. Suitable payloads further include toxins, and biological and chemical warfare agents, for example see Somani, S. M. (ed.), Chemical Warfare Agents, Academic Press, New York (1992)).

In some embodiments, the synthetic membrane-receptor complex does not comprise a payload comprising a synthetic triphosphorylated nucleoside analog. In some embodiments, the synthetic membrane-receptor complex does not comprise a payload comprising 2',3'-dideoxycytidine-5'-triphosphate (ddCTP) and/or 3'-azido-3'-deoxythymidine-5'-triphosphate (AZT-TP).

In some embodiments, the synthetic membrane-receptor complex does not comprise a payload comprising a bisphosphonate.

In some embodiments, the payload is a therapeutic agent, such as a small molecule drug or a large molecule biologic. Large molecule biologics include, but are not limited to, a protein, polypeptide, or peptide, including, but not limited to, a structural protein, an enzyme, a cytokine (such as an interferon and/or an interleukin), a polyclonal or monoclonal antibody, or an effective part thereof, such as an Fv fragment, which antibody or part thereof, may be natural, synthetic or humanized, a peptide hormone, a receptor, or a signaling molecule.

Large molecule biologics are immunoglobulins, antibodies, Fv fragments, etc., that are capable of binding to antigens in an intracellular environment. These types of molecules are known as "intrabodies" or "intracellular antibodies." An "intracellular antibody" or an "intrabody" includes an antibody that is capable of binding to its target or cognate antigen within the environment of a cell, or in an environment that mimics an environment within the cell. Selection methods for directly identifying such "intrabodies" include the use of an in vivo two-hybrid system for selecting antibodies with the ability to bind to antigens inside mammalian cells. Such methods are described in PCT/GB00/00876, incorporated herein by reference. Techniques for producing intracellular antibodies, such as anti-β-galactosidase scFvs, have also been described in Martineau et al., J Mol Biol 280:117-127 (1998) and Visintin et al., Proc. Natl. Acad. Sci. USA 96:11723-1728 (1999).

Large molecule biologics include but is not limited to, at least one of a protein, a polypeptide, a peptide, a nucleic acid, a virus, a virus-like particle, an amino acid, an amino acid analogue, a modified amino acid, a modified amino acid analogue, a steroid, a proteoglycan, a lipid and a carbohydrate or a combination thereof (e.g., chromosomal material comprising both protein and DNA components or a pair or set of effectors, wherein one or more convert another to active form, for example catalytically).

A Large molecule biologic may include a nucleic acid, including, but not limited to, an oligonucleotide or modified oligonucleotide, an antisense oligonucleotide or modified antisense oligonucleotide, an aptamer, a cDNA, genomic DNA, an artificial or natural chromosome (e.g., a yeast artificial chromosome) or a part thereof, RNA, including an siRNA, a shRNA, mRNA, tRNA, rRNA or a ribozyme, or a peptide nucleic acid (PNA); a virus or virus-like particles; a nucleotide or ribonucleotide or synthetic analogue thereof, which may be modified or unmodified.

The large molecule biologic can also be an amino acid or analogue thereof, which may be modified or unmodified or a non-peptide (e.g., steroid) hormone; a proteoglycan; a lipid; or a carbohydrate. If the large molecule biologic is a polypeptide, it can be loaded directly into, e.g., an erythroid cell or a platelet according to the methods described herein. Alternatively, an exogenous nucleic acid encoding a polypeptide, which sequence is operatively linked to transcriptional and translational regulatory elements active in a cell at a target site, may be loaded.

Small molecules, including inorganic and organic chemicals, may also be used as payloads of the synthetic membrane-receptor complexes described herein.

In some embodiments, the small molecule is a pharmaceutically active agent. Useful classes of pharmaceutically active agents include, but are not limited to, antibiotics, anti-inflammatory drugs, angiogenic or vasoactive agents, growth factors and chemotherapeutic (anti-neoplastic) agents (e.g., tumour suppressers).

If a prodrug is loaded into the synthetic membrane-receiver complex in an inactive form it is often useful that the synthetic membrane-receiver complex further comprises a receiver such as an activating polypeptide which converts the inactive prodrug to active drug form. In an embodiment, activating receiver polypeptides include, but are not limited to, viral thymidine kinase (encoded by Genbank Accession No. J02224), carboxypeptidase A (encoded by Genbank Accession No. M27717), α-galactosidase (encoded by Genbank Accession No. M13571), β-gluucuronidase (encoded by Genbank Accession No. M15182), alkaline phosphatase (encoded by Genbank Accession No. J03252 J03512), or cytochrome P-450 (encoded by Genbank Accession No. D00003 N00003), plasmin, carboxypeptidase G2, cytosine deaminase, glucose oxidase, xanthine oxidase, β-glucosidase, azoreductase, t-gutamyl transferase, β-lactamase, and penicillin amidase.

Either the receiver polypeptide or the exogenous gene encoding it may be loaded into, e.g., an erythroid cell or platelet, to generate a synthetic membrane-receptor complex. Both the prodrug and the activating receiver polypeptide may be encoded by genes on the same exogenous nucleic acid. Furthermore, either the prodrug or the the activating receiver polypeptide of the prodrug may be transgenically expressed in a synthetic membrane-receptor complex.

The synthetic membrane-receptor complexes may also be labeled with one or more positive markers that can be used to monitor over time the number or concentration of synthetic membrane-receptor complexes in the blood circulation of an individual. The overall number of synthetic membrane-receptor complexes will decay over time following initial transfusion. In some embodiments, the signal from one or more positive markers are correlated with that of an activated molecular marker, generating a proportionality of signal that is independent of the number of synthetic membrane-receptor complexes remaining in the circulation. Suitable fluorescent compounds include those that are approved by the Food & Drug Administration for human use including but not limited to fluorescein, indocyanin green, and rhodamine B. For example, synthetic membrane-receiver complexes may be non-specifically labeled with fluorescein isothiocyanate (FITC; Bratosin et al., Cytometry 46:351-356 (2001)). For example, a solution of FITC-labeled lectins in phosphate buffered saline (PBS) with 0.2 mM phenylmethysulfonyl fluoride (PMSF) is added to an equal volume of isolated erythroid cells or platelets in the same buffer. The cells are incubated with the FITC-labeled lectins for 1 h at 4° C. in the dark. The lectins hind to sialic acids and beta-galactosyl residues on the surface of the erythroid cells.

Other dyes may be useful for tracking synthetic membrane-receiver complexes in human and non-human circulation. A number of reagents may be used to non-specifically label a synthetic membrane-receiver complex. For example, erythroid cells or platelets may be labeled with PKH26 Red (See, e.g., Bratosin, et al., (1997) Cytometry 30:269-274). Erythroid cells or platelets ($1-3 \times 10^7$ cells) are suspended in 1 ml of diluent and rapidly added to 1 ml or 2 µM PKH26 dissolved in the same diluent. The mixture is mixed by gentle pipetting and incubated at 25° C. for 2-5 min with constant stirring. The labeling may be stopped by adding an equal volume of human serum or compatible protein solution (e.g., 1% bovine serum albumin). After an additional minute, an equal volume of cell culture medium is added and the cells are isolated by centrifugation at 2000×g for 5 min. Cells are washed three times by repeated suspension in cell culture medium and centrifugation. PHK26-labeled synthetic membrane-receptor complexes may be monitored with a maximum excitation wavelength of 551 nm and a maximum emission wavelength of 567 nm.

Synthetic membrane-receiver complexes may be tracked in vivo using VivoTag 680 (VT680; VisEn Medical, Woburn, Mass., USA), a near-infrared fluorochrome with a peak excitation wavelength of 670±5 nm and a peak emission wavelength of 688±5 nm. VT680 also contains an amine reactive NHS ester which enables it to cross-link with proteins and peptides. The surface of cells, e.g., erythroid cells or platelets may be labeled with VT680 (See, e.g., Swirski, et al., (2007) PloS ONE 10:e1075). For example, $4 \times 10^6$ cells/ml are incubated with VT680 diluted in complete culture medium at a final concentration of 0.3 to 300 µg/ml for 30 min at 37° C. The cells are washed twice with complete culture medium after labeling. Cells may be non-specifically labeled based on proteins expressed on the surface of the synthetic membrane-receptor complex. Alternatively, a specific protein, such as a receiver may be labeled with VT680. In some embodiments, a protein or peptide may be directly labeled with VT680 ex vivo and subsequently either attached to the surface of the cell or incorporated into the interior of the cell using methods described herein. In vivo monitoring may, for example, be performed using the dorsal skin fold. Laser scanning microscopy may be performed using, for example, an Olympus IV 100 in which VT680 is excited with a red laser diode of 637 nm and detected with a 660/LP filter. Alternatively, multiphoton microscopy may be performed using, for example, a BioRad Radiance 2100 MP centered around an Olympus BX51 equipped with a 20×/0.95 NA objective lens and a pulsed Ti:Sapphire laser tuned to 820 nm. The latter wavelength is chosen because VT680 has a peak in its two-photon cross-section at 820 nm.

Alternatively or in addition, a synthetic membrane-receiver complex may be labeled with other red and/or near-infrared dyes including, for example, cyanine dyes such as Cy5, Cy5.5, and Cy7 (Amersham Biosciences, Piscataway, N.J., USA) and/or a variety of Alexa Fluor dyes including Alexa Fluor 633, Alexa Fluor 635, Alexa Fluor 647, Alexa Fluor 660, Alexa Fluor 680, Alexa Fluor 700 and Alexa Fluor 750 (Molecular Probes-Invitrogen, Carlsbad, Calif., USA). Additional suitable fluorophores include IRD41 and IRD700 (LI-COR, Lincoln, Nebr., USA), NIR-1 and 1C5-OSu (Dejindo, Kumamotot, Japan), LaJolla Blue (Diatron, Miami, Fla., USA), FAR-Blue, FAR-Green One, and FAR-Green Two (Innosense, Giacosa, Italy), ADS 790-NS and ADS 821-NS (American Dye Source, Montreal, Calif.). Quantum dots (Qdots) of various emission/excitation properties may also be used for labeling synthetic membrane-receiver complexes (See, e.g., Jaiswal et al., Nature Biotech. 21:47-51 (2003)). Many of these fluorophores are available from commercial sources either attached to primary or secondary antibodies or as amine-reactive succinimidyl or monosuccinimidyl esters, for example, ready for conjugation to a protein or proteins either on the surface or inside the synthetic membrane-receiver complex.

Magnetic nanoparticles may be used to track synthetic membrane-receiver complexes in vivo using high resolution MRI (Montet-Abou et al., Molecular Imaging 4:165-171 (2005)). Magnetic particles may be internalized by several mechanisms. Magnetic particles may be taken up by a cell, e.g., an erythroid cell or a platelet through fluid-phase pinocytosis or phagocytosis. Alternatively, the magnetic particles may be modified to contain a surface agent such as, for example, a membrane translocating HIV TAT peptide which promotes internalization. In some instances, a magnetic nanoparticle such as, for example, Feridex IV®, an FDA approved magnetic resonance contrast reagent, may be internalized into, e.g., erythroid cells or platelets in conjunction with a transfection agent such as, for example, protamine sulfate (PRO), polylysine (PLL), and lipofectamine (LFA).

In some embodiments, the synthetic membrane-receiver polypeptide complexes are generated comprising contacting an erythroid cell with a receiver, such as a polypeptide. In some embodiments, the receiver polypeptide is encoded by an exogenous nucleic acid and is expressed by the erythroid cell. In some embodiments, a naturally occurring erythroid cell does not comprise the receiver. For example, a naturally occurring erythroid cell does not express an endogenous polypeptide that is structurally and functionally the same as the receiver polypeptide. In some embodiments, the erythroid cell comprises a receiver that is over-expressed. For example, the receiver is present in substantially higher copy numbers than it would be if it were endogenously expressed by a naturally occurring erythroid cell. In some embodiments, the synthetic membrane-receiver polypeptide complexes are generated by differentiating and maturing the erythroid cells in vitro or in vivo after contacting the cells with a receiver. It is known in the art that erythrocytes undergo a complex process of maturation as they differentiate from precursor cells. The maturation process includes a substantial cytoskeleton and membrane rearrangement and degradation or expulsion of non-essential polypeptides, see e.g., Liu J et al. (2010) Blood 115(10):2021-2027; and Lodish H F et al. (1975) Developmental Biology 47(1):59). For naturally occurring erythrocytes this maturation process happens in vivo, first in the bone marrow and then in circulation as reticulocytes mature into erythrocytes. For cultured erythrocytes this maturation process happens both ex vivo, in culture, and in vivo in circulation as cultured reticulocytes mature into eyrthrocytes (see e.g., Neildez-Nguyen et al. 2002 Nature Biotechnol 20:467). In some embodiments, the synthetic membrane-receiver polypeptide complexes generated from erythroid cells retain their receivers during the maturation process, in vitro or in vivo and the receivers are not lost. In some embodiments, the synthetic membrane-receiver polypeptide complexes generated from erythroid cells retain their receivers after maturation. In some embodiments, fully matured synthetic membrane-receiver polypeptide complexes generated from erythroid cells retain their receiver. The receiver may be retained in vitro, e.g., in culture and/or may be retained in vivo, e.g., after administration to the circulatory system of the subject. In some embodiments, the receiver may be retained by the synthetic membrane-receiver polypeptide complexes for the life of the complex in circulation. These findings are surprising in view of the art which suggested that receivers would be excluded from the erythroid cells during the maturation process. It was further unexpected that receivers would be retained and functionally active when the synthetic membrane-receiver polypeptide complexes generated from erythroid cells are administered to the circulatory system of a subject. In some embodiments culturing of eythroid cells comprising a receiver provides a method of producing a substantially more homogeneous and/or substantially more scalable population of therapeutic synthetic membrane-receiver complexes than is achievable by methods relying upon isolation and modification of non-cultured erythrocytes. Despite a great need for human erythroid cell-based treatment and preventive methods and recognition for its value in the art, no systems derived from modified cultured cells have previously been generated or shown to retain receiver activity in circulation, and the art suggested that such systems would not be achievable. When cultured human erythrocytes have been experimentally administered to a human subject previously they were unmodified (Giarratana et al., Blood 2011, 118:5071).

Targets

Provided herein are synthetic membrane-receiver polypeptide complexes comprising a receiver polypeptide capable of interacting with a target. Further provided herein are synthetic membrane-receiver complexes comprising a non-polypeptide receiver capable of interacting with a target. The synthetic membrane-receiver complexes may be administered to a subject in need thereof to modulate the amount or concentration of a target residing in the circulatory system of the subject. A suitable receiver may be chosen to interact with a specific target. Suitable targets include entities that are associated with a specific disease, disorder, or condition. However, targets may also be chosen independent of a specific disease, disorder, or condition.

In some embodiments, the target is an antibody or antibody-like molecule, for example an autoimmune or a self-antibody, or a foreign antibody, or a therapeutic antibody, including but not limited to, e.g., an antibody against beta-2 glycoprotein 1, an antibody against I/i antigen, an antibody against the NC1 domain of collagen a3 (IV), an antibody against platelet glycoprotein, an antibody against phospholipase A2 receptor, an antibody against erythrocyte glycophorin A, B, or C, or an antibody against erythrocyte Rh antigen.

In some embodiments, the target is a molecule of the complement cascade, for example C1, C1r, C1s, C1q, C2, C2a, C2b, C3, C3a, C3b, C4, C4b, C4a, C3bBb, C3bBb3b, C4b2b, C4b2b3b, C5, C5a, C5b, C6, C7, C8, C9, poly-C9, membrane attack complex. Factor B, Factor D, Properdin, C3, C3a, C3b, iC3b, C3c, C3dg, C3dk, C3e, Bb, Factor I, C1q, C1r, C1s, C4, C4a, C4b, C2, C4 bp, Mannose-Binding Lectin (MBL), MBL-Associated Serine Protease 1 (MASP1), MBL-Associated Serine Protease 2 (MASP2), C5, C5a, C6, C7, C8, C9, CR1, CR2, CR3, CR4, C3aR, C3eR, Decay-accelerating factor (DAF), Membrane cofactor protein (MCP), CD59, C3 Beta chain Receptor, C1 inhibitor, C4 binding protein, Factor I, Factor H.

In some embodiments, the target is an immune complex, for example an IgG immune complex, an IgA immune complex, an IgM immune complex.

In some embodiments, the target is an amyloid placque, for example a placque comprised of beta amyloid, IAPP (Amylin), alpha-synuclein, PrPSc, huntingtin, calcitonin, atrial natriuretic factor, apolipoprotein AI, serum amyloid A, medin, prolactin, transthyretin, lysozyme, beta 2 microglobulin, gelsolin, keratoepithelin, cystatin, immunoglobulin light chain AL, S-IBM.

In some embodiments, the target is a bacterium, for example *Enterococcus, Streptococcus*, or *Mycobacteria, Rickettsia, Mycoplasma, Neisseria meningitides, Neisseria gonorrheoeae, Legionella, Vibrio cholerae, Streptococci, Staphylococcus aureus, Staphylococcus epidermidis, Pseudomonas aeruginosa, Corynobacteria diphtheriae, Clostridium* spp., enterotoxigenic *Eschericia coli*, and *Bacillus anthracis*. Other pathogens for which bacteremia has been reported at some level include the following: *Rickettsia, Bartonella henselae, Bartonella quintana, Coxiella burnetii, chlamydia, Mycobacterium leprae, Salmonella; shigella; Yersinia enterocolitica; Yersinia pseudotuberculosis; Legionella pneumophila; Mycobacterium tuberculosis; Listeria monocytogenes; Mycoplasma* spp.; *Pseudomonas fluorescens; Vibrio cholerae; Haemophilus influenzae; Bacillus anthracis; Treponema pallidum; Leptospira; Borrelia; Corynebacterium diphtheriae; Francisella; Brucella melitensis; Campylobacter jejuni; Enterobacter; Proteus mirabilis; Proteus*; and *Klebsiella pneumoniae*.

In some embodiments, the target is a virus, including but not limited to, those whose infection involves injection of genetic materials into host cells upon binding to cell surface receptors, viruses whose infection is mediated by cell surface receptors. Non-limiting examples of these viruses can be selected from Paramyxoviridae (e.g., pneumovirus, morbillivirus, metapneumovirus, respirovirus or rubulavirus), Adenoviridae (e.g., adenovirus), Arenaviridae (e.g., arenavirus such as lymphocytic choriomeningitis virus), Arteriviridae (e.g., porcine respiratory and reproductive syndrome virus or equine arteritis virus), Bunyaviridae (e.g., phlebovirus or hantavirus), Caliciviridae (e.g., Norwalk virus), Coronaviridae (e.g., coronavirus or torovirus), Filoviridae (e.g., Ebola-like viruses), Flaviviridae (e.g., hepacivirus or flavivirus), Herpesviridae (e.g., simplexvirus, varicellovirus, cytomegalovirus, roseolovirus, or lymphocryptovirus), Orthomyxoviridae (e.g., influenza virus or thogotovirus), Parvoviridae (e.g., parvovirus), Picornaviridae (e.g., enterovirus or hepatovirus), Poxviridae (e.g., orthopoxvirus, avipoxvirus, or leporipoxvirus), Retroviridae (e.g., lentivirus or spumavirus), Reoviridae (e.g., rotavirus), Rhabdoviridae (e.g., lyssavirus, novirhabdovirus, or vesiculovirus), and Togaviridae (e.g., alphavirus or rubivirus). Specific examples of these viruses include human respiratory coronavirus, influenza viruses A-C, hepatitis viruses A to G, and herpes simplex viruses 1-9.

In some embodiments, the target is a parasite, including but not limited to, for example, intestinal or blood-borne parasites, protozoa, trypanosomes; haemoprotozoa and parasites capable of causing malaria; enteric and systemic cestodes including taeniid cestodes; enteric coccidians; enteric flagellate protozoa; filarial nematodes; gastrointestinal and systemic nematodes and hookworms.

In some embodiments, the target is a fungus, including but not limited to, for example, *Candida albicans, Candida glabrata, Aspergillus, T. glabrata, Candida tropicalis, C. krusei*, and *C. parapsilosis*.

In some embodiments, the target is a bacterial toxin, including but not limited to, for example, AB toxin, alpha toxin, anthrax toxin, bacteriocin, botunlinum toxin, cholesterol-dependent cytolysin, *Clostridium botulinum* C3 toxin, *Clostridium difficile* toxin A, *Clostridium difficile* toxin B, *Clostridium* enterotoxin, *Clostridium perfringens* alpha toxin, *Clostridium perfringens* beta toxin, Cord factor, Cry1Ac, Cryptophycin, Delta endotoxin, Diphtheria toxin, Enterotoxin type B, erythrogenic toxin, exfoliatin, haemolysin E, heat-labile enterotoxin, heat-stable enterotoxin, hemolysin, leukocidin, lipopolysaccharide, Listeriolysin O, microcin, Panton-Valentine leucocidin, pathogenicity island, phenol-soluble modulin, pneumolysin, pore-forming toxin, *Pseudomonas* exotoxin, RTX toxin, sakacin, *Staphylococcus aureus* alpha toxin, *Staphylococcus aureus* beta toxin, *Staphylococcus aureus* delta toxin, Streptolysin, Symplocamide A, tabtoxin, tetanolysin, tetanospasmin, thiol-activated cytolysin, tolaasin, toxic shock syndrome toxin, toxoflavin, trehalose dimycolate, verocytotoxin, and vibriocin.

In some embodiments, the target is a prion protein, including but not limited to, for example, PRP, PRPc, PRPsc, PRPres.

In some embodiments, the target is a cytokine or a chemokine or a growth factor, including but not limited to, for example, acylation stimulating protein, adipokine, albinterferon, CCL1, CCL11, CCL12, CCL13, CCL14, CCL15, CCL16, CCL17, CCL18, CCL19, CCL2, CCL20, CCL21, CCL22, CCL23, CCL24, CCL25, CCL26, CCL27, CCL28, CCL3, CCL5, CCL6, CCL7, CCL8, CCL9, colony-stimulating factor, CX3CL1, CX3CR1, CXCL1, CXCL10, CXCL11, CXCL13, CXCL14, CXCL15, CXCL16, CXCL17, CXCL2, CXCL3, CXCL5, CXCL6, CXCL7, CXCL9, erythropoietin, Gc-MAF, granulocyte colony-stimulating factor, granulocyte macrophage colony-stimulating factor, hepatocyte growth factor, IL 10 family, IL 17 family, IL1A, IL1B, interferon, interferon beta 1a, interferon beta 1b, interferon gamma, interferon type I, interferon type II, interferon type III, interleukin, interleukin 1 family, interleukin 1 receptor antagonist, interleukin 10, interleukin 12, interleukin 12 subunit beta, interleukin 13, interleukin 16, interleukin 2, interleukin 23, interleukin 23 subunit alpha, interleukin 34, interleukin 35, interleukin 6, interleukin 7, interleukin 8, interleukin-36, leukemia inhibitory factor, leukocyte-promoting factor, lymphokine, lymphotoxin, lymphotoxin alpha, lymphotoxin beta, macrophage colony-stimulating factor, macrophage inflammatory protein, macrophage-activating factor, monokine, myokine, myonectin, nicotinamide phosphoribosyltransferase, oncostatin M, oprelvekin, platelet factor 4, proinflammatory cytokine, promegapoietin, RANKL, stromal cell-derived factor 1, talimogene laherparepvec, tumor necrosis factor alpha, tumor necrosis factors, XCL1, XCL2, XCR1, angiopoietin, basic fibroblast growth factor, betacellulin, bone morphogenetic protein, brain-derived neurotrophic factor, CCN intercellular signaling protein, CTGF, darbepoetin alfa, endoglin, epidermal growth factor, epoetin alfa, epoetin beta, erythropoietin, FGF15, FGF15/19, fibroblast growth factor, fibroblast growth factor 23, filgrastim, GLIA maturation factor, granulocyte colony-stimulating factor, granulocyte macrophage colony-stimulating factor, growth differentiation factor-9, heberprot-P, hemopoietic growth factors, heparin-binding EGF-like growth factor, hepatocyte growth factor, insulin-like growth factor, insulin-like growth factor 1, insulin-like growth factor 2, keratinocyte growth factor, myostatin, nerve growth factor, neurotrophin-3, neurotrophin-4, oncomodulin, osteopromotive, palifermin, PDGFB, placental growth factor, platelet alpha-granule, platelet-derived growth factor, platelet-derived growth factor receptor, proliferative index, thrombopoietin, transforming growth factor, vascular endothelial growth factor.

In some embodiments, the target is a small molecule, for example a chemical, an amino acid, an atom, an element, an organic acid, <2000 Da, <1000 Da, <500 Da, including but not limited to, for example, iron, copper, calcium, potassium, ethanol, methanol, glycine, alanine, valine, leucine, isoleucine, serine, cysteine, selenocysteine, threonine, methionine, proline, phenylalanine, tyrosine, tryptophan, histidine, lysine, arginine, aspartate, glutamate, asparagine, glutamine.

In some embodiments, the target is a lipid, lipid complex, proteolipid complex, or cholesterol, including but not limited to for example, LDL, VLDL, HDL, HDL2B, triglycerides, LP(a), cholesterol.

In some embodiments, the target is a mammalian cell, including but not limited to, for example, a human cell, a circulating cell, an immune cell, a neutrophil, an eosinophil, a basophil, a lymphocyte, a monocyte, a B cell, a T cell, a CD4+ T cell, a CD8+ T cell, a gamma-delta T cell, a regulatory T cell, a natural killer cell, a natural killer T cell, a macrophage, a Kupffer cell, a dendritic cell, a cancer cell, a cancer stem cell, a circulating tumor cell, a cancer cell from one of the following cancers including, but not limited to, ACUTE lymphoblastic leukaemia (ALL), ACUTE myeloid leukaemia (AML), anal cancer, bile duct cancer, bladder cancer, bone cancer, bowel cancer, brain tumours, breast cancer, cancer of unknown primary, cancer spread to bone, cancer spread to brain, cancer spread to liver, cancer spread to lung, carcinoid, cervical cancer, choriocarcinoma, chronic lymphocytic leukaemia (CLL), chronic myeloid leukaemia (CML), colon cancer, colorectal cancer, endometrial cancer, eye cancer, gallbladder cancer, gastric cancer, gestational trophoblastic tumours (GTT), hairy cell leukaemia, head and neck cancer, hodgkin lymphoma, kidney cancer, laryngeal cancer, leukaemia, liver cancer, lung cancer, lymphoma, melanoma skin cancer, mesothelioma, men's cancer, molar pregnancy, mouth and oropharyngeal cancer, myeloma, nasal and sinus cancers, nasopharyngeal cancer, non hodgkin lymphoma (NHL), oesophageal cancer, ovarian cancer, pancreatic cancer, penile cancer, prostate cancer, rare cancers, rectal cancer, salivary gland cancer, secondary cancers, skin cancer (non melanoma), soft tissue sarcoma, stomach cancer, testicular cancer, thyroid cancer, unknown primary cancer, uterine cancer, vaginal cancer, and vulval cancer.

Sourcing

Synthetic membrane-receiver complexes can be generated by any method described herein. In some embodiments, the steps comprise contacting isolated optionally cultured cells derived from hematopoietic stem cells with a receiver. Hematopoietic stem cells give rise to all of the blood cell types found in mammalian blood including myeloid (monocytes and macrophages, neutorphils, basophils, eosinophils, erythrocytes, megakaryocytes/platelets, dendritic cells) and lymphoid lineages (T-cells, B-cells, NK-cells). Hematopoietic stem cells may be isolated from the bone marrow of adult bones including, for example, femur, hip, rib, or sternum bones. Cells may be obtained directly from the hip, for example, by removal of cells from the bone marrow using aspiration with a needle and syringe. Alternatively, hematopoietic stem cells may be isolated from normal peripheral blood following pre-treatment with cytokines such as, for example, granulocyte colony stimulating factor (G-CSF). G-CSF mobilizes the release of cells from the bone marrow compartment into the peripheral circulation. Other sources of hematopoietic stem cells include umbilical cord blood and placenta.

In some embodiments, the synthetic membrane-receiver complex is generated from megakaryocytes or platelets. In some embodiments, the synthetic membrane-receiver complex is generated from an erythroid cell, such as, e.g. an erythrocyte or a reticulocyte. In some embodiments, the synthetic membrane-receiver complex is not generated from a neutrophil, an eosinophil, or a basophil. In some embodiments, the synthetic membrane-receiver complex is not generated from a monocyte or a macrophage.

In some embodiments, the synthetic membrane-receiver complex is not generated from a CD34$^+$Thy-1$^+$ hematopoietic stem cell or cell populations enriched in CD34$^+$Lin$^-$ or CD34$^+$Thy-1$^+$Lin$^-$ cells.

In some embodiments, the synthetic membrane-receptor complex is not generated from or does not comprise an autologous CD34+ cell.

Isolated hematopoietic stem cells may be cultured, expanded and differentiated ex vivo to provide a variety of source material to generate synthetic membrane-receptor complexes. For example, hematopoietic stem cells isolated from bone marrow, cytokine-stimulated peripheral blood or umbilical cord blood may be expanded and differentiated ex vivo into mature erythrocytes (Giarratana et al., Nature Biotech. 23:69-74 (2005); U.S. Patent Application 2007/0218552). As such, CD34+ cells are isolated from bone marrow or peripheral or cord blood using, for example, magnetic microbead selection and Mini-MACS columns (Miltenyi Biotech). In one example, the cells are subsequently cultured in modified serum-free medium supplemented with 1% bovine serum albumin (BSA), 120 µg/ml iron-saturated human transferrin, 900 ng/ml ferrous sulfate, 90 ng/ml ferric nitrate and 10 µg/ml insulin and maintained at 37° C. in 5% carbon dioxide in air. Expansion and differentiation of the cell culture may occur in multiple steps. For example, in the initial growth step following isolation, the cells may be expanded in the medium described herein in the presence of multiple growth factors including, for example, hydrocortisone, stem cell factor, IL-3, and erythropoietin. In the second stage, the cells may optionally be co-cultured, for example, on an adherent stromal layer in the presence of erythropoietin. In a third stage, the cells may be cultured on an adherent stromal layer in culture medium in the absence of exogenous factors. The adherent stromal layer may be murine MS-5 stromal cells, for example. Alternatively, the adherent stromal layer may be mesenchymal stromal cells derived from adult bone marrow. The adherent stromal cells may be maintained in RPMI supplemented with 10% fetal calf serum, for example. In some embodiments, the erythroid precursor cells and cell populations derived therefrom are not co-cultured with non-erythroid cells, e.g., with an adherent stromal layer, i.e. they are cultured in the absence of non-erythroid cells. In some embodiments, erythroid cells comprising a receiver are cultured in the absence of non-erythroid cells and are differentiated so that greater than 10%, 15%, 20%, 25%, 30%, 35%, 40%, 45%, 50%, 55%, 60%, 65%, 70%, 75%, 80%, 85%, 90%, 95% or greater than 98% of erythroid cells are enucleated and the population of enucleated cells is obtained without an enrichment step, such as gravitational separation, magnetic or fluorescent sorting, irradiation, poisoning of nucleated cells, and the like to select for enucleated cells.

In some instances, it may be desirable to expand and partially differentiate the CD34+ hematopoietic stem cells in vitro and to allow terminal differentiation into mature erythrocytes to occur in vivo (See, e.g., Neildez-Nguyen et al., Nature Biotech. 20:467-472 (2002)). Isolated CD34+ hematopoietic stem cells may be expanded in vitro in the absence of the adherent stromal cell layer in medium containing various factors including, for example, Flt3 ligand, stem cell factor, thrombopoietin, erythropoietin, and insulin growth factor. The resulting erythroid precursor cells may be characterized by the surface expression of CD36 and GPA, and may be transfused into a subject where terminal differentiation to mature erythrocytes is allowed to occur.

In some embodiments, the erythroid cell population comprises a plurality of enucleated functional erythroid cells that comprise a receiver polypeptide that is retained during enucleation. The resulting isolated enucleated functional erythroid cell comprising a receiver polypeptide exhibits substantially the same osmotic membrane fragility as a corresponding isolated, unmodified, uncultured erythroid cell.

In some embodiments, the erythroid cell population comprises a plurality of erythrocyte precursor cells in substantially the same stage of differentiation and/or cell cycle stage, wherein the precursor cells comprise an exogenous nucleic acid encoding a receiver. The majority of erythrocyte precursor cells that comprise an exogenous nucleic acid encoding a receiver are capable of differentiating into mature functional erythrocytes that retain the receiver without retaining the exogenous nucleic acid.

In some embodiments, the primary cells may be collected through venipuncture, capillary puncture, or arterial puncture. From the collected whole blood erythrocytes, platelets or other cells may then be isolated using one, or a combination of techniques including plasma depletion, density gradient, Hetastarch, PrepaCyte-CB, and centrifugation.

In some embodiments, generating a synthetic membrane-receiver complex comprises contacting isolated optionally cultured cells that are autologous and/or allogeneic to the subject with a receiver. For example, erythrocytes allogeneic to the subject include one or more of blood type specific erythrocytes or one or more universal donor erythrocytes. In some embodiments, synthetic membrane-receiver complexes may be generated through fusion of erythrocytes, e.g., between erythrocytes autologous to the subject and one or more allogeneic erythrocytes, liposomes, and/or artificial vesicles.

In certain embodiments, autologous transfusion of synthetic membrane-receiver complexes includes isolating erythrocytes, reticulocytes or hematopoietic stem cells from a subject, generating a suitable synthetic membrane-receiver complex by contacting the cell with a receiver by methods described herein and administering (e.g., by transfusion) the synthetic membrane-receiver complex into the same subject.

In certain embodiments, allogeneic transfusion of synthetic membrane-receiver complexes includes isolating erythrocytes, reticulocytes or hematopoietic stem cells from a donor, generating a suitable synthetic membrane-receiver complex by contacting the cell with a receiver by methods described herein and administering (e.g., by transfusion) the synthetic membrane-receiver complex into a subject that is different from the donor. Where allogeneic cells are used for transfusion, care needs to be taken to use a compatible ABO blood group to prevent an acute intravascular hemolytic transfusion reaction which is characterized by complement activation and lysis of incompatible erythrocytes. The ABO blood types are defined based on the presence or absence of the blood type antigens A and B, monosaccharide carbohydrate structures that are found at the termini of oligosaccharide chains associated with glycoproteins and glycolipids on the surface of the erythrocytes (reviewed in Liu et al., Nat. Biotech. 25:454-464 (2007)). Group 0 erythrocytes lack either of these antigenic monosaccharide structures. Subjects with group A erythrocytes have naturally occurring antibodies to group B erythrocytes whereas subjects with group B erythrocytes have antibodies to group A erythrocytes. Blood group AB subjects have neither antibody and blood group O individuals have both. Subjects with either anti-A and/or anti-B antibodies cannot receive a transfusion of blood containing the corresponding antigen. Because group O erythrocytes contain neither A nor B antigens, they can be safely transfused into recipients of any ABO blood group, e.g., group A, B, AB, or O recipients. Group O erythrocytes are considered universal and may be used in all blood transfusions. In contrast, group A erythrocytes may be given to group A and AB recipients, group B erythrocytes may be given to group B and AB recipients, and group AB erythrocytes may only be given to AB recipients. In embodiments in which synthetic membrane-receiver complexes are generated by connecting erythrocytes or their precursors with a receiver the sourced erythrocytes or their precursors are matched for compatibility with the recipient.

In some instances, it may be beneficial to convert a synthetic membrane-receiver complex comprising a non-group O erythrocyte to a universal blood type. Enzymatic removal of the immunodominant monosaccharides on the surface of group A and group B erythrocytes may be used to generate a population of group O-like synthetic membrane-receiver complexes (See, e.g., Liu et al., Nat. Biotech. 25:454-464 (2007)). Group B synthetic membrane-receiver complexes may be converted using an α-galactosidase derived from green coffee beans. Alternatively or in addition, α-N-acetylgalactosaminidase and α-galactosidase enzymatic activities derived from *E. meningosepticum* bacteria may be used to respectively remove the immunodominant A and B antigens (Liu et al., Nat. Biotech. 25:454-464 (2007)), if present on the synthetic membrane-receiver complexes. In one example, packed red blood cells isolated as described herein, are incubated in 200 mM glycine (pH 6.8) and 3 mM NaCl in the presence of either α-N-acetylgalactosaminidase and α-galactosidase (about 300 μg/ml packed red blood cells) for 60 min at 26° C. After treatment, the red blood cells are washed by 3-4 rinses in saline with centrifugation and ABO-typed according to standard blood banking techniques.

In specific embodiments, the synthetic membrane-receiver complexes described herein may be generated in the following way. First, erythroid precursor cells are isolated. These cells may alternatively be autologous to the patient or from substantially universal donor blood. For example, the cells may be ABO type O, rhesus factor Rh r/r, Duffy –/–, and large Kell antigen K1 negative. In the course of differentiation from erythroid precursor cell to erythroid cell, an exogenous nucleic acid encoding the receiver is introduced. the exogenous nucleic acid encoding the receiver can be under the control of an erythroid-specific promoter, such as a GATA-1 promoter (see e.g., Repik et al., Clin Exp Immunol 2005, 140:230). the exogenous nucleic acid encoding the receiver can be introduced in any way known in the art, for example, as plasmid DNA, virus, or mRNA. Nucleic acid introduction can be achieved by a variety of standard methods, e.g., transfection, transduction, or electroporation.

In specific embodiments, the synthetic membrane-receiver complexes described herein may be generated by contacting platelets with a receiver. Each day an adult human produces $2 \times 10^{11}$ red blood cells, and about one-half as many white cells and platelets. In humans, nearly all blood cell production occurs in the red bone marrowthat represents a hierarchical developmental system composed of hematopoietic stem cells, intermediate level progenitors and maturing cells committed to each lineage.

Although the morphology of all the major blood cell types is similar through their initial development stages, megakaryocytes, cells committed to platelet production, are marked by an obvious structural and functional departure beyond the blast cell level of differentiation growing to a size 10 times the diameter of most other bone marrow and blood cells, and containing up to 128 times the normal chromosomal complement, these cells give rise to blood platelets. After a series of normal cell divisions, the developing megakaryocyte precursor enters a unique cell cycle characterized by a brief (about 1 h) G1 phase, a typical (7 h) S phase, a very brief (~45 min) G2 phase, followed by the endomitotic phase (an aborted M phase). Once the cell develops a highly polyploid nucleus, it also develops demarcation membranes necessary for cytoplasmic fragmentation. This event is accompanied by expression of glycoprotein GPIIbIIIa (platelet fibrinogen receptor; Papayannopoulou et al., Exp. Hematol., 24: 660-9, 1996) and GPIb (von Willibrand factor receptor; Kaushansky et al., Nature, 369: 568-571, 1994), the granules that contain ADP, serotonin, -thromboglobulin, and other substances critical for mature platelet function. Finally, highly polyploid megakaryocytes undergo cytoplasmic partitioning, allowing the release of thousands of platelets (Choi et al., Blood, 85: 402-413, 1995; Cramer et al., Blood, 89: 2336-2346, 1997).

Like all blood cell precursors, megakaryocytes are derived from pluripotent marrow stem cellsthat retain the capacity to extensively self-renew, or to differentiate into all of the elements of the blood. Platelet production is in part regulated by signaling mechanisms induced by interaction between thrombopoietin (TPO) and its cellular receptor TPOR/MPUc-MPL.

Thrombopoietin (TPO) is a hematopoietic growth factor involved in stimulation of megakaryocytopoiesis and platelet production. TPO is expressed in liver and kidney, and, in response to platelet demand, its expression may be also upregulated in the bone marrow microenvironment (Kato et al., Stem Cells, 16: 322-328, 1998; McCarty et al., Blood, 86:3668-3675, 1995). As TPO expression is mostly constitutive, the TPO levels are believed to be regulated by sequestering by platelets (Fielder et al., Blood 87: 2154, 1996).

The gene encoding TPO has been cloned and characterized (Kuter et al., Proc. Natl. Acad. Sci. USA, 91:11104-11108, 1994; Bartley et al., Cell, 77:1117-1124, 1994; Kaushansky et al., Nature, 369:568-571, 1994; Wendling et al., Nature, 369:571-574, 1994, and de Sauvage et al., Nature, 369:533-538, 1994). Human TPO (hTPO) cDNA encodes a 353 amino acid-long polypeptide. The full-length hTPO secreted from mammalian cells after cleavage of the signal peptide consists of 332 amino acids. Although the predicted molecular mass of this protein is 38 kD, the molecular masses reported from measurements of material in serum or in culture fluid from recombinant cells vary from 18 to 85 kD (glycosylation, and post-translational proteolytic processing).

The cell surface receptor for TPO (TPOR/MPL/c-MPL) is a product of the protooncogene c-mpl, a homologue of v-mpl, an envelope protein of the myeloproliferative leukaemia virus (MPLV) shown to induce a pan-myeloid disorder (Wendling, Virol., 149:242-246, 1986). The human c-mpl gene codes for a protein of 635 aa having a predicted molecular weight of 71 kD (Vigon et al., Proc. Natl. Acad. Sci. USA, 89:5640-44, 1992; Mignotte et al., Genomics, 20: 5-12, 1994).

Mice rendered null for the expression of either TPO or its receptor (TPOR/MPL/c-MPL) manifest a severe thrombocytopenic phenotype (Gurney et al., Science, 265: 1445, 1994; Kaushansky et al., J. Clin. Invest., 96: 1683, 1995; de Sauvage et al., J. Exp. Med., 183: 651, 1996).

Multiple cytokines (e.g., stem cell factor [SCF], IL-1, IL-3, IL-6, IL-11, leukaemia inhibiting factor [LIP], G-CSF, GM-CSF, M-CSF, erythropoietin (EPO), kit ligand, and -interferon) have been shown to possess thrombocytopoietic activity.

The resulting platelets are small disc-shaped cell fragments which undergo a rapid transformation when they encounter sites of vascular damage. They become more spherical and extrude pseudopodia, their fibrinogen receptors are activated leading to aggregation, and they release their granule contents and eventually they form a plug which is responsible for primary hemostasis (Siess, W., Physiol. Rev. 69: 58-178, 1989). Activation of platelets is also implicated in the pathogenesis of unstable angina, myocardial infarction and stroke (Packham, M. A., Can J. Physiol Pharmacol. 72: 278-284).

Several physiological substances are involved in the activation of platelets such as collagen, which is exposed at the subendothelial surfaces, thrombin, generated by the coagulation cascade, and thromboxane A2 ($TXA_2$) and ADP, which are released from activated platelets. Collagen binds to several platelet membrane proteins including integrin $\alpha 2\beta 1$ leading to platelet activation through the release of $TXA_2$ and ADP (Shattil, S. J., et al., Curr. Opin. Cell Biol. 6: 695-704, 1994). In contrast, thrombin, $TXA_2$, and ADP, activate G-protein coupled receptors directly and induce platelet aggregation and granule release (Hourani, S. M, and Cusack, N. J., Pharmacol. Rev. 43: 243-298, 1991). The major events involved in platelet activation are believed to be the result of the activation of β-isoforms of phospholipase C (PLC) leading to the generation of inositol 1,4,5 triphosphate and diacylglycerol. Platelets mainly contain two isoforms, PLC-β2 and PLC-β3.

Platelet receptors which mediate platelet adhesion and aggregation are located on the two major platelet surface glycoprotein complexes. These complexes are the glycoprotein Ib-IX complex which facilitates platelet adhesion by binding von Willebrand factor (vWF), and the glycoprotein IIb-IIIa complex which links platelets into aggregates by binding to fibrinogen. Patients with the Bernard-Soulier syndrome, a congenital bleeding disorder, show deficient platelet adhesion due to a deficiency in the glycoprotein Ib-IX complex which binds vWF, mild thrombocytopenia, and large lymphocoid platelets.

Glycoprotein V (GPV) is a major (≈12,000 molecules/platelet), heavily glycosylated platelet membrane protein (Mr 82,000). Exposure of platelets to thrombin liberates a 69 kDa soluble fragment termed GPVfl. GPV can interact non-covalently with the GPIb-IX complex a complex formed by the non-covalent association of GPIb (consisting of GPIbα, a 145 kDa protein, disulfide linked to GPIbβ, a 24 kDa protein) with GPIX (a 22 kDa protein). The binding sites for von Willebrand factor and for thrombin on the GPIb-IX complex have been localized on GPIbα. Since thrombin is now known to activate platelets by cleaving the thrombin receptor (Vu et. al., Cell 64:1057-1068 (1990)), a G-protein coupled receptor, it is unknown whether thrombin cleaves GPV incidently as a consequence of thrombin binding to GPIbα, or whether this cleavage has a physiological role. GPIBα, GPIBβ, and GPIX contain one or more homologous 24 amino acid leucine-rich domains. These domains are also found in a large family of leucine-rich glycoproteins (LRG).

GPV is a marker for the megakaryocytic cell lineage. A monoclonal antibody specific for GPV (SW16) does not bind to red cells, leukocytese endothelial cells, or cell lines such as HEL or MEG-01 which are known to express platelet megakaryocyte markers.

Mature GPV is composed of 543 amino acids which contain a single transmembrane domain, a short cytoplasmic domain (16 residues) and a large extracellular domain with 8 potential N-glycosylation sites. Analysis of the extracellular domain revealed the presence of 15 tandem Leu-rich repeats of 24 amino acids with homology to GPIbα, and identified a cleavage site for thrombin near the C-terminus with homology to the Aα chain of fibrinogen.

Culturing

Sources for generating synthetic membrane-receptor complexes described herein include circulating cells such as erythroid cells. A suitable cell source may be isolated from a subject as described herein from patient-derived hematopoietic or erythroid progenitor cells, derived from immortalized erythroid cell lines, or derived from induced pluripotent stem cells, optionally cultured and differentiated. Methods for generating erythrocytes using cell culture techniques are well known in the art, e.g., Giarratana et al., Blood 2011, 118:5071, Huang et al., Mol Ther 2013, epub ahead of print September 3, or Kurita et al., PLOS One 2013, 8:e59890. Protocols vary according to growth factors, starting cell lines, culture period, and morphological traits by which the resulting cells are characterized. Culture systems have also been established for blood production that may substitute for donor transfusions (Fibach et al. 1989 Blood 73:100). Recently, CD34+ cells were differentiated to the reticulocyte stage, followed by successful transfusion into a human subject (Giarratana et al., Blood 2011, 118:5071).

Provided herein are culturing methods for erythroid cells and synthetic membrane-receiver complexes derived from erythroid cells. Erythroid cells can be cultured from hematopoietic progenitor cells, including, for example, CD34+ hematopoietic progenitor cells (Giarratana et al., Blood 2011, 118:5071), induced pluripotent stem cells (Kurita et al., PLOS One 2013, 8:e59890), and embryonic stem cells (Hirose et al. 2013 Stem Cell Reports 1:499). Cocktails of growth and differentiation factors that are suitable to expand and differentiate progenitor cells are known in the art. Examples of suitable expansion and differentiation factors include, but are not limited to, stem cell factor (SCF), an interleukin (IL) such as IL-1, IL-2, IL-3, IL-4, IL-5, IL-6, IL-7, IL-8, IL-9, IL-11, IL-12, CSF, G-CSF, thrombopoietin (TPO), GM-CSF, erythropoietin (EPO), Flt3, Flt2, PIXY 321, and leukemia inhibitory factor (LIF).

Erythroid cells can be cultured from hematopoietic progenitors, such as CD34+ cells, by contacting the progenitor cells with defined factors in a multi-step culture process. For example, erythroid cells can be cultured from hematopoietic progenitors in a three-step process.

The first step may comprise contacting the cells in culture with stem cell factor (SCF) at 1-1000 ng/mL, erythropoietin (EPO) at 1-100 U/mL, and interleukin-3 (IL-3) at 0.1-100 ng/mL. The first step optionally comprises contacting the cells in culture with a ligand that binds and activates a nuclear hormone receptor, such as e.g., the glucocorticoid receptor, the estrogen receptor, the progesterone receptor, the androgen receptor, or the pregnane x receptor. The ligands for these receptors include, for example, a corticosteroid, such as, e.g., dexamethasone at 10 nM-100 μM or hydrocortisone at 10 nM-100 μM; an estrogen, such as, e.g., beta-estradiol at 10 nM-100 μM; a progestogen, such as, e.g., progesterone at 10 nM-100 μM, hydroxyprogesterone at 10 nM-100 μM, 5a-dihydroprogesterone at 10 nM-100 μM, 11-deoxycorticosterone at 10 nM-100 μM, or a synthetic progestin, such as, e.g., chlormadinone acetate at 10 nM-100 μM; an androgen, such as, e.g., testosterone at 10 nM-100 μM, dihydrotestosterone at 10 nM-100 μM or androstenedione at 10 nM-100 μM; or a pregnane x receptor ligand, such as, e.g., rifampicin at 10 nM-100 μM, hyperforin at 10 nM-100 St. John's Wort (hypericin) at 10 nM-100 μM, or vitamin E-like molecules, such as, e.g., tocopherol at 10 nM-100 The first step may also optionally comprise contacting the cells in culture with an insulin-like molecule, such as, e.g., insulin at 1-50 µg/mL, insulin-like growth factor 1 (IGF-1) at 1-50 µg/mL, insulin-like growth factor 2 (IGF-2) at 1-50 µg/mL, or mechano-growth factor at 1-50 µg/mL. The first step further may optionally comprise contacting the cells in culture with transferrin at 0.1-5 mg/mL.

The first step may optionally comprise contacting the cells in culture with one or more interleukins (IL) or growth factors such as, e.g., IL-1, IL-2, IL-4, IL-5, IL-6, IL-7, IL-8, IL-9, IL-11, IL-12, granulocyte colony-stimulating factor (G-CSF), macrophage colony-stimulating factor (M-CSF), granulocyte-macrophage colony-stimulating factor (GM-CSF), thrombopoietin, fibroblast growth factor (FGF), platelet-derived growth factor (PDGF), transforming growth factor beta (TGF-B), tumor necrosis factor alpha (TNF-A), megakaryocyte growth and development factor (MGDF), leukemia inhibitory factor (LIF), and Flt3 ligand. Each interleukin or growth factor may typically be supplied at a concentration of 0.1-100 ng/mL. The first step may also optionally comprise contacting the cells in culture with serum proteins or non-protein molecules such as, e.g., fetal bovine serum (1-20%), human plasma (1-20%), plasmanate (1-20%), human serum (1-20%), albumin (0.1-100 mg/mL), or heparin (0.1-10 U/mL).

The second step may comprise contacting the cells in culture with stem cell factor (SCF) at 1-1000 ng/mL and erythropoietin (EPO) at 1-100 U/mL. The second step may also optionally comprise contacting the cells in culture with an insulin-like molecule, such as e.g., insulin at 1-50 µg/mL, insulin-like growth factor 1 (IGF-1) at 1-50 µg/mL, insulin-like growth factor 2 (IGF-2) at 1-50 µg/mL, or mechano-growth factor at 1-50 µg/mL. The second step may further optionally comprise contacting the cells in culture with transferrin at 0.1-5 mg/mL. The second may also optionally comprise contacting the cells in culture with serum proteins or non-protein molecules such as, e.g., fetal bovine serum (1-20%), human plasma (1-20%), plasmanate (1-20%), human serum (1-20%), albumin (0.1-100 mg/mL), or heparin (0.1-10 U/mL).

The third step may comprise contacting the cells in culture with erythropoietin (EPO) at 1-100 U/mL. The third step may optionally comprise contacting the cells in culture with stem cell factor (SCF) at 1-1000 ng/mL. The third step may further optionally comprise contacting the cells in culture with an insulin-like molecule, such as e.g., insulin at 1-50 µg/mL, insulin-like growth factor 1 (IGF-1) at 1-50 µg/mL, insulin-like growth factor 2 (IGF-2) at 1-50 µg/mL, or mechano-growth factor at 1-50 µg/mL. The third step may also optionally comprise contacting the cells in culture with transferrin at 0.1-5 mg/mL. The third step may also optionally comprise contacting the cells in culture with serum proteins or non-protein molecules such as, e.g., fetal bovine serum (1-20%), human plasma (1-20%), plasmanate (1-20%), human serum (1-20%), albumin (0.1-100 mg/mL), or heparin (0.1-10 U/mL).

In some embodiments, methods of expansion and differentiation of the synthetic membrane-receptor complexes do not include culturing the synthetic membrane-receptor complexes in a medium comprising a myeloproliferative receptor (mpl) ligand.

The culture process may optionally comprise contacting cells by a method known in the art with a molecule, e.g., a DNA molecule, an RNA molecule, a mRNA, an siRNA, a microRNA, a lncRNA, a shRNA, a hormone, or a small molecule, that activates or knocks down one or more genes. Target genes can include, for example, genes that encode a transcription factor, a growth factor, or a growth factor receptor, including but not limited to, e.g., GATA1, GATA2, CMyc, hTERT, p53, EPO, SCF, insulin, EPO-R, SCF-R, transferrin-R, insulin-R.

In one embodiment, CD34+ cells are placed in a culture containing varying amounts of IMDM, FBS, glutamine, BSA, holotransferrin, insulin, dexamethasone, β-estradiol, IL-3, SCF, and erythropoietin, in three separate differentiation stages for a total of 22 days.

In one embodiment, CD34+ cells are placed in a culture containing varying amounts of IMDM, FBS, glutamine, BSA, holotransferrin, insulin, dexamethasone, β-estradiol, IL-3, SCF, and thrombopoietin, in three separate differentiation stages for a total of 14 days.

In one embodiment, CD34+ cells are placed in a culture containing varying amounts of IMDM, FBS, glutamine, BSA, holotransferrin, insulin, dexamethasone, β-estradiol, IL-3, SCF, and GCSF, in three separate differentiation stages for a total of 15 days.

Compositions

Provided herein are pharmaceutical compositions comprising synthetic membrane-receptor complexes that are suitable for administration to a subject. The pharmaceutical compositions generally comprise a population of synthetic membrane-receiver complexes and a pharmaceutically-acceptable carrier in a form suitable for administration to a subject. Pharmaceutically-acceptable carriers are determined in part by the particular composition being administered, as well as by the particular method used to administer the composition. Accordingly, there is a wide variety of suitable formulations of pharmaceutical compositions comprising a population of synthetic membrane-receptor complexes. (See, e.g., Remington's Pharmaceutical Sciences, Mack Publishing Co., Easton, Pa. 18th ed. (1990)). The pharmaceutical compositions are generally formulated as sterile, substantially isotonic and in full compliance with all Good Manufacturing Practice (GMP) regulations of the U.S. Food and Drug Administration.

Pharmaceutically-acceptable excipients include excipients that are generally safe, non-toxic, and desirable, including excipients that are acceptable for veterinary use as well as for human pharmaceutical use. Such excipients can be solid, liquid, semisolid, or, in the case of an aerosol composition, gaseous.

Examples of carriers or diluents include, but are not limited to, water, saline, Ringer's solutions, dextrose solution, and 5% human serum albumin. The use of such media and compounds for pharmaceutically active substances is well known in the art. Except insofar as any conventional media or compound is incompatible with the synthetic membrane-receiver complexes described herein, use thereof in the compositions is contemplated. Supplementary therapeutic agents may also be incorporated into the compositions. Typically, a pharmaceutical composition is formulated to be compatible with its intended route of administration. The synthetic membrane-receptor complexes can be administered by parenteral, topical, intravenous, oral, subcutaneous, intraarterial, intradermal, transdermal, rectal, intracranial, intraperitoneal, intranasal; intramuscular route or as inhalants. The synthetic membrane-receptor complexes can optionally be administered in combination with other therapeutic agents that are at least partly effective in treating the disease, disorder or condition for which the synthetic membrane-receiver complexes are intended.

Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial compounds such as benzyl alcohol or methyl parabens; antioxidants such as ascorbic acid or sodium bisulfite; chelating compounds such as ethylenediaminetetraacetic acid (EDTA); buffers such as acetates, citrates or phosphates, and compounds for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, e.g., water, ethanol, polyol (e.g., glycerol, propylene glycol, and liquid polyethylene glycol, and the like), and suitable mixtures thereof. The proper fluidity can be maintained, e.g., by the use of a coating such as lecithin, by the maintenance of the required particle size in the case of dispersion and by the use of surfactants. Prevention of the action of microorganisms can be achieved by various antibacterial and antifungal compounds, e.g., parabens, chlorobutanol, phenol, ascorbic acid, thimerosal, and the like. In many cases, it will be preferable to include isotonic compounds, e.g., sugars, polyalcohols such as manitol, sorbitol, sodium chloride in the composition. Prolonged absorption of the injectable compositions can be brought about by including in the composition a compound which delays absorption, e.g., aluminum monostearate and gelatin.

Sterile injectable solutions can be prepared by incorporating the synthetic membrane-receiver complexes in an effective amount and in an appropriate solvent with one or a combination of ingredients enumerated herein, as desired. Generally, dispersions are prepared by incorporating the synthetic membrane-receiver complexes into a sterile vehicle that contains a basic dispersion medium and any desired other ingredients. In the case of sterile powders for the preparation of sterile injectable solutions, methods of preparation are vacuum drying and freeze-drying that yields a powder of the active ingredient plus any additional desired ingredient from a previously sterile-filtered solution thereof. The synthetic membrane-receiver complexes can be administered in the form of a depot injection or implant preparation which can be formulated in such a manner to permit a sustained or pulsatile release of the synthetic membrane-receiver complexes, their receiver(s) and/or their oprional payload(s).

Oral compositions generally include an inert diluent or an edible carrier. They can be enclosed in gelatin capsules or compressed into tablets. For the purpose of oral therapeutic administration, the synthetic membrane-receiver complexes can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding compounds, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating compound such as alginic acid, Primogel, or corn starch; a lubricant such as magnesium stearate or Sterotes; a glidant such as colloidal silicon dioxide; a sweetening compound such as sucrose or saccharin; or a flavoring compound such as peppermint, methyl salicylate, or orange flavoring.

For administration by inhalation, the synthetic membrane-receiver complexes are delivered in the form of an aerosol spray from pressured container or dispenser which contains a suitable propellant, e.g., a gas such as carbon dioxide, or a nebulizer.

Systemic administration of compositions comprising synthetic membrane-receiver complexes can also be by transmucosal or transdermal means. For transmucosal or transdermal administration, penetrants appropriate to the barrier to be permeated are used in the formulation. Such penetrants are generally known in the art, and include, e.g., for transmucosal administration, detergents, bile salts, and fusidic acid derivatives. Transmucosal administration can be accomplished through the use of nasal sprays or suppositories. For transdermal administration, the modified red blood cells are formulated into ointments, salves, gels, or creams as generally known in the art.

The synthetic membrane-receiver complexes can also be prepared as pharmaceutical compositions in the form of suppositories (e.g., with conventional suppository bases such as cocoa butter and other glycerides) or retention enemas for rectal delivery.

In some embodiments, the synthetic membrane-receiver complexes are prepared with carriers that will decrease the rate with which synthetic membrane-receiver complexes are eliminated from the body of a subject. For example, controlled release formulation are suitable, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc.

In one embodiment the pharmaceutical composition comprising synthetic membrane-receiver polypeptide complexes is administered intravenously into a subject that would benefit from the pharmaceutical composition. In other embodiments, the composition is administered to the lymphatic system, e.g., by intralymphatic injection or by intranodal injection (see e.g., Senti et al., 2008 PNAS 105(46):17908), or by intramuscular injection, by subcutaneous administration, by direct injection into the thymus, or into the liver.

In one embodiment, the pharmaceutical composition comprising synthetic membrane-receiver polypeptide complexes is administered as a liquid suspension. In one embodiment the pharmaceutical composition is administered as a coagulated formulation that is capable of forming a depot following administration, and in a preferred embodiment slowly release synthetic membrane-receiver polypeptide complexes into circulation, or in a preferred embodiment remain in depot form.

In one embodiment, the pharmaceutical composition comprising synthetic membrane-receiver complexes is stored using methods and buffer compositions that are capable of maintaining viability of the synthetic membrane-receiver complexes. For example, deoxygenation prior to storage to maintain an anaerobic state, manipulation of pH, supplementation of metabolic precursors, manipulation of osmotic balance, increasing of the volume of the suspending medium, and/or reduction of oxidative stress by adding protective molecules can be used to maintain the viability of the synthetic membrane-receiver complexes. Several studies employing a combination of these strategies have reported maintenance of viability of erythrocytes allowing an extension of storage beyond 6 weeks (see e.g., Yoshida and Shevkoplyas, Blood Transfus 2010 8:220).

Pharmaceutically acceptable carriers or excipients may be used to deliver the synthetic membrane-receiver polypeptides described herein. Excipient refers to an inert substance used as a diluent or vehicle. Pharmaceutically acceptable carriers are used, in general, with a compound so as to make the compound useful for a therapy or as a product. In general, for any substance, a pharmaceutically acceptable carrier is a material that is combined with the substance for delivery to a subject. Conventional pharmaceutical carriers, aqueous, powder or oily bases, thickeners and the like may be necessary or desirable. In some cases the carrier is essential for delivery, e.g., to solubilize an insoluble compound for liquid delivery; a buffer for control of the pH of the substance to preserve its activity; or a diluent to prevent loss of the substance in the storage vessel. In other cases, however, the carrier is for convenience, e.g., a liquid for more convenient administration. Pharmaceutically acceptable salts of the compounds described herein may be synthesized according to methods known to those skilled in the arts.

Typically, pharmaceutically acceptable compositions are highly purified to be free of contaminants, are biocompatible and not toxic, and are suited to administration to a subject. If water is a constituent of the carrier, the water is highly purified and processed to be free of contaminants, e.g., endotoxins.

The pharmaceutically acceptable carrier may be lactose, dextrose, sucrose, sorbitol, mannitol, starch, gum acacia, calcium phosphate, alginates, gelatin, calcium silicate, micro-crystalline cellulose, polyvinylpyrrolidone, cellulose, water, syrup, methyl cellulose, methylhydroxy benzoate, propylhydroxy benzoate, talc, magnesium stearate, and/or mineral oil, but is not limited thereto. The pharmaceutical composition may further include a lubricant, a wetting agent, a sweetener, a flavor enhancer, an emulsifying agent, a suspension agent, and/or a preservative.

Provided are pharmaceutical compositions containing synthetic membrane-receiver complexes having effective levels of receivers. Such compositions contain a plurality of synthetic membrane-receiver complexes, e.g., $1\times10^3$ complexes, or $1\times10^4$, $1\times10^5$, $1\times10^6$, $1\times10^7$, $1\times10^8$, $1\times10^9$, $1\times10^{10}$, $1\times10^{11}$, $1\times10^{12}$, or greater than $1\times10^{12}$ complexes. In specific examples, synthetic membrane-receiver complexes generated from erythroid cells may be administered as packed red blood cells in a saline solution at a concentration of 10%, 20%, 30%, 40%, 50%, 60%, 70%, 80%, 90%, or greater than 90% mass to volume ratio (% m/v). The time of administration to a patient may range from 10 minutes to four hours, or more.

In specific examples, synthetic membrane-receiver complexes generated from erythroid cells can be stored in an appropriate buffer, e.g., an FDA-approved anticoagulant preservative solution such as anticoagulant citrate-dextrose A (ACD-A), citrate-phosphate dextrose (CPD), Citratephosphate-dextrose-dextrose (CP2D), or citrate-phosphate-dextrose-adenine (CPDA-1). The compositions may be stored for up to 21 days.

Alternatively, synthetic membrane-receiver complexes generated from erythroid cells can be stored in an approved additive solution, e.g., AS-1 (Adsol), AS-3 (Nutricel), AS-5 (Optisol), or AS-7 (SOLX).

Alternatively, synthetic membrane-receiver complexes generated from erythroid cells can stored in a glycerol cryoprotective solution. The compositions may be frozen and stored for up to 10 years. Frozen cells may be thawed and deglycerolized by successive washing steps, for example with 0.9% sodium chloride before use.

Provided herein are compositions and pharmaceutical compositions comprising a plurality of cultured functional erythroid cells that comprise a receiver. The compositions and pharmaceutical compositions may comprise a solution of appropriate storage buffer such as, e.g., anticoagulant citrate-dextrose A. The compositions and pharmaceutical compositions comprising the plurality of cultured functional erythroid cells that comprise a receiver may additionally comprise an approved additive such as, e.g., Adsol. The compositions and pharmaceutical compositions comprising the plurality of cultured functional erythroid cells that comprise receiver may additionally comprise a glycerol cryoprotective solution for frozen storage.

In one embodiment, the synthetic membrane-receiver polypeptide complex is able to form a multi-complex aggregate, e.g., a dimer, a trimer, a multimer, with another synthetic membrane-receiver polypeptide complex.

In one embodiment the synthetic membrane-receiver polypeptide complex is able to form a multi-complex aggregate, e.g., a dimer, a trimer, a multimer, with component of the circulatory system, e.g an erythrocyte, a reticulocyte, a platelet, a macrophage, a lymphocyte, a T cell, a B cell, a mast cell.

The dosing and frequency of the administration of the synthetic membrane-receiver complexes and pharmaceutical compositions thereof can be determined by the attending physician based on various factors such as the severity of disease, the patient's age, sex and diet, the severity of any inflammation, time of administration, and other clinical factors. In one example, an intravenous administration is initiated at a dose which is minimally effective, and the dose is increased over a pre-selected time course until a positive effect is observed. Subsequently, incremental increases in dosage are made limiting to levels that produce a corresponding increase in effect while taking into account any adverse affects that may appear.

Non-limited examples of suitable dosages can range, for example, from $1\times10^{10}$ to $1\times10^{14}$, from $1\times10^{11}$ to $1\times10^{13}$, or from $5\times10^{11}$ to $5\times10^{12}$ synthetic membrane-receiver complexes. Specific examples include about $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, $1\times10^{12}$, or more synthetic membrane-receiver complexes. Each dose of synthetic membrane-receiver complexes can be administered at intervals such as once daily, once weekly, twice weekly, once monthly, or twice monthly.

"Complex-based proportional dosage" is the number of synthetic membrane-receiver complexes administered as a dose relative to a naturally occurring quantity of circulating entities. The circulating entities may be cells, e.g., erythrocytes, reticulocytes, or lymphocytes, or targets, e.g., antigens, antibodies, viruses, toxins, cytokines, etc. The units are defined as synthetic membrane-receiver complex per circulating entity, ie SCMRC/CE. This dosage unit may include $10^{-7}$, $10^{-6}$, $10^{-5}$, $10^{-4}$, $10^{-3}$, $10^{-2}$, $10^{-1}$, 1, 10, $10^2$, $10^3$, $10^4$, $10^5$, $10^6$, $10^7$, $10^8$, $10^9$.

The pharmaceutical compositions described herein comprise a synthetic membrane-receiver complex and optionally a pharmaceutically active or therapeutic agent. The therapeutic agent can be a biological agent, a small molecule agent, or a nucleic acid agent.

Dosage forms are provided that comprise a pharmaceutical composition comprising a synthetic membrane-receiver complex described herein. In some embodiments, the dosage form is formulated as a liquid suspension for intravenous injection.

Medical devices are provided that comprise a container holding a pharmaceutical composition comprising a synthetic membrane-receiver complex described herein and an applicator for intravenous injection of the pharmaceutical composition to a subject.

Medical kits are provided that comprise a pharmaceutical composition comprising a synthetic membrane-receiver complex described herein and a medical device for intravenous injection of the pharmaceutical composition to a subject.

A pharmaceutically acceptable suspension of synthetic membrane-receiver complexes is preferably packaged in a volume of approximately 10 to approximately 250 ml. The packaging can be a syringe or an IV bag suitable for transfusions. Administration of the suspension is carried out, e.g., by intravenous or intra-arterial injection, optionally using a drip from an IV bag or the like. The administration is typically carried out intravenously in the arm or via a central catheter. For administrations exceeding 50 ml use of a drip is preferred.

Processes and Properties

In some embodiments, the membrane-receiver complex is generated using a precursor hematopoietic cell, e.g., a CD34+ cell, an erythrocyte, a platelet, a megakaryocyte, or a neutrophil as a source. In some embodiments, the precursor hematopoietic cell is isolated from a human donor by a GMP-compliant process. In some embodiments, the starting cells are sourced from an autologous donor. In some embodiments, the starting cells are sourced from an allogeneic donor. The donor may be typed for blood cell antigen polymorphisms and/or the donor is genotyped for blood cell antigens. The donor can be a universal blood donor. In some embodiments, the donor has the Bombay phenotype, i.e. does not express the H antigen. In some embodiments, the donor has ABO blood type O and is Rh-negative.

In some embodiments, the membrane-receiver complex is generated using CD34+ hematopoietic progenitor cells, mobilized peripheral CD34+ cells, or bone marrow-derived CD34+ cells as a source for the starting material. In some embodiments, the starting cells are derived from umbilical cord blood, are induced pluripotent stem cells or are embryonic stem cells.

The synthetic membrane-receiver complex may be cultured. Cultured complexes can be scaled up from bench-top scale to bioreactor scale. For example, the complexes are cultured until they reach saturation density, e.g., $1 \times 10^5$, $1 \times 10^6$, $1 \times 10^7$, or greater than $1 \times 10^7$ complexes per ml. Optionally, upon reaching saturation density, the complexes can be transferred to a larger volume of fresh medium. The membrane-receiver complexes may be cultured in a bioreactor, such as, e.g., a Wave-type bioreactor, a stirred-tank bioreactor. Various configurations of bioreactors are known in the art and a suitable configuarion may be chosen as desired. Configurations suitable for culturing and/or expanding populations of synthetic membrane-receiver complexes can easily be determined by one of skill in the art without undue experimentation. The bioreactor can be oxygenated. The bioreactor may optionally contain one or more impellers, a recycle stream, a media inlet stream, and control components to regulate the influx of media and nutrients or to regulate the outflux of media, nutrients, and waste products.

In some embodiments, the bioreactor may contain a population of human functional erythroid cells comprising a receiver that shed their intracellular DNA over the course of the culture process. For example, the bioreactor may contain a population of human erythroid cells, enucleated erythroid cells, and pyrenocytes after culture. In a specific embodiment, the human erythroid cells and enucleated erythroid cells comprise a receiver and the receiver is retained by the enucleated erythroid cell, whereas the exogenous nucleic acid encoding the receiver is not retained by the enucleated cell. In certain embodiments, the enucleated functional erythroid cell comprising the receiver exhibits substantially the same osmotic membrane fragility as a corresponding isolated unmodified, uncultured erythroid cell.

In one embodiment. The population of synthetic membrane-receiver complexes generated from erythroid cells or erythroid cell precursors in the bioreactor undergo a total expansion of greater than 20,000-fold in 14 days or greater. In some embodiments, the receiver is introduced into a cultured or freshly isolated erythroid cell precursor and after introduction of an exogenous nucleic acid encoding the receiver the population of synthetic membrane-receiver complexes generated from the erythroid cell precursors in the bioreactor expands in the bioreactor from the precursor cells by more than 20,000-fold.

In some embodiments, the bioreactor is a Wave bioreactor or a impeller-driven agitator. The bioreactor may be aerated by means of a sparger. In one embodiment, the bioreactor is disposable. In one embodiment, the bioreactor is CIP (cleaned in place). The final complexes number of synthetic membrane-receiver complexes that may be obtained in a bioreactor setting as described herein can be greater than $10^9$, $10^{10}$, $10^{11}$, $10^{12}$, $10^{13}$ or greater than $10^{13}$ complexes. The density of synthetic membrane-receiver complexes may be monitored during culture by measuring cell density by hemacytometer counting or by optical density reading at 600 nm. Optionally, the culture process is monitored for pH levels, oxygenation, agitation rate, and/or recycle rate.

The identity of the membrane-receiver complexes can be assessed by in vitro assays. For example, the identity of the membrane-receiver complexes is assessed by counting the number of complexes in a population, e.g., by microscopy, by flow cytometry, or by hemacytometry. Alternatively or in addition, the identity of the membrane-receiver complexes is assessed by analysis of protein content of the complex, e.g., by flow cytometry, Western blot, immunoprecipitation, fluorescence spectroscopy, chemiluminescence, mass spectrometry, or absorbance spectroscopy. In one embodiment, the protein content assayed is a non-surface protein, e.g., an integral membrane protein, hemoglobin, adult hemoglobin, fetal hemoglobin, embryonic hemoglobin, a cytoskeletal protein. In one embodiment, the protein content assayed is a surface protein, e.g., a differentiation marker, a receptor, a co-receptor, a transporter, a glycoprotein. In one embodiment, the surface protein is selected from the list including, but not limited to, glycophorin A, CKIT, transferrin receptor, Band3, Kell, CD45, CD46, CD47, CD55, CD59, CR1. In some embodiments, the identity of the membrane-receiver complexes is assessed by analysis of the receiver content of the complex, e.g., by flow cytometry, Western blot, immunoprecipitation, fluorescence spectroscopy, chemiluminescence, mass spectrometry, or absorbance spectroscopy. For example, the identity of the membrane-receiver complexes can be assessed by the mRNA content of the complexes, e.g., by RT-PCR, flow cytometry, or northern blot. The identity of the membrane-receiver complexes can be assessed by nuclear material content, e.g., by flow cytometry, microscopy, or southern blot, using, e.g., a nuclear stain or a nucleic acid probe. Alternatively or in addition, the identity of the membrane-receiver complexes is assessed by lipid content of the complexes, e.g by flow cytometry, liquid chromatography, or by mass spectrometry.

In some embodiments, the identity of the membrane-receiver complexes is assessed by metabolic activity of the complexes, e.g by mass spectrometry, chemiluminescence, fluorescence spectroscopy, absorbance spectroscopy. Metabolic acitivity can be assessed by ATP consumption rate and/or the metabolic activity is assessed measuring 2,3-diphosphoglycerate (2,3-DPG) level in the synthetic membrane-receiver complex. The metabolic activity can be assessed as the rate of metabolism of one of the following, including but not limited to, Acetylsalicylic acid, N-Acetylcystein, 4-Aminophenol, Azathioprine, Bunolol, Captopril, Chlorpromazine, Dapsone, Daunorubicin, Dehydroepiandrosterone, Didanosin, Dopamine, Epinephrine, Esmolol, Estradiol, Estrone, Etoposide, Haloperidol, Heroin, Insulin, Isoproterenol, Isosorbide dinitrate, LY 217896, 6-mercaptopurine, Misonidazole, Nitroglycerin, Norepinephrine, Para-aminobenzoic acid. In some embodiments, the identity of the membrane-receiver complexes is assessed by partitioning of a substrate by the complexes, e.g by mass spectrometry, chemiluminescence, fluorescence spectroscopy, or absorbance spectroscopy. The substrate can be one of the following, including but not limited to, Acetazolamide, Arbutine, Bumetamide, Creatinine, Darstine, Desethyldorzolamide, Digoxigenin digitoxoside, Digoxin-16'-glucuronide, Epinephrine, Gentamycin, Hippuric acid, Metformin, Norepinephrine, p-Aminohippuric acid, Papaverine, Penicillin G, Phenol red, Serotonin, Sulfosalicylic acid, Tacrolimus, Tetracycline, Tucaresol, and Vancomycin.

In one embodiment, the population of synthetic membrane-receiver omplexes is differentiated from a precursor cell or complex. In this embodiment, the differentiation state of the population of synthetic membrane-receiver complexes is assessed by an in vitro assay. The in vitro assays include those described herein for assessing the identity of the complexes, including but not limited to expansion rate, number, protein content or expression level, mRNA content or expression level, lipid content, partition of a substrate, catalytic activity, or metabolic activity.

In some embodiments, the membrane-receiver complexes are cultured and the differentiation state of the complexes is assessed at multiple time points over the course of the culture process.

Synthetic membrane-receiver complexes may be generated using reticulocytes as a source for starting material. The purity of isolated reticulocytes may be assessed using microscopy in that reticulocytes are characterized by a reticular (mesh-like) network of ribosomal RNA that becomes visible under a microscope with certain stains such as new methylene blue or brilliant cresyl blue. Surface expression of transferrin receptor (CD71) is also higher on reticulocytes and decreases and they mature to erythrocytes, allowing for enrichment and analysis of reticulocyte populations using anti-CD71 antibodies (See, e.g., Miltenyi CD71 microbeads product insert No. 130-046-201). Alternatively, analysis of creatine and hemoglobin A1C content and pyruvate kinase, aspartate aminotransferase, and porphobilinogen deaminase enzyme activity may be used to assess properties of the isolated reticulocytes relative to mature erythrocytes (See, e.g., Brun et al., Blood 76:2397-2403 (1990)). For example, the activity of porphobilinogen deaminase is nearly 9 fold higher whereas the hemoglobin A1C content is nearly 10 fold less in reticulocytes relative to mature erythrocytes.

In some embodiments, cells suitable for generating synthetic membrane-receiver complexes are differentiated ex vivo and/or in vivo from one or more stem cells. In one embodiment, the one or more stem cells are one or more hematopoietic stem cells. Various assays may be performed to confirm the ex vivo differentiation of cultured hematopoietic stem cells into reticulocytes and erythrocytes, including, for example, microscopy, hematology, flow cytometry, deformability measurements, enzyme activities, and hemoglobin analysis and functional properties (Giarratana et al., Nature Biotech. 23:69-74 (2005)). The phenotype of cultured hematopoietic stem cells may be assessed using microscopy of cells stained, for example, with Cresyl Brilliant blue. Reticulocytes, for example, exhibit a reticular network of ribosomal RNA under these staining conditions whereas erythrocytes are devoid of staining. Enucleated cells may also be monitored for standard hematological variables including mean corpuscular volume (MCV; femtoliters (fL)), mean corpuscular hemoglobin concentration (MCHC; %) and mean corpuscular hemoglobin (MCH; pg/cell) using, for example, an XE2100 automat (Sysmex, Roche Diagnostics).

In some embodiments, the synthetic membrane-receiver complexes are assessed for their basic physical properties, e.g., size, mass, volume, diameter, buoyancy, density, and membrane properties, e.g., viscosity, deformability fluctuation, and fluidity.

In one embodiment, the diameter of the synthetic membrane-receiver complexes is measured by microscopy or by automated instrumentation, e.g., a hematological analysis instrument. In one embodiment the diameter of the synthetic membrane-receiver complexes is between about 1-20 microns. In one embodiment, the diameter of the synthetic membrane-receiver complexes is at least in one dimension between about 1-20 microns. In one embodiment, the diameter of the synthetic membrane-receiver complexes is less than about 1 micron. In one embodiment, the diameter of the complexes in one dimension is larger than about 20 microns. In one embodiment, the diameter of the synthetic membrane-receiver complexes is between about 1 micron and about 20 microns, between about 2 microns and about 20 microns between about 3 microns and about 20 microns between about 4 microns and about 20 microns between about 5 microns and about 20 microns between about 6 microns and about 20 microns, between about 5 microns and about 15 microns or between about 10 microns and about 30 microns.

In one embodiment, the mean corpuscular volume of the synthetic membrane-receiver complexes is measured using a hematological analysis instrument. In one embodiment the volume of the mean corpuscular volume of the complexes is greater than 10 fL, 20 fL, 30 fL, 40 fL, 50 fL, 60 fL, 70 fL, 80 fL, 90 fL, 100 fL, 110 fL, 120 fL, 130 fL, 140 fL, 150 fL, or greater than 150 fL. In one embodiment the mean corpuscular volume of the complexes is less than 30 fL, 40 fL, 50 fL, 60 fL, 70 fL, 80 fL, 90 fL, 100 fL, 110 fL, 120 fL, 130 fL, 140 fL, 150 fL, 160 fL, 170 fL, 180 fL, 190 fL, 200 fL, or less than 200 fL. In one embodiment the mean corpuscular volume of the complexes is between 80-100 femtoliters (fL).

In one embodiment the average buoyant mass of the synthetic membrane-receiver complexes (pg/cell) is measured using a suspended microchannel resonatory or a double suspended microchannel resonatory (see e.g., Byun et al PNAS 2013 110(19):7580 and Bryan et al. Lab Chip 2014 14(3):569).

In one embodiment the dry density of the synthetic membrane-receiver complexes is measured by buoyant mass in an H2O-D2O exchange assay (see e.g., Feijo Delgado et al., PLOS One 2013 8(7):e67590).

In some embodiments, the synthetic membrane-receiver complexes have an average membrane deformability fluctuation of standard deviation greater than 10, 20, 30, 40, 50, 60, 70, 80, 90, 100 or greater than 100 mrad as measured by spatial light interference microscopy (SLIM) (see e.g., Bhaduri et al., Sci Reports 2014, 4:6211).

In one embodiment, the average membrane viscosity of a population of synthetic membrane-receiver complexes is measured by detecting the average fluorescence upon incubation with viscosity-dependent quantum yield fluorophores (see e.g., Haidekker et al. Chem & Biol 2001 8(2):123).

In one embodiment, the membrane fluidity of the synthetic membrane-receiver complexes is measured by fluorescence polarization, e.g., with BMG Labtech POLARstar Omega microplate reader.

For example, to measure deformability reticulocytes may be separated from nucleated cells on day 15 of culture, for example, by passage through a deleukocyting filter (e.g., Leucolab LCG2, Macopharma) and subsequently assayed using ektacytometry. The enucleated cells are suspended in 4% polyvinylpyrrolidone solution and then exposed to an increasing osmotic gradient from 60 to 450 mosM. Changes in the laser diffraction pattern (deformability index) of the cells are recorded as a function of osmolarity, to assess the dynamic deformability of the cell membrane. The maximum deformability index achieved at a physiologically relevant osmolarity is related to the mean surface area of erythrocytes.

In some embodiments, the synthetic membrane-receiver complexes are analyzed for hemoglobin contents. Assays of hemoglobin may be used to assess the phenotype of differentiated cells (Giarratana et al., Nature Biotech. 23:69-74 (2005)). For example, high performance liquid chromatography (HPLC) using a Bio-Rad Variant II Hb analyzer (Bio-Rad Laboratories) may be used to assess the percentage of various hemoglobin fractions. Oxygen equilibrium may be measured using a continuous method with a double-wavelength spectrophotometer (e.g., Hemox analyzer, TCS). The binding properties of hemoglobin may be assessed using flash photolysis. In this method, the rebinding of CO to intracellular hemoglobin tetramers are analyzed at 436 nm after photolysis with a 10 nanosecond pulse at 532 nm.

The synthetic membrane-receiver complexes described herein can be purified following manufacture if desired. Many suitable methods of purification are known in the art. For example, the synthetic membrane-receiver complexes are purified by centrifugation, magnetophoresis, irradiation, acoustophoresis, and chemical or physical enucleation. In one embodiment synthetic membrane-receiver complexes are purified by ex vivo maturation with, e.g., a stromal cell co-culture. In one embodiment, synthetic membrane-receiver complexes are purified by chemical or enzymatic treatment of complexes, e.g by treatment with a deglycosylation enzyme.

In one embodiment the synthetic membrane-receiver polypeptide complexes are purified by disabling any residual replicative potential of the membrane-receiver polypeptide complexes. In one embodiment the synthetic membrane-receiver polypeptide complexes are subjected to radiation, e.g., X rays, gamma rays, beta particles, alpha particles, neutrons, protons, elemental nuclei, UV rays in order to damage residual replication-competent nucleic acids.

Ionizing radiation is energy transmitted via X rays, gamma rays, beta particles (high-speed electrons), alpha particles (the nucleus of the helium atom), neutrons, protons, and other heavy ions such as the nuclei of argon, nitrogen, carbon, and other elements. X rays and gamma rays are electromagnetic waves like light, but their energy is much higher than that of light (their wavelengths are much shorter). Ultraviolet (UV) light is a radiation of intermediate energy that can damage cells but UV light differs from the forms of electromagnetic radiation mentioned above in that it does not cause ionization (loss of an electron) in atoms or molecules, but rather excitation (change in energy level of an electron). The other forms of radiation—particles—are either negatively charged (electrons), positively charged (protons, alpha rays, and other heavy ions), or electrically neutral (neutrons).

Radiation-induced ionizations may act directly on the cellular component molecules or indirectly on water molecules, causing water-derived radicals. Radicals react with nearby molecules in a very short time, resulting in breakage of chemical bonds or oxidation (addition of oxygen atoms) of the affected molecules. The major effect in cells is DNA breaks. Since DNA consists of a pair of complementary double strands, breaks of either a single strand or both strands can occur. However, the latter is believed to be much more important biologically. Most single-strand breaks can be repaired normally thanks to the double-stranded nature of the DNA molecule (the two strands complement each other, so that an intact strand can serve as a template for repair of its damaged, opposite strand). In the case of double-strand breaks, however, repair is more difficult and erroneous rejoining of broken ends may occur. These so-called mis-repairs result in induction of mutations, chromosome aberrations, or cell death.

Deletion of DNA segments is the predominant form of radiation damage in cells that survive irradiation. It may be caused by (1) misrepair of two separate double-strand breaks in a DNA molecule with joining of the two outer ends and loss of the fragment between the breaks or (2) the process of cleaning (enzyme digestion of nucleotides—the component molecules of DNA) of the broken ends before rejoining to repair one double-strand break.

Radiations differ not only by their constituents (electrons, protons, neutrons, etc.) but also by their energy. Radiations that cause dense ionization along their track (such as neutrons) are called high-linear-energy-transfer (high-LET) radiation, a physical parameter to describe average energy released per unit length of the track. (See the accompanying figure.) Low-LET radiations produce ionizations only sparsely along their track and, hence, almost homogeneously within a cell. Radiation dose is the amount of energy per unit of biological material (e.g., number of ionizations per cell). Thus, high-LET radiations are more destructive to biological material than low-LET radiations—such as X and gamma rays—because at the same dose, the low-LET radiations induce the same number of radicals more sparsely within a cell, whereas the high-LET radiations—such as neutrons and alpha particles—transfer most of their energy to a small region of the cell. The localized DNA damage caused by dense ionizations from high-LET radiations is more difficult to repair than the diffuse DNA damage caused by the sparse ionizations from low-LET radiations.

In one embodiment, a population of synthetic membrane-receiver polypeptide complexes are subjected to gamma irradiation using an irradiation dose of more than 1, 5, 10, 15, 20, 25, 30, 35, 40, 50, 60, 70, 80, 90, 100, or more than 100 kGy.

In one embodiment, a population of synthetic membrane-receiver polypeptide complexes are subjected to X-ray irradiation using an irradiation dose of more than 0.1, 0.5, 1, 5, 10, 15, 20, 25, 30, 35, 40, 50, 60, 70, 80, 90, 100, 200, 300, 400, 500, 600, 700, 800, 900, 1000, 2000, 3000, 4000, 5000, 6000, 7000, 8000, 9000, 10000, or greater than 10000 mSv.

The purity of a population of synthetic membrane-receiver complexes can be assessed by measuring the homogeneity of the population. In one embodiment, the average distribution width of the synthetic membrane-receiver complexes is measured by a hematological analysis instrument. In one embodiment, the population of synthetic membrane-receiver complexes has a reticulocyte to non-reticulocyte ratio greater than 10, 100, 1000, $10^4$, $10^5$, $10^6$, or greater than $10^6$. The homogeneity of the population of synthetic membrane-receiver complexes may be assessed by measuring the stromal cell content of the population. In one embodiment, the population of synthetic membrane-receiver complexes has less than 1 ppb of stromal cells. Alternatively or in addition, the homogeneity of the population of synthetic membrane-receiver complexes is assessed by measuring the viral titer and/or a bacterial colony forming potential of the population.

In one embodiment the homogeneity of a population of synthetic membrane-receiver complexes is assessed by an in vitro assay. The in vitro assays include those described herein for assessing the identity of the complexes, including but not limited to expansion rate, number, protein content or expression level, mRNA content or expression level, lipid content, partition of a substrate, catalytic activity, or metabolic activity.

Mature erythrocytes for use in generating the synthetic membrane-receiver complexes may be isolated using various methods such as, for example, a cell washer, a continuous flow cell separator, density gradient separation, fluorescence-activated cell sorting (FACS), Miltenyi immunomagnetic depletion (MACS), or a combination of these methods (See, e.g., van der Berg et al., Clin. Chem. 33:1081-1082 (1987); Bar-Zvi et al., J. Biol. Chem. 262: 17719-17723 (1987); Goodman et al., Exp. Biol. Med. 232:1470-1476 (2007)).

Erythrocytes may be isolated from whole blood by simple centrifugation (See, e.g., van der Berg et al., Clin. Chem. 33:1081-1082 (1987)). For example, EDTA-anticoagulated whole blood may be centrifuged at 800×g for 10 min at 4° C. The platelet-rich plasma and buffy coat are removed and the red blood cells are washed three times with isotonic saline solution (NaCl, 9 g/L).

Alternatively, erythrocytes may be isolated using density gradient centrifugation with various separation mediums such as, for example, Ficoll, Hypaque, Histopaque, Percoll, Sigmacell, or combinations thereof. For example, a volume of Histopaque-1077 is layered on top of an equal volume of Histopaque-1119. EDTA-anticoagulated whole blood diluted 1:1 in an equal volume of isotonic saline solution (NaCl, 9 g/L) is layered on top of the Histopaque and the sample is centrifuged at 700×g for 30 min at room temperature. Under these conditions, granulocytes migrate to the 1077/1119 interface, lymphocytes, other mononuclear cells and platelets remain at the plasma/1077 interface, and the red blood cells are pelleted. The red blood cells are washed twice with isotonic saline solution.

Alternatively, erythrocytes may be isolated by centrifugation using a Percoll step gradient (See, e.g., Bar-Zvi et al., J. Biol. Chem. 262:17719-17723 (1987)). For example, fresh blood is mixed with an anticoagulant solution containing 75 mM sodium citrate and 38 mM citric acid and the cells washed briefly in Hepes-buffered saline. Leukocytes and platelets are removed by adsorption with a mixture of α-cellulose and Sigmacell (1:1). The erythrocytes are further isolated from reticulocytes and residual white blood cells by centrifugation through a 45/75% Percoll step gradient for 10 min at 2500 rpm in a Sorvall SS34 rotor. The erythrocytes are recovered in the pellet while reticulocytes band at the 45/75% interface and the remaining white blood cells band at the 0/45% interface. The Percoll is removed from the erythrocytes by several washes in Hepes-buffered saline. Other materials that may be used to generate density gradients for isolation of erythrocytes include OptiPrep™, a 60% solution of iodixanol in water (from Axis-Shield, Dundee, Scotland).

Erythrocytes may be separated from reticulocytes, for example, using flow cytometry (See, e.g., Goodman el al., Exp. Biol. Med. 232:1470-1476 (2007)). In this instance, whole blood is centrifuged (550×g, 20 min, 25° C.) to separate cells from plasma. The cell pellet is resuspended in phosphate buffered saline solution and further fractionated on Ficoll-Paque (1.077 density), for example, by centrifugation (400×g, 30 min, 25° C.) to separate the erythrocytes from the white blood cells. The resulting cell pellet is resuspended in RPMI supplemented with 10% fetal bovine serum and sorted on a FACS instrument such as, for example, a Becton Dickinson FACSCalibur (BD Biosciences, Franklin Lakes, N.J., USA) based on size and granularity.

Erythrocytes may be isolated by immunomagnetic depletion (See, e.g., Goodman, el al., (2007) Exp. Biol. Med. 232:1470-1476). In this instance, magnetic beads with cell-type specific antibodies are used to eliminate non-erythrocytes. For example, erythrocytes are isolated from the majority of other blood components using a density gradient as described herein followed by immunomagnetic depletion of any residual reticulocytes. The cells are pre-treated with human antibody serum for 20 min at 25° C. and then treated with antibodies against reticulocyte specific antigens such as, for example, CD71 and CD36. The antibodies may be directly attached to magnetic beads or conjugated to PE, for example, to which magnetic beads with anti-PE antibody will react. The antibody-magnetic bead complex is able to selectively extract residual reticulocytes, for example, from the erythrocyte population.

Erythrocytes may also be isolated using apheresis. The process of apheresis involves removal of whole blood from a patient or donor, separation of blood components using centrifugation or cell sorting, withdrawal of one or more of the separated portions, and transfusion of remaining components back into the patient or donor. A number of instruments are currently in use for this purpose such as for example the Amicus and Alyx instruments from Baxter (Deerfield, Ill., USA), the Trima Accel instrument from Gambro BCT (Lakewood, Colo., USA), and the MCS+9000 instrument from Haemonetics (Braintree, Mass., USA). Additional purification methods may be necessary to achieve the appropriate degree of cell purity.

In some embodiments, the synthetic membrane-receiver complexes are differentiated ex vivo and/or in vivo from one or more reticulocytes. Reticulocytes may be used to generate synthetic membrane-receiver complexes. Reticulocytes are immature red blood cells and compose approximately 1% of the red blood cells in the human body. Reticulocytes develop and mature in the bone marrow. Once released into circulation, reticulocytes rapidly undergo terminal differentiation to mature erythrocytes. Like mature erythrocytes, reticulocytes do not have a cell nucleus. Unlike mature erythrocytes, reticulocytes maintain the ability to perform protein synthesis. In some embodiments, exogenous nucleic acid (such as mRNA) encoding a receiver is introduced into reticulocytes to generate synthetic membrane-receiver complexes.

Reticulocytes of varying age may be isolated from peripheral blood based on the differences in cell density as the reticulocytes mature. Reticulocytes may be isolated from peripheral blood using differential centrifugation through various density gradients. For example, Percoll gradients may be used to isolate reticulocytes (See, e.g., Noble el al., Blood 74:475-481 (1989)). Sterile isotonic Percoll solutions of density 1.096 and 1.058 g/ml are made by diluting Percoll (Sigma-Aldrich, Saint Louis, Mo., USA) to a final concentration of 10 mM triethanolamine, 117 mM NaCl, 5 mM glucose, and 1.5 mg/ml bovine serum albumin (BSA). These solutions have an osmolarity between 295 and 310 mOsm. Five milliliters, for example, of the first Percoll solution (density 1.096) is added to a sterile 15 ml conical centrifuge tube. Two milliliters, for example, of the second Percoll solution (density 1.058) is layered over the higher density first Percoll solution. Two to four milliliters of whole blood are layered on top of the tube. The tube is centrifuged at 250×g for 30 min in a refrigerated centrifuge with swing-out tube holders. Reticulocytes and some white cells migrate to the interface between the two Percoll layers. The cells at the interface are transferred to a new tube and washed twice with phosphate buffered saline (PBS) with 5 mM glucose, 0.03 mM sodium azide and 1 mg/ml BSA. Residual white blood cells are removed by chromatography in PBS over a size exclusion column.

Alternatively, reticulocytes may be isolated by positive selection using an immunomagnetic separation approach (See, e.g., Brun et al., Blood 76:2397-2403 (1990)). This approach takes advantage of the large number of transferrin receptors that are expressed on the surface of reticulocytes relative to erythrocytes prior to maturation. Magnetic beads coated with an antibody to the transferrin receptor may be used to selectively isolate reticulocytes from a mixed blood cell population. Antibodies to the transferrin receptor of a variety of mammalian species, including human, are available from commercial sources (e.g., Affinity BioReagents, Golden, Colo., USA; Sigma-Aldrich, Saint Louis, Mo., USA). The transferrin antibody may be directly linked to the magnetic beads. Alternatively, the transferrin antibody may be indirectly linked to the magnetic beads via a secondary antibody. For example, mouse monoclonal antibody 10D2 (Affinity BioReagents, Golden, Colo., USA) against human transferrin may be mixed with immunomagnetic beads coated with a sheep anti-mouse immunoglobulin G (Dynal/Invitrogen, Carlsbad, Calif., USA). The immunomagnetic beads are then incubated with a leukocyte-depleted red blood cell fraction. The beads and red blood cells are incubated at 22° C. with gentle mixing for 60-90 min followed by isolation of the beads with attached reticulocytes using a magnetic field. The isolated reticulocytes may be removed from the magnetic beads using, for example, DETACHaBEAD® solution (from Invitrogen, Carlsbad, Calif., USA). Alternatively, reticulocytes may be isolated from in vitro growth and maturation of CD34+ hematopoietic stem cells using the methods described herein.

Terminally-differentiated, enucleated erythrocytes can be separated from other cells based on their DNA content. In a non-limiting example, cells are first labeled with a vital DNA dye, such as Hoechst 33342 (Invitrogen Corp.). Hoechst 33342 is a cell-permeant nuclear counterstain that emits blue fluorescence when bound to double-stranded DNA. Undifferentiated precursor cells, macrophages or other nucleated cells in the culture are stained by Hoechst 33342, while enucleated erythrocytes are Hoechst-negative. The Hoechst-positive cells can be separated from enucleated erythrocytes by using fluorescence activated cell sorters or other cell sorting techniques. The Hoechst dye can be removed from the isolated erythrocytes by dialysis or other suitable methods.

A population of synthetic membrane-receiver complexes can be purified by reducing the nuclear material content of the population of complexes. For example, the enucleation rate of the population of complexes is increased, and/or the number of enucleated synthetic membrane-receiver complexes is increased or enriched.

Populations of synthetic membrane-receiver complexes can be incubated with a small molecule, e.g., an actin inhibitor, e.g., cytochalasin A, B, C, D, E, F, H, J, and then centrifuged to remove nuclear material. Alternatively or in addition, a population of synthetic membrane-receiver complexes can be mechanically manipulated by passing through progressively smaller size-restrictive filters to remove nuclear material. The population of synthetic membrane-receiver complexes may also be incubated on a fibronectin-coated plastic surface to increase the removal of nuclear material. In one embodiment, the population of synthetic membrane-receiver complexes is incubated in co-culture with stromal cells, e.g., macrophages, to increase the removal of nuclear material.

In some embodiments, the population of synthetic membrane-receiver complexes is greater than 5%, 10%, 15%, 20%, 25%, 30%, 35%, 40%, 45%, 50%, 55%, 60%, 65%, 70%, 75%, 80%, 85%, 90%, 95%, 99%, 99.5%, 99.9%, or greater than 99.9% enucleated.

In some embodiments, the synthetic membrane-receiver complexes are not co-cultured with support cells, e.g., with an adherent stromal layer. In some embodiments, the population of synthetic membrane-receiver complexes is generated by contacting erythroid cells with a receiver and differentiating the erythroid cells to obtain a population of enucleated cells comprising the receiver. The population of synthetic membrane-receiver complexes is obtained without an enrichment step, such as gravitational separation, magnetic or fluorescent sorting, irradiation, poisoning of nucleated cells, and the like to select for enucleated cells.

In some embodiments, the population of synthetic membrane-receiver complexes is comprised of greater than 5%, 10%, 15%, 20%, 25%, 30%, 35%, 40%, 45%, 50%, 55%, 60%, 65%, 70%, 75%, 80%, 85%, 90%, 95%, 99%, 99.5%, 99.9%, or greater than 99.9% of synthetic membrane-receiver complexes that lack nuclear material as assessed by an assay to detect nuclear material such as those described herein.

In some embodiments, the presence, biological activity and/or function of a receiver, such as a receiver polypeptide exhibited by synthetic membrane-receiver complexes is assessed. Many suitable assays are available and known in the art.

In one embodiment, the receiver is a polypeptide on the surface of the synthetic membrane-receiver complex. The presence of the receiver can be assessed by assays including but not limited to flow cytometry, western blotting, RT-PCR, Northern blotting, Coombs rosetting, mass spectrometry. In one embodiment, the receiver is a polypeptide in the interior of the synthetic membrane-receiver complex. The presence of the receiver can be assessed by assays including but not limited to Western blotting, RT-PCR, Norther blotting, PCR, Southern blotting, mass spectrometry.

In one embodiment, the receiver is a nucleic acid on the surface of the synthetic membrane-receiver complex. The presence of the receiver can be assessed by assays including but not limited to flow cytometry, flow cytometry with a homologous fluorescent probe, southern blotting, northern blotting, PCR. In one embodiment, the receiver is a nucleic acid in the interior of the synthetic membrane-receiver complex. The presence of the receiver can be assessed by assays including but not limited to southern blotting, northern blotting, PCR.

In one embodiment, the receiver is a small molecule on the surface of the synthetic membrane-receiver complex. The presence of the receiver can be assessed by assays including but not limited to flow cytometry, mass spectrometry. In one embodiment, the receiver is a small molecule in the interior of the synthetic membrane-receiver complex. The presence of the receiver can be assessed by assays including but not limited to nass spectrometry, fluorescence spectroscopy.

In one embodiment, the receiver is a lipid in the membrane of the synthetic membrane-receiver complex. The presence of the receiver can be assessed by assays including but not limited to mass spectrometry, flow cytometry, membrane solubility, fluorescence polarization, spatial light interferences microscopy.

In one embodiment, the receiver is fluorescent or is fused to a fluoresecent molecule or is co-expressed from an exogenous nucleic acid (e.g., in a vector) with a fluorescent reporter protein like GFP. The presence of the receiver in or on the synthetic membrane-receiver complex can be assessed by assays including but not limited to flow cytometry, fluorescence spectroscopy, absorbance spectroscopy.

In one embodiment, the receiver is a gaseous molecule. The presence of the receiver in or on the synthetic membrane-receiver complex can be assessed by assays including but not limited to chemiluminescence assays, mass spectroscopy.

The presence of the receiver in or on the synthetic membrane-receiver complex can be assessed by flow cytometry in a quantitative fashion using calibration beads such as commercially available cytometry calibration beads to quantify the number of receivers on an individual complex. Alternatively or in addition, the presence of the receiver in or on the synthetic membrane-receiver complex can be assessed by Western blot in a quantitative fashion using a standard of known concentration that is detectable using the same detection reagents as the receiver, and in this way the number of receivers on an individual complex can be quantified.

In some embodiments, the presence of two or more different receivers can be assessed by the same or different methods, either simultaneously, in sequential fashion, or in parallel. For example, in one embodiment a receiver on the surface can be assessed by flow cytometry using an antibody specific to the receiver and a different receiver not on the surface that is fluoresecent can be assessed by fluorescent signal using a different channel in flow cytometry. In a different example, a receiver on the surface can be assessed by flow cytometry and a different receiver not on the surface can be assessed by Western blot.

In a specific embodiment, the receiver is retained on the synthetic membrane-receiver complex following terminal differentiation of the cell source. For example, the membrane-receiver complex is generated from a cultured erythroid cell and the expression or presence of the receiver is assessed following terminal differentiation of the cell by a suitable method, e.g., by flow cytometry, Western blot, immunoprecipitation, fluorescence spectroscopy, chemiluminescence, Southern blot, Northern blot, or absorbance spectroscopy.

In a specific embodiment, the receiver is retained on the synthetic membrane-receiver complex following circulation in vivo after administration of the synthetic membrane-receiver complex to a subject. The synthetic membrane-receiver complex can be injected into a laboratory animal or animal model, such as a mouse intravenously, e.g., via the tail vein, or is injected into a human intravenously. Then blood is drawn and the presence of the receiver on the synthetic membrane-receiver complex is assessed by suitable assay, e.g., by flow cytometry, Western blot, immunoprecipitation, fluorescence spectroscopy, chemiluminescence, Southern blot, Northern blot, or absorbance spectroscopy.

In some embodiments, the biological activity of the receiver in or on the synthetic membrane-receiver complex, the overall biological activity of the complex, and the overall activity of a population of complexes can be assessed by in vitro assays.

In some embodiments, the activity of the synthetic membrane-receiver complex is rapidly iterated using a model cell line. For example, a library of suitable receivers is expressed in a model cell line, e.g., HEK293T or K562, and the activity is assessed via a suitable assay; then the best receiver candidate, e.g., the one that is expressed at the highest level or one that demonstrates the highest activity in the suitable assay, is expressed, e.g., in cultured erythroid cells to generate synthetic membrane-receiver complexes.

In one embodiment, the activity of the synthetic membrane receiver complex is rapidly iterated using a cultured mouse erythroid cell model. For example, a library of suitable receivers is expressed in cultured mouse erythroid cells; activity is assessed in a suitable mouse model of disease or a suitable mouse model system for assessing activity; the best receiver candidate, e.g., the one that is expressed at the highest level or the one that demonstrates the highest activity in the suitable assay, is then expressed, e.g., in cultured erythroid cells to generate synthetic membrane-receiver complex.

In some instances, the receiver is an enzyme and the activity of the receiver can be assessed by an enzymatic assay in which the disappearance of a specific substrate molecule is detected or the appearance of a specific product molecule is detected. Such assays include but are not limited to, colorimetric assays, mass spectrometry, HPLC, fluorescent assays.

For example, a) the receiver is adenosine deaminase (ADA) and the enzymatic assay detects the conversion of adenosine to inosine; b) the receiver is phenylalanine hydroxylase (PAH) and the assay detects the conversion of phenylalanine to tyrosine; c) the receiver is phenylalanine ammonia lyase (PAL) and the assay detects the conversion of phenylalanine to trans-cinnamic acid; d) the receiver is thymidine phosphorylase (TP) and the assay detects the conversion of thymidine to thymine and 2-deoxy-ribose; e) the receiver is Purine nucleoside phosphorylase (PNP) and the assay detects the conversion of inosine to hypoxanthine, adenosine into adenine, and guanosine into guanine; f) the receiver is homogentisate 1,2-dioxygenase (HDG) and the assay detects the conversion of homogentisate to maleylacetoacetate; g) the receiver is cystathionine beta synthase and the assay detects the conversion of serine and homocysteine to cystathionine; h) the receiver is oxalate oxidase and the assay detects the oxidation of oxalate.

In some embodiments, activity of the synthetic membrane-receiver complex is assessed in an animal model, for example a mouse model, and immunodeficient mouse, or an NSG mouse, of a disease, for example a metabolic disease or an enzyme deficiency, or that can demonstrate the effect of the synthetic membrane-receiver complex, for example a mouse into which a substrate is injected and the product of the receiver-mediated conversion measured.

In one embodiment, the receiver is complement receptor 1 (CR1) polypeptide, a derivative or functional fragment thereof. The activity of the CR1 receiver can be assessed in several ways including, for example, the specific capture of immune complexes by the CR1 receiver, the efficient transfer of the immune complexes to macrophages, or the in vivo clearance of immune complexes from a mouse.

Functionality of erythroid cells overexpressing CR1 receiver may be assessed by one or more processes: capture of immune complexes on the erythroid cell surface comprising CR1 receiver, release of the immune complexes to macrophages while sparing the erythroid cell comprising CR1 receiver, and proper circulation of the erythroid cells comprising CR1 receiver. These three parameters can be assayed in vitro. Immune complex capture assays are described in the art, e.g., Oudin et al., J Immunol 2000 and Schifferli et al., J Immunol 1991. For example, labeled immune complexes are incubated with erythroid cells expressing native CR1 or CR1 receiver polypeptide or a fragment thereof and the number of immune complexes captured by the erythroid cells is assayed by flow cytometry. Macrophage transfer assays are described in the art, e.g., Kuhn et al., J Immunol 1998. For example, labeled immune complexes loaded onto erythrocytes expressing native CR1 or CR1 receiver polypeptide or a fragment thereof are incubated with macrophages. The transfer of immune complex from erythrocyte surface to macrophage, and the consumption or sparing of erythrocytes by macrophages, can be measured by flow cytometry. Proper circulation can be predicted by analyzing erythroid cell morphology and deformability. Morphology of erythroid cells expressing native CR1 or CR1 receiver polypeptide or a fragment thereof can be assessed by eye using standard microscopy techniques, as described e.g., by Giarratana et al., Blood 2011 and Repik et al., Clin Exp Immunol 2005. Deformability of erythroid cells expressing native CR1 or CR1 receiver polypeptide or a fragment thereof can be assessed by ektacytometry, also known as laser-assisted optical rotational cell analysis (LORCA), as described e.g., Giarratana et al., Blood 2011.

For example, a synthetic membrane-CR1 receiver complex (the complex comprises a CR1 polypeptide receiver) is incubated with immune complexes, such as in vivtro generated immune complexes or patient-derived immune complexes. The capture of the immune complexes by the CR1 receiver is assessed by, for example, flow cytometry using a fluorescent marker in the immune complex or by flow cytometry using a secondary detection agent against an element of the immune complex.

In one embodiment, the synthetic membrane-CR1 receiver complex is first incubated wih immune complexes and then incubated with macrophages, such as primary macrophages, primary monocytes, cultured macrophages, cultured monocytpes, U937 cells, PMA-activated U937 cells, AA9 cells, RAW 264.7 cells, J774 Cells, THP1 cells, KG-1 cells, NR8383 cells, MV-4-11 cells, 3D4/31 cells, MD cells, Fcwf-4 cells, DH82 cells. The macrophages are assayed by, for example, flow cytometry or radiography, for the presence of immune complexes transferred by the synthetic membrane-CR1 receiver complex. The transfer of captured immune complexes from cultured erythroid cells to macrophages is a standard assay in the art, see for example: Repik et al. 2005 Clin Exp Immunol. 140:230; Li et al. 2010 Infection Immunity 78(7):3129.

In one embodiment, activity of the synthetic membrane-CR1 receiver complex is assessed in an animal model. For example, a suitable mouse model may be used, such as an immunodeficient mouse, or an NSG mouse. The mouse disease model can be for example an immune complex disease, such as lupus. Mouse models include NZBWF1/J, MRL/MpJ, MRL/MpJ-Fas(lpr), Smn.C3-Fasl/J, NZM2410/Aeg, 129S4-Cd48, Cg-Sle1, NZM-Sle1 Sle2 Sle3/LmoJ, and BXSB.129P2. Alternatively or in addition, a disease phenotype may be introduced into a mouse, e.g., by injection of immune complexes. The synthetic membrane-CR1 receiver complexes may be injected into any suitable mouse (or other animal model) to test one or more biological effects of the complex, e.g., the clearance of the injected immune complexes by the synthetic membrane-CR1 receiver complex.

In some embodiments, the synthetic membrane-receiver complex comprising a CR1 receiver is not generated in a mouse and/or are not generated from mouse erythroid cells. In some embodiments, the synthetic membrane-receiver complex comprising a CR1 receiver is not generated in a laboratory animal and/or are not generated from an erythroid cells derived from a laboratory animal.

In one embodiment, the receiver is a complement regulatory molecule or has complement regulatory activity. This activity of the receiver can be assessed by both in vitro and in vivo assays. For instance, the activity of the receiver can be assessed by measuring the reduction in an in vitro complement activation assay, e.g., CH50 assay that measures complement-mediated lysis of sensitized sheep erythroctyes, or AH50 assay that measured alternate pathway complement-mediated lysis of non-sensitized rabbit erythrocytes. Alternatively, the activity of the receiver can be assessed by detecting the cleavage or absence of cleavage, which may or may not expose a neoepitope, of a recombinant complement component that has been incubated with the receiver, including but not limited to e.g., the cleavage of recombinant C2 into C2a and C2b, the cleavage of factor B into factor Ba and factor Bb, the cleavage of factor C3b into iC3bH and iC3bL, the cleavage of C3bBb into C3b and Bb, the cleavage of C4bBb into C4b and Bb, or the cleavage of factor C4b into iC4bH and iC4bL. The cleavage or absence of cleavage of a suitable recombinant complement component can be assessed by protein analysis methods known in the art including, but not limited to, e.g., chromatography, gel electrophoresis, ELISA, and western blotting. Suitable in vivo assays for receiver activity include injection of the synthetic membrane-receiver complex into animal, for example a mouse, and examining the deposition of complement factors, for example membrane attack complex, by histological staining.

In one embodiment, the receiver is capable of binding or capturing a target and the activity of the receiver can be assessed by detecting the captured target on the receiver in vitro or in vivo.

In one embodiment, the synthetic membrane-receiver complex is incubated with the target in vitro, and the capture of the target by the receiver is detectected using an in vitro assay including but not limited to, for example, flow cytometry, immunohistochemistry, magnetic separation, radiography, colony-forming assays, microscopy.

In one embodiment, the synthetic membrane-receiver complex is incubated with the target in vitro, and the capture of the target by the receiver is detected using an in vitro co-culture assay including but not limited to for example a macrophage consumption assay of opsonized receiver complex, a T cell activation assay, a B cell stimulation assay, a mast cell degranulation assay, an infectious potential assay.

In an embodiment, the synthetic membrane-receiver complex is incubated with the target in vitro, and the release or off-rate of the captured target is measured using an in vitro assay including but not limited to, for example, flow cytometry, immunohistochemistry, magnetic separation, radiography, colony-forming assays, microscopy.

The capture of the target by the synthetic membrane-receiver complex can be assayed in an in vivo assay, for example in an animal, including a mouse model of diseases in which the target is naturally present in the mouse. Suitable diseases include bacterial infections, viral infections, fungal infections, immune complex diseases, self-antibody diseases, hyperlipidemia, hyperglycemia. In other mouse models, the target is administered to the mouse externally, e.g., by injection or by feeding. In these assays, the capture of the target by the synthetic membrane-receiver complex is assayed either by examining the animal, e.g the plasma, the tissue, for reduction or retention of the target, or by isolating or collecting the receiver complex from the animal, e.g., from the blood, from the plasma, from a tissue, and assaying the presence of the target on the receiver using an in vitro assay including, but not limited to, for example, flow cytometry, immunohistochemistry, magnetic separation, radiography, colony-forming assays, microscopy.

In some embodiments, the receiver is capable of binding or capturing a target and substantially increasing the clearance of the target in vivo, or substantially reducing the concentration of the target in circulation. The activity of the receiver on the synthetic membrane-receiver complex can be assessed by detecting the enhanced clearance of the target in vitro or in vivo.

In one embodiment, the synthetic membrane-receiver complex is incubated with the target in vitro, and the capture of the target by the receiver is detectected using an in vitro assay including but not limited to, for example, flow cytometry, immunohistochemistry, magnetic separation, radiography, colony-forming assays, microscopy. Subsequently, the synthetic membrane-receiver complex is incubated in a co-culture assay with a cell known to promote clearance, for example a macrophage or a monocyte, and the clearance of the target and receiver complex is assessed by, for example, flow cytometry, immunohistochemistry, magnetic separation, radiography, colony-forming assays, microscopy.

In one embodiment, the synthetic membrane-receiver complex is incubated with the target in vitro, and the capture of the target by the receiver is detectected using an in vitro assay including but not limited to, for example, flow cytometry, immunohistochemistry, magnetic separation, radiography, colony-forming assays, microscopy. Subsequently, the synthetic membrane-receiver complex is incubated in a physical system that mimics the clearance mechanism of the complex in vivo, for example an artificial spleen, a microchannel, a packed column, a resin, a tissue explant, a centrifuge, and the clearance of the target and receiver complex is assessed by, for example, flow cytometry, immunohistochemistry, magnetic separation, radiography, colony-forming assays, microscopy.

In one embodiment, the clearance of the target by the synthetic membrane-receiver complex is assayed in an in vivo assay, for example in an animal, including, for example, a mouse model of diseases in which the target is naturally present in the mouse, for example bacterial infection, viral infection, fungal infection, immune complex disease, self-antibody disease, hyperlipidemia, hyperglycemia, or for example, a mouse model in which the target is administered to the mouse externally, e.g., by injection or by feeding. In these assays, the clearance of the target by the receiver complex is assayed either by examining the animal, e.g the plasma, the tissue, for reduction of the target, or by isolating or collecting the synthetic membrane-receiver complex from the animal, e.g., from the blood, from the plasma, from a tissue, and assaying the presence of the target on the receiver using an in vitro assay including, but not limited to, for example, flow cytometry, immunohistochemistry, magnetic separation, radiography, colony-forming assays, microscopy.

In some embodiments, the synthetic membrane-receiver complex is capable of delivering a suitable receiver to a specific subcellular compartment, for example a lysosome.

For example, a receiver may be delivered to the lysosomal compartment of a target cell, e.g., a macrophage. The successful delivery of the receiver to the lysosomal compartment of a target cell is assessed by microscopy and the detection of punctate spots corresponding to a fluorescent receiver or fluorescent receiver detection agent. Alternatively or in addition, the successful delivery of the receiver to the lysosomal compartment of a target cell is assessed by microscopy and the colocalization of a fluorescent receiver detection agent with a fluorescent detection agent for a known lysosomal marker, e.g., lysotracker, LAMP-1.

In some embodiments, the receiver is an enzyme that can degrade toxic components that have built up in the lysosome of a cell exhibiting the genotype or phenotype of, or derived from a patient with, a lysosomal storage disease. For example, the receiver is capable of degrading the toxic material built up in the cell and rescue the cell phenotype, e.g., preventing cell death.

The population of synthetic membrane-receiver complexes can be assessed for the inability of the complexes to replicate, the ability of the complexes to circulate safely through the vasculature, and the lack of immunogenicity of the complexes.

In some embodiments, the safety of the population of synthetic membrane-receiver complexes is assessed by measuring the replication potential of the population of complexes using a suitable in vitro or in vivo assay. For example, tests for a substantial inability of the synthetic membrane-receiver complexes to self-replicate include: a) a susbstanital inability to form a tumor when injected into an immunocompromised mouse; b) a substantial inability to form a colony when cultured in soft agar; c) a substantial inability to incorporate thymidine in a thymidine incorporation assay; d) a substantial lack of positive signal upon transfection with DNA encoding a fluorescent reporter, e.g., less than 10%, 1%, 0.1%, 0.01%, 0.001%, 1 ppm, 100 ppb, 10 ppb, 1 ppb, 100 ppt, 10 ppt, 1 ppt, or less than 1 ppt positive signal; e) a substantial lack of positive signal upon staining with a nuclear dye, e.g., less than 10%, 1%, 0.1%, 0.01%; and 0.001%, 1 ppm, 100 ppb, 10 ppb, 1 ppb, 100 ppt, 10 ppt, 1 ppt, or less than 1 ppt positive signal; f) a substantial lack of positive signal upon staining with cell markers of hematological malignancy, e.g., CKIT, CD34, EpCam, e.g., less than 10%, 1%, 0.1%, 0.01%, 0.001%, 1 ppm, 100 ppb, 10 ppb, 1 ppb, 100 ppt, 10 ppt, 1 ppt, or less than 1 ppt positive signal. In certain embodiments, synthetic membrane-receiver complexes are provided that do not contain a substantial amount of a replicating nucleic acid.

In some embodiments, the safety of the population of synthetic membrane-receiver complexes is assessed by measuring the ability of an administered complex to circulate in vivo (in the circulatory system of a subject) without causing substantial vascular occlusion or induction of the clotting cascade. Optionally, the circulation pharmacokinetics of the synthetic membrane-receiver complexes may be assessed.

In one embodiment, the circulation pharmacokinetics of the synthetic membrane-receiver complexes is assessed by injecting the complex into an animal intravenously, such as a mouse. The mouse can be an NSG (nod-SCID-gamma) immunodeficient mouse. The mouse is depleted of macrophages prior to injection with the complex, e.g., by intraperitoneal injection of human red blood cells, or by intravenous injection with clodronate liposomes. The synthetic membrane-receiver complexes can be labeled with a fluoresecent dye, e.g., CFSE. After injection of the complexes, blood is drawn and the number of synthetic membrane-receiver complexes remaining is assessed by, e.g., flow cytometry, western blot, and the clearance rate of the synthetic membrane-receiver complexes is deduced from these data. Human red blood cells can be injected into the same animal model as the synthetic membrane-receiver complexes and the clearance rates of the complexes and human red blood cells are compared.

In one embodiment, the risk of activation of the clotting cascade by the synthetic membrane-receiver polypeptide complex is assessed with an in vitro assay. In one embodiment, the synthetic membrane-receiver polypeptide complex is incubated with human blood and clotting cascade activation is assessed by measuring the time required for coagulation in the presence of kaolin, negatively-charged phospholipids, and calcium (activated partial thromboplastn time (aPTT) test), see e.g., Exner and Rickard, Biomedicine 1977 27(2):62, or by measuring the time required for coagulation in the presence of thromboplastin and calcium (prothrombin time (PT) test), see e.g., Jaques and Dunlop 1945, Am J Physiol 145:67. The normal range for the aPTT test is approximately 25-38 seconds. The normal range for the PT test is approximately 10-12 seconds.

In one embodiment, any adverse events induced by the synthetic membrane-receiver complexes are assessed by injecting the complex into an animal intravenously and assessing the activation of the clotting cascade. The level of clotting cascade induction is assessed by drawing blood and assessing the levels of clotting cascade components in the plasma by, e.g., Western Blot or ELISA. The clotting cascade components are typically fibrinogen breakdown products, e.g., fibrinopeptide A and fibrinopeptide B. For example, the level of clotting cascade induction is assessed by drawing blood and assessing the levels of clotting activity in the plasma by platelet activation assay, e.g., incubating the plasma with platelets and assessing the activation of the platelets by flow cytometry, e.g., by staining for markers of activation, e.g., by staining for PAC-1, CD62p, or CD40L.

In one embodiment, any adverse events induced by the synthetic membrane-receiver complexes are assessed by injecting the complex into an animal intravenously and assessing the activation of inflammatory pathways. The level of inflammation can be assessed by drawing blood and assessing the levels of inflammatory cytokines in the plasma by, e.g., Western Blot or ELISA. In one embodiment, the inflammatory citokines are interferon gamma, tumor necrosis factor alpha, or IL-12 fragment p70.

In one embodiment, any adverse events induced by the synthetic membrane-receiver complexes are assessed by injecting the complex into an animal intravenously and assessing the status of tissues, e.g., liver, spleen, heart, lungs, brain, skin, kidneys. The status of tissue can be assessed by gross necropsy, dissection of the tissue, histological staining, and imaging by microscopy.

In one embodiment, the ability of the synthetic membrane-receiver complex to circulate in vivo without causing substantial vascular occlusion or activation of the clotting cascade is assessed by measuring the deformability of the complex. The deformability of the synthetic membrane-receiver complex is assessed using an in vitro assay. For example, the assay is an osmotic fragility assay. Mechanical fragility of the synthetic membrane-receiver complex can be assessed by measuring the structural integrity in response to shear stress in a Couett-type shearing system. In one embodiment, the deformability of the synthetic membrane-receiver complex is assessed using an Ektacytometer. In one embodiment, the deformability of the synthetic membrane-receiver complex is assessed by measuring the elongation index at a defined pressure by laser diffraction using a laser-assisted optical rotational cell analyzer (LORCA) instrument. In one embodiment, the deformability of the synthetic membrane-receiver complex is assessed by measuring the transit time through a series of micron-scale constrictions of defined dimensions at a fixed pressure in a microfluidic device. In one embodiment, the deformability of the synthetic membrane-receiver complex is assessed by measuring the survival rate through a series of micron-scale constrictions of defined dimensions at a fixed pressure in a microfluidic device. The microfluidic device can be selected from one of the following, including but not limited to, a poly dimethyl siloxane (PDMS) chip with micron-scale constrictions (e.g., Hoelzle et al. J Vis Exp 2014 91:e51474); a chip with funnel-shaped constrictions (e.g., Guo et al. Lab Chip 2012 12:1143); a PDMS chip with pillars (e.g., Zhang et al. PNAS 2012 109(46):18707); or an in vitro artificial spleen microbead packed column (Guillaume DePlaine et al., Blood 2011, 117(8)).

In one embodiment, the ability of the synthetic membrane-receiver complex to circulate in vivo without causing substantial vascular occlusion or activation of the clotting cascade is assessed by measuring the vascular occlusion of the complex. Vascular occlusion of the synthetic membrane-receiver complex can be assessed using an in vitro assay. For example, the vascular occlusion of the synthetic membrane-receiver complex is assessed using an ex vivo assay. The synthetic membrane-receiver complex is incubated at a 1:1 ratio with reference human red blood cells and induction of multi-cell rosettes are assessed by light microscopy in comparison to a reference assay with Rh-mismatched blood. The vascular occlusion of the synthetic membrane-receiver complex is assessed by measuring the adhesion of the complex to human vascular endothelial cells under flow conditions, see e.g., Kaul D K, Finnegan E, and Barabino G A (2009) Microcirculation 16(1):97-111. Alternatively or in addition, vascular occlusion is assessed by measuring the peripheral resistance unit (PRU) increase in an ex vivo perfusion assay of rat vascular endothelium, see e.g., Kaul, Fabry and Nagel, PNAS 1989, 86:3356. Further, vascular occlusion is assessed by intravital microscopy, see e.g., Zennadi et al. 2007 Blood 110(7):2708. Vascular occlusion may also be assessed by measuring flow rates and adhesion of the complex in vitro graduated height flow chambers, see e.g., Zennadi et al 2004, Blood 104(12):3774.

In some embodiments, the safety of the population of synthetic membrane-receiver complexes is assessed by measuring the immunogenicity of the population of complexes using a suitable in vitro or in vivo assay.

For example, the population of synthetic membrane-receiver complexes a) does not induce agglutination in a Coombs test using serum from the intended recipient subject or b) does not induce agglutination in a Coombs test using pooled human serum.

In one embodiment, the population of synthetic membrane-receiver complexes is derived from a progenitor cell that has been genotyped for the predominant blood group antigens and matched to the blood group antigen genotype of the recipient.

In one embodiment, the population of synthetic membrane-receiver complexes comprises a receiver or other exogenous protein that has less than 10%, 1%, 0.1%, 0.01%, 0.001%, or less than 0.001% predicted T cell reactivity by an in silico T cell epitope prediction algorithm.

In one embodiment, the population of synthetic membrane-receiver complexes comprises a receiver or other exogenous protein that has less than 10%, 1%, 0.1%, 0.01%, 0.001%, or less than 0.001% reactivity in an in vitro T cell activation assay, e.g., Antitope Inc. EpiScreen assay.

For example, synthetic membrane-receiver complexes derived from erythrocytes can be centrifuged and resuspended in appropriate solution (e.g., standard AS-3 solution) for infusion into subjects in need thereof. In some embodiments, the synthetic membrane-receiver complexes to be infused have the same ABO type as that of the recipient to minimize the risk of infusion-associated immune reactions. The synthetic membrane-receiver complexes can also be pretreated to remove blood type-specific antigens or otherwise reduce antigenicities. Methods suitable for this purpose include, but are not limited to, those described in U.S. Patent Application Publication Nos. 20010006772 and 20030207247.

Methods of Treatment and Prevention

Provided herein are methods of modulating the circulatory concentration of a target to treat or prevent a disease, disorder or condition associated with the presence, absence, elevated or depressed concentration of the target in the circulatory system of a subject. The subject may suffer from the disease, disorder or condition or may be at risk of developing the disease, disorder or condition. The methods provided herein include the administration of a suitable synthetic membrane-receiver polypeptide complex described herein in an amount effective to substantially modulate the circulatory concentration of the target, thereby preventing or treating the disease, disorder or condition. In some embodiments, the synthetic membrane-receiver polypeptide complex is formulated as a pharmaceutical composition. In some embodiments, the pharmaceutical composition is formulated for intravenous injection to the subject. The compositions may be administered once to the subject. Alternatively, multiple administrations may be performed over a period of time. For example, two, three, four, five, or more administrations may be given to the subject. In some embodiments, administrations may be given as needed, e.g., for as long as symptoms associated with the disease, disorder or condition persist. In some embodiments, repeated administrations may be indicated for the remainder of the subject's life. Treatment periods may vary and could be, e.g., no longer than a year, six months, three months, two months, one month, two weeks, one week, three days, two days, or no longer than one day.

In some embodiments, the compositions are administered at least twice over a treatment period such that the disease, disorder or condition is treated, or a symptom thereof is decreased. In some embodiments, the compositions are administered at least twice over a treatment period such that the disease, disorder or condition is treated, or a symptom thereof is prevented. In some embodiments, the pharmaceutical composition is administered a sufficient number of times over a treatment period such that the circulatory concentration of the target is substantially decreased during the treatment period. In some embodiments, the pharmaceutical composition is administered a sufficient number of times over a treatment period such that the circulatory concentration of the target self-antibody is substantially decreased during the treatment period such that one or more symptoms of the self-antibody mediated disease, disorder or condition is prevented, decreased or delayed. In some embodiments, decreasing the circulatory concentration of the target includes decreasing the peak concentration, while in others it includes decreasing the average concentration. In some embodiments, a substantial decrease during the treatment period can be determined by comparing a pretreatment or post-treatment period in the human subject, or by comparing measurements made in a population undergoing treatment with a matched, untreated control population. In some embodiments, the circulatory concentration of the target is decreased by at least about 1%, 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, 99.5%, 99.9%, 99.99%, or greater than 99.99% during part or the entirety of the treatment period. In some embodiments, the circulatory concentration of the target is decreased by at least about 1%, 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, 99.5%, 99.9%, 99.99%, or greater than 99.99% within about 1, 5, 10, 15, 20, 30, 40, or 50 minutes, or about 1, 2, 3, 4, 5, 6, 7, 8, 9, 10, 11, 12, 13, 14, 15, 16, 17, 18, 19, 20, 21, 22, or 23 hours, or 1, 2, 3, 4, 5, or 6 days or about 1, 2, 3, 4, 5, or 6 weeks of the administration.

In some embodiments, the pharmaceutical composition is administered a sufficient number of times over a treatment period such that the circulatory concentration of the target is decreased at a rate greater than i) the endogenous clearance rate of the target\by the human subject, or ii) the endogenous production rate of the target by the human subject, or iii) both i) and ii). In some embodiments, the pharmaceutical composition is administered a sufficient number of times a treatment period such that the circulatory concentration of the target is substantially decreased for at least about one week, two weeks, three weeks, four weeks, one month, two months, three months, four months, five months, six months, or greater than six months. In some embodiments, the pharmaceutical composition is administered a sufficient number of times a treatment period such that the circulatory concentration of the target is substantially decreased for a period of time at least as long as the treatment period.

In some embodiments, the pharmaceutical composition is administered at a frequency sufficient to effectively reduce the circulatory concentration of the target below a level that is associated with a symptom of the disease, disorder or condition.

In some embodiments, the time interval between administrations within a treatment period is no longer than the period in which the number of synthetic membrane-receiver complexes in circulation is reduced to less than about 5%, 10%, 15%, 20%, 25%, 30%, 35%, 40%, 45%, 50%, 55%, 60%, 65%, 70%, 75%, 80%, 85%, 90%, or 95% of the number of synthetic membrane-receiver complexes present in the administered pharmaceutical composition.

Diseases, disorders and conditions associated with targets in the circulatory system that may be treated or prevented by administering synthetic membrane-receiver polypeptide complexes are described herein.

Diseases, disorders and conditions associated with targets in the circulatory system that may be treated or prevented by administering synthetic membrane-receiver polypeptide complexes include, but are not limited to: self-antibody-mediated diseases, complement dysregulation-associated diseases, immune complex associated diseases, amyloidoses, diseases associated with infectious agents or pathogens (e.g., bacterial, fungal, viral, parasitic infections), disease associated with toxic proteins, diseases associated with the accumulation of lipids, diseases associated with apoptotic, necrotic, aberrant or oncogenic mammalian cells, and metabolic diseases.

Provided herein, in some embodiments, are methods for the treatment or prevention of diseases or conditions that are associated with targets (e.g., molecules or entities) that reside, at least in part, in the circulatory system. The methods comprise, in certain embodiments, administering to a subject in need thereof functional erythroid cells comprising a receiver, populations of functional erythroid cells comprising a receiver, or compositions, preferably pharmaceutical compositions comprising functional erythroid cells comprising a receiver, in an amount effective to treat or prevent the disease or condition that is associated with molecules or entities that reside, at least in part, in the circulatory system.

Methods are provided for the treatment or prevention of inflammation and diseases associated with inflammation, including sepsis, autoimmune disease, cancer, and microbial infections, the methods comprising, administering to a subject in need thereof an erythrocyte comprising an immune-modulatory receiver in an amount effective to treat or prevent the inflammation or an associated disease. In some embodiments, an erythrocyte comprises an immunomodulatory receiver that comprises a chemokine or cytokine receptor. In a particular embodiment, the chemokine receptor is DARC.

Methods are provided for the modulation of chemokine homeostasis at sites of inflammation, the methods comprising, administering to a subject in need thereof an erythrocyte comprising a chemokine-modulatory receiver in an amount effective to modulate chemokine homeostasis at sites of inflammation. In some embodiments, the erythrocyte comprising a chemokine-modulatory receiver comprises a receiver that comprises a chemokine receptor. In a particular embodiment, the chemokine receptor is DARC. In some embodiments, the site of inflammation is vascular. (Darbonne, J Clinical Invet, 1991).

Further provided are methods of inducing toxin clearance. The methods include administering to a subject in need thereof a population of functional erythroid cells comprising a receiver that is capable of interacting with a toxin, such as e.g., an antibody, scFv or nanobody receiver, in an amount effective to clear toxins from circulation. Such methods may be employed to sequester the toxin and reduce the amount of tissue damage that would otherwise occur within the vasculature and dissipating its pathogenic effects in a less acute manner.

In some embodiments, provided are methods of treating diseases, including, but not limited to, metabolic diseases, cancers, clotting and anti-clotting diseases. The methods include administering to a subject in need thereof a pharmaceutical composition of functional erythroid cells comprising a receiver provided herein in an amount sufficient to treat the metabolic disease, the cancer, the clotting disease or anti-clotting disease of the subject.

In certain embodiments, synthetic membrane-receiver polypeptide complexes exhibit one or more receiver polypeptides on their surface, exposed to the environment the circulatory system of the subject.

In other embodiments, the synthetic membrane-receiver polypeptide complexes comprise one or more receiver polypeptides facing the unexposed side of the synthetic membrane-receiver polypeptide complex.

The receiver polypeptide may interact with targets that are present in the circulatory system. The interaction of the receiver with the target may include, but is not limited to: i) binding of the receiver to the target; ii) degrading the target, iii) cleaving the target; iv) sequestering the target, and/or v) catalytically converting the target.

For example, the receiver polypeptide may be an antibody, a single-chain variable fragment, a nanobody, a diabody, a darpin, a lyase, a hydrolase, a protease, or a nuclease.

In some embodiments, the synthetic membrane-receiver complex comprises a receiver that is not a polypeptide. In some embodiments, the receiver comprises a carbohydrate (e.g., a GAG), a lipid, DNA, a RNA, a peptide nucleic acid (PNA), or a non-protein ligand, drug or substrate that is capable of interacting with the target.

In some embodiments, the interaction between the receiver and the target leads to a direct or indirect reduction of the concentration of the target in the circulatory system. For example, a receiver may directly convert a target into a different product. The receiver may have a catalytic activity toward the target, such as cleaving, degrading, etc. The conversion may be from a target to a degradation product, from a toxic or harmful target to a non-toxic product, etc. The catalytic activity of the receiver may also involve addition of one or more chemical groups to the target. Modification of the target by the receiver may cause, directly or indirectly, e.g., de/phosphorylation, de/ubiquitination, de/methylation, glycosylation, etc. on the target. The receiver may indirectly cause a second modification on the target if the receiver put a first modification that leads to a second modification, e.g., by a different enzyme. Any such modifications may then lead, e.g., to the degradation of the target or to a conversion of the target to a non-harmful or less harmful product. In some embodiments, a decrease in target concentration may be directly or indirectly associated with an increase in a non-target compound. For example, a toxic metabolite may be converted into a non-toxic or less toxic metabolite. In another example, a target may be converted into a product that is lacking or is present in an depressed amount. In this case, a disease, disorder or condition may be associated with the lack of or depressed amount of the non-target compound and conversion of the target, e.g., by a catalytic action of the synthetic membrane-receiver polypeptide complex is capable of increasing the amount of the non-target compound effective to treat the disease, disorder or condition.

In other examples, the receiver may bind to the target and keep it sequestered, e.g., being associated with the synthetic membrane-receiver polypeptide complex. The sequestration may inhibit an activity harbored by the target, e.g., a harmful activity, such as that exerted by a self-antibody which may be causative of an autoimmune disease, or a bacterial toxin that may cause sepsis, etc. Alternatively or in addition, upon sequestration or binding of the target the target is redistributed in the circulatory system of the subject according to the distribution of the synthetic membrane-receiver polypeptide complex. This may significantly limit the volume of distribution of the target, and thus potentially its harmful or adverse impact. The target may be degraded or accumulated at a specific site or organ in the body of the subject directed by the turnover or half-life and distribution of the synthetic membrane-receiver polypeptide complex.

The administration of the pharmaceutical composition may be sufficient to substantially decrease the concentration or amount of the target molecule in circulation during the treatment period, wherein the substantial decrease can be determined in comparison to a pre-treatment or post-treatment period in the human subject, or via comparison of measurements made in a population undergoing treatment as compared to a matched untreated control population. The substantial decrease of the target molecule can include a substantial decrease of the peak concentration or amount of the target molecule present in a human patient or a substantial decrease in the average concentration or amount of the target molecule present in a human patient.

In some embodiments, provided are methods for treating diseases that are marked by periodic flares, wherein a flare is defined as a recurrence of symptoms or an onset of more severe symptoms. Diseases marked by periodic flares include self-antibody mediated diseases, immune complex associated diseases, autoimmune diseases, including for example lupus, rheumatoid arthritis, and goodpasture syndrome.

In some embodiments, provided are methods comprising administering the pharmaceutical composition to a patient a sufficient number of times over a treatment period such that the time between flares is reduced compared to an individual who does not receive the pharmaceutical composition.

In some embodiments, provided are methods comprising administering the pharmaceutical composition to a patient a sufficient number of times over a treatment period such that the severity of the flares is reduced compared to an individual who does not receive the pharmaceutical composition.

In some embodiments, methods of treatment and prevention using synthetic membrane-receiver complexes generated from erythroid cells described herein do not comprise the step of detecting the erythroid cell in vivo, e.g., through a detection agent that is associated with the erythroid cell.

In some embodiments, the synthetic membrane-receiver complex is not generated from a human donor pluripotent hematopoietic stem cell. In some embodiments, a population of synthetic membrane-receiver complexes is not expanded in a bioreactor. In some embodiments, the population of synthetic membrane-receiver complexes after expansion and/or differentiation does not comprise a single species of differentiated human blood cells. In some embodiments, the synthetic membrane-receiver complex is not a differentiated, mature human blood cell. In some embodiments, the synthetic membrane-receiver complex is not generated from a blood cell derived from a universal donor, e.g. blood type O, Rh factor negative.

In some embodiments, a synthetic membrane-ADA polypeptide receiver complex is not used to treat severe combined immune deficiency (ADA-SCID).

In some embodiments, the methods of treatments described herein do not comprise administering a synthetic membrane-receiver complex generated from an erythroid cell that is contacted with a polypeptide receiver in an amount effective to induce immune tolerance to the polypeptide receiver in a subject.

Suitable targets include biological compounds, inorganic or organic compounds. Suitable targets may range in size from less than 100 Da, less than 250 Da, less than 500 Da, less than 1000 Da to targets of more than 1 kDa. Targets can be, e.g., polypeptides, lipids, carbohydrates, nucleic acids, small molecules, metabolites and elements. In some embodiments, the target is an antibody, a complement factor, an immune complex, a serum amyloid protein, a bacterial pathogen, a fungal pathogen, a viral pathogen, or an infected, pathogenic, apoptotic, necrotic, aberrant or oncogenic mammalian cell.

Diseases, disorders and conditions associated with targets in the circulatory system that may be treated or prevented by administering synthetic membrane-receiver polypeptide complexes include, but are not limited to: self-antibody-mediated diseases, complement dysregulation-associated diseases, immune complex associated diseases, amyloidoses, diseases associated with infectious agents or pathogens (e.g., bacterial, fungal, viral, parasitic infections), disease associated with toxic proteins, diseases associated with the accumulation of lipids, diseases associated with apoptotic, necrotic, aberrant or oncogenic mammalian cells, and metabolic diseases.

In some embodiments, provided are methods of treating diseases, including, but not limited to, metabolic diseases, cancers, clotting and anti-clotting diseases. The methods include administering to a subject in need thereof a pharmaceutical composition of erythrocyte cells comprising a receiver provided herein in an amount sufficient to treat the metabolic disease, the cancer, the clotting disease or anti-clotting disease of the subject.

Self-Antibody Mediated Diseases

In some embodiment, the synthetic membrane-receiver polypeptide complexes described herein may be used to treat or prevent diseases, disorders or conditions that are associated with self-antibodies.

In specific embodiments, methods are provided for reducing the circulatory concentration of a target self-antibody in a subject (e.g., a human) suffering from or at risk of developing a self-antibody mediated disease, disorder or condition. The methods include administering a pharmaceutical composition comprising a synthetic membrane-receiver polypeptide complex described herein. The pharmaceutical composition is administered in an amount effective to substantially reduce the circulatory concentration of the target self-antibody. In certain embodiments, the administration is carried out intravenously.

In certain embodiments, synthetic membrane-receiver polypeptide complexes are administered that comprise a receiver that specifically binds and sequesters a target self-antibody that is present in the circulatory system of the subject.

In certain embodiments, the pharmaceutical composition will reduce the target self-antibody load in the circulatory system, thereby reducing the burden of the disease, disorder or condition associated with the presence or elevated concentration of the target self-antibody. Diseases associated with target self-antibodies include, but are not limited to, Goodpasture syndrome, membranous glomerulonephropathy, antiphospholipid syndrome (APS), catastrophic antiphospholipid syndrome (CAPS), and those listed in table 6 and table 8.

Self-antibody mediated diseases arise from an abnormal immune response of the body against substances and tissues normally present in the body. This may be restricted to certain organs (e.g., in autoimmune thyroiditis) or involve a particular tissue in different places, e.g., Goodpasture syndrome, which may affect the basement membrane in both the lung and the kidney. The treatment of self-antibody mediated diseases typically includes immunosuppressive medications that decrease the immune response, such as cyclophosphamide and rituximab. In certain embodiments, treatment with the pharmaceutical compositions described herein is combined with one or more immunosuppressive medications, and effective agents may be, e.g., co-administered or co-formulated.

In healthy subjects, the immune system is able to recognize and ignore the body's own healthy proteins, cells, and tissues, and does not overreact to non-threatening substances in the environment, such as foods. If the immune system ceases to recognize one or more of the body's normal constituents as "self" it may produce pathological self-antibodies, i.e. antibodies that recognize "self" antigens. These self-antibodies are directed against the body's own healthy cells, tissues, and/or organs, and may cause inflammation and tissue damage.

In certain embodiments, synthetic membrane-receiver polypeptide complexes are provided that comprise receivers comprising epitopes capable of being recognized by target self-antibodies. For example, the target self-antibody may specifically recognizes glycoprotein (GP Ib-IX, IIb-IIIa, IV, or Ia-IIa), the NC1 domain of collagen α3 (IV), B2 glycoprotein-1, or phospholipase A2 receptor, and the receiver polypeptide may comprise an antigenic polypeptide selected from the group.

Target self-antibodies sequestered by the synthetic membrane-receiver polypeptide complexes may be cleared from circulation, e.g., through the reticulo-endothelial system. Sequestration and/or degradation of the target self-antibody may reduce the degree of inflammation that is normally caused when the self-antibody interacts with "self" tissues.

In one embodiment the disease or condition is antiphospholipid syndrome, the receiver is beta2-glycoprotein-1 or fragment thereof, and the target is pathogenic self-antibody against beta2-glycoprotein-1.

In one embodiment the disease or condition is catastrophic antiphospholipid syndrome, the receiver is beta2-glycoprotein-1 or fragment thereof, and the target is pathogenic self-antibody against beta2-glycoprotein-1.

In one embodiment the disease or condition is cold agglutinin disease, the receiver is I/i antigen or fragment thereof, and the target is pathogenic self-antibody against I/i antigen.

In one embodiment the disease or condition is Goodpasture syndrome, the receiver is a3 NC1 domain of collagen (IV) or fragment thereof, and the target is pathogenic self-antibody against a3 NC1 domain of collagen (IV).

In one embodiment the disease or condition is immune thrombocytopenia purpura, the receiver is platelet glycoproteins (Ib-IX, IIb-IIIc, IV, Ia-IIa) or fragment thereof, and the target is pathogenic self-antibody against platelet glycoprotein.

In one embodiment the disease or condition is membranous nephropathy, the receiver is phospholipase A2 receptor or fragment thereof, and the target is pathogenic self-antibody against phospholipase A2 receptor.

In one embodiment the disease or condition is warm antibody hemolytic anemia, the receiver is glycophorin A, glycophorin B, and/or glycophorin C, Rh antigen or fragment thereof, and the target is pathogenic self-antibody against glycophorins and/or Rh antigen.

Exemplary self-antibody diseases are Goodpasture syndrome, catastrophic antiphospholipid syndrome, and membranous glomerulopathy.

1. Goodpasture Syndrome

In some embodiment, subjects may be identified as having received or would benefit from receiving treatment for Goodpasture Syndrome. Subjects suffering from or at risk of developing Goodpasture Syndrome may be administered a pharmaceutical composition comprising the synthetic membrane-receiver polypeptide complex described herein to treat or prevent disease.

In one embodiment, the synthetic membrane-receiver polypeptide complex comprises a receiver comprising α3IV collagen (COL4A3), or a derivative or functional fragment thereof. A suitable receiver may be exhibited on the surface of the synthetic membrane-receiver polypeptide complex. COL4A3 is normally found on kidney cells and presents a target to which self-antibodies associated with Goodpasture syndrome have been shown to bind.

COL4A3 is found in air sacs in the lungs and glomeruli of the kidneys. Self-antibodies associated with Goodpasture syndrome are directed against the glomerular basement membrane and can cause kidney damage. Where the disorder is triggered by a viral respiratory infection or by intake of hydrocarbon solvents the resulting immune response can cause bleeding in the air sacs of the lungs and inflammation in the kidney's glomeruli.

2. Catastrophic Antiphospholipid Syndrome (CAPS)

In some embodiment, subjects may be identified as having received or would benefit from receiving treatment for antiphospholipid syndrome (APS). Subjects suffering from or at risk of developing APS may be administered a pharmaceutical composition comprising the synthetic membrane-receiver polypeptide complex described herein to treat or prevent disease.

In one embodiment, the synthetic membrane-receiver polypeptide complex comprises a receiver comprising β2-glycoprotein 1 (b2GPI), or a derivative or functional fragment thereof. A suitable receiver may be exhibited on the surface of the synthetic membrane-receiver polypeptide complex. b2GPI is normally found on endothelial cells and presents a target to which self-antibodies associated with APS have been shown to bind.

Antiphospholipid syndrome (APS) is a multisystem self-antibody mediated condition characterized by vascular thrombosis and/or pregnancy loss associated with persistently positive antiphospholipid antibodies (aPL). Catastrophic APS (CAPS) is the most severe form of APS with multiple organ involvement developing over a short period of time, usually associated with microthrombosis. 'Definite' and 'probable' CAPS have been defined based on the preliminary classification criteria; however, aPL-positive patients with multiple organ thromboses and/or thrombotic microangiopathies are encountered who do not fulfill these criteria. Previous APS diagnosis and/or persistent clinically significant aPL positivity is of great importance for the CAPS diagnosis; however, almost half of the patients who develop CAPS do not have a history of aPL positivity.

3. Membranous Glomerulopathy (MGN)

In some embodiment, subjects may be identified as having received or would benefit from receiving treatment for membranous glomerulopathy (MGN), also called membranous glomerulonephritis membranous nephritis (MN). Subjects suffering from or at risk of developing MGN may be administered a pharmaceutical composition comprising the synthetic membrane-receiver polypeptide complex described herein to treat or prevent disease.

In one embodiment, the synthetic membrane-receptor polypeptide complex comprises a receiver comprising phospholipase A2 receptor, or a derivative or functional fragment thereof. A suitable receiver may be exhibited on the surface of the synthetic membrane-receptor polypeptide complex. Phospholipase A2 receptor is normally found on podocytes and presents a target to which self-antibodies associated with MGN have been shown to bind.

The term membranous nephritis, or membranous glomerulonephritis, is used to describe a chronic glomerular disease that on light, immunofluorescence, and electron microscopy study of renal tissue shows a set of distinct morphologic features in glomeruli, including thickened glomerular basement membrane (GBM) and GBM spikes, granular staining for IgG and complement along the periphery of glomerular all capillary loops, and electron-dense subepithelial deposits corresponding to the granular IgG staining.

Clinically, most patients present with nephrotic syndrome or have proteinuria detected on a routine urinalysis. Idiopathic MN occurs in all age groups and races and both sexes all over the world and is a leading cause of nephrotic syndrome among Caucasian adults. Spontaneous remission of the disease is common in children but also occurs in adults. Although several immunosuppressive drugs often are used to treat individual patients, with or without treatment, nearly a third of patients progress to end-stage renal disease.

Complement Dysregulation-Associated Diseases

In some embodiment, the synthetic membrane-receiver polypeptide complexes described herein may be used to treat or prevent diseases, disorders or conditions that are associated with complement dysregulation.

In specific embodiments, methods are provided for reducing the circulatory concentration of a target complement protein in a subject (e.g., a human) suffering from or at risk of developing a disease, disorder or condition associated with complement dysregulation. The methods include administering a pharmaceutical composition comprising a synthetic membrane-receiver polypeptide complex described herein. The pharmaceutical composition is administered in an amount effective to substantially reduce the circulatory concentration of the target complement protein. In certain embodiments, the administration is carried out intravenously.

In certain embodiments, synthetic membrane-receiver polypeptide complexes are administered that comprise a receiver that specifically binds and sequesters a target complement protein that is present in the circulatory system of the subject.

In certain embodiments, the therapeutic compositions of the invention provide functional erythroid cells comprising receivers in compositions that are useful to treat, prevent, or reduce the severity of a disease, disorder or condition associated with complement pathophysiology or improper immune complex clearance.

In specific embodiments, methods are provided for reducing the circulatory concentration of a target complement protein in a subject (e.g., a human) suffering from or at risk of developing a disease, disorder or condition associated with complement dysregulation. The methods include administering a pharmaceutical composition comprising a synthetic membrane-receiver polypeptide complex described herein. The pharmaceutical composition is administered in an amount effective to substantially reduce the circulatory concentration of the target complement protein. In certain embodiments, the administration is carried out intravenously.

In certain embodiments, synthetic membrane-receiver polypeptide complexes are administered that comprise a receiver that specifically binds and sequesters a target complement protein that is present in the circulatory system of the subject.

Provided are therapeutic compositions present in an amount effect to treat a disease or condition associated with complement over-activation such as systemic lupus erythematosus, ischemia reperfusion injury, organ transplantation, myocardial infarction, rheumatoid arthritis, scleroderma, polyarteritis nodosa, serum sickness, arthus reaction, farmer's lung, Henoch-Schonlein purpura, bacterial endocarditis, vasculitis, and other Type III Hypersensitivity conditions. Further provided are therapeutic compositions present in an amount able to treat an infectious disease in which opsonized pathogen is present in the blood, such as carbapenem-resistant enterobacteriaceae, drug resistant *Neisseria gonorrhoeae*, fully resistant *streptococcus pneumonia*, drug resistant tuberculosis, generalized bacterial sepsis, human immunodeficiency virus infection, hepatitis B virus infection, or malaria. In a further embodiment, provided are therapeutic compositions present in an amount effect to treat a complement factor deficiency-associated disease such as cofactor H deficiency, paroxysmal nocturnal hemoglobinuria, factor B deficiency, factor D deficiency, C1q deficiency, C1r deficiency, C4 deficiency, C2 deficiency, C3 deficiency, C5 deficiency, C6 deficiency, C7 deficiency, factor I deficiency, factor D deficiency, MBL deficiency, MASP2 deficiency, CD55 deficiency, CD59 deficiency, and other deficiencies in genes associate with complement activity including but not limited to those listed in table 6 and table 8.

In certain embodiments, the pharmaceutical composition will reduce the target complement protein load in the circulatory system, thereby reducing the burden of the disease, disorder or condition associated with the presence or elevated concentration of the target complement protein. Diseases associated with complement dysregulation include, but are not limited to, atypical hemolytic uremic syndrome (aHUS), paroxysmal nocturnal hemoglobinuria (PNH), age-related macular degeneration (AMD), complement factor I (CFI) deficiency and those listed in table 6 and table 8.

In certain embodiments, the receiver polypeptide may specifically interact with a complement protein selected from the group consisting of: C1q, C1r, C1s, C2, C3, C3a, C3b, C4, C5, C5a, C5b, C6, C7, C8, and C9, Factor B, Factor D, Properdin, iC3b, C3c, C3dg, C3dk, C3e, Bb, C4a, C4b, and in table 5 and table 10.

In certain embodiments, the receiver polypeptide may comprise CD46, CD55, CD59, factor H, CR1, factor I, CR1, CR2, CR3, CR4, C3aR, C3eR, Decay-accelerating factor (DAF), Membrane cofactor protein (MCP), C3 Beta chain Receptor, C1 inhibitor, C4 binding protein, and those listed in table 10.

Homologous restriction factormicrobial protein NalP, microbial protein SpeB, microbial protein EspP, a derivative or a functional fragment thereof. Alternatively or in addition, the receiver polypeptide may comprise one or more complement control protein (CCP) modules and/or short consensus repeats (SCR) of different origin.

The complement system is composed of more than 32 proteins including 7 serum and 9 membrane regulatory proteins, 1 serosal regulatory protein, and 8 cell membrane receptors that bind complement fragments. Activation of complement occurs with the initiation of an inflammatory reaction, most of which occurs in the intravascular space. The soluble components of complement are present in the circulation and also in body fluids and tissues. In addition to the specific activation induced by antigen-antibody complexes, complement is activated through the pattern recognition receptors, which have the ability to discriminate between self and non-self antigens based on repeating patterns of molecular structure (pathogen-associated molecular patterns) present on the surface of pathogens. Complement-activating pattern recognition receptors include mannose-binding lectin (MBL), ficolins, C-reactive protein, Clq, and natural IgM (IgM).

Excessive, deregulated, or chronic inflammation can initiate or contribute to several pathologies. For example, the activation of complement during an inflammatory reaction contributes to inflammation-driven tissue injury, which occurs in the ischemia/reperfusion (I/R) setting, vasculitides of various etiologies, nephritis, and arthritis. A deficiency in complement components may also result in tissue injury, as observed in autoimmune reactions. Further, alterations in the expression of complement regulatory proteins may lead to excessive complement activation and can also contribute to tissue injury.

In one embodiment the disease or condition is age-related macular degeneration, the receiver is a suitable complement regulatory protein or fragment thereof, and the target is active complement.

In one embodiment the disease or condition is atypical hemolytic uremic syndrome, the receiver is complement factor H, or a suitable complement regulatory protein or fragment thereof, and the target is active complement.

In one embodiment the disease or condition is Complement Factor I deficiency, the receiver is Complement Factor I, a suitable complement regulatory protein or fragment thereof, and the target is active complement.

In one embodiment the disease or condition is paroxysmal nocturnal hemoglobinuria, the receiver is a suitable complement regulatory protein or fragment thereof, and the target is active complement.

In one embodiment the disease or condition is autoimmune hemolytic anemia, the receiver is a suitable complement regulatory molecule or fragment thereof, and the target is active complement.

In one embodiment the disease or condition is non-alcoholic steatohepatitis, the receiver is a suitable complement regulatory molecule or fragment thereof, and the target is active complement.

1. Paroxysmal Nocturnal Hemoglobinuria (PNH)

In some embodiments, subjects may be identified as having received or would benefit from receiving treatment for paroxysmal nocturnal hemoglobinuria (PNH). Subjects suffering from or at risk of developing PNH may be administered a pharmaceutical composition comprising the synthetic membrane-receiver polypeptide complex described herein to treat or prevent disease.

In one embodiment, the synthetic membrane-receiver polypeptide complex comprises a receiver comprising a complement regulatory protein, such as cofactor H, or a derivative or functional fragment thereof. A suitable receiver may be exhibited on the surface of the synthetic membrane-receiver polypeptide complex and may be administered to reduce inflammation.

Paroxysmal nocturnal hemoglobinuria is an acquired disorder that leads to the premature death and impaired production of blood cells. The disorder affects erythrocytes, leukocytes, and platelets (thrombocytes). PNH affects both sexes equally and can occur at any age, although it is most often diagnosed in young adulthood.

People with paroxysmal nocturnal hemoglobinuria have sudden, recurring episodes of symptoms (paroxysmal symptoms), which may be triggered by stresses on the body, such as infections or physical exertion. During these episodes, red blood cells are prematurely destroyed (hemolysis). Affected individuals may pass dark-colored urine due to the presence of hemoglobin (hemoglobinuria). In many, but not all cases, hemoglobinuria is most noticeable in the morning, upon passing urine that has accumulated in the bladder during the night (nocturnal).

The premature destruction of red blood cells results in a deficiency of these cells in the blood (hemolytic anemia), which can cause signs and symptoms such as fatigue, weakness, abnormally pale skin (pallor), shortness of breath, and an increased heart rate. People with PNH may also be prone to infections due to a deficiency of white blood cells.

Abnormal platelets associated with PNH can cause problems in the blood clotting process. As a result, people with this disorder may experience abnormal blood clotting (thrombosis), especially in large abdominal veins; or, less often, episodes of severe bleeding (hemorrhage).

2. Atypical Hemolytic Uremic Syndrome (aHUS)

In some embodiments, subjects may be identified as having received or would benefit from receiving treatment for atypical hemolytic uremic syndrome (aHUS). Subjects suffering from or at risk of developing aHUS may be administered a pharmaceutical composition comprising the synthetic membrane-receiver polypeptide complex described herein to treat or prevent disease.

In one embodiment, the synthetic membrane-receiver polypeptide complex comprises a receiver comprising a complement regulatory protein, such as cofactor I, or a derivative or functional fragment thereof. A suitable receiver may be exhibited on the surface of the synthetic membrane-receiver polypeptide complex and may be administered to reduce inflammation.

Atypical hemolytic uremic syndrome (aHUS) is a rare syndrome of hemolysis, thrombocytopenia, and renal insufficiency. Genetic mutations in the alternate pathway of complement is the cause in more than 60% of patients affected by this thrombotic microangiopathy. aHUS may be treated using plasma therapy, complement blockade, and/or liver transplantation. Because aHUS shares many of the presenting characteristics of the other thrombotic microangiopathies, and confirmatory genetic results are not available at the time of presentation, the diagnosis relies heavily on the recognition of a clinical syndrome consistent with the diagnosis in the absence of signs of an alternate cause of thrombotic microangiopathy.

3. Age-Related Macular Degeneration (AMD)

In some embodiments, subjects may be identified as having received or would benefit from receiving treatment for age related macular degeneration (AMD). Subjects suffering from or at risk of developing AMD may be administered a pharmaceutical composition comprising the synthetic membrane-receiver polypeptide complex described herein to treat or prevent disease.

In one embodiment, the synthetic membrane-receiver polypeptide complex comprises a receiver comprising a complement regulatory protein, such as CD55 and CD59, or a derivative or functional fragment thereof. A suitable receiver may be exhibited on the surface of the synthetic membrane-receiver polypeptide complex and may be administered to reduce inflammation.

Age related macular degeneration (AMD) is a common form of blindness in the western world and genetic variations of several complement genes, including the complement regulator Factor H, the central complement component C3, Factor B, C2, and also Factor I confer a risk for the disease. However deletion of a chromosomal segment in the Factor H gene cluster on human chromosome 1, which results in the deficiency of the terminal pathway regulator CFHR1, and of the putative complement regulator CFHR3 has a protective effect for development of AMD. The Factor H gene encodes two proteins Factor H and FHL1 which are derived from alternatively processed transcripts. In particular a sequence variation at position 402 of both Factor H and FHL1 is associated with a risk for AMD. A tyrosine residue at position 402 represents the protective and a histidine residue the risk variant. AMD is considered a chronic inflammatory disease, which can be caused by defective and inappropriate regulation of the continuously activated alternative complement pathway. This activation generates complement effector products and inflammatory mediators that stimulate further inflammatory reactions. Defective regulation can lead to formation of immune deposits, drusen and ultimately translate into damage of retinal pigment epithelial cells, rupture of the interface between these epithelial cells and the Bruch's membrane and vision loss.

Immune Complex-Associated Diseases

In some embodiments, the synthetic membrane-receiver polypeptide complexes described herein may be used to treat or prevent diseases, disorders or conditions that are associated with immune complexes or improper immune complex clearance.

In specific embodiments, methods are provided for reducing the circulatory concentration of a target immune complex in a subject (e.g., a human) suffering from or at risk of developing a disease, disorder or condition associated with immune complexes. The methods include administering a pharmaceutical composition comprising a synthetic membrane—complement receptor 1 (CR1) receiver complex. The pharmaceutical composition is administered in an amount effective to substantially reduce the circulatory concentration of the target immune complex. In certain embodiments, the administration is carried out intravenously.

In certain embodiments, synthetic membrane—complement receptor 1 (CR1) receiver complexes are administered that specifically bind and sequester a target immune complex that is present in the circulatory system of the subject.

In some embodiments, functional erythroid cells comprising a receiver that comprises complement receptor 1 (CR1) may be administered to a subject exhibiting immune complexes in circulation. For example, a population of functional erythroid cells comprising a receiver that comprises complement receptor 1 (CR1) can bind C3b within an immune complex and removal and clearance from circulation can occur through the liver.

Compositions comprising erythrocyte-bound CR1 receiver, such as a plurality of functional erythroid cells comprising elevated levels of CR1, is preferably administered to a subject having been diagnosed with or being suspected of having a disease state that has resulted from an overabundance of immune complex formation or that has caused a reduction or depletion in the native CR1 level, such as an immune complex-associated disorder or disease.

In certain embodiments, the pharmaceutical composition will reduce the target immune complex load in the circulatory system, and/or prevent the deposition of immune complexes in sensitive soft tissue, thereby reducing the burden of the disease, disorder or condition associated with the presence or elevated concentration of the target immune complex. Diseases associated with complement dysregulation include, but are not limited to, systemic lupus erythematosus (SLE), lupus nephritis, IgA nephropathy, Dense Deposit Disease, lupus nephritis, Goodpasture's syndrome, membranoproliferative glomerulonephritis, immune complex vasculitis, cold agglutinin disease, polymyositis, acute pulmonary hemorrhage, membranous glomerulonephritis, membranous glomerulonephritis, rapidly-progressive glomerulonephritis, post-streptococcal glomerulonephritis, post-staphylococcal glomerulonephritis, Pauci-immune glomerulonephritis, blood hyperviscosity syndrome, and cutaneous leukocytoclastic angiitis and those listed in table 6 and table 8.

In certain embodiments, the target immune complex comprises i) IgM or IgG, and ii) C3b and/or C4b.

In certain embodiments, the CR1 receiver comprises one or more complement control protein (CCP) modules, short consensus repeats (SCR) and/or long homologous repeats (LHRs). In some embodiments, the CR1 receiver comprises a functional fragment of the full-length CR1 polypeptide.

Type III, or immune-complex, reactions are characterized by tissue damage caused by the activation of complement in response to antigen-antibody (immune) complexes (IgG and IgM) that are deposited in tissues. Once the antigen-antibody complexes form, they are deposited in various tissues of the body, especially the blood vessels, kidneys, lungs, skin, and joints. Deposition of the immune complexes causes an inflammatory response, which leads to the release of tissue-damaging enzymes and interleukin-1, which induces fever. Immune complexes underlie many autoimmune diseases, such as systemic lupus erythematosus (an inflammatory disorder of connective tissue), most types of glomerulonephritis (inflammation of the capillaries of the kidney), and rheumatoid arthritis.

Type III hypersensitivity reactions can be provoked by inhalation of antigens into the lungs. A number of conditions are attributed to this type of antigen exposure, including farmer's lung, caused by fungal spores from moldy hay; pigeon fancier's lung, resulting from proteins from powdery pigeon dung; and humidifier fever, caused by normally harmless protozoans that can grow in air-conditioning units and become dispersed in fine droplets in climate-controlled offices. In each case, the person will be sensitized to the antigen with IgG antibodies to the agent circulating in the blood. Inhalation of the antigen will stimulate the reaction and cause chest tightness, fever, and malaise, symptoms that usually pass in a day or two but recur when the individual is re-exposed to the antigen. Permanent damage is rare unless individuals are exposed repeatedly. Some occupational diseases of workers who handle cotton, sugarcane, or coffee waste in warm countries have a similar cause, with the sensitizing antigen usually coming from fungi that grow on the waste rather than the waste itself.

In one embodiment the disease or condition is IgA nephropathy, the receiver is Complement receptor 1 or fragment thereof, and the target is Immune complexes.

In one embodiment the disease or condition is lupus nephritis, the receiver is Complement receptor 1 or fragment thereof, and the target is immune complex.

In one embodiment the disease or condition is systemic lupus erythematosus, the receiver is Complement receptor 1 or fragment thereof, and the target is immune complex.

1. Systemic Lupus Erythematosus (SLE)

In some embodiments, subjects may be identified as having received or would benefit from receiving treatment for systemic lupus erythematosus (SLE). Subjects suffering from or at risk of developing SLE may be administered a pharmaceutical composition comprising the synthetic membrane-CR1 receiver complex to treat or prevent disease.

In certain embodiments, the CR1 receiver interacts with the target C3b, a constituent of a circulating immune complex. In some embodiments, the immune complex once bound to the synthetic membrane-CR1 receiver complex is degraded through the reticulo-endothelial system.

Systemic lupus erythematosus (SLE) is a chronic inflammatory disease that has protean manifestations and follows a relapsing and remitting course. More than 90% of cases of SLE occur in women, frequently starting at childbearing age. SLE is a chronic autoimmune disease that can affect almost any organ system; thus, its presentation and course are highly variable, ranging from indolent to fulminant. In childhood-onset SLE, there are several clinical symptoms more commonly found than in adults, including malar rash, ulcers/mucocutaneous involvement, renal involvement, proteinuria, urinary cellular casts, seizures, thrombocytopenia, hemolytic anemia, fever, and lymphadenopathy. In adults, Raynaud pleuritis and sicca are twice as common as in children and adolescents. A presentation of a triad of fever, joint pain, and rash in a woman of childbearing age should prompt investigation into the diagnosis of SLE.

SLE is an autoimmune disorder characterized by multi-system inflammation with the generation of self-antibodies. Self-antibodies may be present for many years before the onset of the first symptoms of SLE. Further, T cells from patients with lupus show defects in both signaling and effector function (e.g., decreased secretion of interleukin (IL)-2). T-cell abnormalities offer targets for therapy, e.g., belimumab, which targets the B-lymphocyte stimulator (BLys) signaling pathway.

Many clinical manifestations of SLE are mediated by circulating immune complexes that form with antigens in various tissues or the direct effects of antibodies to cell surface components. Immune complexes form in the microvasculature, leading to complement activation and inflammation. Moreover, antibody-antigen complexes deposit on the basement membranes of skin and kidneys. In active SLE, this process has been confirmed by demonstration of complexes of nuclear antigens such as DNA, immunoglobulins, and complement proteins at these sites. Self-antibodies (e.g., lupus anticoagulant (LA), and anti-ribosomal P antibodies) can be used as biomarkers to determine future neuropsychiatric events in SLE.

Other indications include the presence of serum antinuclear antibodies (ANAs) which are found in nearly all individuals with active SLE. Antibodies to native double-stranded DNA (dsDNA) are relatively specific for the diagnosis of SLE. Cytotoxic T cells and suppressor T cells (which would normally down-regulate immune responses) are decreased. The generation of polyclonal T-cell cytolytic activity is impaired. Helper (CD4$^+$) T cells are increased. A lack of immune tolerance is observed in animal lupus models.

2. IgA Nephropathy

In some embodiments, subjects may be identified as having received or would benefit from receiving treatment for IgA nephropathy. Subjects suffering from or at risk of developing IgA nephropathy may be administered a pharmaceutical composition comprising the synthetic membrane-CR1 receiver complex to treat or prevent disease.

In certain embodiments, the CR1 receiver interacts with the target C3b, a constituent of a circulating IgA immune complex. In some embodiments, the immune complex once bound to the synthetic membrane-CR1 receiver complex is degraded through the reticulo-endothelial system.

IgA nephropathy also known as Berger's disease is a kidney disease associated with the accumulation of IgA-immune complexes. The presence of the immune complexes triggers a local inflammation that reduces the kidneys' ability to filter waste, excess water and electrolytes from the blood. Kidney damage may be indicated by blood and protein in urine, high blood pressure and swollen feet.

IgA nephropathy usually progresses slowly over many years. Some subjects present blood in their urine without developing problems, some eventually achieve complete remission, and others develop end-stage kidney failure.

IgA nephropathy is the most common glomerulonephritis worldwide. Clinically, it is characterized by hematuria and proteinuria; about 20-30% of the IgAN patients develop progressive renal failure within 10-20 years from the onset of disease. Histologically, the glomerular mesangium contains deposits of IgA1, the C3 component of complement, and less frequently, IgG and/or IgM. Circulating immune complexes (CICs) composed of IgA1, C3, and IgG are involved in the pathogenesis of the disease.

Serum IgA1 from IgAN patients may exhibit alterations in the glycan side chains. Human IgA1 contains N- and O-linked glycans. IgA1 from IgAN patients display altered glycan moieties, usually with a reduced content of galactose (Gal). The Gal-deficient IgA1 may be present in CICs with IgG. IgA1 from sera of IgAN patients exhibit increased binding to lectins specific for a terminal GalNAc, such as *Helix aspersa* (HAA) or *Helix pomatia* (HPO).

Amyloidoses

In some embodiment, the synthetic membrane-receiver polypeptide complexes described herein may be used to treat or prevent amyloidosis. In some embodiments, membrane-receiver complexes are used that do not contain a receiver polypeptide. The receiver can for example be a glycosaminoglycans (GAG).

In specific embodiments, methods are provided for reducing the circulatory concentration of a target serum amyloid protein in a subject (e.g., a human) suffering from or at risk of developing amyloid plaques. The methods include administering a pharmaceutical composition comprising a synthetic membrane-receiver complex described herein. The pharmaceutical composition is administered in an amount effective to substantially reduce the circulatory concentration of the target serum amyloid protein. In certain embodiments, the administration is carried out intravenously.

In certain embodiments, synthetic membrane-receiver complexes are administered that comprise a receiver that specifically binds, sequesters and/or degrades a target serum amyloid protein or target amyloid plaque that is present in the circulatory system of the subject.

In certain embodiments, the pharmaceutical composition will reduce the target serum amyloid protein or amyloid plaque load in the circulatory system, e.g., preventing their deposition in soft tissue, thereby reducing the burden of the amyloidosis. Amyloidoses include, but are not limited to, AA amyloidosis, light chain (AL) amyloidosis, beta-2 microglobulin amyloidosis and those listed in table 6 and table 8.

In certain embodiments, the receiver polypeptide may specifically interact with a target serum amyloid protein selected from the group consisting of: amyloid P protein, amyloid A protein, light chain, misfolded transthyretin, and fibrinogen alpha chain.

Amyloidosis is a rare disease associated with amyloid plaques build up. Amyloidosis can affect different organs such as, e.g., the heart, kidneys, liver, spleen, nervous system and digestive tract. Severe amyloidosis can lead to life-threatening organ failure.

Acquired systemic amyloidosis is thought to be the cause of death in about 1 in 1,000 persons in Western countries and is most common in the elderly. Systemic AL amyloidosis is the most common and serious type, accounting for over 60% of cases. Dialysis-related $\beta_2$-microglobulin amyloidosis affects about 1 million patients worldwide. Senile transthyretin (ATTR) amyloidosis, which predominantly involves the heart, occurs in about one quarter of persons older than 80 years.

In one embodiment the disease or condition is AA amyloidosis, the receiver is an an antibody-like binder to serum amyloid A protein or serum amyloid P component or fragment thereof, and the target is serum amyloid A protein and amyloid placques.

In one embodiment the disease or condition is beta2 microglobulin amyloidosis, the receiver is an antibody-like binder to beta-2 microglobulin or serum amyloid P component or fragment thereof, and the target is beta-2 microglobulin or amyloid placques.

In one embodiment the disease or condition is light chain amyloidosis, the receiver is an antibody-like binder to light chain, serum amyloid P component or fragment thereof, and the target is antibody light chain or amyloid placques.

1. AA Amyloidosis

In some embodiments, subjects may be identified as having received or would benefit from receiving treatment for AA amyloidosis. Subjects suffering from or at risk of developing AA amyloidosis may be administered a pharmaceutical composition comprising the synthetic membrane—receiver polypeptide complexes described herein to treat or prevent disease.

AA amyloidosis is a complication of chronic infections and inflammatory diseases or any condition that leads to long-term overproduction of the acute phase reactant SAA. The amyloid fibrils are composed of an N-terminal cleavage fragment of SAA (the AA protein). AA amyloidosis occurs in 1% to 5% of patients with rheumatoid arthritis, juvenile idiopathic arthritis and Crohn's disease. Tuberculosis and leprosy are also important causes of AA amyloidosis in some parts of the world. Most patients present with proteinuria, and liver and gastrointestinal involvement may occur with time.

2. AL Amyloidosis

In some embodiments, subjects may be identified as having received or would benefit from receiving treatment for AL amyloidosis. Subjects suffering from or at risk of developing AL amyloidosis may be administered a pharmaceutical composition comprising the synthetic membrane—receiver polypeptide complexes described herein to treat or prevent disease.

Systemic AL occurs in about 2% of people with monoclonal B-cell dyscrasias. AL fibrils are derived from monoclonal immunoglobulin light chains, affecting usually the kidneys, heart, liver and peripheral nerves.

3. β2-Microglobulin Amyloidosis

In some embodiments, subjects may be identified as having received or would benefit from receiving treatment for β2-Microglobulin amyloidosis. Subjects suffering from or at risk of developing β2-Microglobulin amyloidosis may be administered a pharmaceutical composition comprising the synthetic membrane—receiver polypeptide complexes described herein to treat or prevent disease.

$\beta_2$-Microglobulin amyloid deposition occurs in patients with dialysis-dependent chronic renal failure, mainly affecting articular and periarticular structures. It typically causes arthralgia of the shoulders, knees, wrists and small joints of the hand; joint swelling and carpal tunnel syndrome. The amyloid fibril precursor protein is $\beta_2$-microglobulin, which is the invariant chain of the major histocompatibility complex (MHC) class I molecule and is expressed by all nucleated cells. Since it is normally filtered freely at the glomerulus, reabsorbed and catabolized by proximal tubular cells, decreasing renal function causes a proportionate rise in its concentration. Disease-related amyloidosis (DRA) is present in 20% to 30% of patients within 3 years of starting dialysis for end-stage renal failure.

In some embodiments, membrane-receiver complexes that do not contain a receiver polypeptide are used for treatment of an amyloidosis and or for the reduction of a serum amyloid protein or amyloid plaque. In one embodiment, the synthetic membrane-receiver complex comprises a receiver comprising a glycosaminoglycans (GAG), or a derivative or functional fragment thereof. A suitable receiver may be exhibited on the surface of the synthetic membrane-receiver complex and may be administered to bind a circulating amyloidogenic precursors. In certain embodiments, amyloid deposits are prevented from forming.

In one embodiment, the synthetic membrane-receiver polypeptide complex comprises a receiver comprising a serum amyloid P-component (SAP), or a derivative or functional fragment thereof. A suitable receiver may be exhibited on the surface of the synthetic membrane-receiver polypeptide complex and may be administered to prevent amyloids from aggregating. Serum amyloid P-component (protein SAP) has been described to bind in vitro to isolated amyloid fibrils of both primary and secondary types.

Infectious Agent-Mediated Diseases and Conditions

In some embodiments, the synthetic membrane-receiver polypeptide complexes described herein may be used to treat or prevent diseases, disorders or conditions that are associated with infectious agents.

In some embodiments, functional erythroid cells comprising a receiver specific for circulating pathogens are administered to a subject in need thereof in an amount effective to treat an infectious disease in which opsonized pathogen is present in the blood, such as carbapenem-resistant enterobacteriaceae, drug resistant *Neisseria gonorrhoeae*, fully resistant *Streptococcus pneumoniae*, drug resistant tuberculosis, generalized bacterial sepsis, human immunodeficiency virus infection, hepatitis B virus infection, or malaria. In some embodiments, functional erythroid cells comprise a receiver specific for circulating pathogens that include, but are not limited to, the targets in table 5.

In specific embodiments, methods are provided for reducing the circulatory concentration of a target infectious agent in a subject (e.g., a human) suffering from or at risk of developing an infectious disease. The methods include administering a pharmaceutical composition comprising a synthetic membrane-receiver polypeptide complex described herein. The pharmaceutical composition is administered in an amount effective to substantially reduce the circulatory concentration of the target infectious agent. In certain embodiments, the administration is carried out intravenously.

In certain embodiments, synthetic membrane-receiver polypeptide complexes are administered that comprise a receiver that specifically binds, sequesters, and/or degrades an infectious agent, such as a bacterium, a virus, a fungus, or a parasite that is present in the circulatory system of the subject.

In certain embodiments, synthetic membrane-receiver polypeptide complexes are administered to reduce the plasma titer of the infectious agent, e.g., virus titer.

In certain embodiments, synthetic membrane-receiver polypeptide complexes are administered to reduce the ability of the infectious agent to access enough host cells per unit of time. A decrease in the rate of infection of host cells may correlate with an increasing inability of the infectious agent to perpetuate the infection or perpetuate the deleterious effect to the subject host. The infection may be suppressed and/or contained.

In certain embodiments, the pharmaceutical composition will reduce the target infectious agent load in the circulatory system, slowing or stopping the infection and aiding the immune system in its defense, thereby reducing the burden of the infectious disease. Infectious diseases include, but are not limited to, Hepatitis A, Hepatitis B, Hepatitis C, HIV, Ebola, *C. difficile, C. botulinum*, Anthrax, *E. coli, mycobacterium tuberculosis, Candida*, malaria and those listed in table 6 and table 8.

In one embodiment the disease or condition is Anthrax (*B. anthracis*) infection, the receiver is an antibody-like binder to *B. anthracis* surface protein or fragment thereof, and the target is *B. anthracis*.

In one embodiment the disease or condition is *C. botulinum* infection, the receiver is an antibody-like binder to *C. botulinum* surface protein or fragment thereof, and the target is *C. botulinum*.

In one embodiment the disease or condition is *C. difficile* infection, the receiver is an antibody-like binder to *C. difficile* surface protein or fragment thereof, and the target is *C. difficile*.

In one embodiment the disease or condition is *Candida* infection, the receiver is an antibody-like binder to *candida* surface protein or fragment thereof, and the target is *candida*.

In one embodiment the disease or condition is *E. coli* infection, the receiver is an antibody-like binder to *E. coli* surface protein or fragment thereof, and the target is *E. coli*.

In one embodiment the disease or condition is Ebola infection, the receiver is an antibody-like binder to Ebola surface protein or fragment thereof, and the target is Ebola.

In one embodiment the disease or condition is Hepatitis B (HBV) infection, the receiver is an antibody-like binder to HBV surface protein or fragment thereof, and the target is HBV.

In one embodiment the disease or condition is Hepatitis C (HCV) infection, the receiver is an antibody-like binder to HCV surface protein or fragment thereof, and the target is HCV.

In one embodiment the disease or condition is Human immunodeficiency virus (HIV) infection, the receiver is an antibody-like binder to HIV envelope proteins or CD4 or CCR5 or or fragment thereof, and the target is HIV.

In one embodiment the disease or condition is *M. tuberculosis* infection, the receiver is an antibody-like binder to *M. tuberculosis* surface protein or fragment thereof, and the target is *M. tuberculosis*.

In one embodiment the disease or condition is malaria (*P. falciparum*) infection, the receiver is an antibody-like binder to *P. falciparum* surface protein or fragment thereof, and the target is *P. falciparum*.

1. Bacterial Infections

In some embodiments, subjects may be identified as having received or would benefit from receiving treatment for a bacterial infection. Subjects suffering from or at risk of developing a bacterial infection may be administered a pharmaceutical composition comprising the synthetic membrane-receiver polypeptide complex described herein to treat or prevent disease.

In some embodiments, the target is a bacterium. In certain embodiments, the target comprises a bacterial antigen. In some embodiments, the bacterial antigen comprises a cell surface antigen, a secreted toxin, or a secreted bacterial antigen.

Bacteremia is the presence of bacteria in the blood. Gram-negative bacteremia secondary to infection usually originates in the genitourinary system or GI tract, or the skin in patients with decubitus ulcers. Chronically ill and immunocompromised patients have an increased risk of gram-negative bacteremia. They may also develop bacteremia with gram-positive cocci, anaerobes, and fungi. Staphylococcal bacteremia is common in injection drug users. *Bacteroides* bacteremia may develop in patients with infections of the abdomen and the pelvis, particularly the female genital tract. The bacteria most likely to cause bacteremia include members of the *Staphylococcus, Streptococcus, Pseudomonas, Haemophilus*, and *Eshericha coli* (*E. coli*) genera.

Bacterial infectious diseases that can be treated by the pharmaceutical compositions comprising a synthetic membrane-receiver polypeptide complex described herein include, but are not limited to, *Mycobacteria, Rickettsia, Mycoplasma, Neisseria meningitides, Neisseria gonorrheoeae, Legionella, Vibrio cholerae, Streptococci, Staphylococcus aureus, Staphylococcus epidermidis, Pseudomonas aeruginosa, Corynobacteria diphtheriae, Clostridium* spp., enterotoxigenic *Eschericia coli*, and *Bacillus anthracis*. Other pathogens for which bacteremia has been reported include: *Rickettsia, Bartonella henselae, Bartonella quintana, Coxiella burnetii, chlamydia, Mycobacterium leprae, Salmonella; shigella; Yersinia enterocolitica; Yersinia pseudotuberculosis; Legionella pneumophila; Mycobacterium tuberculosis; Listeria monocytogenes; Mycoplasma* spp.; *Pseudomonas fluorescens; Vibrio cholerae; Haemophilus influenzae; Bacillus anthracis; Treponema pallidum; Leptospira; Borrelia; Corynebacterium diphtheriae; Francisella; Brucella melitensis; Campylobacter jejuni; Enterobacter; Proteus mirabilis; Proteus*; and *Klebsiella pneumoniae*.

In some embodiments, a membrane-receiver polypeptide complex may be used to treat the infectious bacterial disease. A suitable receiver polypeptide may comprise, for example, CD14 or a functional fragment thereof. CD14 is associated with monocyte/macrophages and binds lipopolysaccharide associated with gram negative bacteria as well as lipoteichoic acid associated with the gram positive bacteria *Bacillus subtilis*. Other suitable receivers may comprise adenylate cyclase (*Bordatella pertussis*), Gal alpha 1-4Gal-containing isoreceptors (*E. coli*), glycoconjugate receptors (enteric bacteria), Lewis(b) blood group antigen receptor (*Heliobacter pylori*), CR3 receptor, protein kinase receptor, galactose N-acetylgalactosamine-inhibitable lectin receptor, chemokine receptor (*Legionella*), annexin I (*Leishmania mexicana*), ActA protein (*Listeria monocytogenes*), meningococcal virulence associated Opa receptors (*Meningococcus*), acute over ($\alpha$)5$\beta$3 integrin (*Mycobacterium avium*-M), heparin sulphate proteoglycan receptor, CD66 receptor, integrin receptor, membrane cofactor protein, CD46, GM1, GM2, GM3, and CD3 (*Neisseria gonorrhoeae*), KDEL receptor (*Pseudomonas*), epidermal growth factor receptor (*Samonella typhiurium*), $\beta$1 integrin (*Shigella*), nonglycosylated J774 receptor (Streptococci) or combinations or functional fragments thereof.

In some embodiments, the synthetic membrane-receiver complex may comprise more than one receiver. One receiver may function to interact with the target, while the other receiver may modify the target, e.g., disrupting the integrity of the target, marking the target for degradation and/or inactivating the target. For example, if the target is a bacterium, one receiver functions to interact with the target bacterium (e.g., through an interaction with an epitope if the receiver comprises an antibody-like function). The other receiver may be capable of breaching the cell membrane of the bacterium. Suitable second receivers include, for example, lysozymes, bacteriocidal permeability increasing peptides, proteases, and other pore forming antimicrobials. For example, a lysozyme receiver may hydrolyse 1,4-beta-linkages between N-acetylmuramic acid and N-acetyl-D-glucosamine residues in a peptidoglycan and between N-acetyl-D-glucosamine residues in chitodextrins of certain bacteria.

Alternatively, a second receiver may comprise a bacteriostatic or bactericidal agent that may be contacted with the bacterium. Yet another alternative is that the synthetic membrane-receiver complex comprises (e.g., through loading) a bacteriostatic or bactericidal agent that may be contacted with the bacterium. Examples of bacteriostatic or bactericidal agents that may be associated with a receiver or the complex include, but are not limited to, beta-lactam compounds (penicillin, methicillin, nafcillin, oxacillin, cloxacillin, dicloxacilin, ampicillin, ticarcillin, amoxicillin, carbenicillin, piperacillin); cephalosporins & cephamycins (cefadroxil, cefazolin, cephalexin, cephalothin, cephapirin, cephradine, cefaclor, cefamandole, cefonicid, cefuroxime, cefprozil, loracarbef, ceforanide, cefoxitin, cefmetazole, cefotetan, cefoperazone, cefotaxime, ceftazidine, ceftizoxine, ceftriaxone, cefixime, cefpodoxime, proxetil, cefdinir, cefditoren, pivoxil, ceftibuten, moxalactam, cefepime); other beta-lactam drugs (aztreonam, clavulanic acid, sulbactam, tazobactam, ertapenem, imipenem, meropenem); cell wall membrane active agents (vancomycin, teicoplanin, daptomycin, fosfomycin, bacitracin, cycloserine); tetracyclines (tetracycline, chlortetracycline, oxytetracycline, demeclocycline, methacycline, doxycycline, minocycline, tigecycline); macrolides (erythromycin, clarithromycin, azithromycin, telithromycin); clindamycin; choramphenicol; quinupristin-dalfopristin; linezolid; aminoglycosides (streptomycin, neomycin, kanamycin, amikacin, gentamicin, tobramycin, sisomicin, netilmicin); spectinomycin; sulfonamides (sulfacytine, sulfisoxazole, silfamethizole, sulfadiazine, sulfamethoxazole, sulfapyridine, sulfadoxine); trimethoprim; pyrimethamine; trimethoprim-sulfamethoxazole; fluoroquinolones (ciprofloxacin, gatifloxacin, gemifloxacin, levofloxacin, lomefloxacin, moxifloxacin, norfloxacin, ofloxacin); colistimethate sodium, methenamine hippurate, methenamine mandelate, metronidazole, mupirocin, nitrofurantoin, and polymyxin B. Examples of antimycobacteria drugs include, but are not limited to: isoniazid, rifampin, rifabutin, rifapentine, pyrazinamide, ethambutol, ethionamide, capreomycin, clofazimine, and dapsone.

In some embodiments, methods of treatment of bacterial infectious diseases are provided comprising co-administration of one or more bacteriostatic or bactericidal agents and the synthetic membrane-receiver complex described herein, wherein co-administration includes administration of the bacteriostatic or bactericidal agent before, after or concurrent with administration of the synthetic membrane-receiver complex.

In some embodiments, methods of treatment of bacterial infectious diseases are provided comprising administration of a pharmaceutical composition comprising one or more bacteriostatic or bactericidal agents and the synthetic membrane-receiver complex described herein.

In some embodiments, the receiver may sequester the target bacterium and distribute it in the circulatory system without directly modifying the target. In certain embodiments, the synthetic membrane-receiver complex may subject the associated target bacterium to degradation by the reticulo-endothelial system.

2. Fungal Infections

In some embodiments, subjects may be identified as having received or would benefit from receiving treatment for a fungal infection. Subjects suffering from or at risk of developing a fungal infection may be administered a pharmaceutical composition comprising the synthetic membrane-receiver polypeptide complex described herein to treat or prevent disease.

In some embodiments, the target is a fungus. In certain embodiments, the target comprises a fungal antigen. In some embodiments, the fungal antigen comprises a cell surface antigen, a secreted toxin, or a secreted fungal antigen.

Fungemia (also known as candidemia, candedemia, and invasive candidiasis) is the presence of fungi or yeasts in the blood. The most commonly known pathogen is *Candida albicans*, causing roughly 70% of fungemias, followed by *Candida glabrata* with 10%, and *Aspergillus* with 1%. Infections with *T. glabrata, Candida tropicalis, C. krusei*, and *C. parapsilosis* may also occur.

In some embodiments, a membrane-receiver polypeptide complex may be used to treat the infectious fungal disease. In some embodiments, the synthetic membrane-receiver complex may comprise more than one receiver. One receiver may function to interact with the target, while the other receiver may modify the target, e.g., disrupting the integrity of the target, marking the target for degradation and/or inactivating the target. The second receiver may comprise an antifungal agent that may be contacted with the fungus. In another embodiment, the synthetic membrane-receiver complex comprises (e.g., through loading) an antifungal agent that may be contacted with the fungus.

Examples of antifungal agents that may be associated with a receiver or the complex include, but are not limited to, allylamines; terbinafine; antimetabolites; flucytosine; azoles; fluconazole; itraconazole; ketoconazole; ravuconazole; posaconazole; voriconazole; glucan synthesis inhibitors; caspofungin; micafungin; anidulafungin; polyenes; amphotericin B; amphotericin B Lipid Complex (ABLC); amphotericin B Colloidal Dispersion (ABCD); liposomal amphotericin B (L-AMB); liposomal nystatin; and griseofulvin.

In some embodiments, methods of treatment of fungal infectious diseases are provided comprising co-administration of one or more antifungal agents and the synthetic membrane-receiver complex described herein, wherein co-administration includes administration of the antifungal agent before, after or concurrent with administration of the synthetic membrane-receiver complex.

In some embodiments, methods of treatment of bacterial infectious diseases are provided comprising administration of a pharmaceutical composition comprising one or more antifungal agents and the synthetic membrane-receiver complex described herein.

In some embodiments, the receiver may sequester the target fungus and distribute it in the circulatory system without directly modifying the target. In certain embodiments, the synthetic membrane-receiver complex may subject the associated target fungus to degradation by the reticulo-endothelial system.

3. Parasite Infections

In some embodiments, subjects may be identified as having received or would benefit from receiving treatment for a parasitic infection. Subjects suffering from or at risk of developing a parasitic infection may be administered a pharmaceutical composition comprising the synthetic membrane-receiver polypeptide complex described herein to treat or prevent disease.

In some embodiments, the target is a parasite. In certain embodiments, the target comprises a parasitic antigen. In some embodiments, the parasitic antigen comprises a cell surface antigen, a secreted toxin, or a secreted parasitic antigen. Suitable targets include intestinal or blood-borne parasites, including protozoa.

Typically, blood-borne parasites are transmitted through an arthropod vector. Most important arthropod for transmitting parasitic infections are mosquitoes. Mosquitoes carry malaria and filarial nematodes. Biting flies transmit African trypanosomiasis, leishmaniasis and several kinds of filariasis. Examples of parasites include, but are not limited to, trypanosomes; haemoprotozoa and parasites capable of causing malaria; enteric and systemic cestodes including taeniid cestodes; enteric coccidians; enteric flagellate protozoa; filarial nematodes; gastrointestinal and systemic nematodes and hookworms.

In some embodiments, a membrane-receiver polypeptide complex may be used to treat the parasitic infection. In some embodiments, the synthetic membrane-receiver complex may comprise more than one receiver. One receiver may function to interact with the target, while the other receiver may modify the target, e.g., disrupting the integrity of the target, marking the target for degradation and/or inactivating the target. The second receiver may comprise an anti-parasitic agent that may be contacted with the fungus. In another embodiment, the synthetic membrane-receiver complex comprises (e.g., through loading) an anti-parasitic agent that may be contacted with the fungus.

Examples of anti-parasitic agents that may be associated with a receiver or the complex include, but are not limited to, antiprotozoal agents; eflornithine; furazolidone; melarsoprol; metronidazole; omidazole; paromomycin sulfate; pentamidine; pyrimethamine; tinidazole; antimalarial agents; quinine; chloroquine; amodiaquine; pyrimethamine; sulphadoxine; proguanil; mefloquine; halofantrine; primaquine; artemesinin and derivatives thereof; doxycycline; clindamycin; benznidazole; nifurtimox; antihelminthics; albendazole; diethylcarbamazine; mebendazole; niclosamide; ivermectin; suramin; thiabendazole; pyrantel pamoate; levamisole; piperazine family; praziquantel; triclabendazole; octadepsipeptides; and emodepside.

In some embodiments, methods of treatment of parasitic infectious diseases are provided comprising co-administration of one or more anti-parasitic agents and the synthetic membrane-receiver complex described herein, wherein co-administration includes administration of the anti-parasitic agent before, after or concurrent with administration of the synthetic membrane-receiver complex.

In some embodiments, methods of treatment of parasitic infectious diseases are provided comprising administration of a pharmaceutical composition comprising one or more anti-parasitic agents and the synthetic membrane-receiver complex described herein.

In some embodiments, the receiver may sequester the target parasite and distribute it in the circulatory system without directly modifying the target. In certain embodiments, the synthetic membrane-receiver complex may subject the associated target parasite to degradation by the reticulo-endothelial system.

4. Viral Infections

In some embodiments, subjects may be identified as having received or would benefit from receiving treatment for a viral infection. Subjects suffering from or at risk of developing a viral infection may be administered a pharmaceutical composition comprising the synthetic membrane-receiver polypeptide complex described herein to treat or prevent disease.

In some embodiments, the target is a virus. In certain embodiments, the target comprises a viral antigen. In some embodiments, the viral antigen comprises an envelope antigen or a capsid antigen. Suitable viral targets include adenovirus, coxsackievirus, hepatitis a virus, poliovirus, epstein-barr virus, herpes simplex, type 1, herpes simplex, type 2, human cytomegalovirus, human herpesvirus, type 8, varicella-zoster virus, hepatitis B virus, hepatitis C viruses, human immunodeficiency virus (HIV), influenza virus, measles virus, mumps virus, parainfluenza virus, respiratory syncytial virus, papillomavirus, rabies virus, and Rubella virus. Other suitable viral targets include Paramyxoviridae (e.g., pneumovirus, morbillivirus, metapneumovirus, respirovirus or rubulavirus), Adenoviridae (e.g., adenovirus), Arenaviridae (e.g., arenavirus such as lymphocytic choriomeningitis virus), Arteriviridae (e.g., porcine respiratory and reproductive syndrome virus or equine arteritis virus), Bunyaviridae (e.g., phlebovirus or hantavirus), Caliciviridae (e.g., Norwalk virus), Coronaviridae (e.g., coronavirus or torovirus), Filoviridae (e.g., Ebola-like viruses), Flaviviridae (e.g., hepacivirus or flavivirus), Herpesviridae (e.g., simplexvirus, varicellovirus, cytomegalovirus, roseolovirus, or lymphocryptovirus), Orthomyxoviridae (e.g., influenza virus or thogotovirus), Parvoviridae (e.g., parvovirus), Picornaviridae (e.g., enterovirus or hepatovirus), Poxviridae (e.g., orthopoxvirus, avipoxvirus, or leporipoxvirus), Retroviridae (e.g., lentivirus or spumavirus), Reoviridae (e.g., rotavirus), Rhabdoviridae (e.g., lyssavirus, novirhabdovirus, or vesiculovirus), and Togaviridae (e.g., alphavirus or rubivirus). Specific examples of these viruses include human respiratory coronavirus, influenza viruses A-C, hepatitis viruses A to G, and herpes simplex viruses 1-9.

In some embodiments, a membrane-receiver polypeptide complex may be used to treat the viral infection. In some embodiments, the synthetic membrane-receiver complex may comprise more than one receiver. One receiver may function to interact with the target, while the other receiver may modify the target, e.g., disrupting the integrity of the target, marking the target for degradation and/or inactivating the target.

For example, if the target is a virus, one receiver functions to interact with the target virus (e.g., through an interaction with a viral epitope if the receiver comprises an antibody-like function). The other receiver may be capable of breaching the viral envelope or capsid. Suitable second receivers include, for example, antiviral agents, proteases, nucleases, antisense molecules, ribozymes, RNAi molecules (e.g., siRNA or shRNA), or other molecules that are toxic or detrimental to the virus.

The second receiver may comprise an anti-viral agent that may be contacted with the virus. In another embodiment, the synthetic membrane-receiver complex comprises (e.g., through loading) an anti-viral agent that may be contacted with the virus.

Examples of anti-viral agents that may be associated with a receiver or the complex include, but are not limited to, thiosemicarbazones; metisazone; nucleosides and nucleotides; acyclovir; idoxuridine; vidarabine; ribavirin; ganciclovir; famciclovir; valaciclovir; cidofovir; penciclovir; valganciclovir; brivudine; ribavirin, cyclic amines; rimantadine; tromantadine; phosphonic acid derivatives; foscarnet; fosfonet; protease inhibitors; saquinavir; indinavir; ritonavir; nelfinavir; amprenavir; lopinavir; fosamprenavir; atazanavir; tipranavir; nucleoside and nucleotide reverse transcriptase inhibitors; zidovudine; didanosine; zalcitabine; stavudine; lamivudine; abacavir; tenofovir disoproxil; adefovir dipivoxil; emtricitabine; entecavir; non-nucleoside reverse transcriptase inhibitors; nevirapine; delavirdine; efavirenz; neuraminidase inhibitors; zanamivir; oseltamivir; moroxydine; inosine pranobex; pleconaril; and enfuvirtide.

In some embodiments, methods of treatment of viral infectious diseases are provided comprising co-administration of one or more anti-viral agents and the synthetic membrane-receiver complex described herein, wherein co-administration includes administration of the anti-viral agent before, after or concurrent with administration of the synthetic membrane-receiver complex.

In some embodiments, methods of treatment of viral infectious diseases are provided comprising administration of a pharmaceutical composition comprising one or more antiviral agents and the synthetic membrane-receiver complex described herein.

In some embodiments, the receiver may sequester the target virus and distribute it in the circulatory system without directly modifying the target. In certain embodiments, the synthetic membrane-receiver complex may subject the associated target virus to degradation by the reticulo-endothelial system.

Conditions Associated with Toxins and Poisons

In some embodiments, the synthetic membrane-receiver polypeptide complexes described herein may be used to treat or prevent toxic conditions or poisoning caused by toxins or poisons.

Sepsis and septic shock, which represent major causes of mortality in modern intensive care medicine, are caused by an inadequate inflammatory and immunological host response to bacterial infection. Evidence suggests that the systemic spread of microbial toxins, rather than bacteremia itself, is the crucial event in the pathogenesis. The endothelium is a main target of bacterial toxins. The resulting endothelial dysfunction is believed to contribute to the underlying pathomechanisms and the collapse of homeostasis of organ function.

Bacterial toxins targeting endothelial cells severely alter the behavior of extravascular cells and circulating leukocytes via excessive formation of vasoactive mediators and overexpression of adhesion molecules (Grandel, Crit Rev Immunol, 2003).

Pore-forming toxins (PFTs) are one of the most common protein toxins found in nature. These toxins disrupt cells by forming pores in cellular membranes and altering their permeability. In bacterial infections, attack by PFTs is a major virulence mechanism. It has been demonstrated that the inhibition of the pore-forming a-toxin can reduce the severity of *Staphylococcus aureus* infections, and similar PFT-targeted strategies have shown therapeutic potential against other pathogens, including *Escherichia coli, Listeria monocytogenes, Bacillus anthracis* and *Streptococcus pneumoniae*. As well as their role in bacterial pathogenesis, PFTs are commonly used in venomous attacks by animals such as sea anemones, scorpions and snakes. Over 80 families of PFTs have been identified, displaying diverse molecular structures and distinctive epitopic targets (Zhang, Nature Nano, 2013).

A number of biomolecules show interactions with endotoxins, such as lipopolysaccharide-binding protein (LBP), bactericidal/permeability-increasing protein (BPI), amyloid P component, cationic protein, or the enzyme employed in the biological endotoxin assay (anti-LPS) factor from Limulus amebocyte lysate (LAL). These proteins are directly involved in the reaction of many different species upon administration of endotoxin.

In one embodiment, functional erythroid cells comprise a receiver that comprises an amino acid sequence derived from lipopolysaccharide binding protein (LBP). A population of functional erythroid cells comprising a receiver that comprises an amino acid sequence derived from lipopolysaccharide binding protein (LBP) may be administered to a subject in need thereof in an amount effective to remove immunogenic lipopolysaccharide that may be in circulation as a result of a microbial infection.

Further provided are methods of inducing toxin clearance. The methods include administering to a subject in need thereof a population of functional erythroid cells comprising a receiver that is capable of interacting with a toxin, such as e.g., an antibody, scFv or nanobody receiver, in an amount effective to clear toxins from circulation. The compositions comprising functional erythroid cells that comprise the toxin-specific receiver may be administered to subjects that exhibit levels of toxic metabolites or infectious agents such as anthrax, botulinum, cytokines, sarin, hemolysin, venoms, and including, but not limited to, those in table 5.

In one embodiment, functional erythroid cells comprise a receiver that comprises an amino acid sequence derived from the endotoxin receptor CD14. A population of functional erythroid cells comprising a receiver that comprises an amino acid sequence derived from the endotoxin receptor CD14 may be administered to a subject in need thereof in an amount effective to bind to a target endotoxin in circulation. Such methods may be employed to sequester the toxin and reduce the amount of tissue damage that would otherwise occur within the vasculature and dissipating its pathogenic effects in a less acute manner.

In one embodiment, the receiver interacts with cell-free circulating DNA. In one embodiment, the functional erythroid cell expresses exogenous gene encoding a receiver comprising an amino acid sequence derived from a DNA-interacting polypeptide, such as, e.g., DNase, a transcription factor DNA binding domain or histone fragments. The DNase, DNA binding domain or histone fragment may be expressed as a fusion protein. In other embodiments, the DNAse, DNA binding domain, histone fragment or another receiver with affinity to circulating DNA is loaded into or onto the erythroid cell. In one embodiment, the receiver is a DNase, DNA binding domain or histone fragment that is localized extracellularly.

A hallmark of apoptosis is DNA degradation, in which chromosomal DNA is first cleaved into large fragments (50-300 kb) and subsequently into multiples of nucleosomal units (180-200 bp) (Nagata, Cell Death Differ, 2003). The contents of apoptotic cells are ingested by phagocytes or neighboring cells and the DNA is completely digested by DNase II in lysosomes (Nagata, Cell Death Differ, 2003). Thus, DNA fragments released by apoptosis may be removed before appearing in the circulation. In instances where the engulfment of apoptotic bodies is impaired or cell death is increased an inflammatory response may occur. For example, autoimmunity occurs frequently in cancer and other conditions involving increased circulating DNA (Viorritto, Clin Immunol, 2007).

Extracellular DNA, or circulating cell free DNA (cf-DNA), is present in blood plasma. These cf-DNAs, at least part of them, are believed to originate from cancer cells and contain a number of cancer specific entities, including oncogenes, tumor suppressor genes, aberrant microsatellites, aberrant DNA methylation genes, and rearranged chromosomal DNA. The term, 'genometastasis' has been proposed to describe the phenomena of an apoptotic body containing DNA that horizontally enters and transforms healthy cells (Garcia-Olmo, Expert Opinion on Bio Therapy, 2012).

In certain embodiments, functional erythroid cells comprising a receiver specific for circulating DNA are administered to a subject in need thereof in an amount effective to treat a DNA-driven pathogenesis, such as systemic lupus erythematosus and cancers suspected of genometastasis. In some embodiments, functional erythroid cells comprise an extracellular receiver comprising DNAse fused to the N terminal of glycophorin A such that it is capable of degrading circulating DNA within the vasculature.

In specific embodiments, methods are provided for reducing the circulatory concentration of a target toxin or poison in a subject (e.g., a human) suffering from or at risk of developing a toxic condition or poisoning. The methods include administering a pharmaceutical composition comprising a synthetic membrane-receiver polypeptide complex described herein. The pharmaceutical composition is administered in an amount effective to substantially reduce the circulatory concentration of the target toxin or poison. In certain embodiments, the administration is carried out intravenously.

In certain embodiments, synthetic membrane-receiver polypeptide complexes are administered that comprise a receiver that specifically binds, sequesters, and/or degrades a toxin or poison, such as a pathogenic toxin, a venom, a prion protein, a cytokine, a metal (e.g., heavy metal), or an alcohol (e.g., methanol) that is present in the circulatory system of the subject. Conditions associated with toxins or poisons include, but are not limited to bacterial toxin-induced shock, spider venom-induced shock, prion diseases, cytokine storm, iron poisoning, copper poisoning, Wilson disease, heavy metal poisoning, methanol poisoning and those listed in table 6 and table 8.

Further provided are methods of inducing toxin clearance. In specific embodiments, the methods include administering to a subject in need thereof a pharmaceutical composition of erythrocyte cells comprising a receiver provided herein in an amount sufficient to induce toxin clearance in the subject. The compositions may be administered to subjects that exhibit levels of toxic metabolites or infectious agents such as anthrax, botulinum, cytokines, sarin, hemolysin, venoms, and those included, but not limited to table 5.

In one embodiment the disease or condition is alpha hemolysin poisoning, the receiver is an antibody-like binder to alpha hemolysin or fragment thereof, and the target is alpha hemolysin.

In one embodiment the disease or condition is antrax toxin poisoning, the receiver is an antibody-like binder to anthrax toxin or fragment thereof, and the target is anthrax toxin.

In one embodiment the disease or condition is bacterial toxin-induced shock, the receiver is an antibody-like binder to bacterial toxin or fragment thereof, and the target is bacterial toxin.

In one embodiment the disease or condition is botulinum toxin poisoning, the receiver is an antibody-like binder to botulinum toxin or fragment thereof, and the target is botulinum toxin.

In one embodiment the disease or condition is prion disease caused by PRP, the receiver is an antibody-like binder to prion protein PRP or fragment thereof, and the target is prion protein PRP.

In one embodiment the disease or condition is prion disease caused by PRPc, the receiver is an antibody-like binder to prion protein PRPc or fragment thereof, and the target is prion protein PRPc.

In one embodiment the disease or condition is prion disease caused by PRPsc, the receiver is an antibody-like binder to prion protein PRPsc or fragment thereof, and the target is prion protein PRPsc.

In one embodiment the disease or condition is prion disease cuased by PRPres, the receiver is an antibody-like binder to prion protein PRPres or fragment thereof, and the target is prion protein PRPres.

In one embodiment the disease or condition is sepsis or cytokine storm, the receiver is an antibody-like binder to cytokines or duffy antigen receptor of chemokines (DARC) or fragment thereof, and the target is cytokines.

Wilson's disease is caused by a failure of copper metabolism and a buildup of copper in liver, brain, and other organs. Copper chelators are used clinically, for example D-penicillamine, but they suffer from short half-lives that reduce their therapeutic efficacy. In one embodiment, the receiver on the surface of a synthetic membrane-receiver complex is D-penicillamine. Administration of the synthetic membrane-receiver complex will allow D-penicillamine to remain in circulation for substantially longer than free D-penicillamine, thus capturing copper for a longer period of time and providing a clinical benefit in Wilson's disease.

In one embodiment the disease or condition is spider venom poisoning, the receiver is an antibody-like binder to spider venom or fragment thereof, and the target is spider venom.

1. Toxins

In some embodiment, subjects may be identified as having received or would benefit from receiving treatment for botulinum toxin (BTX) poisoning. Subjects suffering from or at risk of developing BTX poisoning may be administered a pharmaceutical composition comprising the synthetic membrane-receiver polypeptide complex described herein to treat or prevent disease.

In one embodiment, the synthetic membrane-receiver polypeptide complex comprises a receiver comprising an antibody domain or antibody-like domain that binds to BTX of any of the types A-H, or a derivative or functional fragment thereof. A suitable receiver may be exhibited on the surface of the synthetic membrane-receiver polypeptide complex. The suitable receiver is capable of binding to BTX and preventing BTX from carrying out its function.

BTX is produced by *Clostridium botulinum* and is a potent neurotoxin with an estimated human lethal dose of 1.3-2.1 ng/kg intravenously (Arnon et al. 2001 J Am Med Assoc 285(8):1059). BTX is a protease that attacks one of the fusion proteins (SNAP-25, syntaxin or synaptobrevin) at a neuromuscular junction, preventing vesicles from anchoring to the membrane to release acetylcholine. By inhibiting acetylcholine release, the toxin interferes with nerve impulses and causes flaccid (sagging) paralysis of muscles.

2. Prions—Creutzfeldt-Jakob Disease

In some embodiment, subjects may be identified as having received or would benefit from receiving treatment for Creutzfeldt-Jakob Disease (CJD) caused by prion protein in the scrapie form (PrPsc). Subjects suffering from or at risk of developing CJD may be administered a pharmaceutical composition comprising the synthetic membrane-receiver polypeptide complex described herein to treat or prevent disease.

In one embodiment, the synthetic membrane-receiver polypeptide complex comprises a receiver comprising an antibody domain or antibody-like domain that binds to PrPsc or a derivative or functional fragment thereof. A suitable receiver may be exhibited on the surface of the synthetic membrane-receiver polypeptide complex. The suitable receiver is capable of binding to PrPsc and preventing PrPsc from carrying out its function.

PrPsc is a misfolded form of PrP that can induce normal PrP to misfold in an autocatalytic fashion. PrPsc is protease resistant and forms insoluble aggregates and fibrils that damage cells. In CJD, the PrPsc aggregates and fibrils lead to rapid neurodegeneration, causing the brain tissue to develop holes and take on a sponge-like texture.

3. Cytokines

In some embodiment, subjects may be identified as having received or would benefit from receiving treatment for sepsis. Subjects suffering from or at risk of developing sepsis poisoning may be administered a pharmaceutical composition comprising the synthetic membrane-receiver polypeptide complex described herein to treat or prevent disease.

In one embodiment, the synthetic membrane-receiver polypeptide complex comprises one or more receivers comprising an antibody domain, antibody-like domain, or cytokine receptor domain that bind to one or more of the cytokines tumor necrosis factor alpha (TNFa), interferon gamma (IFNg), or interleukin-2 (IL-2) or a derivative or functional fragment thereof. A suitable receiver may be exhibited on the surface of the synthetic membrane-receiver polypeptide complex. The suitable receiver is capable of binding to the cytokine and preventing the cytokine from carrying out its function, e.g., by preventing the cytokine from biding to its native receptor.

Cytokines like TNFa, IFNg, and IL-2 are produced by immune cells in response to infection and are powerful inflammatory stimuli for other immune cells. In sepsis, a serious bacterial infection induces whole-body inflammation driven by a storm of cytokines, which triggers multi-organ failure, acute respiratory distress, heart failure, encephalopathy, and edema.

Diseases and Conditions Associated with the Accumulation of Lipids or Cholesterols In some embodiments, the synthetic membrane-receiver polypeptide complexes described herein may be used to treat or prevent diseases and conditions associated with the accumulation of lipids or cholesterols.

In one embodiment, the receiver interacts with one or more lipids. In one embodiment, the functional erythroid cell expresses a exogenous gene encoding an amino acid sequence derived from a lipase. The lipase may be expressed as a full-length protein or a fragment thereof. The lipase may be expressed as a fusion protein. In other embodiments, the lipase protein receiver or another receiver with affinity to lipids is loaded into or onto the erythroid cell. The lipase protein receiver or the other receiver with affinity to lipids may be localized intracellularly or extracellularly. In one embodiment, the receiver comprises an amino acid sequence derived from lipoprotein lipase.

Hyperlipidemia or hyperlipoproteinemia is an excess of lipids, largely cholesterol and triglycerides, in the blood. Lipids travel in the blood attached to proteins to remain dissolved while in circulation. Hyperlipidemia, in general, can be divided into two subcategories; hypercholesterolemia, in which there is a high level of cholesterol and hypertriglyceridemia, in which there is a high level of triglycerides, the most common form of fat. Excess LDL cholesterol contributes to the blockage of arteries, which eventually leads to heart attack. Population studies have shown that the higher the level of LDL cholesterol, the greater the risk of heart disease.

Hyperlipidemia usually has no noticeable symptoms and tends to be discovered during routine examination or evaluation for atherosclerotic cardiovascular disease. However, deposits of cholesterol (known as xanthomas) may form under the skin (especially around the eyes or along the Achilles tendon) in individuals with familial forms of the disorder or in those with very high levels of cholesterol in the blood. Individuals with hypertriglyceridemia may develop numerous pimple-like lesions across their body. Extremely high levels of triglycerides may also result in pancreatitis, a severe inflammation of the pancreas that may be life-threatening.

In certain embodiments, functional erythroid cells comprise a receiver that is capable of interacting with a lipid, or has affinity to a target lipid or target lipid-associated molecule listed in table 5. In certain embodiments, a population of functional erythroid cells comprising a receiver that is capable of interacting with a lipid or comprising a receiver that comprises an amino acid sequence derived from lipoprotein lipase is administered to a subject in need thereof in an amount effective to treat or prevent hyperlipidernia.

In certain embodiments, a population of functional erythroid cells comprising a receiver that is capable of interacting with a lipid or comprising a receiver that comprises an amino acid sequence derived from lipoprotein lipase is administered to a subject in need thereof in an amount effective to remove chylomicrons, which are lipoprotein particles consisting of lipids, protein, and cholesterol, from the blood circulation. In some embodiments, the receiver is lipoprotein lipase and the receiver is localized on the surface of the erythroid cell. In certain embodiments, a population of functional erythroid cells comprising a receiver that comprises an amino acid sequence derived from lipoprotein lipase is administered to a subject in need thereof in an amount effective to treat, alleviate or prevent lipoprotein lipase deficiency. Familial lipoprotein lipase deficiency is a group of rare genetic disorders in which a person lacks the ability to break down lipids, which causes a large amount of fat to build up in the blood.

In specific embodiments, methods are provided for reducing the circulatory concentration of a target lipid or cholesterol in a subject (e.g., a human) suffering from or at risk of developing a disease or condition associated with the accumulation of lipids or cholesterols. The methods include administering a pharmaceutical composition comprising a synthetic membrane-receiver polypeptide complex described herein. The pharmaceutical composition is administered in an amount effective to substantially reduce the circulatory concentration of the target lipid or cholesterol. In certain embodiments, the administration is carried out intravenously.

In certain embodiments, synthetic membrane-receiver polypeptide complexes are administered that comprise a receiver that specifically binds, sequesters, and/or degrades a target lipid or cholesterol, or a complex or aggregate that comprises a lipid or cholesterol, that is present in the circulatory system of the subject. Reduction in the amount or concentration of circulating lipids or cholesterols and associated complexes therewith may reduce or alleviate cardiovascular and other circulatory problems. Diseases or conditions associated with the accumulation of lipids or cholesterols include, but are not limited to lipoprotein lipase deficiency, hypercholesterolemia, coronary artery disease and those listed in table 6 and table 8.

In one embodiment the disease or condition is hypercholesterolemia, the receiver is an antibody-like binder to low-density lipoprotein (LDL), LDL receptor or fragment thereof, and the target is LDL.

In one embodiment the disease or condition is hypercholesterolemia, the receiver is an antibody-like binder to high-density lipoprotein (HDL) or HDL receptor or fragment thereof, and the target is HDL.

In one embodiment the disease or condition is lipoprotein lipase deficiency, the receiver is lipoprotein lipase or fragment thereof, and the target is chilomicrons and very low density lipoproteins (VLDL).

Lipoprotein Lipase Deficiency (Glybera)

In some embodiment, subjects may be identified as having received or would benefit from receiving treatment for lipoprotein lipase deficiency. Subjects suffering from or at risk of developing lipoprotein lipase deficiency may be administered a pharmaceutical composition comprising the synthetic membrane-receiver polypeptide complex described herein to treat or prevent disease.

In one embodiment, the synthetic membrane-receiver polypeptide complex comprises a receiver comprising the enzyme lipoprotein lipase or a derivative or functional fragment thereof. A suitable receiver may be exhibited on the surface of the synthetic membrane-receiver polypeptide complex. The suitable receiver is capable of hydrolyzing triglycerides in lipoproteins, such as those found in chylomicrons and very low-density lipoproteins (VLDL), into two free fatty acids and one monoacylglycerol molecule.

Lipoprotein lipase deficiency is a rare disorder in which afflicted individuals lack the ability to produce lipoprotein lipase enzymes necessary for effective breakdown of fatty acids. The disorder usually presents in childhood and is characterized by very severe hypertriglyceridemia with episodes of abdominal pain, recurrent acute pancreatitis, eruptive cutaneous xanthomata, and hepatosplenomegaly. Clearance of chylomicrons from the plasma is impaired, causing triglycerides to accumulate in plasma and the plasma to have a milky appearance. Symptoms usually resolve with restriction of total dietary fat to <20 grams/day Diseases and Conditions Associated with Infected, Aberrant or Oncogenic Cells In some embodiments, the synthetic membrane-receiver polypeptide complexes described herein may be used to treat or prevent diseases and conditions associated with infected, aberrant or oncogenic cells, such as, e.g., cancer.

In one embodiment, the receiver interacts with a cancer stem cell (CSC) or another cancer-associated circulatory cell. In one embodiment, the functional erythroid cell expresses a exogenous gene encoding an antibody, scFv or nanobody specific for a CSC antigen. The antibody, scFv or nanobody may be expressed as a fusion protein. In other embodiments, the antibody, scFv or nanobody receiver or another receiver with affinity to circulating cancer cells is loaded into or onto the erythroid cell. In one embodiment, the receiver is an antibody, scFv or nanobody that is localized extracellularly. In certain embodiments, the antibody, scFv or nanobody receiver is specific for a CSC antigen selected from CD44, CD47, and MET.

Cancer stem cells (CSCs), which comprise a small fraction of cancer cells, are believed to constitute the origin of most human tumors. One of the key steps in the metastatic cascade is the migration of tumor cells away from the primary tumor, and CSCs are likely associated with this migration. Most adult tissues maintain some aspect of migratory capacity through the ability to generate an epithelial to mesenchymal transition (EMT)-like process during wound healing, tissue regeneration and organ fibrosis. It has been hypothesized that CSCs may also activate their migration through the process of EMT.

A number of studies have linked circulating tumor cells (CTCs) to tumor progression in a variety of solid tumors, and CTC enumeration has begun to be utilized as a prognostic tool in patients with metastatic breast (Cristofanilli et al., 2004), colon (Cohen et al., 2008) and prostate cancer (Danila et al., 2007). Potentially, a fraction of CTCs have CSC activity, and it is hypothesized that CSCs in a primary tumor which enter the circulation become circulating CSCs and remain so until they lodge or home to a target organ. CTCs isolated from patients with melanomas have been found to generate metastases in xenotransplantation models (Ma et al., 2010, Shiozawa, Pharm and Thera, 2013).

The vasculature is a powerful conduit for the proliferation of various circulating tumor cells, metastases, and cancer stem cells. In certain embodiments, functional erythroid cells comprising a receiver specific for circulating cancer cells are administered to a subject in need thereof in an amount effective to treat or prevent metastases. In certain embodiments, populations of functional erythroid cells comprising a receiver specific for circulating cancer cells are administered to a subject in need thereof in an amount effective to interact with CSCs or CTCs to clear them from circulation, e.g., by facilitating degradation in the liver. In some embodiments, functional erythroid cells comprise an antibody, scFv, or nanobody receiver specific for CD44, CD47, or MET (three characteristic surface antigens of CTC). Suitable cancer cells that may be cleared by the erythroid cells described herein include, but are not limited to, cells associated with the cancers listed in table 5 and table 8.

In specific embodiments, methods are provided for reducing the circulatory concentration of a target cell in a subject (e.g., a human) suffering from or at risk of developing a disease or condition associated with an infected, aberrant or oncogenic cell. The methods include administering a pharmaceutical composition comprising a synthetic membrane-receiver polypeptide complex described herein. The pharmaceutical composition is administered in an amount effective to substantially reduce the circulatory concentration of the target cell. In certain embodiments, the administration is carried out intravenously.

In certain embodiments, synthetic membrane-receiver polypeptide complexes are administered that comprise a receiver that specifically binds, sequesters, and/or degrades a target cell, such as an infected, aberrant or oncogenic cell that is present in the circulatory system of the subject. Reduction in the amount or concentration of circulating target cells may reduce or alleviate conditions associated with the infected, aberrant or oncogenic cell, such as, e.g., an infection or cancer. Diseases or conditions associated with infected, aberrant or oncogenic cells include, but are not limited to cancer and those listed in table 6 and table 8.

In one embodiment the disease or condition is cancer, the receiver is an antibody-like binder to CD44 or fragment thereof, and the target is a circulating tumor cell.

In one embodiment the disease or condition is cancer, the receiver is an antibody-like binder to EpCam or fragment thereof, and the target is a circulating tumor cell.

In one embodiment the disease or condition is cancer, the receiver is an antibody-like binder to Her2 or fragment thereof, and the target is a circulating tumor cell.

In one embodiment the disease or condition is cancer, the receiver is an antibody-like binder to EGFR or fragment thereof, and the target is a circulating tumor cell.

In one embodiment the disease or condition is cancer (B cell), the receiver is an antibody-like binder to CD20 or fragment thereof, and the target is a cancerous B cell.

In one embodiment the disease or condition is cancer (B cell), the receiver is an antibody-like binder to CD19 or fragment thereof, and the target is a cancerous B cell.

Circulating Cancer Cell

In some embodiment, subjects may be identified as having received or would benefit from receiving treatment for cancer. Subjects suffering from or at risk of developing cancer may be administered a pharmaceutical composition comprising the synthetic membrane-receiver polypeptide complex described herein to treat or prevent disease.

In one embodiment, the synthetic membrane-receiver polypeptide complex comprises a receiver comprising an antibody domain or antibody-like domain that binds to a circulating cancer cell, e.g., a proliferative B cell, via a cancer cell specific receptor, e.g., CD19, or a derivative or functional fragment thereof. A suitable receiver may be exhibited on the surface of the synthetic membrane-receiver polypeptide complex. The suitable receiver is capable of binding to CD19 on the circulating cancer cell and promoting the clearance of the CD19-expressing cancer cell.

CD19 is a common receptor to B cells, and is a validated marker for B cell cancers including B cell leukemias and lymphomas (Scheuermann and Racila, (1995) Leukemia and Lymphoma 18 (5): 385-397. It is increasingly understood to play an additional role in the proliferation of B cells in cancer by stabilizing the Myc oncoprotein (Chung et al. 2012, J Clin Invest 122(6):2257). In B cell cancers, proliferative B cells overwhelm lymph nodes and bone marrow. Strategies to target and clear these B cells, including antibody therapy (Rituximab), are accepted as part of the standard of care.

Tumor metastasis is the main driver of cancer mortality and therapies targeting metastasis are limited in number, mechanism of action and efficacy. Hematogenous tumor cell spreading (via bloodstream) is a common route for many carcinomas and is a highly complex process involving primary site detachment, migration, transport into the bloodstream, tumor cell adhesion in the vasculature and proliferation at the metastatic site.

Diseases and Conditions Associated with a Metabolic Defect

In some embodiments, the synthetic membrane-receiver polypeptide complexes described herein may be used to treat or prevent diseases and conditions associated with a metabolic defect. A schematic example of a synthetic membrane-receiver polypeptide complex is shown in FIG. 13A.

As described herein, many small molecule metabolites can diffuse across the membrane of, e.g., erythroid cells comprising a suitable receiver, or are actively transported by defined transmembrane channels (see, e.g., Tunnicliff, Comp. Biochem. Physiol. 1994). Some metabolites, however, may require additional assistance to reach the intracellularly localized receiver enzyme, thus the synthetic membrane-receiver complex may optionally comprise a transporter.

In one embodiment, the surface exposed receiver polypepdide may shuttle the substrate across the cell membrane into the synthetic membrane-receiver complex, e.g., an erythroid cell comprising a receiver. The functional erythroid cell comprising a receiver may contain multiple receiver polypeptides, including, but not limited to, the receiver polypeptides listed in Table 7. The receiver polypeptides may increase the cell's capabilities to transport metabolites or other substrates across the membrane. For example, a Glut1 transporter may be contained in the functional erythroid cell's membrane in combination with an intracellularly expressed receiver glucokinase, such that the erythroid cell internalizes and phosphorylates an amount of glucose greater than that of a non-modified erythroid cell. Erythroid cells comprising a receiver glucokinase may be used to reduce blood glucose levels. Diabetes mellitus type II is associated with hyperglycemia as a result of insulin resistance and relative lack of insulin. The hyperglycemia may be alleviated by erythroid cells comprising a receiver glucokinase that capture glucose through surface-localized, receiver Glut1 and phosphorylation by an intracellularly localized, receiver glucokinase. Modified glucose may be unable to exit the cell. The synthetic membrane-receiver complex acts as a "buffer" to respond to hyperglycemic conditions.

Optionally, a second receiver polypeptide may be present in the functional erythroid cell that exhibits increase transport capabilities. The second receiver polypeptide may be localized intracellularly. The second intracellularly localized receiver polypeptide can enzymatically modify, convert, change or otherwise alter the taget substrate that was shuttled into the cell by the first receiver polypeptide localized on the cell surface.

In specific embodiments, methods are provided for modulating the circulatory concentration of a target metabolite in a subject (e.g., a human) suffering from or at risk of developing a disease or condition associated with a metabolic defect. The methods include administering a pharmaceutical composition comprising a synthetic membrane-receiver polypeptide complex described herein. The pharmaceutical composition is administered in an amount effective to substantially modulate the circulatory concentration of the target metabolite. In some embodiments, the target metabolite is present or present in elevated levels in circulation and the amount or concentration of the target metabolite is reduced. For example if the level or concentration of a metabolite is toxic, the toxic target metabolite may be degraded or the toxic target metabolite may be converted into another non-toxic product (e.g., by catalytic action of the receiver). In some embodiments, a non-target metabolite is absent or present in depressed levels in circulation and a target metabolite is converted to the non-target metabolite so that its level or concentration is increased. In such embodiments, the absence of depressed levels of the non-target metabolite is associated with the metabolic disease or disorder and conversion of the target metabolite to the non-target metabolite can at least partially restore or replenish the level or concentration of the non-target metabolite, thereby treating or preventing the metabolic disease. In certain embodiments, the administration is carried out intravenously. Diseases or conditions associated with a metabolic defect include, but are not limited to mitochondrial neurogastrointestinal encephalomyopathy (MNGIE), adenosine deaminase (ADA) deficiency, purine nucleoside phosphorylase (PNP) deficiency, phenylketonuria, alkaptonuria, homocystinuria, primary hyperoxaluria and those listed in table 6 and table 8.

In specific embodiments, methods of treating a metabolic disease include administering to a subject in need thereof a pharmaceutical composition of erythrocyte cells comprising a receiver provided herein in an amount sufficient to treat the metabolic disease. The compositions may be administered to subjects that exhibit disorders of carbohydrate metabolism, amino acid metabolism, organic acid metabolism, mitochondrial metabolism, fatty acid metabolism, purine-pyrimidine metabolism, steroid metabolism, peroxisomal function, lysosomal storage, or urea cycle. Of these disorders, specific indications include ADA-SCID, primary hyperoxaluria, and phenylketonuria, as well as, but not limited to, the conditions listed in table 6 and table 8.

In one embodiment the disease or condition is 3-methyl-crotonyl-CoA carboxylase deficiency, the receiver is 3-methylcrotonyl-CoA carboxylase or fragment thereof, and the target is 3-hydroxyvalerylcarnitine, 3-methylcrotonyl-glycine (3-MCG) and 3-hydroxyisovaleric acid (3-HIVA).

In one embodiment the disease or condition is acute intermittent porphyria, the receiver is porphobilinogen deaminase or fragment thereof, and the target is porphobilinogen.

In one embodiment the disease or condition is adenine phosphoribosyltransferase deficiency, the receiver is adenine phosphoribosyltransferase or fragment thereof, and the target is insoluble purine 2,8-dihydroxyadenine.

In one embodiment the disease or condition is adenosine deaminase deficiency, the receiver is adenosine deaminase or fragment thereof, and the target is adenosine.

In one embodiment the disease or condition is alkaptonuria, the receiver is homogentisate oxidase or fragment thereof, and the target is homogentisate.

In one embodiment the disease or condition is argininemia, the receiver is ammonia monooxygenase or fragment thereof, and the target is ammonia.

In one embodiment the disease or condition is argininosuccinate aciduria, the receiver is ammonia monooxygenase or fragment thereof, and the target is ammonia.

In one embodiment the disease or condition is citrullinemia type I, the receiver is ammonia monooxygenase or fragment thereof, and the target is ammonia.

In one embodiment the disease or condition is citrullinemia type II, the receiver is ammonia monooxygenase or fragment thereof, and the target is ammonia.

In one embodiment the disease or condition is glutaric acidemia type I, the receiver is lysine oxidase or fragment thereof, and the target is 3-hydroxyglutaric and glutaric acid (C5-DC) amd lysine.

In one embodiment the disease or condition is gout with hyperuricemia, the receiver is uricase or fragment thereof, and the target is uric acid (urate crystals).

In one embodiment the disease or condition is hemolytic anemia due to pyrimidine 5' nucleotidase deficiency, the receiver is pyrimidine 5' nucleotidase or fragment thereof, and the target is pyrimidines.

In one embodiment the disease or condition is homocystinuria, the receiver is Cystathionine B synthase or fragment thereof, and the target is homocysteine.

In one embodiment the disease or condition is hyperammonemia/ornithinemia/citrullinemia (ornithine transporter defect), the receiver is ammonia monooxygenase or fragment thereof, and the target is ammonia.

In one embodiment the disease or condition is isovaleric acidemia, the receiver is leucine metabolizing enzyme or fragment thereof, and the target is leucine.

In one embodiment the disease or condition is Lesch-Nyhan syndrome, the receiver is uricase or fragment thereof, and the target is uric acid.

In one embodiment the disease or condition is maple syrup urine disease, the receiver is a leucine metabolizing enzyme or fragment thereof, and the target is leucine.

In one embodiment the disease or condition is methylmalonic acidemia (vitamin b12 non-responsive), the receiver is methylmalonyl-CoA mutase or fragment thereof, and the target is methylmalonate.

In one embodiment the disease or condition is mitochondrial neurogastrointestinal encephalomyopathy (MNGIE), the receiver is thymidine phosphorylase or fragment thereof, and the target is thymidine.

In one embodiment the disease or condition is phenylketonuria, the receiver is phenylalanine hydroxylase, phenylalanine ammonia lyase or fragment thereof, and the target is phenylalanine.

In one embodiment the disease or condition is primary hyperoxaluria, the receiver is oxalate oxidase or fragment thereof, and the target is oxalate.

In one embodiment the disease or condition is propionic acidemia, the receiver is a propionate convertase or fragment thereof, and the target is proprionyl coA.

In one embodiment the disease or condition is purine nucleoside phosphorylase deficiency, the receiver is purine nucleoside phosphorylase or fragment thereof, and the target is Inosine and/or dGTP.

In one embodiment the disease or condition is transferase deficient galactosemia (galactosemia type 1), the receiver is galactose dehydrogenase or fragment thereof, and the target is galactose-1-phosphate.

In one embodiment the disease or condition is tyrosinemia type 1, the receiver is tyrosine phenol-lyase or fragment thereof, and the target is tyrosine.

1. Adenosine Deaminase (ADA) Deficiency

In some embodiments, subjects may be identified as having received or would benefit from receiving treatment for adenosine deaminase (ADA) deficiency. Subjects suffering from or at risk of developing ADA deficiency may be administered a pharmaceutical composition comprising the synthetic membrane-receiver polypeptide complex described herein to treat or prevent disease.

In one embodiment, the synthetic membrane-receiver polypeptide complex comprises a receiver comprising adenosine deaminase (ADA) or a derivative or functional fragment thereof. A suitable receiver may be exhibited on the surface or on the unexposed side of the synthetic membrane-receiver polypeptide complex and may be administered to convert deoxy-adenosine to deoxy-inosine, thereby preventing the build-up of toxic deoxy-adenosine levels.

In certain embodiments, compositions comprising a plurality of functional erythroid cells comprising an adenosine deaminase (ADA) receiver are provided. Such compositions may be used to treat subjects that exhibit ADA-severe combined immunodeficiency (SCID).

Subjects that exhibit an ADA-deficiency are experiencing a build-up of deoxy-adenosine in the body's tissues. The high deoxy-adenosine levels are toxic to immature leukocytes. As a consequence, the subject's adaptive immune response is impaired, which makes them highly susceptible to infection. ADA is an endogenous enzyme produced by a wide variety of cells, including erythrocytes. ADA is responsible for converting deoxy-adenosine to deoxy-inosine, thereby preventing the build-up of toxic deoxy-adenosine levels. Available enzyme replacement therapies source ADA from bovine intestine. The foreign-sourced ADA is subject to immunogenic reactions and inhibitor development. Inhibitor development may occur when a subject's immune system develops the ability to clear and/or alter a therapeutic molecule such that its therapeutic effect is decreased. In addition, the emergence of new variant Creutzfeldt-Jakob disease has raised concerns about sourcing ADA from bovine intestine (Booth 2009, Biologics: Targets and Therapy).

In certain embodiments, provided herein are compositions comprising a plurality of functional erythroid cells comprising an adenosine deaminase (ADA) receiver which may be administered to ADA-SCID subjects to elevate the level of ADA over that of the endogenous levels of existing wild type cells in the ADA-SCID subject. Most ADA-SCID subjects severely lack a functioning deoxy-adenosine metabolism. The erythroid cells may contain exogenous ADA within their intracellular space. The intracellularly localized exogenous ADA receiver polypeptide may then convert deoxy-adenosine to deoxy-inosine, thereby lowering the levels of deoxy-adenosine. Deoxy-adenosine crosses the cell membrane, is converted to deoxy-inosine, and diffuses back into circulation. This may be sufficient to preserve immature leukocyte populations, thereby treating the disease. In some embodiments, the adenosine deaminase receiver is expressed as a fusion to the C terminus of hemoglobin beta such that the ADA is retained in the functional erythroid cell during enucleation. Alternatively, the ADA gene is fused to the part of the gene encoding the C terminus of glycophorin A such that upon expression it is tethered to the intracellular portion of the transmembrane antigen.

2. Phenylketonuria (PKU)

In some embodiments, subjects may be identified as having received or would benefit from receiving treatment for phenylketonuria (PKU). Subjects suffering from or at risk of developing PKU may be administered a pharmaceutical composition comprising the synthetic membrane-receiver polypeptide complex described herein to treat or prevent disease.

In one embodiment, the synthetic membrane-receiver polypeptide complex comprises a receiver comprising phenylalanine ammonia lyase (PAL) or a derivative or functional fragment thereof.

In another embodiment, the synthetic membrane-receiver polypeptide complex comprises a receiver comprising phenylalanine hydroxylase (PAH) or a derivative or functional fragment thereof.

A suitable receiver may be exhibited on the surface or on the unexposed side of the synthetic membrane-receiver polypeptide complex and may be administered to convert phenylalanine to tyrosine, thereby preventing the build-up of toxic phenylalanine levels to treat or prevent PKU.

In specific embodiments, compositions comprising a plurality of functional erythroid cells comprising a phenylalanine ammonia lyase (PAL) receiver are provided. Such compositions may be used to treat subjects that exhibit or are diagnosed with phenylketonuria (PKU).

Subjects diagnosed with PKU are deficient in phenylalanine ammonia hydroxylase (PAH) activity due to an enzyme mutation or production deficiency. PAH, along with its cofactor tetrahydrobiopterin, is responsible for converting phenylalanine to tyrosine. PAH deficiency leads to phenylalanine accumulation and is associated with several neurological disorders.

PAL is an enzyme isolated from plants, yeast, and fungi *chrysanthemi*. PAL is a large, 270 kDa enzyme that can elicit a strong immunogenic reaction. It is also quickly cleared from the body, therefore requiring large, frequent infusions. Even in its pegylated form, PAL only remains in circulation for approximately three days. The short half-life makes PAL treatment difficult for patients to adhere to (Gamez, Molecular Therapy 2005).

In certain embodiments, provided herein are compositions comprising a plurality of functional erythroid cells comprising a phenylalanine ammonia lyase (PAL) receiver, which may be administered to phenylketonuria (PKU) subjects to treat phenylalanine accumulation. The functional erythroid cells may contain exogenous PAL within their intracellular space. The intracellularly localized exogenous PAL polypeptide may then convert phenylalanine to trans-cinnamic acid, a benign metabolite, thereby lowering the levels of phenylalanine. Phenylalanine crosses the cell membrane, is converted to trans-cinnamic acid, and diffuses back into circulation. This may be sufficient to reduce phenylalanine concentrations in the blood.

In specific embodiments, compositions comprising a plurality of functional erythroid cells comprising a phenylalanine hydroxylase (PAH) receiver are provided. Such compositions may be used to treat subjects that exhibit or are diagnosed with phenylketonuria (PKU). PAH is an enzyme that can be isolated from bacteria or mammals. PAH from *Chromobacterium violaceum* is a monomeric ~30 kDa protein (Yew et al. 2013 Mol Gen Metab 109:339).

In certain embodiments, provided herein are compositions comprising a plurality of functional erythroid cells comprising a phenylalanine hydroxylase (PAH) receiver, which may be administered to phenylketonuria (PKU) subjects to treat phenylalanine accumulation. The functional erythroid cells may contain exogenous PAH within their intracellular space. The intracellularly localized exogenous PAH polypeptide may then convert phenylalanine to tyrosine, thereby lowering the levels of phenylalanine. Phenylalanine crosses the cell membrane, is converted to tyrosine, which diffuses back into circulation. This may be sufficient to reduce phenylalanine concentrations in the blood.

3. MNGIE

In some embodiment, subjects may be identified as having received or would benefit from receiving treatment for Mitochondrial Neurogastrointestinal Encephalopathy (MNGIE). Subjects suffering from or at risk of developing MNGIE may be administered a pharmaceutical composition comprising the synthetic membrane-receiver polypeptide complex described herein to treat or prevent disease.

In one embodiment, the synthetic membrane-receiver polypeptide complex comprises a receiver comprising the enzyme thymidine phosphorylase (TP) or a derivative or functional fragment thereof. A suitable receiver may be exhibited on the surface of the synthetic membrane-receiver polypeptide complex. A suitable receiver may be contained in the interior of the synthetic membrane-receiver polypeptide complex. The suitable receiver is capable of catalyzing the phosphorylation of thymidine or deoxyuridine to thymine or uracil.

In MNGIE, aberrant thymidine metabolism leads to impaired replication or maintenance of mtDNA, causing mtDNA depletion, deletion, or both (Nishino et al. 1999 Science 283:689). The disease is characterized by progressive gastrointestinal dysmotility and cachexia manifesting as early satiety, nausea, dysphagia, gastroesophageal reflux, postprandial emesis, episodic abdominal pain and/or distention, and diarrhea; ptosis/ophthalmoplegia or ophthalmoparesis; hearing loss; and demyelinating peripheral neuropathy manifesting as paresthesias (tingling, numbness, and pain)

and symmetric and distal weakness more prominently affecting the lower extremities. There is no treatment for MNGIE. Management is supportive and includes attention to swallowing difficulties and airway protection; domperidone for nausea and vomiting; celiac plexus block with bupivicaine to reduce pain; bolus feedings, gastrostomy, and parenteral feeding for nutritional support; antibiotics for intestinal bacterial overgrowth; morphine, amitriptyline, gabapentin, and phenytoin for neuropathic symptoms; specialized schooling arrangements; and physical and occupational therapy.

4. Lysosomal Enzyme Deficiency

The synthetic complexes described herein can be useful for the treatment of Lysosomal storage disorders. In one embodiment a synthetic membrane-receiver polypeptide complex comprises a receiver, e.g., an enzyme that is active in cell lysosomes and can degrade accumulated toxic compounds, e.g., proteins, polypeptides, carbohydrates, or lipids, in lysosomes of cells with a deficiency in a lysosomal enzyme. The receiver will act by reducing the amount of toxic compound accumulated in the lysosomes of these cells, thus reducing the burden of the disease. Lysosomal storage disorders include, but are not limited to, mucopolysaccharidosis I, Gaucher Disease, Fabry Disease, Pompe Disease and those listed in table 6 and table 8.

In one embodiment, subjects may be identified as having received or would benefit from receiving treatment for Gaucher's disease. Subjects suffering from or at risk of developing Gaucher's disease may be administered a pharmaceutical composition comprising the synthetic membrane-receiver polypeptide complex described herein to treat or prevent disease.

In one embodiment, the synthetic membrane-receiver polypeptide complex comprises a receiver comprising the enzyme glucocerebrosidase or a derivative or functional fragment thereof. A suitable receiver may be exhibited on the surface of the synthetic membrane-receiver polypeptide complex or in the interior of the synthetic membrane-receiver polypeptide complex. The suitable receiver is capable of cleaving by hydrolysis the beta-glucosidic linkage of the chemical glucocerebroside, a sphingolipid.

Gaucher's disease is caused by a hereditary deficiency of the enzyme glucocerebrosidase. When the enzyme is defective, glucocerebroside accumulates in white blood cells, spleen, liver, kidneys, lungs, brain, and bone marrow. The disorder is characterized by bruising, fatigue, anemia, low blood platelets, and enlargement of the liver and spleen. Manifestations may include enlarged spleen and liver, liver malfunction, skeletal disorders and bone lesions that may be painful, severe neurologic complications, swelling of lymph nodes and (occasionally) adjacent joints, distended abdomen, a brownish tint to the skin, anemia, low blood platelets, and yellow fatty deposits on the white of the eye (sclera). Persons affected most seriously may also be more susceptible to infection.

Several lysosomal storage disorders are addressable by methods of treatment described herein. For example: In one embodiment the disease or condition is aspartylglucosaminuria (208400), the receiver is N-aspartylglucosaminidase or fragment thereof, and the target is glycoproteins. In one embodiment the disease or condition is cerebrotendinous xanthomatosis (cholestanol lipidosis; 213700), the receiver is sterol 27-hydroxylase or fragment thereof, and the target is lipids, cholesterol, and bile acid. In one embodiment the disease or condition is ceroid lipofuscinosis adult form (CLN4, Kufs' disease; 204300), the receiver is palmitoyl-protein thioesterase-1 or fragment thereof, and the target is lipopigments. In one embodiment the disease or condition is ceroid lipofuscinosis infantile form (CLN1, Santavuori-Haltia disease; 256730), the receiver is palmitoyl-protein thioesterase-1 or fragment thereof, and the target is lipopigments. In one embodiment the disease or condition is ceroid lipofuscinosis juvenile form (CLN3, Batten disease, Vogt-Spielmeyer disease; 204200), the receiver is lysosomal transmembrane CLN3 protein or fragment thereof, and the target is lipopigments. In one embodiment the disease or condition is ceroid lipofuscinosis late infantile form (CLN2, Jansky-Bielschowsky disease; 204500), the receiver is lysosomal pepstatin-insensitive peptidase or fragment thereof, and the target is lipopigments. In one embodiment the disease or condition is ceroid lipofuscinosis progressive epilepsy with intellectual disability (600143), the receiver is transmembrane CLN8 protein or fragment thereof, and the target is lipopigments. In one embodiment the disease or condition is ceroid lipofuscinosis variant late infantile form (CLN6; 601780), the receiver is transmembrane CLN6 protein or fragment thereof, and the target is lipopigments. In one embodiment the disease or condition is ceroid lipofuscinosis variant late infantile form, Finnish type (CLN5; 256731), the receiver is lysosomal transmembrane CLN5 protein or fragment thereof, and the target is lipopigments. In one embodiment the disease or condition is cholesteryl ester storage disease (CESD), the receiver is lisosomal acid lipase or fragment thereof, and the target is lipids and cholesterol. In one embodiment the disease or condition is congenital disorders of N-glycosylation CDG Ia (solely neurologic and neurologic-multivisceral forms; 212065), the receiver is phosphomannomutase-2 or fragment thereof, and the target is N-glycosylated protein. In one embodiment the disease or condition is congenital disorders of N-glycosylation CDG Ib (602579), the receiver is mannose (Man) phosphate (P) isomerase or fragment thereof, and the target is N-glycosylated protein. In one embodiment the disease or condition is congenital disorders of N-glycosylation CDG Ic (603147), the receiver is dolicho-P-Glc:Man9GlcNAc2-PP-dolichol glucosyltransferase or fragment thereof, and the target is N-glycosylated protein. In one embodiment the disease or condition is congenital disorders of N-glycosylation CDG Id (601110), the receiver is dolicho-P-Man:Man5GlcNAc2-PP-dolichol mannosyltransferase or fragment thereof, and the target is N-glycosylated protein. In one embodiment the disease or condition is congenital disorders of N-glycosylation CDG Ie (608799), the receiver is dolichol-P-mannose synthase or fragment thereof, and the target is N-glycosylated protein. In one embodiment the disease or condition is congenital disorders of N-glycosylation CDG If (609180), the receiver is protein involved in mannose-P-dolichol utilization or fragment thereof, and the target is N-glycosylated protein. In one embodiment the disease or condition is congenital disorders of N-glycosylation CDG Ig (607143), the receiver is dolichyl-P-mannose:Man-7-GlcNAc-2-PP-dolichyl-α-6-mannosyltransferase or fragment thereof, and the target is N-glycosylated protein. In one embodiment the disease or condition is congenital disorders of N-glycosylation CDG Ih (608104), the receiver is dolichyl-P-glucose:Glc-1-Man-9-GlcNAc-2-PP-dolichyl-α-3-glucosyltransferase or fragment thereof, and the target is N-glycosylated protein. In one embodiment the disease or condition is congenital disorders of N-glycosylation CDG Ii (607906), the receiver is α-1,3-Mannosyltransferase or fragment thereof, and the target is N-glycosylated protein. In one embodiment the disease or condition is congenital disorders of N-glycosylation CDG IIa (212066), the receiver is mannosyl-α-1,6-glycoprotein-β-1,2-N-acetylglucosminyltransferase or fragment thereof, and the target is N-glycosylated protein. In one embodiment the disease or condition is congenital disorders of N-glycosylation CDG IIb (606056), the receiver is glucosidase I or fragment thereof, and the target is N-glycosylated protein. In one embodiment the disease or condition is congenital disorders of N-glycosylation CDG IIc (Rambam-Hasharon syndrome; 266265, the receiver is GDP-fucose transporter-1 or fragment thereof, and the target is N-glycosylated protein. In one embodiment the disease or condition is congenital disorders of N-glycosylation CDG IId (607091), the receiver is β-1,4-galactosyltransferase or fragment thereof, and the target is N-glycosylated protein. In one embodiment the disease or condition is congenital disorders of N-glycosylation CDG IIe (608779), the receiver is oligomeric golgi complex-7 or fragment thereof, and the target is N-glycosylated protein. In one embodiment the disease or condition is congenital disorders of N-glycosylation CDG Ij (608093), the receiver is UDP-GlcNAc:dolichyl-P NAcGlc phosphotransferase or fragment thereof, and the target is N-glycosylated protein. In one embodiment the disease or condition is congenital disorders of N-glycosylation CDG Ik (608540), the receiver is β-1,4-mannosyltransferase or fragment thereof, and the target is N-glycosylated protein. In one embodiment the disease or condition is congenital disorders of N-glycosylation CDG Il (608776), the receiver is α-1,2-mannosyltransferase or fragment thereof, and the target is N-glycosylated protein. In one embodiment the disease or condition is congenital disorders of N-glycosylation, type I (pre-Golgi glycosylation defects), the receiver is α-1,2-mannosyltransferase or fragment thereof, and the target is N-glycosylated protein. In one embodiment the disease or condition is cystinosis, the receiver is cystinosin (lysosomal cystine transporter) or fragment thereof, and the target is cysteine. In one embodiment the disease or condition is Fabry's disease (301500), the receiver is trihexosylceramide a-galactosidase or fragment thereof, and the target is globotriaosylceramide. In one embodiment the disease or condition is Farber's disease (lipogranulomatosis; 228000), the receiver is ceramidase or fragment thereof, and the target is lipids. In one embodiment the disease or condition is Fucosidosis (230000), the receiver is α-L-fucosidase or fragment thereof, and the target is fucose and complex sugars. In one embodiment the disease or condition is galactosialidosis (Goldberg's syndrome, combined neuraminidase and β-galactosidase deficiency; 256540), the receiver is protective protein/cathepsin A (PPCA) or fragment thereof, and the target is lipids and glycoproteins. In one embodiment the disease or condition is Gaucher's disease, the receiver is glucosylceramide β-glucosidase or fragment thereof, and the target is sphingolipids. In one embodiment the disease or condition is glutamyl ribose-5-phosphate storage disease (305920), the receiver is ADP-ribose protein hydrolase or fragment thereof, and the target is glutamyl ribose 5-phosphate. In one embodiment the disease or condition is glycogen storage disease type 2 (Pompe's disease), the receiver is alpha glucosidase or fragment thereof, and the target is glycogen. In one embodiment the disease or condition is GM1 gangliosidosis, generalized, the receiver is ganglioside β-galactosidase or fragment thereof, and the target is acidic lipid material, gangliosides. In one embodiment the disease or condition is GM2 activator protein deficiency (Tay-Sachs disease AB variant, GM2A; 272750), the receiver is GM2 activator protein or fragment thereof, and the target is gangliosides. In one embodiment the disease or condition is GM2 gangliosidosis, the receiver is Ganglioside β-galactosidase or fragment thereof, and the target is gangliosides. In one embodiment the disease or condition is infantile sialic acid storage disorder (269920), the receiver is Na phosphate cotransporter, sialin or fragment thereof, and the target is sialic acid. In one embodiment the disease or condition is Krabbe's disease (245200), the receiver is galactosylceramide β-galactosidase or fragment thereof, and the target is sphingolipids. In one embodiment the disease or condition is lysosomal acid lipase deficiency (278000), the receiver is lysosomal acid lipase or fragment thereof, and the target is cholesteryl esters and triglycerides. In one embodiment the disease or condition is metachromatic leukodystrophy (250100), the receiver is arylsulfatase A or fragment thereof, and the target is sulfatides. In one embodiment the disease or condition is mucolipidosis ML II (I-cell disease; 252500), the receiver is N-Acetylglucosaminyl-1-phosphotransfeerase catalytic subunit or fragment thereof, and the target is N-linked glycoproteins. In one embodiment the disease or condition is mucolipidosis ML III (pseudo-Hurler's polydystrophy), the receiver is N-acetylglucosaminyl-1-phosphotransfeerase or fragment thereof, and the target is N-linked glycoproteins. In one embodiment the disease or condition is mucolipidosis ML III (pseudo-Hurler's polydystrophy) Type III-A (252600), the receiver is catalytic subunit or fragment thereof, and the target is N-linked glycoproteins. In one embodiment the disease or condition is mucolipidosis ML III (pseudo-Hurler's polydystrophy) Type III-C(252605), the receiver is substrate-recognition subunit or fragment thereof, and the target is N-linked glycoproteins. In one embodiment the disease or condition is mucopolysaccharidosis MPS I H/S (Hurler-Scheie syndrome; 607015), the receiver is α-1-iduronidase or fragment thereof, and the target is glycosaminoglycans. In one embodiment the disease or condition is mucopolysaccharidosis MPS I-H (Hurler's syndrome; 607014), the receiver is α-1-iduronidase or fragment thereof, and the target is glycosaminoglycans. In one embodiment the disease or condition is mucopolysaccharidosis MPS II (Hunter's syndrome; 309900), the receiver is iduronate sulfate sulfatase or fragment thereof, and the target is glycosaminoglycans. In one embodiment the disease or condition is mucopolysaccharidosis MPS III (Sanfilippo's syndrome) Type III-A (252900), the receiver is Heparan-S-sulfate sulfamidase or fragment thereof, and the target is glycosaminoglycans. In one embodiment the disease or condition is mucopolysaccharidosis MPS III (Sanfilippo's syndrome) Type III-B (252920), the receiver is N-acetyl-D-glucosaminidase or fragment thereof, and the target is glycosaminoglycans. In one embodiment the disease or condition is mucopolysaccharidosis MPS III (Sanfilippo's syndrome) Type III-C (252930), the receiver is acetyl-CoA-glucosaminide N-acetyltransferase or fragment thereof, and the target is glycosaminoglycans. In one embodiment the disease or condition is mucopolysaccharidosis MPS III (Sanfilippo's syndrome) Type III-D (252940), the receiver is N-acetyl-glucosamine-6-sulfate sulfatase or fragment thereof, and the target is glycosaminoglycans. In one embodiment the disease or condition is mucopolysaccharidosis MPS I-S(Scheie's syndrome; 607016), the receiver is α-1-iduronidase or fragment thereof, and the target is glycosaminoglycans. In one embodiment the disease or condition is mucopolysaccharidosis MPS IV (Morquio's syndrome) Type IV-A (253000), the receiver is galactosamine-6-sulfate sulfatase or fragment thereof, and the target is glycosaminoglycans. In one embodiment the disease or condition is mucopolysaccharidosis MPS IV (Morquio's syndrome) Type IV-B (253010), the receiver is β-galactosidase or fragment thereof, and the target is glycosaminoglycans. In one embodiment the disease or condition is mucopolysaccharidosis MPS IX (hyaluronidase deficiency; 601492), the receiver is hyaluronidase or fragment thereof, and the target is glycosaminoglycans. In one embodiment the disease or condition is mucopolysaccharidosis MPS VI (Maroteaux-Lamy syndrome; 253200), the receiver is N-acetyl galactosamine α-4-sulfate sulfatase (arylsulfatase B) or fragment thereof, and the target is glycosaminoglycans. In one embodiment the disease or condition is mucopolysaccharidosis MPS VII (Sly's syndrome; 253220), the receiver is β-glucuronidase or fragment thereof, and the target is glycosaminoglycans. In one embodiment the disease or condition is mucosulfatidosis (multiple sulfatase deficiency; 272200), the receiver is sulfatase-modifying factor-1 or fragment thereof, and the target is sulfatides. In one embodiment the disease or condition is Niemann-Pick disease type A, the receiver is sphingomyelinase or fragment thereof, and the target is sphingomyelin. In one embodiment the disease or condition is Niemann-Pick disease type B, the receiver is sphingomyelinase or fragment thereof, and the target is sphingomyelin. In one embodiment the disease or condition is Niemann-Pick disease Type C1/Type D (257220), the receiver is NPC1 protein or fragment thereof, and the target is sphingomyelin. In one embodiment the disease or condition is Niemann-Pick disease Type C2 (607625), the receiver is epididymal secretory protein 1 (HE1; NPC2 protein) or fragment thereof, and the target is sphingomyelin. In one embodiment the disease or condition is prosaposin deficiency (176801), the receiver is prosaposin or fragment thereof, and the target is sphingolipids. In one embodiment the disease or condition is pycnodysostosis (265800), the receiver is cathepsin K or fragment thereof, and the target is kinins. In one embodiment the disease or condition is sandhoffs disease; 268800, the receiver is β-hexosaminidase B or fragment thereof, and the target is gangliosides. In one embodiment the disease or condition is saposin B deficiency (sulfatide activator deficiency), the receiver is saposin B or fragment thereof, and the target is sphingolipids. In one embodiment the disease or condition is saposin C deficiency (Gaucher's activator deficiency), the receiver is saposin C or fragment thereof, and the target is sphingolipids. In one embodiment the disease or condition is Schindler's disease Type I (infantile severe form; 609241), the receiver is N-acetyl-galactosaminidase or fragment thereof, and the target is glycoproteins. In one embodiment the disease or condition is Schindler's disease Type II (Kanzaki disease, adult-onset form; 609242), the receiver is N-acetyl-galactosaminidase or fragment thereof, and the target is glycoproteins. In one embodiment the disease or condition is Schindler's disease Type III (intermediate form; 609241), the receiver is N-acetyl-galactosaminidase or fragment thereof, and the target is glycoproteins. In one embodiment the disease or condition is sialidosis (256550), the receiver is neuraminidase 1 (sialidase) or fragment thereof, and the target is mucopolysaccharides and mucolipids. In one embodiment the disease or condition is sialuria Finnish type (Salla disease; 604369), the receiver is Na phosphate cotransporter, sialin or fragment thereof, and the target is sialic acid. In one embodiment the disease or condition is sialuria French type (269921), the receiver is UDP-N-acetylglucosamine-2-epimerase/N-acetylmannosamine kinase, sialin or fragment thereof, and the target is sialic acid. In one embodiment the disease or condition is sphingolipidosis Type I (230500), the receiver is ganglioside β-galactosidase or fragment thereof, and the target is sphingolipids. In one embodiment the disease or condition is sphingolipidosis Type II (juvenile type; 230600), the receiver is ganglioside β-galactosidase or fragment thereof, and the target is sphingolipids. In one embodiment the disease or condition is sphingolipidosis Type III (adult type; 230650), the receiver is ganglioside β-galactosidase or fragment thereof, and the target is sphingolipids. In one embodiment the disease or condition is Tay-Sachs disease; 272800, the receiver is β-hexosaminidase A or fragment thereof, and the target is gangliosides. In one embodiment the disease or condition is Winchester syndrome (277950), the receiver is metalloproteinase-2 or fragment thereof, and the target is mucopolysaccharides. In one embodiment the disease or condition is Wolman's disease, the receiver is lysosomal acid lipase or fragment thereof, and the target is lipids and cholesterol. In one embodiment the disease or condition is α-mannosidosis (248500), type I (severe) or II (mild), the receiver is α-D-mannosidase or fragment thereof, and the target is carbohydrates and glycoproteins. In one embodiment the disease or condition is β-mannosidosis (248510), the receiver is β-D-mannosidase or fragment thereof, and the target is carbohydrates and glycoproteins.

Selective Starvation of Metabolites

In some embodiments, the synthetic membrane-receiver polypeptide complexes described herein may be used to treat or prevent cancers.

In specific embodiments, methods are provided for reducing the circulatory concentration of a target metabolite, such as an amino acid cell in a subject (e.g., a human) suffering from or at risk of developing a cancer. The target metabolite is essential for survival of the cancer cell but not for survival of a healthy, normal cell. In certain embodiments, the cancer cell is thereby selectively starved of the critical metabolite but healthy normal cells are spared because the metabolite is non-critical for those cells. The methods include administering a pharmaceutical composition comprising a synthetic membrane-receiver polypeptide complex described herein. The pharmaceutical composition is administered in an amount effective to substantially reduce the circulatory concentration of the target metabolite. In certain embodiments, the administration is carried out intravenously. Diseases that benefit from a selective starvation of a target metabolites include cancers such as acute lymphoblastic leukemia, acute myeloblastic leukemia, pancreatic adenocarcinoma, p53-null solid tumors and those listed in table 6 and table 8.

In specific embodiments, provided are methods of treating cancer that include administering to a subject in need thereof a pharmaceutical composition of erythrocyte cells that comprise a receiver provided herein in an amount sufficient to treat cancer. The compositions comprising functional erythroid cells that comprise a chemotherapeutic or a receiver polypeptides capable of treating tumors and liquid cancers, may be administered to subjects that exhibit a cancers, including adrenal, anal, bile duct, bladder, bone, central nervous system, breast, leukemia, liver, lung, lymphoma, multiple myeloma, osteosarcoma, pancreatic, and those listed in, but not limited to, table 6 and table 8.

In one embodiment the disease or condition is acute lymphoblastic leukemia, the receiver is asparaginase or fragment thereof, and the target is asparagine.

In one embodiment the disease or condition is acute myeloblastic leukemia, the receiver is asparaginase or fragment thereof, and the target is asparagine.

In one embodiment the disease or condition is p53-null solid tumor, the receiver is serine dehyrdatase or serine hydroxymethyl transferase or fragment thereof, and the target is serine.

In one embodiment the disease or condition is pancreatic adenocarcinoma, the receiver is asparaginase or fragment thereof, and the target is asparagine.

Acute Lymphoblastic Leukemia (ALL)

In some embodiments, subjects may be identified as having received or would benefit from receiving treatment for acute lymphoblastic leukemia (ALL). Subjects suffering from or at risk of developing ALL may be administered a pharmaceutical composition comprising the synthetic membrane-receiver polypeptide complex described herein to treat or prevent disease.

In one embodiment, the synthetic membrane-receiver polypeptide complex comprises a receiver comprising asparaginase or a derivative or functional fragment thereof. A suitable receiver may be exhibited on the surface or on the unexposed side of the synthetic membrane-receiver polypeptide complex and may be administered to reduce the concentration of asparagine in circulation thereby depriving a cancer cell lacking the ability to synthesize L-asparagine and relying on the local environment for the amino acid of asparagine.

In specific embodiments, compositions comprising a plurality of functional erythroid cells comprising an asparaginase receiver are provided. Such compositions may be used to treat subjects that exhibit or are diagnosed with acute lymphoblastic leukemia (ALL).

Tumor cells lack the ability to synthesize L-asparagine and rely on their local environment for the amino acid. Asparaginase is an enzyme that can be isolated from both *Escherichia coli* and *Erwinia chrysanthemi*. The foreign-sourced asparaginase is subject to immunogenic reactions that can generate life-threatening human anti-bacterial antibody responses (Avramis, Anticancer Res., 2009 January; 29(1):299-302). It has provided therapeutic benefit as a stand-alone enzyme replacement therapy, but inhibitor development is a common result of chronic treatment.

In specific embodiments, provided herein are compositions comprising a plurality of functional erythroid cells comprising an asparaginase receiver which may be administered to ALL subjects to deprive the cancer cells of asparagine. The functional erythroid cells may contain exogenous asparaginase within their intracellular space. The intracellularly localized exogenous asparaginase polypeptide may then convert asparagine to aspartate, thereby lowering the levels of asparagine. Asparagine crosses the cell membrane, is converted to aspartate, and diffuses back into circulation. This may be sufficient to create a local deficiency in the critical nutrient and starving tumor cells.

Diseases and Conditions Associated with Vascular Deficiencies

In some embodiments, the synthetic membrane-receiver polypeptide complexes described herein may be used to treat or prevent diseases and conditions associated with vascular deficiencies, e.g., of a vascular protein. A schematic example of this aspect of the invention is shown in FIG. 13B.

In some embodiments, the surface exposed receiver polypepdide may interact with a target substrate and can modify, convert, change or otherwise alter the target substrate. Alternatively, the surface exposed receiver polypepdide is cleaved from the surface of the synthetic membrane-receiver complex in response to a specific microenvironment or molecule. In one embodiment, the receiver's catalytic activity may be initiated after cleavage.

In some embodiments, the synthetic membrane-receiver complexes comprise a receiver and optionally comprise a payload, such as a therapeutic agent, that can be released upon lysis of the synthetic membrane-receiver complex. The payload may be an enzyme, protein, antibody, or small molecule. The lytic event may be triggered by a stimulus in the microenvironment in which the synthetic membrane-receiver complex is present. The stimulus may, for example, recruit membrane-targeting enzymes, trigger the complement system to lyse the synthetic membrane-receiver complex, or mark the complex for destruction. Alternatively, in embodiments in which the synthetic membrane-receiver complex is generated from a cell, e.g., an erythroid cell, the synthetic membrane-receiver complex may be modified to undergo apoptosis when exposed to a specific stimulus or once a certain period of time has passed. A schematic example is shown in FIG. 13C.

In specific embodiments, methods are provided for reducing the circulatory concentration of a target vascular protein in a subject (e.g., a human) suffering from or at risk of developing a disease or condition associated with a vascular deficiency. The methods include administering a pharmaceutical composition comprising a synthetic membrane-receiver polypeptide complex described herein. The synthetic membrane-receiver polypeptide complex may comprise a receiver that can degrade, cleave, or convert a vascular protein. In some embodiments, a function of a missing vascular enzyme (a non-target) is restored. In some embodiments, the amount of the target vascular protein is reduced to effectively restore the homeostatic balance of vascular proteins to levels effective to treat or prevent the disease or condition. In certain embodiments, the administration is carried out intravenously. Diseases or conditions associated with vascular deficiencies include, but are not limited to thrombotic thrombocytopenic purpura, hemophilia A, hemophilia B, von Willebrand disease and those listed in table 6 and table 8.

In specific embodiments, provided are methods of treating a clotting disease or anti-clotting disease. The methods include administering to a subject in need thereof a pharmaceutical composition of erythrocyte cells that comprise a receiver provided herein in an amount sufficient to treat the clotting disease or anti-clotting disease. The compositions may be administered to subjects that exhibit hemophilia type A, hemophilia type B, hemophilia Type C, von Willebrand disease, Factor II deficiency, Factor V deficiency, Factor VII deficiency, Factor X deficiency, Factor XII deficiency, thrombophilia, pulmonary embolism, stroke, and those disease or deficiencies included in, but not limited to, table 6 and table 8.

In one embodiment the disease or condition is hemophilia A, the receiver is factor VIII or fragment thereof, and the target is thrombin (factor II a) or factor X.

In one embodiment the disease or condition is hemophilia B, the receiver is factor IX or fragment thereof, and the target is factor XIa or factor X.

In one embodiment the disease or condition is thrombotic thrombocytopenic purpura, the receiver is ADAMTS13 or fragment thereof, and the target is ultra-large von Willebrand factor (ULVWF).

Hemophilia

In some embodiments, subjects may be identified as having received or would benefit from receiving treatment for hemophilia. Subjects suffering from or at risk of developing hemophilia may be administered a pharmaceutical composition comprising the synthetic membrane-receiver polypeptide complex described herein to treat or prevent disease.

In one embodiment, the synthetic membrane-receiver polypeptide complex comprises a receiver comprising coagulation factor VIII or a derivative or functional fragment thereof. A suitable receiver may be exhibited on the surface of the synthetic membrane-receiver polypeptide complex and may be administered to provide factor VIII function to subjects exhibiting hemophilia A.

In one embodiment, the synthetic membrane-receiver polypeptide complex comprises a receiver comprising coagulation factor IX or a derivative or functional fragment thereof. A suitable receiver may be exhibited on the surface of the synthetic membrane-receiver polypeptide complex and may be administered to provide factor IX function to subjects exhibiting hemophilia B.

Hemophilia is a common bleeding disorder (occurring in approximately 1:10,000 males) in which causes severe internal bleeding that often leads to death because the patient's blood doesn't clot normally. Hemophilia usually is inherited with patients displaying severe uncontrollable bleeding events beginning at birth and re-occurring throughout the individual's life. Although there are several types of clotting factors that work together with platelets to help the blood coagulate, people with hemophilia usually have quantitative or qualitative defects in the proteins that encode coagulation factor VIII (hemophilia A) or factor IX (hemophilia B) that prevent normal hemostasis. Hemophilia usually occurs in males because Factors VIII and IX are located on the X chromosome (although with rare exceptions females who inherit a defective X chromosome each from an affected father and mother who is a carrier for the disease). About 1 in 10,000 individuals are born with hemophilia each year all over the world.

Hemostasis is the complex physiological process that leads to the cessation of bleeding. Platelets, plasma proteins, blood vessels and endothelial cells each play an important role in the events that immediately follow tissue injury and which, under normal circumstances, results in the rapid formation of a clot. Central to this is the coagulation cascade, a series of proteolytic events in which certain plasma proteins (or coagulation factors) are sequentially activated in a "cascade" by another previously activated coagulation factor, leading to the rapid generation of thrombin. The large quantities of thrombin produced in this cascade then function to cleave fibrinogen into the fibrin peptides that are required for clot formation.

The coagulation factors circulate as inactive single-chain zymogens, and are activated by cleavage at one or more positions to generate a two-chain activated form of the protein. Factor VII (FVII), a vitamin K-dependent plasma protein, initially circulates in the blood as a zymogen. The FVII zymogen is activated by proteolytic cleavage at a single site, Arg152-Ile153, resulting is a two-chain protease linked by a single disulphide bond (FVIIa). FVIIa binds its cofactor, tissue factor (TF), to form a complex in which FVIIa can efficiently activate factor X (FX) to FXa, thereby initiating the series of events that result in fibrin formation and hemostasis.

The blood coagulation pathway, in part, involves the formation of an enzymatic complex of Factor VIIIa (FVIIIa) and Factor IXa (FIXa) (Xase complex) on the surface of platelets. FIXa is a serine protease with relatively weak catalytic activity without its cofactor FVIIIa. The Xase complex cleaves Factor X (FX) into Factor Xa (FXa), which in turn interacts with Factor Va (FVa) to cleave prothrombin and generate thrombin.

About 9 out of 10 people who have hemophilia have type A. Hemophilia A is a bleeding disorder caused by mutations and/or deletions in the Factor VIII (FVIII) gene resulting in a deficiency of FVIII activity. In some cases, patients have reduced levels of FVIII due to the presence of FVIII inhibitors, such as anti-FVIII antibodies. Hemophilia A is characterized by spontaneous hemorrhage and excessive bleeding after trauma. Over time, the repeated bleeding into muscles and joints, which often begins in early childhood, results in hemophilic arthropathy and irreversible joint damage. This damage is progressive and can lead to severely limited mobility of joints, muscle atrophy and chronic pain (Rodriguez-Merchan, E. C., Semin. Thromb. Hemost. 29:87-96 (2003)).

The disease can be treated by replacement therapy targeting restoration of FVIII activity to 1 to 5% of normal levels to prevent spontaneous bleeding (see, e.g., Mannucci, P. M., et al., N. Engl. J. Med. 344: 1773-9 (2001), herein incorporated by reference in its entirety). There are plasma-derived and recombinant FVIII products available to treat bleeding episodes on-demand or to prevent bleeding episodes from occurring by treating prophylactically. Based on the half-life of these products (10-12 hr) (White G. C., et al., Thromb. Haemost. 77:660-7 (1997); Morfmi, M., Haemophilia 9 (suppl 1):94-99; discussion 100 (2003)), treatment regimens require frequent intravenous administration, commonly two to three times weekly for prophylaxis and one to three times daily for on-demand treatment (Manco-Johnson, M. J., et al, N. Engl. J. Med. 357:535-544 (2007)), each of which is incorporated herein by reference in its entirety. Such frequent administration is painful and inconvenient.

Although on-demand treatment is frequently used, there is a trend toward prophylaxis and the prevention of joint damage (Blanchette P, et al., Haemophilia 2004: 10; 679-683, Manco-Johnson, M J, et al., N. Engl. J. Med. 2007; 357:535-544). Current FVIII products are administered every two to three days for prophylaxis due to the relatively short half-life of 10-12 hr in order to maintain a FVIII:C above 1% in patients (Morfini, M, Haemophilia 2003; 9 (suppl 1):94-99; discussion 100, White G C, et al, Thromb. Haemost. 1997:77:660-7, Blanchette, P, et al, J. Thromb. Haemost. 2008 August; 6(8): 1319-26). Longer-acting FVIII therapies that provide prolonged protection from bleeding would represent an improvement in the quality of life for patients with hemophilia A.

Strategies to extend the half-life of clotting factors include pegylation (Rostin J, et al, Bioconj. Chem. 2000; 11:387-96), glycopegylation (Stennicke H R, et al, Thromb. Haemost. 2008; 100:920-8), formulation with pegylated liposomes (Spira J, et al, Blood 2006; 108:3668-3673, Pan J, et al, Blood 2009; 114:2802-2811) and conjugation with albumin (Schulte S., Thromb. Res. 2008; 122 Suppl 4:S14-9).

Under normal conditions, activated platelets provide the lipid surface supporting coagulation. Since platelets are activated by thrombin, which is formed at sites of vascular injury, coagulation processes are restricted to the sites of injuries. However, it is undesirable to provide the body with peptides that are general substitutes for procoagulant lipids as this would cause systemic coagulation and ultimately lead to disseminated intravascular coagulation (DIC).

U.S. Pat. Nos. 7,109,170 and 6,624,289 disclose regions of the FIXa protease domain that interact with FVIIIa and that comprise the FVIIIa binding site of FIXa. The peptides inhibit binding of FIXa to FVIIIa. The disclosed peptides may be useful as anticoagulants for preventing or treating thrombosis.

US20010014456A1 discloses binding molecules for human FVIII and FVIII-like proteins. These polypeptides bind FVIII and/or FVIII-like polypeptides and are useful for the detection and purification of human FVIII and/or FVIII-like polypeptides from solutions such as blood or conditioned media.

In U.S. Pat. No. 7,033,590 FIX/FIXa activating antibodies and antibody derivatives are used for increasing the amidolytic activity of FIXa, and for treating blood coagulation disorders such as hemophilia A and hemorrhagic diathesis.

U.S. Pat. No. 7,084,109 discloses FVIIa antagonists that are peptides and inhibit FVIIa activity. The peptides may be useful for the prevention of arterial thrombosis in combination with thrombolytic therapy.

Hemophilia can be mild, moderate, or severe, depending on how much normal functional clotting factor is present in the blood. About 7 out of 10 people who have hemophilia A have the severe form of the disorder.

Hemophilia B (also known as Christmas disease) is one of the most common inherited bleeding disorders in the world. It results in decreased in vivo and in vitro blood clotting activity and requires extensive medical monitoring throughout the life of the affected individual.

In the absence of intervention, the afflicted individual may suffer from spontaneous bleeding in the joints, which produces severe pain and debilitating immobility. Bleeding into muscles results in the accumulation of blood in those tissues. Spontaneous bleeding in the throat and neck may cause asphyxiation if not immediately treated. Bleeding into the urine, and severe bleeding following surgery, minor accidental injuries, or dental extractions also are prevalent.

Hemophilia B is caused by a deficiency in Factor IX that may result from either the decreased synthesis of the Factor IX protein or a defective molecule with reduced activity.

Human FIX, one member of the group of vitamin K-dependent polypeptides, is a single-chain glycoprotein with a molecular weight of 57 kDa, which is secreted by liver cells into the blood stream as an inactive zymogen of 415 amino acids. It contains 12 γ-carboxy-glutamic acid residues localized in the N-terminal Gla-domain of the polypeptide. The Gla residues require vitamin K for their biosynthesis. Following the Gla domain there are two epidermal growth factor domains, an activation peptide, and a trypsin-type serine protease domain. Further posttranslational modifications of FIX encompass hydroxylation (Asp 64), N-(Asn157 and Asn167) as well as 0-type glycosylation (Ser53, Ser61, Thr159, Thr169, and Thr172), sulfation (Tyr155), and phosphorylation (Ser158). FIX is converted to its active form, Factor IXa, by proteolysis of the activation peptide at Arg145-Ala146 and Arg180-Val181 leading to the formation of two polypeptide chains, an N-terminal light chain (18 kDa) and a C-terminal heavy chain (28 kDa), which are held together by one disulfide bridge. Activation cleavage of Factor IX can be achieved in vitro e.g., by Factor XIa or Factor VIIa/TF. Factor IX is present in human plasma in a concentration of 5-10 µg/ml. Terminal plasma half-life of Factor IX in humans was found to be about 15 to 18 hours (White G C et al. 1997. Recombinant factor IX. Thromb Haemost. 78: 261-265; Ewenstein B M et al. 2002. Pharmacokinetic analysis of plasma-derived and recombinant F IX concentrates in previously treated patients with moderate or severe hemophilia B. Transfusion 42: 190-197).

The treatment of hemophilia B occurs by replacement of the missing clotting factor by exogenous factor concentrates highly enriched in Factor IX. However, generating such a concentrate from blood is difficult. Purification of Factor IX from plasma (plasma derived Factor IX; pdFIX) almost exclusively yields active Factor IX. However, such purification of FIX from plasma is very difficult because FIX is only present in low concentration in plasma (Andersson, Thrombosis Research 7: 451 459 (1975). Further, purification from blood requires the removal or inactivation of infectious agents such as HIV and HCV. In addition, pdFIX has a short half-life and therefore requires frequent dosing. Recombinant FIX (rFIX) is also available, but suffers from the same short half-life and need for frequent dosing (e.g., 2-3 times per week for prophylaxis) as pdFIX.

A recombinant FVIIa product is marketed by Novo Nordisk (NovoSeven). Recombinant FVIIa has been approved for the treatment of hemophilia A or B patients that have inhibitors to FVIII or FIX, and is used to stop bleeding episodes or prevent bleeding associated with trauma and/or surgery, as well as being approved for the treatment of patients with congenital FVII deficiency. FVIIa therapy leaves significant unmet medical need, because an average of 3 doses of FVIIa over a 6 hour time period are required to manage acute bleeding episodes in hemophilia patients.

Complications of replacement therapy include developing antibodies response to the normal therapeutic protein that is foreign to the patient's immune system (known as inhibitor formation), which ultimately leads to inactivation or destruction of the clotting factor and uncontrolled bleeding in about 30% of patients, developing viral infections from human clotting factors (from blood contaminated with HIV or Hepatitis from infected blood donors especially in third world countries), very expensive costs of the replacement protein which has a very short half-life (days) which requires frequent re-administration to subside a severe vascular injury and damage to joints, muscles, or other parts of the body resulting from delays in treatment.

In specific embodiments, provided herein are platelets comprising a receiver polypeptide capable of treating or preventing clotting diseases, including hemophilia. Suitable receiver polypeptides include clotting factors, e.g., Factor VIII and/or Factor IX. Human Factor VIII has the accession number NM 000132.3 and Human Factor IX has the accession number NM 000133.3.

In some embodiments, methods of treatment of hemophilia are provided comprising co-administration of one or more recombinant factors (e.g., recombinant FIX, FIXa, FVIII, and FVIIa) and the synthetic membrane-receiver complex described herein, wherein co-administration includes administration of the recombinant factor before, after or concurrent with administration of the synthetic membrane-receiver complex.

In some embodiments, methods of treatment of viral infectious diseases are provided comprising administration of a pharmaceutical composition comprising one or more recombinant factors (e.g., recombinant FIX, FIXa, FVIII, and FVIIa) and the synthetic membrane-receiver complex described herein.

In some embodiments, a single treatment is utilized to provide long-term protection against episodes of bleeding. In some embodiments that treat hemophilia, treatment is performed on a regular basis (e.g., weekly, monthly, yearly, once every 2, 3, 4, 5 or more years, and the like) in order to prevent episodes of bleeding. In some embodiments, treatment is only administered when episodes of abnormal bleeding occur (e.g., following accidents, prior to or following surgery, etc,). In some embodiments, maintenance therapy is administered in combination with extra therapy when episodes of abnormal bleeding occur.

Thrombotic Thrombocytopenic Purpura

In some embodiment, subjects may be identified as having received or would benefit from receiving treatment for Thrombotic Thrombocytopenic Purpura (TTP). Subjects suffering from or at risk of developing TTP may be administered a pharmaceutical composition comprising the synthetic membrane-receiver polypeptide complex described herein to treat or prevent disease.

In one embodiment, the synthetic membrane-receiver polypeptide complex comprises a receiver comprising the protease ADAMTSI3 or a derivative or functional fragment thereof. A suitable receiver may be exhibited on the surface of the synthetic membrane-receiver polypeptide complex. The suitable receiver is capable of cleaving ultra-large von Willebrand Factor (UL-VWF) multimers into smaller multimers.

Circulating multimers of UL-VWF increase platelet adhesion to areas of endothelial injury, particularly at arteriole-capillary junctions. Red blood cells passing the microscopic clots are subjected to shear stress which damages their membranes, leading to intravascular hemolysis, which in turn leads to anaemia and schistocyte formation. Reduced blood flow due to thrombosis and cellular injury results in end organ damage. Current therapy is based on support and plasmapheresis to replenish blood levels of the enzyme.

EXAMPLES

Example 1

Gene Assembly

DNA encoding the following genes—glycophorin A (Uniprot ID P02724), Kell (Uniprot ID P23276), antibody scFv against hepatitis B surface antigen (Bose et al. 2003 Mol Immunol 40(9):617, GenBank ID AJ549501.1), adenosine deaminase (Uniprot ID P00813), phenylalanine hydroxylase from *Chromobacterium violaceum* (GenBank ID AF146711.1), complement receptor 1 (Uniprot ID P17927), CD46 (GenBank: BAA12224.1), CD55 (Uniprot ID P08174), CD59 (Uniprot ID P13987), green fluorescent protein (Uniprot ID P42212), thymidine phosphorylase (Uniprot ID P19971), glucocerebrosidase (Uniprot ID P04062), beta2 glycoprotein 1 (Uniprot ID P02749), phospholipase a2 receptor (Uniprot ID Q13018), collagen alpha-3(IV) (Uniprot ID Q01955), serum amyloid P (Uniprot ID P02743), lipoprotein lipase (Uniprot ID P06858), asparaginase (Uniprot ID P00805), factor IX (Uniprot ID F2RM35), ADAMTS13 (Uniprot ID Q76LX8)—were purchased as cDNA from Dharmacon (GE Life Sciences) or synthesized de novo by DNA2.0 and Genscript.

1. Single Gene Cloning (CR1)

Genes were assembled into expression vectors by standard molecular biology methods known in the art. The gene for complement receptor 1 (CR1) was synthesized by a commercial vendor (DNA2.0) and supplied in a standard cloning vector (pJ series). The gene was amplified out of the pJ vector by polymerase chain reaction (PCR) using oligos with non-homologous terminal sequences to prepare for insertion into the mammalian expression vector (System Biosciences, pM series): the upstream oligo consisted of 25 nt homologous to the upstream pM insertion site and 25 nt homologous to the start of CR1; the downstream oligo consisted of 25 nt homologous to the downstream pM insertion site and 25 nt homologous to the end of CR1. The amplified product was purified by gel electrophoresis (Qiagen). The pM vector was linearized by PCR with tail-to-tail oligos homologous to the upstream and downstream insertion sites and purified by PCR purification (Qiagen). The CR1 amplicon was ligated into the linearized pM vector by Gibson assembly, described in detail in Gibson 2011, Methods Enzymology Vol 498, p. 394. Sequences were confirmed by Sanger sequencing.

2. Fusion of Two Genes (Membrane Kell-scFv)

The gene for Kell was purchased as cDNA and supplied in a standard cloning vector (pJ series). The gene for an antibody scFv specific to hepatitis B surface antigen (scFv, described in Bose 2003, Molecular Immunology 40:617) was synthesized by a commercial vendor (DNA2.0) and supplied in a standard cloning vector (pJ series). The genes was amplified out of the pJ vectors by polymerase chain reaction (PCR) using oligos with non-homologous terminal sequences to prepare for insertion into the mammalian expression vector (System Biosciences, pM series). Kell was amplified with an upstream oligo consisting of 25 nt homologous to the upstream pM insertion site and 25 nt homologous to the 5' terminus of Kell, and a downstream oligo consisting of 25 nt homologous to the 5' terminus of scFv and 25 nt homologous to the 3' terminus of Kell. scFv was amplified with an upstream oligo consisting of 25 nt homologous to the 3' terminus of Kell insertion site and 25 nt homologous to the 5' terminus of scFv, and a downstream oligo consisting of 25 nt homologous to the downstream pM insertion site and 25 nt homologous to the 3' terminus of scFv. The amplified products were purified by gel electrophoresis (Qiagen). The pM vector was linearized by PCR with tail-to-tail oligos homologous to the upstream and downstream insertion sites and purified by PCR purification (Qiagen). The Kell and scFv amplicons were ligated into the linearized pM vector by one-pot Gibson assembly, described in detail in Gibson 2011, Methods Enzymology Vol 498, p. 394. Sequences were confirmed by Sanger sequencing.

3. Linker-Assembly Between Genes (Kell-Scfv)

The gene for Kell was purchased as cDNA and supplied in a standard cloning vector (pJ series). The gene for an antibody scFv specific to hepatitis B surface antigen (scFv, described in Bose 2003, Molecular Immunology 40:617) was synthesized by a commercial vendor (DNA2.0) and supplied in a standard cloning vector (pJ series). The genes was amplified out of the pJ vectors by polymerase chain reaction (PCR) using oligos with non-homologous terminal sequences to prepare for insertion into the mammalian expression vector (System Biosciences, pM series). Kell was amplified with an upstream oligo consisting of 25 nt homologous to the upstream pM insertion site and 25 nt homologous to the 5' terminus of Kell; and a downstream oligo consisting of 25 nt homologous to the 5' terminus of scFv, 24 nt encoding a (GlyGlyGlySer)×2 (SEQ ID NO: 23) spacer, and 25 nt homologous to the 3' terminus of Kell. scFv was amplified with an upstream oligo consisting of 25 nt homologous to the 3' terminus of Kell insertion site, 24 nt encoding a (GlyGlyGlySer)×2_(SEQ ID NO: 23) spacer, and 25 nt homologous to the 5' terminus of scFv; and a downstream oligo consisting of 25 nt homologous to the downstream pM insertion site and 25 nt homologous to the 3' terminus of scFv. The amplified products were purified by gel electrophoresis (Qiagen). The pM vector was linearized by PCR with tail-to-tail oligos homologous to the upstream and downstream insertion sites and purified by PCR purification (Qiagen). The Kell and scFv amplicons were ligated into the linearized pM vector by one-pot Gibson assembly, described in detail in Gibson 2011, Methods Enzymology Vol 498, p. 394. Sequences were confirmed by Sanger sequencing.

4. Epitope Tag Attachment (Kell-scFv)

The gene for Kell was purchased as cDNA and supplied in a standard cloning vector (pJ series). The gene for an antibody scFv specific to hepatitis B surface antigen (scFv, described in Bose 2003, Molecular Immunology 40:617) was synthesized by a commercial vendor (DNA2.0) and supplied in a standard cloning vector (pJ series). The genes was amplified out of the pJ vectors by polymerase chain reaction (PCR) using oligos with non-homologous terminal sequences to prepare for insertion into the mammalian expression vector (System Biosciences, pM series). Kell was amplified with an upstream oligo consisting of 25 nt homologous to the upstream pM insertion site and 25 nt homologous to the 5' terminus of Kell; and a downstream oligo consisting of 25 nt homologous to the 5' terminus of scFv, 24 nt encoding a (GlyGlyGlySer)×2 (SEQ ID NO: 23) spacer, and 25 nt homologous to the 3' terminus of Kell. scFv was amplified with an upstream oligo consisting of 25 nt homologous to the 3' terminus of Kell insertion site, 24 nt encoding a (GlyGlyGlySer)×2 (SEQ ID NO: 23) spacer, and 25 nt homologous to the 5' terminus of scFv; and a downstream oligo consisting of 25 nt homologous to the downstream pM insertion site, the 27 nt sequence tacccctatgacgtgcccgactatgcc (Seq. ID No. 8) encoding an HA epitope tag, and 25 nt homologous to the 3' terminus of scFv. The amplified products were purified by gel electrophoresis (Qiagen). The pM vector was linearized by PCR with tail-to-tail oligos homologous to the upstream and downstream insertion sites. The downstream primer additionally contained the 27 nt sequence tacccctatgacgtgcccgactatgcc (Seq. ID No. 8) encoding an HA epitope tag. The linearized vector was purified by PCR purification (Qiagen). The Kell and scFv amplicons were ligated into the linearized pM vector by one-pot Gibson assembly, described in detail in Gibson 2011, Methods Enzymology Vol 498, p. 394. Sequences were confirmed by Sanger sequencing.

5. Fusion of Two Genes (Reporter Assembly) (GPA-HA)

The genes for complement receptor 1 (CR1) and green fluorescent protein (GFP) were synthesized by a commercial vendor (DNA2.0) and supplied in standard cloning vectors (pJ series). The CR1 gene was amplified out of the pJ vector by polymerase chain reaction (PCR) using oligos with non-homologous terminal sequences to prepare for insertion into the mammalian expression vector (System Biosciences, pM series): the upstream oligo consisted of 25 nt homologous to the upstream pM insertion site and 25 nt homologous to the start of CR1; the downstream oligo consisted of 54 nt homologous to the viral-derived T2A sequence gagggcagaggaagtcttctaacatgcggtgacgtggaggsgsstcccggccct (Seq. ID No. 7). The GFP gene was amplified out of the pJ vector by polymerase chain reaction (PCR) using oligos with non-homologous terminal sequences to prepare for insertion into the mammalian expression vector (System Biosciences, pM series): the upstream oligo consisted of 54 nt homologous to the viral-derived T2A sequence gagggcagaggaagtcttctaacatgcggtgacgtggaggsgsstcccggccct (Seq. ID No. 7) and 25 nt homologous to the start of GFP; the downstream oligo consisted of 25 nt homologous to the downstream pM insertion site and 25 nt homologous to the end of GFP. The amplified products were purified by gel electrophoresis (Qiagen). The pM vector was linearized by PCR with tail-to-tail oligos homologous to the upstream and downstream insertion sites and purified by PCR purification (Qiagen). The CR1 and GFP amplicons were ligated together and into the linearized pM vector by Gibson assembly, described in detail in Gibson 2011, Methods Enzymology Vol 498, p. 394. Sequences were confirmed by Sanger sequencing.

Example 2 mRNA Assembly

A gene of interest is cloned into the multiple cloning site of the pSP64 vector (Promega) using standard molecular biology methods. The vector is digested with EcoRI (NEB) to generate a linearized dsDNA vector containing the SP6 promoter, gene of interest, and 30 nucleotide long poly-A tail. mRNA is synthesized by reaction with SP6 RNA polymerase (Promega) according to manufacturer's instructions, including recommended concentrations of 5' cap analog (ARCA) to synthesize capped mRNA transcript. The reaction mixture is then treated with DNAse to digest the template vector (Riboprobe from Promega) and the mRNA is purified using the EZNA MicroElute RNA Clean-Up kit (Omega).

Example 3

Cell Culture

1. Human Red Blood Cells (RBCs)

CD34 cells are isolated from peripheral blood by supermagnetic microbead selection by the use of Mini-MACS columns (Miltenyi Biotec; 94%+/−3% purity). The cells are cultured in erythroid differentiation medium (EDM) on the basis of IMDM supplemented with stabilized glutamine, 330 μg/mL holo-human transferrin, 10 μg/mL recombinant human insulin, 2 IU/mL heparin, and 5% solvent/detergent virus-inactivated plasma. The expansion procedure comprises 3 steps. In the first step (day 0 to day 7), $10^4$/mL CD34+ cells are cultured in EDM in the presence of 1 μM hydrocortisone, 100 ng/mL SCF, 5 ng/mL IL-3, and 3 IU/mL EPO. On day 4, 1 volume of cell culture is diluted in 4 volumes of fresh medium containing SCF, IL-3, EPO, and hydrocortisone. In the second step (day 7 to day 11), the cells are resuspended at $10^5$/mL in EDM supplemented with SCF and EPO. In the third step (day 11 to day 18), the cells are cultured in EDM supplemented with EPO alone. Cell counts are adjusted to $7.5 \times 10^5$ to $1 \times 10^6$ and $5$-$10 \times 10^6$ cells/mL on days 11 and 15, respectively. Beyond day 18, the culture medium containing EPO is renewed twice a week. The cultures are maintained at 37° C. in 5% CO2 in air.

2. Mouse Red Blood Cells

Methods of culturing mouse erythroid cells from mouse fetal liver erythroid progenitors are known in the art, see e.g., Shi et al. 2014, PNAS 2014 111(28):10131.

Mouse erythroid progenitors are isolated from fetal livers. Fetal livers are purchased from Charles River Labs. Livers are put in 1ml PBS on ice. Pipette up and down to get a single-cell suspension solution and pass by a 70 um strainer (BD Falcon 35-2235). Rinse the mesh with 1 ml PBS. Combine the flow through (1ml per embryo). Pellet the cells at 1.5 k RPM for 5 min, re-suspend with red cell lysis buffer (Ammonium Chloride Solution from Stemcell), and incubate on ice for 10 mins. Pellet the cells at 1.5 k RPM for 5 min, remove the lysis buffer, and re-suspend with 10 ml PBS-2% FBS. Add chromPure Rat IgG (Jackson ImmunoResearch, #012-000-003) at 50 ul/mouse and incubate at 4 C for 5 min. Add Biotinylated anti-mouse TER119 (BD Pharmingen, #553672) at (at 1 ul/l*$10^6$ cells) and incubate at 4 C for 15 min. Add Ms Lineage Panel (Fisher Scientific (Thermo Fisher Scientific) # BDB559971) to the cells at (2 ul/l*$10^6$ cells) and incubate at 4 C for 15 min. Washing once with 10× volume of PBS/and Spin the cells with 1.5 k RPM for 5 min at 4 degree. Add Streptavidin Particles Plus—DM (magnetic beads) (BD Pharmigen, #557812) (5 ul/l*$10^6$ cells) and incubate at 4 C for 30 min. Prepare 2-4 FACS tubes on a magnetic holder. Aliquot 2 ml cells into each tube (4 ml in total), and carefully take the cells out of the tube and put into the other tube on the other side avoiding the disruption of the magnetic stick beads. Repeat the same procedure and take the Ter119 negative and linkage negative cells to a new tube. Concentrate the cells, and resuspend the cells with 50-100 ul PBS (2% FBS).

Purified erythroid progenitors are cultured in differentiation medium comprising (for 40 mL): IMDM: 29 ml, FBS (Stem Cell): 6 ml (Final 15%), 10% BSA in IMDM (Stem Cell): 4 ml (Final 1%), 10 mg/ml Holo-transferrin: 2000 ul (Final: 500 ug/ml), 100*L-Glutamine: 400 ul, 100* penicillin streptomycin: 400 ul, 10 U/ul Epo: 2 ul (Final: 0.5 U/ml), 10 mg/ml Insulin: 40 ul (Final: 10 ug/ml). Culture $2*10^5$ cells/ml in the differentiation medium in 24 wells plate at 37 C. After a total culture of 44-48 hours, analyses are performed, for example by flow cytometry as performed herein. Enucleated red blood cells are gated out using (Hoechst stain) for differentiation profile analysis. A successful culture will yield 16 fold increase.

3. Platelets

Donated CD34+ cells are acquired from the Fred Hutchinson Cancer Research Center. The CD34+ enriched cells are plated in a serum-free medium at $2\text{-}4\times10^4$ cells/mL and medium refreshment is done on day 4 by adding an equal volume of media. On day 6, cells are counted and analyzed: $1.5\times10^5$ cells are washed and placed in 1 mL of the same medium supplemented with a cytokine cocktail consisting of TPO 30 ng/mL, SCF 1 ng/mL, interleukin (IL)-6 7.5 ng/mL and IL-9 13.5 ng/mL] to induce megakaryocyte differentiation. At day 10, ½-¼ of the suspension culture is replaced with fresh medium. All cytokines are purchased from Peprotech. The cultures are incubated in a humidified atmosphere (10% CO2) at 39° C. for the first 6 days of culture and 37° C. for the last 8 days. Viable nucleated cells are counted with a hemocytometer (0.4% trypan blue; Invitrogen, Burlington, ON, Canada).

Clonogenic progenitor cells (CPC) are assayed using MethoCult H4436 for myeloid CPC, and MegaCult-C for colony-forming unitmegakaryocyte (CFU-Mk), according to manufacturer's instructions (StemCell Technologies, Vancouver, BC, Canada). To assess differentiation, cells are stained with antibodies against CD61m CD42b, CD41, CD61, and CD49b by flow cytometry using a FACS-Calibur (Becton Dickinson). For cell cycle analysis, cells are rinsed with phosphate-buffered saline (PBS), fixed with formaldehyde 2% (Sigma, St Louis, Mo., USA) for 5 min and permeabilized with 0.1% of Triton X-100 (Bio-Rad, Hercules, Calif., USA). Cells are then marked with mAb-Ki-67-FITC (BD Bioscience, San Jose, Calif., USA), washed and resuspended in 0.5 mL PBS-1% fetal bovine serum (FBS)-0.01% azide 7-amino-actinomycin D (7-AAD) following the manufacturer's instructions (BD Biosciences).

Example 4

Cell Isolation

1. Primary RBCs

Whole blood is collected using aseptic techniques in tubes containing low molecular weight heparin, dalteparin sodium (9 units/mL blood). Blood is centrifuged at 5000×g for 5 minutes and after removal of plasma and buffy coat (both can be retained for later use), the erythrocytes are washed twice in cold (4 C) phosphate buffered saline (PBS) with centrifugation. The resultant red blood cell population is stored at 4 C in CPDA-1 anticoagulant or a glycerol solution for long-term preservation.

2. Primary Platelets

Whole blood (40 ml) is collected in 3.8% sodium citrate (1:9 citrate to blood vol/vol) from healthy individuals under an appropriate IRB protocol. Blood is centrifuged at 200 g for 15 minutes to isolate platelet-rich plasma (PRP). Platelets are then washed in modified Tyrode's buffer (containing 138 mM NaCl, 5.5 mM dextrose, 12 mM NaHCO3, 0.8 mM CaCl2, 0.4 mM MgCl2, 2.9 mM KCl2, 0.36 mM Na2HPO4 and 20 mM Hepes, pH 7.4) in presence of 1 µM prostaglandin I2, and resuspended in the same buffer.

Example 5

Irradiation of Primary or Cultured Cell

Irradiation of a population of synthetic membrane-receiver complexes can be performed to ensure that they are incapable of replication. Such protocols are similar to those known in the art for irradiating cells, e.g., primary red blood cells. Briefly, one unit (350 ml) of whole blood is taken and divided into two aliquots of 175 ml each, 10 such units are thus divided into 20 aliquots. One aliquot (175 ml) from each unit of blood is subjected to gamma irradiation of 25 Gy, and not exceeding 50 Gy, by a self-contained gamma cell irradiator (GammaCell 1000, Theratronics). The blood is then stored at 4 C under conventional blood banking conditions. Sampling is done from these 10 irradiated and 10 non-irradiated blood bags on days 0, 7, 14, and 21 with the help of sampling site coupler (Fenwal, USA). Tests for cell proliferation are conducted, including a thymidine incorporation assay to quantify any mitotic potential. Supernatant is assayed for free hemoglobin by absorbance spectroscopy, and for free lactate dehydrogenase by colorimetric assay (Pierce) to evaluate levels of cell lysis.

Example 6

Enucleation of Erythroid Cells

Erythroid cells are grown to semiconfluence (1 to $4\times10^4$ cells per cm2) on 12-mm diameter coverslips coated with collagen in IMDM medium supplemented with 100 units/ml of penicillin and 100 units/ml of streptomycin. The collagen is necessary to prevent all the cells from falling off the coverslip during centrifugation. Cells are grown to monolayers ($5\times10^4$ cells per cm2) on coverslips either in the same medium or in Dulbecco's modified Eagle's medium with 10% calf serum. It is not necessary to coat the cell coverslips with collagen. In order to enucleate the cells, the coverslips are inverted (cell side down) and placed into the bottom of 15-ml Corex centrifuge tubes containing 2-5 ml of medium with 10 g of cytochalasin B per ml. The centrifuge tubes with the coverslips are placed immediately into a Sorvall RC-2 centrifuge that has been warmed to 37 C by spinning the (SS 34) rotor with the head in place for about 1 hr at 10,000 rpm (with the temperature regulator set at 37-39°). The length of time and speed of centrifugation are crucial factors for successful enucleation. Cells are spun at 9000 rpm for 1 hr at 37±20 and cells are spun at 6500 rpm for 50 min at 37±–20. After centrifugation, the coverslips are removed from the centrifuge and placed cell side up into 35-mm (Falcon) tissue culture dishes (Biolquest) containing 3 ml of medium without cytochalasin B. Within 30-60 min at 370, the cells are morphologically normal and 90-99% lacked nuclei. Enucleated cells are removed from the coverslips by treatment with trypsin-EDTA (Grand Island Biological Co.) and the cells are suspended in normal medium. The enucleated cells are then replated in small drops on 22-mm2 coverslips kept in 35-mm tissue culture dishes and placed in an incubator. At time intervals after replating, the coverslips are mounted on slides (12) and observations on the enucleates are made with Zeiss phase contrast, polarized light, and Nomarski optics.

Example 7

Contacting of Cells

1. Nucleic Acid—Transfection

The nucleic acid of interest is scaled up to provide approximately 5 ug nucleic acid per 10^5 complexes to be loaded, e.g., a cell, such as an erythroid cell, a platelet, or a hematopoietic precursor cell. The nucleic acid is diluted in Opti-MEM Medium (Life Technologies) at a ratio of 1 ug to 50 uL medium. The diluted nucleic is then combined with a transfection reagent (Trans-IT for DNA, Trans-IT mRNA for mRNA, Trans-IT siRNA for siRNA, Mirus Bio) at a 1:1 volume ratio and allowed to form complexes for 5 minutes at room temperature. The nucleic acid complex is added to cells for 12-24 hours. Optionally, after this period of time, the media can be exchanged with fresh media such that the transfection reagents are no longer present.

2. Nucleic Acid—Viral Transduction

The gene of interest is cloned into the multiple cloning site of lentivirus vector pCDH with the MSCV promoter sequence from System Biosciences.

Lentivirus is produced in 293T cells by transfecting the cells with lipofectamine. 5×10^6 293T cells (Lenti-X 293T Cell Line, Clontech catalog #632180) are plated in a P10 petri dish the day before transfection. Cell confluency should be around 70%. One plate is transfected per construct. 20 μl (10 μg) pPACKH1 (System Biosciences) plasmid mix+2 μg lenti construct+20 μl Plus reagent (LifeTechnologies, Catalog #11514-015) are combined in 400 μl Optimem and incubated 15 min at RT. 30 μl of LF2000 (LifeTechnologies, Catalog #11668-019) is diluted into 400 μl Optimem, added dropwise to DNA mix, and incubated for 15 min RT. DNA mix is added to cells (cells are in 9 ml of Optimem). Cells are incubated for 6 hours and then the medium is changed to DMEM/10% FBS. The virus supernatant is collected 48 hours post-transfection by centrifugation at 1,500 rpm for 5 minutes. The supernatant is collected and frozen in 1 ml aliquots at −80° C.

Target cells are transduced at day 3-7 of the culture process described herein. 5×10^5 cultured cells are plated in 500 μL of medium containing 20 μg/mL polybrene in a 24-well plate. For each virus, cells are transduced in triplicate wells. Virus supernatant is added in another 500 μL of medium and the sample is mixed by pipetting. Infection is achieved by spinoculation, spinning the plate at 2000 rpm for 90 minutes at room temperature. After spinoculation, the cells are incubated at 37 C overnight, and the next day 1 mL of fresh IMDM medium with appropriate cytokines is added.

3. Nucleic Acid—Cationic Polymer

An mRNA ecoding the transgene of interest, and including an upstream promoter sequence and a downstream poly A tail, can be purchased from multiple commercial vendors (e.g., IDT-DNA, Coralville Iowa). RNA transfections are carried out using RNAIMax (Invitrogen, Carlsbad, Calif.) or TRANSIT-mRNA (Mims Bio, Madison, Wis.) cationic lipid delivery vehicles. RNA and reagent are first diluted in Opti-MEM basal media (Invitrogen, Carlsbad, Calif.). 100 ng/uL RNA is diluted 5× and 5 μL, of RNAIMax per μg of RNA is diluted 10×. The diluted components are pooled and incubated 15 minutes at room temperature before they are dispensed to culture media. For TRANSIT-mRNA transfections, 100 ng/uL RNA is diluted 10× in Opti-MEM and BOOST reagent is added (at a concentration of 2 μL, per μg of RNA), TRANSIT-mRNA is added (at a concentration of 2 μL, per μg of RNA), and then the RNA-lipid complexes are delivered to the culture media after a 2-minute incubation at room temperature. RNA transfections are performed in Nutristem xenofree hES media (STEMGENT®, Cambridge, Mass.) or Opti-MEM plus 2% FBS. Successful introduction of the mRNA transcript into host cells can be monitored using various known methods, such as a fluorescent label or reporter protein, such as Green Fluorescent Protein (GFP). Successful transfection of a modified mRNA can also be determined by measuring the protein expression level of the target polypeptide by e.g., Western Blotting or immunocytochemistry. Similar methods may be followed for large volume scale-up to multi-liter (5-10,000 L) culture format following similar RNA-lipid complex ratios.

4. Nucleic Acid—Electroporation mRNA ecoding the transgene of interest, and including an upstream promoter sequence and a downstream poly A tail, can be purchased from multiple commercial vendors (e.g., IDT-DNA, Coralville Iowa). Electroporation parameters are optimized by transfecting erythroid lineage cells with mRNA transcripts and measuring transfection efficiency by quantitative RT-PCR with primers designed to specifically detect the exogenous transcripts. For certain cells preparations, discharging a 150 uF capacitor into 2.5×10^6 cells suspended in 50 μl of Opti-MEM (Invitrogen, Carlsbad, Calif.) in a standard electroporation cuvette with a 2 mm gap is sufficient for repeated delivery in excess of 10,000 copies of modified mRNA transcripts per cell, as determined using the standard curve method, while maintaining high viability (>70%). Cell density may vary from 1×10^6 cell/50 μl to a density of 2.5×10^6 cells/500 and require from 110V to 145V to transfect cells with similar efficiencies measured in transcript copies per cell. Large multi-liter (5-10,000 L) electroporation may be performed similar to large volume flow electroporation strategies similar to methods described with the above described constraints (Li et al., 2002; Geng et al., 2010).

5. Polypeptide—Liposome

Cells, including primary terminally-differentiated cells e.g., erythrocytes, can be loaded with exogenous protein on their surface and in their cytoplasm. The loading of proteins can be performed using liposomes.

Lipids (Pro-Ject reagent, Pierce) in organic solvent were dried under nitrogen into a thin film in glass scintillation vial. Approximately 2 uL lipids were used per 10^5 cells. Polyclonal mouse IgG (Abcam) was labeled with Dylight-650 (Pierce) per manufacturer's instructions. Protein solution at 0.1 mg/mL in PBS was added to the dried lipid mixture. The solution was pipetted several times, incubated for 5 minutes at room temperature, then vortexed vigorously to generate encapsulating liposomes. Serum-free medium was added to bring the total volume to 500 uL per 10^5 cells. The liposomal mixture was then incubated with the cells for 3-4 hours at 37 C.

FIG. 1A-FIG. 1F shows the loading of an exogenous protein, in this case fluorescently-labeled IgG, into primary erythrocytes with liposomes. The loading is measured by flow cytometry. The loading is dose-dependent, as 0.06% of cells are fluorescent without liposomes, ~60% of cells are fluorescent at a low liposome dose, and ~85% of cells are fluorescent at a high liposome dose. The data in FIG. 1A-FIG. 1F is strong proof that exogenous proteins can be loaded into erythroid cells with liposomes.

6. Polypeptide—Mechanical Disruption

Cells may be loaded using a microfluidic device containing 1 µm, 2 µm, 3 µm, 4 µm, 5 µm, 10 µm wide channels that transiently porate the cells, allowing a payload to enter when the cells are pressured through the system.

The silicon-based devices are fabricated at the Massachusetts Institute of Technology microfabrication facility using photolithography and deep reactive ion etching techniques. In this process, 6" silicon wafers with a 450-µm thickness are treated with hexamethyldisilazane, spin coated with photoresist (OCG934; FujiFilm) for 60 s at 3,000 rpm, exposed to UV light (EV1; EVG) through a chrome mask with theconstriction channel design, and developed in AZ405 (AZ Electronic Materials) solution for 100 s. After 20 min of baking at 90° C., the wafer is etched by deep reactive ion etching (SPTS Technologies) to the desired depth (typically 15 µm). The process is repeated on the opposite side of the wafer (i.e., the one not containing the etched channels) using a different mask, which contains the access hole patterns, and using a thicker photoresist AZ9260 (AZ Electronic Materials). Wet oxidation is then used to grow 100-200 nm of silicon oxide before the wafer is anodically bonded to a Pyrex wafer and diced into individual devices. Before each experiment, devices are visually inspected and mounted onto a holder with inlet and outlet reservoirs (all designed in-house and produced by Firstcut). These reservoirs interface with the device using Buna-N O-rings (McMaster-Carr) to provide proper sealing. The inlet reservoir is connected to a home-made pressure regulator system using Teflon tubing to provide the necessary driving force to push material through the device. A population of erythroid cells is first suspended in the desired delivery buffer [growth medium, PBS, or PBS supplemented with 3% FBS and 1% F-68 Pluronics (Sigma)], mixed with the desired delivery material, and placed in the device's inlet reservoir. This reservoir is connected to a compressed air line controlled by a regulator, and the selected pressure (0-70 psi) is used to drive the fluid through the device. Treated cells are then collected from the outlet reservoir. Cells are incubated at room temperature in the delivery solution for 5-20 min after treatment to ensure hole closure before being subjected to any further treatment. To deliver fluorescently labeled phenylalanine ammonia hydroxylase (PAH), the experiments are conducted as described above such that the delivery buffer contained 0.1-0.3 mg/mL PAH. GFP knockdown is measured as the percentage reduction in a cell population's average fluorescence intensity relative to untreated controls.

7. Polypeptide—Surface Conjugation

The cell surface is treated with Traut's reagent (2-iminothiolane HCl, Pierce) to thiolate primary amines. Traut's reagent is dissolved in Tris buffer pH 8 with EDTA to prevent oxidation of sulfhydryls. Approximately 1 pmol Traut's reagent is used to treat $10^6$ cells. Incubate Traut's reagent with cells for 1 hour at room temperature. Remove excess or unreacted reagent by centrifugation and washing the cells. The number of available sulfhydryl groups can be measured using Ellman's Reagent. In the meantime, treat suitable receiver polypeptide with amine-to-sulfhydryl crosslinker, such as SMCC (Pierce) according to manufacturer's instructions. Excess crosslinking reagent is removed by desalting. The maleimide-functionalized protein is then incubated with the thiolated cells for several hours. Unreacted protein is separated from the conjugated cells by centrifugation and washing.

8. Polypeptide—Non-Covalent Surface Attachment

The gene for an antibody scFv against hepatitis B surface antigen (scFv, described in Bose 2003, Molecular Immunology 40:617) is fused to a 6-histidine (SEQ ID NO: 27) affinity tag and to the gene encoding the polypeptide sequence that binds mouse glycophorin A, HWMVLP-WLPGTLDGGSGCRG (SEQ ID NO: 28), in a mammalian expression vector (Genlantis). The full fusion protein is produced by transient transfection of HEK-293T cells using standard methods and purified on a Ni-NTA affinity resin (Pierce) according to manufacturer's instructions. The purified fusion protein is incubated with mouse erythrocytes at >100 nM concentration to allow for rapid equilibration and binding of the peptide to glycophorin A.

9. Polypeptide—Lipid Insertion into Membrane

Traut's reagent (Thermo Fisher) is used to generate sulfhydryl groups on an amine-containing suitable receiver polypeptide molecule following manufacturer's protocol. The reaction mixture is incubated for 1 h at room temperature (RT) on a shaker and washed through a spin desalting column (Zeba, MWCO 7K, Thermo Scientific) following the manufacturer's instructions to remove the unreacted Traut's reagent. The generation of sulfhydryl groups on the modified polypeptide is quantified using Ellman's Reagent (Pierce) based on the manufacturer's protocol.

DSPE-PEG$_{3400}$-mal ($1\times10^{-3}$ M in PBS, 4 µL, molar ratio lipid:Polypeptide=1:1) (all lipids purchased from Avanti Polar Lipids and stored as chloroform solution under argon at −20 C) are added to the desalted polypeptide solution and incubated at RT on a shaker. After 1 h, the sample solution is filtered using a centrifugal filter device (Microcon, Millipore Co.) at 14 000 g for 15 min at 4° C. to remove the small molecules and suspended in 600 µL PBS (1 mg/mL polypeptide).

200 µL of whole blood is suspended in 1000 µL PBS and spun at 1500 g for 30 s, repeated four times. Finally, the RBCs are suspended in 800 µL PBS. The conjugation of RBC/DSPE-PEG-Polypeptide is prepared by mixing the above RBCs suspensions and various amounts of DSPE-PEG-Polypeptide solution (1 mg per mL) followed by incubation for 15-30 min at 37° C. The mixture is kept for 5 min at room temperature, then washed three times in PBS and resuspended to a final RBC concentration of $5\times10^8$ per mL. An automated cell counter (Countess, Invitrogen) is used to measure the cell concentration.

10. Polypeptide—Hypotonic Loading

A suitable receiver polypeptide, in this instance mouse IgG, was purchased from Abcam and was added at 0.25 mg/mL to a RBC suspension in isotonic solution at a hematocrit (Hct) of 70%. The suspension was dialyzed in 250 mL of a hypotonic solution containg 10 mM sodium phosphate pH 7.4, 10 mM sodium bicarbonate, and 20 mM glucose, stirred at 15 rpm for 1 hour at 4 C. The cells were then isotonically resealed by adding 1/10 volume of resealing solution comprising 5 mM adenine, 100 mM inosine, 100 mM sodium pyruvate, 100 mM sodium phosphate, 100 mM glucose, 12% (w/v) NaCl at pH 7.4. Cells were then incubated at 37 C for 30 minutes.

11. Polypeptide—Cell-Penetrating Peptide

The manufacture of protamine-conjugated polypeptide is known in the art, see e.g., Kwon et al. 2009 J Contr Rel 139(3):182. 5 mg/ml of Low Molecular Weight Protamine (LMWP) in 50 mM HEPES buffer (pH 8) is mixed with the heterobifunctional cross-linker 3-(2-pyridyldithio)propionic acid N-hydroxysuccinimide (SPDP, Sigma-Aldrich) at a 1:10 molar ratio in DMSO and shaken for 1 h at room temperature. The reaction mixture is then treated with 50 mM dithiothreitol (DTT, Sigma-Aldrich) and the thiolated LMWP is purified by HPLC on a heparin affinity column. The product is collected by ultrafiltration, lyophilized, and stored at −20° C. until further use.

For conjugation, 5 mg/ml suitable receiver polypeptide is mixed with SPDP (40 µl of 0.1 M SPDP in ethanol to 1 ml protein solution) in phosphate buffer, and stirred at room temperature for 1 h. Unreacted SPDP is removed by rapid desalting and buffer exchange by FPLC with 0.1 M phosphate buffer (pH 7.4). Activated polypeptide is then conjugated with a 10-fold molar excess of the above-prepared LMWP-SH for 24 h at 4° C. The LMWP-polypeptide conjugates are isolated by ion-exchange chromatography using a heparin affinity column followed by five rounds of centrifugal filtration (molecular weight cut-off: 5,000 Da). Pooled LMWP-polypeptide conjugates are concentrated, and the degree of conjugation determined by MALDI-TOF mass spectroscopy.

For uptake experiments, fresh sheep erythrocytes (MP Biomedicals, Solon, Ohio) are suspended in Hank's balanced salt solution (HBSS) at a density of $5 \times 10^8$ cells/ml, and are then incubated with a 0.5 mg/ml solution of the LMWP-polypeptide conjugates for 30 min at room temperature under gentle shaking. RBCs are then washed with HBSS and stored at 2-8 C.

12. Polypeptide—Chemical Permeability $3 \times 10^8$ RBCs were preincubated for 30 min with chlorpromazine (Sigma Aldrich) at 200 µM in Ringer's solution. Afterwards, the suitable receiver polypeptide was added in Ringer's solution (1 to 4 µM) to a final volume of 400 µl and incubated for 30 min at room temperature under mild agitation. After incubation, cells were washed twice, resuspended in Ringer and collected for analysis.

13. Polypeptide—Enzymatic Conjugation

Cell surface enzymatic conjugations with sortase are known in the art, see e.g., Shi et al PNAS 2014 111(28): 10131. To label the GPA N terminus with polypeptide, 30 uL of 500 uM *S aureus* sortase and 1 mM polypeptide with LPETGG (SEQ ID NO: 29) at the C terminus is preincubated in 50 mM Tris pH 7.5, 150 mM NaCl, on ice for 15 minutes and added to $5 \times 10^7$ RBCs in DMEM. The sortase and cell mixture is incubated on ice for 30 min with occasional gentle mixing, then spun at 500×g for 2 min at 4 C to remove buffer/DMEM, then washed three times with 1 mL of ice-cold PBS.

14. Gas

The following steps are taken to load erythroid cells with nitric oxide (NO). To avoid oxidative side reactions or S-nitrosylation of erythrocytic proteins other than Hb by S-nitrocysteine (CSNO), S-nitrosothiol (SNO)Hb is synthesized in intact RBCs by (i) addition of aqueous NO to fully deoxygenated RBCs to yield Fe-nitrosylHb [HbFe(II)NO]; (ii) washing under anaerobic conditions; and (iii) reoxygenation, effecting intraerythrocytic intramolecular transfer of NO from heme [Fe(II)NO] to Cys-B93. Sulfanilamide [SA; 3.4% (wt_vol)] in 0.4MHCl is prepared with and without 1% (wt/vol) HgCl2, as is 0.1% (wt/vol) of N-(1-naphthyl) ethylenediamine (NED). Equal volumes of SNOHb are added to SA with or without HgCl2 and then reacted with NED. [SNO] is determined from the difference in absorbance (540 nm) using colorimetry.

15. Small Molecule (Cytoplasm)

Liposomal ProJect reagent (Pierce) is dried under nitrogen into a thin film in glass scintillation vials. Approximately 2 uL reagent is needed per $10^5$ cells. Solution of small molecule of interest in PBS is added to the dried liposome reagent. The solution is pipetted several times, incubated for 5 minutes at room temperature, then vortexed vigorously to generate encapsulating liposomes. Serum-free medium is added to bring the total volume to 500 uL per $10^5$ cells. The liposomal mixture is incubated with the cells for 3-4 hours at 37° C.

16. Small Molecule (Surface)

The conjugation of small molecules to the surface of cells using chemical functionalities is well known in the art, see e.g., Hermanson G T, Bioconjugation Techniques $2^{nd}$ Ed, ISBN 978-0123705013. Briefly, the small molecule of interest is provided with an amine-reactive functional group, such as NHS ester, for example NHS ester biotin (Pierce). The small molecule of interest is stored in organic solvent to prevent hydrolysis of the NHS ester functional group. The small molecule of interest is incubated with cells in aqueous medium in large molar excess (at least 10 pmol for $10^6$ cells) to drive conjugation to primary amines on the cell surface. After 1 hr incubation, the excess unreacted molecule is removed by centrifugation and washing of the cells.

Example 8

Assessment of Polypeptide Presence

1. Fluorescent Transgene

Erythroid cells were cultured as described herein. A transgene encoding glycophorin A with an HA tag on the C-terminus fused to GFP with an intervening viral T2A peptide was constructed by Gibson assembly as described herein. The transgene was introduced into the erythroid cells by lentiviral transduction as described herein. Two days after transduction, cells were collected, washed in PBS buffer, and analyzed on a flow cytometer (Attune, Life Technologies). Transduction efficiency was assessed as the percentage of GFP-positive cells in the population.

2. Cell Surface Proteins

For cell surface proteins, the level of protein expression can be detected as early as 2 days after transfection by flow cytometry with antibodies specific for the protein or for a co-expressed epitope tag. Erythroid cells were cultured as described herein. A transgene encoding glycophorin A with an HA tag at the N-terminus was constructed by Gibson assembly as described herein. The transgene was introduced into the erythroid cells by lentiviral transduction as described herein. Two days after transduction, cells were collected, washed in PBS buffer, and stained with 1:50 dilution of mouse anti-HA antibody (Abcam) for 1 hr. Cells were washed and then stained with a 1:100 dilution of alexa 488-labeled goat anti-mouse secondary antibody (Life Technologies) for 30 minutes on ice. Cells were washed and analyzed on a flow cytometer (Attune, Life Technologies). Transduction efficiency was assessed as the percentage of alexa 488-positive cells in the population.

3. Intracellular Proteins

For intracellular proteins, the level of protein expression can be detected as early as 8-12 hours after transfection by Western Blot. Erythroid cells were cultured as described herein. A transgene encoding adenosine deaminase with an HA tag at the C-terminus was constructed by Gibson assembly as described herein. The transgene was introduced into the erythroid cells by lentiviral transduction as described herein. Two days after transduction, cells were collected, washed in PBS buffer, and lysed in RIPA cell lysis buffer (Pierce). Cell lysate was denatured by boiling in 100 mM DTT, then loaded onto a NuPage SDS-PAGE pre-cast gel. After electrophoresis and transfer to nitrocellulose membrane, protein bands were developed by staining with 1:5000 dilution of mouse anti-HA antibody (Abcam) followed by 1:5000 dilution of goat anti-mouse HRP (Pierce), and subsequent treatment with HRP substrate (SuperSignal, Pierce). Images were captured using an Amersham imager (GE healthcare).

Example 9

Assessment of Small Molecule Presence

Eyrthrocytes from a normal human donor were purchased (Research Blood Components). Cells were then biotinylated with NHS-biotin (Sigma) per manufacturer's instructions using 0.02× volumes of 2 mM stock biotin reagent for 30 minutes at room temperature. Anti-biotin antibody (Abcam) was fluorescently labeled with Dylight 650 (Pierce). Labeling efficiency of the cells was assessed by flow cytometry as described herein using the labeled anti-biotin antibody as a detection marker.

Example 10

Assessment of Gas Level

A standard protocol is used to determine $NO_2^-$ and $NO_3^-$-levels in the three blood components, see e.g., Yang et al. 2003, Free Radic Res 37(1):1. Briefly, a "stop solution" ($K_3Fe(CN)_6$, N-ethylmaleimide, water, NP40) is added to blood to maintain nitrite levels until sample analysis. A 1:4 dilution of "stop solution" to blood is vortexed and placed on dry ice. At the time of sample analysis, a 1:1 dilution of 99.9% pure methanol and thawed sample is centrifuged for 2 min at 13,000 rpm; the supernatant is immediately injected into the chemiluminescent nitric oxide analyzer (NOA, Sievers, Model 280 NO analyzer, Boulder, Colo.) using helium as the carrier gas. The triiodide (I3-) ozone-based chemiluminescent assay is used to analyze nitrite levels. To analyze nitrate, deionized water (Millipore CQ-Gard, Bedford, Mass.) is added to blood to lyse cells. A 9:1 dilution of deionized water to blood is vortexed and placed on dry ice. At the time of sample analysis, a 3:1 dilution of pure HPLC grade ethanol and thawed sample is centrifuged, and the supernatant is immediately analyzed using a Vanadium(III) chloride chemiluminescent assay, see e.g., Ewing and Janero, 1998 Free Radic Biol Med 25(4-5):621. The VC13 reaction solution is maintained at 90° C. with helium as the carrier gas. 1 µM nitrite and nitrate solutions are used to generate standard curves for comparisons and adjustments of sample nitrite and nitrate concentrations.

A thiol-stabilization solution (NEM-DPTA; $K_3Fe(CN)_6$, N-ethylmaleimide, Diethylenetriaminepenta acetic acid, NP40, water) is added to blood to maintain SNOHb and HbNO levels by inhibiting additional thiol reactions. A 4:1 dilution of NEM-DPTA to blood is vortexed and placed on dry ice. A 9:1 dilution of sample and 5% acid sulfanilamide (AS) is incubated for 5 min; half is injected into the NOA (I3-assay) to give combined SNOHb and HbNO levels. The remaining sample is incubated with 50 mM $HgCl_2$, then incubated again with 5% AS, and injected into the NOA to give HbNO levels.

Example 11

Assessment of Expression and Activity

The expression of exogenous proteins in and on cultured cells can be assessed quantitatively by flow cytometry (if the protein is expressed on the surface) or by Western blot (for proteins expressed in the cytoplasm).

1. Quantitative Flow Cytometry

Anti-mouse Fc-binding quantitative flow cytometry beads (Simply Cellular Calibration) were purchased from Bangs Labs. Fluorescently labeled mouse antibodies against relevant cell surface receptors—glycophorin A, Ckit, and transferrin receptor—were purchased from BioLegend. Fluorescently labeled mouse antibody against the HA epitope tag was purchased from Life Technologies. Erythroid cells were cultured as described herein. A transgene encoding glycophorin A with an HA tag at the N-terminus was constructed by Gibson assembly as described herein. The transgene was introduced into the erythroid cells by lentiviral transduction as described herein. At least two days after transduction, $2 \times 10^5$ cells were collected, washed in PBS buffer, and stained with 1:100 dilution of one of the above-listed antibodies for 1 hr. Cells were washed and analyzed on a flow cytometer (Attune, Life Technologies). The protocol was repeated for each of the four antibodies listed above. Quantification was performed according to manufacturer's instructions. Briefly, one drop of each of the five bead samples was incubated with 1:100 dilution of an above-listed antibody. The beads were incubated for 1 hr, washed in PBS, and analyzed on a flow cytometer (Attune, Life Technologies). The protocol was repeated for each of the four antibodies listed above. Calibration curves were fit using the manufacturer's provided excel spreadsheets, from which quantification of fluorescence intensity for the cell-based signals was derived.

2. Quantitative Western Blot

Erythroid cells were cultured as described herein. A transgene encoding adenosine deaminase with an HA tag at the C-terminus was constructed by Gibson assembly as described herein. The transgene was introduced into the erythroid cells by lentiviral transduction as described herein. Two days after transduction, cells were collected, washed in PBS buffer, and lysed in RIPA cell lysis buffer (Pierce).

The transgene was introduced into HEK293T cells by transient transfection using lipofectamine 2000 (Life technologies). Cells were cultured for one week and the supernatant was harvested. Recombinant protein was purified on an HA affinity column (Pierce) according to manufacturer's instructions. Protein concentration was assessed by absorbance at 280 nm.

Western blotting was performed as described herein. In addition to the cell lysate samples, known amounts of the recombinant adenosine deaminase were run on the same gel. Following image collection, the intensity of the recombinant bands were used to generate a standard curve to quantify the amount of protein present in the cell samples.

Figure 2:
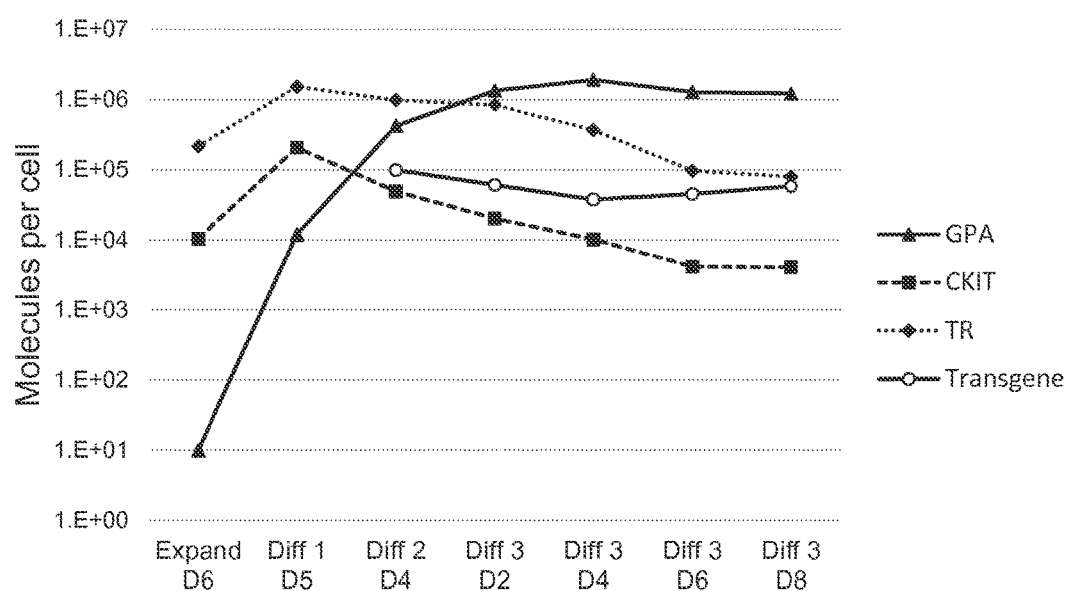
FIG. 2 is a plot of cell surface expression levels assessed by quantitative flow cytometry. The plot shows of various cell surface receptors—glycophorin A (solid triangles), cKIT (dashed squares), transferrin receptor (dotted diamonds)—and an exogenous surface transgene (open circles) during the course of erythroid cell differentiation.

The robust expression of transgenes at high levels has important implications for the therapeutic capacity of the final cell population. FIG. 2 quantifies the expression of three surface proteins indicative of differentiation and one exogenous transgene by quantitative flow cytometry, and demonstrates that the transgene is robustly expressed at a high level.

Erythroid cells in culture were collected at seven time points during a four-stage in vitro differentiation process. At the first time point ("Expand D6") the cells are nucleated hematopoietic precursors. By the final time point ("Diff 3 D8") the cells are predominantly enucleated erythroid cells. GPA (solid triangles), a canonical marker of erythroid cells, starts low in the precursor cells and rapidly reaches $>1 \times 10^6$ copies per cell. CKIT (dashed squares), a receptor for stem cell factor, starts high then decreases to $<1 \times 10^4$ copies per cell as differentiation ensues. TR (dotted diamonds), necessary for the transport of iron into erythroid cells, increases initially then gradually declines to <1×10^5 copies per cell. The transgene (open circles) is introduced at the end of the second differentiation stage ("Diff 1") and is steadily expressed at approximately 1×10^5 copies per cell throughout differentiation. The above data demonstrate that transgenes are robustly expressed in cultured cells.

The expression of exogenous proteins in and on cultured cells can be assessed by flow cytometry (if the protein is expressed on the surface) as described herein, or by Western blot (for proteins expressed in the cytoplasm) as described herein. In instances where an exogenous gene is in a single-transcript construct that contains a downstream fluorescent reporter protein, the fluorescence of the reporter protein can be used as a proxy for expression of the upstream gene, and assessed by flow cytometry as described herein.

Figure 3A:
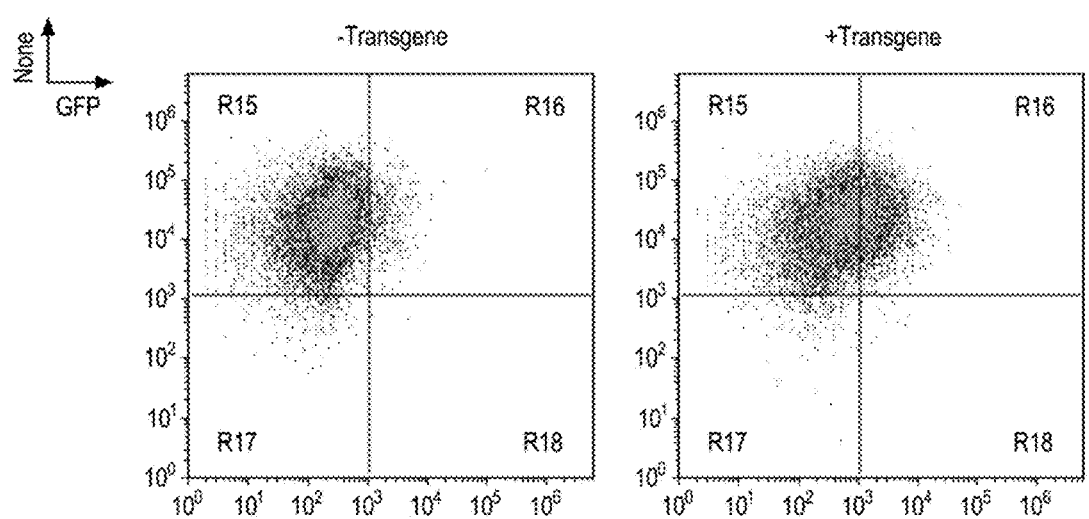
FIG. 3A-FIG. 3AP is a collection of flow cytometry plots and Western blots that demonstrate the expression of a vast array of exemplary receivers on the surface, in the cytoplasm, as fusions, and as intact proteins, in three cell types, enucleated erythroid cells, nucleated erythroid precursor cells, and erythroleukemic cells.
Figure 3B:
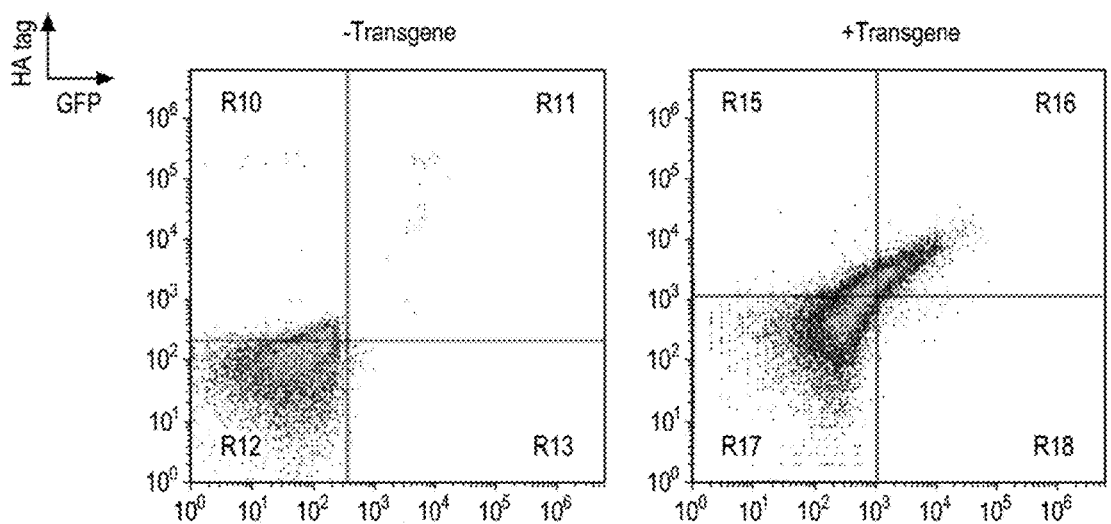
FIG. 3B—Expression of glycophorin A with an HA epitope tag at the N terminus between the leader sequence and the body of the gene assessed by anti-HA staining.
Figure 3C:
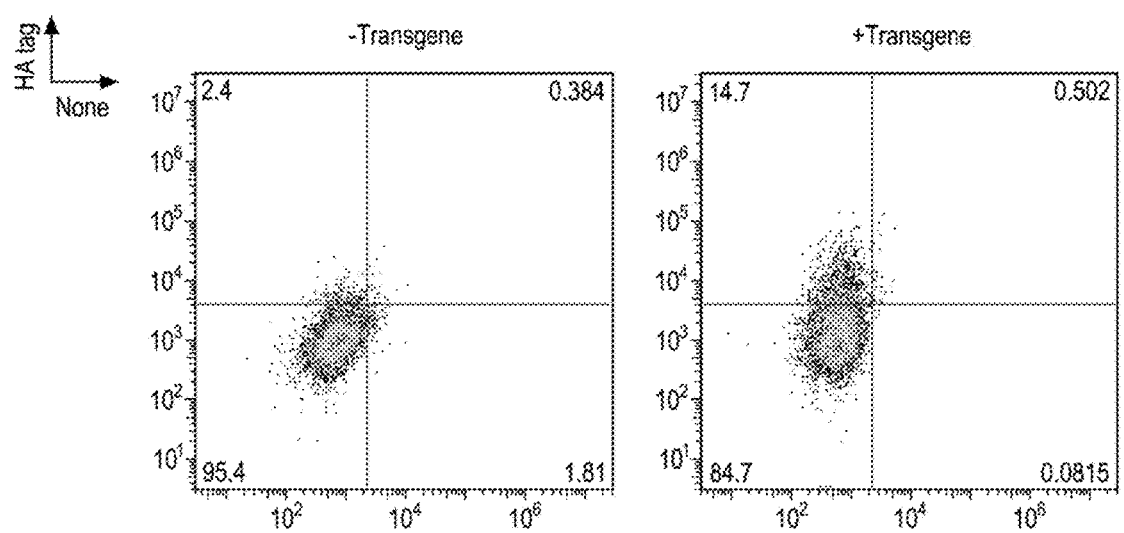
FIG. 3C—Expression of complement receptor 1-derived fragment of ~70 kDa with an HA epitope tag at the N terminus assessed by anti-HA staining.
Figure 3D:
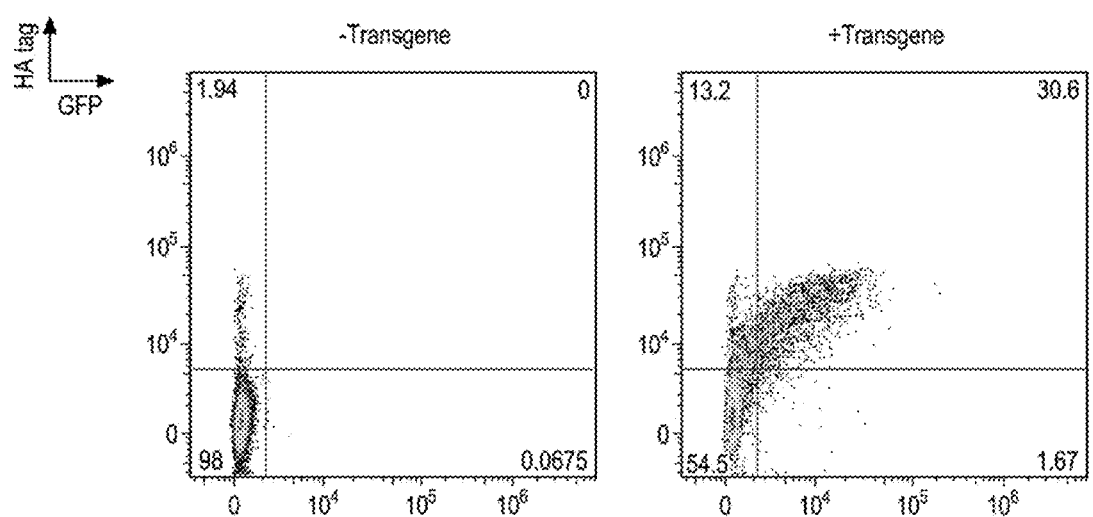
FIG. 3D—Expression of antibody scFv as N terminal fusion to glycophorin A assessed by anti-HA staining.
Figure 3E:
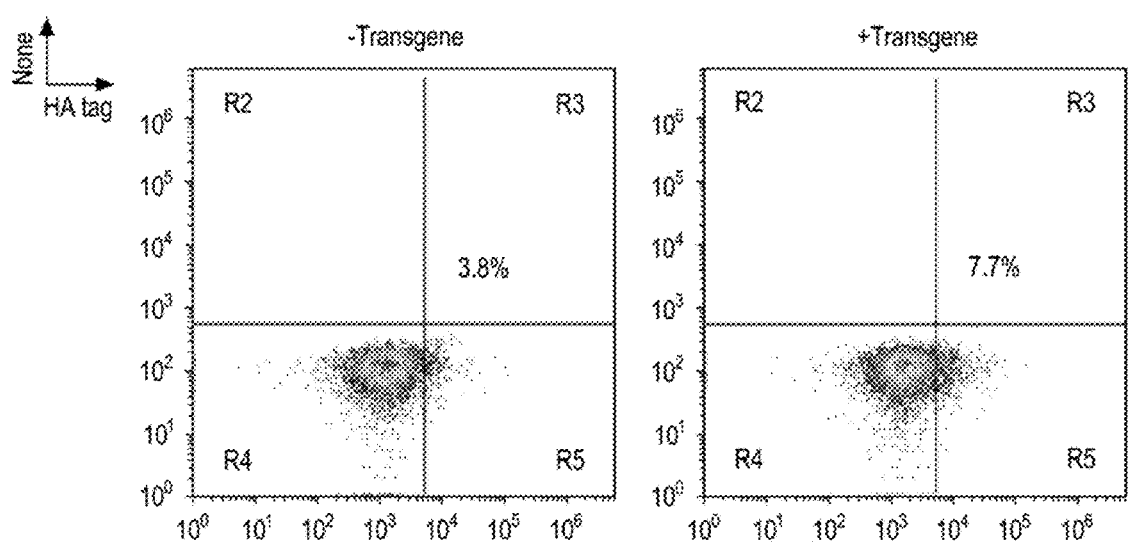
FIG. 3E—Expression of antibody scFv fused to C terminus of Kell-derived fragment of 71 amino acids assessed by anti-HA staining.
Figure 3F:
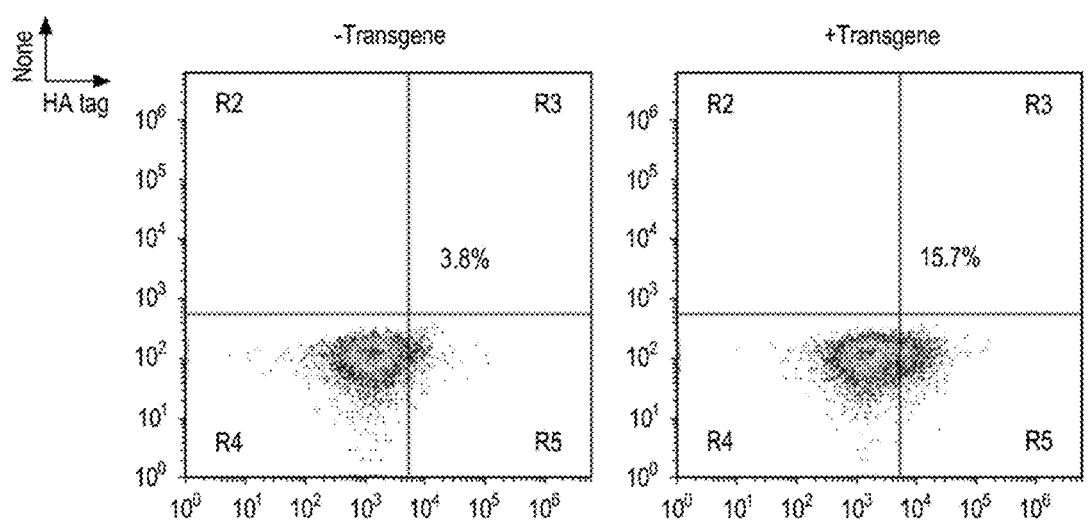
FIG. 3F—Expression of antibody scFv fused to C terminus of Kell-derived fragment of 79 amino acids assessed by anti-HA staining.
Figure 3G:
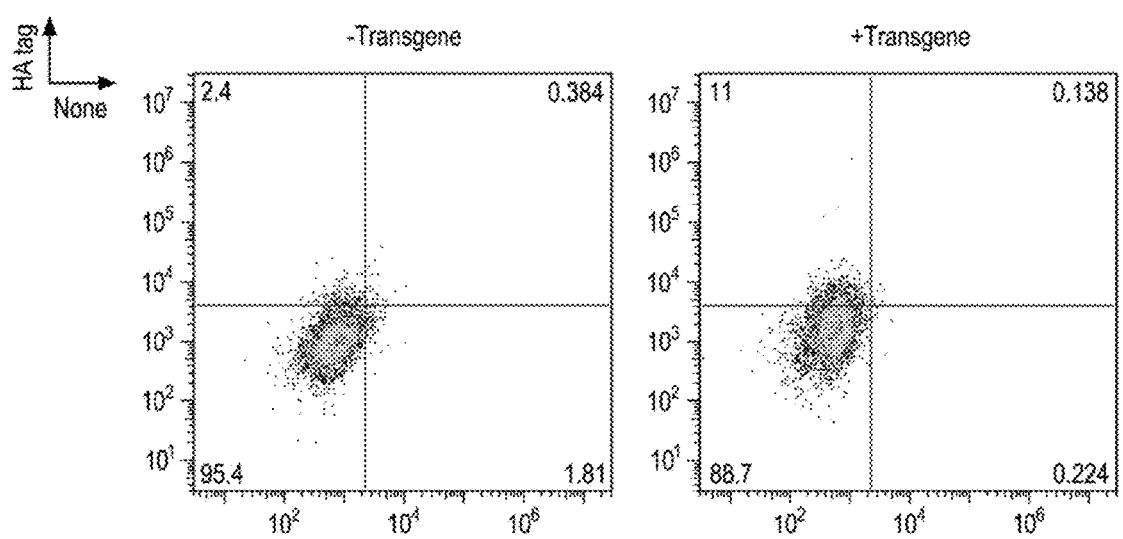
FIG. 3G—Expression of CD55 with HA epitope tag at the extracellular N terminus after the leader sequence assessed by anti-HA staining.
Figure 3H:
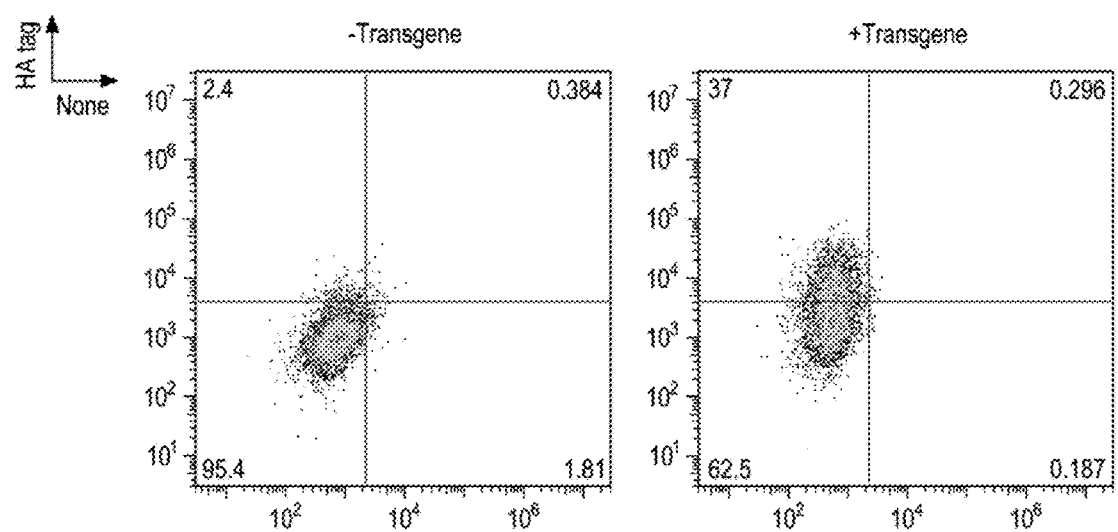
FIG. 3H—Expression of CD59 with HA epitope tag at the extracellular N terminus after the leader sequences assessed by anti-HA staining.
Figure 3L:
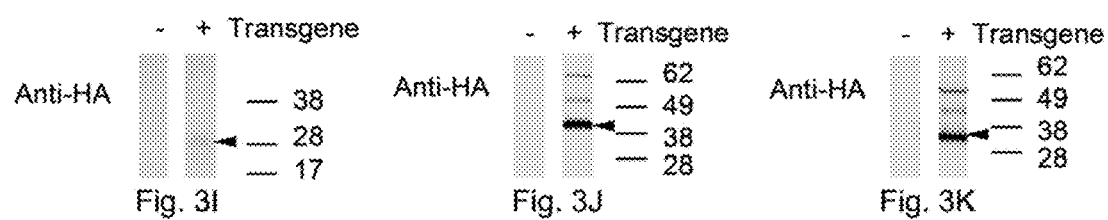
FIG. 3L—Cytoplasmic expression of phenylalanine hydroxylase fused to adenosine deaminase and an HA tag assessed by anti-HA Western blot.
Figure 3L:
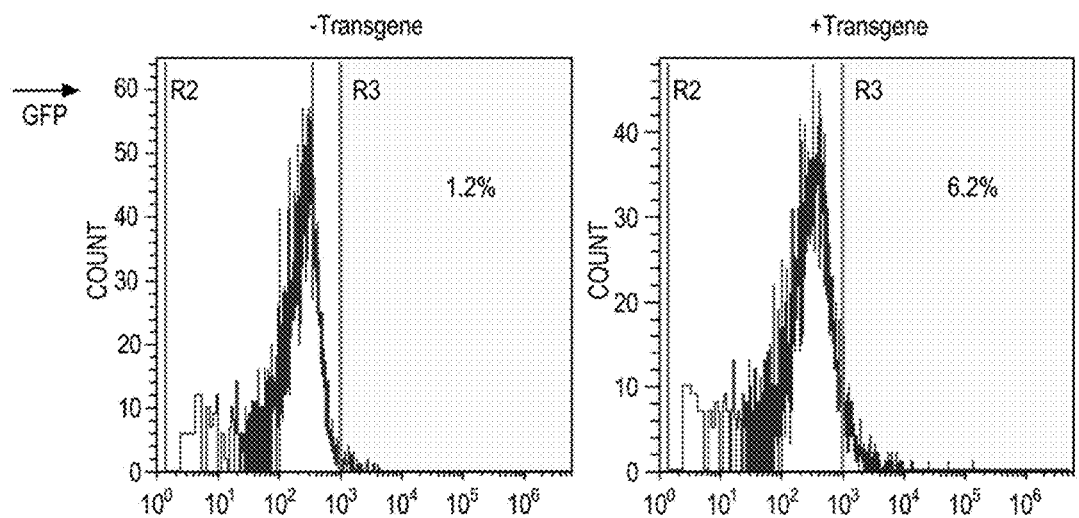
Figure 3M:
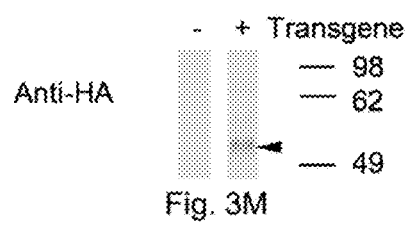
FIG. 3M—Cytoplasmic expression of adenosine deaminase fused to the intracellular C terminus of glycophorin A assessed by anti-HA Western blot. Expected size approximately 55 kDa.
Figure 3N:
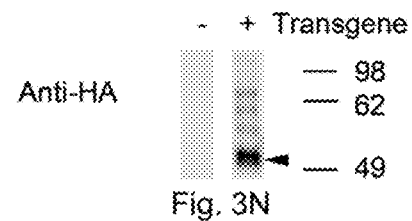
-FIG. 3N shows the exogenous expression of surface and cytoplasmic proteins on enucleated cultured erythroid cells.
Figure 3O:
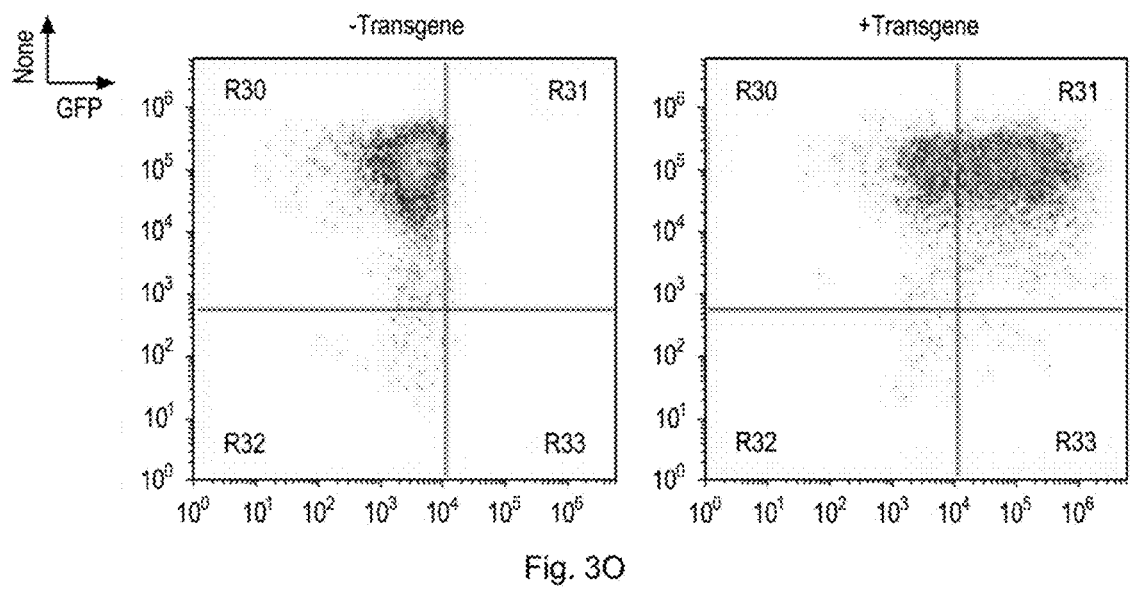
Figure 3P:
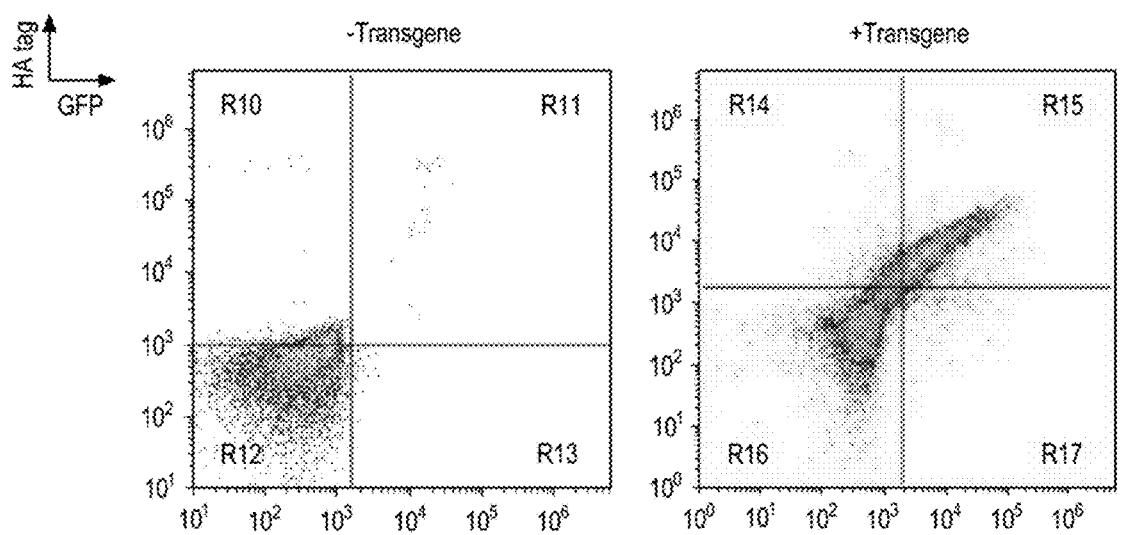
FIG. 3P—Expression of glycophorin A with an HA epitope tag at the N terminus between the leader sequence and the body of the gene assessed by anti-HA staining.
Figure 3Q:
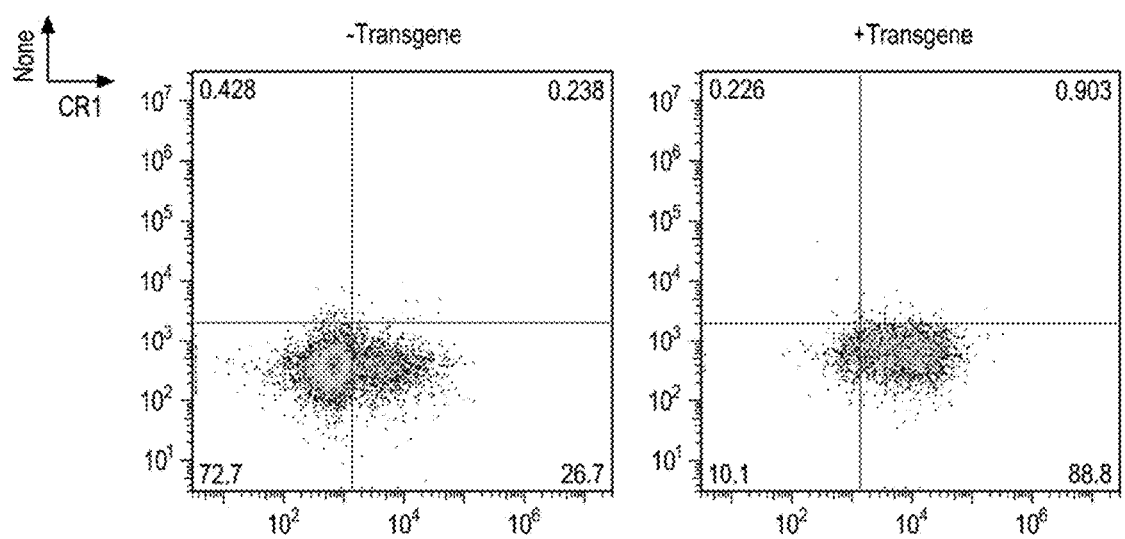
FIG. 3Q—Overexpression of complement receptor 1 assessed by anti-CR1 staining.
Figure 3R:
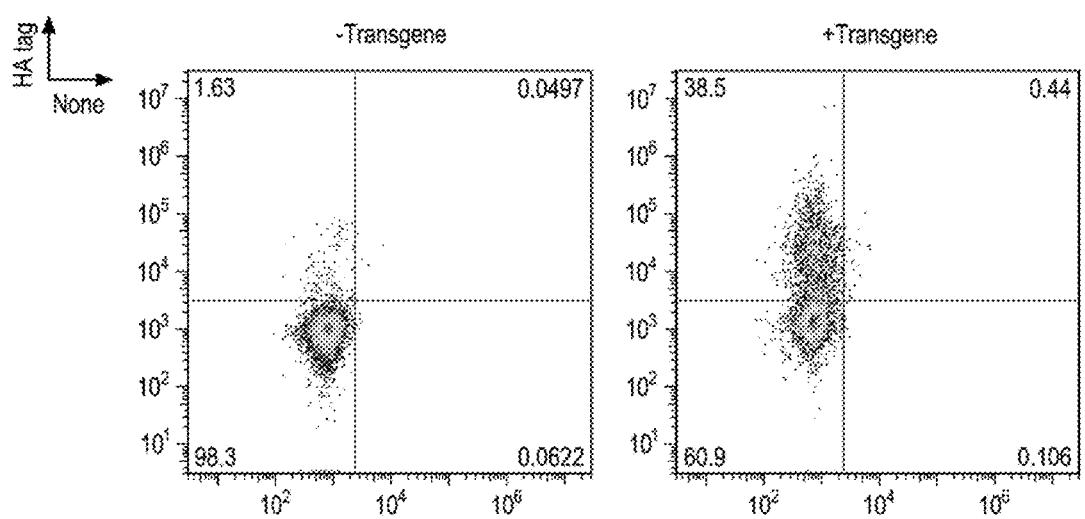
FIG. 3R—Expression of complement receptor 1-derived fragment of ~70 kDa with an HA epitope tag at the N terminus assessed by anti-HA staining.
Figure 3S:
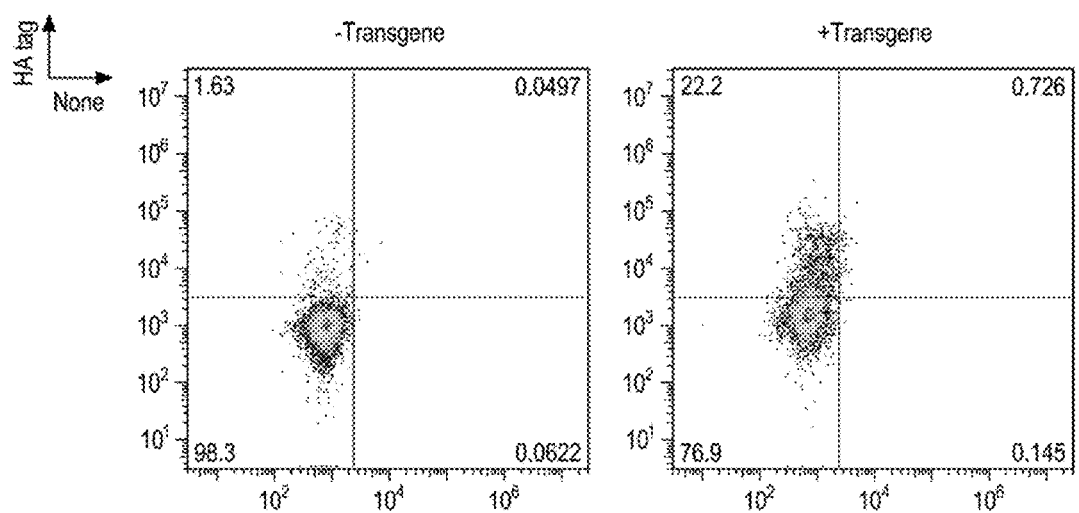
FIG. 3S—Expression of complement receptor 1-derived fragment of ~210 kDa with an HA epitope tag at the N terminus assessed by anti-HA staining.
Figure 3T:
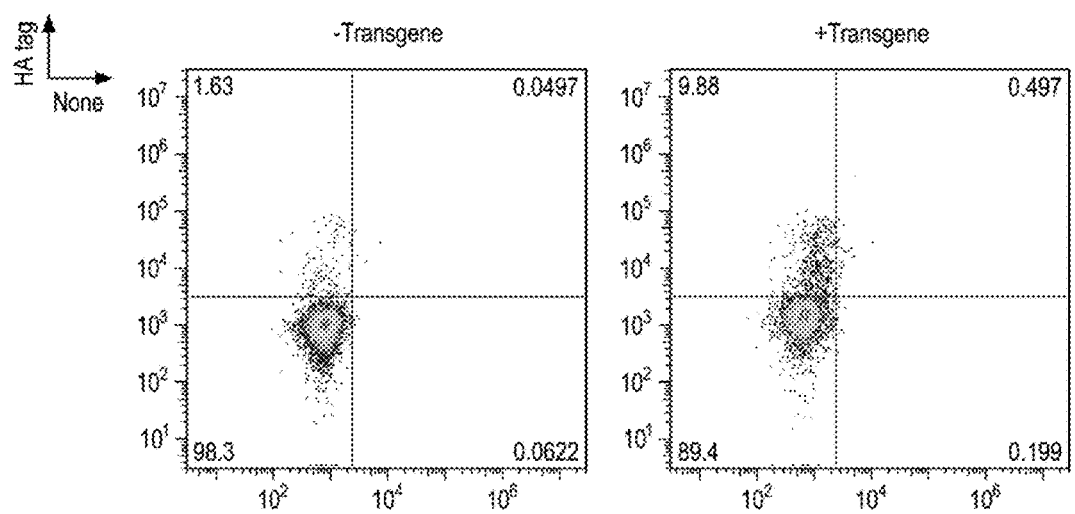
FIG. 3T—Expression of complement receptor 1-derived fragment of ~230 kDa fused to the N terminus of glycophorin A with an HA epitope tag at the N terminus assessed by anti-HA staining.
Figure 3U:
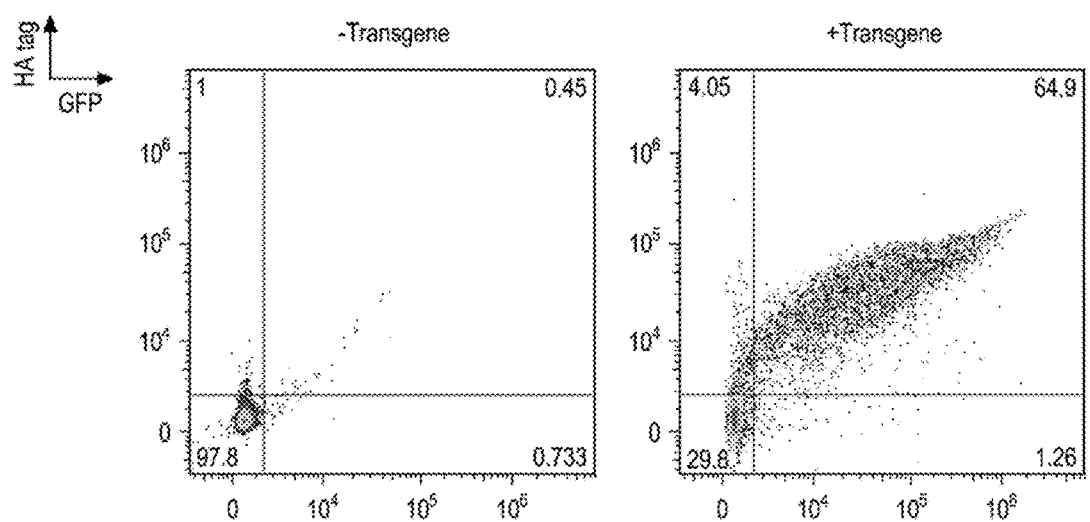
FIG. 3U—Expression of antibody scFv as N terminal fusion to glycophorin A assessed by anti-HA staining.
Figure 3V:
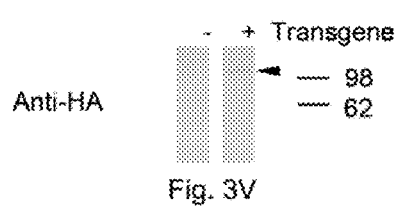
FIG. 3V—Expression of antibody scFv fused to the extracellular C terminus of Kell, assessed by anti-HA staining. Expected size approximately 108 kDa.
Figure 3W:
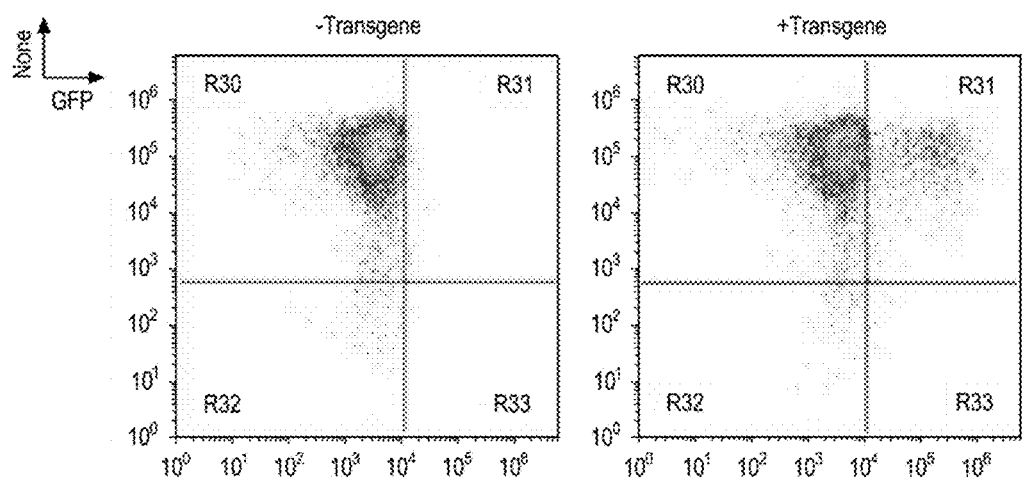
FIG. 3W—Expression of HA tag fused to the extracellular C terminus of Kell, assessed by anti-HA staining.
Figure 3X:
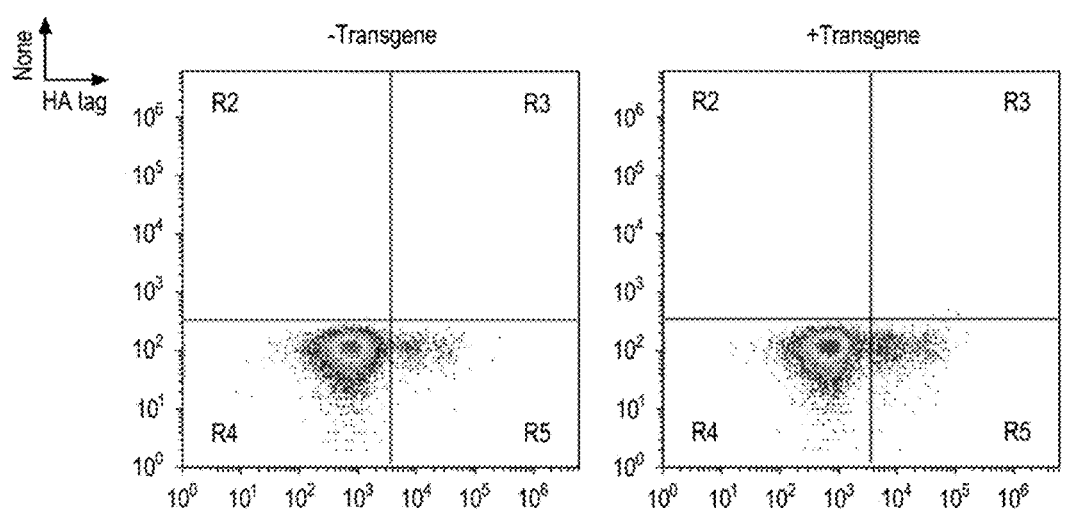
FIG. 3X—Expression of Kell-derived fragment of 71 amino acids with HA tag at the C (extracellular) terminus assessed by anti-HA staining.
Figure 3Y:
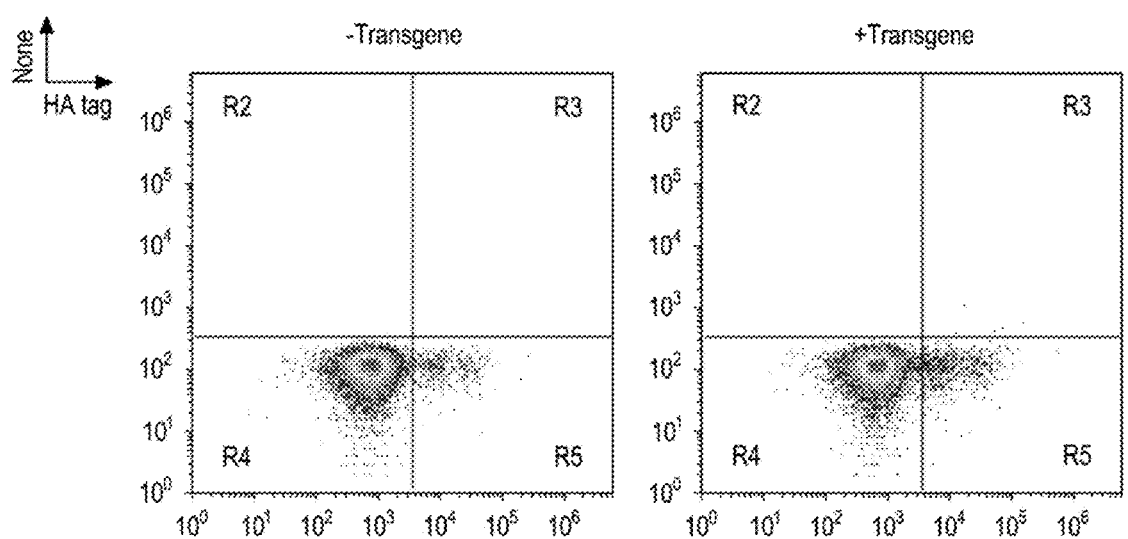
FIG. 3Y—Expression of Kell-derived fragment of 79 amino acids with HA tag at the C terminus assessed by anti-HA staining.
Figure 3Z:
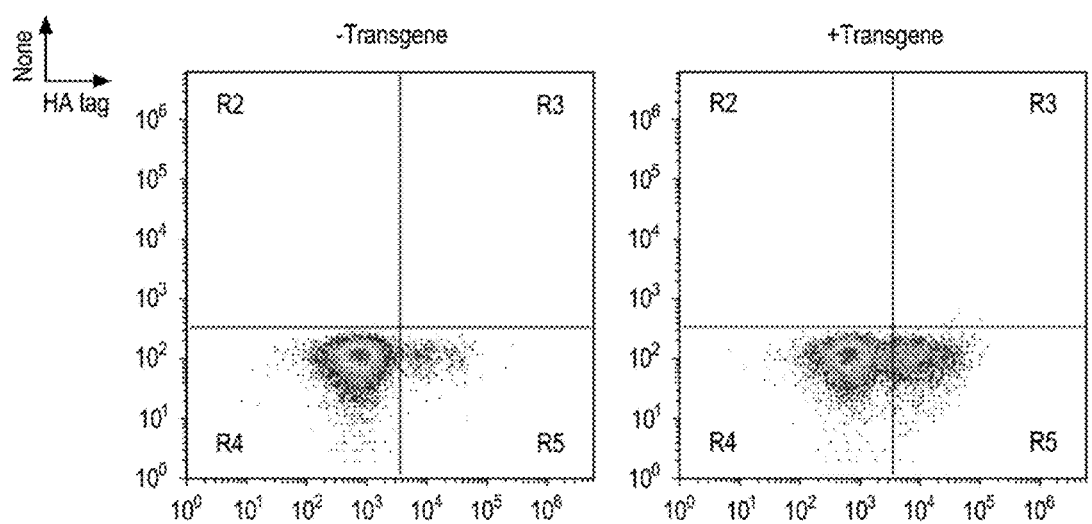
FIG. 3Z—Expression of antibody scFv fused to C terminus of Kell-derived fragment of 71 amino acids assessed by anti-HA staining.
Figure 3A:
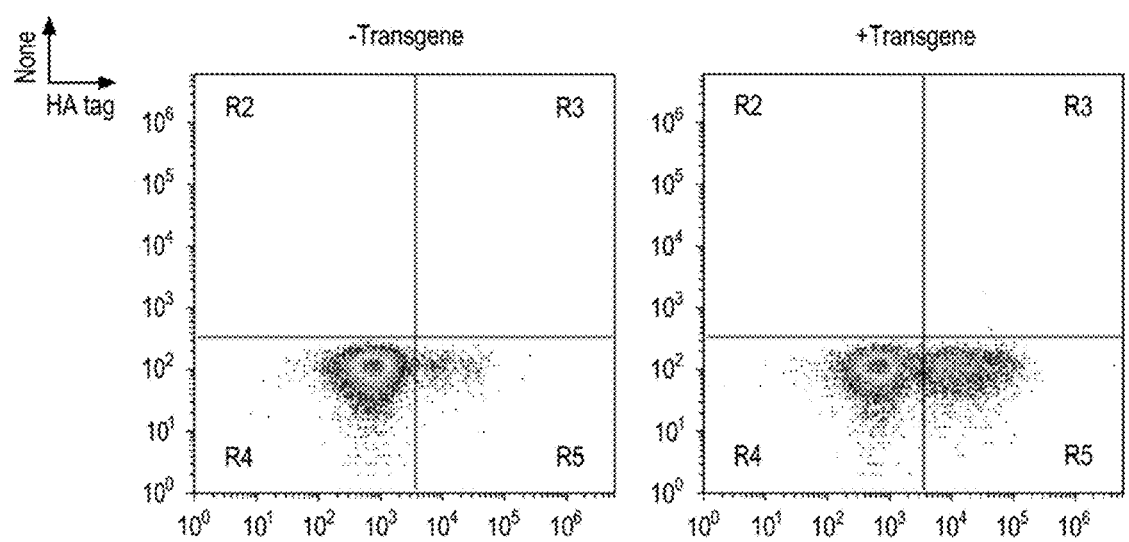
Figure 3A:
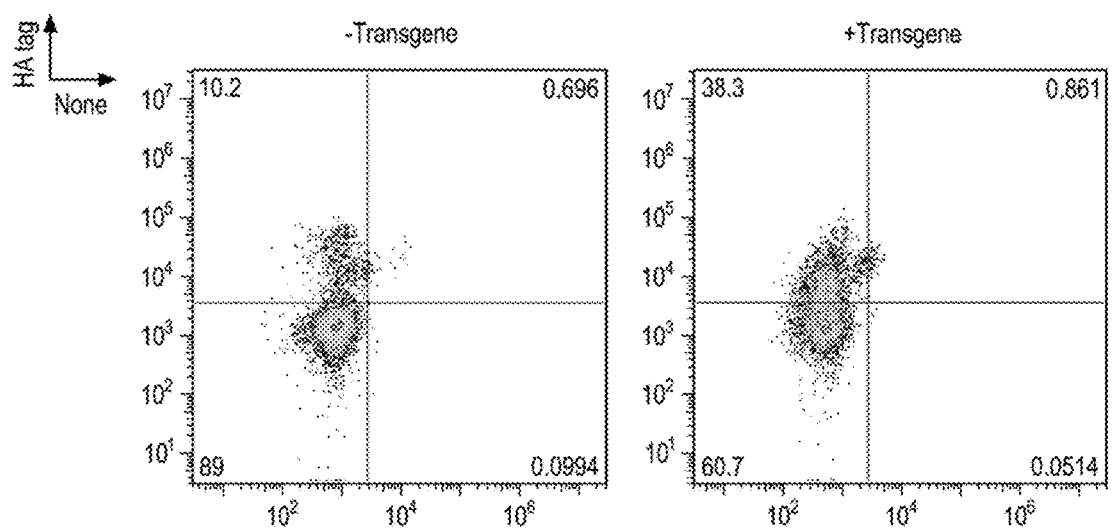
Figure 3A:
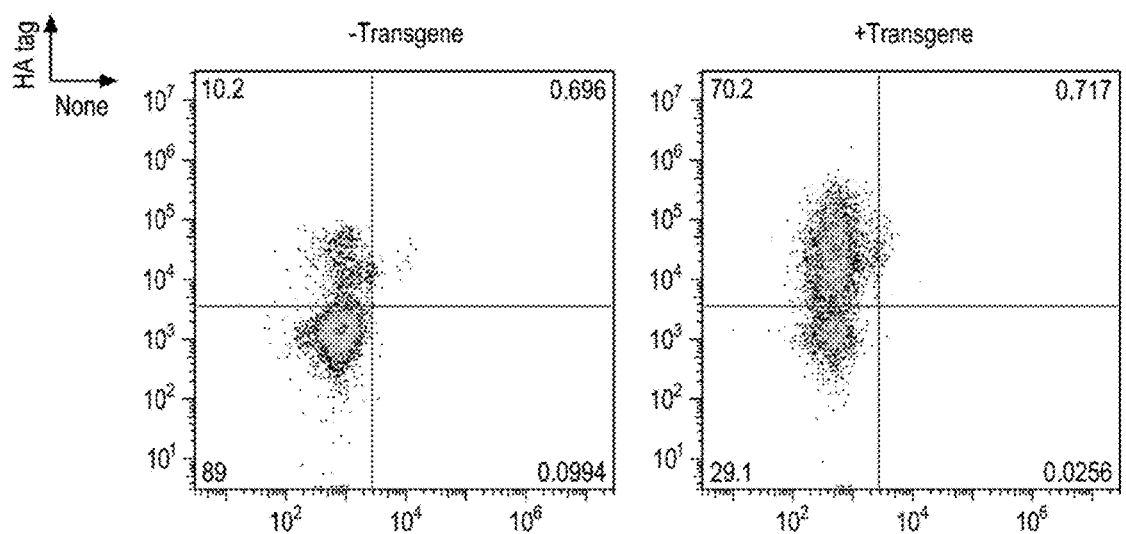
Figure 3A:
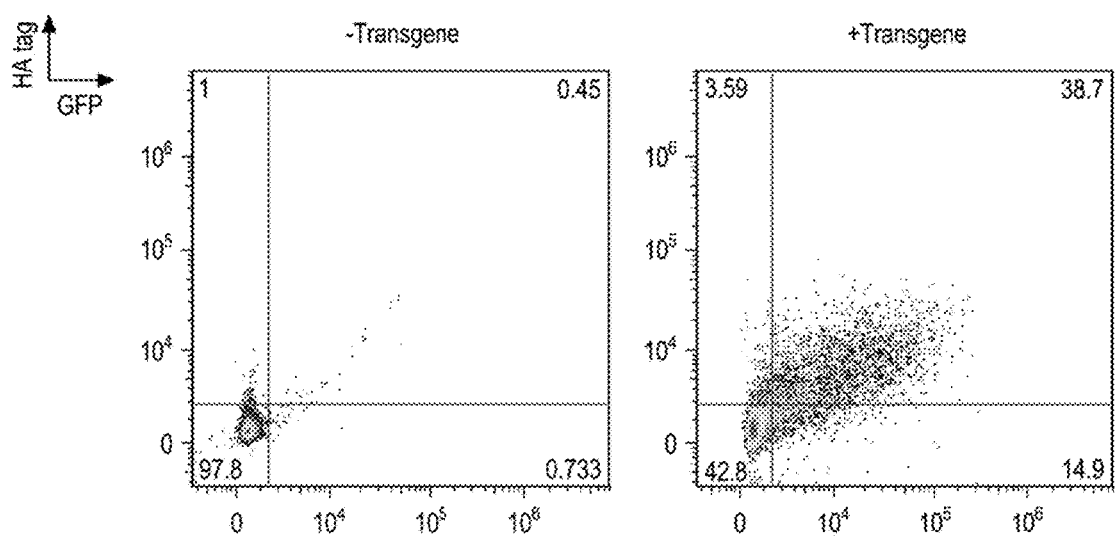
Figure 3A:
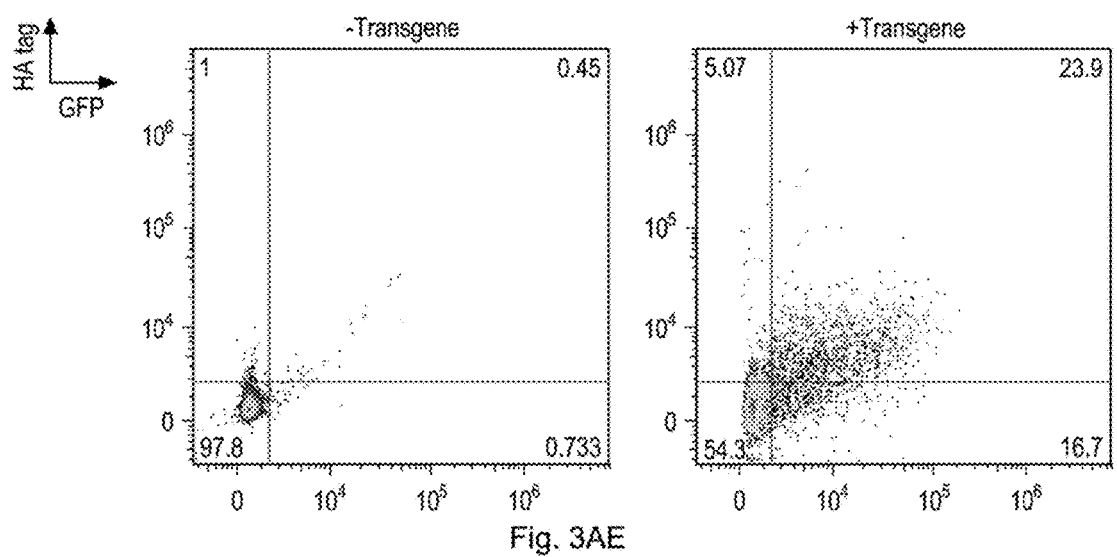
Figure 3A:
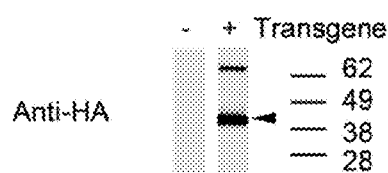
Figure 3A:
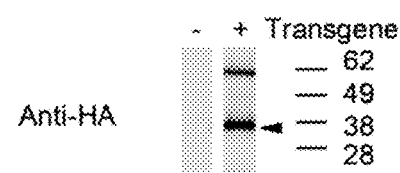
Figure 3A:
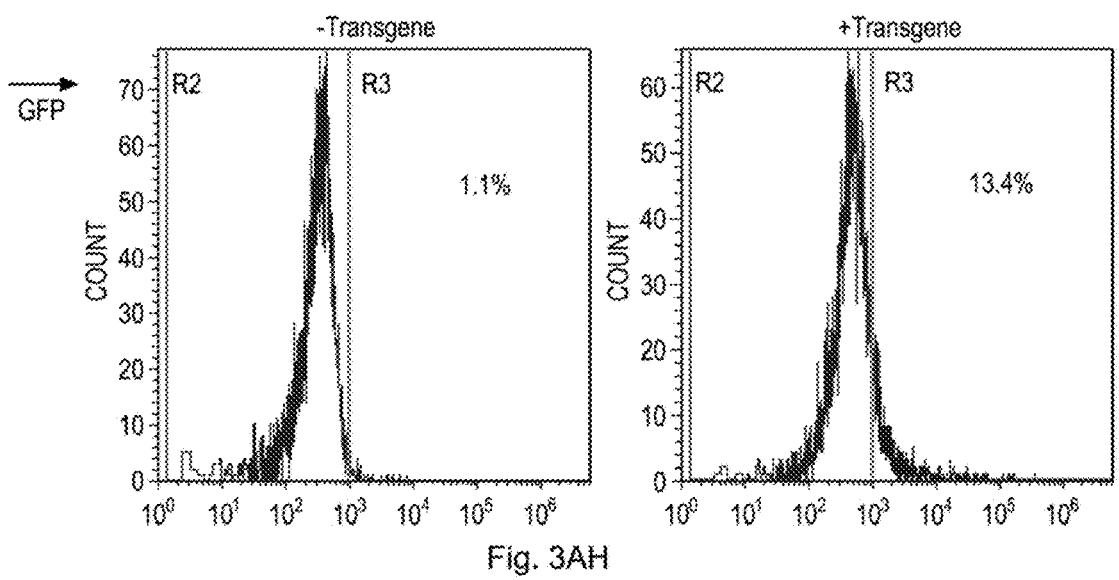
Figure 3A:
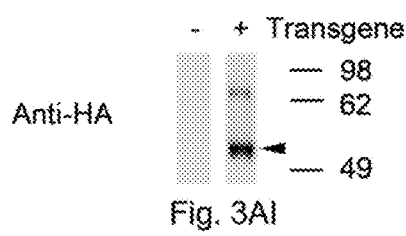
Figure 3A:
Figure 3A:
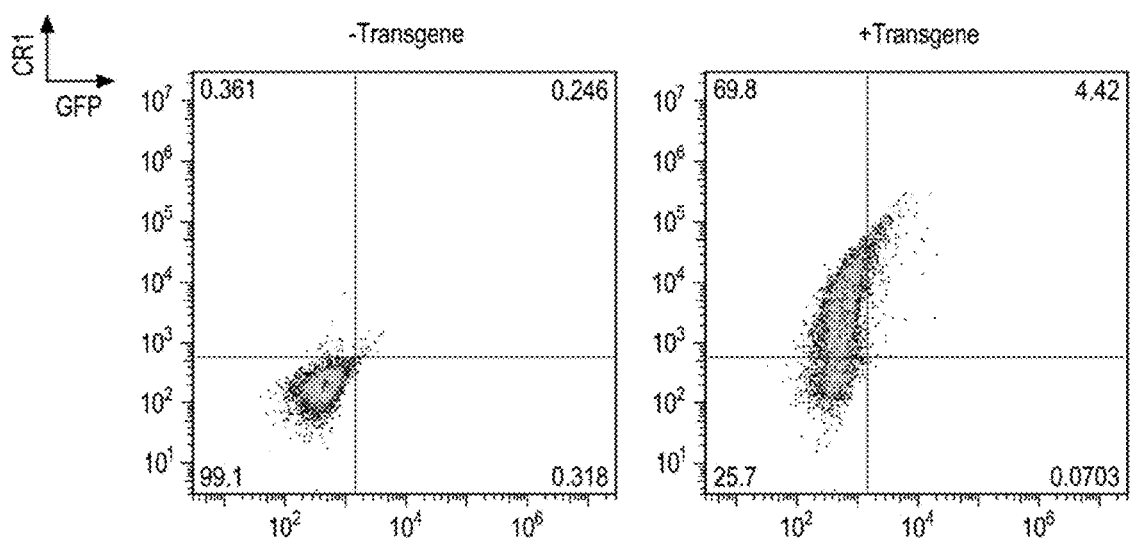
Figure 3A:
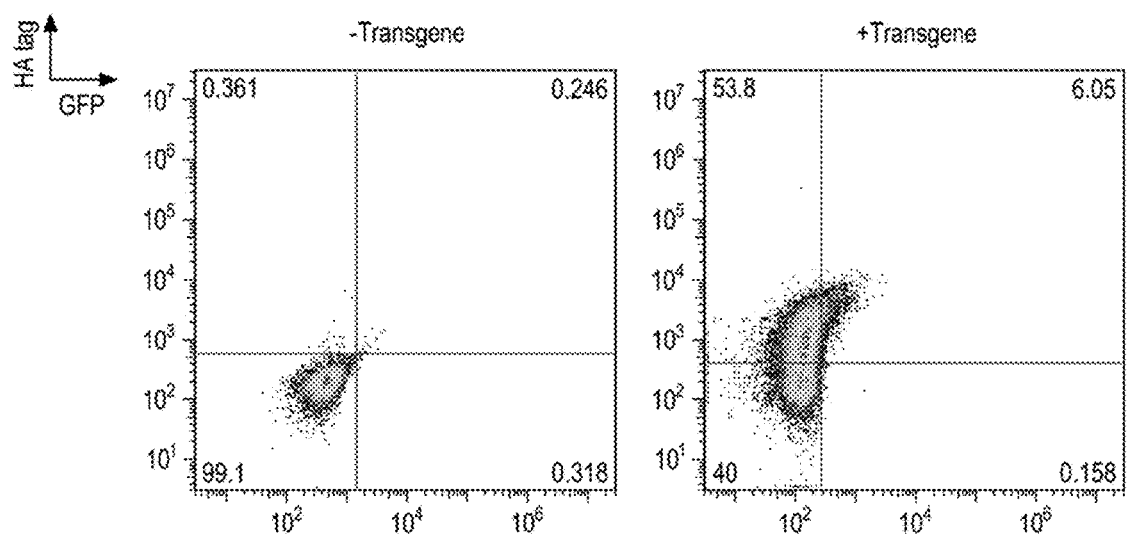
Figure 3A:
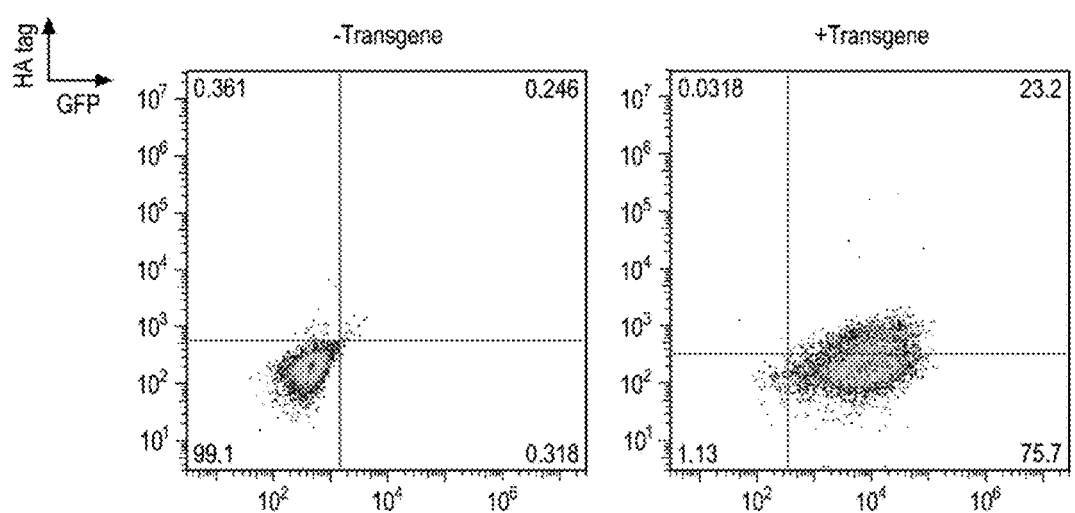
Figure 3A:
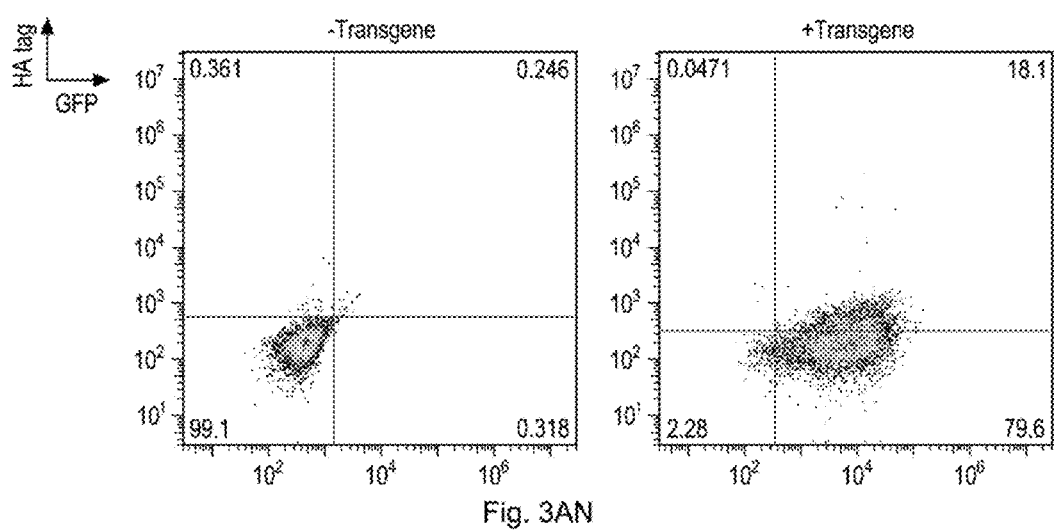
Figure 3A:
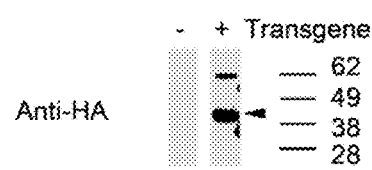
Figure 3A:
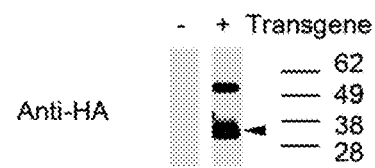

FIG. 3 A-FIG. 3N shows the exogenous expression of surface and cytoplasmic proteins on enucleated cultured erythroid cells. The above data conclusively demonstrate that multiple protein classes—including cytoplasmic, surface, intact, fusions to type I membrane proteins, fusions to type II membrane proteins, fusions to GPI-linked membrane proteins, intracellular fusions, overexpressed, and de novo expressed—can be expressed on multiple cell types including cultured enucleated erythroid cells, cultured nucleated erthyroid precursor cells, and K562 erythroleukemia cells.

FIG. 3B and FIG. 3D demonstrate the simultaneous expression of two exogenous proteins in an enucleated cultured cell.

In FIG. 3B, Erythroid cells were cultured as described herein. A transgene construct encoding glycophorin A signal sequence, an HA epitope tag, glycophorin A coding sequence, viral T2A cleavable sequence and GFP was assembled by Gibson assembly as described herein. The transgene was introduced into the erythroid cells by lentiviral transduction as described herein. The cells were cultured to terminal differentiation as described herein. Cells were analyzed by flow cytometry as described herein, using a fluorescent anti-HA antibody and GFP fluorescence to detect expression of both transgenes.

In FIG. 3D, Erythroid cells were cultured as described herein. A transgene construct encoding glycophorin A signal sequence, antibody scFv specific to hepatitis B surface antigen, HA epitope tag, glycophorin A coding sequence, viral T2A cleavable sequence and GFP was assembled by Gibson assembly as described herein. The transgene was introduced into the erythroid cells by lentiviral transduction as described herein. The cells were cultured to terminal differentiation as described herein. Cells were analyzed by flow cytometry as described herein, using a fluorescent anti-HA antibody and GFP fluorescence to detect expression of both transgenes.

Example 12

Expression of Protein from mRNA in Platelets

The expression in platelets of exogenous proteins translated from exogenous transfected mRNA was measured by flow cytometry. In brief, platelet-enriched serum was centrifuged at 190 g for 15 minutes to remove erythrocytes and leukocytes. The supernatant was then spun for an additional 5 minutes at 2500 g to pellet platelets. Platelets were resuspended in 5 mL of Tyrode's buffer with 1 uM prostaglandin, washed, and resuspended in 750 uL of Tyrode's buffer with 1 uM prostaglandin. mRNA encoding the gene of interest, in this example GFP, was mixed with lipofectamine at a 1:1 mg/mL ratio. The mixture was incubated for 5 minutes, then added to the washed platelet population. The combination was incubated for 24 hours at room temperature with slow rocking. Platelet expression of the transgene was assayed by flow cytometry measuring GFP fluorescence. Surface proteins can also be assayed by flow cytometry. Cytoplasmic or other intracellularly-expressed proteins can also be assayed by Western blot.

There is therapeutic relevance to introducing exogenous proteins into and onto platelets. Since platelets do not possess a nucleus or RNA transcription machinery, DNA transfection is not a viable means of inducing exogenous protein expression in platelets. However, mRNA transfection and translation is a way of introducing exogenous proteins into cells. It is thought that platelets contain mRNA translation machinery, but until now it was not known whether they are able to accept and translate exogenous mRNA into protein.

Figure 4A:
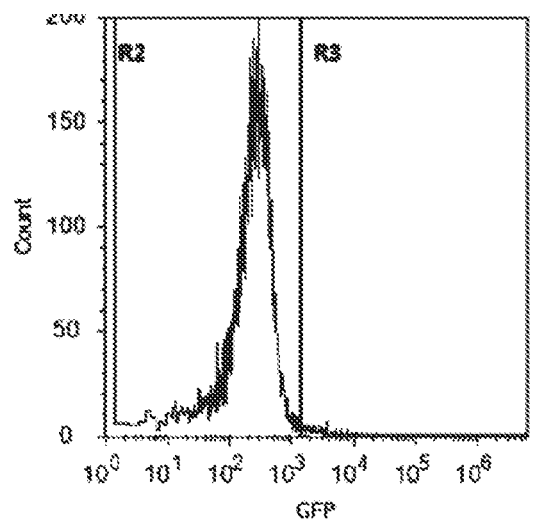
FIG. 4A-FIG. 4C is a collection of flow cytometry histograms that measure fluorescence in primary platelets that have been transfected with mRNA encoding a fluorescent protein (GFP).
Figure 4B:
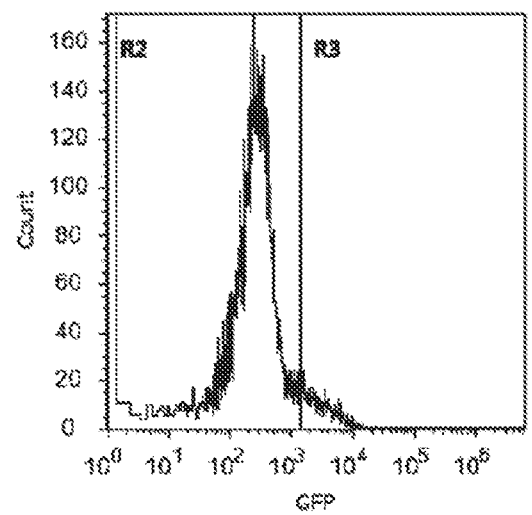
Figure 4C:
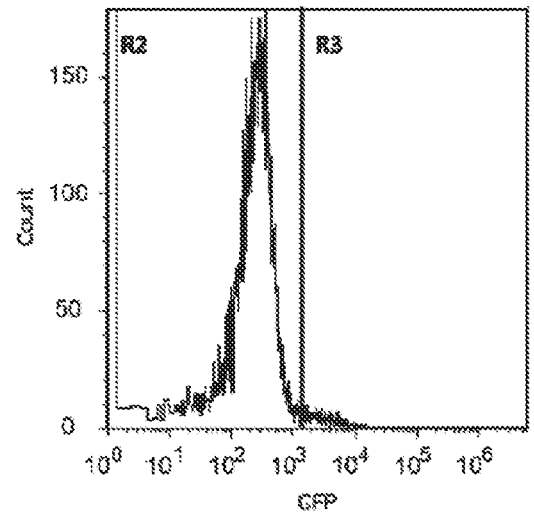

FIG. 4A-FIG. 4C is a collection of flow cytometry plots that demonstrate the translation of exogenous mRNA encoding a transgene, in this case GFP, by platelets. The GFP is detected by fluorescence in the FL1 channel after excitation with a 488 nm laser. (FIG. 4A) Untransfected platelets (1.7% GFP+). (FIG. 4B) Platelets transfected with 3 ug GFP mRNA (8.6% GFP+). (FIG. 4C) Platelets transfected with 6.8 ug GFP mRNA (3.3% GFP+).

The data conclusively demonstrate, for the first time, the translation of exogenous mRNA into exogenous protein by platelets.

Example 13

Activity of Enzymes

FIG. 5A-FIG. 5D demonstrates the activity for enzymes contained on erythroid cells. Biochemical activity of cytoplasmic enzymes was assessed by Western blot for retention of a protein over the course of differentiation. Biological activity of cytoplasmic enzymes was assessed by in vitro enzymatic activity assay.

FIG. 5A-FIG. 5D shows the activity of two different intracellular enzymes expressed in cultured erythroid cells.

1. Adenosine Deaminase.

A transgene encoding adenosine deaminase with an HA tag at the C-terminus was constructed by Gibson assembly as described herein. The transgene was introduced into HEK-293T cells by lipofectamine transfection (Life Technologies) as described herein. Enzymatic activity is assayed using a protocol derived from Helenius 2012, Biochim Biophys Acta 1823(10):1967, in which a specific mixture of enzymes convert purines into uric acid and H2O2 followed by fluorometric detection of the generated H2O2. In brief, two days after transfection, cells were collected, media aspirated, and Krebs Ringer phosphate glucose (KRPG; comprising: 145 mM NaCl, 5.7 mM sodium phosphate, 4.86 mM KCl, 0.54 mM CaCl2, 1.22 mM MgSO4, and 5.5 mM glucose; pH 7.35) added to the cells at 2×10^5 cells/mL. Adenosine was added at 50 uM. After reaction for 6 hours, supernatant was collected and heat inactivated for 5 minutes at 60 C. Aliquots of supernatant were transferred to wells in a white 96-well microplate containing 0.25 U/ml bacterial purine nucleoside phosphorylase (PNP) and 0.15 U/ml microbial xanthine oxidase (XO), both from Sigma. After 20 min incubation at RT, 30 μl of H2O2-detecting mixture containing HRP (final concentration 1 U/ml, Sigma) and Amplex Red reagent (60 μM, Invitrogen, Molecular Probes)

was added to the microwells, followed by measurement of the fluorescence intensity at the emission and excitation wavelengths of 545 and 590 nm, respectively (Tecan Infinite M200).

2. Phenylalanine Hydroxylase

Erythroid cells were cultured as described herein. A transgene encoding phenylalanine hydroxylase with an HA tag at the C-terminus was constructed by Gibson assembly as described herein. The transgene was introduced into the erythroid cells by lentiviral transduction as described herein. Two days after transduction, cells were collected, washed in PBS buffer, and lysed in RIPA cell lysis buffer (Pierce). Cell lysates (64 ug total protein) were added to 1 mL reaction buffer containing 100 mM Tris-HCl, pH 7.5, 4 mM DTT, 4 mM Phenylalanine, 33 μg catalase, and 0.4 mM DMPH4 (all from Sigma). Reactions were run overnight at 37 C. After incubation, samples were de-proteinized by centrifugal filtration in an Amicon Ultra-4 Centrifugal Filter 10 KD (Millipore UFC801024) spinning at 3700 rpm for 10 min. Samples were collected and assayed for tyrosine concentration by absorbance at 540 nm.

Figure 5A:
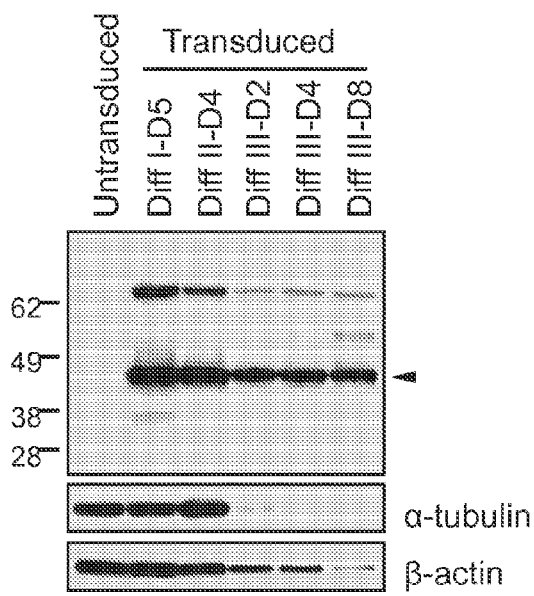
FIG. 5A-FIG. 5C shows protein expression and enzymatic activity of transgenic erythroid cells in culture.
Figure 5B:
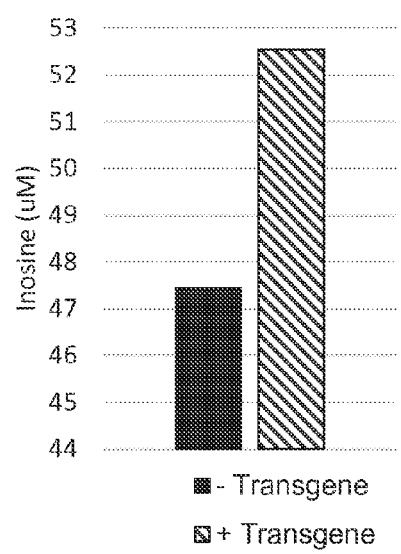
Figure 5C:
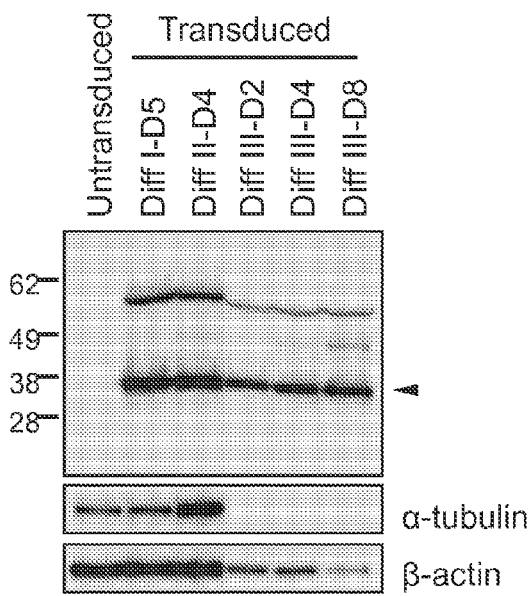

Both of these exogenous proteins were retained through the end of terminal differentiation, a non-trivial feat given that it is well-known in the field that erythroid cells undergo a rigorous program of elimination of proteins unnecessary for basic function (Liu J et al. (2010) Blood 115(10):2021-2027, Lodish H F et al. (1975) Developmental Biology 47(1):59). In FIG. 5A, the exogenously over-expressed protein adenosine deaminase is detected by anti-HA Western blot at various time points over the course of differentiation, from nucleated precursor cells ("Diff I D5") through to enucleated erythroid cells ("Diff III D8"). In FIG. 5C, the exogenously expressed microbial protein phenylalanine hydroxylase is detected by anti-HA Western blot at various time points over the course of differentiation, from nucleated precursor cells ("Diff I D5") through to enucleated erythroid cells ("Diff III D8").

Figure 5D:
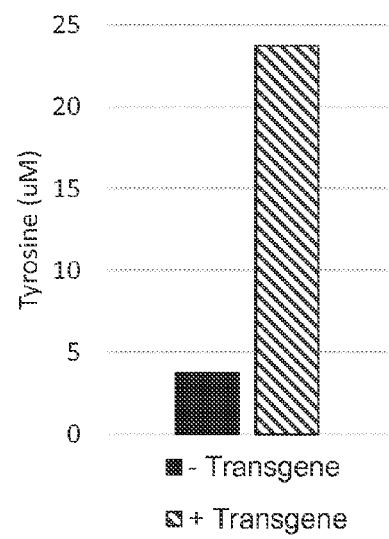
(FIG. 5D) is a bar chart of tyrosine produced from phenylalanine by lysates of cultured phenylalanine hydroxylase-expressing enucleated erythroid cells.

Additionally, both of these enzymes maintained their ability to enzymatically convert substrate into product. FIG. 5B shows the enzymatic conversion of adenosine to inosine by intact adenosine deaminase-expressing 293T cells. FIG. 5D shows the enzymatic conversion of phenylalanine to tyrosine by lysates of cultured phenylalanine hydroxylase-expressing enucleated erythroid cells.

These data conclusively demonstrate that exogenous enzymes are retained on erythroid cells throughout the culture process and that they are enzymatically active in erythroid cells, which has profound therapeutic implications.

Example 14

Activity of CR1

Figure 6A:
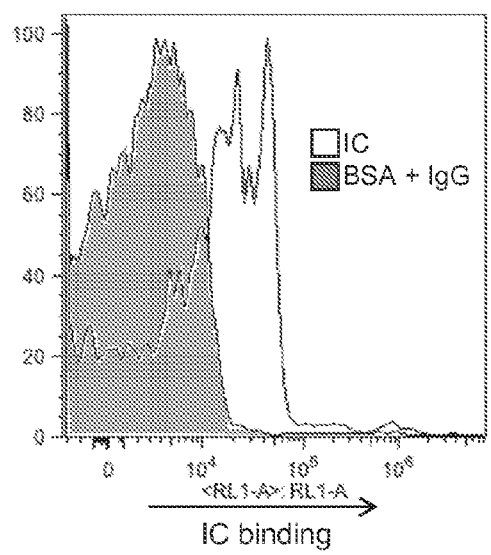
FIG. 6A-FIG. 6B shows immune complex capture and transfer to macrophages by cultured erythroid cells that overexpress complement receptor 1 (CR1).
Figure 6B:
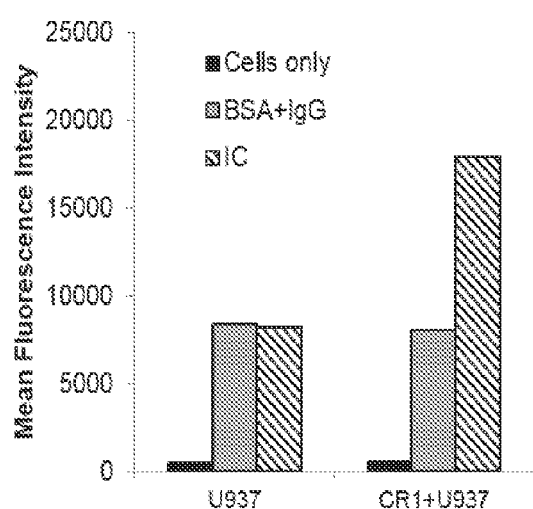

FIG. 6A-FIG. 6B shows both biochemical and biological activity for complement receptor 1 (CR1) over-expressed on the surface of cultured erythroid cells. Biochemical activity of CR1 was assessed by flow cytometry for binding to an immune complex. Biological activity of CR1 was assessed by transfer of immune complexes to macrophages in a co-culture assay.

1. Immune Complex Binding of CR1-Expressing Cells.

Erythroid cells were cultured as described herein. A transgene construct encoding complement receptor 1 (CR1) was constructed by Gibson assembly as described herein. The transgene was introduced into the erythroid cells by lentiviral transduction as described herein. Transgene expression levels were assessed by flow cytometry as described herein using an anti-CR1 antibody (Abcam). The cells were cultured to terminal differentiation as described herein.

Dylight 650-labeled bovine serum albumin (BSA-650) was incubated with polyclonal rabbit anti-BSA (Abcam) in an excess of antibody for 30 minutes at room temp. The complexes were then mixed with human serum at a 1:1 volume ratio for 30 minutes at 37 C. Control complexes were either not mixed with human serum or mixed with heat-inactivated human serum.

Complexes were incubated with the CR1-expressing cells for 30 minutes at 37 C. Cells were washed and analyzed by flow cytometry for capture of immune complexes by detecting Dylight 650 fluorescence.

2. Immune Complex Transfer to Macrophages

Cultured U937 monocytes were activated by incubation with 100 nM phorbol myristate acetate (PMA) for 24 hours at 37 C. Cells coated with immune complexes (see above) were incubated with activated U937 macrophages for 30 minutes at 37 C. The co-culture was analyzed by flow cytometry. Macrophages were identified by FSC/SSC gating. Presence of immune complex on macrophages was analyzed by detecting Dylight 650 fluorescence in the macrophage population.

FIG. 6A-FIG. 6B shows the biochemical and biological activity of complement receptor 1 (CR1) exogenously over-expressed on cultured erythroid cells.

FIG. 6A shows the biochemical activity of CR1, defined as the capture of immune complexes in vitro. The black histogram shows the capture of BSA-based immune complexes by CR1 over-expressed on cultured erythroid cells. The shaded histogram shows the minimal background binding to complexes of BSA and IgG that lack human complement, demonstrating that the binding event is CR1-mediated.

FIG. 6B shows the biological activity of CR1, defined as the transfer of captured immune complexes from cultured erythroid cells to macrophages. This is a standard assay in the field, see: Repik et al. 2005 Clin Exp Immunol. 140:230; Li et al. 2010 Infection Immunity 78(7):3129. Transfer is assessed by flow cytometry and measured as the intensity of labeled immune complex-derived fluorescence on macrophages. In this assay, macrophages that are incubated with no immune complexes (black bars) do not become fluorescent. Macrophages that are incubated with complexes of BSA and IgG that lack complement (and therefore do not bind CR1) take up only a small amount of immune complex (solid gray bars), independent of the presence of cultured CR1-overexpressing erythroid cells. This uptake is likely due to Fc-gamma receptors on the U937 cells interacting with the Fc regions of the IgG molecules. Macrophages that are incubated with immune complexes (BSA+IgG+complement) in the absence of CR1-overexpressing cells (hashed bar, left) take up the same amount of immune complex as in the absence of complement, likely by the same Fc-gamma mediated method. However, the macrophages that are incubated with immune complexes in the presence of CR1-overexpressing cells (hashed bar, right) take up nearly double the number of immune complexes as measured by fluorescence.

These data conclusively demonstrate that CR1 overexpression on cultured erythroid cells enables the capture of immune complexes on said erythroid cells, facilitates the transfer of immune complexes from erythroid cells to macrophages, and significantly increases the rate and number of immune complexes taken up by macrophages.

Example 15

Activity of scFv

FIG. 7A-FIG. 7D shows the biochemical and biological activity of antibody scFv exogenously expressed on the surface of cultured erythroid cells as a fusion to the transmembrane protein GPA.

Erythroid cells were cultured as described herein. A transgene construct encoding the leader sequence of glycophorin A, an antibody scFv specific to hepatitis B surface antigen (scFv, described in Bose 2003, Molecular Immunology 40:617), an HA epitope tag, a [Gly-3-Ser]2 flexible linker, and the body of glycophorin A was assembled by Gibson assembly as described herein. The transgene was introduced into the erythroid cells by lentiviral transduction as described herein. Transgene expression was assessed by flow cytometry as described herein using an anti-HA antibody (Abcam). The cells were cultured to terminal differentiation as described herein. Biochemical activity of the antibody scFv was assessed by flow cytometry for binding to the target protein, in this case hepatitis B surface antigen (HBsAg). Recombinant HBsAg protein (Abcam) was labeled with Dylight-650 fluorophore (Pierce). scFv-expressing cells were incubated with 100 nM labeled protein, washed in PBS, and analyzed for Dylight 650 fluorescence by flow cytometry as described herein.

Biological activity of the antibody scFv was assessed by in vivo capture of HBsAg detected by flow cytometry. Recombinant HBsAg protein (Abcam) was labeled with Dylight-650 fluorophore (Pierce). scFv-expressing cells were fluorescently labeled with CFSE (Sigma). Immunocompromised NSG mice (Jackson labs) were injected with ~400 pmol of the labeled HBsAg into the tail vein. A few minutes later, the same mice were injected with $2 \times 10^7$ scFv-expressing cells. Blood was collected by submandibular puncture at regular intervals in an EDTA-containing tube. Collected blood cells were washed and analyzed by flow cytometry as described herein. Human cells were identified as those that were CFSE positive. Capture of HBsAg was detected as Dylight 650 fluorescence on the human cells.

FIG. 7A-FIG. 7B show the biochemical activity of antibody scFv, defined as the binding of its cognate antigen, hepatitis B surface antigen (HBsAg). In FIG. 7A, cells that express (black) or do not express (gray shaded) the antibody scFv are incubated with 450 nM HBsAg and stained with biotinylated anti-HBsAg antibody and fluorescent streptavidin. Cells that express the antibody scFv (~45% of the cells in this culture) bind to the antigen. In FIG. 7B, cells that express the antibody scFv are incubated with various concentrations of HBsAg and stained as above, showing that the binding event is dose-dependent with an affinity of approximately 10 nM.

Figure 7C:
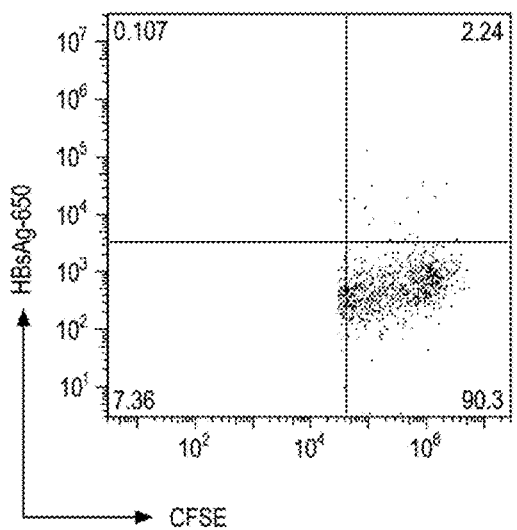
Figure 7D:
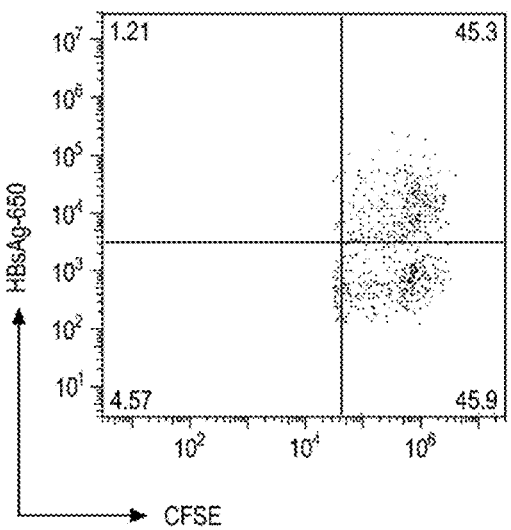

FIG. 7C-FIG. 7D show the biological activity of antibody scFv, defined as the capture of cognate antigen HBsAg while in circulation in a mouse. In this experiment, immunocompromised NSG mice were injected with ~400 pmol fluorescently-labeled HBsAg via the tail vein. Five minutes later, cultured enucleated erythroid cells (7C) or cultured enucleated erythroid cells that expressed exogenous antibody scFv (7D) were injected via the tail vein. Prior to injection, all cultured cells were labeled with CFSE fluorescent dye. Blood was collected 6 hours later, analyzed on a flow cytometer, and gated on CFSE+ human cells. Bare cultured cells did not bind to HBsAg (7C), whereas antibody scFv-expressing cells do bind to HBsAg (7D). Consistently with the biochemical activity experiment, approximately 45% of the cells in this culture express antibody-scFv.

These data demonstrate that the antibody scFv is biochemically active when expressed on the surface of cultured erythroid cells and that the antibody scFv on the erythroid cell is able to bind its target in vivo when in circulation. This has profound implications for therapeutic approaches in which the capture, sequestration, and clearance of a substance in circulation is desired.

Example 16

Activity—Circulating Clearance

FIG. 8A-FIG. 8D shows both biochemical and biological activity for surface molecule capture agents used for circulating clearance of a target.

Biochemical activity of the capture agents, in this case HA polypeptide and biotin, was assessed by flow cytometry for binding to the target protein, in this case anti-HA antibody and anti-biotin antibody. Biological activity of the capture agents was assessed by in vivo capture and clearance of target protein as detected by flow cytometry and plasma protein quantification.

1. Capture of Anti-Biotin Antibody by Chemically-Modified Cells

Eyrthrocytes from a normal human donor were purchased (Research Blood Components). Cells were labeled with CFSE (Sigma) per manufacturer's instructions for 20 minutes at 37 C. Cells were then biotinylated with NHS-biotin (Sigma) per manufacturer's instructions using 0.02 volumes of 2 mM stock biotin reagent for 30 minutes at room temperature. Anti-biotin antibody (Abcam) was fluorescently labeled with Dylight 650 (Pierce). Labeling efficiency of the cells was assessed by flow cytometry using the labeled anti-biotin antibody and CFSE fluorescence as detection markers. 250 ug labeled antibody was injected into an NSG mouse (Jackson Labs) intravenously via the tail vein. Four hours later $1 \times 10^8$ biotinylated cells were injected intravenously via the tail vein. Blood was collected by submandibular puncture at regular intervals in an EDTA-containing tube. Collected blood cells were washed and analyzed by flow cytometry as described herein. Human cells were identified as those that were CFSE positive. Capture of anti-biotin antibody was detected as Dylight 650 fluorescence on the human cells. Plasma from the blood draw was analyzed by ELISA using a biotin-coated microplate (Pierce) per manufacturer's instructions to detect the level of antibody in circulation.

2. Capture of Anti-HA Antibody by Transgenic Cultured Cells

Erythroid cells were cultured as described herein. A transgene construct encoding glycophorin A signal sequence, an HA epitope tag, glycophorin A coding sequence, viral T2A cleavable sequence and GFP was assembled by Gibson assembly as described herein. The transgene was introduced into the erythroid cells by lentiviral transduction as described herein. The cells were cultured to terminal differentiation as described herein. Cells were analyzed by flow cytometry as described herein, using an anti-HA antibody (Life Technologies) fluorescently labeled with Dylight 650 (Pierce) and GFP fluorescence to detect expression of both transgenes. 250 ug labeled anti-HA antibody was injected into an NSG mouse (Jackson Labs) intravenously via the tail vein. Four hours later $1 \times 10^8$ cultured cells were injected intravenously via the tail vein. Blood was collected by submandibular puncture at regular intervals in an EDTA-containing tube. Collected blood cells were washed and analyzed by flow cytometry as described herein. Human cells were identified as those that were CFSE positive. Capture of anti-HA antibody was detected as Dylight 650 fluorescence on the human cells. Plasma from the blood draw was analyzed by ELISA using an HA peptide-coated microplate (Pierce) per manufacturer's instructions to detect the level of antibody in circulation.

FIG. 8A-FIG. 8D shows biochemical and biological activity of (FIG. 8A-FIG. 8B) the polpeptide HA expressed on the surface of cultured erythroid cells as a fusion to GPA and of (FIG. 8C-FIG. 8D) biotin chemically conjugated to the surface of primary erythrocytes. Biochemical activity is defined as the capture of a target protein in vitro. Biological activity is defined as the enhanced clearance of a target protein in vitro.

Figure 8A:
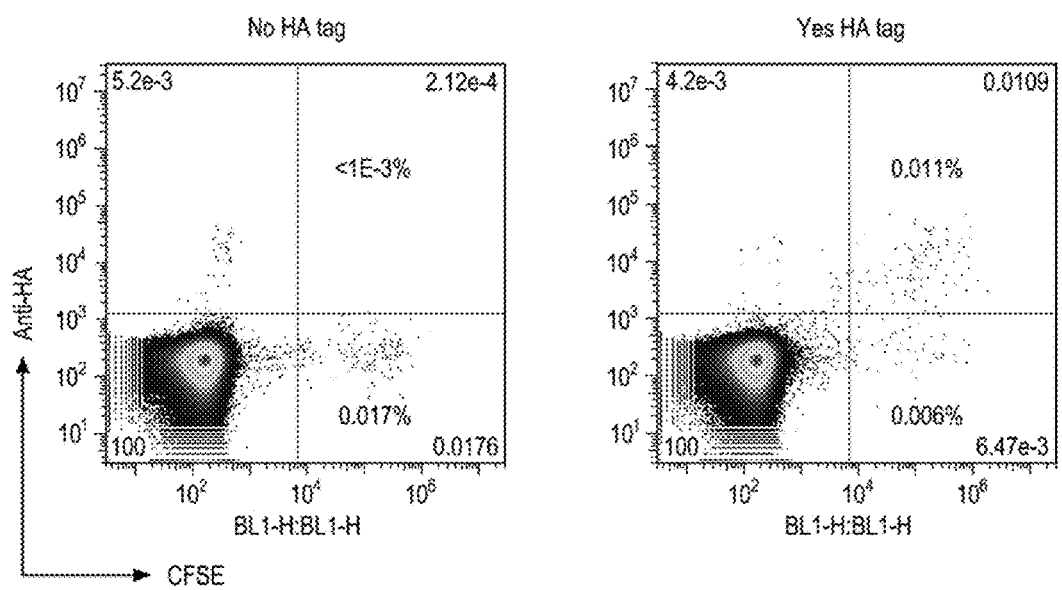
FIG. 8A-FIG. 8D shows the specific clearance of circulating antibodies mediated by membrane-receiver complexes in vivo.

In FIG. 8A, the HA polypeptide, expressed as a fusion to the N terminus of GPA, captures a mouse anti-HA antibody in vivo. NSG mice were injected with fluorescently-labeled mouse anti-HA antibody, followed by injection of cultured human erythroid cells that either do not (left) or do (right) express HA epitope tag on their surface as a fusion to GPA. Blood was drawn and cells analyzed on the flow cytometer. The x-axis measures CFSE fluorescence. The y-axis measures anti-HA antibody Dylight 650 fluorescence. CFSE-positive cultured human erythrocytes are observed in both samples, but only the cells expressing the HA epitope tag are able to capture circulating anti-HA antibody.

Figure 8B:
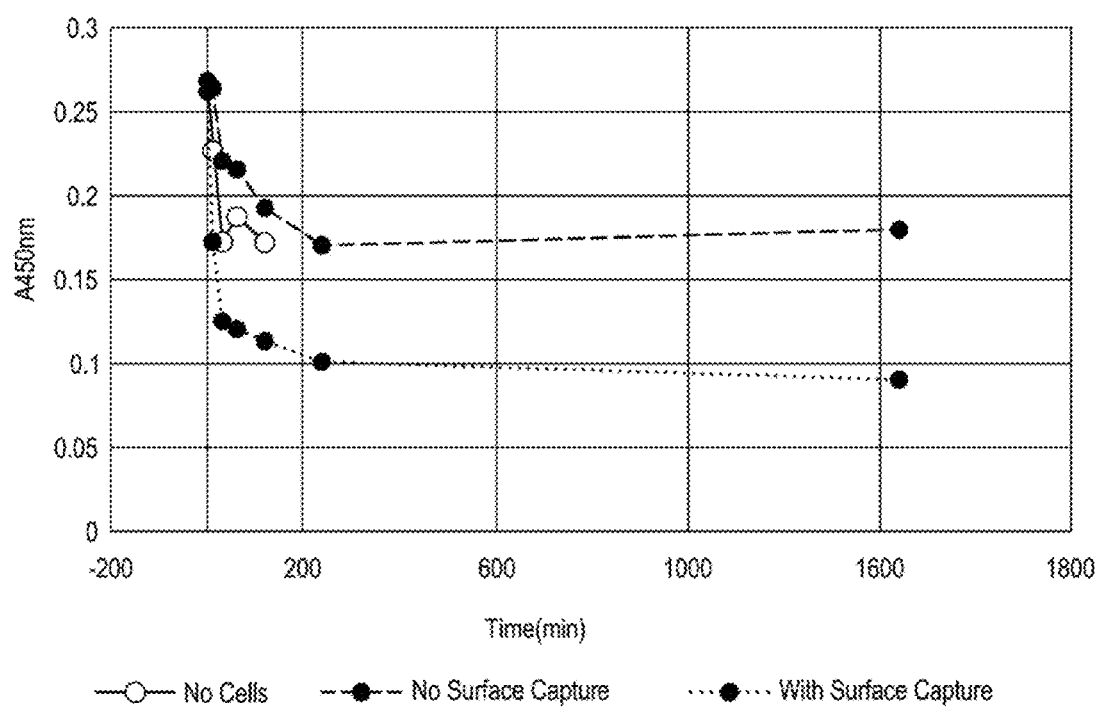

In FIG. 8B, mice were injected with anti-HA antibody then then optionally with cultured human erythroid cells that either do not or do express HA peptide on their surface as a fusion to GPA. Plasma was collected at multiple time points and the level of anti-HA antibody in plasma was assessed by ELISA using an HA peptide-coated plate as a substrate. Mice injected with anti-HA antibody alone (open circles, solid line—this mouse died after 120 minutes of causes unrelated to treatment) or with anti-HA antibody followed by cells that do not express HA peptide on their surface (dashed line) have significant antibody in circulation out to 24 hours post injection of cells. In contrast, mice injected with anti-HA antibody followed by cells that express HA peptide on their surface are depleted of target antibody within minutes. This data conclusively demonstrates that the target antibody is rapidly and specifically cleared from circulation by cultured erythroid cells that express receiver polypeptide on their surface.

Figure 8C:
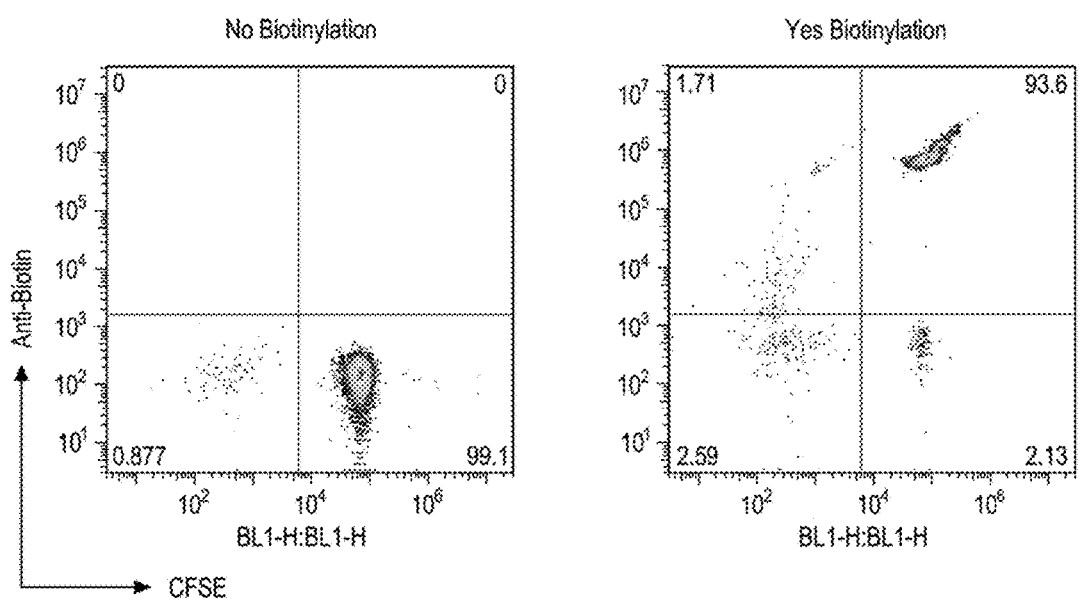

In FIG. 8C, the biotin molecule, conjugated to the surface of erythroid cells by amine functionalization chemistry, captures a mouse anti-biotin antibody. In both of these cases capture was assessed by flow cytometry. Cells that are CFSE labeled and biotinylated show up as double positive when stained with a fluorescent anti-biotin antibody (lower dot plot), whereas CFSE-labeled cells that are not biotinylated only show up as single positive (upper dot plot).

Figure 8D:
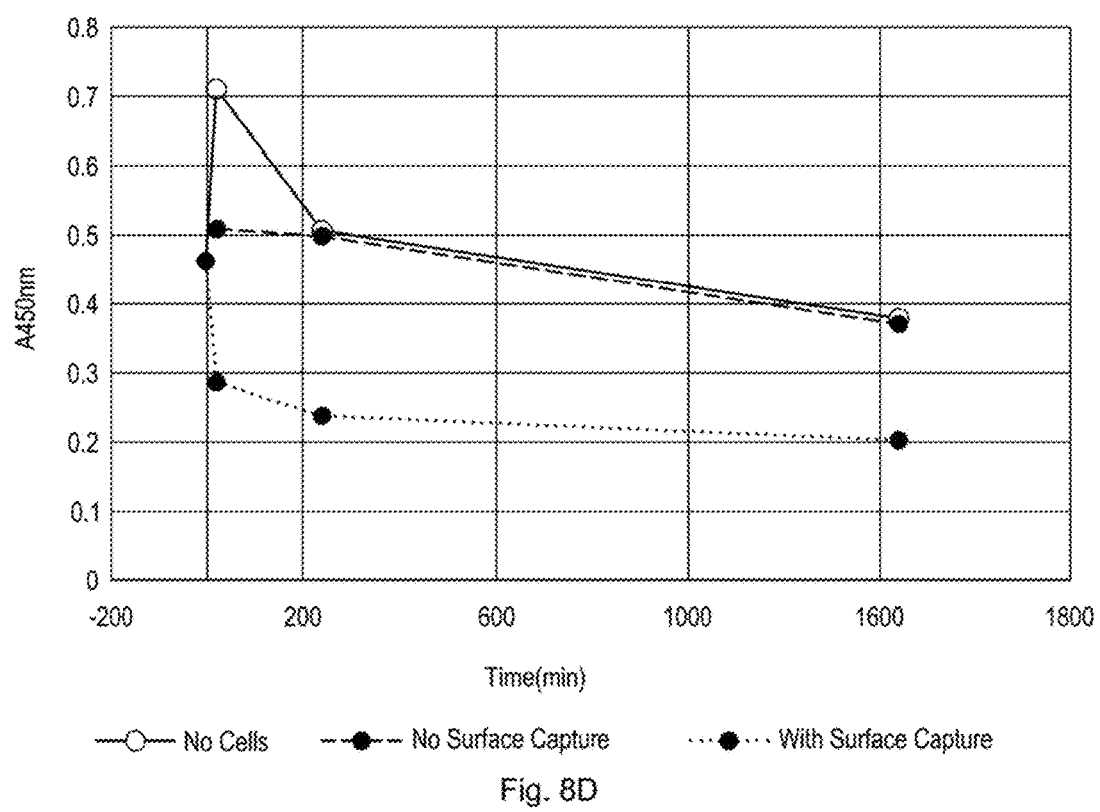

In FIG. 8D, mice were injected with anti-biotin antibody then then optionally with cultured human erythroid cells that either are not or are conjugated to biotin on their surface. Plasma was collected at multiple time points and the level of anti-biotin antibody in plasma was assessed by ELISA using a biotin-coated plate as a substrate. Mice injected with anti-biotin antibody alone (open circles, solid line) or with anti-biotin antibody followed by cells that are not conjugated to biotin on their surface (dashed line) have significant antibody in circulation out to 24 hours post injection of cells. In contrast, mice injected with anti-biotin antibody followed by cells that are conjugated to biotin on their surface are depleted of target antibody within minutes. This data conclusively demonstrates that target antibodies are rapidly and specifically cleared from circulation by cultured erythroid cells that contain receiver polypeptide on their surface.

Together the data conclusively demonstrate that suitable receivers on membrane-receiver complexes are able to bind their target molecules in vivo and mediate rapid circulating clearance of target molecules when in circulation, which has profound therapeutic implications.

Example 17

Activity of Complement Regulators

The complement regulatory activity of the synthetic membrane-receiver complexes is assessed by standard CH50 and AH50 assays known in the art (see e.g., Kabat et al. 1961 Exp Immunochem pp. 133-239 and Platts-Mills et al. 1974 J Immunol 113:348).

Briefly, the CH50 assay utilizes sheep erythrocytes (SRBC) as target cells. Briefly, a suspension containing $1\times10^9$ SRBC/ml is prepared in the GVB(2+) buffer (gelatin/Veronal-buffered saline with Ca2+ and Mg2+), pH 7.35. Hemolysin (rabbit anti-sheep antiserum) is titrated to determine the optimal dilution to sensitize SRBC. Diluted hemolysin (1:800) is mixed with an equal volume of SRBC ($1\times10^9$ SRBC/ml), and the whole is incubated at 37° C. for 15 minutes. This results in $5\times10^8$/ml antibody-coated erythrocytes (EA). EA (100 µl) are incubated with 100 µl of five serial twofold dilutions (1:20, 1:40, 1:80, 1:160, and 1:320) of the normal human serum (NHS) or similar dilution of the mixture of NHS and the membrane-receiver complex at 37° C. for 1 hour. NHS incubated with GVB2+ buffer is used as the control. Background control is obtained by incubating EA with buffer alone (serum is not added), and total lysis (100% hemolysis) is determined by adding distilled water to EA. The reaction is stopped using 1.2 ml of ice-cold 0.15 M NaCl, the mixture is spun to pellet the unlysed cells, and the optical density of the supernatant is determined spectrophotometrically (412 nm). The percentage of hemolysis is determined relative to the 100% lysis control. Complement activity is quantitated by determining the serum dilution required to lyse 50% of cells in the assay mixture. The results are expressed as the reciprocal of this dilution in CH50 units/ml of serum.

Briefly, the AH50 assay depends on lysis of unsensitized rabbit erythrocytes (Erab) by human serum by activation of the alternative pathway. Activation of the calcium-dependent classical pathway is prevented by addition of the calcium chelator ethylene glycol tetraacetic acid (EGTA) to the assay buffer, and magnesium, necessary for both pathways, is added to the buffer. Briefly, a cell suspension of rabbit RBC ($2\times10^8$ cell/ml) is prepared in the GVB-Mg2+-EGTA buffer. A serial 1.5-fold dilution (1:4, 1:6, 1:9, 1:13.5, and 1:20.25) of normal human serum (NHS) or similar dilution of the mixture of NHS and the membrane-receiver complex are prepared in GVB-Mg2+-EGTA buffer, and 100 µl of each serum dilution is added to 50 µl of standardized Erab. NHS incubated with GVB-Mg2+-EGTA buffer is used as the control. The mixture is then incubated at 60 minutes at 37° C. in a shaking water bath to keep cells in suspension, and 1.2 ml of ice-cold NaCl (0.15 M) is used to stop the reaction. The tubes are spun at 1250 g, at 4° C., for 10 minutes to pellet the cells, and the optical density of the supernatant is determined spectrophotometrically (412 nm). Background control has 100 µl GVB-Mg2+-EGTA buffer, and 50 µl Erab and does not exceed 10% of the total lysis. In the total lysis control tube 100 µl of distilled water is added to 50 μl Erab suspension, and the percentage of hemolysis is determined relative to 100% lysis control. The results of the assay are calculated and complement activity is quantitated by determining the serum dilution required to lyse 50% of cells in the assay mixture. The results are expressed as the reciprocal of this dilution in AH50 units/ml of serum.

Example 18

Activity of Platelet-Loaded Thymidine Phosphorylase

A transgene encoding thymidine phosphorylase with an HA tag at the C-terminus is constructed by Gibson assembly as described herein. Platelets are cultured from precursor cells as described herein. The transgene is introduced into the cultured platelet precursor cells by lentiviral transduction as described herein. Expression of thymidine phosphorylase within the cultured platelets is assessed by Western blotting using an anti-HA detection antibody, as described herein.

Thymidine phosphorylase activity is determined in platelet samples by quantifying the rate of conversion of thymidine to thymine. Preliminary experiments are conducted to determine the linear metabolite formation kinetics with respect to time and enzyme dilution; the method is shown to be linear for up to 16 min, over a thymine phosphorylase range of 4.0-719 nmol/min/ml (corresponding to a sample dilution range of 10-9088). Lysates of pre-dialysis samples cultured platelet and control platelet samples are prepared by diluting thawed samples 1:710 with 125 mM Tris-HCl, pH 7.4. Twenty-five ul of the platelet lysate is then added to 100 ul sodium phosphate buffer (100 mM, pH 6.5) and 25 ul thymidine standard (10 mM), mixed and incubated at 37 C for 10 min. The reaction is terminated with 25 ul of 40% TCA. Assay blanks are prepared by adding TCA to the sodium phosphate buffer/thymidine incubation mixture prior to adding the platelet lysate. Samples are centrifuged at 13,400×g for 2 min, and the supernatant washed twice with water-saturated diethyl ether with 2 min on a shaker to extract the TCA. To avoid ether interfering with HPLC separation, effective removal is achieved by exposing the matrix to the air for 5 min to allow evaporation of the ether. A sample volume of 10 ul is injected into the HPLC.

Chromatographic separation of substrate and product is achieved using reversed phase chromatography with isocratic elution using a Waters Alliance HPLC 2795 system. A pre-packed C18column (Spherisorb ODS 125 mm×4.6 mm ID, 5 um particle size, Waters) is used as the stationary stage. Analytes are eluted using a mobile phase of ammonium acetate (40 mM) with the ion-pairing agent tetrabutyl ammonium hydrogen sulphate (5 mM) adjusted to pH 2.70 with HCl, delivered at a flow rate of 1.0 ml/min, with a run time of 8 min. UV detection is at 254 nm and 0.1 absorbance units full scale. Metabolites are identified by comparing spectra with pure standards.

Example 19

Activity of Platelet-Displayed Goodpasture Antigen

A transgene encoding collagen alpha-3(IV) (COL4A3) NC1 domain antigen fused to the N terminus of CD42b (GP1B, genbank AAH27955.1) with an intervening HA tag is constructed by Gibson assembly as described herein. Platelets are cultured from precursor cells as described herein. The transgene is introduced into the cultured platelet precursor cells by lentiviral transduction as described herein. Expression of the exogenous antigen on the cultured platelets is assessed by flow cytometry using an anti-HA detection antibody as described herein.

Serum is collected from a patient suffering from Goodpasture's syndrome, and the serum is tested for anti-COL4A3 antibodies by commercial ELISA (MyBioSource COL4A3 ELISA Kit). The binding capacity of the antigen-expressing platelets is assessed by flow cytometry as described herein, using this anti-COL4A3 serum as the primary detection antibody and fluorescent anti-human IgG as the secondary detection antibody.

Platelet-facilitated clearance of a circulating antigen in vivo is modeled in a mouse using the antigen-expressing platelets. NSG mice are injected with 100 uL of mouse anti-human COL4A3 antibody (Creative BioMart) fluorescently labeled with Dylight 650 dye. CFSE-labeled cultured platelets ($10^8$ per mouse) that express the exogenous antigen are then injected via the tail vein. Blood is drawn from a submandibular location at 10 min, 30 min, 2 h, 12 h, and 24 h. Blood is centrifuged to collect the platelet-rich fraction, which is then stained and analyzed by flow cytometry as described herein. Antibody capture by platelets is determined by tracking the CFSE-Dylight 650 double positive population.

Example 20

Activity In Vivo (Mouse)

Mouse erythroid cells are cultured as described herein. Erythroid precursor cells are transduced with a suitable receiver polypeptide transgene, e.g., encoding complement receptor 1 (CR1) using a lentivirus as described herein. Cells are cultured to terminal differentiation as described herein. The presence of the exogenous protein in the cells is assessed by flow cytometry as described herein. The cells are labeled with a fluorescent die, e.g., CFSE (Sigma Aldrich) per manufacturer's instructions to aid in their detection. The cells are injected into a NZBWF1/J mouse model of lupus, or other appropriate model of disease or activity corresponding to the suitable receiver polypeptide, approximately $1 \times 10^8$ cells injected via the tail vein. Blood is collected at multiple time points by submandibular puncture. Immune complex levels in the plasma are detected by Raji cell assay, see e.g., Theofilopoulos et al. 976, J Clin Invest 57(1):169. Pharmacokinetics of the cultured cells are assessed by flow cytometry as described herein, by tracking the percentage of CFSE fluorescent cells in the drawn blood sample. Mouse overall health is assessed by gross necropsy, including histology of kidney tissue to track reduction of immune complex deposition and inflammation-mediated damage.

Example 21

Rapid Screening

Cell lines, e.g., 293T and K562, have shorter expression and culturing cycles (~1 day) compared to cultured erythroid cells (days-weeks). These cell lines can be used to rapidly iterate through a gene library encoding suitable receiver polypeptides to identify the receiver polypeptide with the highest expression or activity.

A library of suitable receiver polypeptide transgenes, e.g., full-length and shorter variants of complement receptor 1 (CR1), are constructed by polymerase chain reaction and Gibson assembly as described herein. The library of transgenes is transfected into HEK293T cells in a parallel fashion in a microtiter plate using lipofectamine as described herein and transduced into K562 cells using lentivirus as described herein. The expression of the receivers is assessed by flow cytometry as described herein after 24-48 hours. The activity of each of the receivers in the library is assessed by capture of fluorescent immune complex detected with flow cytometry as described herein, and by the transfer of fluorescent immune complexes to cultured monocytes detected with flow cytometry as described herein. The receivers from the library that are most functional—e.g., are highest expressed, capture most immune complexes, or best transfer immune complexes to monocytes—are then individually transduced into parallel erythroid cell cultures as described herein using lentivirus as described herein. The expression of each receiver on cultured erythroid cells is assessed by flow cytometry as described herein The activity of each receiver on cultured erythroid cells is assessed by capture of fluorescent immune complex detected with flow cytometry as described herein, and by the transfer of fluorescent immune complexes to cultured monocytes detected with flow cytometry as described herein.

Example 22

Assessment of Clearance Rate of RBC In Vivo

The clearance rate of erythroid cells was assessed in vivo in an immunocompromised mouse model. NSG mice were treated at day −1 with 100 uL of clordonate liposome (Clodrosomes.com) solution to selectively deplete macrophages. Cells were labeled with the fluorescent tag CFSE and approximately $1 \times 10^8$ cells were injected into each mouse via the tail vein. At regular intervals blood was collected by submandibular puncture and blood cells were collected. Cells were co-stained with anti-human GPA antibodies and analyzed by flow cytometry. Human erythroid cells were distinguished from mouse erythroid cells by CFSE signal and by human GPA signal.

Figure 9A:
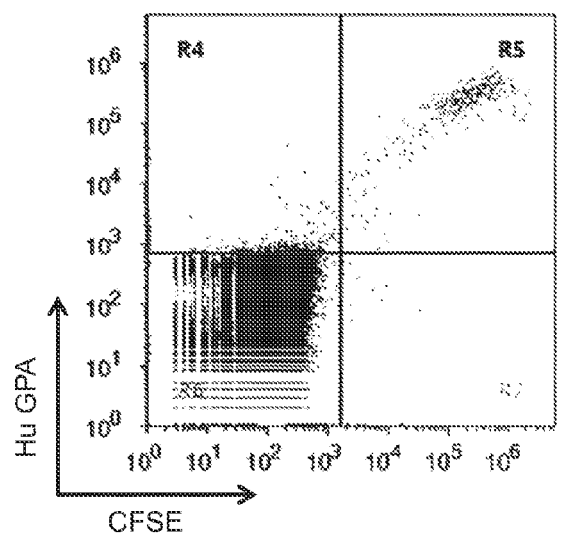
FIG. 9A-FIG. 9B shows the clearance rate of cultured human erythroid cells in a mouse.
Figure 9B:
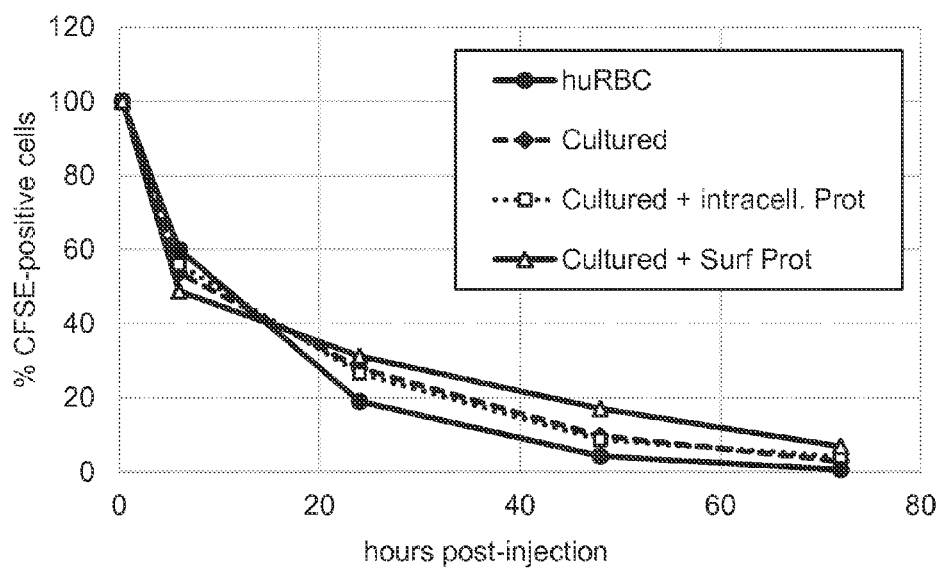

For therapeutic applications, it is important that cultured erythroid cells and cultured erythroid cells containing exogenous protein either intracellularly or on the surface circulate normally in vivo. This is shown in FIG. 9A-FIG. 9B using a standard immunocompromised mouse model. In FIG. 9A, blood collected from an injected mouse is analyzed on the flow cytometer. Cultured human erythroid cells are identified in the top right quadrant of the plot, double-positive for CFSE and human-GPA. In FIG. 9B, mice were injected with human red blood cells (solid circles), cultured enucleated erythroid cells (dashed diamonds), cultured enucleated erythroid cells that express an intracellular exogenous protein (dotted squares) and cultured enucleated erythroid cells that express a surface exogenous protein (open triangles). The clearance rate of the human cells is measured as the percentage of CFSE+ cells remaining over time, scaled to the initial time point (20 minutes post injection). There is no significant difference in clearance rate between the four samples.

These data clearly demonstrates that cultured enucleated erythroid cells have substantially similar circulation to normal human red blood cells. Furthermore, exogenous proteins expressed either in the intracellular space or on the surface of the cells do not substantially affect the circulation behavior of these cells. This is an important result for therapeutic translation of the technology.

Example 23

Assessment of Adverse Circulatory Events

The incidence of adverse events caused by cultured eyrthroid cells in circulation were assessed by detection of fibrinogen breakdown products in blood and histology in animals injected with cultured erythroid cells.

Detection of Fibrinogen Breakdown Products. Mice were injected with cultured erythroid cells as described herein. Blood was collected from mice by submandibular puncture in an EDTA-containing tube. Cells were separated by centrifugation and plasma was collected. The levels of fibrinogen breakdown products fibrinopeptide A and fibrinopeptide B were measured in mouse plasma by ELISA (MyBiosource) following manufacturer's instructions.

Histology. Tissue samples from the same mice were collected following necropsy. Tissues were trimmed, embedded in paraffin wax, and sectioned. Tissue sections were stained by H&E staining and trichrome staining. Microscope images were taken at 10× and 20× magnification.

For therapeutic applications, it is important that cultured erythroid cells and cultured erythroid cells that contain exogenous proteins (either intracellularly or on the surface) not induce adverse events, such as activation of the clotting cascade and tissue thrombus formation.

Figure 10A:
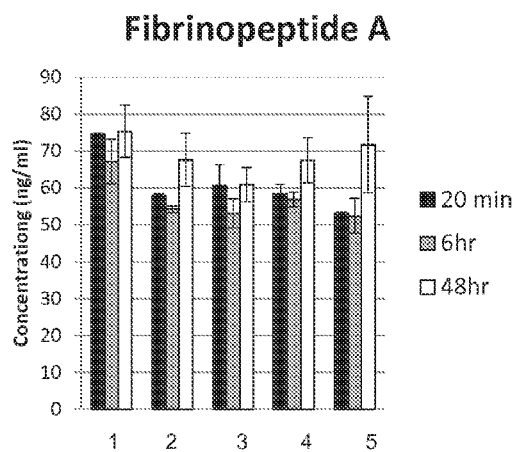
FIG. 10A-FIG. 10D is an assessment of adverse events following injection of cultured human erythroid cells into a mouse.
Figure 10B:
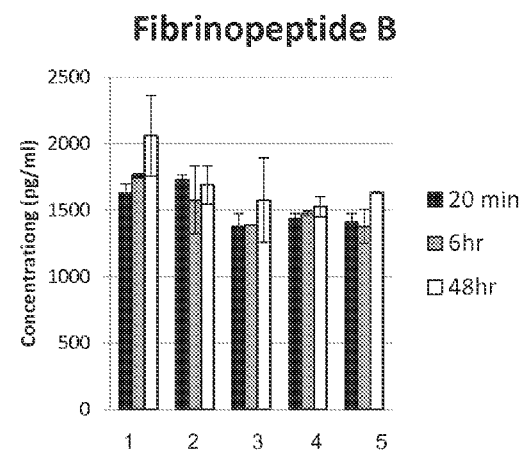

FIGS. 10A and 10B show the levels of fibrinopeptide A and B in mouse plasma for mice injected with (1) human red blood cells, (2) cultured enucleated erythroid cells, (3) cultured enucleated erythroid cells expressing an intracellular exogenous protein, (4) cultured enucleated erythroid cells expressing a surface exogenous protein, and (5) recombinant protein alone. The levels of fibrinopeptide A and B, a marker of fibrinogen breakdown and activation of the clotting cascade, are substantially similar for all samples.

Figure 10C:
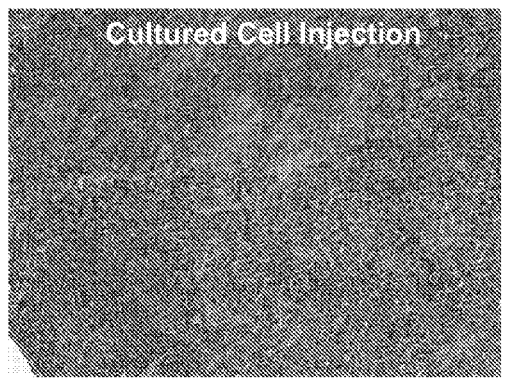
Figure 10D:
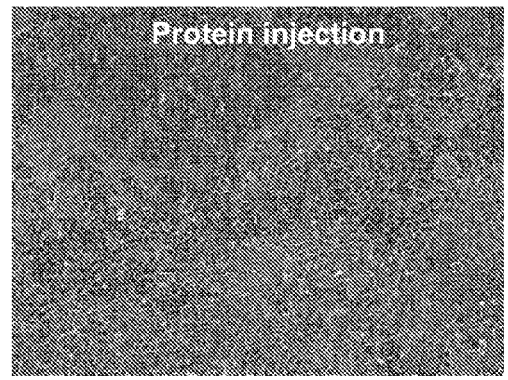

FIG. 10C and FIG. 10D show histologically stained sections of spleen for a mouse injected with cultured enucleated erythroid cells (FIG. 10C) and recombinant protein (FIG. 10D). There is no substantial difference between the tissue, and no identifiable tissue damage in spleen, liver, lung, brain, heart, and kidney was observed between any of the samples.

These data conclusively demonstrate that cultured erythroid cells, with or without exogenous protein, do not induce any adverse events while in circulation in mice.

Example 24

Assessment of Exogenous Protein Retention in Circulation

The retention of exogenous proteins in and on cultured enucleated erythroid cells was assessed by flow cytometry and Western blotting.

1. Retention of Exogenous Protein Assessed by Flow Cytometry

Erythroid cells were cultured as described herein. A transgene construct encoding glycophorin A signal sequence, antibody scFv specific to hepatitis B surface antigen, HA epitope tag, and glycophorin A coding sequence was assembled by Gibson assembly as described herein. The transgene was introduced into the erythroid cells by lentiviral transduction as described herein. The cells were cultured to terminal differentiation as described herein. Cells were fluorescently labeled with CFSE and injected into an immunocompromised NSG mouse (Jackson Labs) via the tail vein (1×10^8 cells per mouse). At regular intervals blood was collected by submandibular puncture. Collected cells were stained with a fluorescent anti-HA antibody (Abcam), and analyzed by flow cytometry. Human cells were identified as CFSE+ cells, and exogenous protein retention was assessed by the fraction of CFSE+ cells that also stained positive for the epitope tag.

2. Retention of Exogenous Protein Assessed by Western Blot

Erythroid cells were cultured as described herein. A transgene construct encoding adenosine deaminase and an HA epitope tag was assembled by Gibson assembly as described herein. The transgene was introduced into the erythroid cells by lentiviral transduction as described herein. The cells were cultured to terminal differentiation as described herein. Cells were fluorescently labeled with CFSE and injected into an immunocompromised NSG mouse (Jackson Labs) via the tail vein (1×10^8 cells per mouse). At regular intervals blood was collected by submandibular puncture. Collected cells were washed, lysed, and analyzed by Western blot as described herein with a detection antibody against the HA epitope tag.

For therapeutic applications, it is important that cultured erythroid cells that contain exogenous proteins either intracellularly or on the surface retain these transgenes when in circulation. This feat is non-trivial given that it is widely hypothesized in the field that erythroid cells undergo a rigorous program of maturation and elimination of proteins unnecessary for basic function when in circulation as they mature (Liu J et al. (2010) Blood 115(10):2021-2027, Lodish H F et al. (1975) Developmental Biology 47(1):59).

Figure 11A:
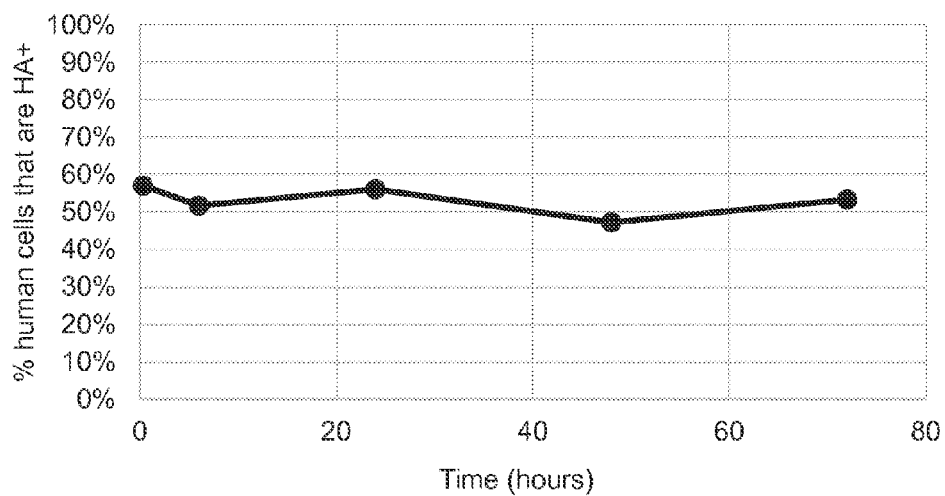
FIG. 11A-FIG. 11B tracks the expression of exogenous protein on cultured erythroid cells in circulation.
Figure 11B:
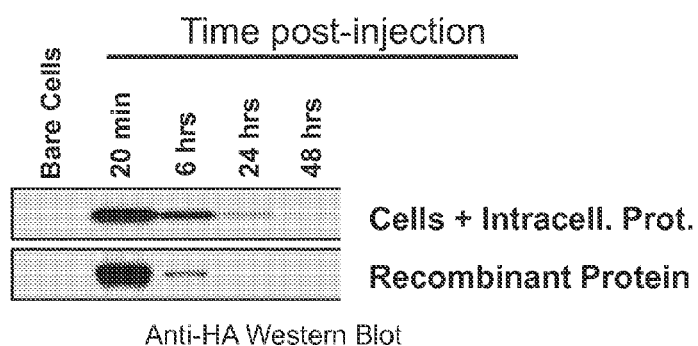

FIG. 11A-FIG. 11B shows that exogenous proteins expressed in and on cultured enucleated erythroid cells were retained in circulation. In FIG. 11A, mice were injected with cultured enucleated erythroid cells that expressed antibody scFv on their surface. The percentage of antibody scFv-positive cells began and remained steadily at approximately 50% through the duration of the multi-day circulation study. In FIG. 11B, mice were injected either with cultured enucleated erythroid cells that expressed a cytoplasmic enzyme with an HA tag or with recombinant enzyme with an HA tag. When analyzed by Western blot, it is clear that the enzyme retained within the cultured cell for the duration of the experiment. The decrease in band intensity is attributable to the clearance of cells during the experiment, not from the removal of exogenous enzyme from said cells.

The data clearly demonstrate that exogenous proteins expressed in and on culture enucleated erythroid cells are retained in and on the cells in circulation, which has tremendous and unprecedented implications for therapeutic relevance.

Example 25

Assessment of Half-Life Extension In Vivo

Erythroid cells were cultured as described herein. A transgene construct encoding adenosine deaminase and an HA epitope tag was assembled by Gibson assembly as described herein. The transgene was introduced into the erythroid cells by lentiviral transduction as described herein. The cells were cultured to terminal differentiation as described herein. Cells were fluorescently labeled with CFSE and injected into an immunocompromised NSG mouse (Jackson Labs) via the tail vein (1×10^8 cells per mouse). At regular intervals blood was collected by submandibular puncture. Collected cells were washed, lysed, and analyzed by Western blot as described herein with a detection antibody against the HA epitope tag.

A transgene encoding adenosine deaminase with an HA tag at the C-terminus was constructed by Gibson assembly as described herein. The transgene was introduced into HEK-293T cells by lipofectamine transfection (Life Technologies) as described herein. The protein was purified from the cell culture supernatant after 7 days using an HA affinity resin (Pierce) according to manufacturer's instructions. Protein concentration was assessed by absorbance of light at 280 nm. Protein (40 ug) was injected into an immunocompromised NSG mouse (Jackson Labs) via the tail vein. At regular intervals blood was collected by submandibular puncture. Plasma was analyzed by Western blot as described herein with a detection antibody against the HA epitope tag.

In FIG. 11B, mice were injected either with cultured enucleated erythroid cells that expressed a cytoplasmic enzyme with an HA tag or with recombinant enzyme with an HA tag. When analyzed by Western blot, it is clear that the enzyme's circulating half-life is significantly extended when expressed within a circulating cell compared to when injected in soluble form.

Example 26

Assessment of Clearance Rate In Vivo—Platelets

A population of exogenous thymidine phosphorylase expressing platelets is cultured using the herein detailed procedure and is labeled with CFSE and injected into an NSG mouse via the tail vein. A population of native human-sourced platelets is similarly labeled with CFSE and injected into another mouse. Samples are taken from both mice at 10 min, 1 h, 4 h, 8 h, 24 h, and 48 h and flow cytometry is used to quantify platelet circulation levels. The half-life of natural vs cultured platelets is compared.

Example 27

Assessment of Adverse Circulatory Events—Platelets

For therapeutic applications, it is important that cultured platelets and cultured platelets that contain exogenous proteins (either intracellularly or on the surface) not induce adverse events, such as activation of the clotting cascade and tissue thrombus formation. Upon injection of cultured platelets into an NSG mouse via the tail vein, fibrinogen breakdown products fibrinopeptide A and fibrinopeptide B are detected in mouse plasma by ELISA following manufacturer's protocol (MyBiosource). Tissue samples from NSG mice are collected following necropsy. Tissues are trimmed, embedded in paraffin wax, and sectioned. Tissue sections are stained by H&E staining and trichrome staining. Microscope images are taken at 10× and 20× magnification and assessed by a trained pathologist for any pathogenic features.

Example 28

Assessment of Exogenous Protein Retention in Circulation—Platelets

The retention of exogenous proteins in and on cultured platelets is assessed by flow cytometry and Western blotting.

CFSE labeled platelets that contain intracellular exogenous protein are injected into a mouse via the tail vein. At regular intervals blood is collected by submandibular puncture. Blood is centrifuged to isolate the platelet-rich plasma, which is then lysed, and analyzed by Western blot with staining for an epitope tag present on the exogenous protein.

Example 29

Acquisition of Donor Cells for Production

After obtaining informed consent, healthy CD34+ stem cell donors receive rhG-CSF (Granocyte or Neupogen), 10 ug/kg/day s.c., for 5 days for peripheral blood stem cell mobilization and then undergo apheresis for 2 consecutive days to collect mobilized CD34+ HSC. Mononuclear cells (MNC) are isolated from mobilized peripheral blood by Ficoll density gradient centrifugation and are split in two parts. One part is used to purify CD34+ cells by using anti-CD34-coated magnetic beads (Miltenyi Biotec, Inc., Germany), relative to Miltenyi protocol. The purity of the CD34+ fractions is controlled. CD34+-enriched HSC are then used immediately in the two-step culture method or frozen until use in the one-step culture method.

Complete medium (CM) used is RPMI 1640 (Eurobio, France), supplemented with 2 mM L-glutamine and 100 IU/ml penicillin-streptomycin (Gibco, Grand Island, N.Y., USA) and 10% heat-inactivated FBS (Gibco). IMDM (Gibco), supplemented with 10% heat-inactivated FBS, is used for expansion. Recombinant human stem cell factor (rhSCF), thrombopoietin (TPO), fetal liver tyrosine kinase 3 ligand (Flt-3L), GM-CSF, and TNF-alpha are purchased from R&D Systems (Minneapolis, Minn., USA).

Example 30

Scale-Up for Production

Erythroid cells are scaled up in volume progressively, maintaining the cells at a density of between $1 \times 10^5$ and $2 \times 10^6$ cells/mL in static culture. Expansion stage is seeded at $10^5$/ml and includes 3-7 progressive volume transfers; 100 ml, 500 ml, 1 L, 10L, 50L, 100L, 100L. During the course of production the cell media includes a combination of IMDM, FBS, BSA, holotransferrin, insulin, glutamine, dexamethasone, beta estradiol, IL-3, SCF, and erythropoietin. When the cells reach a volume appropriate for seeding the production bioreactor, they are transferred to the production bioreactor for final scale-up and differentiation.

Example 31

Culturing Cells in a Bioreactor (Wave)

The WAVE Bioreactor 2/10 system is set up according to the operator manual. In brief, the Cellbag is assembled on the rocking unit, which is placed on the perfusion module. After inflating the bag with air, the weight is set to zero. Subsequently, the bag is filled with the appropriate amount of culturing media and incubated for at least two hours, allowing the media to reach 37 C. The media and cells are transferred to the bag via a transfer flask, a special designed DURAN glass bottle with two ports. In the upper part of the flask, a filter is connected to the port. In the other port, by the bottom of the flask, a tube is assembled. The tube one the transfer flask is coupled with the feed connection on the Cellbag. The transfer flask is maintained in a LAF hood, to decrease the risk of contamination.

Before perfusion is started, tubing and containers for harvest and feed are connected to the Cellbag. Tubing is prepared as follows; a 50 or 70 cm long Saniflex ASTP-ELP silicone tubing (Gore/Saniflex AB), with an inner and outer diameter of 3.2 respectively 6.4 mm, is equipped with male luer lock connections in both ends. The silicone tubing is connected to one end of a C-Flex tube, via a female luer lock. At the other end of the C-Flex tube a male luer lock is assembled and tubings are thereafter autoclaved. Luer locks are held in place with zip-ties on all tubes. Prior to perfusion, the silicone part is connected to the Cellbag and the C-Flex part to a 5 L container (Hyclone Labtainer) for both feed and harvest. All connections are performed in a laminar airflow cabinet.

Control of environmental and metabolic factors can alter the expression or activity of transcription factors and gene regulatory proteins of erythroid cells in culture, see e.g., Csaszar et al., 2009 Biotechnol Bioeng 103(2):402; Csaszar et al. 2012 Cell Stem Cell 10(2):218. To provide control over inputs and outputs in the reactor a micro-volume delivery system is created, a key component of which is a 60-80 cm long fused silica capillary (#TSP100375, Polymicro Technologies) with an internal diameter of 100 um. At the input end, the capillary is fed with a luer-lok tip stock syringe (#309585 BD) connected via a PEEK luer to a MicroTight adapter (#P-662, Upchurch Scientific). The stock syringe is loaded on a Model 33 Twin Syringe Pump (#553333, Harvard Apparatus), kept in a refrigerator at 4 C. At the output end, the capillary enters the bioreactor: a two port FEP cell culture bag (#2PF-0002, VueLife) placed on an orbital shaker in a cell culture incubator at 37 C with 5% $CO_2$. The capillary is fed through a self-sealing rubber septa (#B-IIS, InterLink) with a needle, into the midpoint of the bioreactor. The opposing connector on the bioreactor is replaced with an additional self-sealing rubber septa. Stock syringes and delivery capillaries are blocked overnight before use with a solution of PBS with 10% fetal bovine serum to prevent protein adhesion to syringe and capillary walls.

National Instruments LabVIEW 7.1 is used to create a program to control the syringe pump's injections. The program's basic dosing strategy is an initial injection to concentration L1 followed by wait time t1 and subsequent injections, each to concentration L2 and followed by wait time t2, repeated for n times. The user inputs the flow rate, the stock concentration, the initial culture volume, the desired concentration after injections, the time between injections, and the total number of injections.

Example 32

Assess Expansion and Differentiation of Cultured Erythroid Cells

It is important to assess the expansion, differentiation, and enucleation in vitro differentiated cells to ensure that the introduction of a transgene does not negatively affect the quality of the cells in culture. Expansion is assessed by cell counting. Differentiation is assessed by flow cytometry, Western blot, and RT-PCR. Enucleation is assessed by flow cytometry.

Assessing Expansion Rate by Cell Counting. Erythroid cells are cultured as described herein. At various time points, cells are collected, washed with PBS, and counted using a Countess Automatic Cell Counter instrument (Life Technologies). The expansion rate of the cells is determined by the growth in number of cells over time.

Assessing Differentiation by Flow Cytometry. Erythroid cells are cultured as described herein. At various time points, cells are collected, washed with PBS, and stained with 1:100 dilutions of fluorescent antibodies against the cell surface markers GPA (CD235a), CKIT (CD117), and TR (CD71), purchased from Life Technologies. Labeled cells were analyzed by flow cytometry as described herein.

Assessing Differentiation by Western Blot. Erythroid cells are cultured as described herein. At various time points, cells are collected, washed with PBS, lysed with RIPA buffer, and analyzed by Western Blot as described herein using antibodies for differentiation markers GATA1, GATA2, Band3, CD44, and actin (Abcam).

Assessing Enucleation by Flow Cytometry. Erythroid cells are cultured as described herein. At various time points, cells are collected, washed with PBS, and stained with a fluorescent antibody against glycophorin A (Life Technologies) and the nucleic acid stain DRAQ5 (Pierce) at manufacturer-recommended dilutions, and analyzed on an Attune flow cytometer as described herein.

Assessing Enucleation by Microscopy (Benzidine-Giemsa). Erythroid cells were cultured as described herein. At various time points, cells were collected, washed with PBS, and spun onto slides using a Cytospin (Thermo Scientific). Cells were fixed cells after cytospin with −20 C methanol for 2 min at room temp, rinsed with water, and air-dried. A benzidine tablet (Sigma#D5905) was dissolved with 10 mL PBS, to which 10 μL of H2O2 was added. The solution was filtered with a 0.22 um syringe filter. The cell spot on the slide was covered with 300-500 uL of benzidine solution, incubated at room temperature for 1 hr, then washed with water. Giemsa stain was diluted (Sigma#GS500) 1:20 with water. The cell spot on the slide was covered with 300-500 uL Giemsa solution, incubated at room temperature for 40 minutes, washed with water, and air-dried. Slides were then mounted and sealed before imaging on a microscope.

Figure 12A:
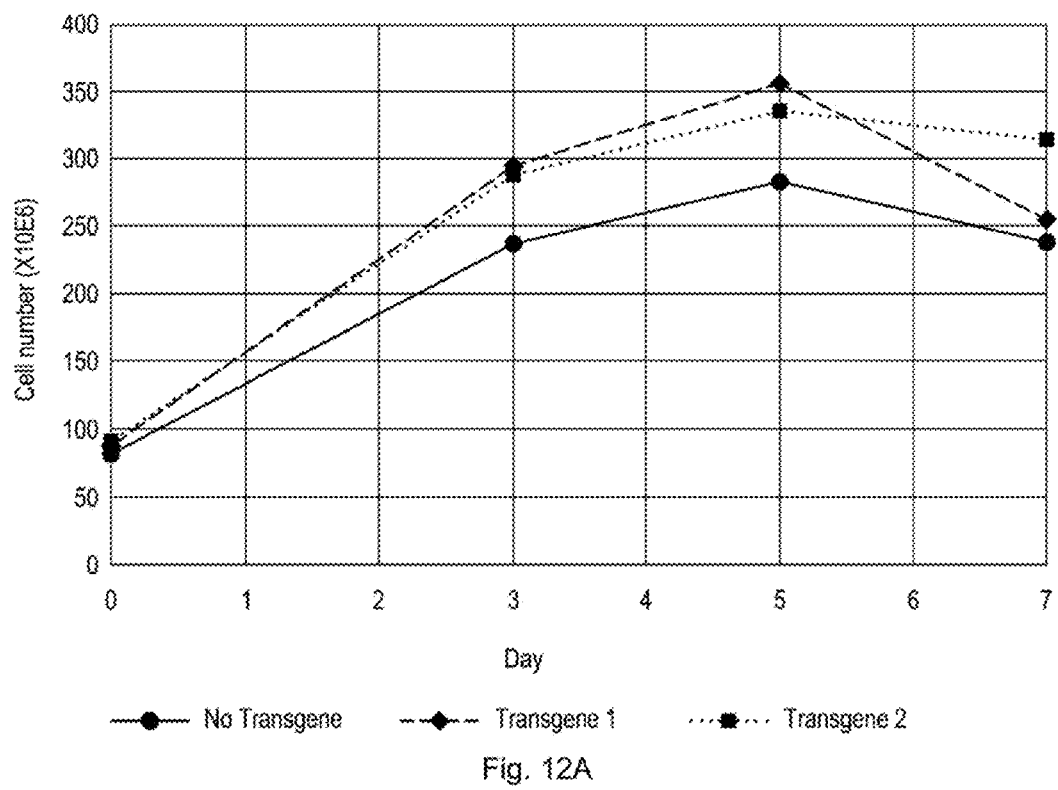
FIG. 12A-FIG. 12C is an assessment of expansion and differentiation of cultured human erythroid cells.

FIG. 12A shows the expansion rate of erythroid cells in culture during a seven day window of expansion and differentiation for cells that contain transgenes (dashed line and dotted line) and cells that do not contain a transgene (solid line). Of note, the expansion rate of cultured cells that contain a transgene is indistinguishable from that of cells that do not contain a transgene.

Figure 12B:
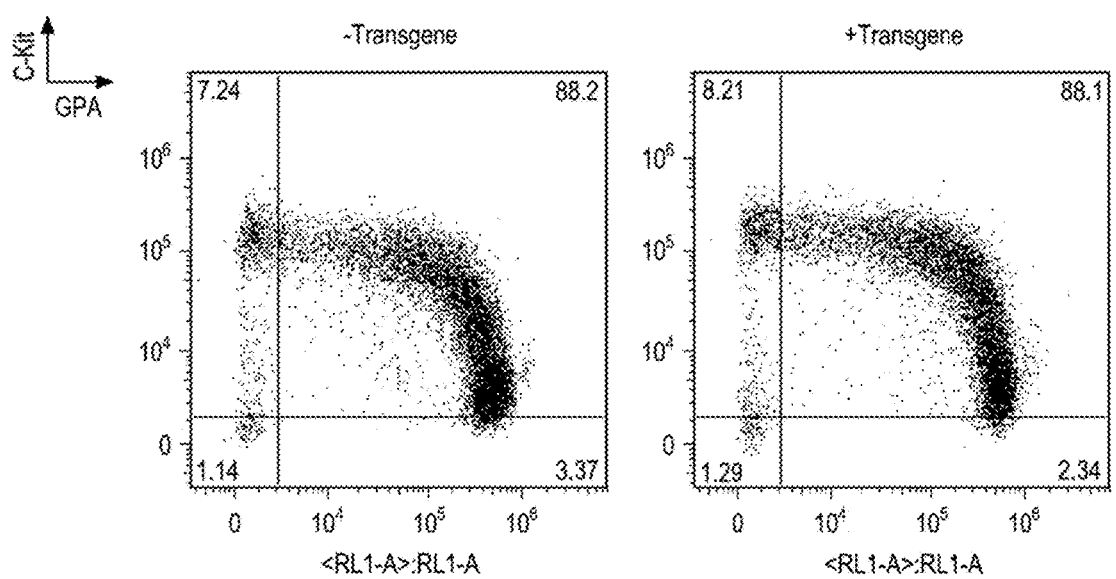

FIG. 12B is a collection of flow cytometry plots for cells stained with antibodies against the cell surface differentiation markers GPA and CKIT. At this particular stage of differentiation, the culture is losing its CKIT expression and increasing its GPA expression as the cells approach terminal maturation. Of note, cultured cells that contain a transgene are indistinguishable from those that do not contain a transgene by this metric of differentiation.

Figure 12C:
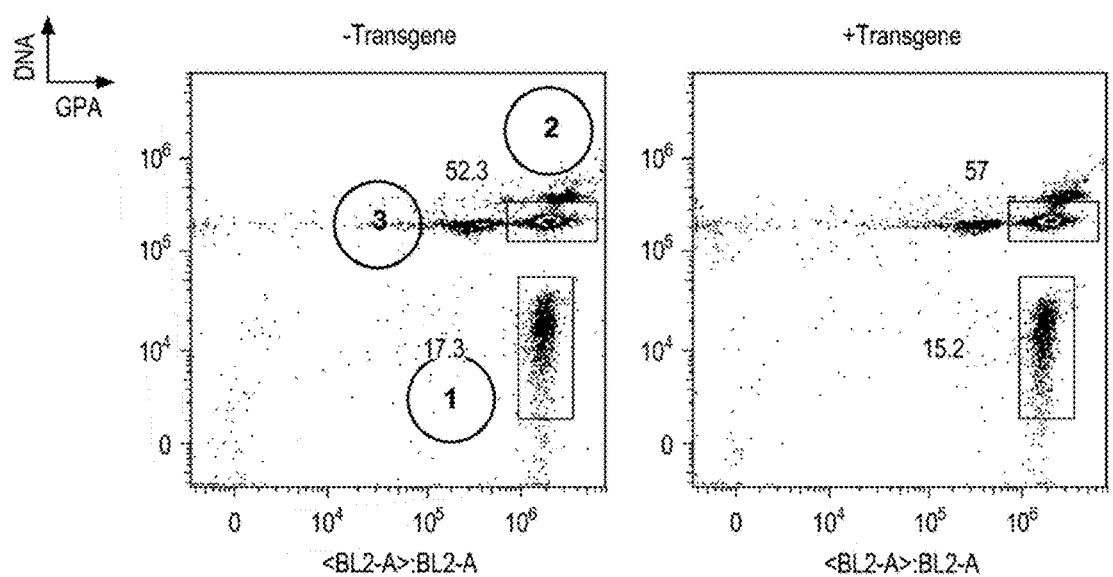

FIG. 12C is a collection of flow cytometry plots for cells stained with an antibody against the surface marker GPA and a fluorescent DNA stain. Three cell populations are evident: (1) cells that are GPA-high and DNA-low, comprising enucleated erythroid cells; (2) cells that are GPA-high and DNA-high, comprising erythroid cells that still contain genetic material; and (3) cells that are GPA-low and DNA-high, comprising pyrenocytes or the membrane-encapsulated ejected nuclei from enucleated cells. Of note, cultured cells that contain a transgene are indistinguishable from those that do not contain a transgene by this metric of enucleation.

The introduction of a transgene into cell culture does not noticeably affect the rate of expansion, the differentiation, or the rate of enucleation of the cells in culture.

Example 33

Assess Hemoglobin Content

1. Total Hemoglobin

Erythrocyte hemoglobin content was determined by Drabkin's reagent (Sigma-Aldrich, product D5941) per manufacturer's instructions. Briefly, blood cells were combined with the reagent in an aqueous buffer, mixed thoroughly, and absorbance of light at a wavelength of 540 nm was measured using a standard spectrophotometer. A soluble hemoglobin standard curve was used to quantify the hemoglobin content in the cells.

2. Hemoglobin Typing by RT-PCR

Cells were lysed and total RNA is collected. Reverse Transcription was carried out with the SuperScript First-Strand Synthesis System for RT-PCR (Life Technologies) according to manufacturer's protocol. Briefly, total RNA (5 ug) was incubated with 150 ng random hexamer primer and 10 nmol dNTP mix in 10 uL H2O for five minutes at 65 C then 1 minute on ice. The reaction master mixture was prepared with 2 uL 10× RT buffer, 4 uL of 25 mM MgCl2, 2 uL of 0.1 M DTT, and 1 uL of RNAseOUT. The reaction mixture was added to the RNA/primer mixture, mixed briefly, and then placed at room temperature for 2 min. 1 uL (50 units) of SuperScript II RT was added to each tube, mixed, and incubated at 25□C for 10 min. The reaction was incubated at 42 C for 50 min, heat inactivated at 70 C for 15 min, then stored on ice. 1 uL RNase H was added and incubated at 37 C for 20 min. This reaction product, the $1^{st}$ strand cDNA, was then stored at −20 C until needed for RT-PCR reaction.

Primers to amplify the different hemoglobin genes and control genes were purchased from IDT-DNA. The primers were as follows: hHBB_F—tcctgaggagaagtctgccgt (Seq. ID No. 9); hHBB_R—ggagtggacagatccccaaag (Seq. ID No. 10); hHBA_F1—tctcctgccgacaagaccaa (Seq. ID No. 11); hHBA_R1—gcagtggcttagcttgaagttg (Seq. ID No. 12); hHBA_F2—caacttcaagctaagccactgc (Seq. ID No. 13); hHBA_R2—cggtgctcacagaagccag (Seq. ID No. 14); hHBD_F—gactgctgtcaatgccctgt (Seq. ID No. 15); hHBD_R—aaaggcacctagcaccttctt (Seq. ID No. 16); hHBG2_F—cactggagctacagacaagaaggtg (Seq. ID No. 17); hHBG2_R—tctcccaccatagaagataccagg (Seq. ID No. 18); hHBE_F—aagagcctcaggatccagcac (Seq. ID No. 19); hHBE_R—tcagcagtgatggatggacac (Seq. ID No. 20); h18S-RNA-F—cgcagctaggaataatggaatagg (Seq. ID No. 21); h18S-RNA-R—catggcctcagttccgaaa (Seq. ID No. 22).

An RT PCR reaction mix was prepared with 25 uL SYBR Green Mix (2×) (Applied Biosystems), 0.5 uL $1^{st}$ strand cDNA, 2 uL forward/reverse primer pair mix (each primer at 5 pmol/uL), in a total volume of 50 uL H2O. Reactions were run in an ABI Prism SDS 7000 instrument (applied biosystems) using the following amplification cycle: 50 C 2 min, 1 cycle; 95 C 10 min, 1 cycle; 95 C 15 s→60 C 30 s→72 C 30 s, 40 cycles; 72 C 10 min, 1 cycle. Dissociation curve analysis and RT-PCR results was performed with the SDS 7000 instrument.

Example 34

Assess Differentiation of Cultured Platelets—FACS

The differentiation state of platelets in culture can be assessed by flow cytometry. Megakaryocytes (MKs) represent a distinct cellular morphology that precedes terminal platelet differentiation. To determine the extent of maturation toward MKs, 1×10^6 cultured cells (LAMA-84 and CD34+ cells) are washed and then labeled with (a) anti-CD41-FITC (GpIIb/IIIa; BD Bioscience, San Jose, Calif., USA) or anti CD71-FITC or (b) anti-CD33-FITC, anti-CD41-PE, anti-CD45-PerCp and CD34-APC (Beckman Coulter, Fullerton, Calif., USA), and analyzed for the percentage of CD41 cells generated.

To determine the amount of ploidy, differentiated LAMA-84 cells are fixed overnight in 75% ethanol at 4° C. and labeled with propidium iodide (PI, 50 µg/ml) and analyzed using the FACScalibur (Becton Dickinson), whereas day 14 differentiated CD34+ cells are analyzed quantitatively under a microscope after May-Grunwald/Giemsa staining by quantitating the number of nuclei per cell and specific morphology of MKs with this stain. Only cells with MK morphology are analyzed. The presence of multinucleated cells in the cytospin preparation is indicative of the presence of polyploid MKs. Differentiated CD34+ cells are assessed for the presence of multinucleated mature MKs by morphology.

Example 35

Assess Differentiation of Cultured Platelets—qPCR

The differentiation state of platelets in culture can be assessed by quantitative PCR. Platelet RNA is extracted to further characterize the cultured cells. Total RNA is extracted using TRIzol reagent (Invitrogen). The purity of each platelet preparation is assessed by PCR analysis of platelet (GPIIIa) and leukocyte (CD45) markers. The integrity of platelet RNA is assessed using Bioanalyzer 2100 (Agilent) prior to further analyses.

Total RNA is collected from cell lysate and a cDNA library is generated using a commercial synthesis kit (Clontech). The labeled cDNAs are quantified with the Quant-iT PicoGreen dsDNA Kit (Invitrogen) and diluted to 3 pM for loading into a single lane and sequencing on an Illumina 1G Genome Analyzer (Solexa).

Raw sequences are filtered through serial quality control criteria. First, the presence of at least 6 nt of the 3' Solexa adapter is verified. The sequence reads that did not comply with this criterion are discarded, whereas the others are trimmed to remove the adapter sequence harbored at the 3' end. The remaining tags are further filtered regarding their length (>10 nt), copy number (>4 reads) and readability (<9 non-identified nucleotides, annotated N). Reads complying with all those criteria are subsequently defined as usable reads.

All the usable reads are aligned to pre-microRNAs extracted from miRBase database. Sequence tags that matched perfectly to more than one precursor are distributed equally among them. In order to account for Drosha and Dicer imperfect cleavage, any sequence tag that perfectly matched the pre-microRNA in the mature microRNA region, allowing up to 4 nt shift as compared to the reference mature microRNA position, is considered as a mature microRNA. The microRNA expression level is defined as the number of reads mapping each mature microRNA normalized to the total number of usable reads, considering that the overall number of small RNAs is invariant. The relative abundance of each microRNA is defined as the number of reads mapping each microRNA compared to the total number of reads mapping mature microRNAs.

Example 36

Purification by Centrifugation

Cultured cell fractions can be purified and separated from nuclei and contaminating alternate-density cell types via centrifugation. Cells are centrifuged at 200 g for 15 minutes to isolate an erythrocyte and reticulocyte rich fraction. The supernatant is pipetted off and the desirable cell fraction is then washed in modified Tyrode's buffer (containing 138 mM NaCl, 5.5 mM dextrose, 12 mM NaHCO3, 0.8 mM MgCl2, 0.4 mM MgCl2, 2.9 mM KCl2, 0.36 mM Na2HPO4 and 20 mM Hepes, pH 7.4) in presence of 1 µM prostaglandin I2, and resuspended in the same buffer.

Example 37

Purification by Chemical Enucleation

Enucleation of cultured cells can be stimulated by chemical additives to the culture, which can help increase the enucleated fraction of cells prior to purification. Erythroid cells are cultured as described herein. 48 hours prior to collection, cells are incubated with 210 mM Me2SO. Cells are then collected by centrifugation at 350×g for 5 min at room temperature, resuspended at a level of 3×105 cells per ml in fresh medium containing 210 mM Me2SO and 5 ug/mL of cytochalasin B (or other actin or nucleus manipulating molecule, ie. p38 MAPK, psoralens) and incubated at 37 C. The proportion of cells without nuclei is assessed by flow cytometry as described herein, using DRAQ5 as a nucleic acid stain and antibodies against glycophorin A as an erythroid surface marker of differentiation.

Example 38

Purification by Acoustophoresis

Several mechanical separation systems may be used to obtain a uniform cell population. Free flow acoustophoresis represents one mechanical separation method (Petersson 2007, American Chemical Society). While suspended in saline solution (0.9 mg/mL) with nutrient additives, including CsCl (0.22 g/mL), is added to the saline solution. A sample suspension containing cultured erythroid cells is processed using an acoustophoresis chip (Cell-Care) with two active outlets (flow rate 0.10 mL/min per outlet).

Syringe pumps (WPI SP260P, World Precision Instruments Inc., Sarasota, Fla.) are used to control the flow rates in the chip. All outlets are individually connected to high-precision glass syringes (1005 TLL and 1010 TLL, Hamilton Bonaduz AG, Bonaduz, Switzerland) via the injectors using Teflon tubing, allowing independent control of the outlet flow rates. The clean fluid inlet is connected to a syringe pump and the cell suspension inlet to a 50-mm-long piece of Teflon tubing (0.3-mm i.d.) with its other end submerged in a beaker from which the sample suspension is aspirated at a rate defined by the difference between the net outlet flow and the clean fluid inlet flow.

The ultrasound used to induce the standing wave between the walls of the separation channel is generated using a 20×20 mm piezoelectric ceramic (Pz26, Ferroperm Piezoceramics AS, Kvistgard, Denmark) attached to the back side of the chip. Ultrasonic gel (Aquasonic Clear, Parker Laboratories Inc., Fairfield, N.J.) ensures a good acoustic coupling between the two. The piezoelectric ceramic is actuated via a power amplifier (model 75A250, Amplifier Research, Souderton, Pa.) connected to a function generator (HP 3325A, Hewlett-Packard Inc., Palo Alto, Calif.). Even though the acoustic waves enter the chip from the back side, a standing wave is induced between the side walls of the separation channel as a result of the coupling of the mechanical vibrations along the three axes of the crystal structure.

The separation process is monitored using a standard microscope and a wattmeter (43 Thruline Wattmeter, Bird Electronic Corp., Cleveland, Ohio). The process can subsequently be controlled by tuning the signal frequency, the actuation power, and the flow rates.

The cell size distributions in the samples are analyzed using a Coulter counter (Multisizer 3, Beckman Coulter Inc., Fullerton, Calif.). Each sample is mixed with an electrolyte (Isoton II, Beckman Coulter Inc.) and analyzed using a 100-um aperture. The level of hemolysis, i.e., the concentration of free hemoglobin from damaged red cells, is measured using a photometer (Plasma/low HB Photometer, HemoCue AB, Angelholm, Sweden).

Example 39

Purification by Ex Vivo Maturation

Erythroid cells that are not fully mature can be driven to maturity by ex vivo incubation in a system that mimics the natural in vivo maturation triggers.

1. Co-Culture with Stromal Cells

In the final stage of culture, erythroid cells are cultured on an adherent stromal layer in fresh medium without cytokines. The cultures are maintained at 37 C in 5% CO2 in air. The adherent cell layer consists of either the MS-5 stromal cell line or mesenchymal stromal cells (MSCs) established from whole normal adult bone marrow (see Prockop, DJ (1997) Science 276:71) in RPMI (Invitrogen) supplemented with 10% fetal calf serum. Adherent MSCs are expanded and purified through at least two successive passages prior to use in co-culture.

2. Culture in Fibronectin-Coated Plates

In the final stage of culture, erythroid cells are cultured in plates adsorbed with human fibronectin. To produce these plates, fibronectin (Sigma Aldrich) is reconstituted with 1 mL sterile H2O/mg of protein and allowed to dissolve for at least 30 minutes at 37° C. A small amount of undissolved material may remain. This will not affect product performance. The fibronectin solution is diluted 100× in sterile balanced salt solution and added to the culture surface with a minimal volume. The culture surface is allowed to air dry for at least 45 minutes at room temperature. Excess fibronectin is removed by aspiration.

Example 40

Purification by Magnetophoresis

Strategies for separating, enriching, and/or purifying erythroid cells by magnetophoresis are known in the art, see e.g., Zborowski et al., 2003, Biophys J 84(4) 2638 and Jin & Chalmers 2012, PLOS One 2012 7(8):e39491. A commercial magnetic separation system (QuadroMACS™ Separator combining four MidiMACS™ separation units and LD columns, Miltenyi Biotec, Auburn, Calif.) is used for magnetic erythrocyte enrichment from HSC-derived erythrocyte cultures. Cells are deoxygenated in a Glove-Bag™ inflatable glove chamber (Cole Parmer, Vernon Hills, Ill.), filled with nitrogen (Medipure™ nitrogen, concentration >99%, Praxair, Inc., Danbury, Conn.). Before deoxygenation, all materials and equipment including the separation system, degassed sterile buffer (PBS+2 mM EDTA+0.5% BSA), and sterile collection tubes are placed in the glove bag, which is then tightly sealed. Deoxygenated cultures are loaded directly into a MACS® LD column which was placed in the QuadroMACS™ separator kept under anoxic conditions inside an inflatable glove chamber filled with N2 gas. Cells which pass through the column contained within the magnet are labeled as negative fraction and they are expected to be "non-magnetic", including HSCs and erythroid cells before final maturation. The cells retained in the separation column are labeled as positive fraction, which is "magnetic" and consist of maturing RBC-like cells nearly full of functional hemoglobin. They are eluted from LD column after its removal from the magnet. Once separation is finished, oxygenated cells are reversibly recovered by exposing the collected cells to air.

Example 41

Purification by FACS

A population of erythroid cultured cells is sorted using a Becton-Dickinson Aria Ilu cell sorter. Prior to sorting, cells are collected, washed with PBS, and stained with a fluorescent antibody against glycophorin A (Life Technologies) and the nucleic acid stain DRAQ5 (Pierce) at manufacturer-recommended dilutions. A 100 μm nozzle is used with a drop drive frequency of 28,000 drops/second. The sample threshold rate is approximately 4000 events/second. The temperature control option is used to maintain sample and collection tubes at 4° C. the entire duration of sorting. Additionally, the sample agitation feature is used at 200 rpm to prevent the sample from sedimenting throughout the sort. The sample is sorted in aliquots of approximately 750 μl dispensed from the syringe. Meanwhile, during these pauses the collection tubes are kept at 4° C., protected from the light, and gently mixed prior to resuming sort. The sorted samples are collected into a 12×75 mm borosilicate glass collection tube containing 250 μl DMEM supplemented with 10% FCS.

Example 41

Purification by Enzymatic Treatment of Cells

Allogeneic erythrocyte sourcing may benefit from A and B antigen removal to generate a universally compatible product. This may be facilitated by a set of enzymes capable of selectively cleaving the galactose groups, rendering the erythroid cells more immunogenically favorable.

Two types of recombinant proteins of endo-β-galactosidase, which are originally identified from *Clostridium perfringens*, are produced in *E. coli* BL-21 using standard cloning methods. ABase is prepared for releasing A/B Ag and endo-β-galactosidase C (EndoGalC) for releasing Galα1-3Galβ1-4GlcNAc (Gal Ag), which is known to be highly immunogenic in xenotransplantation, and has a carbohydrate structure resembling the A/B Ag. ABase cleaves Galβ1-4GlcNAc linkage in blood type A [GalNAcα1-3 (Fucα1-2) Galβ1-4GlcNAc] and in blood type B [Galα1-3 (Fucα1-2) Galβ1-4GlcNAc].

Briefly, after cloning of ABase, an expression plasmid with a C-terminal His tag is constructed in the pET-15b vector eabC without signal peptide. This exogenous gene is transformed into *E. coli* BL-21 cells. The enzyme produced in the cells as a soluble protein fraction is purified over a nickel-nitrilotriacetic acid column (QIAGEN GmbH, Hilden, Germany). Finally, 5 mL of purified recombinant ABase is obtained at the concentration of 3.6 mg/mL with the specific activity of 1500 U/mg. One unit of the enzymatic activity is defined as the amount of the enzyme required to hydrolyze 1 µmol of the substrate per min.

The effect of ABase treatment on Ag presence, Ab binding and complement activation is examined. Human AM RBC are digested with ABase and subjected to flow cytometric analysis after incubation with cross-reactive (anti-A or anti-B or anti-A and B containing; type B, type A or type O respectively) human sera. The mean fluorescence intensity (MFI) is used to quantitate the expression level of blood type A, B and Gal Ag. Digestion level is expressed as a percentage of blood type A or B Ag expressed on RBC after incubation in the absence of ABase.

Fresh blood type O sera are pooled from three healthy human volunteers and frozen at $-80°$ C. to preserve endogenous complement activity until used. Heat-inactivated (for 30 min at $56°$ C.) sera are used for analysis of Ab binding. RBC with and without enzyme (ABase) digestion are incubated with 50% blood type O sera (100 µL) diluted with phosphate-buffered saline containing 0.2% bovine serum albumin (PBS/BSA) for 30 min at $37°$ C. After washing, RBC are reacted with FITC-labeled anti-human IgG/IgM (DAKO, Glostrup, Denmark) (×30, 100 µL) for 30 min at $4°$ C. and then subjected to flow cytometric analysis.

The inhibitory effect of enzyme treatment on complement activation is also evaluated by the change of C3d deposition. After RBC are incubated with 50% human sera in the presence of complement activity for 15 min at $37°$ C., RBC are reacted with FITC-labeled rabbit anti-human C3d Ab (DAKO, Glostrup, Denmark) (×100, 100 µL) for 30 min at $4°$ C. and then applied to flow cytometric analysis. The percentage of the control level (in the absence of enzyme) is calculated based on MR to evaluate the inhibitory effect of enzyme treatment on Ab binding and C3d deposition.

Example 42

Purification of Platelets by Centrifugation

Platelets can be purified from mixed cell suspensions by centrifugation. Some 40 ml of whole blood is distributed in blood collection tubes with sodium citrate at 3.2% used as an anticoagulant. The tubes are centrifuged at 400×g for 10 min. After this stage, three layers are clearly demarcated: plasma, red blood cells, and an intermediate zone. The plasma is at the top with the platelets, the red blood cells are at the bottom because of their heavier density; and the fine, whitish intermediate zone consists of larger platelets and leukocytes and is called the buffy coat. Using a Jelco 18G needle, the upper portion of plasma with platelets is drawn off, and the buffy coat is placed into two other tubes, this time with no additives: one tube to produce plasma (P tube) and the other to produce thrombin (T tube). Only 1.5 ml of plasma is used to produce thrombin, to which 0.5 ml of calcium gluconate at 10% is added, with 15 min in a double boiler at $37°$ C. The two tubes are then centrifuged again, this time at 800×g, for the same length of time (T=10 min). After this final centrifugation, the T tube contains a thrombin-rich liquid while the P tube contains the platelet sedimentation and some red blood cells (erythrocyte-platelet clump). The volume is reduced at this stage by removing two-thirds of the total plasma volume. The portion removed is platelet poor, while the remaining portion with the sedimented platelets (that are easily dispersible by stirring) is platelet rich.

Example 43

Thymidine Incorporation

Self-replication potential of a cell population can be assessed using a thymidine incorporation assay known in the art, see e.g., Harkonen et al. 1991 Exp Cell Res 186L288 and Tanaka et al. 1992 PNAS 89:8928.

Briefly, uniformly 13C- and 15N-enriched thymidine [U-13C, 15N-TdR] is obtained from Martek Biosciences (Columbia, Md.), and 3 H-TdR (80 Ci/mmol) is purchased from ICN Radiochemicals (Irvine, Calif.). Media and buffers are obtained from Fisher Scientific (Pittsburgh, Pa.). All enzymes except phosphodiesterase are from Boehinger Mannheim (Indianapolis, Ind.). Phosphodiesterase II is obtained from Worthington Biochemical Corporation (Lakewood, N.J.). High-performance liquid chomatography (HPLC) solvents are from EM Science (Gibbstown, N.J.) and contained <0.1 ppm evaporation residue.

Erythroid cells are cultured as described herein. Following the culture, cells are collected for use in the thymidine incorporation assay.

Cells are labeled with [U-13C, 15N]-TdR at 1.6 µg/ml for 18 h, with the addition of unenriched thymidine to achieve a final thymidine concentration of 1 µM. After they are washed with phosphate-buffered saline, the cells are cultured in supplemented DMEM for 6 h more before 3 H-TdR is added at the indicated concentrations (0.1-10 µCi/ml) for another 18-h incubation. Unlabeled thymidine is added to the samples to bring the final thymidine concentration to 0.13 µM, which is equivalent to the concentration of 3 H-TdR in the samples receiving 10 µCi radiolabel/ml. After removal of 3 H-TdR, the cells are incubated in supplemented DMEM for an additional 6-54 h before isolation of DNA.

DNA is extracted using the modified Puregene DNA isolation kit (Gentra Systems, Minneapolis, Minn.). Based on the number of cells in the sample, a scale-up/scale-down procedure is used to determine the added reagent volumes. For example, when $1 \times 10^7$ cells are used, 21 µl containing 328 µg of proteinase K is added to 3 ml of cell lysis solution. After mixing, the sample is left overnight at room temperature. The following day, 10 µg of RNase is added and the sample is mixed and incubated for 2 h at 37 C. Protein precipitation solution (1 ml) is added, and the sample is incubated on ice for 5 min. After centrifugation for 10 min at 2000 g, the supernatant containing DNA is mixed with 3 ml 100% 2-propanol and gently inverted 50 times or until white threads of DNA became visible. The sample is then centrifuged at 2000 g for 5 min. The resultant DNA pellet is dried for 5 min before washing in 3 ml of 70% ethanol and recentrifugation for 5 min at 2000 g. The final pellet is air-dried and then rehydrated in deionized H2O and quantitated by absorption at 260 nm. The same procedure is applied to CD34+ stem cells as a control for replicative ability.

Any DNA is denatured by boiling for 3 min, then chilled rapidly on ice. The enzymatic hydrolysis procedure is carried out with a DNA concentration of 0.5 mg/ml. The following protocol describes volume of reagent added per milliliter of DNA solution. DNA is hydrolyzed with 10 µl of nuclease P1 (0.5 U/µl) and 5 µl of DNase I (4 U/µl) in 10 µl of buffer containing 200 mM MgCl2, 100 mM ZnCl2, and 1 M Tris, pH 7.2, for 2 h at $45°$ C., followed by addition of 20 µl phosphodiesterase (4 mU/µl) and further incubation for 2 h at 37° C. Finally, 5 µl of 10 M ammonium acetate (pH 9.0) and 10 µl of alkaline phosphatase (1 U/µl) are added, and the samples incubated for another 2 h at 37° C.

The digested DNA sample is filtered with a 0.22-µm nylon filter. This sample is analyzed with the HPLC/CRI/IRMS system, using a 4.6×250 mm Supelcosil LC-18-S HPLC column (Supelco, Bellefonte, Pa.). The same solvent system is used at 1 ml/min and a linear gradient of 5% to 25% B in 15 min.

After separation by HPLC, the deoxynucleosides are analyzed using chemical reaction interface mass spectrometry (CRIMS). In this process, the deoxynucleosides flow into a nebulization and desolvation system driven by a stream of helium, where they emerge as a dry particle beam. The 13CO2/12CO2 abundances from this in-line generated CO2 are determined with a Finnigan/MAT Delta S isotope ratio mass spectrometer (ThermoFinnigan, San Jose, Calif.) and its accompanying Isodat data system. 5-Fluorodeoxyuridine (Sigma) is used as an internal isotope ratio standard.

Isotope ratios (IR in equation that follows) for three nucleosides are obtained from each sample: T, dA, and dG. The enrichment of $CO_2$ evolved from each DNA-derived deoxynucleoside is computed by the equation (13) $CO_2$ (per mil)=1000× (IR experimental—IR std)/IRstd. To maintain the highest level of internal consistency and avoid any interexperimental drift, the isotope ratio for dG is subtracted across all experiments from the isotope ratio for T. The data from the end of the stable-isotope labeling period (day 0) to the end of the washout (day 3) are evaluated.

Example 44

Quantification of Nuclear Material

The number of cells in a mixed population that contain DNA is assessed by flow cytometry using the DNA stain DRAQ5 (Pierce). Cells are incubated with the stain per manufacturer's instructions and analyzed on a flow cytometer, e.g., an Attune cytometer (Life Technologies). The percentage of cells above a predefined threshold of nuclear material content is quantified.

Example 45

Tumorigenicity Assay In Vitro

To assess the replication potential of cells, a soft agar colony formation assay can be performed. In brief, a base agar layer is made by making a 0.5% Agar+1×RPMI+10% FCS solution, all components warmed to 40 C, and adding 1.5 mL of the solution to a 35 mm petri dish. The agar is allowed to solidify for 30 min at room temp before use.

The top agarose layer is prepared by melting 0.7% agarose in a microwave and cooling to 40 C. A 2×RPMI+20% FCS solution is heated to 40 C. Cells are counted and prepared for plating at 5000 cells per plate at a density of 200,000 cells per mL. 0.1 mL of cell suspension is added to 10 mL tubes, followed by 3 mL of the warm 0.7% Agarose and 3 mL of the warm RPMUFCS solution. The solution is mixed gently by swirling and added (1.5 mL) to each of three or four replicate base agar plates.

Plates are incubated at 37 C in a humidified incubator for 10-30 days. Cells are fed 1-2 times per week with cell culture media, 0.75 mL/plate.

To assess colony formation, plates are stained with 0.5 mL of 0.005% Crystal Violet for >1 hr. Colonies are counted using a dissecting microscope.

Example 46

Tumorigenicity Assay In Vivo

Terminally-differentiated cultured erythroid cells are implanted in various animal models to evaluate the potential for tumorigenicity. Several tissues are collected from the various models and analyzed with histological, immunochemical, and fluorescent assays to quantify tumorigenicity.

Animals receive daily intraperitoneal injections of CsA (10 mg/kg, Sandimmune, Novatis Pharma, Nürnberg) starting two days before grafting. For the depletion of NK cells, some rats receive, in addition to CsA intraperitoneal injections of the monoclonal antibody (mAb), anti-NKR-P1A (clone 10/78, mouse $IgG_1$, BD Biosciences, Heidelberg, Germany) or the respective isotype control (clone PPV-06, mouse $IgG_1$, Exbio, Prague, Czech Republic). The anti-NKR-PIA mAb (clone 10/78) is directed against the same epitope as the mAb (clone 3.2.3). One mg of the respective antibodies are given one day before the injection of erythroid cells followed by 0.5 mg at day 4 after cell transplantation.

Blood samples are taken before starting these experiments, at day 0 and 4 days after erythroid cell transplantation, and at autopsy (day 92) in order to determine the proportion of NK cells in the blood by flow cytometry. For the analysis of subcutaneous tumor growth erythroid cells are injected in 100 µl phosphate-buffered saline (PBS) into the flank of the animals. Tumor growth is monitored every second day by palpation and size is recorded using linear calipers. Animals are sacrificed before day 100 when a tumor volume of 1 $cm^3$ in mice and 5 $cm^3$ in rats is reached, when a weight loss of more than 10% occurs, or when any behavioral signs of pain or suffering are observable. Autopsies of all animals are performed.

Murine tissue near the site of injection is immediately frozen in liquid nitrogen or placed in phosphate-buffered 4% formalin for 16 h and then embedded in paraffin. Spleens and lymph nodes are removed for subsequent immunological analyses. The transplantation of erythroid cells into the striatum of unilaterally 6-OHDA-lesioned rats is performed. These animals are sacrificed 6 weeks after transplantation.

Animal tissue is analyzed by flow cytometry. Appropriate fluorescent and PE-conjugated antibodies against established cancer cell biomarkers of CD133, CD3, CD, CD16, CD19, CD20, CD56, CD44, CD24, and CD133 are added to the excised tissues samples and analyzed to quantify tumorigenic potential.

Example 47

Deformability by EKTA

Erythroid cells cultured as described herein are assessed for deformability characteristics relative to natural erythrocyte samples via ektacytometry.

The ektacytometer consists of a Couette-type viscometer combined with a helium-neon laser used to produce a diffraction image of red cells suspended in a viscous fluid between the two cylinders. When the viscometer rotates, normal red cells elongate in the shear field, causing the diffraction image to become elliptical. The ellipticity of the image is measured by quantifying the light intensity along the major (A) and minor (B) axes of the diffraction pattern and expressing this as a ratio (A−B)/(A+B), the deformability index (DI) or elongation index (EI). The viscosity of the medium is chosen to be greater than the internal viscosity of the densest erythroid cells. A 31 g/liter solution of polyvinylpyrrolidone (PVP), mw=360,000, in a phosphate buffer of 0.04 M composed of K2HP04 and KH2P04 in distilled water yields a viscosity of 0.20 poise at 25° C. and 12 poise at 37 C.

Osmolarity is adjusted with NaCl to the desired level and measured in a Roebling freezing-point osmometer. The final pH is varied by using small additions of 1-M solutions of NaOH and HCl and is measured in a Technicon BG I1 blood gas analyzer. Sodium azide is added as a preservative to stock solutions to obtain 0.4 g/l.

The ektacytometer collects three primary metrics from the erythroid cell samples and compares them to native erythrocytes; Osmolality minimum ($O_{min}$), deformability index ($Di_{max}$), and the osmolality at which the DI reaches half of its maximum value ($O_{hyp}$).

$O_{min}$ is related to the surface area to volume ratio of the cell and has been found to equal the 50% hemolysis point in the classical osmotic fragility test.

$Di_{max}$ is the maximum value of the deformability index, normally reached at 290 mosmol (the physiologic osmolality value). This indicates the maximum deformability of the cell under shear stress and is related to a number of factors, such as surface area, volume, internal viscosity, and mechanical properties of the cell membrane.

$O_{hyp}$ is the osmolality at which the DI reaches half of its maximum value. This gives an indication of the position of the hypertonic part of the curve, which is related to the internal viscosity of the cell as well as mechanical properties of the membrane, such as how it will bend under force (stiffness).

The parameters obtained for the cultured erythroid cells are compared to the same values for primary erythroid cells.

Example 48

Deformability by LORCA

The deformability of purified cRBC populations is measured by a laser diffraction technique (LORCA, laser-assisted optical rotational cell analyzer, R&R Mechanotrics). In brief, a highly diluted suspension of cells is sheared in a Couette system with a gap of 0.3 mm between 2 cylinders, one of which is able to rotate to induce shear stresses. A laser beam is passed through the suspension, and the diffraction pattern is measured at 37° C. At low shear stress, the cells are circular disks, whereas at high shear stress, the cells become elliptical. The cell deformability is expressed in terms of the elongation index (EI), which depends on the ellipticity of the deforming cells. Aliquots containing 12.5 uL of pelleted RBC pellets are diluted in 5 mL of polyvinylpyrrolidone solution (molecular weight 360 000). The EI values at 30 Pa (referred to as EImax) and 3 Pa are selected as representative values of the deformability for easy comparison between samples at various shear stresses.

Example 49

Assessment of Vascular Occlusion—Ex Vivo Rat Vasculature

The potential for vascular occlusion of erythroid cells can be assessed with isolated artificially perfused rat vasculature using methods known in the art, see e.g., Kaul et al. 1983, J Clin Invest 72:22. Briefly, in anesthetized (sodium pentabarbitol 30 mg/kg) rats of the Wistar strain, 120-150 g, the right ileocolic artery and vein are cannulated with heparinized (100 uL/mL) silastic tubing at a site 3 cm distant from the ileocolic junction. Under a steady-state perfusion with Ringer's containing 1% bovine serum albumin, the ascending colon and terminal ileum (3 cm each) are sectioned between ties. After hemostatic ties of all vascular connections is achieved, the tissue is isolated. The isolated mesoappendix is gently spread on an optically clear Lucite block on a microscope stage. The entire preparation is covered with a plastic saran wrap except for outlets of cannulas and the microscope objective.

The control arterial perfusion pressure (Ppa) and venous outflow pressures (Pv) are kept constant at 80 and 3.8 mmHg, respectively, and monitored via Statham-Gould P-50 pressure transducers (Stathan Instruments Inc, Oxnard Calif.). The venous outflow (Fv) rate is monitored using a photoelectric dropcounter and expressed in ml/min. A lapse of 10-12 min is allowed for tissue equilibration and stabilization of Fv. Only preparations exhibiting mesoappendix microvasculature free of host blood cells and with a steady Fv of 4.6+/−0.5 (mean+/−SD) are used. The experiments are done at 37 C.

Erythroid cells are isolated as described herein. After control measurements of Ppa and Fv, erythroid cells (0.2 mL, Hct 30%) are gently delivered via an injection port 15 cm distal to site of arterial cannulation, and the changes in Ppa and Fv are recorded on the strip chart of a Grass polygraph (Grass Instrument Co, Quincy Mass.). The tissue preparations are perfused for 10-15 min before the infusion of samples with Ringer's solution to allow stabilization of the tissue and clear the vasculature of the remaining blood cells of the host animal. The resulting obstruction after the infusion of cells can be cleared and the flow restored by briefly (2-3 min) perfusing the vasculature with fully-oxygenated Ringer's solution at high pressure (100 mmHg).

At the end of each experiment the entire tissue preparation (free of cannulas and luminal content) is weighed. Peripheral resistance units (PRU) are calculated and expressed as PRU=$\Delta$P/Q=mmHg/mL/(min-g) where $\Delta$P (mmHg) is the arteriovenous pressure difference and Q (mUmin-g) is the rate of venous outflow per gram of tissue.

In each experiment, pressure-flow recovery time (Tpf) is determined following the bolus infusion of samples. Tpf is defined as the time (seconds) required for Ppa and Fv to return to their base-line levels following the delivery of a given sample, and it represents total transit time throughout the mesoappendix vasculature. The parameter values obtained for cultured erythroid cells are compared to the values obtained for primary erythroid cells.

Example 50

Assessment of Vascular Occlusion—In Vitro Flow Chamber

Methods to assess vascular occlusion of erythroid cells using in vitro graduated height flow chambers are known in the art, see e.g., Zennadi et al 2004, Blood 104(12):3774.

Briefly, graduated height flow chambers are used to quantitate the adhesion of erythroid cells to endothelial cells (ECs). Slides coated with ECs are washed with Hanks balanced saline solution (HBSS) with 1.26 mM Ca2+, 0.9 mM Mg2+(Gibco, Grand Island, N.Y.) warmed previously to 37° C. and then fit into a variable height flow chamber.

The flow chamber is mounted on the stage of an inverted phase contrast microscope (Diaphot; Nikon, Melville, N.Y.) connected to a thermoplate (Tokai Hit, Fujinomiya-shi, Japan) set at 37° C. Cells are observed using a video camera (RS Photometrics, Tucson, Ariz.) attached to the microscope and connected to a Macintosh G4 computer (Apple, Cupertino, Calif.). Erythroid cells are cultured as described herein, and labeled with fluorescent dye PKH 26 red fluorescent cell linker kit (Sigma) following the manufacturer's instructions. Cells (3 mL) suspended at 0.2% (vol/vol) in HBSS with Ca2+, Mg2+ are infused into the flow chamber and allowed to adhere to the slide for 15 minutes without flow. Before exposure to flow, a minimum of 3 fields at each of 7 different locations along a line oriented normal to future flow are examined for the total number of fluorescent cells. Fluid flow (HBSS with Ca2+, Mg2+) is then started using a calibrated syringe pump. After exposure to flow, the fields are again examined and the number of adherent cells counted. The fraction of adherent cells is presented as follows: Number of cells attached after exposure to flow/ Cells present per field before flow. The wall shear stress is calculated as follows: tw=(6 μQ)/(wH [×]2), in which τw indicates wall shear stress (dyne/cm2); Q, volumetric flow rate (cm3/s); μ, media viscosity; w, width of the flow channel; and H(x), height of the flow chamber as a function of position along the microscope slide.

Example 51

Assessment of Vascular Occlusion—Intravital Microscopy

Methods to assess vascular occlusion of erythroid cells using intravital microscopy are known in the art, see e.g., Zennadi et al. 2007 Blood 110(7):2708.

Briefly, general anesthesia of a test animal is achieved by intraperitoneal injection of 100 mg/kg ketamine (Abbott Laboratory, Chicago, Ill.) and 10 mg/kg xylazine (Bayer, Shawnee Mission, Kans.). A double-sided titanium frame window chamber is surgically implanted into the dorsal skin fold under sterile conditions using a laminar flow hood. Surgery involves carefully removing the epidermal and dermal layers of one side of a dorsal skin fold, exposing the blood vessels of the subcutaneous tissue adjacent to the striated muscles of the opposing skin fold, and then securing the 2 sides of the chamber to the skin using stainless steel screws and sutures. A glass window is placed in the chamber to cover the exposed tissue and secured with a snap ring. Subsequently, animals are kept at 32° C. to 34° C. until in vivo studies were performed 3 days after surgery.

Anesthetized animals with window chambers are placed on the stage of an Axoplan microscope (Carl Zeiss, Thornwood, N.Y.); temperature is maintained at 37° C. using a thermostatically controlled heating pad. All infusions are through the dorsal tail vein. Erythroid cells are cultured as described herein. Cells are then labeled with Dil or DiO (Molecular Probes, Eugene, Oreg.) dyes per manufacturer's instructions. Labeled cells (300 μL; hematocrit [Hct] 0.50 [50%] in PBS with Ca2+ and Mg2+) are infused, and RBC adhesion and blood flow dynamics are observed in subdermal vessels for at least 30 minutes using LD Achroplan 20×/0.40 Korr and Fluar 590.25 objectives. Microcirculatory events and cell adhesion are simultaneously recorded using a Trinitron Color video monitor (PVM-1353 MD; Sony, Tokyo, Japan) and JVC video cassette recorder (BR-S3784; VCR King, Durham, N.C.) connected to a digital video camera C2400 (Hamamatsu Photonics KK, Hamamatsu City, Japan). Thirty segments of venules are examined for each set of conditions. Arterioles are distinguished from venules based on (1) observation of divergent flow as opposed to convergent flow; (2) birefringent appearance of vessel walls using transillumination, which is characteristic of arteriolar vascular smooth muscle; and (3) relatively straight vessel trajectory without evidence of tortuosity.

Measurement of red cell flux and adhesion is performed by examining videotapes produced using×20 magnification. Cell adherence is quantitated by considering cells attached to the vessel walls and immobile for 1 minute. The percentage of the length of vessels with diameters up to 25 μm or more than 25 μm, occupied by SS RBCs, is quantified as follows: % venular length occupied by SS RBCs=(length of vessel wall with adherent cells/total length of the vessel segments analyzed)×100. Changes in RBC flux are calculated as follows: flux=number of circulating fluorescent human RBCs crossing a single point marked on vessels less than 50 μm in diameter per minute.

Example 52

Assessment of Vascular Occlusion—Platelets

Methods to assess vascular occlusion of platelets using human vascular endothelial cells (HUVECs) can be adapted from similar methods for eythroctyes. Briefly, a 2-mL volume of 0.05% hematocrit suspension is added to confluent HUVECs on tissue culture Petri dish. The cone-and-plate apparatus is assembled within 1 min after addition of platelets and placed on a Nikon Diaphot-TMD invertedphase contrast microscope (Southern Micro Instruments, Atlanta, Ga.). The motor is started to turn the cone, and adherence is continuously monitored at 0.1 or 1 dyne/cm2 shear stress for 30 min. Temperature is maintained constant at 37° C. by an air curtain incubator (Nicholson Precision Instruments, Inc., Bethesda, Md.) blowing on the adhesion apparatus. Platelet adherence is visualized and recorded every 5 min by focusing on 8 different fields of view for 20 sec per field for each time point. The entire experiment is viewed under 400× total magnification through a CCD-72 series camera (Dage-MTI, Inc., Michigan City, Ind.) and recorded on videotape with a SVO 2000 video cassette recorder (Sony Electronics, San Jose, Calif.). Adherence is quantified off-line at the end of each experiment by counting individual adherent cells during manual playback of recorded video images. The cell counts in 8 fields for each time point are averaged and normalized to adherent red cells per square millimeter of endothelium.

Example 53

Assessment of Mass/Volume/Density with Resonator

A dual suspended microchannel resonator (SMR) system is used to characterize the mass, volume, and density of a population of terminally-differentiated erythroid cells based on Bryan et al, *LabChip*, 2014. At the start of a cell density measurement, the system is first flushed with filtered Percoll media, which serves as the high density fluid. Next, the sample bypass is filled with a dilute cell sample, and the vial heights at the sample inlet and outlet are adjusted to direct fluid flow into the first SMR. Pressure at the high density fluid inlet is used to set the density of Fluid 2, and pressure at the waste outlet controls the overall flow speed in the device. To minimize the likelihood of size biasing due to heavier cells settling at the bottom of the sample vial or tubing, a fresh sample is introduced at regular intervals by flushing the sample bypass channel. Data is acquired via LabVIEW and processed with MATLAB.

Cell concentration is monitored using a Coulter counter. Cell measurements are performed on cultures grown to 5×10^5-1×10^6 cells/ml. High density fluid introduced for measurement in the second SMR is formulated as a solution of 50% (v/v) Percoll (Sigma), 1.38% (w/v) powdered L15 media (Sigma), 0.4% (w/v) glucose, 100 IU penicillin, and 100 μg mL-1 streptomycin. Media pH is adjusted to 7.2. This Percoll media is stored at 4° C. and filtered immediately prior to use in the dual SMR.

Example 54

Assessment of Phosphatidyl Serine Content by Annexin V

Erythroid cells are cultured as described herein. 50 μL cell suspension is washed in Ringer solution containing 5 mM $CaCl_2$ and then stained with Annexin-V-FITC (1:200 dilution; ImmunoTools, Friesoythe, Germany) in this solution at 37° C. for 20 min under protection from light. Cells are washed and stained by flow cytometry as described herein, and annexin-V fluorescence intensity is measured with an excitation wavelength of 488 nm and an emission wavelength of 530 nm. Relative phosphatidyl serine exposure is assessed from annexin-V fluorescence.

Example 55

Assessment of Lipid Content by Chromatography

Lipids are extracted from washed synthetic membrane-receiver complexes by three extractions with methanol-chloroform 1:1 at room temperature in the presence of the antioxidant BHT (Sigma Aldrich). The pooled extracts are washed with 0.05 M KCl in the method of Folch, Lees and Sloane Stanley 1957, J Biol Chem 226:497. Briefly, for the first extraction, 15 mL methanol containing 0.05 mg/mL BHT are added to the washed complexes in a centrifuge tube and allowed to stand for 30 min with occasional stirring to break up sediment. 15 mL of chloroform is then added and the mixture is allowed to stand for 30 min with occasional stirring to break up clumps. The tubes are centrifuged for 5 minutes at 1500 g and the supernatant fractions decanted into separatory funnels fitted with Teflon stopcocks. The second and third extractions are performed similarly with 15 mL of the methanol-BHT added to the residue followed by 15 mL of chloroform, except the extracts stand for only 10 minutes with occasional stirring after each addition. After centrifugation, the supernatant fractions are pooled in a separatory funnel then 48 mL of chloroform and 28 mL of 0.05 M KCl are added and mixed. The mixture is allowed to stand overnight in darkness at 4 C for phase separation. After being rewarmed to room temperature, the lower of the two clear phases is collected and evaporated to dryness in vacuo at 40 C in a rotary vacuum evaporator. The lipid is transferred quantitatively to a 10 mL volumetric flask with chloroform and stored at −22 C.

The concentration of free cholesterol in the lipid extract is determined as follows. The lipid extract is chromatographed on a 0.5 mm layer of Silica Gel HR (Brinkmann Instruments, Inc., Westbury, N.Y.) in hexane-diethyl ether-glacial acetic acid 80:20:1, the TLC plate is stained by spraying with 2,7-dichlorofluorescein solution (see below), the free cholesterol spot is scraped into a conical centrifuge tube and extracted once with 2.0 nil and three times with 1.0 ml of chloroform, the extract is evaporated to dryness in vacuo at 40° C. in a rotary vacuum evaporator, and the cholesterol is estimated by the ferric chloride method of Mann 1961 Clin Chem 7:275 without saponification. A free cholesterol standard, prepared from a commercial certified reagent grade material by isolation through the dibromide derivative (see e.g., Fieser J Amer Chem Soc 1953 75:5421), is taken through the chromatographic procedure and estimated with each set of determinations. The values for free cholesterol are corrected in each determination for the recovery of the standard, which averaged 95%. The TLC is necessary to remove the BHT, which otherwise interferes with the ferric chloride method by producing a brown product that absorbed at 560 nm.

The phospholipid distribution is determined in triplicate by TLC of aliquots of the total lipid extract at 4° C. on Silica Gel HR, 0.5 mm thick, in chloroformmethanol-glacial acetic acid-water 25:15:4:2 to which is added BHT at a concentration of 50 mg/100 ml to prevent autoxidation during chromatography; the TLC plates are prepared with water ("neutral" plates). Use of a "wedged-tip technique" for applying the lipid sample at the origin of the plate (see e.g., Stahl 1965 Thin-Layer Chromatography, Academic Press Inc.) results in excellent separations of the individual phospholipids. In particular, the method provides complete separation between phosphatidyl ethanolamine (PE), phosphatidyl serine (PS), lecithin, and sphingomyelin; a discrete spot migrates between PS and lecithin that is identified as phosphatidyl inositol (PI). The spots are made visible in UV light by spraying with a solution of 2,7-dichlorofluorescein (33.3 mg/100 ml of aqueous 2 mM NaOH) and then scraping directly into Kramer-Gittleman tubes, where the phospholipids are digested at 190° C. for 60 min with 1.0 ml of 70% perchloric acid. The remainder of the procedure is performed as described above, except that after color development, the silica gel is removed by centrifugation at 3000 g for 5 min and the absorbancy is determined on the clear supernatant solution. Corrections are made for the absorbancy of corresponding areas of blank lanes.

Gas-liquid chromatography is performed on hexane-dissolved samples with a Barber-Colman instrument, model 5000, equipped with paired 8-ft columns of EGSS-X (an ethylene glycol succinate polyester combined with a silicone) 8% on Gas-Chrom P, 100-120 mesh (Applied Science Laboratories Inc.) and dual flame ionization detectors. The nitrogen flow rate is 50 ml/min at the inlet. The column temperature is maintained at 165 OC for 10 min after injection of the sample, then increased at 2 C/min to 200° C.

Example 56

Assessment of Membrane Viscosity

The membrane viscosity of a population of cells can be assessed by fluorescence photobleaching assay. A 0.5-ml sample of erythroid cells is collected and washed once in HEPES-buffered saline (132 mM NaCl, 4.7 mM KCl, 2.0 mM CaCl2, 1.2 mM MgSO4, 20 mM HEPES, adjusted to pH 7.4). The packed cells are then washed once in 145 mM NaCl −10 mM NaHCO3, pH 9.5, and resuspended in the same buffer with 1 mg/ml DTAF (obtained from Research Organics, Cleveland, Ohio). The cells are incubated on ice for 1 h, then washed twice in 50 mM glycine −95 mM NaCl-10 mM NaHCO3, pH 9.5, to remove any dye that has not bound covalently to protein. Finally, the cells are washed twice and resuspended to ~2% hematocrit in HEPES-buffered saline with 1 mg/ml bovine serum albumin. The same treatment is applied to control native erythrocytes.

The flow chamber is mounted on the stage of a Leitz Diavert (Rockleigh, N.J.) inverted microscope equipped for incident-light fluorescence microscopy. The dichroic mirror and excitation/emission filters are the standard combination for use with fluorescein dyes (Leitz designation 12), with excitation wavelength in the range 450-490 nm. The objective is an oil immersion type with 100× magnification and 1.25 numerical aperture. A 100 watt high pressure mercury arc lamp (Osram, Munich) with an appropriate power supply and housing (Oriel, Stamford, Conn.) serves as the fluorescence excitation source.

A computer-controlled electronic shutter (Vincent Associates, Rochester, N.Y.) limits the exposure duration and is synchronized with a photon-counting electronic system for measuring fluorescence intensity. The field diaphragm of the incident light illuminator is used to limit excitation to a circular area of diameter 20-40 urn. At regular intervals, an output pulse from the computer causes the shutter to open for a typical duration of 20 ms. Light from the brief fluorescent image is split with a series of prisms so that half the light is directed to a low-light-level SIT video camera (Model 66-SIT, Dage-MTI, Michigan City, Ind.) and half to a photomultiplier tube (Model 8850, RCA, Harrison, N.J.) enclosed in an ambient temperature housing. During the time that the electronic shutter is open, a video image processor (Model 794, Hughes Aircraft, Carlsbad, Calif.) is triggered to acquire the fluorescent image, providing a video snapshot that can be monitored to ensure that the subject remains in focus and that no foreign object intrudes into the field of view. Distances on the video screen are measured with a video caliper and calibrated by comparison with the video image of a stage micrometer. Also during the time the shutter is open, the photomultiplier signal is processed with the photon-counting technique. An amplifier/discriminator (Model AD6, Pacific Instruments, Concord, Calif.) generates a digital logic pulse for each signal pulse above a given magnitude, and those digital pulses are counted on a 100-MHz gated counter (Model 770, EG&G Ortec, Oak Ridge, Tenn.). The microcomputer controls the gating, resetting, and recording of the photon count.

A typical experiment consists of a number of preliminary fluorescence measurements made during brief (20 ms) pulses of excitation light, followed by an extended period of illumination (typically 30 s) during which the samples cells are bleached, followed by another series of brief exposures, every 15-30 s, until the fluorescence appears to have completed its recovery.

The recovery time and other parameter values obtained for cultured erythroid cells are compared to the same values obtained for primary erythroid cells.

Example 57

Assessment of Mean Corpuscular Volume with Advia Hematology Analyzer

The Mean corpuscular volume (MCV) of the cultured erythroid cells is measured using electrical impedance in an Advia 120 hematology analyzer (Siemens Healthcare). The results are compared to that of natural human erythrocytes.

Example 58

Pathogen Testing of Cultured Erythroid Cells

RT-PCR is used to quantify adventitious virus presence in cultured erythroid cell populations and confirm non-contamination (Assay No. 003000.BSV, BioReliance). Sterility testing of unprocessed and final bulk, final vials, prebanking cells, and cell and virus banks is performed by directly inoculating the erythroid population into 2 different types of media that support the growth of aerobic and anaerobic bacteria respectively. Samples are incubated for 14 days followed by testing for microbial contaminants per BioReliance Sterility Testing protocol USP 71.

Example 59

Assessment of Osmotic Fragility

Osmotic fragility is evaluated to measure the resistance of the erythroid cells to lysis when exposed to hypotonic solutions. Solutions of NaCl in water were made at concentrations spanning 0% to 1%. Cells were incubated in each of the salt solutions for 15 minutes. The samples were centrifuged to pellet intact cells. Supernatant was assayed for hemoglobin content by absorption of light at 540 nm using a spectrophotometer. The point at which 50% hemolysis occurs is calculated and compared to the value obtained for primary erythrocytes.

Example 60

Assessment of Rosetting/Immunogenicity

The direct antiglobulin test, also known as Coombs test, assesses the agglutination or resetting of erythroid cells caused by the binding of polyclonal antibodies from serum to surface antigens on the cell. It can be performed with pooled human serum for general allogeneic immunogenicity assessment, or with serum from the intended recipient for specific immunogenicity prediction.

In brief, add 1-2 drops of cells stored in an EDTA tube to a reaction tube. Wash this tube three times with isotonic saline. After the third wash, prepare a 3% suspension from the washed cells. Label 2 tubes A and B. Add one drop of the washed 3% suspension to each tube. Wash these tubes one more time. When decanting, position the tubes so that the cell button is on top. This will prevent too many cells from being lost in the washing process. Drain well, and blot dry with a biowipe. Immediately add one drop human test serum to both tubes, and shake to mix. Allow the B tube to incubate at room temperature 5 minutes. Centrifuge the A tube for the time calibrated for the Coombs spin on the serofuge. Immediately resuspend gently and examine for agglutination using the lighted agglutination viewer (Beckton Dickinson). If the A tube is positive, it is not necessary to read the B tube nor is it necessary to examine the A tube microscopically. If the A tube is negative by lighted agglutination viewer, examine for agglutination under the microscope. If the A tube was negative through the microscopic reading, centrifuge the B tube after its incubation period and repeat steps 2-4 with the B tube sample. If the B tube is negative as well, add one drop of IgG-coated Coombs Control Cells (Check Cells) to the tube and centrifuge. Examine for agglutination. Agglutination should be present in this step, or the test is invalid.

If there is no agglutination in any of the steps before addition of the check cells (ccc), the test is interpreted as negative. If agglutination is observed in any of the steps before addition of the check cells, the test is interpreted as positive.

Example 61

Assessment of Oxygen-Binding Capacity

Equilibrium oxygen binding curves at 37° C. are determined in a tonometer linked to a 1-cm path length cuvette. Spectral measurements are performed with a spectrophotometer (Cary 50; Variant Inc), and the temperature is controlled with a Peltier module. Analyses are performed in 50 mM bis-Tris buffer (pH 7.2) containing 140 mM NaCl and 2 mM glucose. After thorough deoxygenation under nitrogen, the red cell suspensions are equilibrated at different partial pressures of oxygen by injection of known volumes of pure oxygen into the tonometer through a rubber cap with a Hamilton syringe. The fractional saturation is estimated by simulation of the absorption spectra in the visible and Soret regions as a linear combination of the fully deoxygenated and oxygenated spectra of the RBC suspension by least squares regression.

Example 62

Assessment of Metabolic State of Cells

The erythroid cell population may be verified as metabolically active using a variety of different enzyme based assays to quantify important metabolic end products. Active glycolysis is a crucial metabolic pathway to assess and may be measured with the following assay (Glycolysis cell-based assay kit, Cayman Chemical, Item 600450).

450 ul of assay buffer is aliquoted into a test tube, followed by 50 uL of the L-Lactic acid standard asnd mixed thoroughly. A titration curve is constructed using the lactic acid concentration standard, beginning with a 1 mM dilution.

Cells are added to a 96 well plate and centrifuged at 1000 RPM for 5 minutes. 100 uL of the standards are transferred into a separate 96 well plate. 90 uL of assay buffer is then added to each well. 10 ul of supernatant in each cell well is then transferred to corresponding new wells. Add 100 ul of reaction solution to each well using a repeating pipettor. The plates are then incubated on an orbital shaker for 30 minutes at RT. The absorbance isread at 490 nm with a plate reader. Results are compared to natural cells to identify any metabolic differences.

Example 63

Assessment of Platelet Aggregation

Aggregation propensity of cultured or primary sourced platelets can be monitored. Platelets are submitted to swirling analysis by shaking them in front of a light source, with the results expressed as presence or absence of birefringence. The units of platelet concentrates produced with a volume of 50-70 mL are left to rest for one hour and placed in a linear shaker (C-Mar®) at 70 rpm at a controlled temperature of 22±2° C. (71.6±3.6° F.).

The tests of platelets concentrates (platelet count, platelet aggregation and pH) are carried out on days 1, 3 and 5 after processing; a leukocyte count is performed only on day 1 and the microbiological control is performed only on the 5th day of storage. In order to obtain aliquots from samples of platelet concentrates, a sterile connection (Haemonetics®) is used which ensured the integrity of the environment. Platelet aggregation is achieved using the turbidimetric aggregometry technique using a dual-channel Chronolog (Crono-Log Corporation®) within four hours of blood collection. For this, the cells are initially obtained through light centrifugation at 1000 rpm for five minutes, and then centrifuged at 3000 rpm for fifteen minutes (Eppendorf®). Samples are subjected to a platelet count in an automatic counter (Human Count®).

After adjusting the platelet concentration, aggregation is evaluated using different concentrations of inducing agonists: collagen 2.0 µg/mL and ADP 7.0 µg/mL (Crono-Log Corporation®). For each test, 400 µL of PRP and 400 µL of PPP are used, each one in a different cuvette after waiting for spontaneous aggregation. The aggregation curve is observed after five minutes of stimulation by inducing agonists, and soon after, aggregation is measured and expressed as a percentage according to the curves formed during the tests. The result of the test is commonly expressed as a percentage of aggregation by the quantity of light transmitted through the test solution; aggregation is classified as normal, low or high.

Example 64

Autologous Culture Process

The culture of erythroid cells using autologously sourced progenitor CD34+ cells is done to optimize cell immunocompatibility for patients. CD34+ cells from the bone marrow are mobilized to the periphery in a patient using GM-CSF as described herein. Between $10^6$-$10^8$ CD34+ cells are collected and cultured using the aforementioned 22 day protocol using defined media. During Day 4 the cells are transfected with a lentiviral vector containing a gene that codes for the expression of a therapeutic agent. Upon completion of the culturing protocol, the cells are purified and assessed across several quality control metrics including physical properties that correlate with circulation viability, immunogenicity, replicative potential, purity, and therapeutic dose. The cells are then stored in appropriate stabilizing solution and formulated in a syringe or appropriate delivery vehicle. The cells are then infused into the same patient that donated the initial CD34+ cells.

Example 65

Autologous Loading Process

For the preparation of therapeutic erythroid cells loaded with a suitable receiver, autologously sourced erythrocytes can be used to optimize cell immunocompatibility for patients. Blood is drawn from the patient and centrifuged at 5000 g for 20 minutes. The buffy coat is removed and the remaining red cells are re-suspended in anticoagulant buffer at a density of $10^8$ cells/nil, giving a total of $10^10$ cells. The cells are loaded with a therapeutic receiver of interest by one of the methods described above. Upon completion of the loading protocol, the cells are purified and assessed across several quality control metrics including physical properties that correlate with circulation viability, immunogenicity, replicative potential, purity, and therapeutic dose. The cells are then stored in appropriate stabilizing solution and formulated in a syringe or appropriate delivery vehicle. The cells are infused into the same patient that donated the initial erythrocytes.

Example 66

Allogeneic Culture Process

To create a scalable, universal therapeutic, etyrhoid cells can be cultured from an allogeneic source. The culture of erythroid cells using allogeneically sourced progenitor CD34+ cells is done to streamline the process and culture a volume of therapeutic capable of treating patients at scale. Donors are blood-typed for major blood antigens, including A, B, Rh to identify universal donors (e.g., O Rh— or Bombay Rh—). CD34+ cells from the bone marrow are mobilized to the periphery in a suitable donor using GM-CSF as described herein. Between $10^6$-$10^8$ CD34+ cells are collected and cultured using the aforementioned 22 day protocol using defined media. During Day 4 the cells are transfected with a lentiviral vector containing a gene that codes for the expression of a therapeutic agent. Upon completion of the culturing protocol, the cells are purified and assessed across several quality control metrics including physical properties that correlate with circulation viability, immunogenicity, replicative potential, purity, and therapeutic dose. The cells are then stored in appropriate stabilizing solution and formulated in a syringe or appropriate delivery vehicle. The cells are then infused into patients irrespective of their major blood groups.

Example 67

Allogeneic Loading Process

The culture of erythroid cells using allogeneically sourced progenitor CD34+ cells is done to streamline the process to prepare larger volumes of therapeutic cells capable of treating patients at scale. Donors are blood-typed for major blood antigens, including A, B, Rh to identify universal donors (e.g., O Rh— or Bombay Rh—). The cells are loaded with a therapeutic receiver of interest by one of the methods described above. Upon completion of the loading protocol, the cells are purified and assessed across several quality control metrics including physical properties that correlate with circulation viability, immunogenicity, replicative potential, purity, and therapeutic dose. The cells are then stored in appropriate stabilizing solution and formulated in a syringe or appropriate delivery vehicle. The cells are then infused into patients irrespective of their major blood groups.

Example 68

Storage

1. Storage in Refrigerated Buffer Solution

Standard protocols for the storage of red blood cells are known in the art, see e.g., Meryman and Hornblower 1986, Transfusion 26(6):500. The standard protocol for the storage of red blood cells (for up to 42 days) is the collection of blood into anticoagulant solutions (citrate-dextrose-phosphate). Erythroid cells are cultured as described herein. Red cell concentrates are prepared by the removal of plasma by centrifugation. The cells are stored at 4±2° C. in a slightly hypertonic additive solution, SAGM (sodium, adenine, glucose, mannitol, 376 mOsm/L).

2. Storage in Frozen Buffer Solution

Methods for glycerolization, freezing, and thawing of erythroid cells are known in the art, see e.g., Meryman and Hornblower 1977 Transfusion 17(5):4348. Human blood in citrate phosphate dextrose is glycerolized and frozen within 4 days of collection. To prepare glycerolized RBCs, approximately 10 mL of whole blood is first centrifuged at 1,400 g for 10-15 min, and the plasma is removed. The resulting packed cells are then glycerolized in two steps using an aqueous glycerol solution with the following composition: 57.1 g glycerol, 0.03 g potassium chloride, 0.085 g magnesium chloride hexahydrate, 0.08 g disodium phosphate, and 1.6 g sodium lactate in a total volume of 100 mL, adjusted to a pH of 6.8.42 In the first step, 1.5 mL of this glycerol solution is added drop-wise to the packed cells with gentle agitation over a period of 3 min. The mixture is then allowed to equilibrate undisturbed for at least 5 min. In the second glycerolization step, 5 mL of the glycerol solution is added drop-wise while the mixture is gently agitated over a 3-min period, yielding a final glycerol composition of ~40% w/v. The entire glycerolization process is carried out at room temperature. The glycerolized RBCs are then divided into aliquots of 0.6-1.1 mL in cryogenic vials, placed in a NalgeneVR Cryo "Mr. Frosty" freezing container (Thermo Scientific, NC), and stored in a −80 C freezer for at least 12 h and up to 10 years. Frozen RBCs are thawed by placing the cryogenic vial in a 37 C water bath for 1 min. All glycerolized blood samples are used in deglycerolization experiments within 2 h of thawing.

3. Formulation as Syringe

The cell population may be intravenously administered via a syringe. The therapeutic cells are diluted to a density of $10^7$ cells/ml using standard saline buffer at 37 C such that 100 ml of volume, or $10^9$ cells, are delivered. The cell solution is loaded into a 150 cc syringe, 20 gauge needle and injected into the patient through the basilic vein at 5 cc/min. During injection the patient's vitals are monitored for any immunogenic or clotting reactions.

4. Formulation as Bag

The cell population may be intravenously administered via syringe connected to a bag and drip chamber (i.e. an IV drip). The therapeutic cells are diluted to a density of $10^7$ cells/ml using standard saline buffer at 37 C such that 100 ml of volume, or $10^9$ cells, are delivered. The cell solution is loaded into a 1 L plastic bag, connected to a catheter and allowed to drain via gravity into the patient through the basilic vein. During infusion the patient's vitals are monitored for any immunogenic or clotting reactions.

Example 69

CAPS Catastrophic Antiphospholipid Syndrome

Cells are cultured in the presence of a lentivirus encoding the exogenous transgene β2-Glycoprotein I (b2GPI) (GenBank: X53595.1) fused to the N-terminus of glycophorin A such that the final cell product expresses $>1\times10^5$ copies of the b2GPI receiver on the surface per cell. To ensure that the receiver is functionally expressed, in vitro activity is assessed by flow cytometry. Briefly, cells are incubated with serum from patients with Antiphospholipid Syndrome that have previously tested positive for anti-b2GPI antibodies by ELISA. The cells are washed and labeled with secondary antibodies to detect human primary antibodies bound to their surface and analyzed by flow cytometry for presence of the fluorophore.

The cultured erythroid cell population that over expresses beta-2 glycoprotein I is provided as a treatment for antiphospholipid syndrome in an early phase clinical trial.

A patient diagnosed as having antiphospholipid autoantibodies in circulation is intravenously administered single doses of $10^9$-$10^{11}$ cells once a month for 6-12 months. During the course of treatment patients' thymidine and thymine levels are monitored with daily blood tests and relevant APS symptoms such as thrombotic events and bleeding are documented.

A population of 10^11 erythroid cells expressing between 10K and 100K copies of Beta-2 glycoprotein 1 per cell is stored in a transfusion bag with CPDA-1 and glycerol and stored at −80 C for up to 10 years. Upon treatment, the bag is thawed, centrifuged, and the cells removed and resuspended in saline for administration to a patient. Cells are intravenously administered with a 50 gauge needle at 5 ml/min at 37 C.

Example 70

Goodpasture Disease

Cells are cultured in the presence of a lentivirus encoding the non-collagenous C-terminal domain of the exogenous transgene COL4A3, NC1-COL4A3 (ID: NM_000091.4) fused to the N-terminus of glycophorin A such that the final cell product expresses >1×10^5 copies of the NC1-COL4A3 receiver on the surface per cell as assessed by flow cytometry. To ensure that the receiver is functionally expressed, in vitro activity is assessed by flow cytometry. Briefly, cells are incubated with serum from patients with Goodpasture Syndrome that have previously tested positive for anti-NC1-COL4A3 antibodies by ELISA. The cells are washed and labeled with secondary antibodies to detect human primary antibodies bound to their surface and analyzed by flow cytometry for presence of the fluorophore.

Example 71

Membranous GN

Cells are cultured in the presence of a lentivirus encoding the $4^{th}$-$6^{th}$ extracellular domains of the exogenous transgene phospholipase A2 receptor (PLA2R) (ID: MGC:178179) fused to the N-terminus of glycophorin A such that the final cell product expresses >1×10^5 copies of the PLA2R receiver on the surface per cell as assessed by flow cytometry. To ensure that the receiver is functionally expressed, in vitro activity is assessed by flow cytometry. Briefly, cells are incubated with serum from patients with Membranous Glomerulonephritis (MGN) that have previously tested positive for anti-PLA2R antibodies by ELISA. The cells are washed and labeled with secondary antibodies to detect human primary antibodies bound to their surface and analyzed by flow cytometry for presence of the fluorophore.

Example 72

IgA Nephropathy

Cells are cultured in the presence of a lentivirus encoding the extracellular domain of exogenous transgene complement receptor 1 (CR1) (SEQ ID 2) fused to the N terminus of glycophorin A such that the final cell product expresses >1×10^5 copies of CR1 ectodomain receiver per cell as assessed by flow cytometry. To ensure that the receiver is functionally expressed, the cell is assayed for its ability to bind immune complexes and transfer those complexes to macrophages.

Dylight 650-labeled bovine serum albumin (BSA-650) is incubated with polyclonal rabbit anti-BSA (Abcam) in an excess of antibody for 30 minutes at room temp to generate complexes. The complexes are then mixed with human serum at a 1:1 volume ratio for 30 minutes at 37 C to form immune complexes. Control complexes are either not mixed with human serum or mixed with heat-inactivated human serum. The complexes are then incubated with cells for 30 minutes at 37 C. Cells are washed and analyzed by flow cytometry for capture of immune complexes by detecting Dylight 650 fluorescence.

Cultured U937 monocytes are activated by incubation with 100 nM phorbol myristate acetate (PMA) for 24 hours at 37 C. Cells coated with immune complexes (see above) are incubated with activated U937 macrophages for 30 minutes at 37 C. The co-culture is analyzed by flow cytometry. Macrophages are identified by FSC/SSC gating. Presence of immune complex on macrophages is analyzed by detecting Dylight 650 fluorescence in this cell population.

Example 73

Systemic Lupus Erythematosus

Cells are cultured in the presence of a lentivirus encoding the extracellular domain of exogenous transgene complement receptor 1 (CR1) (SEQ ID 2) fused to the N terminus of glycophorin A such that the final cell product expresses >1×10^5 copies of CR1 ectodomain receiver per cell as assessed by flow cytometry. To ensure that the receiver is functionally expressed, the cell is assayed for its ability to bind immune complexes and transfer those complexes to macrophages.

Dylight 650-labeled bovine serum albumin (BSA-650) is incubated with polyclonal rabbit anti-BSA (Abcam) in an excess of antibody for 30 minutes at room temp to generate complexes. The complexes are then mixed with human serum at a 1:1 volume ratio for 30 minutes at 37 C to form immune complexes. Control complexes are either not mixed with human serum or mixed with heat-inactivated human serum. The complexes are then incubated with cells for 30 minutes at 37 C. Cells are washed and analyzed by flow cytometry for capture of immune complexes by detecting Dylight 650 fluorescence.

Cultured U937 monocytes are activated by incubation with 100 nM phorbol myristate acetate (PMA) for 24 hours at 37 C. Cells coated with immune complexes (see above) are incubated with activated U937 macrophages for 30 minutes at 37 C. The co-culture is analyzed by flow cytometry. Macrophages are identified by FSC/SSC gating. Presence of immune complex on macrophages is analyzed by detecting Dylight 650 fluorescence in this cell population.

Example 74

Paroxysmal Nocturnal Hemoglobinuria

Cells are cultured in the presence of a lentivirus encoding the exogenous transgene CD59 (NCBI Reference Sequence: NM_203330.2) with an N-terminal epitope tag such that the final cell product expresses >1×10^5 copies of CD59 receiver per cell as assessed by flow cytometry. To ensure that the receiver is functionally expressed, the cell is assayed for its ability to inhibit membrane attack complex on sheep erythrocytes in co-culture.

Briefly, fresh sheep erythrocytes in 10% solution of 1× veronal buffered saline (VBS) are sensitized with polyclonal rabbit anti-sheep RBC antibody (haemolysin) for 30 minutes at 30 C. Serial dilutions of cultured cells are added to sensitized sheep erythrocytes. Human serum is added at serial dilutions to each well, starting with 1:4 dilution in VBS. Incubate at 37° C. for 30 minutes, mixing after 15 minutes. Centrifuge the samples at 1,500 g for 5 minutes to sediment the RBCs. Transfer 100 ul of supernatant from each tube to a well in a 96 well flat bottom plate. Add 100 ml of distilled water to each well. Read the absorbance of the samples at 540 nm using a plate spectrophotometer. % lysis is calculated as OD540 (test) −OD540 (blank)/OD540 (total lysis) −OD540 (blank)*100.

Example 75

Atypical Hemolytic Uremic Syndrome

Cells are cultured in the presence of a lentivirus encoding the exogenous transgene CD59 (NCBI Reference Sequence: NM_203330.2) with an N-terminal epitope tag such that the final cell product expresses >1×10^5 copies of CD59 receiver per cell as assessed by flow cytometry. To ensure that the receiver is functionally expressed, the cell is assayed for its ability to inhibit membrane attack complex on sheep erythrocytes in co-culture.

Briefly, fresh sheep erythrocytes in 10% solution of 1× veronal buffered saline (VBS) are sensitized with polyclonal rabbit anti-sheep RBC antibody (haemolysin) for 30 minutes at 30 C. Serial dilutions of cultured cells are added to sensitized sheep erythrocytes. Human serum is added at serial dilutions to each well, starting with 1:4 dilution in VBS. Incubate at 37° C. for 30 minutes, mixing after 15 minutes. Centrifuge the samples at 1,500 g for 5 minutes to sediment the RBCs. Transfer 100 ul of supernatant from each tube to a well in a 96 well flat bottom plate. Add 100 ml of distilled water to each well. Read the absorbance of the samples at 540 nm using a plate spectrophotometer. % lysis is calculated as OD540 (test) −OD540 (blank)/OD540 (total lysis) −OD540 (blank)*100.

Example 76

Age-Related Macular Degeneration

Cells are cultured in the presence of a lentivirus encoding the exogenous transgene CD59 (NCBI Reference Sequence: NM_203330.2) with an N-terminal epitope tag such that the final cell product expresses >1×10^5 copies of CD59 receiver per cell as assessed by flow cytometry. To ensure that the receiver is functionally expressed, the cell is assayed for its ability to inhibit membrane attack complex on sheep erythrocytes in co-culture.

Briefly, fresh sheep erythrocytes in 10% solution of 1× veronal buffered saline (VBS) are sensitized with polyclonal rabbit anti-sheep RBC antibody (haemolysin) for 30 minutes at 30 C. Serial dilutions of cultured cells are added to sensitized sheep erythrocytes. Human serum is added at serial dilutions to each well, starting with 1:4 dilution in VBS. Incubate at 37° C. for 30 minutes, mixing after 15 minutes. Centrifuge the samples at 1,500 g for 5 minutes to sediment the RBCs. Transfer 100 ul of supernatant from each tube to a well in a 96 well flat bottom plate. Add 100 ml of distilled water to each well. Read the absorbance of the samples at 540 nm using a plate spectrophotometer. % lysis is calculated as OD540 (test) −OD540 (blank)/OD540 (total lysis) −OD540 (blank)*100.

Example 77

B Cell Acute Lymphoblastic Leukemia

An antibody scFv is generated based on a full-length anti-CD20 antibody. Splice overlap extension PCR (SOE-PCR) are used to create fully synthetic anti-CD20 variable (V) genes based on the V gene sequences of the murine 2B8 (U.S. Pat. No. 5,736,137). Full-length 2B8 VL and VH genes are then assembled by SOE-PCR to produce a single chain Fv (scFv) with 18-residue long linker (Whitlow 218 linker; GSTSGSGKPGSGEGSTKG (SEQ ID NO: 30)) in VL-VH orientation. Following SOE-PCR which also includes a signal peptide to the 5'-end (upstream) to enable secretion, the construct is cloned into pCR®-2.1-TOPO vector (Invitrogen Corp., Carlsbad, Calif.) and confirmed by sequencing.

Cells are cultured in the presence of a lentivirus encoding the exogenenous anti-CD20 antibody scFv anti-CD20 (Olafsen et al., J Nucl Med 2009, 50(9):1500) fused to the N-terminus of glycophorin A such that the final cell product expresses >1×10^5 copies of anti-CD20 scFv receiver per cell as assessed by flow cytometry. To ensure that the receiver is functionally expressed, in vitro activity is assessed by flow cytometry. Briefly, cells are incubated with soluble CD20 target protein (Abcam) at a range of concentrations. The target proteins are directly labeled with a fluorophore. Incubated cells are washed and analyzed by flow cytometry for presence of the fluorophore.

Example 78

Light Chain Amyloidosis

Cells are cultured in the presence of a lentivirus encoding the exogenous transgene Serum Amyloid P (SAP) component (GenBank: D00097.1) fused to the N terminus of glycophorin A such that the final cell product expresses >1×10^5 copies of SAP receiver per cell as assessed by flow cytometry. To ensure that the receiver is functionally expressed, in vitro activity is assessed by flow cytometry. Briefly, cells are incubated with serum from patients with light chain amyloidosis that are positive for amyloid plaques by anti-Light Chain ELISA. Binding of light chain amyloid plaques to the SAP-displaying cells is detected by secondary labeling with anti-lambda light chain antibodies (Abeam) that are directly labeled with fluorophore. Incubated cells are washed and analyzed by flow cytometry for presence of the fluorophore.

Example 79

Hepatitis B

Cells are cultured in the presence of a lentivirus encoding the exogenous transgene antibody scFv against hepatitis B surface antigen (HBsAg) (SEQ ID No. 1) such that the final cell product expresses >1×10^5 copies of antibody scFv receiver per cell as assessed by flow cytometry. To ensure that the receiver is functionally expressed, in vitro activity is assessed by flow cytometry. Briefly, cells are incubated with target protein HBsAg (Abeam) that is directly labeled with Dylight 650 fluorophore at a range of concentrations. Incubated cells are washed and analyzed by flow cytometry for presence of the fluorophore.

Example 80

ADA-SCID

Adenosine deaminase activity is monitored in vitro using HPLC protocol to detect adenosine and inosine levels. Approximately 10^5 erythroid cells expressing an exogenous, intracellular adenosine deaminase, produced using the aforementioned transfection protocol, are aliquoted into 1 ml wells. 1 mM of adenosine is administered to each well and incubated for 1 hr. The cells are centrifuged and soluble protein is removed from the supernatant using cold methanol precipitation. The supernatant samples are then run on an Agilent 1100 HPLC using a standard inosine and adenosine curve to determine the relative amounts of nucleoside and intracellular enzymatic activity compared to natural cells.

Adenosine deaminase activity is monitored in vivo using HPLC protocol to detect adenosine and inosine levels. An ADA-SCID mouse model is treated with clodronate for 3 days prior to cell therapy administration. 100 ul of $10^8$ ADA expressing human erythroid cells are administered via tail vein injection to the mouse model and blood samples are taken via a submandibular bleed at 10 min, 12 h, 24, h, 48 h, 72 h. The samples are analyzed using HPLC and inosine and adenosine levels are tracked over time.

A population of $10^8$ cultured erythroid cells expressing 10K to 100K copies of ADA per cell is administered via tail vein injection to a cohort of NOD-SCID mice. Prior to injection adenosine and inosine circulation levels are documented. Cells are allowed to circulated for 1 week and blood samples are taken at 10 min, 1 h, 6, h, 12 h, 24, h, 48 h, 96 h, 144 h. Adenosine and inosine levels are tracked.

A patient diagnosed with ADA-SCID is confirmed via genotyping and found to be deficient for ADA activity. Relevant clinical symptoms used in the diagnosis include lymphocyte count, adenosine levels, and infection frequency. The patient is intravenously administered $10^{11}$ erythroid cells cultured from a blood-type matched donor and expressing exogenous ADA diluted in 500 ml of saline solution via gravity drain over the course of 1 hr. The procedure is repeated monthly for 6 months. Patient lymphocyte counts are tracked using immunofluorescence analysis of specific CD antigens, adenosine and inosine levels are monitored using HPLC, and infection rate recorded over the duration of the treatment. Immunogenic response to the transfusion is closely monitored.

The cultured erythroid cell population that over expresses adenosine deaminase is provided as a treatment for ADA-SCID.

A patient diagnosed as deficient for adenosine deaminase is intravenously administered single doses of $10^9$-$10^{11}$ cells once a month for 6-12 months. During the course of treatment patients' adenosine and inosine levels are monitored with daily blood tests and relevant ADA-SCID symptoms such as lymphocyte counts, infections, and skin rashes are documented.

A population of $10^{11}$ erythroid cells expressing between 10K and 100K copies of ADA per cell is stored in a transfusion bag with CPDA-1 and glycerol and stored at −80 C for up to 10 years. Upon treatment, the bag is thawed, centrifuged, and the cells removed and resuspended in saline for administration to a patient. Cells are intravenously administered with a 50 gauge needle at 5 ml/min at 37 C.

Example 81

MNGIE

Thymidine phosphorylase (TP) activity is monitored in vitro using HPLC protocol to detect thymidine and thymine levels. Approximately $10^5$ erythroid cells expressing an exogenous, intracellular thymidine phosphorylase, produced using the aforementioned transfection protocol, are aliquoted into 1 ml wells. 1 mM of thymidine is administered to each well and incubated for 1 hr. The cells are centrifuged and soluble protein is removed from the supernatant using cold methanol precipitation. The supernatant samples are then run on an Agilent 1100 HPLC using a standard thymidine and thymine curve to determine the relative amounts of nucleoside and intracellular enzymatic activity compared to natural cells.

Thymidine phosphorylase activity is monitored in vivo using HPLC protocol to detect thymidine and thymine levels. A TP deficient mouse model is treated with clodronate for 3 days prior to cell therapy administration (Haragushi, Mol. Cell Biol 2002). 100 ul of $10^8$ TP expressing erythroid cells are administered via tail vein injection to the mouse model and blood samples are taken via a submandibular bleed at 10 min, 12 h, 24, h, 48 h, 72 h. The samples are analyzed using HPLC and thymidine and thymine levels are tracked over time.

A patient diagnosed with MNGIE is confirmed via genotyping and found to be deficient for TYMP. Relevant clinical symptoms used in the diagnosis include gastrointestinal motility, early satiety, cachexia, and nausea. The patient is intravenously administered $10^{11}$ erythroid cells cultured from a blood-type matched donor and expressing exogenous TP diluted in 500 ml of saline solution via gravity drain over the course of 1 hr. The procedure is repeated monthly for 6 months. The patient's symptoms are monitored over the duration of the treatment, including thymidine and thymine levels using HPLC.

The cultured erythroid cell population that over expresses thymidine phosphorylase is provided as a treatment for MNGIE.

A patient diagnosed as deficient for thymidine phosphorylase is intravenously administered single doses of $10^9$-$10^{11}$ cells once a month for 6-12 months. During the course of treatment patients' thymidine and thymine levels are monitored with daily blood tests and relevant MNGIE symptoms such as gastrointestinal behavior and cachexia are documented.

A population of $10^{11}$ erythroid cells expressing between 10K and 100K copies of thymidine phosphorylase per cell is stored in a transfusion bag with CPDA-1 and glycerol and stored at −80 C for up to 10 years. Upon treatment, the bag is thawed, centrifuged, and the cells removed and resuspended in saline for administration to a patient. Cells are intravenously administered with a 50 gauge needle at 5 ml/min at 37 C.

Example 82

Gaucher Disease

An in vitro assay is conducted to demonstrate the delivery of β-glucocerebrosidase (GC) to macrophages using GC-loaded, or expressing, erythroid cells. Successful delivery is indicative of potential mechanistic action as a treatment for Gaucher's disease. Primary cultures of macrophages are prepared using a U937 cell line. Erythroid cells are loaded with GC and CFSE using transgene expression methods and standard protocol for small molecule loading, washed with Alsever's solution and added to the macrophages on coverslips at a ratio of 10:1. Plates are centrifuged at 2600 g for 5 min and incubated at 37 C for 30 min. Non-phagocytosed erythroid cells are lysed with hypotonic buffer. Macrophages are washed with PBS and stained with benzidine and Giemsa. The macrophages are then analyzed with FACS for internalized GC and CFSE, as well as accumulated ceramide levels using a diacylglycerol (DAG) kinase assay.

Erythroid cells from mice are washed with Alsever's solution and stained with PKH26 (Sigma Aldrich). Labeled, GC-loaded cells are injected into mice intraperitoneally. Four days after injection spleens are prepared for microscopy and 12 micron sections are visualized using a fluorescent microscope. PKH26 is observed and quantified. In addition, GC-loaded erythroid cells are administered and after 7 days circulating macrophage cell levels are quantified using FACS of respective CD antigens and compared to levels in control mice. Ceramide levels in the macrophage population are quantified using the DAG kinase assay.

A patient is diagnosed with Gaucher's disease according to characteristic symptoms such as; enlarged liver, anemia, thrombocytopenia, lung disease, arthritis, and genetic typing that identifies associated mutant genes. The patient is administered $10^{\wedge}11$ erythroid cells either loaded with or expressing GC. The cells are diluted in 500 ml of saline solution and are administered via gravity drain over the course of 1 hr. The procedure is repeated monthly for 6 months. The patient's symptoms are monitored over the duration of the treatment, including macrophage counts, bleeding and thrombotic events, and macrophage ceramide levels.

Example 83

ALL-Asparaginase

Asparaginase activity is monitored in vitro using HPLC protocol to detect L-asparagine and aspartic acid levels. Approximately $10^{\wedge}5$ erythroid cells expressing an exogenous, intracellular asparaginase, produced using the standard transfection protocol, are aliquoted into 1 ml wells. 1 mM of asparagine is administered to each well and incubated for 1 hr. The cells are centrifuged and soluble protein is removed from the supernatant using cold methanol precipitation. The supernatant samples are then run on an Agilent 1100 HPLC using a standard asparagine and aspartic acid curve to determine the relative amounts of amino acid and intracellular enzymatic activity compared to natural cells.

Asparaginase activity is monitored in vivo using HPLC protocol to detect asparagine and aspartic acid levels. An acute lymphocytic leukemia mouse model created via insertion of a mutant NOTCH1 gene is treated with clodronate for 3 days prior to cell therapy administration (Haragushi, Mol. Cell Biol 2002). 100 ul of $10^{\wedge}8$ asparaginase expressing erythroid cells are administered via tail vein injection to the mouse model and blood samples are taken via a submandibular bleed at 10 min, 12 h, 24, h, 48 h, 72 h. The samples are analyzed using HPLC and asparagine and aspartic acid levels are tracked over time as well as with T cell proliferation behavior demonstrative of leukemia progression.

A patient diagnosed with ALL according to standard symptoms and somatic mutation analysis, including NOTCH1, RAS/PI3K/AKT deregulated signaling is intravenously administered $10^{\wedge}11$ erythroid cells cultured from a blood-type matched donor. The cells express exogenous, intracellular asparaginase diluted in 500 ml of saline solution and are administered via gravity drain over the course of 1 hr. The procedure is repeated monthly for 6 months. The patient's symptoms are monitored over the duration of the treatment, including asparagine and aspartic acid levels using HPLC. Proliferative leukemic cells are quantified using immunofluorescence of blood samples.

Example 84

Thrombotic Thrombocytopenic Purpura

An in vitro assay is conducted to demonstrate the activity of ADAMTS13 expressed on a cultured erythroid cell's membrane. The ADAMTS13 assay is a FRET-inducible system that relies on a synthetic 73-amino-acid peptide, FRETS-VWF73. Cleavage of this substrate between two modified residues relieves the fluorescence quenching in the intact peptide. Incubation of FRETS-VWF73 with cultured erythroid cells, compared to native erythrocytes, demonstrates quantitatively increased fluorescence over time. Quantitative analysis is achieved within a 1-h period using a 96-well format in commercial plate readers with common filters (Kokame, Br J Haematol, 2005).

The mechanistic ability of an ADAMTS13 expressing cultured erythroid cell is demonstrated using an NSG mouse model that is administered clodronate for macrophage depletion. Recombinant, human Von Willebrand factor (VWF) is injected at 10 mM via the tail vein. $10^{\wedge}8$ human erythroid cells expressing ADAMTS13 is subsequently injected and blood samples are taken at 10 min, 1 hr, 4 hr, 8 hr, 24 hr. The serum is assayed for VWF cleavage using gel electrophoresis. Cleavage of the VWF by ADAMTS13 takes place leading to a reduction in multimer sizes. This reduction is visualized by agarose gel electrophoresis followed by Western blotting with a peroxidase-conjugated anti-VWF antibody. The concentration of ADAMTS13 activity in the test sample is established by reference to a series of diluted normal plasma samples.

A patient is diagnosed with thrombotic thrombocytopenia purpura according to characteristic symptoms such as; thrombocytopenia, microangiopathic hemolytic anemia, neurologic symptoms, kidney failure, and genetic typing that identifies associated mutant genes. The patient is administered $10^{\wedge}11$ erythroid cells expressing ADAMTS13 on the surface. The cells are diluted in 500 ml of saline solution and are administered via gravity drain over the course of 1 hr. The procedure is repeated monthly for 6 months. The patient's symptoms are monitored over the duration of the treatment, including VWF multimer levels, bleeding, and thrombotic events.

Example 85

Hemophilia B (FIX)

An in vitro assay is conducted to demonstrate the activity of Factor IX (FIX) expressed on a cultured erythroid cell's membrane. The Factor IXa assay protocol (activated Factor IX, BIOPHEN Factor IXa, Ref. A221812) is used to provide a quantitative chromogenic read out of a sample of erythroid cells. FIXa activity of the erythroid cells is compared to that of both native erythrocytes and human plasma.

A mouse model of hemophilia B (Jackson Laboratories, B6.129P2-F9$^{tm1Dws}$/J) is immunosuppressed with cyclophosphamide and cleared of macrophages with clodronate. The mouse is then injected with $10^{\wedge}8$ human erythroid cells expressing human FIX on the surface. The mouse is bled daily for 2 weeks via the tail vein and clotting time is recorded. Results are compared to a negative control mouse model and a positive control model that receives a single dose of soluble FIX.

A patient is diagnosed with hemophilia B according to characteristic symptoms such as; spontaneous bleeding, gastrointestinal tract hemorrhage, bruising, low circulating Factor IX levels, and genotyping that confirms mutation in the X-linked gene. The patient is administered 10^11 erythroid cells expressing FIX on the surface. The cells are diluted in 500 ml of saline solution and are administered via gravity drain over the course of 1 hr. The procedure is repeated monthly for 6 months. The patient's symptoms are monitored over the duration of the treatment, including FIXa levels, spontaneous bleeding, and thrombotic events.

Example 85

Acute Lymphoblastic Leukemia

Erythroid cells expressing scFv against the leuekemic antigen, Wilms' tumor (WT1), are assayed in vitro for rosetting with primary sourced, WT1 positive, leukemia cells. Cells are cultivated at 3% hematocrit using McCoy's 5A medium enriched with 20% homologous serum, using the method described by Russell et al. 2011 Blood 118(13): e74. The presence of rosettes is detected and quantified using a novel Giemsa subvital staining methodology, modified from techniques applied in van Driessche, Leukemia 2005. The sampled culture suspension is stained with Giemsa (the final stain concentration is 5%) for 15 minutes. A small volume of this suspension (7.5 μl) is used to make a wet mount with 22×32 mm (0.17 mm thickness) glass cover slip. The wet mount is examined immediately with light microscope under oil immersion magnification. The rosetting rate is determined by examining erythroid cells in McCoy's 5A medium enriched with 20% homologous serum.

An NSG mouse model is treated with clodronate to eliminate its macrophage population. The mouse is injected with 10^8 leukemic cells that are positive for WT1. A population of erythroid cells expressing multiple copies of a scFv against WT1 on its surface is injected shortly thereafter and blood samples are taken at 10 min, 1 hr, 4 hr, 12 hr, 24 hr, 48 hr time points. Samples are analyzed using FACS and erythroid-B cell binding is quantified and compared to that of a positive control erythrocyte infused mouse.

A patient diagnosed with acute lymphoblastic leukemia according to characteristic symptoms such as; fatigue, fever loss of weight, anemia, abnormal white blood cell count, and positive bone marrow biopsy. The patient is administered 10^11 erythroid cells expressing anti-WT1 scFv on the surface. The cells are diluted in 500 ml of saline solution and are administered via gravity drain over the course of 1 hr. The procedure is repeated monthly for 6 months. The patient's symptoms are monitored over the duration of the treatment, including leukemic white blood cell counts.

Although the foregoing invention has been described in some detail by way of illustration and example for purposes of clarity of understanding, it will be readily apparent to one of ordinary skill in the art in light of the teachings of this invention that certain changes and modifications can be made thereto without departing from the spirit or scope of the appended claims.

TABLES

TABLE 1

| Erythroid Polypeptides and Non-Receiver Polypeptides | | | |
|---|---|---|---|
| ABO blood groups | Stomatin | Peters | DAF Cromer |
| Aquaporin 3 | Tropomyosin | Rasmussen | Gerbich (GYPC) |
| Aubergers | Glucose transporter | Reid | CD47 |
| Band 3 | Adducin | REIT | Glycophorin A, B, C |
| Basigin | Rabphilin | SARA | Band 3 (AE3) |
| C41 | C1 tetrahydrofolate synthase | Rhesus blood D group | GYPB Ss |
| CD44 | Vel group | Aldolase | C4A, C4B Chido, Rodgers C4 component of complement |
| Cis AB | Lan antigen | Tropomodulin | HLA Bg HLA class I |
| Diego (Di) | At antigen | Arginase | RHAG Rh-associated Ammonium transport glycoprotein |
| Colton antigen | Jr antigen | Creatine kinase | |
| Complement Component 4 | AnWj antigen | B-Cam protein | Colton (Co) Water channel protein |
| alpha(1,3) fucosyltransferase | Sd antigen | Rap1A | ACHE Cartwright (Yt) Acetylcholinesterase |
| CR1 | Batty | Bennett-Goodspeed | Glutathione transferase |
| DAF | Bilkes | P antigen system | Glycophorin C |
| Diego | Wright (Wr) | Rh blood group | Aquaporin |
| Duffy | Box | Xg antigen system | Erythroblast associated membrane protein |
| Hh/Bombay antigen ii antigen | Christiansen alpha(1,2) fucosyltransferase | XK protein Yt/Cartwright antigen system | CD44 Synaptobrevin 2 |
| Indian blood group | HJK | CD58 | Ribonuclease |
| Kell | HOFM | Rh | ABO glycosyl transferases |
| Kidd | JFV | AnWj Adhesion receptor | CD59 |
| Lewis antigen | JONEs | Scianna | CD44 |
| Lutheran antigen | Jensen | Radin | MER2 |
| MNS antigen system | Katagiri | Duodenal cytochrome B | DOK Dombrock ADP-ribosyltransferase |

TABLE 1-continued

Erythroid Polypeptides and Non-Receiver Polypeptides

| | | | |
|---|---|---|---|
| Cost group | Livesay | DARC (Duffy) | SEMA7A JMH Putative adhesion receptor |
| Er group | Milne | CR1 Knops-McCoy | UMOD Sda Tamm-Horsfall protein (uromodulin) |
| Dematin | Oldeide | FP Family | Anion exchanger channel protein (band 3, AE1) |
| Indian (In) | Annexin Family | Tweety Family | CTL Family |
| Kidd (Jk) Urea transporter | Bcl-2 Family | UT Family | DAACS Family |
| FUT3 Lewis (Le) | Bestrophin Family | VIC Family | DASS family |
| Adenosine deaminase | BNip3 Family | AAAP Family | DMT family |
| OK Oka Neurothelin, putative adhesion molecule | CD20 Family | transferrin receptor | ENT Family |
| LW Adhesion receptor | CLIC Family | c-KIT | GPH Family |
| FUT2 Secretor (Se) | Connexin Family | Insulin receptors 1 & 2 | GUP Family |
| FUT1 Hh alpha | CRAC-C Family | Estrogen receptor | LCT Family |
| LU Lutheran (Lu) Adhesion receptor | Ctr Family | Dexamethasone receptor | MC family |
| P1 Glycosyltransferase | E-CIC Family | JAK2 kinase | MET Family |
| XK Kx Putative neurotransmitter transporter | ENaC Family | ABC family | MFS Family |
| XG Xg formerly called PBDX | GIC Family | ArsAB family | MOP Family |
| MIC2 | ICC Family | F-ATPase Family | MTC Family |
| Hemoglobin | Innexin Family | IISP Family | NCS2 Family |
| Ankyrin | IRK-C Family | MPT Family | Nramp Family |
| Spectrin | LIC Family | P-ATPase Family | NSS Family |
| KEL Kell (K, k, Kp, Js) Metalloproteinase | MIP Family | AE family | OAT Family |
| Torkildsen | MIT family | APC Family | OST Family |
| Rab 35 | NSCC2 Family | ArsB Family | Oxa1 Family |
| Ral A binding protein | PCC Family | BASS Family | PiT Family |
| Zona pellucida binding protein | Plamolipin Family | CaCA Family | PNaS Family |
| Lyn B protein | PLB Family | CCC Family | POT Family |
| KIaa1741 protein | PLM Family | CDF Family | RFC Family |
| DC38 | Presenilin Family | CIC Family | RND Family* |
| Calciums transporting ATPase | RIR-CaC Family | CNT Family | SSS Family |
| ACC Family | TRIC Family | CPA1 Family | STRA6 Family |
| Amt Family | TRP-CC Family | CPA2 Family | SulP Family |
| ZIP Family | HCC Family | NIPA Family | N-MDE Family |
| ATP-E Family | LPI Family | PPI Family | Epo receptor |
| dsRNA-T Family | MagT1 Family | PPI2 Family | MgtE Family |

TABLE 2

Erythroid Cells

| | |
|---|---|
| Embryonic stem cells (ESC) | Blastocyte colony-forming cells |
| Cord blood stem cell (CD-SC) | Burst-forming unit erythroid (BFU-E) |
| CD34+ cells | Megakaryocyte-erythroid progenitor (MEP) cell |
| Hematopoietic stem cells (HSC) | Erythroid forming colony unit (CFU-E) |
| Spleen colony forming unit (CFU-S) | Reticulocytes |
| Common myeloid progenitor (CMP) cells capable of forming a granulocyte, erythrocyte, monocyte, or megakaryocyte (CFU-GEMM) | Erythrocytes |
| Any cell of myeloid lineage | Induced pluripotent stem cells (iPSC) |
| Proerythroblast | Mesenchymal stem cell |
| Polychromatophilic erythrocyte | Polychromatic normoblasts |
| Normoblast | Orthochromatic normoblasts |

TABLE 3

Erythroid Promoters

| Promoter | Gene |
|---|---|
| beta globin promoter | beta globin |
| 3' beta-globin enhancer | beta globin |
| beta globin locus control region | beta globin |
| GATA-1 promoter | GATA-1 |
| GYPA promoter | Glycophorin A |
| HK1 promoter | Hexokinase |

TABLE 4

| Sequences of Complement Receptor 1 |
|---|

4A. CR1 isoform S precursor, Homo sapiens NCBI Reference Sequence No. NP_000642.3

(Seq. ID No. 1)

```
   1 mgassprspe pvgppapglp fccggsllav vvllalpvaw gqcnapewlp farptnltde
  61 fefpigtyln yecrpgysgr pfsiiclkns vwtgakdrcr rkscrnppdp vngmvhvikg
 121 iqfgsqikys ctkgyrligs ssatciisgd tviwdnetpi cdripcglpp titngdfist
 181 nrenfhygsv vtyrcnpgsg grkvfelvge psiyctsndd qvgiwsgpap qciipnkctp
 241 pnvengilvs dnrslfslne vvefrcqpgf vmkgprrvkc qalnkwepel pscsrvcqpp
 301 pdvlhaertq rdkdnfspgq evfyscepgy dlrgaasmrc tpqgdwspaa ptcevkscdd
 361 fmgqllngry lfpvnlqlga kvdfvcdegf qlkgssasyc vlagmeslwn ssvpvceqif
 421 cpsppvipng rhtgkplevf pfgktvnytc dphpdrgtsf dligestirc tsdpqgngvw
 481 sspaprcgil ghcqapdhfl faklktqtna sdfpigtslk yecrpeyygr pfsitcldnl
 541 vwsspkdvck rkscktppdp vngmvhvitd iqvgsrinys cttghrligh ssaecilsgn
 601 aahwstkppi cqripcglpp tiangdfist nrenfhygsv vtyrcnpgsg grkvfelvge
 661 psiyctsndd qvgiwsgpap qciipnkctp pnvengilvs dnrslfslne vvefrcqpgf
 721 vmkgprrvkc qalnkwepel pscsrvcqpp pdvlhaertq rdkdnfspgq evfyscepgy
 781 dlrgaasmrc tpqgdwspaa ptcevkscdd fmgqllngry lfpvnlqlga kvdfvcdegf
 841 qlkgssasyc vlagmeslwn ssvpvceqif cpsppvipng rhtgkplevf pfgktvnytc
 901 dphpdrgtsf dligestirc tsdpqgngvw sspaprcgil ghcqapdhfl faldktqtna
 961 sdfpigtslk yecrpeyygr pfsitcldnl vwsspkdvck rkscktppdp vngmvhvitd
1021 iqvgsrinys cttghrligh ssaecilsgn aahwstkppi cqripcglpp tiangdfist
1081 nrenfhygsv vtyrcnpgsg grkvfelvge psiyctsndd qvgiwsgpap qciipnkctp
1141 pnvengilvs dnrslfslne vvefrcqpgf vmkgprrvkc qalnkwepel pscsrvcqpp
1201 pdvlhaertq rdkdnfspgq evfyscepgy dlrgaasmrc tpqgdwspaa ptcevkscdd
1261 fmgqllngry lfpvnlqlga kvdfvcdegf qlkgssasyc vlagmeslwn ssvpvceqif
1321 cpsppvipng rhtgkplevf pfgkavnytc dphpdrgtsf dligestirc tsdpqgngvw
1381 sspaprcgil ghcqapdhfl faklktqtna sdfpigtslk yecrpeyygr pfsitcldnl
1441 vwsspkdvck rkscktppdp vngmvhvitd iqvgsrinys cttghrligh ssaecilsgn
1501 tahwstkppi cqripcglpp tiangdfist nrenfhygsv vtyrcnlgsr grkvfelvge
1561 psiyctsndd qvgiwsgpap qciipnkctp pnvengilvs dnrslfslne vvefrcqpgf
1621 vmkgprrvkc qalnkwepel pscsrvcqpp peilhgehtp shqdnfspgq evfyscepgy
1681 dlrgaaslhc tpqgdwspea prcavkscdd flgqlphgry lfpinlqlga kvsfvcdegf
1741 rlkgssyshc vlvgmrslwn nsvpvcehif cpnppailng rhtgtpsgdi pygkeisytc
1801 dphpdrgmtf nligestirc tsdphgngvw sspaprcels vraghcktpe qfpfasptip
1861 indfefpvgt slnyecrpgy fgkmfsiscl enlvwssved ncrrkscgpp pepfngmvhi
1921 ntdtqfgstv nyscnegfrl igspsttclv sgnnvtwdkk apiceiisce ppptisngdf
1981 ysnnrtsfhn gtvvtyqcht gpdgeqlfel vgersiycts kddqvgvwss pprcistnk
2041 ctapevenai rvpgnrsfft lteiirfrcq pgfvmvgsht vqcqtngrwg pklphcsrvc
2101 qpppeilhge htlshqdnfs pgqevfysce psydlrgaas lhctpqgdws peaprctvks
2161 cddflgqlph grvllpinlq lgakvsfvcd egfrlkgrsa shcvlagmka lwnssvpvce
2221 qifcpnppai lngrhtgtpf gdipygkeis yacdthpdrg mtfnligess irctsdpqgn
```

TABLE 4-continued

Sequences of Complement Receptor 1

```
2281 gvwsspaprc elsvpaacph ppkiqnghyi gghvslylpg mtisyicdpg yllvgkgfif 2341 ctdqgiwsql dhyckevncs fplfmngisk elemkkvyhy gdyvtlkced gytlegspws 2401 qcqaddrwdp plakctsrth dalivgtlsg tiffilliif lswiilkhrk gnnahenpke 2461 vaihlhsqgg ssvhprtlqt neensrvlp
```

4B. CR1 isoform F precursor, Homo sapiens NCBI Reference Sequence No. NP_000564.2

(Seq. ID No. 2)

```
   1 mgassprspe pvgppapglp fccggsllav vvllalpvaw gqcnapewlp farptnitde 61 fefpigtyln yecrpgysgr pfsiiclkns vwtgakdrcr rkscrnppdp vngmvhvikg 121 iqfgsqikys ctkgyrligs ssatciisgd tviwdnetpi cdripcglpp titngdfist 181 nrenfhygsv vtyrcnpgsg grkvfelvge psiyctsndd qvgiwsgpap qciipnkctp 241 pnvengilvs dnrslfslne vvefrcqpgf vmkgprrvkc qalnkwepel pscsrvcqpp 301 pdvlhaertq rdkdnfspgq evfyscepgy dlrgaasmrc tpqgdwspaa ptcevkscdd 361 fmgqllngry lfpvnlqlga kvdfvcdegf qlkgssasyc vlagmeslwn ssvpvceqif 421 cpsppvipng rhtgkplevf pfgktvnytc dphpdrgtsf dligestirc tsdpqgngvw 481 sspaprcgil ghcqapdhfl faklktqtna sdfpigtslk yecrpeyygr pfsitcldnl 541 vwsspkdvck rkscktppdp vngmvhvitd iqvgsrinys cttghrligh ssaecilsgn 601 aahwstkppi cqripcglpp tiangdfist nrenfhygsv vtyrcnpgsg grkvfelvge 661 psiyctsndd qvgiwsgpap qciipnkctp pnvengilvs dnrslfslne vvefrcqpgf 721 vmkgprrvkc qalnkwepel pscsrvcqpp pdvlhaertq rdkdnfspgq evfyscepgy 781 dlrgaasmrc tpqgdwspaa ptcevkscdd fmgqllngry lfpvnlqlga kvdfvcdegf 841 qlkgssasyc vlagmeslwn ssvpvceqif cpsppvipng rhtgkplevf pfgkavnytc 901 dphpdrgtsf dligestirc tsdpqgngvw sspaprcgil ghcqapdhfl faklktqtna 961 sdfpigtslk yecrpeyygr pfsitcldnl vwsspkdvck rkscktppdp vngmvhvitd 1021 iqvgsrinys cttghrligh ssaecilsgn tahwstkppi cqripcglpp tiangdfist 1081 nrenfhygsv vtyrcnlgsr grkvfelvge psiyctsndd qvgiwsgpap qciipnkctp 1141 pnvengilvs dnrslfslne vvefrcqpgf vmkgprrvkc qalnkwepel pscsrvcqpp 1201 peilhgehtp shqdnfspgq evfyscepgy dlrgaaslhc tpqgdwspea prcavkscdd 1261 flgqlphgry lfpinlqlga kvsfvcdegf rlkgssyshc vlvgmrslwn nsvpvcehif 1321 cpnppailng rhtgtpsgdi pygkeisytc dphpdrgmtf nligestirc tsdphgngvw 1381 sspaprcels vraghcktpe qfpfasptip indfefpvgt slnyecrpgy fgkmfsiscl 1441 enlvwssved ncrrkscgpp pepfngmvhi ntdtqfgstv nyscnegfrl igspsttclv 1501 sgnnvtwdkk apiceiisce ppptisngdf ysnnrtsfhn gtvvtyqcht gpdgeqlfel 1561 vgersiycts kddqvgvwss ppprcistnk ctapevenai rvpgnrsfft lteiirfrcq 1621 pgfvmvgsht vqcqtngrwg pklphcsrvc qpppeilhge htlshqdnfs pgqevfysce 1681 psydlrgaas lhctpqgdws peaprctvks cddflgqlph grvllpinlq lgakvsfvcd 1741 egfrlkgrsa shcvlagmka lwnssvpvce qifcpnppai lngrhtgtpf gdipygkeis 1801 yacdthpdrg mtfnligess irctsdpqgn gvwsspaprc elsvpaacph ppkiqnghyi 1861 gghvslylpg mtisyicdpg yllvgkgfif ctdqgiwsql dhyckevncs fplfmngisk 1921 elemkkvyhy gdyvtlkced gytlegspws qcqaddrwdp plakctsrth dalivgtlsg
```

TABLE 4-continued

Sequences of Complement Receptor 1

1981 tiffilliif lswiilkhrk gnnahenpke vaihlhsqgg ssvhprtlqt neensrvlp

4C. Predicted CR1 isoform X1, Homo sapiens, NCBI Reference Sequence No. XP_005273121.1

(Seq. ID No. 3)

```
   1 mclgrmgass prspepvgpp apglpfccgg sllavvvlla lpvawgqcna pewlpfarpt
  61 nitdefefpi gtylnyecrp gysgrpfsii clknsvwtga kdrcrrkscr nppdpvngmv
 121 hvikgiqfgs qikysctkgy rligsssatc iisgdtviwd netpicdrip cglpptitng
 181 dfistnrenf hygsvvtyrc npgsggrkvf elvgepsiyc tsnddqvgiw sgpapqciip
 241 nkctppnven gilvsdnrsl fslnevvefr cqpgfvmkgp rrvkcqalnk wepelpscsr
 301 vcqpppdvlh aertqrdkdn fspgqevfys cepgydlrga asmrctpqgd wspaaptcev
 361 kscddfmgql lngrvlfpvn lqlgakvdfv cdegfqlkgs sasycvlagm eslwnssvpv
 421 ceqifcpspp vipngrhtgk plevfpfgkt vnytcdphpd rgtsfdlige stirctsdpq
 481 gngvwsspap rcgilghcqa pdhflfaklk tqtnasdfpi gtslkyecrp eyygrpfsit
 541 cldnlvwssp kdvckrksck tppdpvngmv hvitdiqvgs rinyscttgh rlighssaec
 601 ilsgnaahws tkppicqrip cglpptiang dfistnrenf hygsvvtyrc npgsggrkvf
 661 elvgepsiyc tsnddqvgiw sgpapqciip nkctppnven gilvsdnrsl fslnevvefr
 721 cqpgfvmkgp rrvkcqalnk wepelpscsr vcqpppdvlh aertqrdkdn fspgqevfys
 781 cepgydlrga asmrctpqgd wspaaptcev kscddfmgql lngrvlfpvn lqlgakvdfv
 841 cdegfqlkgs sasycvlagm eslwnssvpv ceqifcpspp vipngrhtgk plevfpfgkt
 901 vnytcdphpd rgtsfdlige stirctsdpq gngvwsspap rcgilghcqa pdhflfaklk
 961 tqtnasdfpi gtslkyecrp eyygrpfsit cldnlvwssp kdvckrksck tppdpvngmv
1021 hvitdiqvgs rinyscttgh rlighssaec ilsgnaahws tkppicqlcq pppdvlhaer
1081 tqrdkdnfsp gqevfyscep gydlrgaasm rctpqgdwsp aaptcevksc ddfmgqllng
1141 rvlfpvnlql gakvdfvcde gfqlkgssas ycvlagmesl wnssvpvceq ifcpsppvip
1201 ngrhtgkple vfpfgkavny tcdphpdrgt sfdligesti rctsdpqgng vwsspaprcg
1261 ilghcqapdh flfaldktqt nasdfpigts lkyecrpeyy grpfsitcld nlvwsspkdv
1321 ckrkscktpp dpvngmvhvi tdiqvgsrin yscttghrli ghssaecils gntahwstkp
1381 picqripcgl pptiangdfi stnrenfhyg svvtyrcnlg srgrkvfelv gepsiyctsn
1441 ddqvgiwsgp apqciipnkc tppnvengil vsdnrslfsl nevvefrcqp gfvmkgprry
1501 kcqalnkwep elpscsrvcq pppeilhgeh tpshqdnfsp gqevfyscep gydlrgaasl
1561 hctpqgdwsp eaprcavksc ddflgqlphg rvlfpinlql gakvsfvcde gfrlkgssys
1621 hcvlvgmrsl wnnsvpvceh ifcpnppail ngrhtgtpsg dipygkeisy tcdphpdrgm
1681 tfnligesti rctsdphgng vwsspaprce lsvraghckt peqfpfaspt ipindfefpv
1741 gtslnyecrp gyfgkmfsis clenlvwssv edncrrkscg pppepfngmv hintdtqfgs
1801 tvnyscnegf rligspsttc lvsgnnvtwd kkapiceiis ceppptisng dfysnnrtsf
1861 hngtvvtyqc htgpdeqlf elvgersiyc tskddqvgvw ssppprcist nkctapeven
1921 airvpgnrsf ftlteiirfr cqpgfvmvgs htvqcqtngr wgpklphcsr vcqpppeilh
1981 gehtlshqdn fspgqevfys cepsydlrga aslhctpqgd wspeaprctv kscddflgql
2041 phgrvllpin lqlgakvsfv cdegfrlkgr sashcvlagm kalwnssvpv ceqifcpnpp
2101 ailngrhtgt pfgdipygke isyacdthpd rgmtfnlige ssirctsdpq gngvwsspap
2161 rcelsvpaac phppkiqngh yigghvslyl pgmtisyicd pgyllvgkgf ifctdqgiws
```

TABLE 4-continued

Sequences of Complement Receptor 1

```
2221 qldhyckevn csfplfmngi skelemkkvy hygdyvtlkc edgytlegsp wsqcqaddrw 2281 dpplakctsr thdalivgtl sgtiffilli iflswiilkh rkgnnahenp kevaihlhsq 2341 ggssvhprtl qtneensrvl p
```

TABLE 5

Targets

General Classes of Targets

| | | | |
|---|---|---|---|
| Microbes | Polypeptides | DNA | Amino Acids |
| Fungi | Toxins | RNA | Prions |
| Bacteria | Lipids | Parasites | Cytokines |
| Virus | Cells | Cellular debris | Complement-associated molecules |

Complement-Related Targets

| | | | |
|---|---|---|---|
| Immune complexes | C3dg | C4a | C6 |
| Factor B | C3dk | C4b | C7 |
| Factor D | C3e | C2 | C8 |
| Properdin | Bb | C4bp | C9 |
| C3 | membrane attack complex | Mannose-Binding Lectin (MBL) | |
| C3a | C1q | MBL-Associated Serine Protease 1 (MASP1) | |
| C3b | C1r | MBL-Associated Serine Protease 2 (MASP2) | |
| iC3b | C1s | C5 | |
| C3c | C4 | C5a | |

Infectious Disease-Related Targets

| | | | |
|---|---|---|---|
| Lipopolysaccharides | Cell invasion protein | Intermedilysin | Secreted effector protein sptP |
| Zona occludens toxin | Cholera enterotoxin | Invasion protein sipA | Seeligeriolysin |
| Actin polymerization protein RickA | Cysteine protease | Iota toxin component Ia | Serine protease |
| Actin polymerization protein RickA | Cytolethal distending toxin | Ivanolysin | Shiga toxin |
| Adenosine monophosphate-protein transferase vopS | Cytolysin | LepB | Sphingomyelinase |
| adenylate cyclase | Cytotoxic necrotizing factor | Lethal factor | Staphylokinase |
| Adenylate cyclase ExoY | Cytotoxin | Leukotoxin | Streptokinase |
| ADP-ribosyltransferase enzymatic component | Dermonecrotic toxin | Listeriolysin | Streptolysin |
| Aerolysin | Deubiquitinase | Microbial collagenase | Streptopain |
| Alpha-toxin | Diphtheria toxin | Outer membrane protein IcsA autotransporter | Suilysin |
| Alveolysin | Enterohemolysin | Panton-Valentine Leucocidin F | Superantigen |
| Alveolysin | Enterotoxin | Perfringolysin | T3SS secreted effector EspF |
| Anthrolysin O | Epidermal cell differentiation inhibitor | Pertussis toxin | Tetanus toxin |
| Arp2/3 complex-activating protein rickA | Exoenzyme | Phospholipase | Tir |
| Binary ADP-ribosyltransferase CDT toxin | Exotoxin | Plasminogen activator | TolC |
| Botulinum neurotoxin | G-nucleotide exchange factor | Pneumolysin | Toxic shock syndrome toxin |
| C2 toxin, component II | Guanine nucleotide exchange factor sopE | Protective antigen | Zink-carboxypeptidase |
| CagA | Heat stable enterotoxin | Protein kinase | Zink-carboxypeptidase |
| Calmodulin-sensitive adenylate cyclase | IgA-specific serine endopeptidase autotransporter | Pyolysin | Zn-dependent peptidase |
| Cell cycle inhibiting factor | Inositol phosphate phosphatase sopB | RTX toxin | |

TABLE 5-continued

| Targets | | | |
|---|---|---|---|
| Other Molecular Targets | | | |
| G-CSF | IL3 | IL10 | MIP1a |
| GM-CSF | IL4 | IL12 | MIP1b |
| M-CSF | IL5 | IFNa | TGFb |
| IL1a | IL6 | IFNb | TNFa |
| IL1b | IL7 | IFNg | TNFb |
| IL2 | IL8 | Self-antibodies | Non-self antibodies |
| PRP | PRPc | PRPsc | PRPres |
| Lipid & Cell Targets | | | |
| Circulating tumor cells | very low density lipid (VLDL) | triglycerides | Fatty acids |
| Metastases | high density lipoprotein | chylomicrons | Cholesterol |
| Eukaryotic cells | low density lipoprotein | apolipoproteins | |

TABLE 6

| Diseases and Conditions | | | |
|---|---|---|---|
| Cancers | | | |
| Acute lymphoblastic leukaemia (ALL) | Colorectal cancer | Macroglobulinemia, Waldenström | Pleuropulmonary Blastoma, Childhood |
| Acute myeloid leukaemia (AML) | Craniopharyngioma, Childhood | Male Breast Cancer | Pregnancy and Breast Cancer |
| Adrenocortical Carcinoma | Cutaneous T-Cell Lymphoma | Malignant Fibrous Histiocytoma of Bone and Osteosarcoma | Primary Central Nervous System (CNS) Lymphoma |
| AIDS-Related Kaposi Sarcoma | Ductal Carcinoma In Situ (DCIS) | Melanoma | Prostate Cancer |
| AIDS-Related lymphoma | Embryonal Tumors, Childhood | Merkel Cell Carcinoma | Rare cancers |
| Anal Cancer | Endometrial Cancer | Mesothelioma | Rectal Cancer |
| Appendix Cancer | Ependymoma, Childhood | Metastatic Squamous Neck Cancer with Occult Primary | Renal cell carcinoma |
| Astrocytomas, Childhood | Epithelial cancer | Midline Tract Carcinoma Involving NUT Gene | Renal Pelvis and Ureter, Transitional Cell Cancer |
| Atypical Teratoid/Rhabdoid Tumor, Childhood | Esophageal Cancer | Molar pregnancy | Retinoblastoma |
| Basal Cell Carcinoma | Esthesioneuroblastoma, Childhood | Mouth and oropharyngeal cancer | Rhabdomyosarcoma |
| Bile duct cancer | Ewing sarcoma | Multiple Endocrine Neoplasia Syndromes, Childhood | Salivary Gland Cancer |
| Bladder cancer | Extragonadal Germ Cell Tumor | Multiple Myeloma/Plasma Cell Neoplasm | Sarcoma |
| Bone cancer | Extrahepatic Bile Duct Cancer | Mycosis Fungoides | Secondary cancers |
| Bowel cancer | Eye Cancer | Myelodysplastic Syndromes | Sézary Syndrome |
| Brain Stem Glioma, Childhood | Gallbladder Cancer | Myelodysplastic/ Myeloproliferative Neoplasms | Skin Cancer |
| Brain tumours | Gastric cancer | Myeloproliferative Disorders, Chronic | Skin cancer (non melanoma) |
| Breast cancer | Gastrointestinal Carcinoid Tumor | Nasal Cavity and Paranasal Sinus Cancer | Small Cell Lung Cancer |
| Bronchial Tumors, Childhood | Germ Cell Tumor | Nasopharyngeal cancer | Small Intestine Cancer |
| Burkitt Lymphoma | Gestational trophoblastic tumours (GTT) | Neuroblastoma | Soft Tissue Sarcoma |
| Cancer of unknown primary | Glioma | Non-Hodgkin Lymphoma | Squamous Cell Carcinoma |
| Cancer spread to bone | Hairy cell leukaemia | Non-Small Cell Lung Cancer | Squamous Neck Cancer with Occult Primary, Metastatic |

TABLE 6-continued

| Diseases and Conditions | | | |
|---|---|---|---|
| Cancer spread to brain | Head and neck cancer | Oesophageal cancer | Stomach (Gastric) Cancer |
| Cancer spread to liver | Heart Cancer, Childhood | Oral Cancer | Stomach cancer |
| Cancer spread to lung | Hepatocellular (Liver) Cancer | Oral Cavity Cancer | T-Cell Lymphoma, Cutaneous - see Mycosis Fungoides and Sézary Syndrome |
| Carcinoid Tumor | Histiocytosis, Langerhans Cell | Oropharyngeal Cancer | Testicular cancer |
| Carcinoma of Unknown Primary | Hodgkin Lymphoma | Osteosarcoma (Bone Cancer) | Throat Cancer |
| Cardiac (Heart) Tumors, Childhood | Hypopharyngeal Cancer | Osteosarcoma and Malignant Fibrous Histiocytoma | Thymoma and Thymic Carcinoma |
| Central Nervous System Atypical Teratoid/Rhabdoid Tumor, Childhood | Intraocular Melanoma | Ovarian Cancer | Thyroid Cancer |
| Central Nervous System Embryonal Tumors, Childhood | Islet Cell Tumors, Pancreatic Neuroendocrine Tumors | Pancreatic Cancer | Transitional Cell Cancer of the Renal Pelvis and Ureter |
| Central Nervous System, Childhood | Kidney cancer | Pancreatic Neuroendocrine Tumors (Islet Cell Tumors) | Unknown primary cancer |
| Cervical cancer | Langerhans Cell Histiocytosis | Papillomatosis, Childhood | Ureter and Renal Pelvis, Transitional Cell Cancer |
| Chordoma, Childhood | Laryngeal Cancer | Paraganglioma | Urethral Cancer |
| Choriocarcinoma | Leukemia | Parathyroid Cancer | Uterine Cancer, Endometrial |
| Chronic Lymphocytic Leukemia (CLL) | Lip and Oral Cavity Cancer | Penile Cancer | Uterine Sarcoma |
| Chronic myeloid leukaemia (CML) | Liver cancer | Pharyngeal Cancer | Vaginal cancer |
| Chronic Myeloproliferative Disorders | Lobular Carcinoma In Situ (LCIS) | Pheochromocytoma | Vulvar Cancer |
| Colon cancer | Low Malignant Potential Tumor | Pituitary Tumor | Waldenström Macroglobulinemia |
| Lymphoma | Lung Cancer | Plasma Cell Neoplasm/Multiple Myeloma | Wilms Tumor |
| Complement and Immune Complex-Related Diseases | | | |
| Age-related macular degeneration | ANCA-associated vasculitis (Includes Pauci-immune) | Glomerulonephritis - sparse hair - telangiectasis | MYH9-related disease |
| Atypical hemolytic uremic syndrome | Anti-glomerular basement membrane disease (Goodpasture's) | Goodpasture's sndrome | Nail-patella syndrome |
| Autoimmune hemolytic anemia | Arthus Reaction | Granulomatosis with polyangiitis (ANCA and Wegeners) | Nail-patella-like renal disease |
| C1 inhibitor deficiency | Asthma | Guillain-Barre syndrome | Nephritis |
| C1q deficiency | Atypical hemolytic uremic syndrome | Hemolytic angioedema (HAE) | Non-amyloid monoclonal immunoglobulin deposition disease |
| C1r deficiency | Autoimmune inner ear disease (AIED) Sensorineural hearing loss | Henoch-Schonlein purpura | Pauci-immune glomerulonephritis |
| C1s deficiency | Autoimmune uveitis | HIVICK | Pediatric systemic lupus erythematosus |
| C2 deficiency | Autosomal dominant intermediate Charcot-Marie-Tooth disease type E | Hypersensitivty vasculitis | Pierson syndrome |
| C3 deficiency | Behçet disease | Hypocomplementemic urticarial vasculitis | Polyarteritis |
| C4 deficiency | Berger (IgA) Nephropathy | Idiopathic membranous glomerulonephritis | polyarteritis nodosa |

TABLE 6-continued

| Diseases and Conditions | | | |
|---|---|---|---|
| C5 deficiency | Buergers disease | Idiopathic nephrotic syndrome | Polymyalgia rheumatica |
| C6 deficiency | Central nervous system vasculitis | IgA nephropathy (Berger's disease) | Polymyositis |
| C7 deficiency | Choroiditis | IgA nephropathy/vasculitis (Henoch-Schonlein purpura) | Polymyositis/dermatomyositis |
| C8 deficiency | Chronic demyelinating polyneuropathy (CIDP) | Immune thrombocytopenia | Poststaphilococcal glomerulonephritis |
| C9 deficiency | Churg-strauss syndrome | Immunobullous diseases | Poststeptococcal glomerulonephritis |
| CD55 deficiency | Cogan's syndrome | Immunotactoid or fibrillary glomerulopathy | Primary membranoproliferative glomerulonephritis |
| CD59 deficiency | Collagen type III glomerulopathy | Infection-related glomerulonephritis | Rapidly progressive glomerulonephritis (Crescentic) |
| Complement Factor I deficiency | Congenital and infantile nephrotic syndrome | Inflammatory myopathies | Rapidly progressive glomerulonephritis (RPGN) |
| Complement factor-H related 1(CFHR1) deficiency | Congenital membranous nephropathy due to maternal anti-neutral endopeptidase alloimmunization | Juvenile dermatomyositis | Rasmussen syndrome |
| Complement factor-H related 3(CFHR3) deficiency | Cryoglobulinaemia/Cold agglutinin diease | Juvenile polymyositis | Reactive arthritis |
| CR3/CR4 defieciency (leukocyte adhesion deficiency 1) | Cryoglobulinemic vasculitis | Kawasaki disease | Relapsing polychondritis |
| Factor B deficiency | Cutaneous vasculitis | Lipoprotein glomerulopathy | Renal amyloidosis |
| Factor D deficiency | Demyelinating myopathies (paraprotein associated) | Lupus nephritis | Reynolds syndrome |
| Factor H deficiency | Denys-Drash syndrome | Lupus nephropathy | Rheumatoid arthritis |
| Factor I deficiency | Dermatomyositis | May Hegglin anomaly | Sarcoidosis (Nesnier Boeck Schuamann Disease) |
| Ficolin 3 deficiency | Dermatomyositis | Membranoglomerular nephritis | Schimke immuno-osseous dysplasia |
| MASP2 deficiency | Diabetic nephropathy | Membranoproliferative glomerulonephritis | Scleroderma |
| MBL deficiency | Drug-induced immune complex vasculitis | Membranoproliferative glomerulonephritis Type I (MPGN Type I) | Sebastian syndrome |
| Non-alcoholic steatohepatitis | Eosinophilic granulomatosis with polyangiitis (Churgg-Strauss) | Membranoproliferative glomerulonephritis Type II (Dense Deposit Disease, MPGN Type II) | Secondary amyloidosis |
| Paroxysmal nocturnal hemoglobinuria | Epstein Syndrome | Membranoproliferative glomerulonephritis Type III (MPGN Type III) | Severe or recurring C diff colitis |
| Properdin deficencty | Essential mixed cryoglobulinemia | Membranouse glomerulonephritis | Sjogren's syndrome |
| Action myoclonus - renal failure syndrome | Familial Mediterranean fever | Menieres disease | Staphylococcal or streptococcal sepsis |
| Acute respiratory disease syndrome (ARDS)/Severe acute respiratory syndrome (SARS) | Familial renal amyloidosis | Microscopic polyangiitis | Stiff person syndrome |
| Acute serum sickness | Familial steroid-resistant nephrotic syndrome with sensorineural deafness | Minimal change disease | Systemic lupus erythematosus |
| Adult-onset Still disease | Farmer's lung | Mixed connective tissue disease | Systemic sclerosis |
| Age-related macular degeneration | Fechtner Syndrome | Mostly large vessel vasculitis | Takayasu arteritis |

TABLE 6-continued

| Diseases and Conditions | | | |
|---|---|---|---|
| AL amyloidosis | Fibronectin glomerulopathy | mostly medium vessel vasculitis | Toxic epidermal necrolysis (Stevens Johnson syndrome) |
| Alport's syndrome | Fibrosing alveolitis | Mostly small vessel vsculitis | Transplantation/reperfusion (solid organ) |
| Alzheimer's disease | Focal segmental glomerular | Muckle-Wells syndrome | Vasculitis |
| Amyloidosis (AL, AA, MIDD, Other) | Focal segmental glomerulosclerosis | Myasthenia gravis | Wegener's granulomatosis |
| Giant cell arteritis | Frasier syndrome | Galloway-Mowat syndrome | |
| Type 1 diabetes | Myasthenia gravis | Graves' disease | Pernicious anemia |
| Crohn's disease | alopecia areata | thrombocytopenic purpura | Primary biliary cirrhosis |
| Ulcerative colitis | autoimmune hepatitis | Guillain-Barre syndrome | Psoriasis |
| Inflammatory bowel syndrome | autoimmune deramtomyositis | Autoimmune myocarditis | Rheumatoid arthritis |
| Multiple sclerosis | Juvenile idiopathic arthritis | Autoimmune pemphigus | Vitiligo |
| Enzyme Deficiencies & Vascular Diseases | | | |
| 2,4-dienoyl-CoA reductase deficiency | Fabry disease (1:80,000 to 1:117,000) | Isobutyryl-CoA dehydrogenase | Peripheral neuropathy |
| 2-Methyl-3-hydroxy butyric aciduria | Familial hypercholesterolemia (1:500) | Isovaleric acidemia | Peroxisomal disorders (1:50,000; e.g., Zellweger syndrome, neonatal adrenoleukodystrophy, Refsum's disease) |
| 2-methylbutyryl-CoA dehydrogenase | Familial myocardial infarct/stroke | Lactase deficiency (common) | Phenylketonuria |
| 3-hydroxy-3-methylglutaryl (HMG) aciduria | Fatty acid oxidation disorders (1:10,000) | Lesch-Nyhan syndrome | Primary hyperoxaluria |
| 3-methylglutaconic aciduria | Galactokinase deficiency | Lipoprotein lipase deficiency (rare) | Propionic acidemia |
| 3-oxothiolase deficiency (1:100,000) | Galactose epimerase | long-chain l-3-hdroxyacyl-CoA dehydrogenase | Recurrent emesis |
| 4-hydroxybutyric aciduria | Galactosemia | Lysinuric protein intolerance (rare) | Short-chain acyl-CoA dehydrogenase |
| 5,10-methylenetetrahydrofolate reductase deficiency (common) | Galactosemia (1:40,000) | Lysinuric protein intolerance (rare) | Sucrase-isomaltase deficiency (rare) |
| 5-Oxoprolinuria (pyroglutamic aciduria) | Gaucher's disease | Malonic acidemia | Symptoms of pancreatitis |
| Abetalipoproteinemia (rare) | Glutaric acidemia type I | Maple syrup urine disease | Transferase deficient galactosemia (Galactosemia type 1) |
| Acute Intermittent Porphyria | Glutaric acidemia Type II | Medium chain acyl-CoA dehydrogenase | Trifunctional protein deficiency |
| Alkaptonuria | Glutathione Synthetase Deficiency w/ 5-oxoprolinuria | Medium/short chain L-3-hydroxy acyl-CoA dehydrogenase | Tyrosinemia type 1 |
| Argininemia | Glutathione Synthetase Deficiency w/o 5-oxoprolinuria | Medum-chain ketoacyl-coA thiolase | Tyrosinemia type 2 |
| argininosuccinate aciduria | Glycogenolysis disorders (1:20,000) | Metachromatic leukodystrophy (1:100,000) | Tyrosinemia type 3 |
| Benign hyperphenylalaninemia | Glycogenosis, type I (1:70,000) | Metachromatic leukodystrophy (1:100,000) | Upward gaze paralysis |
| beta ketothiolase deficiency | Hemolytic anemia due to adenylate kinase deficiency | Methylmalonic acidemia (Cbl C) | Very long chain acyl-CoA dehydrogenase |

TABLE 6-continued

| Diseases and Conditions | | | |
|---|---|---|---|
| Biopterin cofactor biosynthesis defects | Hemolytic anemia due to deficiency in Glucose 6 phosphate dehydrogenase | Methylmalonic acidemia (Cbl D) | Wilson Disease |
| Biopterin cofactor regeneration defects | Hemolytic anemia due to diphosphoglycerate mutase deficiency | Methylmalonic acidemia (vitamin b12 non-responsive) | Aicardi-Goutieres Syndrome (may be an allelic form of CLE) |
| biotin-unresponsive 3-methylcrotonyl-CoA carboxylase deficiency | Hemolytic anemia due to erythrocyte adenosine deaminase overproduction | Methylmalonic acidemia w/0 homocystinuria | Cutaneous lupus erythematosus |
| Carbamoyl phosphate synthetase | Hemolytic anemia due to glucophosphate isomerase deficiency | Methylmalonic aciduria and homocystinuria | Dermatitis herpetiformis |
| Carnitine acylcarnitine translocase | Hemolytic anemia due to glutathione reductase deficiency | Mitochondrial disorders (1:30,000) | hemophilia A |
| Carnitine palmitoyltransferase I | Hemolytic anemia due to glyceraldehyde-3-phosphate dehydrogenase deficiency | Mitochondrial disorders (1:30,000; e.g., cytochrome-c oxidase deficiency; MELAS syndrome; Pearson's syndrome [all rare]) | hemophilia B |
| Carnitine palmitoyltransferase II | Hemolytic anemia due to pyrimidine 5' nucleotidase deficiency | Mitochondrial disorders (1:30,000; e.g., Leigh disease, Kearns-Sayre syndrome [rare]) | Idiopathic steroid sensitive nephrotic syndrome (same as focal segmental glomerulaosclerosis) |
| Carnitine uptake defect | Hemolytic anemia due to red cell pyruvate kinase deficiency | Mitochondrial disorders (1:30,000; e.g., lipoamide dehydrogenase deficiency [rare]) | Immune thrombocytopenic purpura |
| citrullinemia type I | HHH syndrome (rare) | Mitochondrial disorders (1:30,000; e.g., Pearson's syndrome [rare]) | Myasthenia gravis |
| Citrullinemia type II | homocysteinuria | Multiple carboxylase (holocarboxylase synthetase) | Oligoarticular juvenile arthritis |
| Congenital disorders of glycosylation (rare) | Homocystinuria (1:200,000) | Multiple carboxylase deficiency (e.g., holocarboxylase synthetase [rare]) and biotinidase deficiencies (1:60,000) | Scleroderma |
| D-2-hydroxyglutaricaciduria | hyperammonemia/ornithinemia/citrullinemia (ornithine transporter defect) | Muscle cramps/spasticity | Solar urticaria (maybe protophyria erythema) |
| D-2-hydroxyglutaricaciduria (rare) | Hyperlipoproteinemia, types I and IV (rare) | Myoadenylate deaminase deficiency (1:100,000) | Thrombotic thrombocytopenic purpura |
| Enteropeptidase deficiency (rare) | Hypermethioninemia due to glycine N-methyltransferase deficiency | Niemann-Pick disease, type C (rare) | Tubulointerstitial nephritis with Uveitis/ATIN |
| Ethylmalonic encephalopathy | Hypermethioninemia encephalopathy due to adenosine kinase deficiency Hyperprolinemia | Nonketotic hyperglycinemia | Von willebrand disease |
| Infectious Diseases & agents | | | |
| *Acinetobacter* | Dengue haemorrhagic fever | Infection-induced immune complex vasculitis | Sepsis |
| *Arcobacter butzleri* infection - blood infection | Disseminated infection with *mycobacterium avium* complex - blood infection | *Klebsiella* | *Serratia* |
| *Arcobacter cryaerophilus* infection - blood infection | E. coli | Leprosy/Hansen's disease | *Staphylococcus Aureus* |
| *Arcobacter* infection - blood infection | *Enterobacter* | Malaria | *Stenotrophomonas maltophilia* - blood infection |

TABLE 6-continued

| Diseases and Conditions | | | |
|---|---|---|---|
| Bacteremia | Enterococcus | Meningococcus | Streptococcal Group A invasive disease - blood infection |
| Bacterial endocarditis | Glanders - blood infection | Methicillin Resistant Staphylococcus Aureus | Streptococcus pneumoniae |
| Campylobacter fetus infection - blood infection | Gonorrhea | Pseudomonas | Streptococcus pyogenes |
| Campylobacter jejuni infection - blood infection | Hepatitis | Rhodococcus equi - blood infection | Trypanosomiasis |
| Candida | Human Immunodeficiency Virus | Salmonella | Yellow fever |

Coagulase-negative Staphylococcus

TABLE 7

| Receivers | | | |
|---|---|---|---|
| General Classes of Receivers | | | |
| Ankyrin repeat proteins | Fibronectins | Lyases | |
| Antibodies | Complement receptors | GPI-linked polypeptides | Nanobodies |
| Aptamers | Cyclic peptides | HEAT repeat proteins | Nucleic Acids |
| ARM repeat proteins | DARPins | Hydrolases | Polypeptides |
| Carbohydrates | DNAses | Kinases | Single-chain variable fragments (scFv) |
| Cell surface receptors | Enzymes | Lipoproteins | Tetratricopeptide repeat proteins |
| Complement-Related Receivers | | | |
| C1 inhibitor | C4 binding protein | CR3 | Factor I |
| C3 Beta chain Receptor | CD59 | CR4 | Homologous restriction factor |
| C3aR | CR1 | Decay-accelerating factor (DAF) | Membrane cofactor protein (MCP) |
| C3eR | CR2 | Factor H | PRELP |
| Enzymes | | | |
| triacylglycerol lipase | bile-acid-CoA hydrolase | feruloyl esterase | phosphatidate phosphatase |
| (S)-methylmalonyl-CoA hydrolase | bis(2-ethylhexyl)phthalate esterase | formyl-CoA hydrolase | phosphatidylglycero-phosphatase |
| [acyl-carrier-protein] phosphodiesterase | bisphosphoglycerate phosphatase | fructose-bisphosphatase | phosphatidylinositol deacylase |
| [phosphorylase] phosphatase | Carboxylic-Ester Hydrolases | fumarylacetoacetase | phosphodiesterase I |
| 1,4-lactonase | carboxymethylene-butenolidase | fusarinine-C ornithinesterase | phosphoglycerate phosphatase |
| 11-cis-retinyl-palmitate hydrolase | cellulose-polysulfatase | galactolipase | phosphoglycolate phosphatase |
| 1-alkyl-2-acetylglycerophospho-choline esterase | cephalosporin-C deacetylase | gluconolactonase | phosphoinositide phospholipase C |
| 2'-hydroxybiphenyl-2-sulfinate desulfinase | cerebroside-sulfatase | glucose-1-phosphatase | phospholipase A1 |
| 2-pyrone-4,6-dicarboxylate lactonase | cetraxate benzylesterase | glucose-6-phosphatase | phospholipase A2 |
| 3',5'-bisphosphate nucleotidase | chlorogenate hydrolase | glutathione thiolesterase | phospholipase C |
| 3-hydroxyisobutyryl-CoA hydrolase | chlorophyllase | glycerol-1-phosphatase | phospholipase D |
| 3'-nucleotidase | cholinesterase | glycerol-2-phosphatase | phosphonoacetaldehyde hydrolase |
| 3-oxoadipate enol-lactonase | choline-sulfatase | glycerophosphocholine phosphodiesterase | phosphonoacetate hydrolase |
| 3-phytase | choloyl-CoA hydrolase | Glycosidases, i.e. enzymes that hydrolyse O- and S-glycosyl compounds | phosphonopyruvate hydrolase |

TABLE 7-continued

| Receivers | | | |
|---|---|---|---|
| 4-hydroxybenzoyl-CoA thioesterase | chondro-4-sulfatase | glycosulfatase | phosphoprotein phosphatase |
| 4-methyloxaloacetate esterase | chondro-6-sulfatase | Glycosylases | Phosphoric-diester hydrolases |
| 4-phytase | citrate-lyase deacetylase | histidinol-phosphatase | Phosphoric-monoester hydrolases |
| 4-pyridoxolactonase | cocaine esterase | hormone-sensitive lipase | Phosphoric-triester hydrolases |
| 5'-nucleotidase | cutinase | Hydrolysing N-glycosyl compounds | phosphoserine phosphatase |
| 6-acetylglucose deacetylase | cyclamate sulfohydrolase | Hydrolysing S-glycosyl compounds | poly(3-hydroxybutyrate) depolymerase |
| 6-phosphogluconolactonase | Cysteine endopeptidases | hydroxyacylglutathione hydrolase | poly(3-hydroxyoctanoate) depolymerase |
| a-amino-acid esterase | Cysteine-type carboxypeptidases | hydroxybutyrate-dimer hydrolase | polyneuridine-aldehyde esterase |
| a-Amino-acyl-peptide hydrolases | D-arabinonolactonase | hydroxymethylglutaryl-CoA hydrolase | protein-glutamate methylesterase |
| acetoacetyl-CoA hydrolase | deoxylimonate A-ring-lactonase | iduronate-2-sulfatase | quorum-quenching N-acyl-homoserine lactonase |
| acetoxybutynylbithiophene deacetylase | dGTPase | inositol-phosphate phosphatase | retinyl-palmitate esterase |
| acetylajmaline esterase | dihydrocoumarin hydrolase | juvenile-hormone esterase | Serine dehyrdatase or serine hydroxymethyl transferase |
| acetylalkylglycerol acetylhydrolase | Dipeptidases | kynureninase | Serine endopeptidases |
| acetylcholinesterase | Dipeptide hydrolases | L-arabinonolactonase | serine-ethanolaminephosphate phosphodiesterase |
| acetyl-CoA hydrolase | Dipeptidyl-peptidases and tripeptidyl-peptidases | limonin-D-ring-lactonase | Serine-type carboxypeptidases |
| acetylesterase | Diphosphoric-monoester hydrolases | lipoprotein lipase | S-formylglutathione hydrolase |
| acetylpyruvate hydrolase | disulfoglucosamine-6-sulfatase | L-rhamnono-1,4-lactonase | sialate O-acetylesterase |
| acetylsalicylate deacetylase | dodecanoyl-[acyl-carrier-protein] hydrolase | lysophospholipase | sinapine esterase |
| acetylxylan esterase | Endodeoxyribonucleases producing 3'-phosphomonoesters | mannitol-1-phosphatase | Site specific endodeoxyribonucleases: cleavage is not sequence specific |
| acid phosphatase | Endodeoxyribonucleases producing 5'-phosphomonoesters | Metallocarboxypeptidases | Site-specific endodeoxyribonucleases that are specific for altered bases. |
| Acting on acid anhydrides to catalyse transmembrane movement of substances | Endopeptidases of unknown catalytic mechanism | Metalloendopeptidases. | Site-specific endodeoxyribonucleases: cleavage is sequence specific |
| Acting on acid anhydrides to facilitate cellular and subcellular movement | Endoribonucleases producing 3'-phosphomonoesters | methylphosphothio-glycerate phosphatase | sphingomyelin phosphodiesterase |
| Acting on GTP to facilitate cellular and subcellular movement | Endoribonucleases producing 5'-phosphomonoesters | methylumbelliferyl-acetate deacetylase | S-succinylglutathione hydrolase |
| Acting on phosphorus-nitrogen bonds | Endoribonucleases that are active with either ribo- or deoxyribonucleic acids and produce 3'-phosphomonoesters | monoterpene e-lactone hydrolase | steroid-lactonase |
| Acting on sulfur-nitrogen bonds | Endoribonucleases that are active with either ribo- or deoxyribonucleic acids and produce 5'-phosphomonoesters | N-acetylgalactosamine-4-sulfatase | sterol esterase |
| actinomycin lactonase | Enzymes acting on acid anhydrides | N-acetylgalactosamine-6-sulfatase | steryl-sulfatase |
| acylcarnitine hydrolase | Enzymes Acting on carbon-carbon bonds | N-acetylgalactosaminoglycan deacetylase | succinyl-CoA hydrolase |

TABLE 7-continued

| Receivers | | | |
|---|---|---|---|
| acyl-CoA hydrolase | Enzymes acting on carbon-nitrogen bonds, other than peptide bonds | N-acetylglucosamine-6-sulfatase | sucrose-phosphate phosphatase |
| acylglycerol lipase | Enzymes acting on carbon-phosphorus bonds | N-sulfoglucosamine sulfohydrolase | sugar-phosphatase |
| acyloxyacyl hydrolase | Enzymes acting on carbon-sulfur bonds | oleoyl-[acyl-carrier-protein] hydrolase | Sulfuric-ester hydrolases |
| acylpyruvate hydrolase | Enzymes Acting on ether bonds | Omega peptidases | tannase |
| ADAMTS13 | Enzymes acting on halide bonds | orsellinate-depside hydrolase | Thioester hydrolases |
| Adenosine deaminase | Enzymes acting on peptide bonds (peptidases) | oxaloacetase | Thioether and trialkylsulfonium hydrolases |
| adenylyl-[glutamate-ammonia ligase] hydrolase | Enzymes acting on phosphorus-nitrogen bonds | palmitoyl[protein] hydrolase | Threonine endopeptidases |
| ADP-dependent medium-chain-acyl-CoA hydrolase | Enzymes acting on sulfur-nitrogen bonds | palmitoyl-CoA hydrolase | thymidine phosphorylase |
| ADP-dependent short-chain-acyl-CoA hydrolase | Enzymes acting on sulfur-sulfur bonds | pectinesterase | trehalose-phosphatase |
| ADP-phosphoglycerate phosphatase | Ether hydrolases. | Peptidyl peptide hydrolases | triacetate-lactonase |
| alkaline phosphatase | Exodeoxyribonucleases producing 5'-phosphomonoesters | Peptidyl-amino-acid hydrolases | Triphosphoric-monoester hydrolases |
| all-trans-retinyl-palmitate hydrolase | Exonucleases that are active with either ribo- or deoxyribonucleic acids and produce 3'-phosphomonoesters | Peptidylamino-acid hydrolases or acylamino-acid hydrolases | trithionate hydrolase |
| aminoacyl-tRNA hydrolase | Exonucleases that are active with either ribo- or deoxyribonucleic acids and produce 5'-phosphomonoesters | Peptidyl-dipeptidases | tropinesterase |
| Aminopeptidases | Exoribonucleases producing 3'-phosphomonoesters | phenylacetyl-CoA hydrolase | ubiquitin thiolesterase |
| arylesterase | Exoribonucleases producing 5'-phosphomonoesters. | Phenylalanine ammonia lyase | UDP-sulfoquinovose synthase |
| arylsulfatase | Factor IX | Phenylalanine hydroxylase | uricase |
| Asparaginase | Factor VIII | pheophorbidase | uronolactonase |
| Aspartic endopeptidases | fatty-acyl-ethyl-ester synthase | phloretin hydrolase | wax-ester hydrolase |
| | b-diketone hydrolase | phorbol-diester hydrolase | xylono-1,4-lactonase |

TABLE 8

| Selected Diseases, Receivers and Targets | | | |
|---|---|---|---|
| Category | Disease | Receiver | Target |
| Amyloidoses | AA Amyloidosis | an an antibody-like binder to serum amyloid A protein or serum amyloid P component | Serum amyloid A protein and amyloid placques |
| Amyloidoses | beta2 microgulin amyloidosis | an an antibody-like binder to beta-2 microglobulin or serum amyloid P component | Beta2 microglobulin or amyloid placques |
| Amyloidoses | Light chain amyloidosis | an an antibody-like binder to light chain, serum amyloid P component | Antibody light chain or amyloid placques |
| Cell clearance | Cancer | an an antibody-like binder to CD44 | a circulating tumor cell |
| Cell clearance | Cancer | an an antibody-like binder to EpCam | a circulating tumor cell |
| Cell clearance | Cancer | an an antibody-like binder to Her2 | a circulating tumor cell |

TABLE 8-continued

Selected Diseases, Receivers and Targets

| Category | Disease | Receiver | Target |
|---|---|---|---|
| Cell clearance | Cancer | an an antibody-like binder to EGFR | a circulating tumor cell |
| Cell clearance | Cancer (B cell) | an an antibody-like binder to CD20 | a cancerous B cell |
| Cell clearance | Cancer (B cell) | an an antibody-like binder to CD19 | a cancerous B cell |
| Clearance Ab | Antiphospholipid syndrome | beta2-glycoprotein-1 | pathogenic self-antibody against beta2-glycoprotein-1 |
| Clearance Ab | Catastrophic antiphospholipid syndrome | beta2-glycoprotein-1 | pathogenic self-antibody against beta2-glycoprotein-1 |
| Clearance Ab | Cold agglutinin disease | I/i antigen | Pathogenic self-antibody against I/i antigen |
| Clearance Ab | Goodpasture syndrome | a3 NC1 domain of collagen (IV) | pathogenic self-antibody against a3 NC1 domain of Collagen (IV) |
| Clearance Ab | Immune thrombocytopenia purpura | Platelet Glycoproteins (Ib-IX, IIb-IIIa, IV, Ia-IIa) | pathogenic self-antibody against platelet glycoprotein |
| Clearance Ab | Membranous Nephropathy | Phospholipase A2 receptor | pathogenic self-antibody against phospholipase A2 receptor |
| Clearance Ab | Warm antibody hemolytic anemia | Glycophorin A, glycophorin B, and/or glycophorin C, Rh antigen | pathogenic self-antibody against glycophorins and/or Rh antigen |
| Complement | Age-related macular degeneration | a suitable complement regulatory protein | active complement |
| Complement | Atypical hemolytic uremic syndrome | complement factor H, or a suitable complement regulatory protein | active complement |
| Complement | Autoimmune hemolytic anemia | a suitable complement regulatory molecule | active complement |
| Complement | Complement Factor I deficiency | Complement factor I, a suitable complement regulatory protein | active complement |
| Complement | Non-alcoholic steatohepatitis | a suitable complement regulatory molecule | active complement |
| Complement | Paroxysmal nocturnal hemoglobinuria | a suitable complement regulatory protein | active complement |
| Enzyme | 3-methylcrotonyl-CoA carboxylase deficiency | 3-methylcrotonyl-CoA carboxylase | 3-hydroxyvalerylcarnitine, 3-methylcrotonylglycine (3-MCG) and 3-hydroxyisovaleric acid (3-HIVA) |
| Enzyme | Acute Intermittent Porphyria | Porphobilinogen deaminase | Porphobilinogen |
| Enzyme | Acute lymphoblastic leukemia | Asparaginase | Asparagine |
| Enzyme | Acute lymphocytic leukemia, acute myeloid leukemia | Asparaginase | Asparagine |
| Enzyme | Acute myeloblastic leukemia | Asparaginase | Asparagine |
| Enzyme | Adenine phosphoribosyltransferase deficiency | adenine phosphoribosyltransferase | Insoluble purine 2,8-dihydroxyadenine |
| Enzyme | Adenosine deaminase deficiency | Adenosine deaminase | Adenosine |
| Enzyme | Afibrinogenomia | FI | enzyme replacement |
| Enzyme | Alcohol poisoning | Alcohol dehydrogenase/oxidase | Ethanol |
| Enzyme | Alexander's disease | FVII | enzyme replacement |
| Enzyme | Alkaptonuria | homogentisate oxidase | homogentisate |
| Enzyme | Argininemia | Ammonia monooxygenase | ammonia |
| Enzyme | argininosuccinate aciduria | Ammonia monooxygenase | ammonia |
| Enzyme | citrullinemia type I | Ammonia monooxygenase | ammonia |
| Enzyme | Citrullinemia type II | Ammonia monooxygenase | ammonia |

TABLE 8-continued

| Selected Diseases, Receivers and Targets | | | |
|---|---|---|---|
| Category | Disease | Receiver | Target |
| Enzyme | Complete LCAT deficiency, Fish-eye disease, atherosclerosis, hypercholesterolemia | Lecithin-cholesterol acyltransferase (LCAT) | Cholesterol |
| Enzyme | Cyanide poisoning | Thiosulfate-cyanide sulfurtransferase | Cyanide |
| Enzyme | Diabetes | Hexokinase, glucokinase | Glucose |
| Enzyme | Factor II Deficiency | FII | enzyme replacement |
| Enzyme | Familial hyperarginemia | Arginase | Arginine |
| Enzyme | Fibrin Stabilizing factor Def. | FXIII | enzyme replacement |
| Enzyme | Glutaric acidemia type I | lysine oxidase | 3-hydroxyglutaric and glutaric acid (C5-DC), lysine |
| Enzyme | Gout | Uricase | Uric Acid |
| Enzyme | Gout - hyperuricemia | Uricase | Uric acid (Urate crystals) |
| Enzyme | Hageman Def. | FXII | enzyme replacement |
| Enzyme | Hemolytic anemia due to pyrimidine 5' nucleotidase deficiency | pyrimidine 5' nucleotidase | pyrimidines |
| Enzyme | Hemophilia A | Factor VIII | Thrombin (factor II a) or Factor X |
| Enzyme | Hemophilia B | Factor IX | Factor XIa or Factor X |
| Enzyme | Hemophilia C | FXI | enzyme replacement |
| Enzyme | Hepatocellular carcinoma, melanoma | Arginine deiminase | Arginine |
| Enzyme | Homocystinuria | Cystathionine B synthase | homocysteine |
| Enzyme | hyperammonemia/ornithinemia/citrullinemia (ornithine transporter defect) | Ammonia monooxygenase | Ammonia |
| Enzyme | Isovaleric acidemia | Leucine metabolizing enzyme | leucine |
| Enzyme | Lead poisoning | d-aminolevulinate dehydrogenase | lead |
| Enzyme | Lesch-Nyhan syndrome | Uricase | Uric acid |
| Enzyme | Maple syrup urine disease | Leucine metabolizing enzyme | Leucine |
| Enzyme | Methylmalonic acidemia (vitamin b12 non-responsive) | methylmalonyl-CoA mutase | methylmalonate |
| Enzyme | Mitochondrial neurogastrointestinal encephalomyopathy | thymidine phosphorylase | thymidine |
| Enzyme | Mitochondrial neurogastrointestinal encephalomyopathy (MNGIE) | Thymidine phosphorylase | Thymidine |
| Enzyme | Owren's disease | FV | enzyme replacement |
| Enzyme | p53-null solid tumor | Serine dehyrdatase or serine hydroxymethyl transferase | serine |
| Enzyme | Pancreatic adenocarcinoma | Asparaginase | asparagine |
| Enzyme | Phenylketonuria | Phenylalanine hydroxylase, phenylalanine ammonia lyase | Phenylalanine |
| Enzyme | Primary hyperoxaluria | Oxalate oxidase | Oxalate |
| Enzyme | Propionic acidemia | Propionate conversion enzyme? | Proprionyl coA |
| Enzyme | Purine nucleoside phosphorylase deficiency | Purine nucleoside phosphorylase | Inosine, dGTP |
| Enzyme | Stuart-Power Def. | FX | enzyme replacement |
| Enzyme | Thrombotic Thrombocytopenic Purpura | ADAMTS13 | ultra-large von willebrand factor (ULVWF) |
| Enzyme | Transferase deficient galactosemia (Galactosemia type 1) | galactose dehydrogenase | Galactose-1-phosphate |
| Enzyme | Tyrosinemia type 1 | tyrosine phenol-lyase | tyrosine |
| Enzyme | von Willebrand disease | vWF | enzyme replacement |
| IC clearance | IgA Nephropathy | Complement receptor 1 | Immune complexes |
| IC clearance | Lupus nephritis | Complement receptor 1 | immune complex |
| IC clearance | Systemic lupus erythematosus | Complement receptor 1 | immune complex |
| Infectious | Anthrax (*B. anthracis*) infection | an an antibody-like binder to *B. anthracis* surface protein | *B. anthracis* |
| Infectious | *C. botulinum* infection | an an antibody-like binder to *C. botulinum* surface protein | *C. botulinum* |

TABLE 8-continued

Selected Diseases, Receivers and Targets

| Category | Disease | Receiver | Target |
|---|---|---|---|
| Infectious | C. difficile infection | an antibody-like binder to C. difficile surface protein | C. difficile |
| Infectious | Candida infection | an antibody-like binder to candida surface protein | candida |
| Infectious | E. coli infection | an antibody-like binder to E. coli surface protein | E. coli |
| Infectious | Ebola infection | an antibody-like binder to Ebola surface protein | Ebola |
| Infectious | Hepatitis B (HBV) infection | an antibody-like binder to HBV surface protein | HBV |
| Infectious | Hepatitis C (HCV) infection | an antibody-like binder to HCV surface protein | HCV |
| Infectious | Human immunodeficiency virus (HIV) infection | an antibody-like binder to HIV envelope proteins or CD4 or CCR5 or | HIV |
| Infectious | M. tuberculosis infection | an antibody-like binder to M. tuberculosis surface protein | M. tuberculosis |
| Infectious | Malaria (P. falciparum) infection | an antibody-like binder to P. falciparum surface protein | P. falciparum |
| Lipid | Hepatic lipase deficiency, hypercholesterolemia | Hepatic lipase (LIPC) | Lipoprotein, intermediate density (IDL) |
| Lipid | Hyperalphalipoproteinemia 1 | Cholesteryl ester transfer protein(CETP) | Lipoprotein, high density (HDL) |
| Lipid | hypercholesterolemia | an antibody-like binder to low-density lipoprotein (LDL), LDL receptor | LDL |
| Lipid | hypercholesterolemia | an antibody-like binder to high-density lipoprotein (HDL) or HDL receptor | HDL |
| Lipid | lipoprotein lipase deficiency | lipoprotein lipase | chilomicrons and very low density lipoproteins (VLDL) |
| Lipid | Lipoprotein lipase deficiency, disorders of lipoprotein metabolism | lipoprotein lipase (LPL) | Lipoprotein, very low density (VLDL) |
| Lysosomal storage | Aspartylglucosaminuria (208400) | N-Aspartylglucosaminidase | glycoproteins |
| Lysosomal storage | Cerebrotendinous xanthomatosis (cholestanol lipidosis; 213700) | Sterol 27-hydroxylase | lipids, cholesterol, and bile acid |
| Lysosomal storage | Ceroid lipofuscinosis Adult form (CLN4, Kufs' disease; 204300) | Palmitoyl-protein thioesterase-1 | lipopigments |
| Lysosomal storage | Ceroid lipofuscinosis Infantile form (CLN1, Santavuori-Haltia disease; 256730) | Palmitoyl-protein thioesterase-1 | lipopigments |
| Lysosomal storage | Ceroid lipofuscinosis Juvenile form (CLN3, Batten disease, Vogt-Spielmeyer disease; 204200) | Lysosomal transmembrane CLN3 protein | lipopigments |
| Lysosomal storage | Ceroid lipofuscinosis Late infantile form (CLN2, Jansky-Bielschowsky disease; 204500) | Lysosomal pepstatin-insensitive peptidase | lipopigments |
| Lysosomal storage | Ceroid lipofuscinosis Progressive epilepsy with intellectual disability (600143) | Transmembrane CLN8 protein | lipopigments |
| Lysosomal storage | Ceroid lipofuscinosis Variant late infantile form (CLN6; 601780) | Transmembrane CLN6 protein | lipopigments |
| Lysosomal storage | Ceroid lipofuscinosis Variant late infantile form, Finnish type (CLN5; 256731) | Lysosomal transmembrane CLN5 protein | lipopigments |
| Lysosomal storage | Cholesteryl ester storage disease (CESD) | lisosomal acid lipase | lipids and cholesterol |

TABLE 8-continued

Selected Diseases, Receivers and Targets

| Category | Disease | Receiver | Target |
|---|---|---|---|
| Lysosomal storage | Congenital disorders of N-glycosylation CDG Ia (solely neurologic and neurologic-multivisceral forms; 212065) | Phosphomannomutase-2 | N-glycosylated protein |
| Lysosomal storage | Congenital disorders of N-glycosylation CDG Ib (602579) | Mannose (Man) phosphate (P) isomerase | N-glycosylated protein |
| Lysosomal storage | Congenital disorders of N-glycosylation CDG Ic (603147) | Dolicho-P-Glc:Man9GlcNAc2-PP-dolichol glucosyltransferase | N-glycosylated protein |
| Lysosomal storage | Congenital disorders of N-glycosylation CDG Id (601110) | Dolicho-P-Man:Man5GlcNAc2-PP-dolichol mannosyltransferase | N-glycosylated protein |
| Lysosomal storage | Congenital disorders of N-glycosylation CDG Ie (608799) | Dolichol-P-mannose synthase | N-glycosylated protein |
| Lysosomal storage | Congenital disorders of N-glycosylation CDG If (609180) | Protein involved in mannose-P-dolichol utilization | N-glycosylated protein |
| Lysosomal storage | Congenital disorders of N-glycosylation CDG Ig (607143) | Dolichyl-P-mannose:Man-7-GlcNAc-2-PP-dolichyl-α-6-mannosyltransferase | N-glycosylated protein |
| Lysosomal storage | Congenital disorders of N-glycosylation CDG Ih (608104) | Dolichyl-P-glucose:Glc-1-Man-9-GlcNAc-2-PP-dolichyl-α-3-glucosyltransferase | N-glycosylated protein |
| Lysosomal storage | Congenital disorders of N-glycosylation CDG Ii (607906) | α-1,3-Mannosyltransferase | N-glycosylated protein |
| Lysosomal storage | Congenital disorders of N-glycosylation CDG IIa (212066) | Mannosyl-α-1,6-glycoprotein-β-1,2-N-acetylglucosminyltransferase | N-glycosylated protein |
| Lysosomal storage | Congenital disorders of N-glycosylation CDG IIb (606056) | Glucosidase I | N-glycosylated protein |
| Lysosomal storage | Congenital disorders of N-glycosylation CDG IIc (Rambam-Hasharon syndrome; 266265 | GDP-fucose transporter-1 | N-glycosylated protein |
| Lysosomal storage | Congenital disorders of N-glycosylation CDG IId (607091) | β-1,4-Galactosyltransferase | N-glycosylated protein |
| Lysosomal storage | Congenital disorders of N-glycosylation CDG IIe (608779) | Oligomeric Golgi complex-7 | N-glycosylated protein |
| Lysosomal storage | Congenital disorders of N-glycosylation CDG Ij (608093) | UDP-GlcNAc:dolichyl-P NAcGlc phosphotransferase | N-glycosylated protein |
| Lysosomal storage | Congenital disorders of N-glycosylation CDG Ik (608540) | β-1,4-Mannosyltransferase | N-glycosylated protein |
| Lysosomal storage | Congenital disorders of N-glycosylation CDG Il (608776) | α-1,2-Mannosyltransferase | N-glycosylated protein |
| Lysosomal storage | Congenital disorders of N-glycosylation, type I (pre-Golgi glycosylation defects) | α-1,2-Mannosyltransferase | N-glycosylated protein |
| Lysosomal storage | Cystinosis | Cystinosin (lysosomal cystine transporter) | Cysteine |
| Lysosomal storage | Fabry's disease (301500) | Trihexosylceramide α-galactosidase | globotriaosylceramide |
| Lysosomal storage | Farber's disease (lipogranulomatosis; 228000) | Ceramidase | lipids |
| Lysosomal storage | Fucosidosis (230000) | α-L-Fucosidase | fucose and complex sugars |
| Lysosomal storage | Galactosialidosis (Goldberg's syndrome, combined neuraminidase and β-galactosidase deficiency; 256540) | Protective protein/cathepsin A (PPCA) | lysosomal content |
| Lysosomal storage | Gaucher's disease | Glucosylceramide β-glucosidase | sphingolipids |

TABLE 8-continued

Selected Diseases, Receivers and Targets

| Category | Disease | Receiver | Target |
|---|---|---|---|
| Lysosomal storage | Glutamyl ribose-5-phosphate storage disease (305920) | ADP-ribose protein hydrolase | glutamyl ribose 5-phosphate |
| Lysosomal storage | Glycogen storage disease type 2 (Pompe's disease) | alpha glucosidase | glycogen |
| Lysosomal storage | GM1 gangliosidosis, generalized | Ganglioside β-galactosidase | acidic lipid material, gangliosides |
| Lysosomal storage | GM2 activator protein deficiency (Tay-Sachs disease AB variant, GM2A; 272750) | GM2 activator protein | gangliosides |
| Lysosomal storage | GM2 gangliosidosis | Ganglioside β-galactosidase | gangliosides |
| Lysosomal storage | Infantile sialic acid storage disorder (269920) | Na phosphate cotransporter, sialin | sialic acid |
| Lysosomal storage | Krabbe's disease (245200) | Galactosylceramide β-galactosidase | sphingolipids |
| Lysosomal storage | Lysosomal acid lipase deficiency (278000) | Lysosomal acid lipase | cholesteryl esters and triglycerides |
| Lysosomal storage | Metachromatic leukodystrophy (250100) | Arylsulfatase A | sulfatides |
| Lysosomal storage | Mucolipidosis ML II (I-cell disease; 252500) | N-Acetylglucosaminyl-1-phosphotransfeerase catalytic subunit | N-linked glycoproteins |
| Lysosomal storage | Mucolipidosis ML III (pseudo-Hurler's polydystrophy) | N-acetylglucosaminyl-1-phosphotransfeerase | N-linked glycoproteins |
| Lysosomal storage | Mucolipidosis ML III (pseudo-Hurler's polydystrophy) Type III-A (252600) | Catalytic subunit | N-linked glycoproteins |
| Lysosomal storage | Mucolipidosis ML III (pseudo-Hurler's polydystrophy) Type III-C (252605) | Substrate-recognition subunit | N-linked glycoproteins |
| Lysosomal storage | Mucopolysaccharidosis MPS I H/S (Hurler-Scheie syndrome; 607015) | α-1-Iduronidase | glycosaminoglycans |
| Lysosomal storage | Mucopolysaccharidosis MPS I-H (Hurler's syndrome; 607014) | α-1-Iduronidase | glycosaminoglycans |
| Lysosomal storage | Mucopolysaccharidosis MPS II (Hunter's syndrome; 309900) | Iduronate sulfate sulfatase | glycosaminoglycans |
| Lysosomal storage | Mucopolysaccharidosis MPS III (Sanfilippo's syndrome) Type III-A (252900) | Heparan-S-sulfate sulfamidase | glycosaminoglycans |
| Lysosomal storage | Mucopolysaccharidosis MPS III (Sanfilippo's syndrome) Type III-B (252920) | N-acetyl-D-glucosaminidase | glycosaminoglycans |
| Lysosomal storage | Mucopolysaccharidosis MPS III (Sanfilippo's syndrome) Type III-C (252930) | Acetyl-CoA-glucosaminide N-acetyltransferase | glycosaminoglycans |
| Lysosomal storage | Mucopolysaccharidosis MPS III (Sanfilippo's syndrome) Type III-D (252940) | N-acetyl-glucosaminine-6-sulfate sulfatase | glycosaminoglycans |
| Lysosomal storage | Mucopolysaccharidosis MPS I-S (Scheie's syndrome; 607016) | α-1-Iduronidase | glycosaminoglycans |
| Lysosomal storage | Mucopolysaccharidosis MPS IV (Morquio's syndrome) Type IV-A (253000) | Galactosamine-6-sulfate sulfatase | glycosaminoglycans |
| Lysosomal storage | Mucopolysaccharidosis MPS IV (Morquio's syndrome) Type IV-B (253010) | β-Galactosidase | glycosaminoglycans |
| Lysosomal storage | Mucopolysaccharidosis MPS IX (hyaluronidase deficiency; 601492) | Hyaluronidase deficiency | glycosaminoglycans |

TABLE 8-continued

Selected Diseases, Receivers and Targets

| Category | Disease | Receiver | Target |
| --- | --- | --- | --- |
| Lysosomal storage | Mucopolysaccharidosis MPS VI (Maroteaux-Lamy syndrome; 253200) | N-Acetyl galactosamine α-4-sulfate sulfatase (arylsulfatase B) | glycosaminoglycans |
| Lysosomal storage | Mucopolysaccharidosis MPS VII (Sly's syndrome; 253220) | β-Glucuronidase | glycosaminoglycans |
| Lysosomal storage | Mucosulfatidosis (multiple sulfatase deficiency; 272200) | Sulfatase-modifying factor-1 | sulfatides |
| Lysosomal storage | Niemann-Pick disease type A | Sphingomyelinase | sphingomyelin |
| Lysosomal storage | Niemann-Pick disease type B | Sphingomyelinase | sphingomyelin |
| Lysosomal storage | Niemann-Pick disease Type C1/Type D ((257220) | NPC1 protein | sphingomyelin |
| Lysosomal storage | Niemann-Pick disease Type C2 (607625) | Epididymal secretory protein 1 (HE1; NPC2 protein) | sphingomyelin |
| Lysosomal storage | Prosaposin deficiency (176801) | Prosaposin | sphingolipids |
| Lysosomal storage | Pycnodysostosis (265800) | Cathepsin K | kinins |
| Lysosomal storage | Sandhoff's disease; 268800 | β-Hexosaminidase B | gangliosides |
| Lysosomal storage | Saposin B deficiency (sulfatide activator deficiency) | Saposin B | sphingolipids |
| Lysosomal storage | Saposin C deficiency (Gaucher's activator deficiency) | Saposin C | sphingolipids |
| Lysosomal storage | Schindler's disease Type I (infantile severe form; 609241) | N-Acetyl-galactosaminidase | glycoproteins |
| Lysosomal storage | Schindler's disease Type II (Kanzaki disease, adult-onset form; 609242) | N-Acetyl-galactosaminidase | glycoproteins |
| Lysosomal storage | Schindler's disease Type III (intermediate form; 609241) | N-Acetyl-galactosaminidase | glycoproteins |
| Lysosomal storage | Sialidosis (256550) | Neuraminidase 1 (sialidase) | mucopolysaccharides and mucolipids |
| Lysosomal storage | Sialuria Finnish type (Salla disease; 604369) | Na phosphate cotransporter, sialin | sialic acid |
| Lysosomal storage | Sialuria French type (269921) | UDP-N-acetylglucosamine-2-epimerase/N-acetylmannosamine kinase, sialin | sialic acid |
| Lysosomal storage | Sphingolipidosis Type I (230500) | Ganglioside β-galactosidase | sphingolipids |
| Lysosomal storage | Sphingolipidosis Type II (juvenile type; 230600) | Ganglioside β-galactosidase | sphingolipids |
| Lysosomal storage | Sphingolipidosis Type III (adult type; 230650) | Ganglioside β-galactosidase | sphingolipids |
| Lysosomal storage | Tay-Sachs disease; 272800 | β-Hexosaminidase A | gangliosides |
| Lysosomal storage | Winchester syndrome (277950) | Metalloproteinase-2 | mucopolysaccharides |

TABLE 8-continued

Selected Diseases, Receivers and Targets

| Category | Disease | Receiver | Target |
|---|---|---|---|
| Lysosomal storage | Wolman's disease | lysosomal acid lipase | lipids and cholesterol |
| Lysosomal storage | α-Mannosidosis (248500), type I (severe) or II (mild) | α-D-Mannosidase | carbohydrates and glycoproteins |
| Lysosomal storage | β-Mannosidosis (248510) | β-D-Mannosidase | carbohydrates and glycoproteins |
| Toxic Molecule | alpha hemolysin poisoning | an antibody-like binder to alpha hemolysin | alpha hemolysin |
| Toxic Molecule | antrax toxin poisoning | an antibody-like binder to anthrax toxin | anthrax toxin |
| Toxic Molecule | bacterial toxin-induced shock | an antibody-like binder to bacterial toxin | bacterial toxin |
| Toxic Molecule | botulinum toxin poisoning | an antibody-like binder to botulinum toxin | botulinum toxin |
| Toxic Molecule | Hemochromatosis (iron poisoning) | iron chelator | molecular iron |
| Toxic Molecule | Methanol poisoning | Methanol dehdrogenase | Methanol |
| Toxic Molecule | Nerve gas poisoning | Butyryl cholinesterase | Sarin |
| Toxic Molecule | Prion disease caused by PRP | an antibody-like binder to prion protein PRP | Prion protein PRP |
| Toxic Molecule | Prion disease caused by PRPc | an antibody-like binder to prion protein PRPc | Prion protein PRPc |
| Toxic Molecule | Prion disease caused by PRPsc | an antibody-like binder to prion protein PRPsc | Prion protein PRPsc |
| Toxic Molecule | Prion disease cuased by PRPres | an antibody-like binder to prion protein PRPres | Prion protein PRPres |
| Toxic Molecule | Sepsis or cytokine storm | an antibody-like binder to cytokines or Duffy antigen receptor of chemokines (DARC) | cytokines |
| Toxic Molecule | spider venom poisoning | an antibody-like binder to spider venom | spider venom |
| Toxic Molecule | Wilson disease | copper chelator | molecular copper |

TABLE 9A

| Conjugation methods | |
|---|---|
| Zero-length x-linker | Amine-sulfhydryl x-linker |
| EDC | SPDP, LC-SPDP, sulfo-LC-SPDP |
| EDC plus sulfo NHS | SMPT and sulfo-LC-SMPT |
| CMC | SMCC and sulfo-SMCC |
| DCC | MBS and sulfo-MBS |
| DIC | SIAB and sulfo-SIAB |
| Woodward's reagent K | SMPB and sulfo-SMPB |
| N,N'-carbonyldiimidazole | GMBS and sulfo-GMBS |
| Schiff base + reductive amination | SIAX and SIAXX |
| Homobifunctional NHS esters | SIAC and SIACX |
| DSP | NPIA |
| DTSSP | Carbonyl-sulfydryl x-linker |
| DSS | MPBH |
| BS^3 | M2C2H |
| DST | PDPH |
| Sulfo-DST | amine-photoreactive x-linker |
| BSOCOES | NHS-ASA, Sulfo-NHS-ASA |
| Sulfo-BSOCOES | Sulfo-NHS-LC-ASA |
| EGS | SASD |
| Sulfo-EGS | HSAB and sulfo-HSAB |
| DSG | SANPAH and sulfo-SANPAH |
| DSC | ANB-NOS |
| Homobifunctional Imidoesters | SAND |
| DMA | SADP and sulfo-SADP |
| DMP | Sulfo-SAPB |
| DMS | SAED |
| DTBP | Sulfo-SAMCA |
| Sulfhydryl reactive x-linkers | p-Nitrophenyl diazopyruvate |
| DPDPB | PNP-DTP |
| BMH | sulfhydryl-photoreactive x-linker |
| Difluorobenzene derivatives | ASIB |
| DFDNB | APDP |
| DFDNPS | Benzophenone-4-iodoacetamide |
| Photoreactive x-linker | Benzophenone-4-maleimide |
| BASED | Carbonyl-photoreactive x-linker |
| Homobifunctional aldehydes | ABH |
| Formaldehyde | Carboxylate-photoreactive x-linker |
| Glutaraldehyde | ASBA |
| bis-epoxide | arginine-photoreactive x-linker |
| 1,4-butanediol diglycidyl ether | APG |
| Homobifunctional hydrazides | Bioorthogonal reactions |
| adipic acid dihydrazide | Diels-alder reagent pairs |
| carbohydrazide | Hydrazine-aldehyde reagent pairs |
| Bis-diazonium derivative | Boronic acid salicylhydroxamate |
| o-tolidine diazotized | Click chemistry |
| Bis-diazotized benzidine | Staudinger ligation |

TABLE 9B

| Enzymatic conjugation methods |
|---|
| Sortase |
| DD-transpeptidase |
| Peptidyl transferase |
| G-glutamyl transpeptidase |

TABLE 9B-continued

Enzymatic conjugation methods

D-glutamyl transpeptidase  
Farnesyltransferase  
Prenyltranferase  
Dimethylallyltrans-transferase  
Geranylgeranyl pyrophosphate synthase  
Dehydrodolichol diphosphate synthase

TABLE 9C

Chemistry of reactive groups

| Amine reactions | Thiol reactions | Hydroxyl reactions | Active hydrogen reactions |
|---|---|---|---|
| Isothyocyantes | Haloacetyl and alkl halide derivatives | Epoxides and oxiranes | Diazonium derivatives |
| Isocyanates | Maleimides | Carbonyldiimidazole | Mannich condensation |
| Acyl azides | Aziridines | N,N'0disuccinimidyl carbonate | Iodination reactions |
| NHS esters | Acryloyl derivatives | N-hydroxysuccinimidyl chloroformate | |
| Sulfonyl chlorides | Arylating agents | Oxidation with periodate | |
| Aldehydes and glyoxals | Thil-disulfide exchange reagents | Enzymatic oxidation | Cycloaddition reactions |
| Epoxides and oxiranes | Vinylsulfone derivatives | Alkyl halogens | Diels-Alder reaction |
| Carbonates | Metal-thiol dative bonds | Isocyanates | Complex formation with boronic acid derivatives |

TABLE 10

Complement & Complement Regulatory Molecules
Soluble molecules

Alternative Pathway

Factor B  
Factor D  
Properdin  
C3  
C3a  
C3b  
iC3b  
C3c  
C3dg  
C3dk  
C3e  
Bb  
Factor I

Classical Pathway

C1q  
C1r  
C1s  
C4  
C4a  
C4b  
C2  
C4bp

Lectin Pathway

Mannose-Binding Lectin (MBL)  
MBL-Associated Serine Protease 1 (MASP1)  
MBL-Associated Serine Protease 2 (MASP2)

Late Components

C5  
C5a  
C6  
C7  
C8  
C9

Receptors

CR1  
CR2  
CR3  
CR4  
C3aR  
C3eR  
Decay-accelerating factor (DAF)  
Membrane cofactor protein (MCP)  
CD59  
C3 Beta chain Receptor  
Homologous restriction factor

Control Proteins

C1 inhibitor  
C4 binding protein  
Factor I  
Factor H

What is claimed is:

1. A method of treating a subject having PKU comprising:
    a) obtaining an isolated population of functional erythroid cells comprising a receiver polypeptide, wherein said receiver polypeptide comprises phenylalanine ammonia lyase (PAL), wherein the functional erythroid cells of said isolated population comprising said receiver polypeptide are not hypotonically loaded cells, and
    b) administering to a subject in need thereof a pharmaceutical composition comprising said functional erythroid cells,
        wherein said isolated population of functional erythroid cells comprising said receiver polypeptide must be made by a method comprising the following steps:
        i introducing into a population of cultured or freshly isolated erythroid cell precursors an exogenous nucleic acid encoding said receiver polypeptide, wherein said receiver polypeptide comprises PAL; and
        ii culturing the population of erythroid cell precursors that contain said receiver polypeptide to provide the isolated population of functional erythroid cells comprising said receiver polypeptide.

2. The method of claim 1, wherein the functional erythroid cells reside in circulation for longer than any one of 1, 2, 3, 4, 5, 6, 7, 8, 9, and 10 days.

3. The method of claim 1, wherein the functional erythroid cell resides in circulation for longer than 21 days.

4. The method of claim 1, wherein the receiver polypeptide resides in circulation for substantially the duration of the functional erythroid cell in circulation.

5. The method of claim 1, wherein the receiver polypeptide does not substantially diffuse out of the erythroid cell.

6. The method of claim 1, wherein the receiver polypeptide is glycosylated.

7. The method of claim 1, wherein the functional erythroid cell exhibits substantially the same osmotic membrane fragility as an isolated, unmodified, cultured or uncultured erythroid cell.

8. The method of claim 1, wherein the receiver polypeptide has a size from 500 amino acids to 3000 amino acids.

9. The method of claim 1, wherein the pharmaceutical composition further comprises a pharmaceutically-acceptable excipient or carrier.

10. The method of claim 1 further comprising administering the pharmaceutical composition at least twice over a treatment period such that the PKU is treated, or a symptom thereof is decreased.

11. The method of claim 1, wherein the circulatory concentration of phenylalanine is decreased by at least about 5% during part or the entirety of a treatment period.

12. The method of claim 1, wherein the half-life in circulation of the receiver polypeptide is increased by at least 1.5-fold compared to a pegylated PAL polypeptide.

13. The method of claim 1, wherein the functional erythroid cell comprises at least 50,000 copies of the receiver polypeptide.

14. The method of claim 1, wherein the functional erythroid cell is a reticulocyte or mature erythrocyte.

15. The method of claim 1, wherein the functional erythroid cell lacks the A and B antigen.

16. The method of claim 1, wherein the functional erythroid cell further comprises a CD47, CD55, or CD59 polypeptide in an amount effective for the functional erythroid cell to reside in the circulatory system for longer than any one of 1, 2, 3, 4, 5, 6, 7, 8, 9, and 10 days.

17. The method of claim 16, wherein the effective amount of CD47, CD55, or CD59 polypeptide is any one of $10^3$, $10^4$, $10^5$, and $10^6$ polypeptides per erythroid cell.

18. The method of claim 1, wherein the pharmaceutical composition is administered in an amount effective to reduce the concentration of phenylalanine in the blood.

19. The method of claim 1, wherein the subject is deficient in phenylalanine ammonia hydroxylase (PAH) activity.

20. The method of claim 19, wherein the PAH activity deficiency is associated with a PAH enzyme mutation.

21. The method of claim 1, wherein the pharmaceutical composition further comprises one or more of: an antibacterial compound, an antioxidant, a chelating compound, and an anticoagulant preservative.

* * * * *

SEQUENCE LISTING

<160> NUMBER OF SEQ ID NOS: 30

<210> SEQ ID NO 1
<211> LENGTH: 2489
<212> TYPE: PRT
<213> ORGANISM: Homo sapiens

<400> SEQUENCE: 1

```
Met Gly Ala Ser Ser Pro Arg Ser Pro Glu Pro Val Gly Pro Pro Ala
1               5                   10                  15

Pro Gly Leu Pro Phe Cys Cys Gly Gly Ser Leu Leu Ala Val Val Val
            20                  25                  30

Leu Leu Ala Leu Pro Val Ala Trp Gly Gln Cys Asn Ala Pro Glu Trp
        35                  40                  45

Leu Pro Phe Ala Arg Pro Thr Asn Leu Thr Asp Glu Phe Glu Phe Pro
    50                  55                  60

Ile Gly Thr Tyr Leu Asn Tyr Glu Cys Arg Pro Gly Tyr Ser Gly Arg
65                  70                  75                  80

Pro Phe Ser Ile Ile Cys Leu Lys Asn Ser Val Trp Thr Gly Ala Lys
                85                  90                  95

Asp Arg Cys Arg Arg Lys Ser Cys Arg Asn Pro Pro Asp Pro Val Asn
            100                 105                 110

Gly Met Val His Val Ile Lys Gly Ile Gln Phe Gly Ser Gln Ile Lys
            115                 120                 125

Tyr Ser Cys Thr Lys Gly Tyr Arg Leu Ile Gly Ser Ser Ser Ala Thr
        130                 135                 140

Cys Ile Ile Ser Gly Asp Thr Val Ile Trp Asp Asn Glu Thr Pro Ile
145                 150                 155                 160

Cys Asp Arg Ile Pro Cys Gly Leu Pro Pro Thr Ile Thr Asn Gly Asp
                165                 170                 175

Phe Ile Ser Thr Asn Arg Glu Asn Phe His Tyr Gly Ser Val Val Thr
            180                 185                 190

Tyr Arg Cys Asn Pro Gly Ser Gly Gly Arg Lys Val Phe Glu Leu Val
            195                 200                 205

Gly Glu Pro Ser Ile Tyr Cys Thr Ser Asn Asp Asp Gln Val Gly Ile
        210                 215                 220

Trp Ser Gly Pro Ala Pro Gln Cys Ile Ile Pro Asn Lys Cys Thr Pro
225                 230                 235                 240

Pro Asn Val Glu Asn Gly Ile Leu Val Ser Asp Asn Arg Ser Leu Phe
                245                 250                 255

Ser Leu Asn Glu Val Val Glu Phe Arg Cys Gln Pro Gly Phe Val Met
            260                 265                 270

Lys Gly Pro Arg Arg Val Lys Cys Gln Ala Leu Asn Lys Trp Glu Pro
        275                 280                 285

Glu Leu Pro Ser Cys Ser Arg Val Cys Gln Pro Pro Pro Asp Val Leu
    290                 295                 300

His Ala Glu Arg Thr Gln Arg Asp Lys Asp Asn Phe Ser Pro Gly Gln
305                 310                 315                 320

Glu Val Phe Tyr Ser Cys Glu Pro Gly Tyr Asp Leu Arg Gly Ala Ala
                325                 330                 335

Ser Met Arg Cys Thr Pro Gln Gly Asp Trp Ser Pro Ala Ala Pro Thr
            340                 345                 350

Cys Glu Val Lys Ser Cys Asp Asp Phe Met Gly Gln Leu Leu Asn Gly
        355                 360                 365
```

```
Arg Val Leu Phe Pro Val Asn Leu Gln Leu Gly Ala Lys Val Asp Phe
    370                 375                 380

Val Cys Asp Glu Gly Phe Gln Leu Lys Gly Ser Ser Ala Ser Tyr Cys
385                 390                 395                 400

Val Leu Ala Gly Met Glu Ser Leu Trp Asn Ser Ser Val Pro Val Cys
                405                 410                 415

Glu Gln Ile Phe Cys Pro Ser Pro Val Ile Pro Asn Gly Arg His
            420                 425                 430

Thr Gly Lys Pro Leu Glu Val Phe Pro Phe Gly Lys Thr Val Asn Tyr
        435                 440                 445

Thr Cys Asp Pro His Pro Asp Arg Gly Thr Ser Phe Asp Leu Ile Gly
    450                 455                 460

Glu Ser Thr Ile Arg Cys Thr Ser Asp Pro Gln Gly Asn Gly Val Trp
465                 470                 475                 480

Ser Ser Pro Ala Pro Arg Cys Gly Ile Leu Gly His Cys Gln Ala Pro
                485                 490                 495

Asp His Phe Leu Phe Ala Lys Leu Lys Thr Gln Thr Asn Ala Ser Asp
            500                 505                 510

Phe Pro Ile Gly Thr Ser Leu Lys Tyr Glu Cys Arg Pro Glu Tyr Tyr
        515                 520                 525

Gly Arg Pro Phe Ser Ile Thr Cys Leu Asp Asn Leu Val Trp Ser Ser
    530                 535                 540

Pro Lys Asp Val Cys Lys Arg Lys Ser Cys Lys Thr Pro Pro Asp Pro
545                 550                 555                 560

Val Asn Gly Met Val His Val Ile Thr Asp Ile Gln Val Gly Ser Arg
                565                 570                 575

Ile Asn Tyr Ser Cys Thr Thr Gly His Arg Leu Ile Gly His Ser Ser
            580                 585                 590

Ala Glu Cys Ile Leu Ser Gly Asn Ala Ala His Trp Ser Thr Lys Pro
        595                 600                 605

Pro Ile Cys Gln Arg Ile Pro Cys Gly Leu Pro Pro Thr Ile Ala Asn
    610                 615                 620

Gly Asp Phe Ile Ser Thr Asn Arg Glu Asn Phe His Tyr Gly Ser Val
625                 630                 635                 640

Val Thr Tyr Arg Cys Asn Pro Gly Ser Gly Gly Arg Lys Val Phe Glu
                645                 650                 655

Leu Val Gly Glu Pro Ser Ile Tyr Cys Thr Ser Asn Asp Asp Gln Val
            660                 665                 670

Gly Ile Trp Ser Gly Pro Ala Pro Gln Cys Ile Ile Pro Asn Lys Cys
        675                 680                 685

Thr Pro Pro Asn Val Glu Asn Gly Ile Leu Val Ser Asp Asn Arg Ser
    690                 695                 700

Leu Phe Ser Leu Asn Glu Val Val Glu Phe Arg Cys Gln Pro Gly Phe
705                 710                 715                 720

Val Met Lys Gly Pro Arg Arg Val Lys Cys Gln Ala Leu Asn Lys Trp
                725                 730                 735

Glu Pro Glu Leu Pro Ser Cys Ser Arg Val Cys Gln Pro Pro Pro Asp
            740                 745                 750

Val Leu His Ala Glu Arg Thr Gln Arg Asp Lys Asp Asn Phe Ser Pro
        755                 760                 765

Gly Gln Glu Val Phe Tyr Ser Cys Glu Pro Gly Tyr Asp Leu Arg Gly
    770                 775                 780

Ala Ala Ser Met Arg Cys Thr Pro Gln Gly Asp Trp Ser Pro Ala Ala
```

-continued

```
                785                 790                 795                 800
Pro Thr Cys Glu Val Lys Ser Cys Asp Asp Phe Met Gly Gln Leu Leu
                    805                 810                 815
Asn Gly Arg Val Leu Phe Pro Val Asn Leu Gln Leu Gly Ala Lys Val
                    820                 825                 830
Asp Phe Val Cys Asp Glu Gly Phe Gln Leu Lys Gly Ser Ser Ala Ser
                    835                 840                 845
Tyr Cys Val Leu Ala Gly Met Glu Ser Leu Trp Asn Ser Ser Val Pro
        850                 855                 860
Val Cys Glu Gln Ile Phe Cys Pro Ser Pro Val Ile Pro Asn Gly
865                 870                 875                 880
Arg His Thr Gly Lys Pro Leu Glu Val Phe Pro Phe Gly Lys Thr Val
                    885                 890                 895
Asn Tyr Thr Cys Asp Pro His Pro Asp Arg Gly Thr Ser Phe Asp Leu
                    900                 905                 910
Ile Gly Glu Ser Thr Ile Arg Cys Thr Ser Asp Pro Gln Gly Asn Gly
                    915                 920                 925
Val Trp Ser Ser Pro Ala Pro Arg Cys Gly Ile Leu Gly His Cys Gln
        930                 935                 940
Ala Pro Asp His Phe Leu Phe Ala Lys Leu Lys Thr Gln Thr Asn Ala
945                 950                 955                 960
Ser Asp Phe Pro Ile Gly Thr Ser Leu Lys Tyr Glu Cys Arg Pro Glu
                    965                 970                 975
Tyr Tyr Gly Arg Pro Phe Ser Ile Thr Cys Leu Asp Asn Leu Val Trp
                    980                 985                 990
Ser Ser Pro Lys Asp Val Cys Lys Arg Lys Ser Cys Lys Thr Pro Pro
        995                 1000                1005
Asp Pro Val Asn Gly Met Val His Val Ile Thr Asp Ile Gln Val
        1010                1015                1020
Gly Ser Arg Ile Asn Tyr Ser Cys Thr Thr Gly His Arg Leu Ile
        1025                1030                1035
Gly His Ser Ser Ala Glu Cys Ile Leu Ser Gly Asn Ala Ala His
        1040                1045                1050
Trp Ser Thr Lys Pro Pro Ile Cys Gln Arg Ile Pro Cys Gly Leu
        1055                1060                1065
Pro Pro Thr Ile Ala Asn Gly Asp Phe Ile Ser Thr Asn Arg Glu
        1070                1075                1080
Asn Phe His Tyr Gly Ser Val Val Thr Tyr Arg Cys Asn Pro Gly
        1085                1090                1095
Ser Gly Gly Arg Lys Val Phe Glu Leu Val Gly Glu Pro Ser Ile
        1100                1105                1110
Tyr Cys Thr Ser Asn Asp Asp Gln Val Gly Ile Trp Ser Gly Pro
        1115                1120                1125
Ala Pro Gln Cys Ile Ile Pro Asn Lys Cys Thr Pro Pro Asn Val
        1130                1135                1140
Glu Asn Gly Ile Leu Val Ser Asp Asn Arg Ser Leu Phe Ser Leu
        1145                1150                1155
Asn Glu Val Val Glu Phe Arg Cys Gln Pro Gly Phe Val Met Lys
        1160                1165                1170
Gly Pro Arg Arg Val Lys Cys Gln Ala Leu Asn Lys Trp Glu Pro
        1175                1180                1185
Glu Leu Pro Ser Cys Ser Arg Val Cys Gln Pro Pro Pro Asp Val
        1190                1195                1200
```

-continued

Leu His Ala Glu Arg Thr Gln Arg Asp Lys Asp Asn Phe Ser Pro
1205                1210                1215

Gly Gln Glu Val Phe Tyr Ser Cys Glu Pro Gly Tyr Asp Leu Arg
1220                1225                1230

Gly Ala Ala Ser Met Arg Cys Thr Pro Gln Gly Asp Trp Ser Pro
1235                1240                1245

Ala Ala Pro Thr Cys Glu Val Lys Ser Cys Asp Asp Phe Met Gly
1250                1255                1260

Gln Leu Leu Asn Gly Arg Val Leu Phe Pro Val Asn Leu Gln Leu
1265                1270                1275

Gly Ala Lys Val Asp Phe Val Cys Asp Glu Gly Phe Gln Leu Lys
1280                1285                1290

Gly Ser Ser Ala Ser Tyr Cys Val Leu Ala Gly Met Glu Ser Leu
1295                1300                1305

Trp Asn Ser Ser Val Pro Val Cys Glu Gln Ile Phe Cys Pro Ser
1310                1315                1320

Pro Pro Val Ile Pro Asn Gly Arg His Thr Gly Lys Pro Leu Glu
1325                1330                1335

Val Phe Pro Phe Gly Lys Ala Val Asn Tyr Thr Cys Asp Pro His
1340                1345                1350

Pro Asp Arg Gly Thr Ser Phe Asp Leu Ile Gly Glu Ser Thr Ile
1355                1360                1365

Arg Cys Thr Ser Asp Pro Gln Gly Asn Gly Val Trp Ser Ser Pro
1370                1375                1380

Ala Pro Arg Cys Gly Ile Leu Gly His Cys Gln Ala Pro Asp His
1385                1390                1395

Phe Leu Phe Ala Lys Leu Lys Thr Gln Thr Asn Ala Ser Asp Phe
1400                1405                1410

Pro Ile Gly Thr Ser Leu Lys Tyr Glu Cys Arg Pro Glu Tyr Tyr
1415                1420                1425

Gly Arg Pro Phe Ser Ile Thr Cys Leu Asp Asn Leu Val Trp Ser
1430                1435                1440

Ser Pro Lys Asp Val Cys Lys Arg Lys Ser Cys Lys Thr Pro Pro
1445                1450                1455

Asp Pro Val Asn Gly Met Val His Val Ile Thr Asp Ile Gln Val
1460                1465                1470

Gly Ser Arg Ile Asn Tyr Ser Cys Thr Thr Gly His Arg Leu Ile
1475                1480                1485

Gly His Ser Ser Ala Glu Cys Ile Leu Ser Gly Asn Thr Ala His
1490                1495                1500

Trp Ser Thr Lys Pro Pro Ile Cys Gln Arg Ile Pro Cys Gly Leu
1505                1510                1515

Pro Pro Thr Ile Ala Asn Gly Asp Phe Ile Ser Thr Asn Arg Glu
1520                1525                1530

Asn Phe His Tyr Gly Ser Val Val Thr Tyr Arg Cys Asn Leu Gly
1535                1540                1545

Ser Arg Gly Arg Lys Val Phe Glu Leu Val Gly Glu Pro Ser Ile
1550                1555                1560

Tyr Cys Thr Ser Asn Asp Asp Gln Val Gly Ile Trp Ser Gly Pro
1565                1570                1575

Ala Pro Gln Cys Ile Ile Pro Asn Lys Cys Thr Pro Pro Asn Val
1580                1585                1590

```
Glu Asn Gly Ile Leu Val Ser Asp Asn Arg Ser Leu Phe Ser Leu
    1595                1600                1605

Asn Glu Val Val Glu Phe Arg Cys Gln Pro Gly Phe Val Met Lys
    1610                1615                1620

Gly Pro Arg Arg Val Lys Cys Gln Ala Leu Asn Lys Trp Glu Pro
    1625                1630                1635

Glu Leu Pro Ser Cys Ser Arg Val Cys Gln Pro Pro Pro Glu Ile
    1640                1645                1650

Leu His Gly Glu His Thr Pro Ser His Gln Asp Asn Phe Ser Pro
    1655                1660                1665

Gly Gln Glu Val Phe Tyr Ser Cys Glu Pro Gly Tyr Asp Leu Arg
    1670                1675                1680

Gly Ala Ala Ser Leu His Cys Thr Pro Gln Gly Asp Trp Ser Pro
    1685                1690                1695

Glu Ala Pro Arg Cys Ala Val Lys Ser Cys Asp Asp Phe Leu Gly
    1700                1705                1710

Gln Leu Pro His Gly Arg Val Leu Phe Pro Leu Asn Leu Gln Leu
    1715                1720                1725

Gly Ala Lys Val Ser Phe Val Cys Asp Glu Gly Phe Arg Leu Lys
    1730                1735                1740

Gly Ser Ser Val Ser His Cys Val Leu Val Gly Met Arg Ser Leu
    1745                1750                1755

Trp Asn Asn Ser Val Pro Val Cys Glu His Ile Phe Cys Pro Asn
    1760                1765                1770

Pro Pro Ala Ile Leu Asn Gly Arg His Thr Gly Thr Pro Ser Gly
    1775                1780                1785

Asp Ile Pro Tyr Gly Lys Glu Ile Ser Tyr Thr Cys Asp Pro His
    1790                1795                1800

Pro Asp Arg Gly Met Thr Phe Asn Leu Ile Gly Glu Ser Thr Ile
    1805                1810                1815

Arg Cys Thr Ser Asp Pro His Gly Asn Gly Val Trp Ser Ser Pro
    1820                1825                1830

Ala Pro Arg Cys Glu Leu Ser Val Arg Ala Gly His Cys Lys Thr
    1835                1840                1845

Pro Glu Gln Phe Pro Phe Ala Ser Pro Thr Ile Pro Ile Asn Asp
    1850                1855                1860

Phe Glu Phe Pro Val Gly Thr Ser Leu Asn Tyr Glu Cys Arg Pro
    1865                1870                1875

Gly Tyr Phe Gly Lys Met Phe Ser Ile Ser Cys Leu Glu Asn Leu
    1880                1885                1890

Val Trp Ser Ser Val Glu Asp Asn Cys Arg Arg Lys Ser Cys Gly
    1895                1900                1905

Pro Pro Pro Glu Pro Phe Asn Gly Met Val His Ile Asn Thr Asp
    1910                1915                1920

Thr Gln Phe Gly Ser Thr Val Asn Tyr Ser Cys Asn Glu Gly Phe
    1925                1930                1935

Arg Leu Ile Gly Ser Pro Ser Thr Thr Cys Leu Val Ser Gly Asn
    1940                1945                1950

Asn Val Thr Trp Asp Lys Lys Ala Pro Ile Cys Glu Ile Ile Ser
    1955                1960                1965

Cys Glu Pro Pro Pro Thr Ile Ser Asn Gly Asp Phe Tyr Ser Asn
    1970                1975                1980

Asn Arg Thr Ser Phe His Asn Gly Thr Val Val Thr Tyr Gln Cys
```

-continued

```
           1985                1990                1995
His Thr Gly Pro Asp Gly Glu Gln Leu Phe Glu Leu Val Gly Glu
           2000                2005                2010

Arg Ser Ile Tyr Cys Thr Ser Lys Asp Asp Gln Val Gly Val Trp
           2015                2020                2025

Ser Ser Pro Pro Pro Arg Cys Ile Ser Thr Asn Lys Cys Thr Ala
           2030                2035                2040

Pro Glu Val Glu Asn Ala Ile Arg Val Pro Gly Asn Arg Ser Phe
           2045                2050                2055

Phe Thr Leu Thr Glu Ile Ile Arg Phe Arg Cys Gln Pro Gly Phe
           2060                2065                2070

Val Met Val Gly Ser His Thr Val Gln Cys Gln Thr Asn Gly Arg
           2075                2080                2085

Trp Gly Pro Lys Leu Pro His Cys Ser Arg Val Cys Gln Pro Pro
           2090                2095                2100

Pro Glu Ile Leu His Gly Glu His Thr Leu Ser His Gln Asp Asn
           2105                2110                2115

Phe Ser Pro Gly Gln Glu Val Phe Tyr Ser Cys Glu Pro Ser Tyr
           2120                2125                2130

Asp Leu Arg Gly Ala Ala Ser Leu His Cys Thr Pro Gln Gly Asp
           2135                2140                2145

Trp Ser Pro Glu Ala Pro Arg Cys Thr Val Lys Ser Cys Asp Asp
           2150                2155                2160

Phe Leu Gly Gln Leu Pro His Gly Arg Val Leu Leu Pro Leu Asn
           2165                2170                2175

Leu Gln Leu Gly Ala Lys Val Ser Phe Val Cys Asp Glu Gly Phe
           2180                2185                2190

Arg Leu Lys Gly Arg Ser Ala Ser His Cys Val Leu Ala Gly Met
           2195                2200                2205

Lys Ala Leu Trp Asn Ser Ser Val Pro Val Cys Glu Gln Ile Phe
           2210                2215                2220

Cys Pro Asn Pro Pro Ala Ile Leu Asn Gly Arg His Thr Gly Thr
           2225                2230                2235

Pro Phe Gly Asp Ile Pro Tyr Gly Lys Glu Ile Ser Tyr Ala Cys
           2240                2245                2250

Asp Thr His Pro Asp Arg Gly Met Thr Phe Asn Leu Ile Gly Glu
           2255                2260                2265

Ser Ser Ile Arg Cys Thr Ser Asp Pro Gln Gly Asn Gly Val Trp
           2270                2275                2280

Ser Ser Pro Ala Pro Arg Cys Glu Leu Ser Val Pro Ala Ala Cys
           2285                2290                2295

Pro His Pro Pro Lys Ile Gln Asn Gly His Tyr Ile Gly Gly His
           2300                2305                2310

Val Ser Leu Tyr Leu Pro Gly Met Thr Ile Ser Tyr Ile Cys Asp
           2315                2320                2325

Pro Gly Tyr Leu Leu Val Gly Lys Gly Phe Ile Phe Cys Thr Asp
           2330                2335                2340

Gln Gly Ile Trp Ser Gln Leu Asp His Tyr Cys Lys Glu Val Asn
           2345                2350                2355

Cys Ser Phe Pro Leu Phe Met Asn Gly Ile Ser Lys Glu Leu Glu
           2360                2365                2370

Met Lys Lys Val Tyr His Tyr Gly Asp Tyr Val Thr Leu Lys Cys
           2375                2380                2385
```

```
Glu Asp Gly Tyr Thr Leu Glu Gly Ser Pro Trp Ser Gln Cys Gln
    2390                2395                2400

Ala Asp Asp Arg Trp Asp Pro Pro Leu Ala Lys Cys Thr Ser Arg
    2405                2410                2415

Thr His Asp Ala Leu Ile Val Gly Thr Leu Ser Gly Thr Ile Phe
    2420                2425                2430

Phe Ile Leu Leu Ile Ile Phe Leu Ser Trp Ile Ile Leu Lys His
    2435                2440                2445

Arg Lys Gly Asn Asn Ala His Glu Asn Pro Lys Glu Val Ala Ile
    2450                2455                2460

His Leu His Ser Gln Gly Gly Ser Ser Val His Pro Arg Thr Leu
    2465                2470                2475

Gln Thr Asn Glu Glu Asn Ser Arg Val Leu Pro
    2480                2485

<210> SEQ ID NO 2
<211> LENGTH: 2039
<212> TYPE: PRT
<213> ORGANISM: Homo sapiens

<400> SEQUENCE: 2

Met Gly Ala Ser Ser Pro Arg Ser Pro Glu Pro Val Gly Pro Pro Ala
1               5                   10                  15

Pro Gly Leu Pro Phe Cys Cys Gly Gly Ser Leu Leu Ala Val Val Val
                20                  25                  30

Leu Leu Ala Leu Pro Val Ala Trp Gly Gln Cys Asn Ala Pro Glu Trp
            35                  40                  45

Leu Pro Phe Ala Arg Pro Thr Asn Leu Thr Asp Glu Phe Glu Phe Pro
        50                  55                  60

Ile Gly Thr Tyr Leu Asn Tyr Glu Cys Arg Pro Gly Tyr Ser Gly Arg
65                  70                  75                  80

Pro Phe Ser Ile Ile Cys Leu Lys Asn Ser Val Trp Thr Gly Ala Lys
                85                  90                  95

Asp Arg Cys Arg Arg Lys Ser Cys Arg Asn Pro Pro Asp Pro Val Asn
            100                 105                 110

Gly Met Val His Val Ile Lys Gly Ile Gln Phe Gly Ser Gln Ile Lys
        115                 120                 125

Tyr Ser Cys Thr Lys Gly Tyr Arg Leu Ile Gly Ser Ser Ser Ala Thr
    130                 135                 140

Cys Ile Ile Ser Gly Asp Thr Val Ile Trp Asp Asn Glu Thr Pro Ile
145                 150                 155                 160

Cys Asp Arg Ile Pro Cys Gly Leu Pro Pro Thr Ile Thr Asn Gly Asp
                165                 170                 175

Phe Ile Ser Thr Asn Arg Glu Asn Phe His Tyr Gly Ser Val Val Thr
            180                 185                 190

Tyr Arg Cys Asn Pro Gly Ser Gly Gly Arg Lys Val Phe Glu Leu Val
        195                 200                 205

Gly Glu Pro Ser Ile Tyr Cys Thr Ser Asn Asp Asp Gln Val Gly Ile
    210                 215                 220

Trp Ser Gly Pro Ala Pro Gln Cys Ile Ile Pro Asn Lys Cys Thr Pro
225                 230                 235                 240

Pro Asn Val Glu Asn Gly Ile Leu Val Ser Asp Asn Arg Ser Leu Phe
                245                 250                 255

Ser Leu Asn Glu Val Val Glu Phe Arg Cys Gln Pro Gly Phe Val Met
```

-continued

```
              260                 265                 270
Lys Gly Pro Arg Arg Val Lys Cys Gln Ala Leu Asn Lys Trp Glu Pro
            275                 280                 285
Glu Leu Pro Ser Cys Ser Arg Val Cys Gln Pro Pro Asp Val Leu
        290                 295                 300
His Ala Glu Arg Thr Gln Arg Asp Lys Asp Asn Phe Ser Pro Gly Gln
305                 310                 315                 320
Glu Val Phe Tyr Ser Cys Glu Pro Gly Tyr Asp Leu Arg Gly Ala Ala
                325                 330                 335
Ser Met Arg Cys Thr Pro Gln Gly Asp Trp Ser Pro Ala Ala Pro Thr
            340                 345                 350
Cys Glu Val Lys Ser Cys Asp Asp Phe Met Gly Gln Leu Leu Asn Gly
            355                 360                 365
Arg Val Leu Phe Pro Val Asn Leu Gln Leu Gly Ala Lys Val Asp Phe
            370                 375                 380
Val Cys Asp Glu Gly Phe Gln Leu Lys Gly Ser Ser Ala Ser Tyr Cys
385                 390                 395                 400
Val Leu Ala Gly Met Glu Ser Leu Trp Asn Ser Ser Val Pro Val Cys
                405                 410                 415
Glu Gln Ile Phe Cys Pro Ser Pro Pro Val Ile Pro Asn Gly Arg His
            420                 425                 430
Thr Gly Lys Pro Leu Glu Val Phe Pro Phe Gly Lys Thr Val Asn Tyr
            435                 440                 445
Thr Cys Asp Pro His Pro Asp Arg Gly Thr Ser Phe Asp Leu Ile Gly
            450                 455                 460
Glu Ser Thr Ile Arg Cys Thr Ser Asp Pro Gln Gly Asn Gly Val Trp
465                 470                 475                 480
Ser Ser Pro Ala Pro Arg Cys Gly Ile Leu Gly His Cys Gln Ala Pro
                485                 490                 495
Asp His Phe Leu Phe Ala Lys Leu Lys Thr Gln Thr Asn Ala Ser Asp
            500                 505                 510
Phe Pro Ile Gly Thr Ser Leu Lys Tyr Glu Cys Arg Pro Glu Tyr Tyr
            515                 520                 525
Gly Arg Pro Phe Ser Ile Thr Cys Leu Asp Asn Leu Val Trp Ser Ser
            530                 535                 540
Pro Lys Asp Val Cys Lys Arg Lys Ser Cys Lys Thr Pro Pro Asp Pro
545                 550                 555                 560
Val Asn Gly Met Val His Val Ile Thr Asp Ile Gln Val Gly Ser Arg
                565                 570                 575
Ile Asn Tyr Ser Cys Thr Thr Gly His Arg Leu Ile Gly His Ser Ser
                580                 585                 590
Ala Glu Cys Ile Leu Ser Gly Asn Ala Ala His Trp Ser Thr Lys Pro
            595                 600                 605
Pro Ile Cys Gln Arg Ile Pro Cys Gly Leu Pro Pro Thr Ile Ala Asn
            610                 615                 620
Gly Asp Phe Ile Ser Thr Asn Arg Glu Asn Phe His Tyr Gly Ser Val
625                 630                 635                 640
Val Thr Tyr Arg Cys Asn Pro Gly Ser Gly Gly Arg Lys Val Phe Glu
                645                 650                 655
Leu Val Gly Glu Pro Ser Ile Tyr Cys Thr Ser Asn Asp Asp Gln Val
            660                 665                 670
Gly Ile Trp Ser Gly Pro Ala Pro Gln Cys Ile Ile Pro Asn Lys Cys
            675                 680                 685
```

Thr Pro Pro Asn Val Glu Asn Gly Ile Leu Val Ser Asp Asn Arg Ser
690                 695                 700

Leu Phe Ser Leu Asn Glu Val Val Glu Phe Arg Cys Gln Pro Gly Phe
705                 710                 715                 720

Val Met Lys Gly Pro Arg Arg Val Lys Cys Gln Ala Leu Asn Lys Trp
            725                 730                 735

Glu Pro Glu Leu Pro Ser Cys Ser Arg Val Cys Gln Pro Pro Pro Asp
            740                 745                 750

Val Leu His Ala Glu Arg Thr Gln Arg Asp Lys Asp Asn Phe Ser Pro
            755                 760                 765

Gly Gln Glu Val Phe Tyr Ser Cys Glu Pro Gly Tyr Asp Leu Arg Gly
            770                 775                 780

Ala Ala Ser Met Arg Cys Thr Pro Gln Gly Asp Trp Ser Pro Ala Ala
785                 790                 795                 800

Pro Thr Cys Glu Val Lys Ser Cys Asp Asp Phe Met Gly Gln Leu Leu
            805                 810                 815

Asn Gly Arg Val Leu Phe Pro Val Asn Leu Gln Leu Gly Ala Lys Val
            820                 825                 830

Asp Phe Val Cys Asp Glu Gly Phe Gln Leu Lys Gly Ser Ser Ala Ser
            835                 840                 845

Tyr Cys Val Leu Ala Gly Met Glu Ser Leu Trp Asn Ser Ser Val Pro
850                 855                 860

Val Cys Glu Gln Ile Phe Cys Pro Ser Pro Pro Val Ile Pro Asn Gly
865                 870                 875                 880

Arg His Thr Gly Lys Pro Leu Glu Val Phe Pro Phe Gly Lys Ala Val
            885                 890                 895

Asn Tyr Thr Cys Asp Pro His Pro Asp Arg Gly Thr Ser Phe Asp Leu
            900                 905                 910

Ile Gly Glu Ser Thr Ile Arg Cys Thr Ser Asp Pro Gln Gly Asn Gly
            915                 920                 925

Val Trp Ser Ser Pro Ala Pro Arg Cys Gly Ile Leu Gly His Cys Gln
            930                 935                 940

Ala Pro Asp His Phe Leu Phe Ala Lys Leu Lys Thr Gln Thr Asn Ala
945                 950                 955                 960

Ser Asp Phe Pro Ile Gly Thr Ser Leu Lys Tyr Glu Cys Arg Pro Glu
            965                 970                 975

Tyr Tyr Gly Arg Pro Phe Ser Ile Thr Cys Leu Asp Asn Leu Val Trp
            980                 985                 990

Ser Ser Pro Lys Asp Val Cys Lys Arg Lys Ser Cys Lys Thr Pro Pro
            995                 1000                1005

Asp Pro Val Asn Gly Met Val His Val Ile Thr Asp Ile Gln Val
        1010                1015                1020

Gly Ser Arg Ile Asn Tyr Ser Cys Thr Thr Gly His Arg Leu Ile
        1025                1030                1035

Gly His Ser Ser Ala Glu Cys Ile Leu Ser Gly Asn Thr Ala His
        1040                1045                1050

Trp Ser Thr Lys Pro Pro Ile Cys Gln Arg Ile Pro Cys Gly Leu
        1055                1060                1065

Pro Pro Thr Ile Ala Asn Gly Asp Phe Ile Ser Thr Asn Arg Glu
        1070                1075                1080

Asn Phe His Tyr Gly Ser Val Val Thr Tyr Arg Cys Asn Leu Gly
        1085                1090                1095

```
Ser Arg Gly Arg Lys Val Phe Glu Leu Val Gly Glu Pro Ser Ile
1100                1105                1110

Tyr Cys Thr Ser Asn Asp Asp Gln Val Gly Ile Trp Ser Gly Pro
1115                1120                1125

Ala Pro Gln Cys Ile Ile Pro Asn Lys Cys Thr Pro Pro Asn Val
1130                1135                1140

Glu Asn Gly Ile Leu Val Ser Asp Asn Arg Ser Leu Phe Ser Leu
1145                1150                1155

Asn Glu Val Val Glu Phe Arg Cys Gln Pro Gly Phe Val Met Lys
1160                1165                1170

Gly Pro Arg Arg Val Lys Cys Gln Ala Leu Asn Lys Trp Glu Pro
1175                1180                1185

Glu Leu Pro Ser Cys Ser Arg Val Cys Gln Pro Pro Pro Glu Ile
1190                1195                1200

Leu His Gly Glu His Thr Pro Ser His Gln Asp Asn Phe Ser Pro
1205                1210                1215

Gly Gln Glu Val Phe Tyr Ser Cys Glu Pro Gly Tyr Asp Leu Arg
1220                1225                1230

Gly Ala Ala Ser Leu His Cys Thr Pro Gln Gly Asp Trp Ser Pro
1235                1240                1245

Glu Ala Pro Arg Cys Ala Val Lys Ser Cys Asp Asp Phe Leu Gly
1250                1255                1260

Gln Leu Pro His Gly Arg Val Leu Phe Pro Leu Asn Leu Gln Leu
1265                1270                1275

Gly Ala Lys Val Ser Phe Val Cys Asp Glu Gly Phe Arg Leu Lys
1280                1285                1290

Gly Ser Ser Val Ser His Cys Val Leu Val Gly Met Arg Ser Leu
1295                1300                1305

Trp Asn Asn Ser Val Pro Val Cys Glu His Ile Phe Cys Pro Asn
1310                1315                1320

Pro Pro Ala Ile Leu Asn Gly Arg His Thr Gly Thr Pro Ser Gly
1325                1330                1335

Asp Ile Pro Tyr Gly Lys Glu Ile Ser Tyr Thr Cys Asp Pro His
1340                1345                1350

Pro Asp Arg Gly Met Thr Phe Asn Leu Ile Gly Glu Ser Thr Ile
1355                1360                1365

Arg Cys Thr Ser Asp Pro His Gly Asn Gly Val Trp Ser Ser Pro
1370                1375                1380

Ala Pro Arg Cys Glu Leu Ser Val Arg Ala Gly His Cys Lys Thr
1385                1390                1395

Pro Glu Gln Phe Pro Phe Ala Ser Pro Thr Ile Pro Ile Asn Asp
1400                1405                1410

Phe Glu Phe Pro Val Gly Thr Ser Leu Asn Tyr Glu Cys Arg Pro
1415                1420                1425

Gly Tyr Phe Gly Lys Met Phe Ser Ile Ser Cys Leu Glu Asn Leu
1430                1435                1440

Val Trp Ser Ser Val Glu Asp Asn Cys Arg Arg Lys Ser Cys Gly
1445                1450                1455

Pro Pro Pro Glu Pro Phe Asn Gly Met Val His Ile Asn Thr Asp
1460                1465                1470

Thr Gln Phe Gly Ser Thr Val Asn Tyr Ser Cys Asn Glu Gly Phe
1475                1480                1485

Arg Leu Ile Gly Ser Pro Ser Thr Thr Cys Leu Val Ser Gly Asn
```

-continued

```
            1490                1495                1500
Asn Val Thr Trp Asp Lys Lys Ala Pro Ile Cys Glu Ile Ile Ser
1505                1510                1515
Cys Glu Pro Pro Thr Ile Ser Asn Gly Asp Phe Tyr Ser Asn
1520                1525                1530
Asn Arg Thr Ser Phe His Asn Gly Thr Val Val Thr Tyr Gln Cys
1535                1540                1545
His Thr Gly Pro Asp Gly Glu Gln Leu Phe Glu Leu Val Gly Glu
1550                1555                1560
Arg Ser Ile Tyr Cys Thr Ser Lys Asp Asp Gln Val Gly Val Trp
1565                1570                1575
Ser Ser Pro Pro Pro Arg Cys Ile Ser Thr Asn Lys Cys Thr Ala
1580                1585                1590
Pro Glu Val Glu Asn Ala Ile Arg Val Pro Gly Asn Arg Ser Phe
1595                1600                1605
Phe Thr Leu Thr Glu Ile Ile Arg Phe Arg Cys Gln Pro Gly Phe
1610                1615                1620
Val Met Val Gly Ser His Thr Val Gln Cys Gln Thr Asn Gly Arg
1625                1630                1635
Trp Gly Pro Lys Leu Pro His Cys Ser Arg Val Cys Gln Pro Pro
1640                1645                1650
Pro Glu Ile Leu His Gly Glu His Thr Leu Ser His Gln Asp Asn
1655                1660                1665
Phe Ser Pro Gly Gln Glu Val Phe Tyr Ser Cys Glu Pro Ser Tyr
1670                1675                1680
Asp Leu Arg Gly Ala Ala Ser Leu His Cys Thr Pro Gln Gly Asp
1685                1690                1695
Trp Ser Pro Glu Ala Pro Arg Cys Thr Val Lys Ser Cys Asp Asp
1700                1705                1710
Phe Leu Gly Gln Leu Pro His Gly Arg Val Leu Leu Pro Leu Asn
1715                1720                1725
Leu Gln Leu Gly Ala Lys Val Ser Phe Val Cys Asp Glu Gly Phe
1730                1735                1740
Arg Leu Lys Gly Arg Ser Ala Ser His Cys Val Leu Ala Gly Met
1745                1750                1755
Lys Ala Leu Trp Asn Ser Ser Val Pro Val Cys Glu Gln Ile Phe
1760                1765                1770
Cys Pro Asn Pro Pro Ala Ile Leu Asn Gly Arg His Thr Gly Thr
1775                1780                1785
Pro Phe Gly Asp Ile Pro Tyr Gly Lys Glu Ile Ser Tyr Ala Cys
1790                1795                1800
Asp Thr His Pro Asp Arg Gly Met Thr Phe Asn Leu Ile Gly Glu
1805                1810                1815
Ser Ser Ile Arg Cys Thr Ser Asp Pro Gln Gly Asn Gly Val Trp
1820                1825                1830
Ser Ser Pro Ala Pro Arg Cys Glu Leu Ser Val Pro Ala Ala Cys
1835                1840                1845
Pro His Pro Pro Lys Ile Gln Asn Gly His Tyr Ile Gly Gly His
1850                1855                1860
Val Ser Leu Tyr Leu Pro Gly Met Thr Ile Ser Tyr Ile Cys Asp
1865                1870                1875
Pro Gly Tyr Leu Leu Val Gly Lys Gly Phe Ile Phe Cys Thr Asp
1880                1885                1890
```

-continued

```
Gln Gly Ile Trp Ser Gln Leu Asp His Tyr Cys Lys Glu Val Asn
    1895                1900                1905

Cys Ser Phe Pro Leu Phe Met Asn Gly Ile Ser Lys Glu Leu Glu
    1910                1915                1920

Met Lys Lys Val Tyr His Tyr Gly Asp Tyr Val Thr Leu Lys Cys
    1925                1930                1935

Glu Asp Gly Tyr Thr Leu Glu Gly Ser Pro Trp Ser Gln Cys Gln
    1940                1945                1950

Ala Asp Asp Arg Trp Asp Pro Pro Leu Ala Lys Cys Thr Ser Arg
    1955                1960                1965

Thr His Asp Ala Leu Ile Val Gly Thr Leu Ser Gly Thr Ile Phe
    1970                1975                1980

Phe Ile Leu Leu Ile Ile Phe Leu Ser Trp Ile Ile Leu Lys His
    1985                1990                1995

Arg Lys Gly Asn Asn Ala His Glu Asn Pro Lys Glu Val Ala Ile
    2000                2005                2010

His Leu His Ser Gln Gly Gly Ser Ser Val His Pro Arg Thr Leu
    2015                2020                2025

Gln Thr Asn Glu Glu Asn Ser Arg Val Leu Pro
    2030                2035

<210> SEQ ID NO 3
<211> LENGTH: 2361
<212> TYPE: PRT
<213> ORGANISM: Homo sapiens

<400> SEQUENCE: 3

Met Cys Leu Gly Arg Met Gly Ala Ser Pro Arg Ser Pro Glu Pro
1               5                   10                  15

Val Gly Pro Pro Ala Pro Gly Leu Pro Phe Cys Cys Gly Gly Ser Leu
                20                  25                  30

Leu Ala Val Val Val Leu Leu Ala Leu Pro Val Ala Trp Gly Gln Cys
                35                  40                  45

Asn Ala Pro Glu Trp Leu Pro Phe Ala Arg Pro Thr Asn Leu Thr Asp
    50                  55                  60

Glu Phe Glu Phe Pro Ile Gly Thr Tyr Leu Asn Tyr Glu Cys Arg Pro
65                  70                  75                  80

Gly Tyr Ser Gly Arg Pro Phe Ser Ile Ile Cys Leu Lys Asn Ser Val
                85                  90                  95

Trp Thr Gly Ala Lys Asp Arg Cys Arg Arg Lys Ser Cys Arg Asn Pro
                100                 105                 110

Pro Asp Pro Val Asn Gly Met Val His Val Ile Lys Gly Ile Gln Phe
    115                 120                 125

Gly Ser Gln Ile Lys Tyr Ser Cys Thr Lys Gly Tyr Arg Leu Ile Gly
    130                 135                 140

Ser Ser Ser Ala Thr Cys Ile Ile Ser Gly Asp Thr Val Ile Trp Asp
145                 150                 155                 160

Asn Glu Thr Pro Ile Cys Asp Arg Ile Pro Cys Gly Leu Pro Pro Thr
                165                 170                 175

Ile Thr Asn Gly Asp Phe Ile Ser Thr Asn Arg Glu Asn Phe His Tyr
                180                 185                 190

Gly Ser Val Val Thr Tyr Arg Cys Asn Pro Gly Ser Gly Gly Arg Lys
    195                 200                 205

Val Phe Glu Leu Val Gly Glu Pro Ser Ile Tyr Cys Thr Ser Asn Asp
```

```
              210                 215                 220
Asp Gln Val Gly Ile Trp Ser Gly Pro Ala Pro Gln Cys Ile Ile Pro
225                 230                 235                 240

Asn Lys Cys Thr Pro Pro Asn Val Glu Asn Gly Ile Leu Val Ser Asp
            245                 250                 255

Asn Arg Ser Leu Phe Ser Leu Asn Glu Val Val Glu Phe Arg Cys Gln
        260                 265                 270

Pro Gly Phe Val Met Lys Gly Pro Arg Arg Val Lys Cys Gln Ala Leu
    275                 280                 285

Asn Lys Trp Glu Pro Glu Leu Pro Ser Cys Ser Arg Val Cys Gln Pro
290                 295                 300

Pro Pro Asp Val Leu His Ala Glu Arg Thr Gln Arg Asp Lys Asp Asn
305                 310                 315                 320

Phe Ser Pro Gly Gln Glu Val Phe Tyr Ser Cys Glu Pro Gly Tyr Asp
            325                 330                 335

Leu Arg Gly Ala Ala Ser Met Arg Cys Thr Pro Gln Gly Asp Trp Ser
        340                 345                 350

Pro Ala Ala Pro Thr Cys Glu Val Lys Ser Cys Asp Asp Phe Met Gly
    355                 360                 365

Gln Leu Leu Asn Gly Arg Val Leu Phe Pro Val Asn Leu Gln Leu Gly
370                 375                 380

Ala Lys Val Asp Phe Val Cys Asp Glu Gly Phe Gln Leu Lys Gly Ser
385                 390                 395                 400

Ser Ala Ser Tyr Cys Val Leu Ala Gly Met Glu Ser Leu Trp Asn Ser
            405                 410                 415

Ser Val Pro Val Cys Glu Gln Ile Phe Cys Pro Ser Pro Pro Val Ile
        420                 425                 430

Pro Asn Gly Arg His Thr Gly Lys Pro Leu Glu Val Phe Pro Phe Gly
    435                 440                 445

Lys Thr Val Asn Tyr Thr Cys Asp Pro His Pro Asp Arg Gly Thr Ser
450                 455                 460

Phe Asp Leu Ile Gly Glu Ser Thr Ile Arg Cys Thr Ser Asp Pro Gln
465                 470                 475                 480

Gly Asn Gly Val Trp Ser Ser Pro Ala Pro Arg Cys Gly Ile Leu Gly
            485                 490                 495

His Cys Gln Ala Pro Asp His Phe Leu Phe Ala Lys Leu Lys Thr Gln
        500                 505                 510

Thr Asn Ala Ser Asp Phe Pro Ile Gly Thr Ser Leu Lys Tyr Glu Cys
    515                 520                 525

Arg Pro Glu Tyr Tyr Gly Arg Pro Phe Ser Ile Thr Cys Leu Asp Asn
530                 535                 540

Leu Val Trp Ser Ser Pro Lys Asp Val Cys Lys Arg Lys Ser Cys Lys
545                 550                 555                 560

Thr Pro Pro Asp Pro Val Asn Gly Met Val His Val Ile Thr Asp Ile
            565                 570                 575

Gln Val Gly Ser Arg Ile Asn Tyr Ser Cys Thr Thr Gly His Arg Leu
        580                 585                 590

Ile Gly His Ser Ser Ala Glu Cys Ile Leu Ser Gly Asn Ala Ala His
    595                 600                 605

Trp Ser Thr Lys Pro Pro Ile Cys Gln Arg Ile Pro Cys Gly Leu Pro
610                 615                 620

Pro Thr Ile Ala Asn Gly Asp Phe Ile Ser Thr Asn Arg Glu Asn Phe
625                 630                 635                 640
```

-continued

```
His Tyr Gly Ser Val Thr Tyr Arg Cys Asn Pro Gly Ser Gly Gly
            645                 650                 655

Arg Lys Val Phe Glu Leu Val Gly Glu Pro Ser Ile Tyr Cys Thr Ser
            660                 665                 670

Asn Asp Asp Gln Val Gly Ile Trp Ser Gly Pro Ala Pro Gln Cys Ile
            675                 680                 685

Ile Pro Asn Lys Cys Thr Pro Pro Asn Val Glu Asn Gly Ile Leu Val
        690                 695                 700

Ser Asp Asn Arg Ser Leu Phe Ser Leu Asn Glu Val Val Glu Phe Arg
705                 710                 715                 720

Cys Gln Pro Gly Phe Val Met Lys Gly Pro Arg Arg Val Lys Cys Gln
                725                 730                 735

Ala Leu Asn Lys Trp Glu Pro Glu Leu Pro Ser Cys Ser Arg Val Cys
            740                 745                 750

Gln Pro Pro Pro Asp Val Leu His Ala Glu Arg Thr Gln Arg Asp Lys
            755                 760                 765

Asp Asn Phe Ser Pro Gly Gln Glu Val Phe Tyr Ser Cys Glu Pro Gly
770                 775                 780

Tyr Asp Leu Arg Gly Ala Ala Ser Met Arg Cys Thr Pro Gln Gly Asp
785                 790                 795                 800

Trp Ser Pro Ala Ala Pro Thr Cys Glu Val Lys Ser Cys Asp Asp Phe
                805                 810                 815

Met Gly Gln Leu Leu Asn Gly Arg Val Leu Phe Pro Val Asn Leu Gln
            820                 825                 830

Leu Gly Ala Lys Val Asp Phe Val Cys Asp Glu Gly Phe Gln Leu Lys
            835                 840                 845

Gly Ser Ser Ala Ser Tyr Cys Val Leu Ala Gly Met Glu Ser Leu Trp
850                 855                 860

Asn Ser Ser Val Pro Val Cys Glu Gln Ile Phe Cys Pro Ser Pro Pro
865                 870                 875                 880

Val Ile Pro Asn Gly Arg His Thr Gly Lys Pro Leu Glu Val Phe Pro
                885                 890                 895

Phe Gly Lys Thr Val Asn Tyr Thr Cys Asp Pro His Pro Asp Arg Gly
            900                 905                 910

Thr Ser Phe Asp Leu Ile Gly Glu Ser Thr Ile Arg Cys Thr Ser Asp
            915                 920                 925

Pro Gln Gly Asn Gly Val Trp Ser Ser Pro Ala Pro Arg Cys Gly Ile
930                 935                 940

Leu Gly His Cys Gln Ala Pro Asp His Phe Leu Phe Ala Lys Leu Lys
945                 950                 955                 960

Thr Gln Thr Asn Ala Ser Asp Phe Pro Ile Gly Thr Ser Leu Lys Tyr
                965                 970                 975

Glu Cys Arg Pro Glu Tyr Tyr Gly Arg Pro Phe Ser Ile Thr Cys Leu
            980                 985                 990

Asp Asn Leu Val Trp Ser Ser Pro Lys Asp Val Cys Lys Arg Lys Ser
            995                 1000                1005

Cys Lys Thr Pro Pro Asp Pro Val Asn Gly Met Val His Val Ile
        1010                1015                1020

Thr Asp Ile Gln Val Gly Ser Arg Ile Asn Tyr Ser Cys Thr Thr
        1025                1030                1035

Gly His Arg Leu Ile Gly His Ser Ser Ala Glu Cys Ile Leu Ser
        1040                1045                1050
```

-continued

```
Gly Asn Ala Ala His Trp Ser Thr Lys Pro Pro Ile Cys Gln Leu
    1055                1060                1065

Cys Gln Pro Pro Pro Asp Val Leu His Ala Glu Arg Thr Gln Arg
    1070                1075                1080

Asp Lys Asp Asn Phe Ser Pro Gly Gln Glu Val Phe Tyr Ser Cys
    1085                1090                1095

Glu Pro Gly Tyr Asp Leu Arg Gly Ala Ala Ser Met Arg Cys Thr
    1100                1105                1110

Pro Gln Gly Asp Trp Ser Pro Ala Ala Pro Thr Cys Glu Val Lys
    1115                1120                1125

Ser Cys Asp Asp Phe Met Gly Gln Leu Leu Asn Gly Arg Val Leu
    1130                1135                1140

Phe Pro Val Asn Leu Gln Leu Gly Ala Lys Val Asp Phe Val Cys
    1145                1150                1155

Asp Glu Gly Phe Gln Leu Lys Gly Ser Ser Ala Ser Tyr Cys Val
    1160                1165                1170

Leu Ala Gly Met Glu Ser Leu Trp Asn Ser Ser Val Pro Val Cys
    1175                1180                1185

Glu Gln Ile Phe Cys Pro Ser Pro Pro Val Ile Pro Asn Gly Arg
    1190                1195                1200

His Thr Gly Lys Pro Leu Glu Val Phe Pro Phe Gly Lys Ala Val
    1205                1210                1215

Asn Tyr Thr Cys Asp Pro His Pro Asp Arg Gly Thr Ser Phe Asp
    1220                1225                1230

Leu Ile Gly Glu Ser Thr Ile Arg Cys Thr Ser Asp Pro Gln Gly
    1235                1240                1245

Asn Gly Val Trp Ser Ser Pro Ala Pro Arg Cys Gly Ile Leu Gly
    1250                1255                1260

His Cys Gln Ala Pro Asp His Phe Leu Phe Ala Lys Leu Lys Thr
    1265                1270                1275

Gln Thr Asn Ala Ser Asp Phe Pro Ile Gly Thr Ser Leu Lys Tyr
    1280                1285                1290

Glu Cys Arg Pro Glu Tyr Tyr Gly Arg Pro Phe Ser Ile Thr Cys
    1295                1300                1305

Leu Asp Asn Leu Val Trp Ser Ser Pro Lys Asp Val Cys Lys Arg
    1310                1315                1320

Lys Ser Cys Lys Thr Pro Pro Asp Pro Val Asn Gly Met Val His
    1325                1330                1335

Val Ile Thr Asp Ile Gln Val Gly Ser Arg Ile Asn Tyr Ser Cys
    1340                1345                1350

Thr Thr Gly His Arg Leu Ile Gly His Ser Ser Ala Glu Cys Ile
    1355                1360                1365

Leu Ser Gly Asn Thr Ala His Trp Ser Thr Lys Pro Pro Ile Cys
    1370                1375                1380

Gln Arg Ile Pro Cys Gly Leu Pro Pro Thr Ile Ala Asn Gly Asp
    1385                1390                1395

Phe Ile Ser Thr Asn Arg Glu Asn Phe His Tyr Gly Ser Val Val
    1400                1405                1410

Thr Tyr Arg Cys Asn Leu Gly Ser Arg Gly Arg Lys Val Phe Glu
    1415                1420                1425

Leu Val Gly Glu Pro Ser Ile Tyr Cys Thr Ser Asn Asp Asp Gln
    1430                1435                1440

Val Gly Ile Trp Ser Gly Pro Ala Pro Gln Cys Ile Ile Pro Asn
```

-continued

```
            1445                1450                1455
Lys Cys Thr Pro Pro Asn Val Glu Asn Gly Ile Leu Val Ser Asp
        1460                1465                1470
Asn Arg Ser Leu Phe Ser Leu Asn Glu Val Val Glu Phe Arg Cys
        1475                1480                1485
Gln Pro Gly Phe Val Met Lys Gly Pro Arg Val Lys Cys Gln
        1490                1495                1500
Ala Leu Asn Lys Trp Glu Pro Glu Leu Pro Ser Cys Ser Arg Val
        1505                1510                1515
Cys Gln Pro Pro Pro Glu Ile Leu His Gly Glu His Thr Pro Ser
        1520                1525                1530
His Gln Asp Asn Phe Ser Pro Gly Gln Glu Val Phe Tyr Ser Cys
        1535                1540                1545
Glu Pro Gly Tyr Asp Leu Arg Gly Ala Ala Ser Leu His Cys Thr
        1550                1555                1560
Pro Gln Gly Asp Trp Ser Pro Glu Ala Pro Arg Cys Ala Val Lys
        1565                1570                1575
Ser Cys Asp Asp Phe Leu Gly Gln Leu Pro His Gly Arg Val Leu
        1580                1585                1590
Phe Pro Leu Asn Leu Gln Leu Gly Ala Lys Val Ser Phe Val Cys
        1595                1600                1605
Asp Glu Gly Phe Arg Leu Lys Gly Ser Ser Val Ser His Cys Val
        1610                1615                1620
Leu Val Gly Met Arg Ser Leu Trp Asn Asn Ser Val Pro Val Cys
        1625                1630                1635
Glu His Ile Phe Cys Pro Asn Pro Pro Ala Ile Leu Asn Gly Arg
        1640                1645                1650
His Thr Gly Thr Pro Ser Gly Asp Ile Pro Tyr Gly Lys Glu Ile
        1655                1660                1665
Ser Tyr Thr Cys Asp Pro His Pro Asp Arg Gly Met Thr Phe Asn
        1670                1675                1680
Leu Ile Gly Glu Ser Thr Ile Arg Cys Thr Ser Asp Pro His Gly
        1685                1690                1695
Asn Gly Val Trp Ser Ser Pro Ala Pro Arg Cys Glu Leu Ser Val
        1700                1705                1710
Arg Ala Gly His Cys Lys Thr Pro Glu Gln Phe Pro Phe Ala Ser
        1715                1720                1725
Pro Thr Ile Pro Ile Asn Asp Phe Glu Phe Pro Val Gly Thr Ser
        1730                1735                1740
Leu Asn Tyr Glu Cys Arg Pro Gly Tyr Phe Gly Lys Met Phe Ser
        1745                1750                1755
Ile Ser Cys Leu Glu Asn Leu Val Trp Ser Ser Val Glu Asp Asn
        1760                1765                1770
Cys Arg Arg Lys Ser Cys Gly Pro Pro Pro Glu Pro Phe Asn Gly
        1775                1780                1785
Met Val His Ile Asn Thr Asp Thr Gln Phe Gly Ser Thr Val Asn
        1790                1795                1800
Tyr Ser Cys Asn Glu Gly Phe Arg Leu Ile Gly Ser Pro Ser Thr
        1805                1810                1815
Thr Cys Leu Val Ser Gly Asn Asn Val Thr Trp Asp Lys Lys Ala
        1820                1825                1830
Pro Ile Cys Glu Ile Ile Ser Cys Glu Pro Pro Pro Thr Ile Ser
        1835                1840                1845
```

```
Asn Gly Asp Phe Tyr Ser Asn Asn Arg Thr Ser Phe His Asn Gly
    1850            1855                1860
Thr Val Val Thr Tyr Gln Cys His Thr Gly Pro Asp Gly Glu Gln
    1865            1870                1875
Leu Phe Glu Leu Val Gly Glu Arg Ser Ile Tyr Cys Thr Ser Lys
    1880            1885                1890
Asp Asp Gln Val Gly Val Trp Ser Ser Pro Pro Arg Cys Ile
    1895            1900                1905
Ser Thr Asn Lys Cys Thr Ala Pro Glu Val Glu Asn Ala Ile Arg
    1910            1915                1920
Val Pro Gly Asn Arg Ser Phe Phe Thr Leu Thr Glu Ile Ile Arg
    1925            1930                1935
Phe Arg Cys Gln Pro Gly Phe Val Met Val Gly Ser His Thr Val
    1940            1945                1950
Gln Cys Gln Thr Asn Gly Arg Trp Gly Pro Lys Leu Pro His Cys
    1955            1960                1965
Ser Arg Val Cys Gln Pro Pro Glu Ile Leu His Gly Glu His
    1970            1975                1980
Thr Leu Ser His Gln Asp Asn Phe Ser Pro Gly Gln Glu Val Phe
    1985            1990                1995
Tyr Ser Cys Glu Pro Ser Tyr Asp Leu Arg Gly Ala Ala Ser Leu
    2000            2005                2010
His Cys Thr Pro Gln Gly Asp Trp Ser Pro Glu Ala Pro Arg Cys
    2015            2020                2025
Thr Val Lys Ser Cys Asp Asp Phe Leu Gly Gln Leu Pro His Gly
    2030            2035                2040
Arg Val Leu Leu Pro Leu Asn Leu Gln Leu Gly Ala Lys Val Ser
    2045            2050                2055
Phe Val Cys Asp Glu Gly Phe Arg Leu Lys Gly Arg Ser Ala Ser
    2060            2065                2070
His Cys Val Leu Ala Gly Met Lys Ala Leu Trp Asn Ser Ser Val
    2075            2080                2085
Pro Val Cys Glu Gln Ile Phe Cys Pro Asn Pro Pro Ala Ile Leu
    2090            2095                2100
Asn Gly Arg His Thr Gly Thr Pro Phe Gly Asp Ile Pro Tyr Gly
    2105            2110                2115
Lys Glu Ile Ser Tyr Ala Cys Asp Thr His Pro Asp Arg Gly Met
    2120            2125                2130
Thr Phe Asn Leu Ile Gly Glu Ser Ser Ile Arg Cys Thr Ser Asp
    2135            2140                2145
Pro Gln Gly Asn Gly Val Trp Ser Ser Pro Ala Pro Arg Cys Glu
    2150            2155                2160
Leu Ser Val Pro Ala Ala Cys Pro His Pro Pro Lys Ile Gln Asn
    2165            2170                2175
Gly His Tyr Ile Gly Gly His Val Ser Leu Tyr Leu Pro Gly Met
    2180            2185                2190
Thr Ile Ser Tyr Ile Cys Asp Pro Gly Tyr Leu Leu Val Gly Lys
    2195            2200                2205
Gly Phe Ile Phe Cys Thr Asp Gln Gly Ile Trp Ser Gln Leu Asp
    2210            2215                2220
His Tyr Cys Lys Glu Val Asn Cys Ser Phe Pro Leu Phe Met Asn
    2225            2230                2235
```

-continued

```
Gly Ile Ser Lys Glu Leu Glu Met Lys Lys Val Tyr His Tyr Gly
    2240                2245                2250

Asp Tyr Val Thr Leu Lys Cys Glu Asp Gly Tyr Thr Leu Glu Gly
    2255                2260                2265

Ser Pro Trp Ser Gln Cys Gln Ala Asp Asp Arg Trp Asp Pro Pro
    2270                2275                2280

Leu Ala Lys Cys Thr Ser Arg Thr His Asp Ala Leu Ile Val Gly
    2285                2290                2295

Thr Leu Ser Gly Thr Ile Phe Phe Ile Leu Leu Ile Ile Phe Leu
    2300                2305                2310

Ser Trp Ile Ile Leu Lys His Arg Lys Gly Asn Asn Ala His Glu
    2315                2320                2325

Asn Pro Lys Glu Val Ala Ile His Leu His Ser Gln Gly Gly Ser
    2330                2335                2340

Ser Val His Pro Arg Thr Leu Gln Thr Asn Glu Glu Asn Ser Arg
    2345                2350                2355

Val Leu Pro
    2360

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Tyr Pro Tyr Asp Val Pro Asp Tyr Ala
1               5

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Glu Gln Lys Leu Ile Ser Glu Glu Asp Leu
1               5                   10

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Asp Tyr Lys Asp Asp Asp Asp Lys
1               5

<210> SEQ ID NO 7
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
```
gagggcagag gaagtcttct aacatgcggt gacgtggagg sgsstcccgg ccct	54

<210> SEQ ID NO 8
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
tacccctatg acgtgcccga ctatgcc	27

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
tcctgaggag aagtctgccg t	21

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ggagtggaca gatccccaaa g	21

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tctcctgccg acaagaccaa	20

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gcagtggctt agcttgaagt tg	22

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13

```
caacttcaag ctaagccact gc                                            22
```

<210> SEQ ID NO 14
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14

```
cggtgctcac agaagccag                                                19
```

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15

```
gactgctgtc aatgccctgt                                               20
```

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16

```
aaaggcacct agcaccttct t                                             21
```

<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17

```
cactggagct acagacaaga aggtg                                         25
```

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18

```
tctcccacca tagaagatac cagg                                          24
```

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19

```
aagagcctca ggatccagca c                                             21
```

-continued

```
<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
tcagcagtga tggatggaca c                                             21

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
cgcagctagg aataatggaa tagg                                          24

<210> SEQ ID NO 22
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
catggcctca gttccgaaa                                                19

<210> SEQ ID NO 23
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gly Gly Gly Ser Gly Gly Gly Ser
1               5

<210> SEQ ID NO 24
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gly Gly Gly Gly Ser Gly Gly Gly Gly Ser Gly Gly Gly Gly Ser
1               5                   10                  15

<210> SEQ ID NO 25
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
```

```
<223> OTHER INFORMATION: Any amino acid

<400> SEQUENCE: 25

Leu Pro Xaa Thr Gly
1               5

<210> SEQ ID NO 26
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid

<400> SEQUENCE: 26

Leu Pro Xaa Thr Ala
1               5

<210> SEQ ID NO 27
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 27

His His His His His His
1               5

<210> SEQ ID NO 28
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

His Trp Met Val Leu Pro Trp Leu Pro Gly Thr Leu Asp Gly Gly Ser
1               5                   10                  15

Gly Cys Arg Gly
            20

<210> SEQ ID NO 29
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Leu Pro Glu Thr Gly Gly
1               5

<210> SEQ ID NO 30
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 30

Gly Ser Thr Ser Gly Ser Gly Lys Pro Gly Ser Gly Glu Gly Ser Thr
1               5                   10                  15
Lys Gly
```